US012553037B2

(12) United States Patent
Fernandes et al.

(10) Patent No.: US 12,553,037 B2
(45) **Date of Patent: *Feb. 17, 2026**

(54) ENGINEERED CLASS 2, TYPE V REPRESSOR SYSTEMS

(71) Applicant: Scribe Therapeutics Inc., Alameda, CA (US)

(72) Inventors: Jason Fernandes, Redwood City, CA (US); Ross White, Concord, CA (US); Sean Higgins, Alameda, CA (US); Sarah Denny, San Francisco, CA (US); Benjamin Oakes, El Cerrito, CA (US); Emeric Jean Marius Charles, Berkeley, CA (US)

(73) Assignee: Scribe Therapeutics Inc., Alameda, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/612,882

(22) Filed: Mar. 21, 2024

(65) Prior Publication Data

US 2024/0254466 A1 Aug. 1, 2024

Related U.S. Application Data

(63) Continuation of application No. PCT/US2022/076774, filed on Sep. 21, 2022.

(60) Provisional application No. 63/321,517, filed on Mar. 18, 2022, provisional application No. 63/246,543, filed on Sep. 21, 2021.

(51) Int. Cl.

| | |
|---|---|
| ***C12N 9/22*** | (2006.01) |
| ***A61K 48/00*** | (2006.01) |
| ***C12N 9/10*** | (2006.01) |
| ***C12N 15/11*** | (2006.01) |
| ***C12N 15/86*** | (2006.01) |
| ***C12N 15/88*** | (2006.01) |
| ***C12N 15/90*** | (2006.01) |

(52) U.S. Cl.

CPC .............. *C12N 9/22* (2013.01); *A61K 48/005* (2013.01); *C12N 9/1007* (2013.01); *C12N 15/11* (2013.01); *C12N 15/86* (2013.01); *C12N 15/88* (2013.01); *C12N 15/907* (2013.01); *C07K 2319/00* (2013.01); *C12N 2310/20* (2017.05); *C12N 2750/14143* (2013.01)

(58) Field of Classification Search

CPC .......... C12N 9/22; C12N 15/11; C12N 15/88; C12N 2310/20; C12N 2830/005

See application file for complete search history.

(56) References Cited

U.S. PATENT DOCUMENTS

| | | | |
|---|---|---|---|
| 5,208,036 | A | 5/1993 | Eppstein et al. |
| 5,264,618 | A | 11/1993 | Felgner et al. |
| 5,279,833 | A | 1/1994 | Rose |
| 5,283,185 | A | 2/1994 | Epand et al. |
| 5,405,783 | A | 4/1995 | Pirrung et al. |
| 5,412,087 | A | 5/1995 | Mcgall et al. |
| 5,445,934 | A | 8/1995 | Fodor et al. |
| 5,695,937 | A | 12/1997 | Kinzler et al. |
| 5,785,992 | A | 7/1998 | Ansell et al. |
| 6,919,204 | B2 | 7/2005 | Wolffe et al. |
| 7,001,768 | B2 | 2/2006 | Wolffe |
| 7,008,780 | B2 | 3/2006 | Pomerantz et al. |
| 7,368,551 | B2 | 5/2008 | Li et al. |
| 8,450,107 | B1 | 5/2013 | Zhang et al. |
| 8,735,153 | B2 | 5/2014 | Wolffe et al. |
| 9,738,593 | B2 | 8/2017 | Ansell et al. |
| 9,834,791 | B2 | 12/2017 | Zhang et al. |
| 10,106,490 | B2 | 10/2018 | Du |
| 10,166,298 | B2 | 1/2019 | Ansell et al. |
| 10,221,127 | B2 | 3/2019 | Du et al. |
| 10,266,850 | B2 | 4/2019 | Doudna et al. |
| 10,570,415 | B2 | 2/2020 | Doudna et al. |
| 10,704,060 | B2 | 7/2020 | Gersbach et al. |
| 10,968,253 | B2 | 4/2021 | Ohlmann et al. |
| 11,015,210 | B2 | 5/2021 | Faust et al. |
| 11,072,782 | B2 | 7/2021 | Cathomen et al. |
| 11,219,634 | B2 | 1/2022 | Prieve et al. |
| 11,312,955 | B2 | 4/2022 | Berry et al. |
| 11,434,476 | B2 | 9/2022 | Jaenisch et al. |
| 11,434,491 | B2 | 9/2022 | Chen et al. |
| 11,560,555 | B2 | 1/2023 | Oakes et al. |
| 11,795,472 | B2 | 10/2023 | Doudna et al. |
| 11,873,504 | B2 | 1/2024 | Doudna et al. |
| 12,084,692 | B2 | 9/2024 | Oakes et al. |
| 12,163,125 | B2 | 12/2024 | Vijayakumar et al. |

(Continued)

FOREIGN PATENT DOCUMENTS

| | | | |
|---|---|---|---|
| EP | 0 805 819 | B1 | 2/2012 |
| EP | 3 004 370 | A2 | 4/2016 |

(Continued)

OTHER PUBLICATIONS

US 12,018,249 B2, 06/2024, Vijayakumar et al. (withdrawn)

Yeo et al (An enhanced CRISPR repressor for targeted mammalian gene regulation. Nat Methods. Aug. 2018 ; 15(8): 611-616) (Year: 2018).*

Liu et al (Engineering cell signaling using tunable CRISPR-Cpf1-based transcription factors. Nature Communications, vol. 8, 2017). (Year: 2017).*

Schmitges et al (Multiparameter functional diversity of human C2H2 zinc finger proteins. Genome Res. 2016 26: 1742-1752) (Year: 2016).*

KRAB domain sequence in ZNF73 protein (available through UniProt since Feb. 19, 2014, attached in PTO-892) (Year: 2014).*

(Continued)

*Primary Examiner* — Emily A Cordas
*Assistant Examiner* — Matasha Dhar
(74) *Attorney, Agent, or Firm* — COOLEY LLP

(57) ABSTRACT

The disclosure relates to gene repressor systems comprising catalytically-dead Class 2 CRISPR proteins and one or more transcription repressor domains linked to the catalytically-dead Class 2 CRISPR protein as a fusion protein, as well as a guide ribonucleic acid (gRNA); and methods of making and using same.

26 Claims, 61 Drawing Sheets

Specification includes a Sequence Listing.

(56) References Cited

U.S. PATENT DOCUMENTS

| | | | |
|---|---|---|---|
| 2002/0160940 A1 | 10/2002 | Case et al. | |
| 2003/0082552 A1 | 5/2003 | Wolffe et al. | |
| 2003/0108880 A1 | 6/2003 | Rebar et al. | |
| 2006/0083780 A1 | 4/2006 | Heyes et al. | |
| 2006/0240554 A1 | 10/2006 | Chen et al. | |
| 2007/0059795 A1 | 3/2007 | Moore et al. | |
| 2007/0192880 A1 | 8/2007 | Muyan et al. | |
| 2009/0023153 A1 | 1/2009 | Wolffe et al. | |
| 2011/0071208 A1 | 3/2011 | Maclachlan et al. | |
| 2011/0076335 A1 | 3/2011 | Yaworski et al. | |
| 2011/0117125 A1 | 5/2011 | Hope et al. | |
| 2012/0207744 A1 | 8/2012 | Mendlein et al. | |
| 2016/0304872 A1 | 10/2016 | Elowitz et al. | |
| 2017/0056524 A1 | 3/2017 | Kaestner | |
| 2017/0369870 A1 | 12/2017 | Gill et al. | |
| 2018/0179525 A1 | 6/2018 | Lande et al. | |
| 2018/0258424 A1 | 9/2018 | Greenberg et al. | |
| 2019/0024086 A1 | 1/2019 | Lande et al. | |
| 2019/0032049 A1 | 1/2019 | Naldini et al. | |
| 2019/0127713 A1 | 5/2019 | Gersbach et al. | |
| 2019/0167815 A1 | 6/2019 | Holmes et al. | |
| 2019/0233805 A1 | 8/2019 | Segal et al. | |
| 2019/0336608 A1 | 11/2019 | Baumhof et al. | |
| 2019/0359959 A1 | 11/2019 | Jaenisch et al. | |
| 2019/0376088 A1 | 12/2019 | Yamagata et al. | |
| 2019/0381180 A1 | 12/2019 | Baumhof et al. | |
| 2020/0017879 A1* | 1/2020 | Doudna | C12N 15/62 |
| 2020/0087641 A1 | 3/2020 | Zhang et al. | |
| 2020/0109406 A1 | 4/2020 | Miller et al. | |
| 2020/0121809 A1 | 4/2020 | Hope et al. | |
| 2020/0149039 A1 | 5/2020 | Schuijers et al. | |
| 2020/0339638 A1 | 10/2020 | Nabhan et al. | |
| 2020/0377564 A1 | 12/2020 | Khalil et al. | |
| 2021/0047653 A1 | 2/2021 | Bowlin et al. | |
| 2021/0123034 A1 | 4/2021 | Chavez et al. | |
| 2021/0139918 A1* | 5/2021 | Chen | C12N 9/22 |
| 2021/0260170 A1 | 8/2021 | Yamagata et al. | |
| 2021/0284981 A1 | 9/2021 | Doudna et al. | |
| 2021/0309981 A1 | 10/2021 | Doudna et al. | |
| 2022/0002753 A1 | 1/2022 | Qi et al. | |
| 2022/0177872 A1 | 6/2022 | Oakes et al. | |
| 2022/0220508 A1 | 7/2022 | Oakes et al. | |
| 2022/0233721 A1 | 7/2022 | Yoshimi et al. | |
| 2022/0343485 A1 | 10/2022 | Urata et al. | |
| 2022/0403387 A1 | 12/2022 | Lande et al. | |
| 2023/0028178 A1 | 1/2023 | Doudna et al. | |
| 2023/0036273 A1 | 2/2023 | Joung et al. | |
| 2023/0096554 A1 | 3/2023 | Jaenisch et al. | |
| 2023/0124880 A1 | 4/2023 | Oakes et al. | |
| 2023/0287391 A1 | 9/2023 | Taipale et al. | |
| 2023/0340439 A1 | 10/2023 | Qi et al. | |
| 2023/0340471 A1 | 10/2023 | Naldini et al. | |
| 2023/0407276 A1 | 12/2023 | Doudna et al. | |
| 2024/0026352 A1 | 1/2024 | Gersbach et al. | |
| 2024/0026385 A1 | 1/2024 | Vijayakumar et al. | |
| 2024/0052328 A1 | 2/2024 | Kwon et al. | |
| 2024/0076678 A1 | 3/2024 | Maeder et al. | |
| 2024/0123089 A1 | 4/2024 | Fernandes et al. | |
| 2024/0124537 A1 | 4/2024 | Fernandes et al. | |
| 2024/0139319 A1 | 5/2024 | Lombardo et al. | |
| 2024/0167052 A1 | 5/2024 | Doudna et al. | |
| 2024/0209359 A1 | 6/2024 | Zhang et al. | |
| 2024/0209396 A1 | 6/2024 | Yang et al. | |
| 2024/0376462 A1 | 11/2024 | Vijayakumar et al. | |
| 2024/0392271 A1 | 11/2024 | Fernandes et al. | |
| 2025/0011756 A1 | 1/2025 | Vijayakumar et al. | |
| 2025/0043262 A1 | 2/2025 | Oakes et al. | |
| 2025/0136962 A1 | 5/2025 | Oakes et al. | |

FOREIGN PATENT DOCUMENTS

| | | | |
|---|---|---|---|
| EP | 3 209 783 | B1 | 11/2021 |
| EP | 4 158 009 | | 4/2023 |
| EP | 4 196 505 | | 6/2023 |
| EP | 4 208 545 | | 7/2023 |
| EP | 4 244 345 | | 9/2023 |
| EP | 4 267 743 | | 11/2023 |
| EP | 4 374 004 | | 5/2024 |
| WO | WO-96/10390 | A1 | 4/1996 |
| WO | WO-03/072788 | A1 | 9/2003 |
| WO | WO-2009/127060 | A1 | 10/2009 |
| WO | WO-2013/176772 | A1 | 11/2013 |
| WO | WO-2015/070083 | A1 | 5/2015 |
| WO | WVO-2016/063264 | A1 | 4/2016 |
| WO | WO-2018/064371 | A1 | 4/2018 |
| WO | WO-2018/195555 | A1 | 10/2018 |
| WO | WO-2019/079462 | A1 | 4/2019 |
| WO | WO-2019/204766 | A1 | 10/2019 |
| WO | WO-2020/023529 | A1 | 1/2020 |
| WO | WO-2020/041456 | A1 | 2/2020 |
| WO | WO-2020/247882 | A1 | 12/2020 |
| WO | WO-2020/247883 | A2 | 12/2020 |
| WO | WO-2021/026336 | A2 | 2/2021 |
| WO | WO-2021/026336 | A3 | 2/2021 |
| WO | WO-2021/113772 | A1 | 6/2021 |
| WO | WO-2021/226077 | A2 | 11/2021 |
| WO | WO-2021/247570 | A2 | 12/2021 |
| WO | WO-2021/247570 | A3 | 12/2021 |
| WO | WO-2022/114243 | A1 | 6/2022 |
| WO | WO-2022/119957 | A1 | 6/2022 |
| WO | WO-2022/120095 | A1 | 6/2022 |
| WO | WO-2022/125843 | A1 | 6/2022 |
| WO | WO-2022/140577 | A2 | 6/2022 |
| WO | WO-2022/261149 | A2 | 12/2022 |
| WO | WO-2022/261150 | A2 | 12/2022 |
| WO | WO-2022/261150 | A3 | 12/2022 |
| WO | WO-2023/004338 | A2 | 1/2023 |
| WO | WO-2023/004338 | A3 | 1/2023 |
| WO | WO-2023/023553 | A2 | 2/2023 |
| WO | WO-2023/039378 | A1 | 3/2023 |
| WO | WO-2023/049742 | A2 | 3/2023 |
| WO | WO-2023/049872 | A2 | 3/2023 |
| WO | WO-2023/049872 | A3 | 3/2023 |
| WO | WO-2023/055893 | A1 | 4/2023 |
| WO | WO-2023/093862 | A1 | 6/2023 |
| WO | WO-2023/138617 | A1 | 7/2023 |
| WO | WO-2023/165597 | A1 | 9/2023 |
| WO | WO-2023/173110 | A1 | 9/2023 |
| WO | WO-2023/178280 | A2 | 9/2023 |
| WO | WO-2023/178280 | A3 | 9/2023 |
| WO | WO-2023/215711 | A1 | 11/2023 |
| WO | WO-2023/235818 | A2 | 12/2023 |
| WO | WO-2023/240076 | A1 | 12/2023 |
| WO | WO-2023/241669 | A1 | 12/2023 |
| WO | WO-2023/247789 | A1 | 12/2023 |
| WO | WO-2023/250148 | A1 | 12/2023 |
| WO | WO-2023/250183 | A2 | 12/2023 |
| WO | WO-2023/250183 | A3 | 12/2023 |
| WO | WO-2023/250511 | A2 | 12/2023 |
| WO | WO-2023/250511 | A3 | 12/2023 |
| WO | WO-2024/032681 | A1 | 2/2024 |
| WO | WO-2024/131940 | A1 | 6/2024 |
| WO | WO-2024/206555 | A1 | 10/2024 |
| WO | WO-2024/206565 | A1 | 10/2024 |
| WO | WO-2024/206620 | A1 | 10/2024 |

OTHER PUBLICATIONS

Alerasool et al (An efficient KRAB domain for CRISPRi applications in human cells. Nature Methods | vol. 17 | Nov. 2020 | 1093-1096; cited in IDS dated Mar. 22, 2024) (Year: 2020).*

Nunez et al (Genome-wide programmable transcriptional memory by CRISPR-based epigenome editing. Cell 184, 2503-2519, Apr. 29, 2021; cited in IDS dated Mar. 22, 2024; NPL associated with Chen). (Year: 2021).*

Cao et al (A CRISPR/dCasX-mediated transcriptional programming system for inhibiting the progression of bladder cancer cells by repressing c-MYC or activating TP53. Clin. Transl. Med. 2021;11:e537. First Published Sep. 15, 2021). (Year: 2021).*

Karemaker et al (DNA methyltransferases hitchhiking on chromatin. Swiss Med Wkly. 2020;150:w20329) (Year: 2020).*

NP_001307822.1 (ADD sequence from DNMT3A protein sequence, in PTO-892). (Year: 2016).*

(56) References Cited

OTHER PUBLICATIONS

Conserved Protein Domain Family entry cd07765: KRAB_A-box, https://www.ncbi.nlm.nih.gov/Structure/cdd/cddsrv.cgi?ascbin=8&maxaln=10&seltype=2&uid=cd07765, updated Jan. 17, 2013, printed as pp. 1/2-2/2, (2013), 2 pages.
Hie, B.L. et al. (Apr. 2022). "Evolutionary velocity with protein language models predicts evolutionary dynamics of diverse proteins," Cell Syst. 13:274-285.e6.
Hirakawa, M.P. et al. (Apr. 2020). "Gene editing and CRISPR in the clinic: current and future perspectives," Biosci. Rep. 40(4):BSR20200127, 37 pages.
Hochstrasser, M.L. et al. (2014). "CasA mediates Cas3-catalyzed target degradation during CRISPR RNA-guided interference," PNAS 111:6618-6623.
Margolin, J.F. et al. (May 1994). "Kruppel-associated boxes are potent transcriptional repression domains," PNAS 91(10):4509-4513.
Mlambo, T. et al. (2018). "Designer epigenome modifiers enable robust and sustained gene silencing in clinically relevant human cells," Nucleic Acids Research 46:4456-4468, Supplemental Figures, 15 pages.
NCBI Reference Sequence NM_175629.2 (Jul. 2024). "*Homo sapiens* DNA methyltransferase 3 alpha (DNMT3A), transcript variant 1, mRNA," located at https://www.ncbi.nlm.nih.gov/nuccore/NM_175629.2, retrieved on Jul. 12, 2024, 7 pages.
NCBI Reference Sequence NP_783328.1 (Jul. 2024). "DNA (cytosine-5)-methyltransferase 3A isoform a [*Homo sapiens*]," located at https://www.ncbi.nlm.nih.gov/protein/NP_783328.1, retrieved on Jul. 12, 2024, 4 pages.
NCBI Reference Sequence NM_153759.3 (Jul. 2024). "*Homo sapiens* DNA methyltransferase 3 alpha (DNMT3A), transcript variant 2, mRNA," located at https://www.ncbi.nlm.nih.gov/nuccore/NM_153759.3, retrieved on Jul. 12, 2024, 5 pages.
NCBI Reference Sequence NP_715640.2 (Jul. 2024). "DNA (cytosine-5)-methyltransferase 3A isoform b [*Homo sapiens*]," located at https://www.ncbi.nlm.nih.gov/protein/NP_715640.2, retrieved on Jul. 12, 2024, 3 pages.
NCBI Reference Sequence NM_022552.4 (Jul. 2024). "*Homo sapiens* DNA methyltransferase 3 alpha (DNMT3A), transcript variant 3, mRNA," located at https://www.ncbi.nlm.nih.gov/nuccore/NM_022552, retrieved on Jul. 12, 2024, 8 pages.
NCBI Reference Sequence NP_072046.2 (Jul. 2024). "DNA (cytosine-5)-methyltransferase 3A isoform a [*Homo sapiens*]," located at https://www.ncbi.nlm.nih.gov/protein/NP_072046.2?report=GenPept, retrieved on Jul. 12, 2024, 4 pages.
NCBI Reference Sequence NM_175630.1 (Jul. 2024). "*Homo sapiens* DNA methyltransferase 3 alpha (DNMT3A), transcript variant 4, mRNA," located at https://www.ncbi.nlm.nih.gov/nuccore/NM_175630.1?report=GenBank, retrieved on Jul. 12, 2024, 4 pages.
NCBI Reference Sequence NP_783329.1 (Jul. 2024). "DNA (cytosine-5)-methyltransferase 3A isoform c [*Homo sapiens*]," located at https://www.ncbi.nlm.nih.gov/protein/NP_783329.1, retrieved on Jul. 12, 2024, 3 pages.
NCBI Reference Sequence NM_001320892.1 (Jul. 2024). "*Homo sapiens* DNA methyltransferase 3 alpha (DNMT3A), transcript variant 5, mRNA," located at https://www.ncbi.nlm.nih.gov/nuccore/NM_001320892.2; retrieved on Jul. 12, 2024, 4 pages.
NCBI Reference Sequence NP_001307821.1 (Jul. 2024). "DNA (cytosine-5)-methyltransferase 3A isoform c [*Homo sapiens*]," located at https://www.ncbi.nlm.nih.gov/protein/NP_001307821.1, retrieved on Jul. 12, 2024, 3 pages.
Non-Final Office Action mailed on Jun. 23, 2021, for U.S. Appl. No. 15/521,294, filed Apr. 23, 2017, 24 pages.
Tajima, S. et al. (Nov. 2016). "Domain Structure of the Dnmt1, Dnmt3a, and Dnmt3b DNA Methyltransferases," DNA Methyltransferases—Role and Function, pp. 63-86.
Urrutia, R. (Sep. 2003). "KRAS-containing zinc-finger repressor proteins," Genome Biology, vol. 4, Article No. 231, 8 pages.
Wolf, G. et al. (Oct. 2015). "Spotting the enemy within: Targeted silencing of foreign DNA in mammalian genomes by the Krüppel-associated box zinc finger protein family," Mob DNA 6:17, 20 pages.
U.S. Appl. No. 18/663,845, filed May 14, 2024, by Vijayakumar et al.
Abaandou, L. et al. (2021). "Affecting HEK293 cell growth and production performance by modifying the expression of specific genes," Cells 10:1667, 21 pages.
Alerasool, N. et al. (2020). "An efficient KRAB domain for CRISPRi applications in human cells," Nature Methods 17:1093-1096.
Alignment of SEQ ID No. 8 (2022). DNMT3A sequence disclosed in Siddique, A. N. et al. (2013). J. Mol. Biol. 425:479-491, 2 total pages.
Altschul, S.F. et al. (1990). "Basic local alignment search tool," J. Mol. Biol. 215:403-410.
Amabile, A. et al. (2016). "Inheritable Silencing of Endogenous Genes by Hit-and-Run Targeted Epigenetic Editing," Cell 167:219-232.e14.
Ayyanathan, K. et al. (2003). "Regulated recruitment of HP1 to a euchromatic gene induces mitotically heritable, epigenetic gene silencing: a mammalian cell culture model of gene variegation," Genes and Development 17:1855-1869.
Bailey, T.L. (2021). "STREME: Accurate and versatile sequence motif discovery," Bioinformatics 37:2834-2840.
Braliou, G.G. et al. (2001). "The v-ErbA oncoprotein quenches the activity of an erythroid-specific enhancer," Oncogene 20:775-787.
Brief Communication in Opposition Proceedings for EP Patent No. 3 209 783, dated Dec. 21, 2023, 26 pages.
Broude, E.V. et al. (2007). "p21 (CDKN1A) is a negative regulator of p53 stability," Cell Cycle 6:1468-1471.
Burstein, D. et al. (Feb. 2017). "New CRISPR-Cas systems from uncultivated microbes," Nature 542:237-241. Published online Dec. 22, 2016, with Supplemental Materials, 28 total pages.
Cedar, H. et al. (2009). "Linking DNA methylation and histone modification: Patterns and paradigms," Nat. Rev. Genet. 10:295-304.
Chen, J. et al. (2016). "Production and clinical development of nanoparticles for gene delivery," Mol. Ther. Methods Clin. Dev. 3:16023, 8 pages.
Cortes-Mancera, F.M. et al. (2022). "gene-targeted DNA methylation: Towards long-lasting reprogramming of gene expression?" Adv. Exp. Med. Biol. 1389:515-533.
Das, A.T. et al. (2016). "Tet-On systems for doxycycline-inducible gene expression," Curr. Gene Ther. 16:156-167.
Ding, L. et al. DNA methylation-independent long-term epigenetic silencing with dCRISPR/Cas9 fusion proteins. Life Sci Alliance. Mar. 14, 2022;5(6):e202101321, 11 pages.
Ecco, G. et al. (2017). "KRAB zinc finger proteins," Development 144:2719-2729.
Fiddes, I.T. et al. (2018). "Comparative Annotation Toolkit (CAT)—simultaneous clade and personal genome annotation," Genome Res. 28:1029-1038.
Figures 1-20 filed on Nov. 6, 2015, of granted European Patent No. 3 209 783, 20 total pages.
Fuks, F. (2005). "DNA methylation and histone modifications: Teaming up to silence genes," Curr. Opin. Genet Develop. 15:490-495.
Gilbert, L.A. et al. (2013). "CRISPR-mediated modular RNA-guided regulation of transcription in eukaryotes," Cell 154:442-451.
Gilbert, L.A. et al. (2014). "Genome-scale CRISPR-mediated control of gene repression and activation," Cell 159:647-661.
Haberle, V. et al. (2018). "Eukaryotic core promoters and the functional basis of transcription initiation.," Nat. Rev. Mol. Cell. Biol. 19:621-637, 40 pages provided.
Hofacker, D. et al. Engineering of Effector Domains for Targeted DNA Methylation with Reduced Off-Target Effects. Int J Mol Sci Jan. 13, 2020;21(2):502, 16 pages.
International Search Report mailed on Mar. 30, 2023, for PCT Application No. PCT/US2022/076774, filed on Sep. 21, 2022, 11 pages.
Jackson, A.L. et al. (2003). "Expression profiling reveals off-target gene regulation by RNAi," Nat. Biotechnol. 21:635-637.

(56) References Cited

OTHER PUBLICATIONS

Jain, S. et al. (2021). "TALEN outperforms Cas9 in editing heterochromatin target sites," Nat. Commun. 12:606, 10 total pages.
Kabadi, A.M. et al. (2014). "Engineering synthetic TALE and CRISPR/Cas9 transcription factors for regulating gene expression," Methods 69:188-197.
Kao, T-H. et al. (2014). "Ectopic DNMT3L triggers assembly of a repressive complex for retroviral silencing in somatic cells," J. Virology 88:10680-10695.
Kim, S-H. et al. (2007). "Zinc-fingers and homeoboxes 1 (ZHX1) binds DNA methyltransferase (DNMT) 3B to enhance DNMT3B-mediated transcriptional repression," Biochemical and Biophysical Research Communications 355:318-323.
Kocak, D.D. (2013). "Synthetic Transcription Factors and their Effects on Endogenous DNA Methylation in Human Cells," Thesis submitted in partial fulfillment of the requirements for the degree of Master of Science in the Department of Biomedical Engineering in the Graduate School of Duke University, 35 total pages.
Kotin, R.M. (1994). "Prospects for the use of adeno-associated virus as a vector for human gene therapy," Human Gene Therapy 5:793-801.
Kuhnel, F. et al. (2004). "Tumor-specific adenoviral gene therapy: transcriptional repression of gene expression by utilizing p53-signal transduction pathways," Cancer Gene Therapy 11:28-40.
Letter from D Young & Co. to the European Patent Office (Munich, Germany) dated Dec. 18, 2017, 5 total pages.
Letter from D Young & Co. to the European Patent Office (Munich, Germany) dated Aug. 12, 2019, 4 total pages.
Li, H. et al. (2006). "The Histone Methyltransferase SETDB1 and the DNA Methyltransferase DNMT3A Interact Directly and Localize to Promoters Silenced in Cancer Cells," Journal Biological Chemistry 281:19489-19500.
Li, F. et al. (2007). "Chimeric DNA methyltransferases target DNA methylation to specific DNA sequences and repress expression of target genes," Nucleic Acid Research 35:100-112.
Li, W. et al. (2014). "MAGeCK enables robust identification of essential genes from genome-scale CRISPR/Cas9 knockout screens," Genome Biol. 15:554, 12 total pages.
Liu, X.S. et al. (2016). "Editing DNA methylation in the mammalian genome," Cell 167:233-247.e17.
Liu, J.J. et al. "CasX enzymes comprise a distinct family of RNA-guided genome editors," Nature 566:218-223. Published online Feb. 4, 2019.
Liu, J.J. et al. CasX enzymes comprise a distinct family of RNA-guided genome editors, Nature 568:E8-E10. (Author correction: published online Apr. 3, 2019).
Luo, M.L. et al. (2015). "Repurposing endogenous type I CRISPR-Cas systems for programmable gene repression," Nucl. Acids Res. 43:674-681.
Ma, A-N. et al. (2014). "Targeted gene suppression by inducing de novo DNA methylation in the gene promoter," Epigenetics and Chromatin 7:20, 11 total pages.
Makarova, K.S. et al. (2020). "Evolutionary classification of CRISPR-Cas systems: A burst of class 2 and derived variants," Nat. Rev. Microbiol. 18:67-83.
Mao, Y. et al. (2021). "A high-quality bonobo genome refines the analysis of hominid evolution," Nature 594:77-81.
McDonald, J.I. et al. (2016). "Reprogrammable CRISPR/Cas9-based system for inducing site-specific DNA methylation," Biol. Open 5:866-874.
McInnes, L. et al. (2018). "UMAP: Uniform manifold approximation and projection for dimension reduction," ArXiv e-prints 1802. 03426, pp. 1-63.
Mlambo, T. et al. (2018). "Designer epigenome modifiers enable robust and sustained gene silencing in clinically relevant human cells," Nucleic Acids Research 46:4456-4468.
Moussa, H.F. et al. (2021). "Here to stay: Writing lasting epigenetic memories," Cell 184:2281-2283.
Murphy, K.E. et al. (2016). "The transcriptional repressive activity of KRAB zinc finger proteins does not correlate with their ability to recruit TRIM28," PLoS ONE 11:e0163555, 19 total pages.
Nakamura, M. et al. (2021). "Durable CRISPR-Based Epigenetic Silencing," BioDesign Research 2021, 1-8.
National Cancer Institute (2015). "Cell lines in the In Vitro Screen," 5 total pages.
Noguchi, H. et al. (Jul. 2003). "PDX-1 protein containing its own antennapedia-like protein transduction domain can transduce pancreatic duct and islet cells," Diabetes 52:1732-1737.
Nunez JK et al. Genome-wide programmable transcriptional memory by CRISPR-based epigenome editing. Cell. Apr. 29, 2021,184(9):2503-2519.e17.
O'Geen, H. et al. (2019). "Ezh2-dCas9 and KRAB-dCas9 enable engineering of epigenetic memory in a context-dependent manner," Epigenetics Chromatin. 12:26, 20 pages.
O'Geen, H. et al. (2022). "Determinants of heritable gene silencing for KRAB-dCas9+DNMT3 and Ezh2-dCas9+DNMT3 hit-and-run epigenome editing," Nucl. Acids Res. 50:3239-3253.
Orth, P. et al. (2000). "Structural basis of gene regulation by the tetracycline inducible Tet repressor-operator system," Nat. Struct. Biol, 7:215-219.
Pflueger, C. et al. (2018). "A modular dCas9-SunTag DNMT3A epigenome editing system overcomes pervasive off-target activity of direct fusion dCas9-DNMT3A constructs," Genome Res. 28:1193-1206.
Policarpi, C. et al. (2021). "Epigenetic editing: Dissecting chromatin function in context," BioEssays 43:e2000316, 16 total pages.
Qi, L. S. et al. (Feb. 2013). "Repurposing CRISPR as an RNA-guided platform for sequence-specific control of gene expression," Cell 152:1173-1183.
Rivenbark, A. et al. (2012). "Epigenetic reprogramming of cancer cells via targeted DNA methylation," Epigenetics 7:350-360.
Rives, A. et al. (2021). "Biological structure and function emerge from scaling unsupervised learning to 250 million protein sequences," PNAS 118:e2016239118, 12 total pages.
Rodriguez, D. et al. (2016). "Epigenetic editing: On the verge of reprogramming gene expression at will," Curr. Genet. Med. Rep. 4:170-179.
Schultz, D.C. et al. (2002). "SETDB1: a novel KAP-1-associated histone H3, lysine 9-specific methyltransferase that contributes to HP1-mediated silencing of euchromatic genes by KRAB zinc-finger proteins," Genes Dev. 16:919-932.
Siddique, A.N. et al. (2013). "Targeted methylation and gene silencing of VEGF-A in human cells by using a designed Dnmt3a-Dnmt3L single-chain fusion protein with increased DNA methylation activity," J. Mol. Biol. 425:479-491.
Sigoillot, F.D. et al. (2012). "A bioinformatics method identifies prominent off-targeted transcripts in RNAi screens," Nat. Methods 9:363-366.
Smith, T.F. et al. (1981). "Comparison of biosequences," Adv. Appl. Math. 2:482-489.
Stepper, P. et al. (2017). "Efficient targeted DNA methylation with chimeric dCas9-Dnmt3a-Dnmt3L methyltransferase," Nucleic Acids Res. 45:1703-1713.
Stepper, P. (2020). "CRISPR-Cas9 fusions for synthetic epigenetics," Institut für Biochemie und Technische Biochemie der Universität Stuttgart, 152 pages.
Stoll, G.A. et al. (2022). "Structure and functional mapping of the KRAB-KAP1 repressor complex," bioRxiv, 34 total pages.
Tréhin, R. et al. (Jul. 2004). "Cellular uptake but low permeation of human calcitonin-derived cell penetrating peptides and Tat(47-57) through well-differentiated epithelial models," Pharm. Res. 21:1248-1256.
Tsuchida, C.A. et al. (2022). "Chimeric CRISPR-CasX enzymes and guide RNAs for improved genome editing activity," Mol. Cell 82:1199-1209, 28 pages provided.
Tycko, J. et al. (2020). "High-Throughput Discovery and Characterization of Human Transcriptional Effectors," Cell 183:2020-2035, 38 pages provided.
Valton, J. et al. (2012). "Overcoming transcription activator-like effector (TALE) DNA binding domain sensitivity to cytosine methylation," J. Biol. Chem. 287:38427-38432.

(56) References Cited

OTHER PUBLICATIONS

Vojta, A. et al. (2016). "Repurposing the CRISPR-Cas9 system for targeted DNA methylation," Nucleic Acids Res. 44:5615-5628.
Warren, W.C. et al. (2020). "Sequence diversity analyses of an improved rhesus macaque genome enhance its biomedical utility," Science 370:eabc6617, 26 total pages.
Wender, P.A. et al. (Nov. 2000). "The design, synthesis, and evaluation of molecules that enable or enhance cellular uptake: peptoid molecular transporters," PNAS 97:13003-13008.
Written Opinion of the International Searching Authority mailed on Mar. 30, 2023, for PCT Application No. PCT/US2022/076774, filed on Sep. 21, 2022, 11 pages.
Yang, H. et al. (May 2019). "CasX: a new and small CRISPR gene-editing protein," Cell Res. 29:345-346. Published online Apr. 16, 2019.
Ying, Y. et al. (2015). "The Krüppel-associated box repressor domain induces reversible and irreversible regulation of endogenous mouse genes by mediating different chromatin states," Nucl. Acids Res. 43:1549-1561.
Zender, L. et al. (Jun. 2002). "VP22-mediated intercellular transport of p53 in hepatoma cells in vitro and in vivo," Cancer Gene Ther. 9:489-496.
Zhang, J. et al. (Jun. 1997). "PowerBLAST: a new network BLAST application for interactive or automated sequence analysis and annotation," Genome Res. 7:649-656.
Zhang, Y. et al. (2010). "Chromatin methylation activity of Dnmt3a and Dnmt3a/3L is guided by interaction of the ADD domain with the histone H3 tail.," Nucl. Acids Res. 38:4246-4253.
Zhao, X. et al. (2013). "Intracellular delivery of artificial transcription factors fused to the protein transduction domain of HIV-1 Tat," Protein Expression and Purification 90:27-33.
International Search Report mailed on Aug. 5, 2024, for PCT Application No. PCT/US2024/021866, filed on Mar. 28, 2024, 6 pages.
Margres, M.J. et al. (2021). "The tiger rattlesnake genome reveals a complex genotype underlying a simple venom phenotype," PNAS 118:e2014634118, 12 pages.
NCBI Reference Sequence UNIPROT Q96PE6, ZIM3_Human (2021). Accession No. Q96PE6, 13 pages.
NCBI Reference Sequence NM_022552.4 (2020). "*Homo sapiens* DNA methyltransferase 3 alpha (DNMT3A), transcript variant 3, mRNA," Accession No. NM_022552.4, 7 pages.
NCBI Reference Sequence NP_072046.2 (2021). "DNA (cytosine-5)-methyltransferase 3A isoform a [*Homo sapiens*]," Accession No. NP_072046.2, 5 pages.
NCBI Reference Sequence UNIPROT Q9CWR8, DNM3L_Mouse (2021), Accession No. Q9CWR8, 11 pages.
NCBI Reference Sequence NP_001075164.1 (2021). "DNA (cytosine-5)-methyltransferase 3-like isoform 1[Mus Musculus]," Accession No. NP_001075164.1, 3 pages.
O'Geen, H. et al. (2017). "dCas9-based epigenome editing suggests acquisition of histone methylation is not sufficient for target gene repression," Nucl. Acids Res. 45:9901-9916.
Otani, J. et al. (2009). "Structural basis for recognition of H3K4 methylation status by the DNA methyltransferase 3A ATRX-DNMT3-DNMT3L domain," EMBO Rep. 10(11):1235-1241.
Thakore, P.I. et al. (2018). "RNA-guided transcriptional silencing in vivo with *S. aureus* CRISPR-Cas9 repressors," Nature Communications 9:1674, 9 total pages.
Vonk, F.J. et al. (2013). "The king cobra genome reveals dynamic gene evolution and adaptation in the snake venom system," PNAS 110(51):20651-20656.
Written Opinion of the International Searching Authority mailed on Aug. 5, 2024, for PCT Application No. PCT/US2024/021866, filed on Mar. 28, 2024, 10 pages.
U.S. Appl. No. 18/778,393, filed Jul. 19, 2024, by Oakes et al.
U.S. Appl. No. 18/909,093, filed Oct. 8, 2024, by Oakes et al.
U.S. Appl. No. 18/789,158, filed Jul. 30, 2024, by Vijayakumar et al.
Alhaji, S.Y. et al. (Apr. 2019). "Silencing of transgene expression in mammalian cells by DNA methylation and histone modifications in gene therapy perspective," Biotechnol. Genet. Eng. Rev. 35(1):1-25.
Amabile, A. et al. (May 2015). "Permanent epigenetic silencing of human genes with artificial transcriptional repressors," Molecular Therapy 23(Suppl. 1): S275, 1 page.
Cappelluti, M.A. et al. (Feb. 2024). "Durable and efficient gene silencing in vivo by hit-and-run epigenome editing," Nature 627:416-423.
Cedar, H. (Apr. 1988). "DNA methylation and gene activity," Cell 53(1):3-4.
Chen, X. et al. (2012). "Fusion protein linkers: Property, design and functionality," Advanced Drug Delivery Reviews 65(10):1357-1369.
De Groote, M.L. et al. (Sep. 2012). "Epigenetic editing: Targeted rewriting of epigenetic marks to modulate expression of selected target genes," Nucl. Acids Res. 40(21):10596-10613.
Delrosso, N. et al. (Apr. 2023). "Large-scale mapping and mutagenesis of human transcriptional effector domains," Nature 616(7956):365-372.
Han, H. et al. (2023). "Leverage of nuclease-deficient CasX for preventing pathological angiogenesis," Mol. Ther. Nucl. Acids 33:738-748.
Jia, D. et al. (Sep. 2007). "Structure of Dnmt3a bound to Dnmt3L suggests a model for de novo DNA methylation," Nature 449(7159):248-251.
Makarova, K.S. et al. (Nov. 2015). "An updated evolutionary classification of CRISPR-Cas systems," Nat. Rev. Microbiol. 13(11):722-736.
Mukund, A.X. et al. (Sep. 2023). "High-throughput functional characterization of combinations of transcriptional activators and repressors," Cell Systems 14(9):746-763.
NCBI Reference Sequence UNIPROT P15840 (2025), located at www.uniprot.org/uniprotkb/P15840/entry, retrieved on Feb. 19, 2025, 5 pages.
Quenneville et al. (2012). "The KRAB-ZFP/KAP1 system contributes to the early embryonic establishment of site-specific DNA methylation patterns maintained during development," Cell Rep. 2:766-773.
Schunder, E. et al. (2013). "First indication for a functional CRISPR/Cas system in Francisella Tularensis," Int'l J. Med. Microbiol. 303:51-60.
Tak, Y.E. et al. (Dec. 2017). "Inducible and multiplex gene regulation using CRISPR-Cpf1-based transcription factors," Nature Methods 14(12):1163-1166.
Tang, X. et al. (2017). "A CRISPR-Cpf1 system for efficient genome editing and transcriptional repression in plants," Nature Plants 3:17018, 5 pages.
Vonk, F.J. et al. (2013). "The king cobra genome reveals dynamic gene evolution and adaptation in the snake venom system," PNAS 110(51):20651-20656, Supplemental Information, 68 pages.
Yamazaki, T. et al. (May 2017). "Targeted DNA methylation in pericentromeres with genome editing-based artificial DNA methyltransferase," PLos One 12(5):e0177764, 18 pages.
Yamazaki, T. et al. (Apr. 2007). "Time-lapse and retrospective analysis of DNA methylation in mouse preimplantation embryos by live cell imaging," Dev. Biol. 304(1):409-419.
Zetsche, B. et al. (Oct. 2015). "Cpf1 is a single RNA-guided endonuclease of a class 2 CRISPR-cas system," Cell 163:759-771.
U.S. Appl. No. 18/869,765, filed Nov. 26, 2024, by Zhou et al.
U.S. Appl. No. 19/343,818, filed Sep. 29, 2025, Inventor Fernandes, Jason et al.
U.S. Appl. No. 19/343,824, filed Sep. 29, 2025, Inventor Fernandes, Jason et al.

* cited by examiner

Motif 3:

Motif 5:

Motif 7:

Motif 8:

Generic dXR configuration:

Specificity/Activity with ELXR-ZIM3 for spacer 7.37

Specificity/Activity with ELXR-ZNF10 for spacer 7.37

ENGINEERED CLASS 2, TYPE V REPRESSOR SYSTEMS

CROSS REFERENCE TO RELATED APPLICATIONS

This application is a continuation of International Application No. PCT/US2022/076774, filed Sep. 21, 2022, which claims priority to U.S. provisional applications 63/246,543, filed on Sep. 21, 2021, and 63/321,517, filed on Mar. 18, 2022, the contents of each of which are incorporated herein by reference in their entirety.

INCORPORATION BY REFERENCE OF SEQUENCE LISTING

The contents of the electronic sequence listing (SCRB_034_02US_SeqList_ST26.xml; Size: 63,394,386 bytes; and Date of Creation: Mar. 15, 2024) is herein incorporated by reference in its entirety.

BACKGROUND

Methods of modulating expression of a target gene in a cell are varied. In mammalian systems, cells use a system of chromatin regulators (CRs) and associated histone and DNA modifications to modulate gene expression and establish long-term epigenetic memory. This system is critical in development, aging, and disease, and may provide essential capabilities for incorporating regulation in synthetic biology. In experimental systems, methods such as RNA interference (RNAi) are useful for targeted-gene knockdown and have been widely used for large-scale library screens. RNAi, however, has several limitations. In particular, RNAi-based knockdown suffers from off-target effects, along with incomplete knockdown of the target (Jackson A L, et al. Expression profiling reveals off-target gene regulation by RNAi. Nat Biotechnol. 21:635 (2003)); Sigoillot F D, et al., A bioinformatics method identifies prominent off-targeted transcripts in RNAi screens. Nat Methods. 19:9(4):363 (2012)). Tailored DNA binding proteins such as zinc finger proteins or transcription activator-like effectors (TALEs) linked to transcriptional repressor domains, while able to mediate selective gene suppression, are limited by the fact that each desired target gene necessitates the generation of a new protein.

The advent of CRISPR/Cas systems and the programmable nature of these systems has facilitated their use as a versatile technology for genomic manipulation and engineering. Particular CRISPR proteins are particularly well suited for such manipulation. For example, certain Class 2 CRISPR/Cas systems have a compact size, offering ease of delivery, and the nucleotide sequence encoding the protein is relatively short, an advantage for its incorporation into viral vectors for cellular delivery. However, in certain disease indications, gene silencing, or repression, is preferable to gene editing. The ability to render CasX catalytically-inactive (dCasX) has been demonstrated (WO2020247882A1), which makes it an attractive platform for the generation of fusion proteins capable of gene silencing. Thus, there is a need in the art for additional gene repressor systems (e.g., a dCas protein plus repressor domain) that have been optimized and/or offer improvements over earlier generation gene repressor systems, such as those based on Cas9 for utilization in a variety of therapeutic, diagnostic, and research applications.

SUMMARY

Aspects of the present disclosure are directed to compositions and methods of modulating expression of a target nucleic acid in a cell.

The present disclosure provides compositions of a gene repressor system comprising catalytically-dead Class 2 CRISPR proteins, for example Class 2 Type V CRISPR proteins, linked with one or more transcription repressor domains as a fusion protein and guide ribonucleic acids (gRNA) comprising a targeting sequence complementary to a target nucleic acid sequence of a gene in a cell (dXR:gRNA system), nucleic acids encoding the fusion proteins, vectors encoding or comprising the components of the dXR:gRNA systems, and lipid nanoparticles encoding or encapsidating the components of the dXR:gRNA systems, and methods of making and using the dXR:gRNA systems. The dXR:gRNA systems of the disclosure have utility in methods of gene silencing, or gene repression, in diseases where repression of a gene product is useful to reverse the underlying cause of the disease or to ameliorate the signs or symptoms of the disease, which methods are also provided.

Further features and advantages of certain embodiments of the present disclosure will become more fully apparent in the following description of embodiments and drawings thereof, and from the claims.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
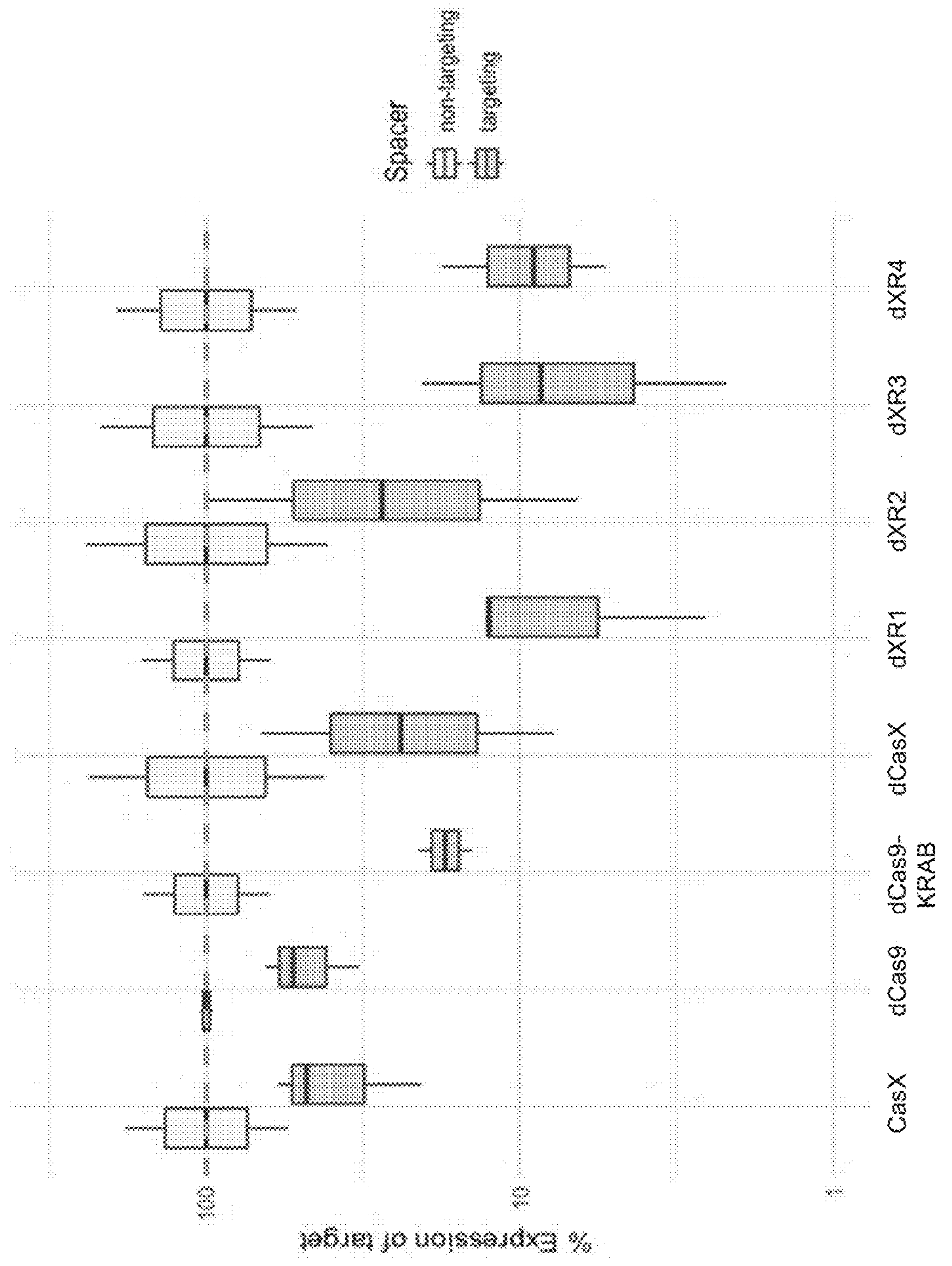
FIG. 1 shows results of an assay evaluating targeting and non-targeting dXR molecules using non-targeting and targeting spacers (left and right bars, respectively), with percentage (%) loss of target mRNA as measured by qPCR in HEK293T cells, as described in Example 1. Data represent ΔΔCt values from biological duplicates.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Unless otherwise defined, all technical and scientific terms used herein have the same meaning as commonly understood by one of ordinary skill in the art to which this invention belongs. Although methods and materials similar or equivalent to those described herein can be used in the practice or testing of the present embodiments, suitable methods and materials are described below. In case of conflict, the patent specification, including definitions, will control. In addition, the materials, methods, and examples are illustrative only and not intended to be limiting. Numerous variations, changes, and substitutions will now occur to those skilled in the art without departing from the invention.

Definitions

The terms "polynucleotide" and "nucleic acid," used interchangeably herein, refer to a polymeric form of nucleotides of any length, either ribonucleotides or deoxyribonucleotides. Thus, terms "polynucleotide" and "nucleic acid" encompass single-stranded DNA; double-stranded DNA; multi-stranded DNA; single-stranded RNA; double-stranded RNA; multi-stranded RNA; genomic DNA; cDNA; DNA-RNA hybrids; and a polymer comprising purine and pyrimidine bases or other natural, chemically or biochemically modified, non-natural, or derivatized nucleotide bases.

"Hybridizable" or "complementary" are used interchangeably to mean that a nucleic acid (e.g., RNA, DNA) comprises a sequence of nucleotides that enables it to non-covalently bind, i.e., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. It is understood that the sequence of a polynucleotide need not be 100% complementary to that of its target nucleic acid sequence to be specifically hybridizable; it can have at least about 70%, at least about 80%, or at least about 90%, or at least about 95% sequence identity and still hybridize to the target nucleic acid sequence. Moreover, a polynucleotide may hybridize over one or more segments such that intervening or adjacent segments are not involved in the hybridization event (e.g., a loop structure or hairpin structure, a 'bulge', 'bubble' and the like).

A "gene," for the purposes of the present disclosure, includes a DNA region encoding a gene product (e.g., a protein, or RNA), as well as all DNA regions which regulate the production of the gene product, whether or not such regulatory element sequences are adjacent to coding and/or transcribed sequences. Accordingly, a gene may include regulatory sequences including, but not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. Coding sequences encode a gene product upon transcription or transcription and translation; the coding sequences of the disclosure may comprise fragments and need not contain a full-length open reading frame. A gene can include both the strand that is transcribed; e.g. the strand containing the coding sequence, as well as the complementary strand.

The term "downstream" refers to a nucleotide sequence that is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

The term "regulatory element" is used interchangeably herein with the term "regulatory sequence," and is intended to include promoters, enhancers, and other expression regulatory elements (e.g., transcription termination signals, such as polyadenylation signals and poly-U sequences). Exemplary regulatory elements include a transcription promoter such as, but not limited to, CMV, CMV+intron A, SV40, RSV, HIV-Ltr, elongation factor 1 alpha (EF1α), MMLV-ltr, internal ribosome entry site (IRES) or P2A peptide to permit translation of multiple genes from a single transcript, metallothionein, a transcription enhancer element, a transcription termination signal, polyadenylation sequences, sequences for optimization of initiation of translation, and translation termination sequences. It will be understood that the choice of the appropriate regulatory element will depend on the encoded component to be expressed (e.g., protein or RNA) or whether the nucleic acid comprises multiple components that require different polymerases or are not intended to be expressed as a fusion protein.

The term "promoter" refers to a DNA sequence that contains an RNA polymerase binding site, transcription start site, TATA box, and/or B recognition element and assists or promotes the transcription and expression of an associated transcribable polynucleotide sequence and/or gene (or transgene). A promoter can be synthetically produced or can be derived from a known or naturally occurring promoter sequence or another promoter sequence. A promoter can be proximal or distal to the gene to be transcribed. A promoter can also include a chimeric promoter comprising a combination of two or more heterologous sequences to confer certain properties. A promoter of the present disclosure can include variants of promoter sequences that are similar in composition, but not identical to, other promoter sequence(s) known or provided herein. A promoter can be classified according to criteria relating to the pattern of expression of an associated coding or transcribable sequence or gene operably linked to the promoter, such as constitutive, developmental, tissue specific, inducible, etc.

The term "enhancer" refers to regulatory element DNA sequences that, when bound by specific proteins called transcription factors, regulate the expression of an associated gene. Enhancers may be located in the intron of the gene, or 5' or 3' of the coding sequence of the gene. Enhancers may be proximal to the gene (i.e., within a few tens or hundreds of base pairs (bp) of the promoter), or may be located distal to the gene (i.e., thousands of bp, hundreds of thousands of bp, or even millions of bp away from the promoter). A single gene may be regulated by more than one enhancer, all of which are envisaged as within the scope of the instant disclosure.

"Operably linked" means with reference to a juxtaposition of two or more components (such as sequence elements), in which the components are arranged such that both components function normally and allow the possibility that at least one of the components can mediate a function that is exerted upon at least one of the other components; e.g., a promoter and an encoding sequence.

"Repressor domain" refers to polypeptide factors that act as regulatory elements on DNA that inhibit, repress, or block transcription of DNA, resulting in repression of gene expression. A repressor domain can be a subunit of a repressor and individual domains can possess different functional properties. In the context of the present disclosure, the linking of a repressor domain to a catalytically inactive CRISPR protein that is paired as a ribonucleoprotein complex (RNP) with a guide RNA with binding affinity to certain regions of a target nucleic acid, can, when bound to the target nucleic acid, prevent transcription from a promoter or otherwise inhibit the expression of a gene. Without wishing to be bound by theory, it is thought that transcriptional repressors can function by a variety of mechanisms, including physically blocking RNA polymerase passage by steric hindrance, altering the polymerase's post-translational modification state, modifying the epigenetic state of the nascent RNA, changing the epigenetic state of the DNA through methylation, changing the epigenetic state of the DNA through histone deacetylation or modulating nucleosome remodeling, or preventing enhancer-promoter interactions, thereby leading to gene silencing or a reduction in the level of gene expression.

As used herein a "catalytically-dead CRISPR protein" refers to a CRISPR protein that lacks endonuclease activity. The skilled artisan will appreciate that a CRISPR protein can be catalytically dead, and still able to carry out additional protein functions, such as DNA binding. Similarly, a "catalytically-dead CasX" refers to a CasX protein that lacks endonuclease activity but is still able to carry out additional protein functions, such as DNA binding.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "enhancers" and "promoters", above).

The term "recombinant polynucleotide" or "recombinant nucleic acid" refers to one which is not naturally occurring; e.g., is made by the artificial combination of two otherwise separated segments of sequence through human intervention. This artificial combination is often accomplished by either chemical synthesis means, or by the artificial manipulation of isolated segments of nucleic acids; e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids; e.g., by genetic engineering techniques.

Similarly, the term "recombinant polypeptide" or "recombinant protein" refers to a polypeptide or protein which is not naturally occurring; e.g., is made by the artificial combination of two otherwise separated segments of amino sequence through human intervention. Thus; e.g., a protein that comprises a heterologous amino acid sequence is recombinant.

As used herein, the term "contacting" means establishing a physical connection between two or more entities. For example, contacting a target nucleic acid sequence with a guide nucleic acid means that the target nucleic acid sequence and the guide nucleic acid are made to share a physical connection; e.g., can hybridize if the sequences share sequence similarity.

"Dissociation constant", or "$K_d$", are used interchangeably and mean the affinity between a ligand "L" and a protein "P"; i.e., how tightly a ligand binds to a particular protein. It can be calculated using the formula $K_d$=[L][P]/[LP], where [P], [L] and [LP] represent molar concentrations of the protein, ligand and complex, respectively.

As used herein, "homology-directed repair" (HDR) refers to the form of DNA repair that takes place during repair of double-strand breaks in cells. This process requires nucleotide sequence homology, and uses a donor template to repair or knock-out a target DNA, and leads to the transfer of genetic information from the donor (e.g., such as the donor template) to the target. Homology-directed repair can result in an alteration of the sequence of the target nucleic acid sequence by insertion, deletion, or mutation if the donor template differs from the target DNA sequence and part or all of the sequence of the donor template is incorporated into the target DNA.

As used herein, "non-homologous end joining" (NHEJ) refers to the repair of double-strand breaks in DNA by direct ligation of the break ends to one another without the need for a homologous template (in contrast to homology-directed repair, which requires a homologous sequence to guide repair). NHEJ often results in the loss (deletion) of nucleotide sequence near the site of the double-strand break.

As used herein "micro-homology mediated end joining" (MMEJ) refers to a mutagenic DSB repair mechanism, which always associates with deletions flanking the break sites without the need for a homologous template (in contrast to homology-directed repair, which requires a homologous sequence to guide repair). MMEJ often results in the loss (deletion) of nucleotide sequence near the site of the double-strand break.

A polynucleotide or polypeptide (or protein) has a certain percent "sequence similarity" or "sequence identity" to another polynucleotide or polypeptide, meaning that, when aligned, that percentage of bases or amino acids are the same, and in the same relative position, when comparing the two sequences. Sequence similarity (sometimes referred to as percent similarity, percent identity, or homology) can be determined in a number of different manners. To determine sequence similarity, sequences can be aligned using the methods and computer programs that are known in the art, including BLAST, available over the world wide web at ncbi.nlm.nih.gov/BLAST. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.); e.g., using default settings, which uses the algorithm of Smith and Waterman (Adv. Appl. Math., 1981, 2, 482-489).

The terms "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence.

A "vector" or "expression vector" is a replicon, such as plasmid, phage, virus, or cosmid, to which another DNA segment, i.e., an "insert", may be attached so as to bring about the replication or expression of the attached segment in a cell.

The term "naturally-occurring" or "unmodified" or "wild type" as used herein as applied to a nucleic acid, a polypeptide, a cell, or an organism, refers to a nucleic acid, polypeptide, cell, or organism that is found in nature.

As used herein, a "mutation" refers to an insertion, deletion, substitution, duplication, or inversion of one or more amino acids or nucleotides as compared to a wild-type or reference amino acid sequence or to a wild-type or reference nucleotide sequence.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

A "host cell," as used herein, denotes a eukaryotic cell, a prokaryotic cell, or a cell from a multicellular organism (e.g., in a cell line), cultured as a unicellular entity, which eukaryotic or prokaryotic cells are used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host The term "tropism" as used herein refers to preferential entry of the virus like particle (VLP or XDP) into certain cell or tissue type(s) and/or preferential interaction with the cell surface that facilitates entry into certain cell or tissue types, optionally and preferably followed by expression (e.g., transcription and, optionally, translation) of sequences carried by the VLP or XDP into the cell.

The terms "pseudotype" or "pseudotyping" as used herein, refers to viral envelope proteins that have been substituted with those of another virus possessing preferable characteristics. For example, HIV can be pseudotyped with vesicular stomatitis virus G-protein (VSV-G) envelope proteins (amongst others, described herein, below), which allows HIV to infect a wider range of cells because HIV envelope proteins target the virus mainly to CD4+ presenting cells.

The term "tropism factor" as used herein refers to components integrated into the surface of an XDP or VLP that provides tropism for a certain cell or tissue type. Non-limiting examples of tropism factors include glycoproteins, antibody fragments (e.g., scFv, nanobodies, linear antibodies, etc.), receptors and ligands to target cell markers.

A "target cell marker" refers to a molecule expressed by a target cell including but not limited to cell-surface receptors, cytokine receptors, antigens, tumor-associated antigens, glycoproteins, oligonucleotides, enzymatic substrates, antigenic determinants, or binding sites that may be present in the on the surface of a target tissue or cell that may serve as ligands for a tropism factor.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

As used herein, "treatment" or "treating," are used interchangeably herein and refer to an approach for obtaining beneficial or desired results, including but not limited to a therapeutic benefit and/or a prophylactic benefit. By therapeutic benefit is meant eradication or amelioration of the underlying disorder or disease being treated. A therapeutic benefit can also be achieved with the eradication or amelioration of one or more of the symptoms or an improvement in one or more clinical parameters associated with the underlying disease such that an improvement is observed in the subject, notwithstanding that the subject may still be afflicted with the underlying disorder.

The terms "therapeutically effective amount" and "therapeutically effective dose", as used herein, refer to an amount of a drug or a biologic, alone or as a part of a composition, that is capable of having any detectable, beneficial effect on any symptom, aspect, measured parameter or characteristics of a disease state or condition when administered in one or repeated doses to a subject such as a human or an experimental animal. Such effect need not be absolute to be beneficial.

As used herein, "administering" is meant a method of giving a dosage of a compound (e.g., a composition of the disclosure) or a composition (e.g., a pharmaceutical composition) to a subject.

A "subject" is a mammal. Mammals include, but are not limited to, domesticated animals, non-human primates, humans, rabbits, mice, rats and other rodents.

All publications, patents, and patent applications mentioned in this specification are herein incorporated by reference to the same extent as if each individual publication, patent, or patent application was specifically and individually indicated to be incorporated by reference.

I. General Methods

The practice of the present invention employs, unless otherwise indicated, conventional techniques of immunology, biochemistry, chemistry, molecular biology, microbiology, cell biology, genomics and recombinant DNA, which can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Where a range of values is provided, it is understood that endpoints are included and that each intervening value, to the tenth of the unit of the lower limit unless the context clearly dictates otherwise, between the upper and lower limit of that range and any other stated or intervening value in that stated range, is encompassed. The upper and lower limits of these smaller ranges may independently be included in the smaller ranges, and are also encompassed, subject to any specifically excluded limit in the stated range. Where the stated range includes one or both of the limits, ranges excluding either or both of those included limits are also included.

Unless defined otherwise, all technical and scientific terms used herein have the same meaning as commonly understood by one of ordinary skill in the art to which this invention belongs. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise.

It will be appreciated that certain features of the disclosure, which are, for clarity, described in the context of separate embodiments, may also be provided in combination in a single embodiment. In other cases, various features of the disclosure, which are, for brevity, described in the context of a single embodiment, may also be provided separately or in any suitable sub-combination. It is intended that all combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

II. Repressor and Epigenetic Long-Term X-Repressor (ELXR) Systems

In a first aspect, the present disclosure provides gene repressor systems comprising a catalytically-dead CRISPR protein linked to one or more repressor domains, and one or more guide ribonucleic acids (gRNA) comprising a targeting sequence complementary to a target nucleic acid sequence of a gene targeted for repression, silencing, or downregulation, wherein the system is capable of binding to a target nucleic acid of the gene and repressing transcription of the gene.

In the context of the present disclosure and with respect to a gene, "repression", "repressing", "inhibition of gene expression", "downregulation", and "silencing" are used interchangeably herein to refer to the inhibition or blocking of transcription of a gene or a portion thereof. A gene product capable of being repressed by the systems of the disclosure include mRNA, rRNA, tRNA, structural RNA or protein encoded by the mRNA. Accordingly, repression of a gene can result in a decrease in production of a gene product. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Transcriptional repression includes both reversible and irreversible inactivation of gene transcription. In some embodiments, repression by the systems of the disclosure comprises any detectable decrease in the production of a gene product in cells, preferably a decrease in production of a gene product by at least about 10%, 20%, 30%, 40%, 50%, 60%, 70%, 80%, 90%, 95%, or 99%, or any integer there between, when compared to untreated cells or cells treated with a comparable system comprising a non-targeting spacer. Most preferably, gene repression results in complete inhibition of gene expression, such that no gene product is detectable. In some embodiments, the repression of transcription by the systems of the embodiments is sustained for at least about 8 hours, at least about 1 day, at least about 1 week, at least about 2 weeks, at least about 3 weeks, at least about 1 month, or at least about 3 months, or at least about 6 months when assessed in an in vitro assay, including cell-based assays. In some embodiments, the repression of transcription by the gene repressor systems of the embodiments is sustained for at least about 1 day, at least about 1 week, at least about 2 weeks, at least about 3 weeks, at least about 1 month, or at least about 3 months, or at least about 6 months when assessed in a subject that has been administered a therapeutically-effective dose of a system of the embodiments described herein. In some embodiments, gene repression by the system results in no or minimal detectable off-target methylation or off-target activity, when assessed in an in vitro assay. In other embodiments, gene repression by the system results in no or minimal detectable off-target methylation or off-target activity, when assessed in a subject that has been administered a therapeutically-effective dose of a system of the embodiments described herein.

In some embodiments, the present disclosure provides systems of catalytically-dead CRISPR proteins linked to one or more repressor domains as a fusion protein and one or more guide ribonucleic acids (gRNA) for use in repressing a target nucleic acid, inclusive of coding and non-coding regions.

In some embodiments, the present disclosure provides systems of catalytically-dead CasX (dCasX) proteins linked to one or more repressor domains as a fusion protein (dXR) and one or more guide ribonucleic acids (gRNA) for use in repressing a target nucleic acid, inclusive of coding and non-coding regions; collectively, a dXR:gRNA system. A gRNA variant and targeting sequence, and a dCasX variant protein and linked repressor domain(s) of any of the embodiments, can form a complex and bind via non-covalent interactions, referred to herein as a ribonucleoprotein (RNP) complex. In some embodiments, the use of a pre-complexed dXR:gRNA RNP confers advantages in the delivery of the system components to a cell or target nucleic acid for repression of the target nucleic acid. In the RNP, the gRNA can provide target specificity to the RNP complex by including a targeting sequence (also referred to as a "spacer") having a nucleotide sequence that is complementary to a sequence of a target nucleic acid. In the RNP, the dCasX protein and linked repressor domain(s) of the pre-complexed dXR:gRNA provides the site-specific activity and is guided to a target site (and further stabilized at a target site) within a target nucleic acid sequence to be modified by virtue of its association with the gRNA. The dCasX protein and linked repressor domain(s) of the RNP complex provides the site-specific activities of the complex such as binding of the target sequence by the dCasX protein and the linked repressor domains provide the repression activity either directly or by the recruitment of other cellular factors.

Provided herein are compositions comprising or encoding the dCasX variant protein and linked repressor domains (dXR), gRNA variants, and dXR:gRNA gene repression pairs of any combination of dXR and gRNA, nucleic acids encoding the dXR and gRNA, as well as delivery modalities comprising the dXR:gRNA or encoding nucleic acids. Also provided herein are methods of making dCasX protein and linked repressor domain(s) and gRNA, as well as methods of using the CasX and gRNA, including methods of gene repression and methods of treatment. The dCasX protein and linked repressor domain(s) and gRNA components of the dXR:gRNA systems and their features, as well as the delivery modalities and the methods of using the compositions for the repression, down-regulation or silencing of a gene are described more fully, below.

III. Repressor Domain Fusion Proteins of the dXR:gRNA Systems

In one aspect, the disclosure relates to fusion proteins comprising one or more repressor domains operably linked to a catalytically dead CRISPR protein, e.g., a catalytically-dead Class 2 CRISPR protein. In some embodiments, the catalytically-dead Class 2 CRISPR protein is a catalytically-dead Class 2, Type V CRISPR protein. In some embodiments, the catalytically-dead CRISPR proteins include Class 2, Type II CRISPR/Cas nucleases such as Cas9. In other cases, the catalytically-dead CRISPR proteins include Class 2, Type V CRISPR/Cas nucleases such as a Cas12a (Cpf1), Cas12b (C2c1), Cas12c (C2c3), Cas12d (CasY), Cas12e (CasX), Cas12f, Cas12g, Cas12h, Cas12i, Cas12j, Cas12k, Cas12l, Cas14, and/or CasΦ. In some embodiments, the catalytically-dead Class 2, Type V CRISPR protein is a catalytically-dead CasX protein (dCasX) selected from the group of sequences of SEQ ID NOS: 17-36 and 59353-59358 as set forth in Table 4, or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, linked to one or more repressor domains, resulting in a dXR fusion protein. In some embodiments, the catalytically-dead Class 2, Type V CRISPR protein is a catalytically-dead CasX protein (dCasX) selected from the group of sequences of SEQ ID NOS: 17-36 and 59353-59358 as set forth in Table 4 linked to one or more repressor domains, resulting in a dXR fusion protein.

In some embodiments, the disclosure provides fusion proteins comprising a first repressor domain as a fusion protein wherein the first repressor domain is a Krüppel-associated box (KRAB) domain which can be fused to a catalytically dead CRISPR protein by linker peptides disclosed herein. In some embodiments, the disclosure provides dXR fusion proteins comprising a first repressor domain as a fusion protein wherein the first repressor domain is a Krüppel-associated box (KRAB) domain which can be fused to the dCasX by linker peptides disclosed herein, resulting in a dXR fusion protein.

Amongst repressor domains that have the ability to repress, or silence genes, the Krüppel-associated box (KRAB) repressor domain is amongst the most powerful in human genome systems (Alerasool, N., et al. An efficient KRAB domain for CRISPRi applications. Nat. Methods 17:1093 (2020)). KRAB domains are present in approximately 400 human zinc finger protein-based transcription factors that upon binding of the dXR to the target nucleic acid, is capable of recruiting additional repressor domains such as, but not limited to, Trim28 (also known as Kap1 or Tif1-beta) that, in turn, assembles a protein complex with chromatin regulators such as CBX5/HP1α and SETDB1 that induce repression of transcription of the gene. SETDB1 is a histone methyltransferase that deposit H3K9me3 marks on histones, which is a mark of heterochromatin (complexes which acetylate histones and deposit active H3K9ac marks are displaced). In some cases, DNA methyltransferases (the DNMT domains DNMT3A and DNMT3L) are subsequently recruited to deposit methylation marks on the DNA so that silencing of the gene will persist after the system complex is no longer bound to the target nucleic acid. The methylation of CpG dinucleotides (CpG) in mammalian cells is catalyzed by the DNA methyltransferases DNMT3a and 3b, which establish DNA methylation patterns, and DNMTL, which maintains the methylation pattern after DNA replication (Zhang, Y., et al. Chromatin methylation activity of Dnmt3a and Dnmt3a/3L is guided by interaction of the ADD domain with the histone H3 tail. Nucleic Acids Research 38:4246 (2010)). Thus, SETDB1 and DNMT3's recruited by the KRAB domain act as co-repressors of the dXR fusion protein (Tatsumi, D., et al. DNMTs and SETDB1 function as co-repressors in MAX-mediated repression of germ cell-related genes in mouse embryonic stem cells. PLoS ONE 13(11): e0205969 (2018)).

Other repressor domains suitable for inclusion in the dXR of the disclosure include DNA methyltransferase 3 alpha (DNMT3A or subdomains thereof), DNMT3A-like protein (DNMT3L or subdomains thereof), DNA methyltransferase 3 beta (DNMT3B), DNA methyltransferase 1 (DNMT1), Friend of GATA-1 (FOG), Mad mSIN3 interaction domain (SID), enhanced SID (SID4X), nuclear receptor corepressor (NcoR), nuclear effector protein (NuE), KOX1 repression domain, the ERF repressor domain (ERD), the SRDX repression domain, histone lysine methyltransferases such as PR/SET domain containing protein (Pr-SET)7/8, lysine methyltransferase 5B (SUV4-20H1), PR/SET domain 2 (RIZ1), histone lysine demethylases such as lysine demethylase 4A (JMJD2A/JHDM3A), lysine demethylase 4B (JMJD2B), lysine demethylase 4C (JMJD2C/GASC1), lysine demethylase 4D (JMJD2D), lysine demethylase 5A (JARID1A/RBP2), lysine demethylase 5B (JARID1B/PLU-1), lysine demethylase 5C (JARID 1C/SMCX), lysine demethylase 5D (JARID1D/SMCY), sirtuin 1 (SIRT1), SIRT2, DNA methylases such as HhaI DNA m5c-methyltransferase (M.HhaI), methyltransferase 1 (MET1), histone H3 lysine 9 methyltransferase G9a (G9a), S-adenosyl-L-methionine-dependent methyltransferases superfamily protein (DRM3), DNA cytosine methyltransferase MET2a (ZMET2), methyl-CpG (mCpG) binding domain 2 (meCP2), Switch independent 3 transcription regulator family member A (SIN3A), histone deacetylase HDT1 (HDT1), n-terminal truncation of methyl-CpG-binding domain containing protein 2 (MBD2B), nuclear inhibitor of protein phosphatase-1 (NIPP1), GLP, chromomethylase 1 (CMT1), chromomethylase 2 (CMT2), heterochromatin protein 1 (HP1A), mixed lineage leukemia protein-5 (MLL5), histone-lysine N-methyltransferase SETDB1 (SETB1), Suppressor Of Variegation 3-9 Homolog 1 (SUV39H1), SUV39H2, euchromatic histone lysine methyltransferase 1 (EHMT1), histone-lysine N-methyltransferase EZH1 (EZH1), EZH2, nuclear receptor binding SET domain protein 1 (NSD1), NSD2, NSD3, ASH1 like histone lysine methyltransferase (ASH1L), tripartite motif containing 28 (TRIM28), Methyltransferase Like 3 (METTL3), METTL4, family with sequence similarity 208 member A (FAM208A), M-Phase Phosphoprotein 8 (MPHOSPH8), SET domain containing 2 (SETD2), histone deacetylase 1 (HDAC1), HDAC2, HDAC3, HDAC8, HDAC4, HDAC5, HDAC7, HDAC9, Periphilin 1 (PPHLN1), and subdomains thereof.

Human genes encoding KRAB zinc-finger proteins include KOX1/ZNF10, KOX8/ZNF708, ZNF43, ZNF184, ZNF91, HPF4, HTF10, HTF34, and the sequences of SEQ ID NOS: 355-888. In some embodiments, the KRAB transcriptional repressor domain of the dXR:gRNA systems is selected from the group consisting of (in all cases, ZNF=zinc finger protein; KRBOX=KRAB box domain containing; ZKSCAN=zinc finger with KRAB and SCAN domains; SSX=SSX family member; KRBA=KRAB-A domain containing; ZFP=zinc finger protein) ZNF343, ZNF10, ZNF337, ZNF334, ZNF215, ZNF519, ZNF485, ZNF214, ZNF33B, ZNF287, ZNF705A, ZNF37A, KRBOX4, ZKSCAN3, ZKSCAN4, ZNF57, ZNF557, ZNF705B, ZNF662, ZNF77, ZNF500, ZNF558, ZNF620, ZNF713, ZNF823, ZNF440, ZNF441, ZNF136, small nuclear ribonucleoprotein polypeptides B and B1 (SNRPB), ZNF735, ZKSCAN2, ZNF619, ZNF627, ZNF333, ATP binding cassette subfamily A member 11 (ABCA11P), PLD5 pseudogene 1 (PLD5P1), ZNF25, ZNF727, ZNF595, ZNF14, ZNF33A, ZNF101, ZNF253, ZNF56, ZNF720, ZNF85, ZNF66, ZNF722P, ZNF486, ZNF682, ZNF626, ZNF100, ZNF93, ZKSCAN1, ZNF257, ZNF729, ZNF208, ZNF90, ZNF430, ZNF676, ZNF91, ZNF429, ZNF675, ZNF681, ZNF99, ZNF431, ZNF98, ZNF708, ZNF732, SSX family member 2 (SSX2), ZNF721, ZNF726, ZNF730, ZNF506, ZNF728, ZNF141, ZNF723, ZNF302, ZNF484, SSX2B, ZNF718, ZNF74, ZNF157, ZNF790, ZNF565, ZNF705G, vomeronasal 1 receptor 107 pseudogene (VN1R107P), solute carrier family 27 member 5 (SLC27A5), ZNF737, SSX4, ZNF850, ZNF717, ZNF155, ZNF283, ZNF404, ZNF114, ZNF716, ZNF230, ZNF45, ZNF222, ZNF286A, ZNF624, ZNF223, ZNF284, ZNF790-AS1, ZNF382, ZNF749, ZNF615, ZFP90, ZNF225, ZNF234, ZNF568, ZNF614, ZNF584, ZNF432, ZNF461, ZNF182, ZNF630, ZNF630-AS1, ZNF132, ZNF420, ZNF324B, ZNF616, ZNF471, ZNF227, ZNF324, ZNF860, ZFP28 zinc finger protein (ZFP28), ZNF470, ZNF586, ZNF235, ZNF274, ZNF446, ZFP1, ZIM3, ZNF212, ZNF766, ZNF264, ZNF480, ZNF667, ZNF805, ZNF610, ZNF783, ZNF621, ZNF8-DT, ZNF880, ZNF213-AS1, ZNF213, ZNF263, zinc finger and SCAN domain containing 32 (ZSCAN32), ZIM2, ZNF597, ZNF786, KRAB-A domain containing 1 (KRBA1), ZNF460, ZNF8, ZNF875, ZNF543, ZNF133, ZNF229, ZNF528, SSX1, ZNF81, ZNF578, ZNF862, ZNF777, ZNF425, ZNF548, ZNF746, ZNF282, ZNF398, ZNF599, ZNF251, ZNF195, ZNF181, RBAK-RBAKDN readthrough (RBAK-RBAKDN), ZFP37, RNA, 7SL, cytoplasmic 526, pseudogene (RN7SL526P), ZNF879, ZNF26, ZSCAN21, ZNF3, ZNF354C, ZNF10, ZNF75D, ZNF426, ZNF561, ZNF562, ZNF846, ZNF782, ZNF552, ZNF587B, ZNF814, ZNF587, ZNF92, ZNF417, ZNF256, ZNF473, ZFP14, ZFP82, ZNF529, ZNF605, ZFP57, ZNF724, ZNF43, ZNF354A, ZNF547, SSX4B, ZNF585A, ZNF585B, ZNF792, ZNF789, ZNF394, ZNF655, ZFP92, ZNF41, ZNF674, ZNF546, ZNF780B, ZNF699, ZNF177, ZNF560, ZNF583, ZNF707, ZNF808, ZKSCAN5, ZNF137P, ZNF611, ZNF600, ZNF28, ZNF773, ZNF549, ZNF550, ZNF416, ZIK1, ZNF211, ZNF527, ZNF569, ZNF793, ZNF571-AS1, ZNF540, ZNF571, ZNF607, ZNF75A, ZNF205, ZNF175, ZNF268, ZNF354B, ZNF135, ZNF221, ZNF285, ZNF419, ZNF30, ZNF304, ZNF254, ZNF701, ZNF418, ZNF71, ZNF570, ZNF705E, KRBOX1, ZNF510, ZNF778, PR/SET domain 9 (PRDM9), ZNF248, ZNF845, ZNF525, ZNF765, ZNF813, ZNF747, ZNF764, ZNF785, ZNF689, ZNF311, ZNF169, ZNF483, ZNF493, ZNF189, ZNF658, ZNF564, ZNF490, ZNF791, ZNF678, ZNF454, ZNF34, ZNF7, ZNF250, ZNF705D, ZNF641, ZNF2, ZNF554, ZNF555, ZNF556, ZNF596, ZNF517, ZNF331, ZNF18, ZNF829, ZNF772, ZNF17, ZNF112, ZNF514, ZNF688, PRDM7, ZNF695, ZNF670-ZNF695, ZNF138, ZNF670, ZNF19, ZNF316, ZNF12, ZNF202, RBAK, ZNF83, ZNF468, ZNF479, ZNF679, ZNF736, ZNF680, ZNF273, ZNF107, ZNF267, ZKSCAN8, ZNF84, ZNF573, ZNF23, ZNF559, ZNF44, ZNF563, ZNF442, ZNF799, ZNF443, ZNF709, ZNF566, ZNF69, ZNF700, ZNF763, ZNF433-AS1, ZNF433, ZNF878, ZNF844, ZNF788P, ZNF20, ZNF625-ZNF20, ZNF625, ZNF606, ZNF530, ZNF577, ZNF649, ZNF613, ZNF350, ZNF317, ZNF300, ZNF180, ZNF415, vomeronasal 1 receptor 1 (VN1R1), ZNF266, ZNF738, ZNF445, ZNF852, ZKSCAN7, ZNF660, myosin phosphatase Rho interacting protein pseudogene 1 (MPRIPP1), ZNF197, ZNF567, ZNF582, ZNF439, ZFP30, ZNF559-ZNF177, ZNF226, ZNF841, ZNF544, ZNF233, ZNF534, ZNF836, ZNF320, KRBA2, ZNF761, ZNF383, ZNF224, ZNF551, ZNF154, ZNF671, ZNF776, ZNF780A, ZNF888, ZNF816-ZNF321P, ZNF321P, ZNF816, ZNF347, ZNF665, ZNF677, ZNF160, ZNF184, ZNF140, ZNF589, ZNF891, ZFP69B, ZNF436, pogo transposable element derived with KRAB domain (POGK), ZNF669, ZFP69, ZNF684, ZNF124, and ZNF496, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto.

In some embodiments, the gene repressor system comprises a single KRAB domain operably linked to the catalytically-dead CRISPR protein as a fusion protein, wherein the KRAB domain is selected from the group of sequences consisting of SEQ ID NOS: 889-2100 and 2332-33239, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In some embodiments, the system comprises a single KRAB domain operably linked to the catalytically-dead CRISPR protein, wherein the KRAB domain is selected from the group of sequences consisting of SEQ ID NOS: 889-2100 and 2332-33239. In some embodiments, the fusion protein of the systems comprises a single KRAB domain operably linked to the catalytically-dead CRISPR protein, wherein the KRAB domain is selected from the group of sequences consisting of SEQ ID NOS: 57746-59342, or a sequence having at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In some embodiments, the fusion protein of the systems comprises a single KRAB domain operably linked to the catalytically-dead CRISPR protein, wherein the KRAB domain is selected from the group of sequences consisting of SEQ ID NOS: 57746-57840, or a sequence having at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In some embodiments, the fusion protein of the systems comprises a single KRAB domain operably linked to the catalytically-dead CRISPR, wherein the KRAB domain is selected from the group of sequences consisting of SEQ ID NOS: 57746-57755, or a sequence having at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In a particular embodiment, the fusion protein of the systems comprises a single KRAB domain operably linked to a catalytically dead Cas9 protein, wherein the KRAB domain is selected from the group of sequences consisting of SEQ ID NOS: 57746-57755, or a sequence having at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto.

In some embodiments, the fusion proteins of the systems comprise a single KRAB domain operably linked by a peptide linker to the catalytically-dead CRISPR protein, wherein the KRAB domain comprises one or more motifs selected from the group consisting of a) $PX_1X_2X_3X_4X_5X_6EX_7$, wherein $X_1$ is A, D, E, or N, $X_2$ is L or V, $X_3$ is I or V, $X_4$ is S, T, or F, $X_5$ is H, K, L, Q, R or W, $X_6$ is L or M, and $X_7$ is G, K, Q, or R; b) $X_1X_2X_3X_4GX_5X_6X_7X_8X_9$, wherein $X_1$ is L or V, $X_2$ is A, G, L, T or V, $X_3$ is A, F, or S, $X_4$ is L or V, $X_5$ is C, F, H, I, L or Y, $X_6$ is A, C, P, Q, or S, $X_7$ is A, F, G, I, S, or V, $X_8$ is A, P, S, or T, and $X_9$ is K or R; c) $QX_1X_2LYRX_3VMX_4$(SEQ ID NO: 59345), wherein $X_1$ is K or R, $X_2$ is A, D, E, G, N, S, or T, $X_3$ is D, E, or S, and $X_4$ is L or R; d) $X_1X_2X_3FX_4DVX_5X_6X_7FX_8X_9X_{10}X_{11}$ (SEQ ID NO: 59346), wherein $X_1$ is A, L, P, or S, $X_2$ is L or V, $X_3$ is S or T, $X_4$ is A, E, G, K, or R, $X_5$ is A or T, $X_6$ is I or V, $X_7$ is D, E, N, or Y, $X_8$ is S or T, $X_9$ is E, P, Q, R, or W, $X_{10}$ is E or N, and $X_{11}$ is E or Q; e) $X_1X_2X_3PX_4X_5X_6X_7X_8X_9X_{10}$, wherein $X_1$ is E, G, or R, $X_2$ is E or K, $X_3$ is A, D, or E, $X_4$ is C or W, $X_5$ is I, K, L, M, T, or V, $X_6$ is I, L, P, or V, $X_7$ is D, E, K, or V, $X_8$ is E, G, K, P, or R, $X_9$ is A, D, R, G, K, Q, or V, and $X_{10}$ is D, E, G, I, L, R, S, or V; f) $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S; g) $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R; h) $X_1PX_2X_3X_4X_5$ $X_6LEX_7X_8X_9X_{10}X_{11}X_{12}$, wherein $X_1$ is K or R, $X_2$ is A, D, E, or N, $X_3$ is I, L, M, or V, $X_4$ is I or V, $X_5$ is F, S, or T, $X_6$ is H, K, L, Q, R, or W, $X_7$ is K, Q, or R, $X_8$ is E, G, or R, $X_9$ is D, E, or K, $X_{10}$ is A, D, or E, $X_{11}$ is L or P, and $X_{12}$ is C or W; or i) $X_1LX_2X_3X_4QX_5X_6$, wherein $X_1$ is C, H, L, Q, or W, $X_2$ is D, G, N, R, or S, $X_3$ is L, P, S, or T, $X_4$ is A, S, or T, $X_5$ is K or R, and $X_6$ is A, D, E, K, N, S, or T, and the KRAB domain comprises a sequence selected from the group consisting of SEQ ID NOS: 57746-59342. In other embodiments, the fusion proteins of the systems comprise a single KRAB domain operably linked to the catalytically-dead CRISPR protein wherein the KRAB domain comprises a first domain comprising the sequence $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S, and a second sequence motif comprises the sequence $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R, and the KRAB domain comprises a sequence selected from the group consisting of SEQ ID NOS: 57746-59342. In other embodiments, the fusion proteins of the systems comprise a single KRAB domain operably linked to the catalytically-dead CRISPR protein wherein the KRAB domain comprises a first domain comprising the sequence $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S, and a second sequence motif comprises the sequence $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R, and the KRAB domain comprises a sequence selected from the group consisting of SEQ ID NOS: 57746-57840. In still other embodiments, the fusion proteins of the systems comprise a single KRAB domain operably linked to the catalytically-dead CRISPR protein wherein the KRAB domain comprises a first domain comprising the sequence $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S, and a second sequence motif comprises the sequence $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R, and the KRAB domain comprises a sequence selected from the group consisting of SEQ ID NOS: 57746-57755.

In some embodiments, the dXR:gRNA system comprises a single KRAB domain operably linked to a catalytically-dead Class 2, Type V CRISPR protein as a fusion protein, wherein the catalytically-dead Class 2, Type V CRISPR protein is a dCasX selected from the group of sequences of SEQ ID NOS: 17-36 and 59353-59358 as set forth in Table 4, or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and wherein the KRAB domain is selected from the group of sequences consisting of SEQ ID NOS: 889-2100 and 2332-33239, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In some embodiments, the system comprises a single KRAB domain operably linked to the dCasX selected from the group of sequences of SEQ ID NOS: 17-36 and 59353-59358 as set forth in Table 4, wherein the KRAB domain is selected from the group of sequences consisting of SEQ ID NOS: 889-2100 and 2332-33239. In some embodiments, the dXR fusion protein of the systems comprises a single KRAB domain operably linked to the dCasX selected from the group of sequences of SEQ ID NOS: 17-36 and 59353-59358 as set forth in Table 4, wherein the KRAB domain is selected from the group of sequences consisting of SEQ ID NOS: 57746-59342, or a sequence having at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In some embodiments, the dXR fusion protein of the systems comprises a single KRAB domain operably linked to the dCasX selected from the group of sequences of SEQ ID NOS: 17-36 and 59353-59358 as set forth in Table 4, wherein the KRAB domain is selected from the group of sequences consisting of SEQ ID NOS: 57746-57840, or a sequence having at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In some embodiments, the dXR fusion protein of the systems comprises a single KRAB domain operably linked to the dCasX selected from the group of sequences of SEQ ID NOS: 17-36 and 59353-59358 as set forth in Table 4, wherein the KRAB domain is selected from the group of sequences consisting of SEQ ID NOS: 57746-57755, or a sequence having at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In a particular embodiment, the dXR fusion protein of the systems comprises a single KRAB domain operably linked to the dCasX of SEQ ID NO: 18 as set forth in Table 4, wherein the KRAB domain is selected from the group of sequences consisting of SEQ ID NOS: 57746-57755, or a sequence having at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In another particular embodiment, the dXR fusion protein of the systems comprises a single KRAB domain operably linked to the dCasX of SEQ ID NO: 25, as set forth in Table 4, wherein the KRAB domain is selected from the group of sequences consisting of SEQ ID NOS: 57746-57755, or a sequence having at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In another particular embodiment, the dXR fusion protein of the systems comprises a single KRAB domain operably linked to the dCasX of SEQ ID NO: 59357, as set forth in Table 4, wherein the KRAB domain is selected from the group of sequences consisting of SEQ ID NOS: 57746-57755, or a sequence having at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In another particular embodiment, the dXR fusion protein of the systems comprises a single KRAB domain operably linked to the dCasX of SEQ ID NO: 59358, as set forth in Table 4, wherein the KRAB domain is selected from the group of sequences consisting of SEQ ID NOS: 57746-57755, or a sequence having at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto.

In some embodiments, the dXR fusion proteins of the systems comprise a single KRAB domain operably linked by a peptide linker to a dCasX selected from the group of sequences of SEQ ID NOS: 17-36 and 59353-59358 as set forth in Table 4, wherein the KRAB domain comprises one or more motifs selected from the group consisting of a) $PX_1X_2X_3X_4X_5X_6EX_7$, wherein $X_1$ is A, D, E, or N, $X_2$ is L or V, $X_3$ is I or V, $X_4$ is S, T, or F, $X_5$ is H, K, L, Q, R or W, $X_6$ is L or M, and $X_7$ is G, K, Q, or R; b) $X_1X_2X_3X_4GX_5X_6X_7X_8X_9$, wherein $X_1$ is L or V, $X_2$ is A, G, L, T or V, $X_3$ is A, F, or S, $X_4$ is L or V, $X_5$ is C, F, H, I, L or Y, $X_6$ is A, C, P, Q, or S, $X_7$ is A, F, G, I, S, or V, $X_8$ is A, P, S, or T, and $X_9$ is K or R; c) $QX_1X_2LYRX_3VMX_4$(SEQ ID NO: 59345), wherein $X_1$ is K or R, $X_2$ is A, D, E, G, N, S, or T, $X_3$ is D, E, or S, and $X_4$ is L or R; d) $X_1X_2X_3FX_4DVX_5X_6X_7FX_8X_9X_{10}X_{11}$ (SEQ ID NO: 59346), wherein $X_1$ is A, L, P, or S, $X_2$ is L or V, $X_3$ is S or T, $X_4$ is A, E, G, K, or R, $X_5$ is A or T, $X_6$ is I or V, $X_7$ is D, E, N, or Y, $X_8$ is S or T, $X_9$ is E, P, Q, R, or W, $X_{10}$ is E or N, and $X_{11}$ is E or Q; e) $X_1X_2X_3PX_4X_5X_6X_7X_8X_9X_{10}$, wherein $X_1$ is E, G, or R, $X_2$ is E or K, $X_3$ is A, D, or E, $X_4$ is C or W, $X_5$ is I, K, L, M, T, or V, $X_6$ is I, L, P, or V, $X_7$ is D, E, K, or V, $X_8$ is E, G, K, P, or R, $X_9$ is A, D, R, G, K, Q, or V, and $X_{10}$ is D, E, G, I, L, R, S, or V; f) $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S; g) $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R; h) $X_1PX_2X_3X_4X_5$ $X_6LEX_7X_8X_9X_{10}X_{11}X_{12}$, wherein $X_1$ is K or R, $X_2$ is A, D, E, or N, $X_3$ is I, L, M, or V, $X_4$ is I or V, $X_5$ is F, S, or T, $X_6$ is H, K, L, Q, R, or W, $X_7$ is K, Q, or R, $X_8$ is E, G, or R, $X_9$ is D, E, or K, $X_{10}$ is A, D, or E, $X_{11}$ is L or P, and $X_{12}$ is C or W; or i) $X_1LX_2X_3X_4QX_5X_6$, wherein $X_1$ is C, H, L, Q, or W, $X_2$ is D, G, N, R, or S, $X_3$ is L, P, S, or T, $X_4$ is A, S, or T, $X_5$ is K or R, and $X_6$ is A, D, E, K, N, S, or T, and the KRAB domain comprises a sequence selected from the group consisting of SEQ ID NOS: 57746-59342. In other embodiments, the dXR fusion proteins of the systems comprise a single KRAB domain operably linked to the dCasX wherein the KRAB domain comprises a first domain comprising the sequence $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S, and a second sequence motif comprises the sequence $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R, and the KRAB domain comprises a sequence selected from the group consisting of SEQ ID NOS: 57746-59342. In other embodiments, the dXR fusion proteins of the systems comprise a single KRAB domain operably linked to the dCasX wherein the KRAB domain comprises a first domain comprising the sequence $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S, and a second sequence motif comprises the sequence $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R, and the KRAB domain comprises a sequence selected from the group consisting of SEQ ID NOS: 57746-57840. In still other embodiments, the dXR fusion proteins of the systems comprise a single KRAB domain operably linked to the dCasX wherein the KRAB domain comprises a first domain comprising the sequence $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S, and a second sequence motif comprises the sequence $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R, and the KRAB domain comprises a sequence selected from the group consisting of SEQ ID NOS: 57746-57755. In a particular embodiment, the dXR fusion protein comprises a sequence selected from the group consisting of SEQ ID NOS: 59508-59567 and 59673-60012. In the foregoing embodiments of the paragraph, the dXR fusion proteins is capable of repressing expression of a reporter gene to a greater extent than a comparable fusion protein comprising a ZNF10 KRAB domain (SEQ ID NO: 59626) when assayed in an in vitro cellular assay, together with a gRNA targeting the reporter gene. In some embodiments, the reporter gene is a B2M locus of a eukaryotic cell such as, but not limited to, an HEK293 cell. In some embodiments, expression of reporter gene is repressed in the in vitro assay by at least about 75%, at least about 80%, at least about 85%, or at least about 90% at day 7 of the assay. Exemplary methods of measuring repression of a reporter gene are provided in the examples, for example, in Example 4.

In some embodiments, the dXR fusion protein is capable of forming a ribonuclear protein complex (RNP) with the gRNA and, upon binding to the target nucleic acid of the cell in a cellular assay, the dXR:gRNA system is capable of repressing transcription of a gene encoded by the target nucleic acid by at least about 10%, at least about 20%, at least about 30%, at least about 40%, at least about 50%, at least about 60%, at least about 70%, at least about 75%, at least about 80%, at least about 85%, at least about 90%, at least about 95%, or at least 99%. In some embodiments, the dXR fusion protein is capable of forming a ribonuclear protein complex (RNP) with the gRNA and, upon binding to the target nucleic acid of the cell in a cellular assay, the system is capable of repressing transcription of a gene encoded by the target nucleic acid, wherein the repression of transcription of the gene is sustained for at least about 8 hours, at least about 1 day, at least about 7 days, at least about 2 weeks, at least about 3 weeks, at least about 1 month, or at least about 2 months.

In some embodiments, the present disclosure provides systems comprising a first and a second repressor domain linked to a catalytically-dead CRISPR protein as a fusion protein, and one or more gRNA comprising a targeting sequence complementary to a target nucleic acid sequence of a gene targeted for silencing, wherein the system is capable of binding the target nucleic acid in a manner that leads to long-term epigenetic modification of the gene so that repression persists even after the system is no longer present on the target nucleic acid. In some embodiments, the first and the second repressor domains are operably linked as a fusion protein, such as to a dCasX of the embodiments described herein. As used herein "epigenetic modification" means a modification to either DNA or histones associated with DNA, wherein the modification is either a direct modification by a component of the system or is indirect by the recruitment of one or more additional cellular components, but in which the DNA target nucleic acid sequence itself is not edited. For example, DNMT3A (or its catalytic domain) directly modifies the DNA by methylating it, whereas KRAB recruits KAP-1/TIF1β corepressor complexes that act as potent transcriptional repressors and can further recruit factors associated with DNA methylation and formation of repressive chromatin, such as heterochromatin protein 1 (HP1), histone deacetylases and histone methyltransferases (Ying, Y., et al. The Krüppel-associated box repressor domain induces reversible and irreversible regulation of endogenous mouse genes by mediating different chromatin states. Nucleic Acids Res. 43(3): 1549 (2015)). Together, the first and second repressor components of the systems work in synchrony to result in an additive or synergistic effect on transcriptional silencing of the targeted gene. In some embodiments, the present disclosure provides systems comprising a first and a second repressor domain operably linked to a dCasX, the first repressor is a KRAB domain of any of the foregoing embodiments, and the second repressor is selected from the group consisting of DNMT3A, DNMT3L, DNMT3B, DNMT1, FOG, SID4X, SID, NcoR, NuE, histone H3 lysine 9 methyltransferase G9a (G9a), methyl-CpG (mCpG) binding domain 2 (meCP2), Switch independent 3 transcription regulator family member A (SIN3A), histone deacetylase HDT1 (HDT1), n-terminal truncation of methyl-CpG-binding domain containing protein 2 (MBD2B), nuclear inhibitor of protein phosphatase-1 (NIPP1), GLP, heterochromatin protein 1 (HP1A), mixed lineage leukemia protein-5 (MLL5), histone-lysine N-methyltransferase SETDB1 (SETB1), Suppressor Of Variegation 3-9 Homolog 1 (SUV39H1), SUV39H2, euchromatic histone lysine methyltransferase 1 (EHMT1), histone-lysine N-methyltransferase EZH1 (EZH1), EZH2, nuclear receptor binding SET domain protein 1 (NSD1), NSD2, NSD3, ASH1 like histone lysine methyltransferase (ASH1L), tripartite motif containing 28 (TRIM28), Methyltransferase Like 3 (METTL3), METTL4, family with sequence similarity 208 member A (FAM208A), M-Phase Phosphoprotein 8 (MPHOSPH8), SET domain containing 2 (SETD2), histone deacetylase 1 (HDAC1), HDAC2, HDAC3, Periphilin 1 (PPHLN1), and subdomains thereof (e.g., the DNMT3A catalytic domain and the ATRX-DNMT3-DNMT3L (ADD) domain are subdomains of DNMT3A, and the DNMT3L interaction domain is a subdomain of DNMT3L).

In some embodiments, the present disclosure provides dXR:gRNA systems comprising a first and a second repressor domain operably linked to a dCasX. In some embodiments, the disclosure provides a dXR fusion protein comprising a dCasX selected from the group of sequences of SEQ ID NOS: 17-36 and 59353-59358 as set forth in Table 4, or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, wherein the first repressor is a KRAB domain selected from the group of sequences consisting of SEQ ID NOS: 889-2100 and 2332-33239, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and wherein the second repressor is a DNMT3A domain that lacks a regulatory subdomain and only maintains a catalytic domain selected from the group consisting of SEQ ID NOS: 33625-57543 and 59450, wherein the transcriptional repressor domains are linked by linker peptide sequences to the catalytically-dead CasX protein or to the other repressor domain. In some embodiments, the dXR comprising a DNMT3A catalytic domain effects methylation exclusively at CpG sequences. In a particular embodiment, the present disclosure provides systems comprising a first and a second repressor domain operably linked to a dCasX comprising the sequence of SEQ ID NO: 18, or a sequence having at least about 65%, at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto, wherein the first repressor is a KRAB domain selected from the group of sequences consisting of SEQ ID NOS: 57746-59342, or is selected from the group consisting of SEQ ID NOS: 57746-57840, or is selected from the group consisting of SEQ ID NOS: 57746-57755, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the second repressor domain is a DNMT3A catalytic domain selected from the group consisting of SEQ ID NOS: 33625-57543 and 59450, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, wherein the transcriptional repressor domains are linked by linker peptide sequences to the catalytically-dead CasX protein or to the other repressor domain. In a particular embodiment, the present disclosure provides systems comprising a first and a second repressor domain operably linked to a dCasX comprising the sequence of SEQ ID NO: 18, wherein the first repressor is a KRAB domain selected from the group of sequences consisting of SEQ ID NOS: 57746-59342, or is selected from the group consisting of SEQ ID NOS: 57746-57840, and the second repressor domain is a DNMT3A catalytic domain selected from the group consisting of SEQ ID NOS: 33625-57543 and 59450, wherein the transcriptional repressor domains are linked by linker peptide sequences to the catalytically-dead CasX protein or to the other repressor domain. In the foregoing embodiments, wherein the fusion protein comprises KRAB and the second transcriptional repressor domain comprises a DNMT3A catalytic domain, upon binding of the RNP of the fusion protein and the gRNA to the target nucleic acid, the system is capable of recruiting one or more of the additional repressor domains of the cell, including the repressor domains listed herein, in order to affect repression of transcription of a gene encoded by the target nucleic acid, such that upon binding of an RNP of the fusion protein and the gRNA to the target nucleic acid, transcription of the gene in the cells is repressed by at least about 10%, at least about 20%, at least about 30%, at least about 40%, at least about 50%, at least about 60%, at least about 70%, at least about 75%, at least about 80%, at least about 85%, at least about 90%, at least about 95%, or at least 99%, or any percentage there between, when assayed in an in vitro assay, including cell-based assays. Most preferably, the epigenetic modification results in complete silencing of gene expression, such that no gene product is detectable. In some embodiments, the repression of transcription by the systems of the embodiments is sustained for at least about 1 day, at least about 1 week, at least about 2 weeks, at least about 3 weeks, at least about 1 month, or at least about 3 months, or at least about 6 months when assessed in an in vitro assay. In some embodiments, the repression of transcription by the systems of the embodiments is sustained for at least about 1 day, at least about 1 week, at least about 2 weeks, at least about 3 weeks, at least about 1 month, or at least about 3 months, at least about 6 months, or at least about 1 year when assessed in a subject that has been administered a therapeutically-effective dose of a system of the embodiments described herein. In some embodiments, use of the system results in no or minimal detectable off-target methylation or off-target activity, when assessed in an in vitro assay. In some embodiments, use of the system results in off-target methylation or off-target activity that is less than about 10%, less than about 9%, less than about 8%, less than about 7%, less than about 6%, less than about 5%, less than about 4%, less than about 3%, less than about 2%, or less than about 1% in the cells. In other embodiments, use of the system results in no or minimal detectable off-target methylation or off-target activity, when assessed in a subject that has been administered a therapeutically-effective dose of a system of the embodiments described herein.

In other embodiments, the disclosure provides gene repressor systems wherein the fusion protein comprises a first, a second, and a third transcriptional repressor domain, wherein the third transcriptional repressor domain is different from the first and the second transcriptional repressor domains. In some embodiments, the present disclosure provides dXR:gRNA systems wherein the dXR comprises a KRAB domain of any of the embodiments described herein as the first repressor domain, a DNMT3A catalytic domain as the second repressor domain and a DNMT3L domain as the third repressor domain. It has been discovered that such dXR fusion proteins, when used in the dXR:gRNA systems, result in epigenetic long-term repression of transcription of target nucleic acid (and such fusion proteins are alternatively referred to herein as "ELXR"). In the foregoing, the DNMT3L helps maintains the methylation pattern after DNA replication. In an exemplary embodiment of the foregoing, the catalytically-dead Class 2 protein is a class 2 Type V CRISPR protein, for example a dCasX selected from the group of sequences of SEQ ID NOS: 17-36 and 59353-59358 as set forth in Table 4 or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the first repressor domain is a KRAB repressor domain selected from the group of sequences of SEQ ID NOS: 889-2100 and 2332-33239, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the second repressor domain is a DNMT3A catalytic domain of DNMT3A, or a sequence variant thereof, including the sequences of SEQ ID NOS: 33625-57543 and 59450, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the third repressor domain is a DNMT3L interaction domain is the sequence of SEQ ID NO: 59625, or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, wherein the fusion protein comprises one or more linker peptides described herein, and wherein the fusion protein is capable of forming an RNP with a gRNA of the system that binds to the target nucleic acid. In a particular embodiment, the present disclosure provides systems comprising a first, a second, and a third repressor domain operably linked to a dCasX comprising the sequence of SEQ ID NO: 18, or a sequence having at least about 65%, at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto, wherein the first domain comprises a KRAB domain comprising one or more motifs selected from the group consisting of a) $PX_1X_2X_3X_4X_5X_6EX_7$, wherein $X_1$ is A, D, E, or N, $X_2$ is L or V, $X_3$ is I or V, $X_4$ is S, T, or F, $X_5$ is H, K, L, Q, R or W, $X_6$ is L or M, and $X_7$ is G, K, Q, or R; b) $X_1X_2X_3X_4GX_5X_6X_7X_8X_9$, wherein $X_1$ is L or V, $X_2$ is A, G, L, T or V, $X_3$ is A, F, or S, $X_4$ is L or V, $X_5$ is C, F, H, I, L or Y, $X_6$ is A, C, P, Q, or S, $X_7$ is A, F, G, I, S, or V, $X_8$ is A, P, S, or T, and $X_9$ is K or R; c) $QX_1X_2LYRX_3VMX_4$ (SEQ ID NO: 59345), wherein $X_1$ is K or R, $X_2$ is A, D, E, G, N, S, or T, $X_3$ is D, E, or S, and $X_4$ is L or R; d) $X_1X_2X_3FX_4DVX_5X_6X_7FX_8X_9X_{10}X_{11}$ (SEQ ID NO: 59346), wherein $X_1$ is A, L, P, or S, $X_2$ is L or V, $X_3$ is S or T, $X_4$ is A, E, G, K, or R, $X_5$ is A or T, $X_6$ is I or V, $X_7$ is D, E, N, or Y, $X_8$ is S or T, $X_9$ is E, P, Q, R, or W, $X_{10}$ is E or N, and $X_{11}$ is E or Q; e) $X_1X_2X_3PX_4X_5X_6X_7X_8X_9X_{10}$, wherein $X_1$ is E, G, or R, $X_2$ is E or K, $X_3$ is A, D, or E, $X_4$ is C or W, $X_5$ is I, K, L, M, T, or V, $X_6$ is I, L, P, or V, $X_7$ is D, E, K, or V, $X_8$ is E, G, K, P, or R, $X_9$ is A, D, R, G, K, Q, or V, and $X_{10}$ is D, E, G, I, L, R, S, or V; f) $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S; g) $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R; h) $X_1PX_2X_3X_4X_5$ $X_6LEX_7X_8X_9X_{10}X_{11}X_{12}$, wherein $X_1$ is K or R, $X_2$ is A, D, E, or N, $X_3$ is I, L, M, or V, $X_4$ is I or V, $X_5$ is F, S, or T, $X_6$ is H, K, L, Q, R, or W, $X_7$ is K, Q, or R, $X_8$ is E, G, or R, $X_9$ is D, E, or K, $X_{10}$ is A, D, or E, $X_{11}$ is L or P, and $X_{12}$ is C or W; or i) $X_1LX_2X_3X_4QX_5X_6$, wherein $X_1$ is C, H, L, Q, or W, $X_2$ is D, G, N, R, or S, $X_3$ is L, P, S, or T, $X_4$ is A, S, or T, $X_5$ is K or R, and $X_6$ is A, D, E, K, N, S, or T, and the KRAB domain comprises a sequence selected from the group consisting of SEQ ID NOS: 57746-59342, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the second repressor domain is a DNMT3A catalytic domain comprising a sequence selected from the group consisting of SEQ ID NOS: 33625-57543 and 59450, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the third repressor is a DNMT3L interaction domain comprising the sequence of SEQ ID NO: 59625, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and wherein the fusion protein comprises one or more linker peptides described herein, and wherein the fusion protein is capable of forming an RNP with a gRNA of the system that binds to the target nucleic acid. In a particular embodiment, the present disclosure provides systems comprising a first, a second, and a third repressor domain operably linked to a dCasX comprising the sequence of SEQ ID NO: 18, or a sequence having at least about 65%, at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto, wherein the first domain comprises a KRAB domain comprising one or more motifs selected from the group consisting of a) $PX_1X_2X_3X_4X_5X_6EX_7$, wherein $X_1$ is A, D, E, or N, $X_2$ is L or V, $X_3$ is I or V, $X_4$ is S, T, or F, $X_5$ is H, K, L, Q, R or W, $X_6$ is L or M, and $X_7$ is G, K, Q, or R; b) $X_1X_2X_3X_4GX_5X_6X_7X_8X_9$, wherein $X_1$ is L or V, $X_2$ is A, G, L, T or V, $X_3$ is A, F, or S, $X_4$ is L or V, $X_5$ is C, F, H, I, L or Y, $X_6$ is A, C, P, Q, or S, $X_7$ is A, F, G, I, S, or V, $X_8$ is A, P, S, or T, and $X_9$ is K or R; c) $QX_1X_2LYRX_3VMX_4$(SEQ ID NO: 59345), wherein $X_1$ is K or R, $X_2$ is A, D, E, G, N, S, or T, $X_3$ is D, E, or S, and $X_4$ is L or R; d) $X_1X_2X_3FX_4DVX_5X_6X_7FX_8X_9X_{10}X_{11}$ (SEQ ID NO: 59346), wherein $X_1$ is A, L, P, or S, $X_2$ is L or V, $X_3$ is S or T, $X_4$ is A, E, G, K, or R, $X_5$ is A or T, $X_6$ is I or V, $X_7$ is D, E, N, or Y, $X_8$ is S or T, $X_9$ is E, P, Q, R, or W, $X_{10}$ is E or N, and $X_{11}$ is E or Q; e) $X_1X_2X_3PX_4X_5X_6X_7X_8X_9X_{10}$, wherein $X_1$ is E, G, or R, $X_2$ is E or K, $X_3$ is A, D, or E, $X_4$ is C or W, $X_5$ is I, K, L, M, T, or V, $X_6$ is I, L, P, or V, $X_7$ is D, E, K, or V, $X_8$ is E, G, K, P, or R, $X_9$ is A, D, R, G, K, Q, or V, and $X_{10}$ is D, E, G, I, L, R, S, or V; f) $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S; g) $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R; h) $X_1PX_2X_3X_4X_5$ $X_6LEX_7X_8X_9X_{10}X_{11}X_{12}$, wherein $X_1$ is K or R, $X_2$ is A, D, E, or N, $X_3$ is I, L, M, or V, $X_4$ is I or V, $X_5$ is F, S, or T, $X_6$ is H, K, L, Q, R, or W, $X_7$ is K, Q, or R, $X_8$ is E, G, or R, $X_9$ is D, E, or K, $X_{10}$ is A, D, or E, $X_{11}$ is L or P, and $X_{12}$ is C or W; or i) $X_1LX_2X_3X_4QX_5X_6$, wherein $X_1$ is C, H, L, Q, or W, $X_2$ is D, G, N, R, or S, $X_3$ is L, P, S, or T, $X_4$ is A, S, or T, $X_5$ is K or R, and $X_6$ is A, D, E, K, N, S, or T, and the KRAB domain comprises a sequence selected from the group consisting of SEQ ID NOS: 57746-57840, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the second repressor domain is a DNMT3A catalytic domain comprising a sequence selected from the group consisting of SEQ ID NOS: 33625-57543 and 59450, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the third repressor is a DNMT3L interaction domain comprising the sequence of SEQ ID NO: 59625, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, wherein the fusion protein comprises one or more linker peptides described herein, and wherein the fusion protein is capable of forming an RNP with a gRNA of the system that binds to the target nucleic acid. In a particular embodiment, the present disclosure provides systems comprising a first, a second, and a third repressor domain operably linked to a dCasX comprising the sequence of SEQ ID NO: 18, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, wherein the KRAB domain comprises one or more motifs selected from the group consisting of a) $PX_1X_2X_3X_4X_5X_6EX_7$, wherein $X_1$ is A, D, E, or N, $X_2$ is L or V, $X_3$ is I or V, $X_4$ is S, T, or F, $X_5$ is H, K, L, Q, R or W, $X_6$ is L or M, and $X_7$ is G, K, Q, or R; b) $X_1X_2X_3X_4GX_5X_6X_7X_8X_9$, wherein $X_1$ is L or V, $X_2$ is A, G, L, T or V, $X_3$ is A, F, or S, $X_4$ is L or V, $X_5$ is C, F, H, I, L or Y, $X_6$ is A, C, P, Q, or S, $X_7$ is A, F, G, I, S, or V, $X_8$ is A, P, S, or T, and $X_9$ is K or R; c) $QX_1X_2LYRX_3VMX_4$ (SEQ ID NO: 59345), wherein $X_1$ is K or R, $X_2$ is A, D, E, G, N, S, or T, $X_3$ is D, E, or S, and $X_4$ is L or R; d) $X_1X_2X_3FX_4DVX_5X_6X_7FX_8X_9X_{10}X_1$ (SEQ ID NO: 59346), wherein $X_1$ is A, L, P, or S, $X_2$ is L or V, $X_3$ is S or T, $X_4$ is A, E, G, K, or R, $X_5$ is A or T, $X_6$ is I or V, $X_7$ is D, E, N, or Y, $X_8$ is S or T, $X_9$ is E, P, Q, R, or W, $X_{10}$ is E or N, and $X_{11}$ is E or Q; e) $X_1X_2X_3PX_4X_5X_6X_7X_8X_9X_{10}$, wherein $X_1$ is E, G, or R, $X_2$ is E or K, $X_3$ is A, D, or E, $X_4$ is C or W, $X_5$ is I, K, L, M, T, or V, $X_6$ is I, L, P, or V, $X_7$ is D, E, K, or V, $X_8$ is E, G, K, P, or R, $X_9$ is A, D, R, G, K, Q, or V, and $X_{10}$ is D, E, G, I, L, R, S, or V; f) $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S; g) $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R; h) $X_1PX_2X_3X_4X_5$ $X_6LEX_7X_8X_9X_{10}X_{11}X_{12}$, wherein $X_1$ is K or R, $X_2$ is A, D, E, or N, $X_3$ is I, L, M, or V, $X_4$ is I or V, $X_5$ is F, S, or T, $X_6$ is H, K, L, Q, R, or W, $X_7$ is K, Q, or R, $X_8$ is E, G, or R, $X_9$ is D, E, or K, $X_{10}$ is A, D, or E, $X_{11}$ is L or P, and $X_{12}$ is C or W; or i) $X_1LX_2X_3X_4QX_5X_6$, wherein $X_1$ is C, H, L, Q, or W, $X_2$ is D, G, N, R, or S, $X_3$ is L, P, S, or T, $X_4$ is A, S, or T, $X_5$ is K or R, and $X_6$ is A, D, E, K, N, S, or T, and the KRAB domain comprises a sequence selected from the group consisting of SEQ ID NOS: 57746-57755, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the second repressor domain is a DNMT3A catalytic domain comprising a sequence selected from the group consisting of SEQ ID NOS: 33625-57543 and 59450, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the third repressor is a DNMT3L interaction domain comprising the sequence of SEQ ID NO: 59625, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and wherein the fusion protein comprises one or more linker peptides described herein, and wherein the fusion protein is capable of forming an RNP with a gRNA of the system that binds to the target nucleic acid. In another particular embodiment, the present disclosure provides systems comprising a first, a second, and a third repressor domain operably linked to a dCasX comprising the sequence of SEQ ID NO: 25, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, wherein the KRAB domain comprises one or more motifs selected from the group consisting of a) $PX_1X_2X_3X_4X_5X_6EX_7$, wherein $X_1$ is A, D, E, or N, $X_2$ is L or V, $X_3$ is I or V, $X_4$ is S, T, or F, $X_5$ is H, K, L, Q, R or W, $X_6$ is L or M, and $X_7$ is G, K, Q, or R; b) $X_1X_2X_3X_4GX_5X_6X_7X_8X_9$, wherein $X_1$ is L or V, $X_2$ is A, G, L, T or V, $X_3$ is A, F, or S, $X_4$ is L or V, $X_5$ is C, F, H, I, L or Y, $X_6$ is A, C, P, Q, or S, $X_7$ is A, F, G, I, S, or V, $X_8$ is A, P, S, or T, and $X_9$ is K or R; c) $QX_1X_2LYRX_3VMX_4$ (SEQ ID NO: 59345), wherein $X_1$ is K or R, $X_2$ is A, D, E, G, N, S, or T, $X_3$ is D, E, or S, and $X_4$ is L or R; d) $X_1X_2X_3FX_4DVX_5X_6X_7FX_8X_9X_{10}X_1$ (SEQ ID NO: 59346), wherein $X_1$ is A, L, P, or S, $X_2$ is L or V, $X_3$ is S or T, $X_4$ is A, E, G, K, or R, $X_5$ is A or T, $X_6$ is I or V, $X_7$ is D, E, N, or Y, $X_8$ is S or T, $X_9$ is E, P, Q, R, or W, $X_{10}$ is E or N, and $X_{11}$ is E or Q; e) $X_1X_2X_3PX_4X_5X_6X_7X_8X_9X_{10}$, wherein $X_1$ is E, G, or R, $X_2$ is E or K, $X_3$ is A, D, or E, $X_4$ is C or W, $X_5$ is I, K, L, M, T, or V, $X_6$ is I, L, P, or V, $X_7$ is D, E, K, or V, $X_8$ is E, G, K, P, or R, $X_9$ is A, D, R, G, K, Q, or V, and $X_{10}$ is D, E, G, I, L, R, S, or V; f) $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S; g) $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R; h) $X_1PX_2X_3X_4X_5$ $X_6LEX_7X_8X_9X_{10}X_{11}X_{12}$, wherein $X_1$ is K or R, $X_2$ is A, D, E, or N, $X_3$ is I, L, M, or V, $X_4$ is I or V, $X_5$ is F, S, or T, $X_6$ is H, K, L, Q, R, or W, $X_7$ is K, Q, or R, $X_8$ is E, G, or R, $X_9$ is D, E, or K, $X_{10}$ is A, D, or E, $X_{11}$ is L or P, and $X_{12}$ is C or W; or i) $X_1LX_2X_3X_4QX_5X_6$, wherein $X_1$ is C, H, L, Q, or W, $X_2$ is D, G, N, R, or S, $X_3$ is L, P, S, or T, $X_4$ is A, S, or T, $X_5$ is K or R, and $X_6$ is A, D, E, K, N, S, or T, and the KRAB domain comprises a sequence selected from the group consisting of SEQ ID NOS: 57746-57755, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the second repressor domain is a DNMT3A catalytic domain comprising a sequence selected from the group consisting of SEQ ID NOS: 33625-57543 and 59450, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the third repressor is a DNMT3L interaction domain comprising the sequence of SEQ ID NO: 59625, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and wherein the fusion protein comprises one or more linker peptides described herein, and wherein the fusion protein is capable of forming an RNP with a gRNA of the system that binds to the target nucleic acid. In another particular embodiment, the present disclosure provides systems comprising a first, a second, and a third repressor domain operably linked to a dCasX comprising the sequence of SEQ ID NO: 59357, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, wherein the KRAB domain comprises one or more motifs selected from the group consisting of a) $PX_1X_2X_3X_4X_5X_6EX_7$, wherein $X_1$ is A, D, E, or N, $X_2$ is L or V, $X_3$ is I or V, $X_4$ is S, T, or F, $X_5$ is H, K, L, Q, R or W, $X_6$ is L or M, and $X_7$ is G, K, Q, or R; b) $X_1X_2X_3X_4GX_5X_6X_7X_8X_9$, wherein $X_1$ is L or V, $X_2$ is A, G, L, T or V, $X_3$ is A, F, or S, $X_4$ is L or V, $X_5$ is C, F, H, I, L or Y, $X_6$ is A, C, P, Q, or S, $X_7$ is A, F, G, I, S, or V, $X_8$ is A, P, S, or T, and $X_9$ is K or R; c) $QX_1X_2LYRX_3VMX_4$ (SEQ ID NO: 59345), wherein $X_1$ is K or R, $X_2$ is A, D, E, G, N, S, or T, $X_3$ is D, E, or S, and $X_4$ is L or R; d) $X_1X_2X_3FX_4DVX_5X_6X_7FX_8X_9X_{10}X_{11}$ (SEQ ID NO: 59346), wherein $X_1$ is A, L, P, or S, $X_2$ is L or V, $X_3$ is S or T, $X_4$ is A, E, G, K, or R, $X_5$ is A or T, $X_6$ is I or V, $X_7$ is D, E, N, or Y, $X_8$ is S or T, $X_9$ is E, P, Q, R, or W, $X_{10}$ is E or N, and $X_{11}$ is E or Q; e) $X_1X_2X_3PX_4X_5X_6X_7X_8X_9X_{10}$, wherein $X_1$ is E, G, or R, $X_2$ is E or K, $X_3$ is A, D, or E, $X_4$ is C or W, $X_5$ is I, K, L, M, T, or V, $X_6$ is I, L, P, or V, $X_7$ is D, E, K, or V, $X_8$ is E, G, K, P, or R, $X_9$ is A, D, R, G, K, Q, or V, and $X_{10}$ is D, E, G, I, L, R, S, or V; f) $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S; g) $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R; h) $X_1PX_2X_3X_4X_5$ $X_6LEX_7X_8X_9X_{10}X_{11}X_{12}$, wherein $X_1$ is K or R, $X_2$ is A, D, E, or N, $X_3$ is I, L, M, or V, $X_4$ is I or V, $X_5$ is F, S, or T, $X_6$ is H, K, L, Q, R, or W, $X_7$ is K, Q, or R, $X_8$ is E, G, or R, $X_9$ is D, E, or K, $X_{10}$ is A, D, or E, $X_{11}$ is L or P, and $X_{12}$ is C or W; or i) $X_1LX_2X_3X_4QX_5X_6$, wherein $X_1$ is C, H, L, Q, or W, $X_2$ is D, G, N, R, or S, $X_3$ is L, P, S, or T, $X_4$ is A, S, or T, $X_5$ is K or R, and $X_6$ is A, D, E, K, N, S, or T, and the KRAB domain comprises a sequence selected from the group consisting of SEQ ID NOS: 57746-57755, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the second repressor domain is a DNMT3A catalytic domain comprising a sequence selected from the group consisting of SEQ ID NOS: 33625-57543 and 59450, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the third repressor is a DNMT3L interaction domain comprising the sequence of SEQ ID NO: 59625, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and wherein the fusion protein comprises one or more linker peptides described herein, and wherein the fusion protein is capable of forming an RNP with a gRNA of the system that binds to the target nucleic acid. In another particular embodiment, the present disclosure provides systems comprising a first, a second, and a third repressor domain operably linked to a dCasX comprising the sequence of SEQ ID NO: 59358, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, wherein the KRAB domain comprises one or more motifs selected from the group consisting of a) $PX_1X_2X_3X_4X_5X_6EX_7$, wherein $X_1$ is A, D, E, or N, $X_2$ is L or V, $X_3$ is I or V, $X_4$ is S, T, or F, $X_5$ is H, K, L, Q, R or W, $X_6$ is L or M, and $X_7$ is G, K, Q, or R; b) $X_1X_2X_3X_4GX_5X_6X_7X_8X_9$, wherein $X_1$ is L or V, $X_2$ is A, G, L, T or V, $X_3$ is A, F, or S, $X_4$ is L or V, $X_5$ is C, F, H, I, L or Y, $X_6$ is A, C, P, Q, or S, $X_7$ is A, F, G, I, S, or V, $X_8$ is A, P, S, or T, and $X_9$ is K or R; c) $QX_1X_2LYRX_3VMX_4$ (SEQ ID NO: 59345), wherein $X_1$ is K or R, $X_2$ is A, D, E, G, N, S, or T, $X_3$ is D, E, or S, and $X_4$ is L or R; d) $X_1X_2X_3FX_4DVX_5X_6X_7FX_8X_9X_{10}X_{11}$ (SEQ ID NO: 59346), wherein $X_1$ is A, L, P, or S, $X_2$ is L or V, $X_3$ is S or T, $X_4$ is A, E, G, K, or R, $X_5$ is A or T, $X_6$ is I or V, $X_7$ is D, E, N, or Y, $X_8$ is S or T, $X_9$ is E, P, Q, R, or W, $X_{10}$ is E or N, and $X_{11}$ is E or Q; e) $X_1X_2X_3PX_4X_5X_6X_7X_8X_9X_{10}$, wherein $X_1$ is E, G, or R, $X_2$ is E or K, $X_3$ is A, D, or E, $X_4$ is C or W, $X_5$ is I, K, L, M, T, or V, $X_6$ is I, L, P, or V, $X_7$ is D, E, K, or V, $X_8$ is E, G, K, P, or R, $X_9$ is A, D, R, G, K, Q, or V, and $X_{10}$ is D, E, G, I, L, R, S, or V; f) $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S; g) $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R; h)

$X_1PX_2X_3X_4X_5$ $X_6LEX_7X_8X_9X_{10}X_{11}X_{12}$, wherein $X_1$ is K or R, $X_2$ is A, D, E, or N, $X_3$ is I, L, M, or V, $X_4$ is I or V, $X_5$ is F, S, or T, $X_6$ is H, K, L, Q, R, or W, $X_7$ is K, Q, or R, $X_8$ is E, G, or R, $X_9$ is D, E, or K, $X_{10}$ is A, D, or E, $X_{11}$ is L or P, and $X_{12}$ is C or W; or i) $X_1LX_2X_3X_4QX_5X_6$, wherein $X_1$ is C, H, L, Q, or W, $X_2$ is D, G, N, R, or S, $X_3$ is L, P, S, or T, $X_4$ is A, S, or T, $X_5$ is K or R, and $X_6$ is A, D, E, K, N, S, or T, and the KRAB domain comprises a sequence selected from the group consisting of SEQ ID NOS: 57746-57755, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the second repressor domain is a DNMT3A catalytic domain comprising a sequence selected from the group consisting of SEQ ID NOS: 33625-57543 and 59450, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the third repressor is a DNMT3L interaction domain comprising the sequence of SEQ ID NO: 59625, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and wherein the fusion protein comprises one or more linker peptides described herein, and wherein the fusion protein is capable of forming an RNP with a gRNA of the system that binds to the target nucleic acid. In some embodiments of the system, the fusion protein components of the system are configured according to a configuration as schematically portrayed in FIG. 7. In some embodiments each of the repressor domains and the dCasX are operably linked, in some cases via a linker, as described herein. In some embodiments, the dXR fusion protein has a configuration of, N-terminal to C-terminal (with reference to the components of Table 45) of configuration 1 (NLS-Linker4-DNMT3A-Linker2-DNMT3L-Linker1-Linker3-dCasX-Linker3-KRAB-NLS), configuration 2 (NLS-Linker3-dCasX-Linker3-KRAB-NLS-Linker1-DNMT3A-Linker2-DNMT3L), configuration 3 (NLS-Linker3-dCasX-Linker1-DNMT3A-Linker2-DNMT3L-Linker3-KRAB-NLS), configuration 4 (NLS-KRAB-Linker3-DNMT3A-Linker2-DNMT3L-Linker1-dCasX-Linker3-NLS), or configuration 5 (NLS-DNMT3A-Linker2-DNMT3L-Linker3-KRAB-Linker1-dCasX-Linker3-NLS). In some embodiments, the dXR fusion protein comprises a sequence selected from the group consisting of SEQ ID NOS: 59508-59517, 59528-59537, 59548-59557, and 59673-59842, or a sequence having or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and wherein the fusion protein is in configuration 1, 4 or 5.

Figure 7:
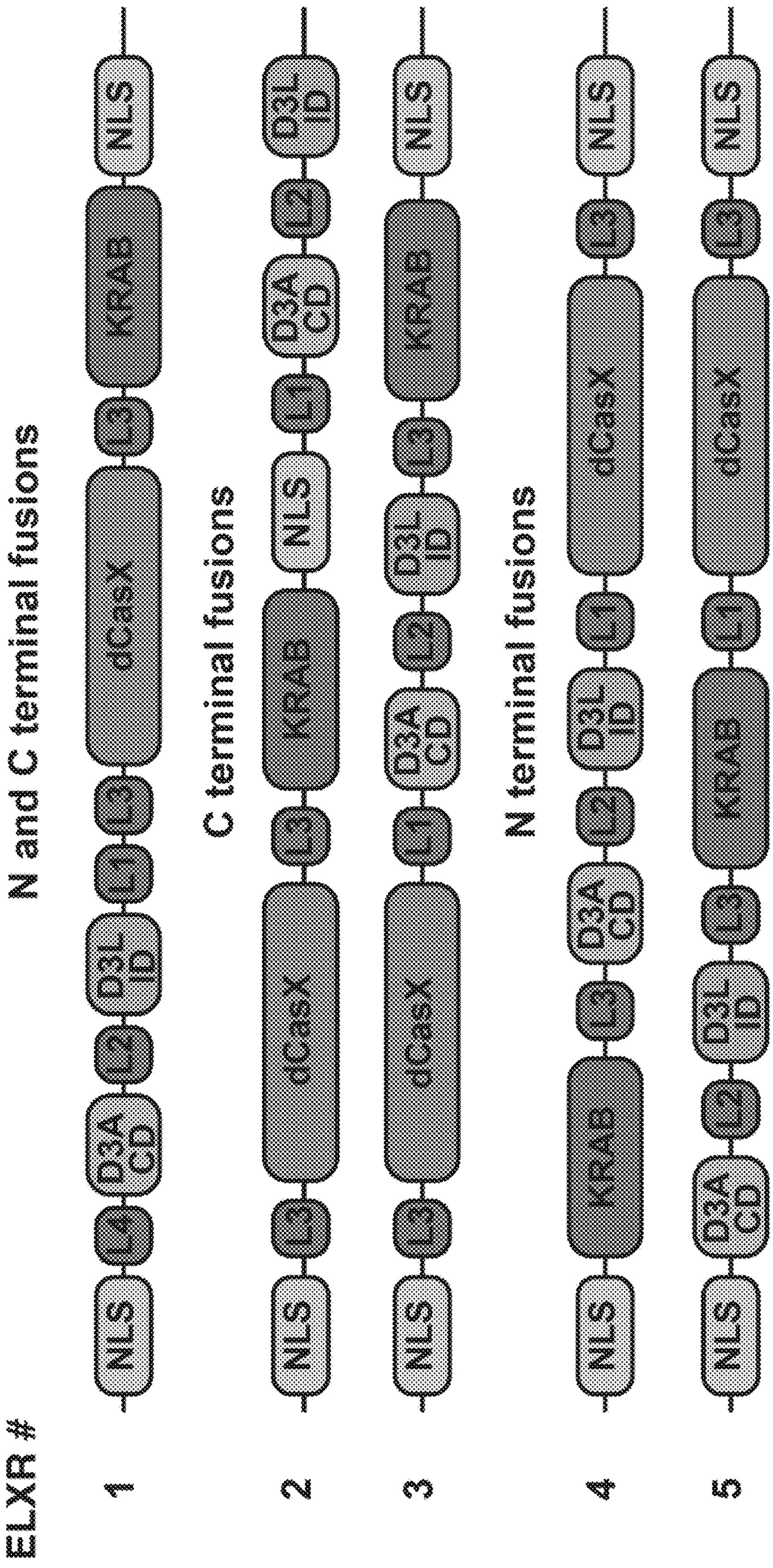
FIG. 7 illustrates the schematics of various configurations of the epigenetic long-term CasX repressor (ELXR) molecules tested for gene repression activity. D3A and D3L denote DNA methyltransferase 3 alpha (DNMT3A) and DNMT3A-like protein (DNMT3L), respectively, as described in Example 6. CD=catalytic domain, ID=interaction domain. L1-L4 are linkers. NLS is the nuclear localization signal. See Tables 24 and 25 for ELXR sequences.
Figure 45:
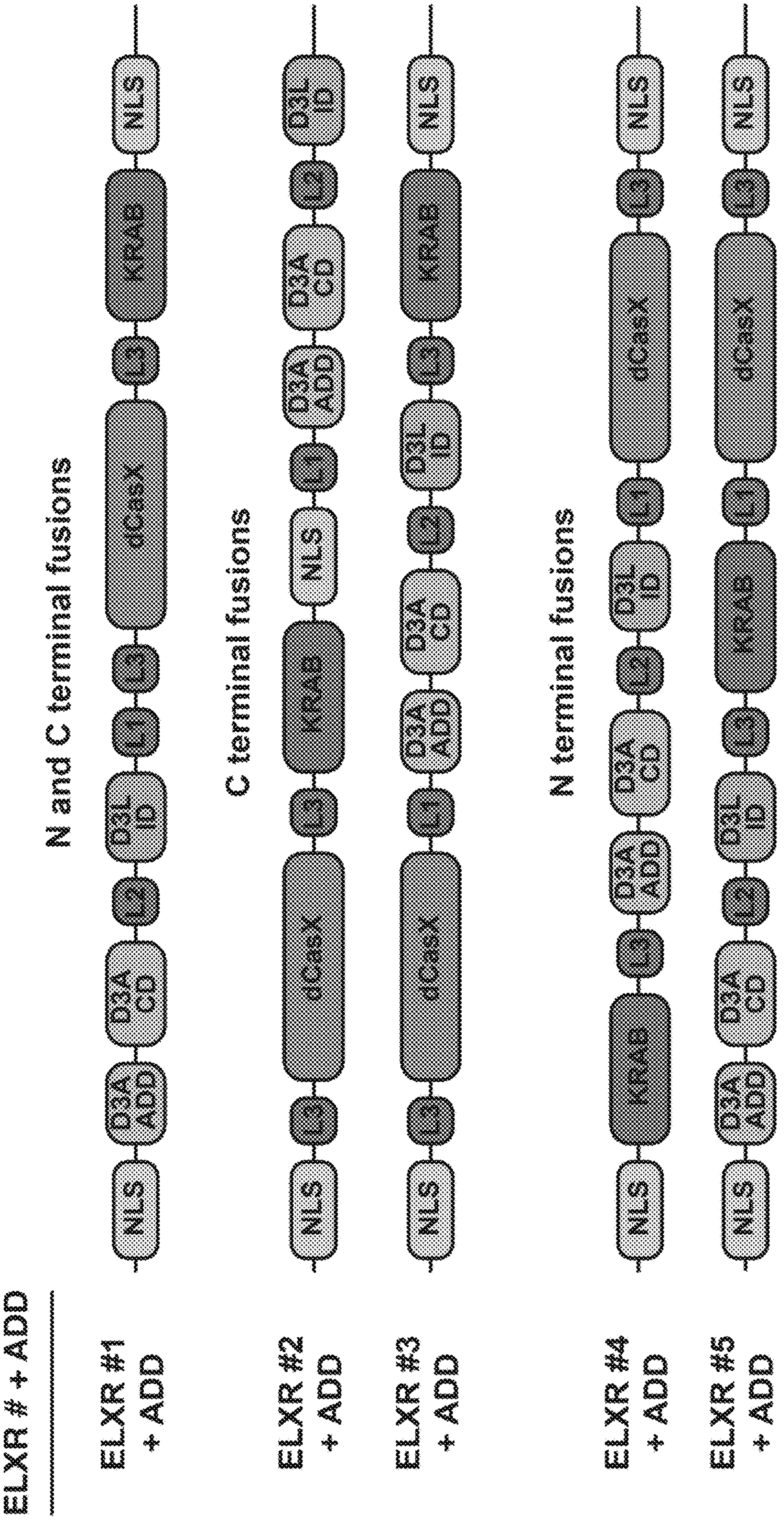
FIG. 45 illustrates the schematics of various configurations of ELXR molecules with the incorporation of the DNMT3A ADD. "D3A ADD", "D3A CD", and "D3L ID" denote the ADD domain of DNMT3A, the catalytic domain of DNMT3A, and the interaction domain of DNMT3L, respectively. L1-L3 are linkers. NLS is the nuclear localization signal.

In some embodiments, the dXR fusion protein comprises an ADD domain as a fourth domain, wherein the C-terminus of the ADD domain is operably to the N-terminus of the DNMT3A catalytic domain, representative configurations of which are schematically portrayed in FIG. 45. In some embodiments, the dXR comprises a dCasX and a first, second, third, and fourth repressor, and the dXR comprises a sequence selected from the group consisting of SEQ ID NOS: 59508-59567 and 59673-60012, or a sequence having or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and wherein the fusion protein comprises one or more linker peptides described herein, and wherein the fusion protein is capable of forming an RNP with a gRNA of the system that binds to the target nucleic acid. In some embodiments of the system comprising a dCasX variant, a first, second, third repressor domain, including the constructs of configurations 1-5, upon binding of an RNP of the fusion protein and the gRNA to the target nucleic acid, the gene is epigenetically modified and transcription of the gene is repressed. In some embodiment, transcription of the gene is repressed by at least about 10%, at least about 20%, at least about 30%, at least about 40%, at least about 50%, at least about 60%, at least about 70%, at least about 75%, at least about 80%, at least about 85%, at least about 90%, at least about 95%, or at least 99%, when assayed in an in vitro assay, including cell-based assays. In some embodiments, the repression of transcription of the gene by the system compositions, including the constructs of configurations 1-5, is sustained for at least about 8 hours, at least about 1 day, at least about 7 days, at least about 2 weeks, at least about 3 weeks, at least about 1 month, or at least about 2 months, when assayed in an in vitro assay, including cell-based assays. In a particular embodiment, dXR configurations 4 and 5, when used in the dXR:gRNA system, result in less off-target methylation or off-target activity in an in vitro assay compared to configuration 1 (as shown in FIGS. 7 and 45). In some embodiments, use of the dXR configurations 4 and 5 (as shown in FIGS. 7 and 45), when used in the dXR:gRNA system, results in off-target methylation or off-target activity that is less than about 10%, less than about 9%, less than about 8%, less than about 7%, less than about 6%, less than about 5%, less than about 4%, less than about 3%, less than about 2%, or less than about 1% in the cells.

In still other embodiments, the present disclosure provides dXR:gRNA systems wherein the dXR comprises a dCasX and a first, second, third, and fourth repressor domain. In some embodiments, the dXR comprises a dCasX selected from the group of sequences of SEQ ID NOS: 17-36 and 59353-59358 as set forth in Table 4 or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the first repressor domain is a KRAB repressor domain selected from the group of sequences of SEQ ID NOS: 889-2100 and 2332-33239, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the second repressor domain is DNMT3A catalytic domain selected from the group of sequences of SEQ ID NOS: 33625-57543 and 59450, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the third repressor domain is a DNMT3L interaction domain having a sequence of SEQ ID NO: 59625, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the fourth domain is a DNMT3A ADD domain of SEQ ID NO: 59452, or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In a particular embodiment, the dXR comprises a dCasX comprises a sequence of SEQ ID NO: 18 as set forth in Table 4 or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the first repressor domain is a KRAB repressor domain selected from the group of sequences of SEQ ID NOS: 889-2100 and 2332-33239, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the second repressor domain is DNMT3A catalytic domain selected from the group of sequences of SEQ ID NOS: 33625-57543 and 59450, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the third repressor domain is a DNMT3L interaction domain having a sequence of SEQ ID NO: 59625, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the fourth domain is a DNMT3A ADD domain of SEQ ID NO: 59452, or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In another particular embodiment, the dXR comprises a dCasX comprises a sequence of SEQ ID NO: 25 as set forth in Table 4 or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the first repressor domain is a KRAB repressor domain selected from the group of sequences of SEQ ID NOS: 889-2100 and 2332-33239, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the second repressor domain is DNMT3A catalytic domain selected from the group of sequences of SEQ ID NOS: 33625-57543 and 59450, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the third repressor domain is a DNMT3L interaction domain having a sequence of SEQ ID NO: 59625, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the fourth domain is a DNMT3A ADD domain of SEQ ID NO: 59452, or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In another particular embodiment, the dXR comprises a dCasX comprises a sequence of SEQ ID NO: 59357 as set forth in Table 4 or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the first repressor domain is a KRAB repressor domain selected from the group of sequences of SEQ ID NOS: 889-2100 and 2332-33239, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the second repressor domain is DNMT3A catalytic domain selected from the group of sequences of SEQ ID NOS: 33625-57543 and 59450, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the third repressor domain is a DNMT3L interaction domain having a sequence of SEQ ID NO: 59625, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the fourth domain is a DNMT3A ADD domain of SEQ ID NO: 59452, or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In another particular embodiment, the dXR comprises a dCasX comprises a sequence of SEQ ID NO: 59358 as set forth in Table 4 or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the first repressor domain is a KRAB repressor domain selected from the group of sequences of SEQ ID NOS: 889-2100 and 2332-33239, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the second repressor domain is DNMT3A catalytic domain selected from the group of sequences of SEQ ID NOS: 33625-57543 and 59450, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the third repressor domain is a DNMT3L interaction domain having a sequence of SEQ ID NO: 59625, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the fourth domain is a DNMT3A ADD domain of SEQ ID NO: 59452, or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto. The ADD domain is known to have two key functions: 1) it allosterically regulates the catalytic activity of DNMT3A by serving as a methyltransferase auto-inhibitory domain, and 2) it recognizes unmethylated H3K4 (H3K4me0). Without wishing to be bound by theory, it is thought that the interaction of the ADD domain with the H3K4me0 mark unveils the catalytic site of DNMT3A, thereby recruiting an active DNMT3A to chromatin to implement de novo methylation at these sites. In a surprising finding, it has been discovered that the addition of the DNMT3A ADD domain to the dXR constructs comprising the DNMT3A catalytic and DNMT3L interaction domains greatly enhances the repression of the target nucleic acid in comparison to dXR constructs lacking the ADD domain. Exemplary data for the improved repression are presented in the Examples.

In a particular embodiment, the present disclosure provides systems comprising a first, a second, a third, and a fourth repressor domain operably linked to a dCasX comprising the sequence of SEQ ID NO: 18, or a sequence having at least about 65%, at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto, wherein the KRAB domain comprises one or more motifs selected from the group consisting of a) $PX_1X_2X_3X_4X_5X_6EX_7$, wherein $X_1$ is A, D, E, or N, $X_2$ is L or V, $X_3$ is I or V, $X_4$ is S, T, or F, $X_5$ is H, K, L, Q, R or W, $X_6$ is L or M, and $X_7$ is G, K, Q, or R; b) $X_1X_2X_3X_4GX_5X_6X_7X_8X_9$, wherein $X_1$ is L or V, $X_2$ is A, G, L, T or V, $X_3$ is A, F, or S, $X_4$ is L or V, $X_5$ is C, F, H, I, L or Y, $X_6$ is A, C, P, Q, or S, $X_7$ is A, F, G, I, S, or V, $X_8$ is A, P, S, or T, and $X_9$ is K or R; c) $QX_1X_2LYRX_3VMX_4$(SEQ ID NO: 59345), wherein $X_1$ is K or R, $X_2$ is A, D, E, G, N, S, or T, $X_3$ is D, E, or S, and $X_4$ is L or R; d) $X_1X_2X_3FX_4DVX_5X_6X_7FX_8X_9X_{10}X_{11}$ (SEQ ID NO: 59346), wherein $X_1$ is A, L, P, or S, $X_2$ is L or V, $X_3$ is S or T, $X_4$ is A, E, G, K, or R, $X_5$ is A or T, $X_6$ is I or V, $X_7$ is D, E, N, or Y, $X_8$ is S or T, $X_9$ is E, P, Q, R, or W, $X_{10}$ is E or N, and $X_{11}$ is E or Q; e) $X_1X_2X_3PX_4X_5X_6X_7X_8X_9X_{10}$, wherein $X_1$ is E, G, or R, $X_2$ is E or K, $X_3$ is A, D, or E, $X_4$ is C or W, $X_5$ is I, K, L, M, T, or V, $X_6$ is I, L, P, or V, $X_7$ is D, E, K, or V, $X_8$ is E, G, K, P, or R, $X_9$ is A, D, R, G, K, Q, or V, and $X_{10}$ is D, E, G, I, L, R, S, or V; f) $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S; g) $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R; h) $X_1PX_2X_3X_4X_5\ X_6LEX_7X_8X_9X_{10}X_{11}X_{12}$, wherein $X_1$ is K or R, $X_2$ is A, D, E, or N, $X_3$ is I, L, M, or V, $X_4$ is I or V, $X_5$ is F, S, or T, $X_6$ is H, K, L, Q, R, or W, $X_7$ is K, Q, or R, $X_8$ is E, G, or R, $X_9$ is D, E, or K, $X_{10}$ is A, D, or E, $X_{11}$ is L or P, and $X_{12}$ is C or W; or i) $X_1LX_2X_3X_4QX_5X_6$, wherein $X_1$ is C, H, L, Q, or W, $X_2$ is D, G, N, R, or S, $X_3$ is L, P, S, or T, $X_4$ is A, S, or T, $X_5$ is K or R, and $X_6$ is A, D, E, K, N, S, or T, and the KRAB domain comprises a sequence selected from the group consisting of SEQ ID NOS: 57746-59342, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the second repressor domain is a DNMT3A catalytic domain sequence selected from the group consisting of SEQ ID NOS: 33625-57543 and 59450, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the third repressor is a DNMT3L interaction domain comprising the sequence of SEQ ID NO: 59625, or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the fourth repressor is an ADD domain comprising the sequence of SEQ ID NO: 59452, or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, wherein the fusion protein comprises one or more linker peptides described herein, and wherein the fusion protein is capable of forming an RNP with a gRNA of the system that binds to the target nucleic acid. The present disclosure provides systems comprising a first, a second, a third, and a fourth repressor domain operably linked to a dCasX comprising the sequence of SEQ ID NO: 18, or a sequence having at least about 65%, at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto, wherein the first repressor domain comprises a KRAB domain comprising one or more motifs selected from the group consisting of a) $PX_1X_2X_3X_4X_5X_6EX_7$, wherein $X_1$ is A, D, E, or N, $X_2$ is L or V, $X_3$ is I or V, $X_4$ is S, T, or F, $X_5$ is H, K, L, Q, R or W, $X_6$ is L or M, and $X_7$ is G, K, Q, or R; b) $X_1X_2X_3X_4GX_5X_6X_7X_8X_9$, wherein $X_1$ is L or V, $X_2$ is A, G, L, T or V, $X_3$ is A, F, or S, $X_4$ is L or V, $X_5$ is C, F, H, I, L or Y, $X_6$ is A, C, P, Q, or S, $X_7$ is A, F, G, I, S, or V, $X_8$ is A, P, S, or T, and $X_9$ is K or R; c) $QX_1X_2LYRX_3VMX_4$ (SEQ ID NO: 59345), wherein $X_1$ is K or R, $X_2$ is A, D, E, G, N, S, or T, $X_3$ is D, E, or S, and $X_4$ is L or R; d) $X_1X_2X_3FX_4DVX_5X_6X_7FX_8X_9X_{10}X_{11}$ (SEQ ID NO:

59346), wherein $X_1$ is A, L, P, or S, $X_2$ is L or V, $X_3$ is S or T, $X_4$ is A, E, G, K, or R, $X_5$ is A or T, $X_6$ is I or V, $X_7$ is D, E, N, or Y, $X_8$ is S or T, $X_9$ is E, P, Q, R, or W, $X_{10}$ is E or N, and $X_{11}$ is E or Q; e) $X_1X_2X_3PX_4X_5X_6X_7X_8X_9X_{10}$, wherein $X_1$ is E, G, or R, $X_2$ is E or K, $X_3$ is A, D, or E, $X_4$ is C or W, $X_5$ is I, K, L, M, T, or V, $X_6$ is I, L, P, or V, $X_7$ is D, E, K, or V, $X_8$ is E, G, K, P, or R, $X_9$ is A, D, R, G, K, Q, or V, and $X_{10}$ is D, E, G, I, L, R, S, or V; f) $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S; g) $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R; h) $X_1PX_2X_3X_4X_5X_6LEX_7X_8X_9X_{10}X_{11}X_{12}$, wherein $X_1$ is K or R, $X_2$ is A, D, E, or N, $X_3$ is I, L, M, or V, $X_4$ is I or V, $X_5$ is F, S, or T, $X_6$ is H, K, L, Q, R, or W, $X_7$ is K, Q, or R, $X_8$ is E, G, or R, $X_9$ is D, E, or K, $X_{10}$ is A, D, or E, $X_{11}$ is L or P, and $X_{12}$ is C or W; or i) $X_1LX_2X_3X_4QX_5X_6$, wherein $X_1$ is C, H, L, Q, or W, $X_2$ is D, G, N, R, or S, $X_3$ is L, P, S, or T, $X_4$ is A, S, or T, $X_5$ is K or R, and $X_6$ is A, D, E, K, N, S, or T, and the KRAB domain comprises a sequence selected from the group consisting of SEQ ID NOS: 57746-57840, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the second repressor domain is a DNMT3A catalytic domain comprising a sequence selected from the group consisting of SEQ ID NOS: 33625-57543 and 59450, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the third repressor is a DNMT3L interaction domain comprising the amino acid sequence of SEQ ID NO: 59625, or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the fourth repressor is an ADD domain comprising the sequence of SEQ ID NO: 59452, or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, wherein the fusion protein comprises one or more linker peptides described herein, and wherein the fusion protein is capable of forming an RNP with a gRNA of the system that binds to the target nucleic acid. The present disclosure provides systems comprising a first, a second, a third, and a fourth repressor domain operably linked to a dCasX comprising the sequence of SEQ ID NO: 18, or a sequence having at least about 65%, at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto, wherein the first repressor domain comprises a KRAB domain comprising one or more motifs selected from the group consisting of a) $PX_1X_2X_3X_4X_5X_6EX_7$, wherein $X_1$ is A, D, E, or N, $X_2$ is L or V, $X_3$ is I or V, $X_4$ is S, T, or F, $X_5$ is H, K, L, Q, R or W, $X_6$ is L or M, and $X_7$ is G, K, Q, or R; b) $X_1X_2X_3X_4GX_5X_6X_7X_8X_9$, wherein $X_1$ is L or V, $X_2$ is A, G, L, T or V, $X_3$ is A, F, or S, $X_4$ is L or V, $X_5$ is C, F, H, I, L or Y, $X_6$ is A, C, P, Q, or S, $X_7$ is A, F, G, I, S, or V, $X_8$ is A, P, S, or T, and $X_9$ is K or R; c) $QX_1X_2LYRX_3VMX_4$ (SEQ ID NO: 59345), wherein $X_1$ is K or R, $X_2$ is A, D, E, G, N, S, or T, $X_3$ is D, E, or S, and $X_4$ is L or R; d) $X_1X_2X_3FX_4DVX_5X_6X_7FX_8X_9X_{10}X_1$ (SEQ ID NO: 59346), wherein $X_1$ is A, L, P, or S, $X_2$ is L or V, $X_3$ is S or T, $X_4$ is A, E, G, K, or R, $X_5$ is A or T, $X_6$ is I or V, $X_7$ is D, E, N, or Y, $X_8$ is S or T, $X_9$ is E, P, Q, R, or W, $X_{10}$ is E or N, and $X_{11}$ is E or Q; e) $X_1X_2X_3PX_4X_5X_6X_7X_8X_9X_{10}$, wherein $X_1$ is E, G, or R, $X_2$ is E or K, $X_3$ is A, D, or E, $X_4$ is C or W, $X_5$ is I, K, L, M, T, or V, $X_6$ is I, L, P, or V, $X_7$ is D, E, K, or V, $X_8$ is E, G, K, P, or R, $X_9$ is A, D, R, G, K, Q, or V, and $X_{10}$ is D, E, G, I, L, R, S, or V; f) $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S; g) $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R; h) $X_1PX_2X_3X_4X_5$ $X_6LEX_7X_8X_9X_{10}X_{11}X_{12}$, wherein $X_1$ is K or R, $X_2$ is A, D, E, or N, $X_3$ is I, L, M, or V, $X_4$ is I or V, $X_5$ is F, S, or T, $X_6$ is H, K, L, Q, R, or W, $X_7$ is K, Q, or R, $X_8$ is E, G, or R, $X_9$ is D, E, or K, $X_{10}$ is A, D, or E, $X_{11}$ is L or P, and $X_{12}$ is C or W; or i) $X_1LX_2X_3X_4QX_5X_6$, wherein $X_1$ is C, H, L, Q, or W, $X_2$ is D, G, N, R, or S, $X_3$ is L, P, S, or T, $X_4$ is A, S, or T, $X_5$ is K or R, and $X_6$ is A, D, E, K, N, S, or T, and the KRAB domain comprises a sequence selected from the group consisting of SEQ ID NOS: 57746-57755, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the second repressor domain is a DNMT3A catalytic domain comprising a sequence selected from the group consisting of SEQ ID NOS: 33625-57543 and 59450, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, the third repressor is a DNMT3L interaction domain comprising the sequence of SEQ ID NOS: 59625, or a sequence variant having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and the fourth repressor is an ADD domain comprising the sequence of SEQ ID NO: 59452, or sequence variants having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and wherein the fusion protein comprises one or more linker peptides described herein, and wherein the fusion protein is capable of forming an RNP with a gRNA of the system that binds to the target nucleic acid. In some embodiments, the dXR fusion protein comprise an ADD domain and a DNMT3A catalytic domain, wherein the C terminus of the ADD domain is operably to the N terminus of the DNMT3A catalytic domain. In some embodiments each of the repressor domains and the dCasX are operably linked, in some cases via a linker, as described herein. In some embodiments, the dXR fusion protein has a configuration of, N-terminal to C-terminal of configuration 1 (NLS-ADD-DNMT3A-Linker2-DNMT3A-Linker1-Linker3-dCasX-Linker3-KRAB-NLS), configuration 2 (NLS-Linker3-dCasX-Linker3-KRAB-NLS-Linker1-ADD-DNMT3A-Linker2-DNMT3L), configuration 3 (NLS-Linker3-dCasX-Linker1-ADD-DNMT3A-Linker2-DNMT3L-Linker3-KRAB-NLS), configuration 4 (NLS-KRAB-Linker3-ADD-DNMT3A-Linker2-DNMT3L-Linker1-dCasX-Linker3-NLS), or configuration 5 (NLS-ADD-DNMT3A-Linker2-DNMT3L-Linker3-KRAB-Linker1-dCasX-Linker3-NLS). In some embodiments of the system, the fusion protein components of the system are configured as schematically portrayed in FIG. 45. In some embodiments, the dXR fusion protein comprises a sequence selected from the group consisting of SEQ ID NOS: 59518-59526, 59538-59547, 59558-59567 and 59843-60012, or a sequence having or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto, and wherein the fusion protein is in configuration 1, 4 or 5.

In some embodiments of the system comprising a dCasX variant, a first, second, third, and fourth repressor domain, upon binding of an RNP of the fusion protein and the gRNA to the target nucleic acid, a gene encoded by the target nucleic acid is epigenetically-modified and transcription of the gene is repressed. In some embodiment, transcription of the gene is repressed by at least about 10%, at least about 20%, at least about 30%, at least about 40%, at least about 50%, at least about 60%, at least about 70%, at least about 75%, at least about 80%, at least about 85%, at least about 90%, at least about 95%, or at least 99%, when assayed in an in vitro assay, including cell-based assays. In some embodiments, the repression of transcription of the gene by the system compositions is sustained for at least about 8 hours, at least about 1 day, at least about 7 days, at least 2 weeks, at least about 3 weeks, at least about 1 month, or at least about 2 months, when assayed in an in vitro assay, including cell-based assays. In a particular embodiment, dXR configurations 4 and 5, when used in the dXR:gRNA system, result in less off-target methylation or off-target activity in an in vitro assay compared to configuration 1. In some embodiments, use of the dXR configurations 4 and 5, when used in the dXR:gRNA system, results in off-target methylation or off-target activity that is less than about 10%, less than about 9%, less than about 8%, less than about 7%, less than about 6%, less than about 5%, less than about 4%, less than about 3%, less than about 2%, or less than about 1% in the cells.

In some embodiments, the transcriptional repressor domains are linked to each other, or to the catalytically-dead CRISPR protein or catalytically-dead Class 2, Type V CRISPR protein (e.g., dCasX) within the fusion protein by linker peptide sequences. In some cases, the one or more transcriptional repressor domains are linked at or near the C-terminus of the catalytically-dead Class 2, Type V CRISPR protein (e.g., dCasX) by linker peptide sequences. In other cases, the one or more transcriptional repressor domains are linked at or near the N-terminus of the catalytically-dead Class 2, Type V CRISPR protein (e.g., dCasX) by linker peptide sequences. In still other cases, a first transcriptional repressor domain is linked at or near the C-terminus of the catalytically-dead Class 2, Type V CRISPR protein (e.g., dCasX) by linker peptide sequences and a second, third, and, optionally, a fourth transcriptional repressor domain is linked at or near the N-terminus of the catalytically-dead Class 2, Type V CRISPR protein. Representative, but non-limiting configurations are schematically portrayed in FIG. 7, FIG. 38, and FIG. 45. In the foregoing, the linker peptide is selected from the group consisting of RS, (G)n (SEQ ID NO: 33240), (GS)n (SEQ ID NO: 33241), (GGS)n (SEQ ID NO: 33242), (GSGGS)n (SEQ ID NO: 33243), (GGSGGS)n (SEQ ID NO: 33244), (GGGS)n (SEQ ID NO: 33245), GGSG (SEQ ID NO: 33246), GGSGG (SEQ ID NO: 33247), GSGSG (SEQ ID NO: 33248), GSGGG (SEQ ID NO: 33249), GGGSG (SEQ ID NO: 33250), GSSSG (SEQ ID NO: 33251), (GP)n (SEQ ID NO: 33252), GPGP (SEQ ID NO: 33253), GGSGGGS (SEQ ID NO: 33254), GSGSGGG (SEQ ID NO: 57628), GGCGGTTCCGGCGGAGGAAGC (SEQ ID NO: 57624), GGCGGTTCCGGCGGAGGTTCC (SEQ ID NO: 57625), GGATCAGGCTCTGGAGGTGGA (SEQ ID NO: 57627), GGAGGGCCGAGCTCTGGCGCACCCCCACCAAGTG-GAGGGTCTCCTGCCGGGTCCCC AACATCTACT-GAAGAAGGCACCAGCGAATCCGCAACGCCCG-AGTCAGGCCCTGGTA CCTCCACAGAACCATCT-GAAGGTAGTGCGCCTGGTTCCCCAGCTG-GAAGCCCTACTT CCACCGAAGAAGGCACGT-CAACCGAACCAAGTGAAGGATCTGCCCCTGGG-ACCAGC ACTGAACCATCTGAG (SEQ ID NO: 57620), SSGNSNANSRGPSFSSGLVPLSLRGSH (SEQ ID NO: 57623), GGPSSGAPPPSGGSPAGSPTSTEEGTSESAT-PESGPGTSTEPSEGSAPGSPAGSPTSTEEGT STEPSEGSAPGTSTEPSE (SEQ ID NO: 57621), TCTAGCGGCAATAGTAACGCTAACAGCCGCGG-GCCGAGCTTCAGCAGCGGCCTGGT GCCGT-TAAGCTTGCGCGGCAGCCAT (SEQ ID NO: 57622), GGP, PPP, PPAPPA (SEQ ID NO: 33255), PPPGPPP (SEQ ID NO: 33256), PPPG (SEQ ID NO: 33257), PPP(GGGS)n (SEQ ID NO: 33258), (GGGS)nPPP (SEQ ID NO: 33259), AEAAAKEAAAKEAAAKA (SEQ ID NO:33260), AEAAAKEAAAKA (SEQ ID NO: 33261), SGSETPGTS-ESATPES (SEQ ID NO: 33262), and TPPKTKRKVEFE (SEQ ID NO: 33263), wherein n is an integer of 1 to 5.

IV. Guide Ribonucleic Acids (gRNA) of the Systems

In another aspect, the disclosure provides guide ribonucleic acids (gRNAs) utilized in the gene repressor systems of the disclosure that have utility, with the other components of the gene repressor systems, in the repression of transcription of genes targeted by the design of the gRNA. The present disclosure provides specifically-designed gRNAs with targeting sequences (or "spacers") that are complementary to (and are therefore able to hybridize with) the target nucleic acid as a component of the gene repression systems, wherein the gRNA is capable of forming a ribonucleoprotein (RNP) complex with the catalytically-dead CRISPR protein (e.g., dCasX) of a fusion protein. In the case of a dCasX variant with linked repressor domains employed in the systems of the disclosure, the dCasX variant has specificity to a protospacer adjacent motif (PAM) sequence comprising a TC motif in the complementary non-target strand, and wherein the PAM sequence is located 1 nucleotide 5' of the sequence in the non-target strand that is complementary to the target nucleic acid sequence in the target strand of the target nucleic acid. The use of a pre-complexed RNP confers advantages in the delivery of the system components to a cell or target nucleic acid sequence for repression of transcription of the target nucleic acid sequence. The dCasX variant protein component of the RNP provides the site-specific activity that is guided to a target site (e.g., stabilized at a target site) within a target nucleic acid sequence by virtue of its association with the guide RNA comprising a targeting sequence complementary to the desired specific location of the target nucleic acid and proximal to the PAM sequence.

It is envisioned that in some embodiments, multiple gRNAs (e.g., multiple gRNAs) are delivered by the system for the repression at different regions of a gene, increasing the efficiency and/or duration of repression, as described more fully, below.

a. Reference gRNA and gRNA Variants

In designing gRNA for incorporation into the gene repressor systems of the disclosure, comprehensive approaches termed Deep Mutational Evolution (DME), deep mutational scanning (DMS), error prone PCR, cassette mutagenesis, random mutagenesis, staggered extension PCR, gene shuffling, or domain swapping, were utilized to, in a systematic way, introduce mutations and variations in the nucleic acid sequence of, first, naturally-occurring gRNA ("reference gRNA"), resulting in gRNA variants with improved properties, then re-applying the approaches to gRNA variants to further evolve and improve the resulting gRNA variants. gRNA variants also include variants comprising one or more chemical modifications. The activity of reference gRNAs may be used as a benchmark against which the activity of gRNA variants are compared, thereby measuring improvements in function or other characteristics of the gRNA variants. In other embodiments, a reference gRNA or gRNA variant may be subjected to one or more deliberate, targeted mutations in order to produce a gRNA variant, for example a rationally-designed variant.

The gRNAs of the disclosure comprise two segments; a targeting sequence and a protein-binding segment. The targeting segment of a gRNA includes a nucleotide sequence (referred to interchangeably as a guide sequence, a spacer, a targeter, or a targeting sequence) that is complementary to (and therefore hybridizes with) a specific sequence (a target site) within the target nucleic acid sequence (e.g., a target ssRNA, a target ssDNA, a strand of a double stranded target nucleic acid, etc.), described more fully below. The targeting sequence of a gRNA is capable of binding to a target nucleic acid sequence, including a coding sequence, a complement of a coding sequence, a non-coding sequence, and to regulatory elements. The protein-binding segment (or "activator" or "protein-binding sequence") interacts with (e.g., binds to) a dCasX protein as a complex, forming an RNP (described more fully, below). The protein-binding segment is alternatively referred to herein as a "scaffold", which is comprised of several regions, described more fully, below.

In the case of a dual guide RNA (dgRNA), the targeter and the activator portions each have a duplex-forming segment, where the duplex forming segment of the targeter and the duplex-forming segment of the activator have complementarity with one another and hybridize to one another to form a double stranded duplex (dsRNA duplex for a gRNA). The term "targeter" or "targeter RNA" is used herein to refer to a crRNA-like molecule (crRNA: "CRISPR RNA") of a CasX dual guide RNA (and therefore of a CasX single guide RNA when the "activator" and the "targeter" are linked together; e.g., by intervening nucleotides). The crRNA has a 5' region that anneals with the tracrRNA followed by the nucleotides of the targeting sequence. Thus, for example, a guide RNA (dgRNA or sgRNA) comprises a guide sequence and a duplex-forming segment of a crRNA, which can also be referred to as a crRNA repeat. A corresponding tracrRNA-like molecule (activator) also comprises a duplex-forming stretch of nucleotides that forms the other half of the dsRNA duplex of the protein-binding segment of the guide RNA. Thus, a targeter and an activator, as a corresponding pair, hybridize to form a dual guide RNA, referred to herein as a "dual-molecule gRNA" or a "dgRNA". Site-specific binding of a target nucleic acid sequence (e.g., genomic DNA) by the dCasX protein and linked repressor domain(s) can occur at one or more locations (e.g., a sequence of a target nucleic acid) determined by base-pairing complementarity between the targeting sequence of the gRNA and the target nucleic acid sequence. Thus, for example, the gRNA of the disclosure have sequences complementarity to and therefore can hybridize with the target nucleic acid that is adjacent to a sequence complementary to a TC PAM motif or a PAM sequence, such as ATC, CTC, GTC, or TTC. Because the targeting sequence of a guide sequence hybridizes with a sequence of a target nucleic acid sequence, a targeting sequence can be modified by a user to hybridize with a specific target nucleic acid sequence, so long as the location of the PAM sequence is considered. In other embodiments, the activator and targeter of the gRNA are covalently linked to one another (rather than hybridizing to one another) and comprise a single molecule, referred to herein as a "single-molecule gRNA," "one-molecule guide RNA," "single guide RNA", "single guide RNA", a "single-molecule guide RNA," a "sgRNA", or a "one-molecule guide RNA".

Collectively, the assembled gRNAs of the disclosure comprise four distinct regions, or domains: the RNA triplex, the scaffold stem, the extended stem, and the targeting sequence that, in the embodiments of the disclosure is specific for a target nucleic acid and is located on the 3' end of the gRNA. The RNA triplex, the scaffold stem, and the extended stem, together, are referred to as the "scaffold" of the gRNA. The foregoing components of the gRNA are described in WO2020247882A1 and WO2022120095, incorporated by reference herein.

b. Targeting Sequence

In some embodiments of the gRNAs of the disclosure, the extended stem loop is followed by a region that forms part of the triplex, and then the targeting sequence (or "spacer") at the 3' end of the gRNA, with the scaffold being that region of the guide 5' relative to the targeting sequence. The targeting sequence targets the CasX ribonucleoprotein holo complex to a specific region of the target nucleic acid sequence of the gene to be repressed, 3' relative to the binding of the RNP. Thus, for example, gRNA targeting sequences of the disclosure have sequences complementarity to, and therefore can hybridize to, a portion of the gene in a nucleic acid in a eukaryotic cell (e.g., a eukaryotic chromosome, chromosomal sequence, a eukaryotic RNA, etc.) as a component of the RNP when the TC PAM motif or any one of the PAM sequences TTC, ATC, GTC, or CTC is located 1 nucleotide 5' to the non-target strand sequence complementary to the target sequence. The targeting sequence of a gRNA can be modified so that the gRNA can target a desired sequence of any desired target nucleic acid sequence, so long as the PAM sequence location is taken into consideration. In some embodiments, the PAM motif sequence recognized by the nuclease of the RNP is TC. In other embodiments, the PAM sequence recognized by the nuclease of the RNP is NTC. In other embodiments, the PAM sequence recognized by the nuclease of the RNP is TTC. In other embodiments, the PAM sequence recognized by the nuclease of the RNP is ATC. In other embodiments, the PAM sequence recognized by the nuclease of the RNP is CTC. In other embodiments, the PAM sequence recognized by the nuclease of the RNP is GTC.

The gene repressor systems of the present disclosure can be designed to target any region of, or proximal to, a gene or region of a gene for which repression of transcription is sought. When the entirety of the gene is to be repressed, designing a guide with a targeting sequence complementary to a sequence encompassing or proximal to the transcription start site (TSS) is contemplated by the disclosure. The TSS selection occurs at different positions within the promoter region, depending on promoter sequence and initiating-substrate concentration. The core promoter serves as a binding platform for the transcription machinery, which comprises Pol II and its associated general transcription factors (GTFs) (Haberle, V. et al. Eukaryotic core promoters and the functional basis of transcription initiation (Nat Rev Mol Cell Biol. 19(10):621 (2018)). Variability in TSS selection has been proposed to involve DNA 'scrunching' and 'anti-scrunching,' the hallmarks of which are: (i) forward and reverse movement of the RNA polymerase leading edge, but not trailing edge, relative to DNA, and (ii) expansion and contraction of the transcription bubble. In some embodiments, the target nucleic acid sequence bound by an RNP of the dXR:gRNA system is within 1 kb of a transcription start site (TSS) in the gene. In some embodiments, the target nucleic acid sequence bound by an RNP of the system is within 20 bp, 50 bp, 100 bp, 150 bp, 200 bp, 250 bp, 500 bps, or 1 kb upstream of a TSS of the gene. In some embodiments, the target nucleic acid sequence bound by an RNP of the system is within 20 bp, 50 bp, 100 bp, 150 bp, 200 bp, 250 bp, 500 bps or 1 kb downstream of a TSS of the gene. In some embodiments, the target nucleic acid sequence bound by an RNP of the system is within 500 bps upstream to 500 bps downstream, or 300 bps upstream to 300 bps downstream of a TSS of the gene. In some embodiments, the target nucleic acid sequence bound by an RNP of the system is within 20 bp, 50 bp, 100 bp, 150 bp, 200 bp, 250 bp, 500 bps, or 1 kb of an enhancer of the gene. In some embodiments, the target nucleic acid sequence bound by an RNP of the system of the disclosure is within 1 kb 3' to a 5' untranslated region of the gene. In other embodiments, the target nucleic acid sequence bound by an RNP of the system is within the open reading frame of the gene, inclusive of introns (if any). In some embodiments, the targeting sequence of a gRNA of the system of the disclosure is designed to be specific for an exon of the gene of the target nucleic acid. In a particular embodiment, the targeting sequence of a gRNA of the system of the disclosure is designed to be specific for exon 1 of the gene of the target nucleic acid. In other embodiments, the targeting sequence of a gRNA of the system of the disclosure is designed to be specific for an intron of the gene of the target nucleic acid. In other embodiments, the targeting sequence of the gRNA of the system of the disclosure is designed to be specific for an intron-exon junction of the gene of the target nucleic acid. In other embodiments, the targeting sequence of the gRNA of the system of the disclosure is designed to be specific for a regulatory element of the gene of the target nucleic acid. In other embodiments, the targeting sequence of the gRNA of the system of the disclosure is designed to be complementary to a sequence of an intergenic region of the gene of the target nucleic acid. In other embodiments, the targeting sequence of a gRNA of the system of the disclosure is specific for a junction of the exon, an intron, and/or a regulatory element of the gene. In those cases where the targeting sequence is specific for a regulatory element, such regulatory elements include, but are not limited to promoter regions, enhancer regions, intergenic regions, 5' untranslated regions (5' UTR), 3' untranslated regions (3' UTR), conserved elements, and regions comprising cis-regulatory elements. The promoter region is intended to encompass nucleotides within 5 kb of the initiation point of the encoding sequence or, in the case of gene enhancer elements or conserved elements, can be thousands of bp, hundreds of thousands of bp, or even millions of bp away from the encoding sequence of the gene of the target nucleic acid. In the foregoing, the targets are those in which the encoding gene of the target is intended to be repressed such that the gene product is not expressed or is expressed at a lower level in a cell. In some embodiments, upon binding of the RNP of the system of the disclosure to the binding location of the target nucleic acid, the system is capable of repressing transcription of the gene 5' to the binding location of the RNP. In other embodiments, upon binding of the RNP of the system to the binding location of the target nucleic acid, the system is capable of repressing transcription of the gene 3' to the binding location of the RNP. In some embodiments, upon binding of the RNP of the system to the binding location of the target nucleic acid, the system is capable of repressing transcription of the gene by at least about 10%, at least about 20%, at least about 30%, at least about 40%, at least about 50%, at least about 60%, at least about 70%, at least about 75%, at least about 80%, at least about 85%, at least about 90%, at least about 95%, or at least 99% greater compared to an untreated gene, when assessed in an in vitro assay. In some embodiments, upon binding of the RNP of the system to the binding location of the target nucleic acid, the system is capable of repressing transcription of the gene for at least about 8 hours, at least about 1 day, at least about 7 days, at least about 2 weeks, at least about 3 weeks, at least about 1 month, at least about 2 months, or at least about 6 months, or at least about 1 year.

In some embodiments, the targeting sequence of a gRNA of the system has between 14 and 20 consecutive nucleotides. In some embodiments, the targeting sequence has 14, 15, 16, 17, 18, 19, or 20 consecutive nucleotides. In some embodiments, the targeting sequence of the gRNA of the system consists of 20 consecutive nucleotides. In some embodiments, the targeting sequence consists of 19 consecutive nucleotides. In some embodiments, the targeting sequence consists of 18 consecutive nucleotides. In some embodiments, the targeting sequence consists of 17 consecutive nucleotides. In some embodiments, the targeting sequence consists of 16 consecutive nucleotides. In some embodiments, the targeting sequence consists of 15 consecutive nucleotides. In some embodiments, the targeting sequence has 14, 15, 16, 17, 18, 19, or 20 consecutive nucleotides and the targeting sequence can comprise 0 to 5, 0 to 4, 0 to 3, or 0 to 2 mismatches relative to the target nucleic acid sequence and retain sufficient binding specificity such that the RNP comprising the gRNA comprising the targeting sequence can form a complementary bond with respect to the target nucleic acid.

In some embodiments, dXR:gRNA a repressor system of the disclosure comprises a first gRNA and further comprises a second (and optionally a third, fourth, fifth, or more) gRNA, wherein the second gRNA or additional gRNA has a targeting sequence complementary to a different or overlapping portion of the target nucleic acid sequence compared to the targeting sequence of the first gRNA such that multiple points in the target nucleic acid are targeted, increasing the ability of the system to effectively repress transcription. It will be understood that in such cases, the second or additional gRNA is complexed with an additional copy of the dXR. By selection of the targeting sequences of the gRNA, defined regions of the target nucleic acid sequence can be repressed using the systems described herein.

c. gRNA Scaffolds

With the exception of the targeting sequence region, the remaining regions of the gRNA are referred to herein as the scaffold. In some embodiments, the gRNA scaffolds are variants of reference gRNA wherein mutations, insertions, deletions or domain substitutions are introduced to confer desirable properties on the gRNA.

In some embodiments, a reference gRNA comprises a sequence isolated or derived from Deltaproteobacteria. In some embodiments, the sequence is a CasX tracrRNA sequence.

Exemplary CasX reference tracrRNA sequences isolated or derived from Deltaproteobacteria may include: ACAUCUGGCGCGUUUAUUCCAUUACUUUG-GAGCCAGUCCCAGCGACUAUGUCGU AUGGACGAAGCGCUUAUUUAUCGGAGA (SEQ ID NO: 6) and ACAUCUGGCGCGUUUAUUCCAUUAC-UUUGGAGCCAGUCCCAGCGACUAUGUCGU AUGGACGAAGCGCUUAUUUAUCGG (SEQ ID NO: 7). Exemplary crRNA sequences isolated or derived from Deltaproteobacteria may comprise a sequence of CCGAUA-AGUAAAACGCAUCAAAG (SEQ ID NO: 33271).

In some embodiments, a reference guide RNA comprises a sequence isolated or derived from Planctomycetes. In some embodiments, the sequence is a CasX tracrRNA sequence. Exemplary reference tracrRNA sequences isolated or derived from Planctomycetes may include: UACUGGCGCUUUUAUCUCAUUAC-UUUGAGAGCCAUCACCAGCGACUAUGUCGUA UGGGUAAAGCGCUUAUUUAUCGGAGA (SEQ ID NO: 8) and UACUGGCGCUUUUAUCUCAUUAC-UUUGAGAGCCAUCACCAGCGACUAUG UCGUAUGGGUAAAGCGCUUAUUUAUCGG (SEQ ID NO: 9). Exemplary crRNA sequences isolated or derived from Planctomycetes may comprise a sequence of UCUCCGAUAAAUAAGAAGCAU-CAAAG (SEQ ID NO: 33272).

In some embodiments, a reference gRNA comprises a sequence isolated or derived from *Candidatus Sungbacteria*. In some embodiments, the sequence is a CasX tracrRNA sequence. Exemplary CasX reference tracrRNA sequences isolated or derived from *Candidatus Sungbacteria* may comprise sequences of: GUUUACACACUCCCUCU-CAUAGGGU (SEQ ID NO: 10), GUUUACACACUCC-CUCUCAUGAGGU (SEQ ID NO: 11), UUUUA-CAUACCCCCUCUCAUGGGAU (SEQ ID NO: 12) and GUUUACACACUCCCUCUCAUGGGGG (SEQ ID NO: 13). Table 1 provides the sequences of reference gRNA tracr, cr and scaffold sequences that, in some embodiments, are modified to create the gRNA of the systems. In some embodiments, the disclosure provides gRNA variant sequences wherein the gRNA has a scaffold comprising a sequence having one or more nucleotide modifications relative to a reference gRNA sequence having a sequence of any one of SEQ ID NOS: 4-16 of Table 1. It will be understood that in those embodiments wherein a vector comprises a DNA encoding sequence for a gRNA, that thymine (T) bases can be substituted for the uracil (U) bases of any of the gRNA sequence embodiments described herein.

TABLE 1

Reference gRNA tracr, cr and scaffold sequences

| SEQ ID NO. | Nucleotide Sequence |
|---|---|
| 4 | ACAUCUGGCGCGUUUAUUCCAUUACUUUGGAGCCAGUCCCAGCGACUAUGUCGUAUGGACGAAGC GCUUAUUUAUCGGAGAGAAACCGAUAAGUAAAACGCAUCAAAG |
| 5 | UACUGGCGCUUUUAUCUCAUUACUUUGAGAGCCAUCACCAGCGACUAUGUCGUAUGGGUAAAGCG CUUAUUUAUCGGAGAGAAAUCCGAUAAAUAAGAAGCAUCAAAG |
| 6 | ACAUCUGGCGCGUUUAUUCCAUUACUUUGGAGCCAGUCCCAGCGACUAUGUCGUAUGGACGAAGC GCUUAUUUAUCGGAGA |
| 7 | ACAUCUGGCGCGUUUAUUCCAUUACUUUGGAGCCAGUCCCAGCGACUAUGUCGUAUGGACGAAGC GCUUAUUUAUCGG |
| 8 | UACUGGCGCUUUUAUCUCAUUACUUUGAGAGCCAUCACCAGCGACUAUGUCGUAUGGGUAAAGCG CUUAUUUAUCGGAGA |
| 9 | UACUGGCGCUUUUAUCUCAUUACUUUGAGAGCCAUCACCAGCGACUAUGUCGUAUGGGUAAAGCG CUUAUUUAUCGG |
| 10 | GUUUACACACUCCCUCUCAUAGGGU |
| 11 | GUUUACACACUCCCUCUCAUGAGGU |
| 12 | UUUUACAUACCCCCUCUCAUGGGAU |
| 13 | GUUUACACACUCCCUCUCAUGGGGG |
| 14 | CCAGCGACUAUGUCGUAUGG |
| 15 | GCGCUUAUUUAUCGGAGAGAAAUCCGAUAAAUAAGAAGC |
| 16 | GGCGCUUUUAUCUCAUUACUUUGAGAGCCAUCACCAGCGACUAUGUCGUAUGGGUAAAGCGCUUA UUUAUCGGA |

d. gRNA Variants

In another aspect, the disclosure relates to guide ribonucleic acid variants (referred to herein as "gRNA variant"), which comprise one or more modifications relative to a reference gRNA scaffold. As used herein, "scaffold" refers to all parts to the gRNA necessary for gRNA function with the exception of the spacer sequence.

In some embodiments, a gRNA variant comprises one or more nucleotide substitutions, insertions, deletions, or swapped or replaced regions relative to a reference gRNA sequence of the disclosure. In some embodiments, a mutation can occur in any region of a reference gRNA scaffold to produce a gRNA variant. In some embodiments, the scaffold of the gRNA variant sequence has at least 50%, at least 60%, or at least 70%, at least 80%, at least 85%, at least about 90%, at least about 95%, at least about 96%, at least about 97%, at least about 98%, or at least about 99% identity to the sequence of SEQ ID NO: 4 or SEQ ID NO: 5.

In some embodiments, a gRNA variant comprises one or more nucleotide changes within one or more regions of the reference gRNA scaffold that improve a characteristic of the reference gRNA. Exemplary regions include the RNA triplex, the pseudoknot, the scaffold stem loop, and the extended stem loop. In some cases, the variant scaffold stem further comprises a bubble. In other cases, the variant scaffold further comprises a triplex loop region. In still other cases, the variant scaffold further comprises a 5' unstructured region. In some embodiments, the gRNA variant scaffold comprises a scaffold stem loop having at least 60% sequence identity, at least 70% sequence identity, at least 80% sequence identity, at least 90% sequence identity, at least 95% sequence identity, or at least 99% sequence identity to SEQ ID NO: 14. In some embodiments, the gRNA variant scaffold comprises a scaffold stem loop having at least 60% sequence identity to SEQ ID NO: 14. In other embodiments, the gRNA variant comprises a scaffold stem loop having the sequence of CCAGCGACUAUGUCGUAGUGG (SEQ ID NO: 33273). In other embodiments, the disclosure provides a gRNA scaffold comprising, relative to SEQ ID NO: 5, a C18G substitution, a G55 insertion, a U1 deletion, and a modified extended stem loop in which the original 6 nt loop and 13 most-loop-proximal base pairs (32 nucleotides total) are replaced by a Uvsx hairpin (4 nt loop and 5 loop-proximal base pairs; 14 nucleotides total) and the loop-distal base of the extended stem was converted to a fully base-paired stem contiguous with the new Uvsx hairpin by deletion of the A99 and substitution of G65U. In the foregoing embodiment, the gRNA scaffold comprises the sequence ACUGGCGCUUUUAUCUGAUUACUUUGAGAGCCAUCACCAGCGACUAUGUCGUAG UGGGUAAAGCUCCCUCUUCGGAGGGAGCAUCAAAG (SEQ ID NO: 33274).

All gRNA variants that have one or more improved characteristics, or add one or more new functions when the variant gRNA is compared to a reference gRNA described herein, are envisaged as within the scope of the disclosure. A representative example of such a gRNA variant appropriate for the gene repressor systems is gRNA variant 174 (SEQ ID NO: 2238). Another representative example of such a gRNA variant appropriate for the gene repressor systems is gRNA variant 235 (SEQ ID NO: 2292). In some embodiments, the gRNA variant adds a new function to the RNP comprising the gRNA variant. In some embodiments, the gRNA variant has an improved characteristic selected from: improved stability; improved solubility; improved transcription of the gRNA; improved resistance to nuclease activity; increased folding rate of the gRNA; decreased side product formation during folding; increased productive folding; improved binding affinity to a dXR fusion protein and linked repressor domain(s); improved binding affinity to a target nucleic acid when complexed with a dXR fusion protein and linked repressor domain(s); and improved ability to utilize a greater spectrum of one or more PAM sequences, including ATC, CTC, GTC, or TTC, in the binding of target nucleic acid when complexed with a dXR fusion protein, and any combination thereof. In some cases, the one or more of the improved characteristics of the gRNA variant is at least about 1.1 to about 100,000-fold improved relative to the reference gRNA of SEQ ID NO: 4 or SEQ ID NO: 5. In other cases, the one or more improved characteristics of the gRNA variant is at least about 1.1, at least about 10, at least about 100, at least about 1000, at least about 10,000, at least about 100,000-fold or more improved relative to the reference gRNA of SEQ ID NO: 4 or SEQ ID NO: 5. In other cases, the one or more of the improved characteristics of the gRNA variant is about 1.1 to 100,00-fold, about 1.1 to 10,00-fold, about 1.1 to 1,000-fold, about 1.1 to 500-fold, about 1.1 to 100-fold, about 1.1 to 50-fold, about 1.1 to 20-fold, about 10 to 100,00-fold, about 10 to 10,00-fold, about 10 to 1,000-fold, about 10 to 500-fold, about 10 to 100-fold, about 10 to 50-fold, about 10 to 20-fold, about 2 to 70-fold, about 2 to 50-fold, about 2 to 30-fold, about 2 to 20-fold, about 2 to 10-fold, about 5 to 50-fold, about 5 to 30-fold, about 5 to 10-fold, about 100 to 100,00-fold, about 100 to 10,00-fold, about 100 to 1,000-fold, about 100 to 500-fold, about 500 to 100,00-fold, about 500 to 10,00-fold, about 500 to 1,000-fold, about 500 to 750-fold, about 1,000 to 100,00-fold, about 10,000 to 100,00-fold, about 20 to 500-fold, about 20 to 250-fold, about 20 to 200-fold, about 20 to 100-fold, about 20 to 50-fold, about 50 to 10,000-fold, about 50 to 1,000-fold, about 50 to 500-fold, about 50 to 200-fold, or about 50 to 100-fold, improved relative to the reference gRNA of SEQ ID NO: 4 or SEQ ID NO: 5. In other cases, the one or more improved characteristics of the gRNA variant is about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 40-fold, 45-fold, 50-fold, 55-fold, 60-fold, 70-fold, 80-fold, 90-fold, 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, 300-fold, 310-fold, 320-fold, 330-fold, 340-fold, 350-fold, 360-fold, 370-fold, 380-fold, 390-fold, 400-fold, 425-fold, 450-fold, 475-fold, or 500-fold improved relative to the reference gRNA of SEQ ID NO: 4 or SEQ ID NO: 5.

In some embodiments, a gRNA variant can be created by subjecting a reference gRNA to a one or more mutagenesis methods, such as the mutagenesis methods described herein, below, which may include Deep Mutational Evolution (DME), deep mutational scanning (DMS), error prone PCR, cassette mutagenesis, random mutagenesis, staggered extension PCR, gene shuffling, or domain swapping, in order to generate the gRNA variants of the disclosure. The activity of reference gRNAs may be used as a benchmark against which the activity of gRNA variants are compared, thereby measuring improvements in function of gRNA variants. In other embodiments, a reference gRNA may be subjected to one or more deliberate, targeted mutations, substitutions, or domain swaps in order to produce a gRNA variant, for example a rationally designed variant. Exemplary gRNA variants produced by such methods are presented in Table 2.

In some embodiments, the gRNA variant comprises one or more modifications compared to a reference guide ribonucleic acid scaffold sequence, wherein the one or more modification is selected from: at least one nucleotide substitution in a region of the reference gRNA; at least one nucleotide deletion in a region of the reference gRNA; at least one nucleotide insertion in a region of the reference gRNA; a substitution of all or a portion of a region of the reference gRNA; a deletion of all or a portion of a region of the reference gRNA; or any combination of the foregoing. In some cases, the modification is a substitution of 1 to 15 consecutive or non-consecutive nucleotides in the reference gRNA in one or more regions. In other cases, the modification is a deletion of 1 to 10 consecutive or non-consecutive nucleotides in the reference gRNA in one or more regions. In other cases, the modification is an insertion of 1 to 10 consecutive or non-consecutive nucleotides in the reference gRNA in one or more regions. In other cases, the modification is a substitution of the scaffold stem loop or the extended stem loop with an RNA stem loop sequence from a heterologous RNA source with proximal 5' and 3' ends. In some cases, a gRNA variant of the disclosure comprises two or more modifications in one region relative to a reference gRNA. In other cases, a gRNA variant of the disclosure comprises modifications in two or more regions. In other cases, a gRNA variant comprises any combination of the foregoing modifications described in this paragraph.

In some embodiments, a 5' G is added to a gRNA variant sequence, relative to a reference gRNA, for expression in vivo, as transcription from a U6 promoter is more efficient and more consistent with regard to the start site when the +1 nucleotide is a G. In other embodiments, two 5' Gs are added to generate a gRNA variant sequence for in vitro transcription to increase production efficiency, as T7 polymerase strongly prefers a G in the +1 position and a purine in the +2 position. In some cases, the 5' G bases are added to the reference scaffolds of Table 1. In other cases, the 5' G bases are added to the variant scaffolds of Table 2.

Table 2 provides exemplary gRNA variant scaffold sequences. In some embodiments, the gRNA variant scaffold comprises any one of the sequences listed in Table 2, or a sequence having at least about 50%, at least about 60%, at least about 70%, at least about 80%, at least about 90%, at least about 95%, at least about 95%, at least about 96%, at least about 97%, at least about 98%, at least about 99% sequence identity thereto. It will be understood that in those embodiments wherein a vector comprises a DNA encoding sequence for a gRNA, that thymine (T) bases can be substituted for the uracil (U) bases of any of the gRNA sequence embodiments described herein.

TABLE 2

Exemplary gRNA Variant Scaffold Sequences

| SEQ ID NO. | Guide No. | Sequence |
|---|---|---|
| 2238 | 174 | ACUGGCGCUUUUAUCUGAUUACUUUGAGAGCCAUCACCAGCGACUAUGUCGUAGUG GGUAAAGCUCCCUCUUCGGAGGGAGCAUCAAAG |
| 2239 | 175 | ACUGGCGCCUUUAUCUCAUUACUUUGAGAGCCAUCACCAGCGACUAUGUCGUAUGG GUAAAGCGCUUACGGACUUCGGUCCGUAAGAAGCAUCAAAG |
| 2240 | 176 | GCUGGCGCUUUUAUCUGAUUACUUUGAGAGCCAUCACCAGCGACUAUGUCGUAGUG GGUAAAGCUCCCUCUUCGGAGGGAGCAUCAAAG |
| 2241 | 177 | ACUGGCGCUUUUAUCUGAUUACUUUGAGAGCCAUCACCAGCGACUAUGUCGUAUGG GUAAAGCUCCCUCUUCGGAGGGAGCAUCAAAG |
| 2242 | 181 | ACUGGCGCCUUUAUCUGAUUACUUUGAGAGCCAUCACCAGCGACUAUGUCGUAUGG GUAAAGCGCUUACGGACUUCGGUCCGUAAGAAGCAUCAAAG |
| 2243 | 182 | ACUGGCGCUUUUAUCUGAUUACUUUGAGAGCCAUCACCAGCGACUAUGUCGUAUGG GUAAAGCGCUUACGGACUUCGGUCCGUAAGAAGCAUCAAAG |
| 2244 | 183 | ACUGGCGCUUUUAUCUGAUUACUUUGAGAGCCAUCACCAGCGACUAUGUCGUAGUG GGUAAAGCGCUUACGGACUUCGGUCCGUAAGAAGCAUCAAAG |
| 2245 | 184 | ACUGGCGCUUUUAUCUGAUUACUUUGAGAGCCAUCACCAGCGACUAUGUCGUAUUG GGUAAAGCUCCCUCUUCGGAGGGAGCAUCAAAG |
| 2246 | 185 | ACUGGCGCUUUUAUCUGAUUACUUUGAGAGCCAUCACCAGCGACUAUGUCGUAUUG GGUAAAGCGCUUACGGACUUCGGUCCGUAAGAAGCAUCAAAG |
| 2247 | 186 | ACUGGCGCCUUUAUCAUCAUUACUUUGAGAGCCAUCACCAGCGACUAUGUCGUAUG GGUAAAGCGCUUACGGACUUCGGUCCGUAAGAAGCAUCAAAG |
| 2248 | 187 | ACUGGCGCUUUUAUCUGAUUACUUUGAGAGCCAUCACCAGCGACUAUGUCGUAGUG GGUAAAGCGCCCUCUUCGGAGGGAAGCAUCAAAG |
| 2249 | 188 | ACUGGCGCUUUUAUCUGAUUACUUUGAGAGCCAUCACCAGCGACUAUGUCGUAGUG GGUAAAGCUCACAUGAGGAUCACCCAUGUGAGCAUCAAAG |
| 2250 | 189 | ACUGGCACUUUUACCUGAUUACUUUGAGAGCCAACACCAGCGACUAUGUCGUAGUG GGUAAAGCUCCCUCUUCGGAGGGAGCAUCAAAG |
| 2251 | 190 | ACUGGCACUUUUAUCUGAUUACUUUGAGAGCCAUCACCAGCGACUAUGUCGUAGUG GGUAAAGCUCCCUCUUCGGAGGGAGCAUCAAAG |

TABLE 2-continued

Exemplary gRNA Variant Scaffold Sequences

| SEQ ID NO. | Guide No. | Sequence |
|---|---|---|
| 2252 | 191 | ACUGGCCCUUUUAUCUGAUUACUUUGAGAGCCAUCACCAGCGACUAUGUCGUAGUG GGUAAAGCUCCCUCUUCGGAGGGAGCAUCAAAG |
| 2253 | 192 | ACUGGCGCUUUUACCUGAUUACUUUGAGAGCCAUCACCAGCGACUAUGUCGUAGUG GGUAAAGCUCCCUCUUCGGAGGGAGCAUCAAAG |
| 2254 | 193 | ACUGGCGCUUUUAUCUGAUUACUUUGAGAGCCAACACCAGCGACUAUGUCGUAGUG GGUAAAGCUCCCUCUUCGGAGGGAGCAUCAAAG |
| 2255 | 195 | ACUGGCACCUUUACCUGAUUACUUUGAGAGCCAACACCAGCGACUAUGUCGUAUGG GUAAAGCGCUUACGGACUUCGGUCCGUAAGAAGCAUCAAAG |
| 2256 | 196 | ACUGGCACCUUUAUCUGAUUACUUUGAGAGCCAUCACCAGCGACUAUGUCGUAUGG GUAAAGCGCUUACGGACUUCGGUCCGUAAGAAGCAUCAAAG |
| 2257 | 197 | ACUGGCCCCUUUAUCUGAUUACUUUGAGAGCCAUCACCAGCGACUAUGUCGUAUGG GUAAAGCGCUUACGGACUUCGGUCCGUAAGAAGCAUCAAAG |
| 2258 | 198 | ACUGGCGCCUUUAUCUGAUUACUUUGAGAGCCAACACCAGCGACUAUGUCGUAUGG GUAAAGCGCUUACGGACUUCGGUCCGUAAGAAGCAUCAAAG |
| 2259 | 199 | GCUGGCGCUUUUAUCUGAUUACUUUGAGAGCCAUCACCAGCGACUAUGUCGUAGUG GGUAAAGCUCCCUCUUCGGAGGGAGCAUCAAAG |
| 2260 | 200 | GACUGGCGCUUUUAUCUGAUUACUUUGAGAGCCAUCACCAGCGACUAUGUCGUAGU GGGUAAAGCUCCCUCUUCGGAGGGAGCAUCAAAG |
| 2261 | 201 | ACUGGCGCCUUUAUCUGAUUACUUUGGAGAGCCAUCACCAGCGACUAUGUCGUAGU GGGUAAAGCUCCCUCUUCGGAGGGAGCAUCAAAG |
| 2262 | 202 | ACUGGCGCAUUUAUCUGAUUACUUUGUGAGCCAUCACCAGCGACUAUGUCGUAGUG GGUAAAGCUCCCUCUUCGGAGGGAGCAUCAAAG |
| 2263 | 203 | ACUGGCGCCUUUAUCUGAUUACUUUGAGAGCCAUCACCAGCGACUAUGUCGUAGUG GGUAAAGCUCCCUCUUCGGAGGGAGCAUCAAAG |
| 2264 | 204 | ACUGGCGCUUUUAUCUGAUUACUUUGGAGAGCCAUCACCAGCGACUAUGUCGUAGU GGGUAAAGCUCCCUCUUCGGAGGGAGCAUCAAAG |
| 2265 | 205 | ACUGGCGCAUUUAUCUGAUUACUUUGAGAGCCAUCACCAGCGACUAUGUCGUAGUG GGUAAAGCUCCCUCUUCGGAGGGAGCAUCAAAG |
| 2266 | 206 | ACUGGCGCUUUUAUCUGAUUACUUUGUGAGCCAUCACCAGCGACUAUGUCGUAGUG GGUAAAGCUCCCUCUUCGGAGGGAGCAUCAAAG |
| 2267 | 207 | ACUGGCGCUUUUAUUCUGAUUACUUUGAGAGCCAUCACCAGCGACUAUGUCGUAGU GGGUAAAGCUCCCUCUUCGGAGGGAGCAUCAAAG |
| 2268 | 208 | ACGGCGCUUUUAUCUGAUUACUUUGAGAGCCAUCACCAGCGACUAUGUCGUAGUGG GUAAAGCUCCCUCUUCGGAGGGAGCAUCAAAG |
| 2269 | 209 | ACUGGCGCUUUUAUAUGAUUACUUUGAGAGCCAUCACCAGCGACUAUGUCGUAGUG GGUAAAGCUCCCUCUUCGGAGGGAGCAUCAAAG |
| 2270 | 210 | ACUGGCGCUUUUAUCUUGAUUACUUUGAGAGCCAUCACCAGCGACUAUGUCGUAGU GGGUAAAGCUCCCUCUUCGGAGGGAGCAUCAAAG |
| 2271 | 211 | ACUGGCGCUUUUAUCUGAUUACUUUGAGAGCCAGCACCAGCGACUAUGUCGUAGUG GGUAAAGCUCCCUCUUCGGAGGGAGCAUCAAAG |
| 2272 | 212 | ACUGGCGCUGUUAUCUGAUUACUUCGAGAGCCAUCACCAGCGACUAUGUCGUAGUG GGUAAAGCUCCCUCUUCGGAGGGAGCAUCGAAG |
| 2273 | 213 | ACUGGCGCUCUUAUCUGAUUACUUCGAGAGCCAUCACCAGCGACUAUGUCGUAGUG GGUAAAGCUCCCUCUUCGGAGGGAGCAUCGAAG |
| 2274 | 214 | ACUGGCGCUUGUAUCUGAUUACUCUGAGAGCCAUCACCAGCGACUAUGUCGUAGUG GGUAAAGCUCCCUCUUCGGAGGGAGCAUCAGAG |
| 2275 | 215 | ACUGGCGCUUCUAUCUGAUUACUCUGAGAGCCAUCACCAGCGACUAUGUCGUAGUG GGUAAAGCUCCCUCUUCGGAGGGAGCAUCAGAG |
| 2276 | 216 | ACUGGCGCUUUGAUCUGAUUACCUUGAGAGCCAUCACCAGCGACUAUGUCGUAGUG GGUAAAGCUCCCUCUUCGGAGGGAGCAUCAAGG |

TABLE 2-continued

Exemplary gRNA Variant Scaffold Sequences

| SEQ ID NO. | Guide No. | Sequence |
|---|---|---|
| 2277 | 217 | ACUGGCGCUUUCAUCUGAUUACCUUGAGAGCCAUCACCAGCGACUAUGUCGUAGUGGGUAAAGCUCCCUCUUCGGAGGGAGCAUCAAGG |
| 2278 | 218 | ACUGGCGCUGUUAUCUGAUUACUUUGAGAGCCAUCACCAGCGACUAUGUCGUAGUGGGUAAAGCUCCCUCUUCGGAGGGAGCAUCAAAG |
| 2279 | 219 | ACUGGCGCUUUUAUCUGAUUACUUUGAGAGCCAUCACCAGCGACUAUGUCGUAGUGGGUAAAGCUCCCUCUUCGGAGGGAGCAUCGAAG |
| 2280 | 220 | ACUGGCGCUUUUAUCUGAUUACUUCGAGAGCCAUCACCAGCGACUAUGUCGUAGUGGGUAAAGCUCCCUCUUCGGAGGGAGCAUCAAAG |
| 2281 | 221 | ACUGGCACUUCUAUCUGAUUACUCUGAGAGCCAUCACCAGCGACUAUGUCGUAUGGGUAAAGCCGCUUACGGACUUCGGUCCGUAAGAGGCAUCAGAG |
| 2282 | 222 | ACUGGCACUUCUAUCUGAUUACUCUGAGAGCCAUCACCAGCGACUAUGUCGUAGUGGGUAAAGCUCCCUCUUCGGAGGGAGCAUCAGAG |
| 2283 | 223 | ACUGGCACCUUUAUCUGAUUACUUUGAGAGCCAUCACCAGCGACUAUGUCGUAUGGGUAAAGCCGCUUACGGACUUCGGUCCGUAAGAGGCAUCAAAG |
| 2284 | 224 | ACUGGCACUUGUAUCUGAUUACUCUGAGAGCCAUCACCAGCGACUAUGUCGUAUGGGUAAAGCCGCUUACGGACUUCGGUCCGUAAGAGGCAUCAGAG |
| 2285 | 225 | ACUGGCACUUGUAUCUGAUUACUCUGAGAGCCAUCACCAGCGACUAUGUCGUAGUGGGUAAAGCUCCCUCUUCGGAGGGAGCAUCAGAG |
| 2286 | 229 | ACUGGCACUUUUAUCUGAUUACUUUGAGAGCCAUCACCAGCGACUAUGUCGUAUGGGUAAAGCGCUUACGGACUUCGGUCCGUAAGAAGCAUCAAAG |
| 2287 | 230 | ACUGGCACUUCUAUCUGAUUACUCUGAGAGCCAUCACCAGCGACUAUGUCGUAUGGGUAAAGCGCUUACGGACUUCGGUCCGUAAGAAGCAUCAGAG |
| 2288 | 231 | ACUGGCGCUUCUAUCUGAUUACUCUGAGAGCCAUCACCAGCGACUAUGUCGUAUGGGUAAAGCCGCUUACGGACUUCGGUCCGUAAGAGGCAUCAGAG |
| 2289 | 232 | ACUGGCACUUCUAUCUGAUUACUCUGAGCGCCAUCACCAGCGACUAUGUCGUAUGGGUAAAGCCGCUUACGGACUUCGGUCCGUAAGAGGCAUCAGAG |
| 2290 | 233 | ACUGGCGCUUCUAUCUGAUUACUCUGAGCGCCAUCACCAGCGACUAUGUCGUAUGGGUAAAGCCGCUUACGGACUUCGGUCCGUAAGAGGCAUCAGAG |
| 2291 | 234 | ACUGGCGCUUCUAUCUGAUUACUCUGAGCGCCAUCACCAGCGACUAUGUCGUAUGGGUAAAGCGCCUUACGGACUUCGGUCCGUAAGGAGCAUCAGAG |
| 2292 | 235 | ACUGGCGCUUCUAUCUGAUUACUCUGAGCGCCAUCACCAGCGACUAUGUCGUAGUGGGUAAAGCCGCUUACGGACUUCGGUCCGUAAGAGGCAUCAGAG |
| 2293 | 236 | ACGGGACUUUCUAUCUGAUUACUCUGAAGUCCCUCACCAGCGACUAUGUCGUAUGGGUAAAGCCGCUUACGGACUUCGGUCCGUAAGAGGCAUCAGAG |
| 2294 | 237 | ACCUGUAGUUCUAUCUGAUUACUCUGACUACAGUCACCAGCGACUAUGUCGUAUGGGUAAAGCCGCUUACGGACUUCGGUCCGUAAGAGGCAUCAGAG |
| 2295 | 238 | ACUGGCGCUUUUAUCUGAUUACUUUGAGAGCCAUCACCAGCGACUAUGUCGUAGUGGGUAAAGCUGCACGGUGGGCGCAGCUUCGGCUGACGGUACACCGUGCAGCAUCAAAG |
| 2296 | 239 | ACUGGCGCUUUUAUCUGAUUACUUUGAGAGCCAUCACCAGCGACUAUGUCGUAGUGGGUAAAGCUGCACGGUGGGCGCAGCUUCGGCUGACGGUACACCGGUGGGCGCAGCUUCGGCUGACGGUACACCGUGCAGCAUCAAAG |
| 2297 | 240 | ACUGGCGCUUUUAUCUGAUUACUUUGAGAGCCAUCACCAGCGACUAUGUCGUAGUGGGUAAAGCUGCACGGUGGGCGCAGCUUCGGCUGACGGUACACCGGUGGGCGCAGCUUCGGCUGACGGUACACCGGUGGGCGCAGCUUCGGCUGACGGUACACCGUGCAGCAUCAAAG |
| 2298 | 241 | ACUGGCGCUUUUAUCUGAUUACUUUGAGAGCCAUCACCAGCGACUAUGUCGUAGUGGGUAAAGCUGCACGGUGGGCGCAGCUUCGGCUGACGGUACACCGGUGGGCGCAGCUUCGGCUGACGGUACACCGGUGGGCGCAGCUUCGGCUGACGGUACACCGGUGGGCGCAGCUUCGGCUGACGGUACACCGUGCAGCAUCAAAG |

TABLE 2-continued

Exemplary gRNA Variant Scaffold Sequences

| SEQ ID NO. | Guide No. | Sequence |
|---|---|---|
| 2299 | 242 | ACUGGCGCUUUUAUCUGAUUACUUUGAGAGCCAUCACCAGCGACUAUGUCGUAGUGGGUAAAGCUGCACGGUGGGCGCAGCUUCGGCUGACGGUACACCGGUGGGCGCAGCUUCGGCUGACGGUACACCGGUGGGCGCAGCUUCGGCUGACGGUACACCGGUGGGCGCAGCUUCGGCUGACGGUACACCGGUGGGCGCAGCUUCGGCUGACGGUACACCGUGCAGCAUCAAAG |
| 2300 | 243 | ACUGGCGCUUUUAUCUGAUUACUUUGAGAGCCAUCACCAGCGACUAUGUCGUAGUGGGUAAAGCUGCACCUAGCGGAGGCUAGGUGCAGCAUCAAAG |
| 2301 | 244 | ACUGGCGCUUUUAUCUGAUUACUUUGAGAGCCAUCACCAGCGACUAUGUCGUAGUGGGUAAAGCUGCACCUCGGCUUGCUGAAGCGCGCACGGCAAGAGGCGAGGUGCAGCAUCAAAG |
| 2302 | 245 | ACUGGCGCUUUUAUCUGAUUACUUUGAGAGCCAUCACCAGCGACUAUGUCGUAGUGGGUAAAGCUGCACCUCUCUCGACGCAGGACUCGGCUUGCUGAAGCGCGCACGGCAAGAGGCGAGGGGCGGCGACUGGUGAGUACGCCAAAAAUUUUGACUAGCGGAGGCUAGAAGGAGAGAGGUGCAGCAUCAAAG |
| 2303 | 246 | ACUGGCGCUUUUAUCUGAUUACUUUGAGAGCCAUCACCAGCGACUAUGUCGUAGUGGGUAAAGCUGCACGGUGCCCGUCUGUUGUGUCGAGAGACGCCAAAAAUUUUGACUAGCGGAGGCUAGAAGGAGAGAGAUGGGUGCCGUGCAGCAUCAAAG |
| 2304 | 247 | ACUGGCGCUUUUAUCUGAUUACUUUGAGAGCCAUCACCAGCGACUAUGUCGUAGUGGGUAAAGCUGCACAUGGAGAGGAGAUGUGCAGCAUCAAAG |
| 2305 | 248 | ACUGGCGCUUUUAUCUGAUUACUUUGAGAGCCAUCACCAGCGACUAUGUCGUAGUGGGUAAAGCUGCACAUGGAGAUGUGCAGCAUCAAAG |
| 2306 | 249 | ACUGGCGCUUUUAUCUGAUUACUUUGAGAGCCAUCACCAGCGACUAUGUCGUAGUGGGUAAAGCUUGGGCGCAGCGUCAAUGACGCUGACGGUACAAGCAUCAAAG |
| 2307 | 250 | ACUGGCGCUUUUAUCUGAUUACUUUGAGAGCCAUCACCAGCGACUAUGUCGUAGUGGGUAAAGCUGCACUAUGGGCGCAGCGUCAAUGACGCUGACGGUACAGGCCACAUGAGGAUCACCCAUGUGGUAUAGUGCAGCAUCAAAG |
| 2308 | 251 | ACUGGCGCUUUUAUCUGAUUACUUUGAGAGCCAUCACCAGCGACUAUGUCGUAGUGGGUAAAGCUGCACUAUGGGCGCAGCUCAUGAGGAUCACCCAUGAGCUGACGGUACAGGCCACAUGAGGAUCACCCAUGUGGUAUAGUGCAGCAUCAAAG |
| 2309 | 252 | ACUGGCGCUUUUAUCUGAUUACUUUGAGAGCCAUCACCAGCGACUAUGUCGUAGUGGGUAAAGCUGCACUAUGGGCGCAGCGUCAAUGACGCUGACGGUACAGGCCACAUGGCAGUCGUAACGACGCGGGUGGUAUAGUGCAGCAUCAAAG |
| 2310 | 253 | ACUGGCGCUUUUAUCUGAUUACUUUGAGAGCCAUCACCAGCGACUAUGUCGUAGUGGGUAAAGCUGCACUAUGGGCGCAGCAAACAUGGCAGUCCUAAGGACGCGGGUUUUGCUGACGGUACAGGCCACAUGGCAGUCGUAACGACGCGGGUGGUAUAGUGCAGCAUCAAAG |
| 2311 | 254 | ACUGGCGCUUUUAUCUGAUUACUUUGAGAGCCAUCACCAGCGACUAUGUCGUAGUGGGUAAAGCUGCACUAUGGGCGCAGACAUGGCAGUCGUAACGACGCGGGUCUGACGGUACAGGCCACAUGAGGAUCACCCAUGUGGUAUAGUGCAGCAUCAAAG |
| 2312 | 255 | ACUGGCGCUUUUAUCUGAUUACUUUGAGAGCCAUCACCAGCGACUAUGUCGUAGUGGGUAAAGCUGCACUAAGGAGUUUAUAUGGAAACCCUUAGUGCAGCAUCAAAG |
| 2313 | 256 | ACUGGCGCUUUUAUCUGAUUACUUUGAGAGCCAUCACCAGCGACUAUGUCGUAGUGGGUAAAGCUCAGGAAGCACUAUGGGCGCAGCGUCAAUGACGCUGACGGUACAGGCCAGACAAUUAUUGUCUGGUAUAGUGCAGCAGCAGAACAAUUUGCUGAGGGCUAUUGAGGCGCAACAGCAUCUGUUGCAACUCACAGUCUGGGGCAUCAAGCAGCUCCAGGCAAGAAUCCUGAGCAUCAAAG |
| 2314 | 257 | ACUGGCGCUUUUAUCUGAUUACUUUGAGAGCCAUCACCAGCGACUAUGUCGUAGUGGGUAAAGCUGCACGCCCUGAAGAAGGGCGUGCAGCAUCAAAG |
| 2315 | 258 | ACUGGCGCUUUUAUCUGAUUACUUUGAGAGCCAUCACCAGCGACUAUGUCGUAGUGGGUAAAGCUGCACGGCUCGUGUAGCUCAUUAGCUCCGAGCCGUGCAGCAUCAAAG |
| 2316 | 259 | ACUGGCGCUUUUAUCUGAUUACUUUGAGAGCCAUCACCAGCGACUAUGUCGUAGUGGGUAAAGCUGCACCCGUGUGCAUCCGCAGUGUCGGAUCCACGGGUGCAGCAUCAAAG |
| 2317 | 260 | ACUGGCGCUUUUAUCUGAUUACUUUGAGAGCCAUCACCAGCGACUAUGUCGUAGUGGGUAAAGCUGCACGGAAUCCAUUGCACUCCGGAUUUCACUAGGUGCAGCAUCAAAG |

TABLE 2-continued

| Exemplary gRNA Variant Scaffold Sequences | | |
|---|---|---|
| SEQ ID NO. | Guide No. | Sequence |
| 2318 | 261 | ACUGGCGCUUUUAUCUGAUUACUUUGAGAGCCAUCACCAGCGACUAUGUCGUAGUGGGUAAAGCUGCACAUGCAUGUCUAAGACAGCAUGUGCAGCAUCAAAG |
| 2319 | 262 | ACUGGCGCUUUUAUCUGAUUACUUUGAGAGCCAUCACCAGCGACUAUGUCGUAGUGGGUAAAGCUGCACAAAACAUAAGGAAAACCUAUGUUGUGCAGCAUCAAAG |
| 2320 | 263 | ACUGGCGCUUCUAUCUGAUUACUCUGAGCGCCAUCACCAGCGACUAUGUCGUAGUGGGUAAAGCCGCUUACGGACUAUGGGCGCAGCGUCAAUGACGCUGACGGUACAGGCCAGACAAUUAUUGUCUGGUAUAGUCCGUAAGAGGCAUCAGAG |
| 2321 | 264 | ACUGGCGCUUCUAUCUGAUUACUCUGAGCGCCAUCACCAGCGACUAUGUCGUAGUGGGUAAAGCCGCUUACGGGUGGGCGCAGCGUCAAUGACGCUGACGGUACAGGCCAGACAAUUAUUGUCUGGUACCCGUAAGAGGCAUCAGAG |
| 2322 | 265 | ACUGGCGCUUCUAUCUGAUUACUCUGAGCGCCAUCACCAGCGACUAUGUCGUAGUGGGUAAAGCCGCUUACGGUAUGGGCGCAGCGUCAAUGACGCUGACGGUACAGGCCACAUGAGGAUCACCCAUGUGGUAUACCGUAAGAGGCAUCAGAG |
| 2323 | 266 | ACUGGCGCUUUUAUCUGAUUACUUUGAGAGCCAUCACCAGCGACUAUGUCGUAGUGGGUAAAGCUCCCUAUGGGCGCAGCGUCAAUGACGCUGACGGUACAGGCCACAUGAGGAUCACCCAUGUGGUAUAGGGAGCAUCAAAG |
| 2324 | 267 | ACUGGCGCUUCUAUCUGAUUACUCUGAGCGCCAUCACCAGCGACUAUGUCGUAGUGGGUAAAGCCGCUUACGGUAUGGGCGCAGCUCAUGAGGAUCACCCAUGAGCUGACGGUACAGGCCACAUGAGGAUCACCCAUGUGGUAUACCGUAAGAGGCAUCAGAG |
| 2325 | 268 | ACUGGCGCUUUUAUCUGAUUACUUUGAGAGCCAUCACCAGCGACUAUGUCGUAGUGGGUAAAGCUCCCUAUGGGCGCAGCUCAUGAGGAUCACCCAUGAGCUGACGGUACAGGCCACAUGAGGAUCACCCAUGUGGUAUAGGGAGCAUCAAAG |
| 2326 | 269 | ACUGGCGCUUCUAUCUGAUUACUCUGAGCGCCAUCACCAGCGACUAUGUCGUAGUGGGUAAAGCCGCUUACGGUAUGGGCGCAGCGUCAAUGACGCUGACGGUACAGGCCACAUGGCAGUCGUAACGACGCGGGUGGUAUACCGUAAGAGGCAUCAGAG |
| 2327 | 270 | ACUGGCGCUUUUAUCUGAUUACUUUGAGAGCCAUCACCAGCGACUAUGUCGUAGUGGGUAAAGCUCCCUAUGGGCGCAGCGUCAAUGACGCUGACGGUACAGGCCACAUGGCAGUCGUAACGACGCGGGUGGUAUAGGGAGCAUCAAAG |
| 2328 | 271 | ACUGGCGCUUCUAUCUGAUUACUCUGAGCGCCAUCACCAGCGACUAUGUCGUAGUGGGUAAAGCCGCUUACGGUAUGGGCGCAGCAAACAUGGCAGUCCUAAGGACGCGGGUUUUGCUGACGGUACAGGCCACAUGGCAGUCGUAACGACGCGGGUGGUAUACCGUAAGAGGCAUCAGAG |
| 2329 | 272 | ACUGGCGCUUUUAUCUGAUUACUUUGAGAGCCAUCACCAGCGACUAUGUCGUAGUGGGUAAAGCUCCCUAUGGGCGCAGCAAACAUGGCAGUCCUAAGGACGCGGGUUUUGCUGACGGUACAGGCCACAUGGCAGUCGUAACGACGCGGGUGGUAUAGGGAGCAUCAAAG |
| 2330 | 273 | ACUGGCGCUUCUAUCUGAUUACUCUGAGCGCCAUCACCAGCGACUAUGUCGUAGUGGGUAAAGCCGCUUACGGUAUGGGCGCAGACAUGGCAGUCGUAACGACGCGGGUCUGACGGUACAGGCCACAUGAGGAUCACCCAUGUGGUAUACCGUAAGAGGCAUCAGAG |
| 2331 | 274 | ACUGGCGCUUUUAUCUGAUUACUUUGAGAGCCAUCACCAGCGACUAUGUCGUAGUGGGUAAAGCUCCCUAUGGGCGCAGACAUGGCAGUCGUAACGACGCGGGUCUGACGGUACAGGCCACAUGAGGAUCACCCAUGUGGUAUAGGGAGCAUCAAAG |
| 57544 | 275 | ACUGGCGCUUUUAUCUGAUUACUUUGAGAGCCAUCACCAGCGACUAUGUCGUAGUGGGUAAAGCUGCACUAUGGGCGCAGCACCUGAGGAUCACCCAGGUGCUGACGGUACAGGCCACCUGAGGAUCACCCAGGUGGUAUAGUGCAGCAUCAAAG |
| 57545 | 276 | ACUGGCGCUUUUAUCUGAUUACUUUGAGAGCCAUCACCAGCGACUAUGUCGUAGUGGGUAAAGCUGCACUAUGGGCGCAGCGCAUGAGGAUCACCCAUGCGCUGACGGUACAGGCCGCAUGAGGAUCACCCAUGCGGUAUAGUGCAGCAUCAAAG |
| 57546 | 277 | ACUGGCGCUUUUAUCUGAUUACUUUGAGAGCCAUCACCAGCGACUAUGUCGUAGUGGGUAAAGCUGCACUAUGGGCGCAGCGCCUGAGGAUCACCCAGGCGCUGACGGUACAGGCCGCCUGAGGAUCACCCAGGCGGUAUAGUGCAGCAUCAAAG |
| 57547 | 278 | ACUGGCGCUUUUAUCUGAUUACUUUGAGAGCCAUCACCAGCGACUAUGUCGUAGUGGGUAAAGCUGCACUAUGGGCGCAGCGCCUGAGCAUCAGCCAGGCGCUGACGGUACAGGCCGCCUGAGCAUCAGCCAGGCGGUAUAGUGCAGCAUCAAAG |

TABLE 2-continued

Exemplary gRNA Variant Scaffold Sequences

| SEQ ID NO. | Guide No. | Sequence |
|---|---|---|
| 57548 | 279 | ACUGGCGCUUUUAUCUGAUUACUUUGAGAGCCAUCACCAGCGACUAUGUCGUAGUGGGUAAAGCUGCACUAUGGGCGCAGCACAUGAGCAUCAGCCAUGUGCUGACGGUACAGGCCACAUGAGCAUCAGCCAUGUGGUAUAGUGCAGCAUCAAAG |
| 57549 | 280 | ACUGGCGCUUUUAUCUGAUUACUUUGAGAGCCAUCACCAGCGACUAUGUCGUAGUGGGUAAAGCUGCACUAUGGGCGCAGCACAUGAGUAUCAACCAUGUGCUGACGGUACAGGCCACAUGAGUAUCAACCAUGUGGUAUAGUGCAGCAUCAAAG |
| 57550 | 281 | ACUGGCGCUUUUAUCUGAUUACUUUGAGAGCCAUCACCAGCGACUAUGUCGUAGUGGGUAAAGCUGCACUAUGGGCGCAGCACAUGAGAAUCAGCCAUGUGCUGACGGUACAGGCCACAUGAGAAUCAGCCAUGUGGUAUAGUGCAGCAUCAAAG |
| 57551 | 282 | ACUGGCGCUUUUAUCUGAUUACUUUGAGAGCCAUCACCAGCGACUAUGUCGUAGUGGGUAAAGCUGCACUAUGGGCGCAGCCCUUGAGGAUCACCCAUGUGCUGACGGUACAGGCCCCUUGAGGAUCACCCAUGUGGUAUAGUGCAGCAUCAAAG |
| 57552 | 283 | ACUGGCGCUUUUAUCUGAUUACUUUGAGAGCCAUCACCAGCGACUAUGUCGUAGUGGGUAAAGCUGCACUAUGGGCGCAGCACUUGAGGAUCACCCAUGUGCUGACGGUACAGGCCACUUGAGGAUCACCCAUGUGGUAUAGUGCAGCAUCAAAG |
| 57553 | 284 | ACUGGCGCUUUUAUCUGAUUACUUUGAGAGCCAUCACCAGCGACUAUGUCGUAGUGGGUAAAGCUGCACUAUGGGCGCAGCACCUGAGGAUCACCCAUGUGCUGACGGUACAGGCCACCUGAGGAUCACCCAUGUGGUAUAGUGCAGCAUCAAAG |
| 57554 | 285 | ACUGGCGCUUUUAUCUGAUUACUUUGAGAGCCAUCACCAGCGACUAUGUCGUAGUGGGUAAAGCUGCACUAUGGGCGCAGCACAUGAGGAUCACCUAUGUGCUGACGGUACAGGCCACAUGAGGAUCACCUAUGUGGUAUAGUGCAGCAUCAAAG |
| 57555 | 286 | ACUGGCGCUUUUAUCUGAUUACUUUGAGAGCCAUCACCAGCGACUAUGUCGUAGUGGGUAAAGCUGCACUAUGGGCGCAGCACAUUAGGAUCACCAAUGUGCUGACGGUACAGGCCACAUUAGGAUCACCAAUGUGGUAUAGUGCAGCAUCAAAG |
| 57556 | 287 | ACUGGCGCUUUUAUCUGAUUACUUUGAGAGCCAUCACCAGCGACUAUGUCGUAGUGGGUAAAGCUGCACUAUGGGCGCAGCACAUUAGGAUCACCGAUGUGCUGACGGUACAGGCCACAUUAGGAUCACCGAUGUGGUAUAGUGCAGCAUCAAAG |
| 57557 | 288 | ACUGGCGCUUUUAUCUGAUUACUUUGAGAGCCAUCACCAGCGACUAUGUCGUAGUGGGUAAAGCUGCACUAUGGGCGCAGCACAUUAGGAUCACCUAUGUGCUGACGGUACAGGCCACAUUAGGAUCACCUAUGUGGUAUAGUGCAGCAUCAAAG |
| 57558 | 289 | ACUGGCGCUUUUAUCUGAUUACUUUGAGAGCCAUCACCAGCGACUAUGUCGUAGUGGGUAAAGCUGCACUAUGGGCGCAGCACAUGAGGAUUACCCAUGUGCUGACGGUACAGGCCACAUGAGGAUUACCCAUGUGGUAUAGUGCAGCAUCAAAG |
| 57559 | 290 | ACUGGCGCUUUUAUCUGAUUACUUUGAGAGCCAUCACCAGCGACUAUGUCGUAGUGGGUAAAGCUGCACUAUGGGCGCAGCACAUGAGGAUAACCCAUGUGCUGACGGUACAGGCCACAUGAGGAUAACCCAUGUGGUAUAGUGCAGCAUCAAAG |
| 57560 | 291 | ACUGGCGCUUUUAUCUGAUUACUUUGAGAGCCAUCACCAGCGACUAUGUCGUAGUGGGUAAAGCUGCACUAUGGGCGCAGCACAUGAGGAUGACCCAUGUGCUGACGGUACAGGCCACAUGAGGAUGACCCAUGUGGUAUAGUGCAGCAUCAAAG |
| 57561 | 292 | ACUGGCGCUUUUAUCUGAUUACUUUGAGAGCCAUCACCAGCGACUAUGUCGUAGUGGGUAAAGCUGCACUAUGGGCGCAGCACAUGAGGACCACCCAUGUGCUGACGGUACAGGCCACAUGAGGACCACCCAUGUGGUAUAGUGCAGCAUCAAAG |
| 57562 | 293 | ACUGGCGCUUUUAUCUGAUUACUUUGAGAGCCAUCACCAGCGACUAUGUCGUAGUGGGUAAAGCUGCACUAUGGGCGCAGCAGAUGAGGAUCACCCAUGGGCUGACGGUACAGGCCAGAUGAGGAUCACCCAUGGGGUAUAGUGCAGCAUCAAAG |
| 57563 | 294 | ACUGGCGCUUUUAUCUGAUUACUUUGAGAGCCAUCACCAGCGACUAUGUCGUAGUGGGUAAAGCUGCACUAUGGGCGCAGCACAUGGGGAUCACCCAUGUGCUGACGGUACAGGCCACAUGGGGAUCACCCAUGUGGUAUAGUGCAGCAUCAAAG |
| 57564 | 295 | ACUGGCGCUUUUAUCUGAUUACUUUGAGAGCCAUCACCAGCGACUAUGUCGUAGUGGGUAAAGCUGCACUAUGGGCGCAGCACAUGAGGAUCACCCAUGUGCUGACGGUACAGGCCACAUGAGGAUCACCCAUGUGGUAUAGUGCAGCAUCAAAG |
| 57565 | 296 | ACUGGCGCUUUUAUCUGAUUACUUUGAGAGCCAUCACCAGCGACUAUGUCGUAGUGGGUAAAGCUCACCUGAGGAUCACCCAGGUGAGCAUCAAAG |
| 57566 | 297 | ACUGGCGCUUUUAUCUGAUUACUUUGAGAGCCAUCACCAGCGACUAUGUCGUAGUGGGUAAAGCUCGCAUGAGGAUCACCCAUGCGAGCAUCAAAG |

TABLE 2-continued

| Exemplary gRNA Variant Scaffold Sequences | | |
|---|---|---|
| SEQ ID NO. | Guide No. | Sequence |
| 57567 | 298 | ACUGGCGCUUUUAUCUGAUUACUUUGAGAGCCAUCACCAGCGACUAUGUCGUAGUG GGUAAAGCUCGCCUGAGGAUCACCCAGGCGAGCAUCAAAG |
| 57568 | 299 | ACUGGCGCUUUUAUCUGAUUACUUUGAGAGCCAUCACCAGCGACUAUGUCGUAGUG GGUAAAGCUCGCCUGAGCAUCAGCCAGGCGAGCAUCAAAG |
| 57569 | 300 | ACUGGCGCUUUUAUCUGAUUACUUUGAGAGCCAUCACCAGCGACUAUGUCGUAGUG GGUAAAGCUCACAUGAGCAUCAGCCAUGUGAGCAUCAAAG |
| 57570 | 301 | ACUGGCGCUUUUAUCUGAUUACUUUGAGAGCCAUCACCAGCGACUAUGUCGUAGUG GGUAAAGCUCACAUGAGUAUCAACCAUGUGAGCAUCAAAG |
| 57571 | 302 | ACUGGCGCUUUUAUCUGAUUACUUUGAGAGCCAUCACCAGCGACUAUGUCGUAGUG GGUAAAGCUCACAUGAGAAUCAGCCAUGUGAGCAUCAAAG |
| 57572 | 303 | ACUGGCGCUUUUAUCUGAUUACUUUGAGAGCCAUCACCAGCGACUAUGUCGUAGUG GGUAAAGCUCCCUUGAGGAUCACCCAUGUGAGCAUCAAAG |
| 57573 | 304 | ACUGGCGCUUUUAUCUGAUUACUUUGAGAGCCAUCACCAGCGACUAUGUCGUAGUG GGUAAAGCUCACUUGAGGAUCACCCAUGUGAGCAUCAAAG |
| 57574 | 305 | ACUGGCGCUUUUAUCUGAUUACUUUGAGAGCCAUCACCAGCGACUAUGUCGUAGUG GGUAAAGCUCACCUGAGGAUCACCCAUGUGAGCAUCAAAG |
| 57575 | 306 | ACUGGCGCUUUUAUCUGAUUACUUUGAGAGCCAUCACCAGCGACUAUGUCGUAGUG GGUAAAGCUCACAUGAGGAUCACCUAUGUGAGCAUCAAAG |
| 57576 | 307 | ACUGGCGCUUUUAUCUGAUUACUUUGAGAGCCAUCACCAGCGACUAUGUCGUAGUG GGUAAAGCUCACAUUAGGAUCACCAAUGUGAGCAUCAAAG |
| 57577 | 308 | ACUGGCGCUUUUAUCUGAUUACUUUGAGAGCCAUCACCAGCGACUAUGUCGUAGUG GGUAAAGCUCACAUUAGGAUCACCGAUGUGAGCAUCAAAG |
| 57578 | 309 | ACUGGCGCUUUUAUCUGAUUACUUUGAGAGCCAUCACCAGCGACUAUGUCGUAGUG GGUAAAGCUCACAUUAGGAUCACCUAUGUGAGCAUCAAAG |
| 57579 | 310 | ACUGGCGCUUUUAUCUGAUUACUUUGAGAGCCAUCACCAGCGACUAUGUCGUAGUG GGUAAAGCUCACAUGAGGAUUACCCAUGUGAGCAUCAAAG |
| 57580 | 311 | ACUGGCGCUUUUAUCUGAUUACUUUGAGAGCCAUCACCAGCGACUAUGUCGUAGUG GGUAAAGCUCACAUGAGGAUAACCCAUGUGAGCAUCAAAG |
| 57581 | 312 | ACUGGCGCUUUUAUCUGAUUACUUUGAGAGCCAUCACCAGCGACUAUGUCGUAGUG GGUAAAGCUCACAUGAGGAUGACCCAUGUGAGCAUCAAAG |
| 57582 | 313 | ACUGGCGCUUUUAUCUGAUUACUUUGAGAGCCAUCACCAGCGACUAUGUCGUAGUG GGUAAAGCUCACAUGAGGACCACCCAUGUGAGCAUCAAAG |
| 57583 | 314 | ACUGGCGCUUUUAUCUGAUUACUUUGAGAGCCAUCACCAGCGACUAUGUCGUAGUG GGUAAAGCUCAGAUGAGGAUCACCCAUGGGAGCAUCAAAG |
| 57584 | 315 | ACUGGCGCUUUUAUCUGAUUACUUUGAGAGCCAUCACCAGCGACUAUGUCGUAGUG GGUAAAGCUCACAUGGGGAUCACCCAUGUGAGCAUCAAAG |
| 59352 | 316 | ACUGGCGCUUCUAUCUGAUUACUCUGAGCGCCAUCACCAGCGACUAUGUCGUAGUG GGUAAAGCUCCCUCUUCGGAGGGAGCAUCAGAG |
| 57585 | 317 | ACUGGCGCUUCUAUCUGAUUACUCUGAGCGCCAUCACCAGCGACUAUGUCGUAGUG GGUAAAGCUCACAUGAGGAUCACCCAUGUGAGCAUCAGAG |
| 57586 | 318 | ACUGGCGCUUCUAUCUGAUUACUCUGAGCGCCAUCACCAGCGACUAUGUCGUAGUG GGUAAAGCUGCACUAUGGGCGCAGCGUCAAUGACGCUGACGGUACAGGCCACAUGA GGAUCACCCAUGUGGUAUAGUGCAGCAUCAGAG |
| 57587 | 319 | ACUGGCGCUUCUAUCUGAUUACUCUGAGCGCCAUCACCAGCGACUAUGUCGUAGUG GGUAAAGCUGCACUAUGGGCGCAGCUCAUGAGGAUCACCCAUGAGCUGACGGUACA GGCCACAUGAGGAUCACCCAUGUGGUAUAGUGCAGCAUCAGAG |

TABLE 2-continued

Exemplary gRNA Variant Scaffold Sequences

| SEQ ID NO. | Guide No. | Sequence |
|---|---|---|
| 57588 | 320 | ACUGGCGCUUCUAUCUGAUUACUCUGAGCGCCAUCACCAGCGACUAUGUCGUAGUG GGUAAAGCUGCACUAUGGGCGCAGACAUGGCAGUCGUAACGACGCGGGUCUGACGG UACAGGCCACAUGAGGAUCACCCAUGUGGUAUAGUGCAGCAUCAGAG |
| 57589 | 321 | ACUGGCGCUUUUAUCUGAUUACUUUGAGAGCCAUCACCAGCGACUAUGUCGUAGUG GGUAAAGCUGCACUAUGGGGCCACAUGAGGAUCACCCAUGUGGUGUACAGCGCAGC GUCAAUGACGCUGACGAUAGUGCAGCAUCAAAG |

In some embodiments, a gRNA variant of the gene repressor systems comprises a sequence of any one of SEQ ID NOs: 2238-2331, 57544-57589, and 59352, set forth in Table 2. In some embodiments, a gRNA variant comprises a sequence of any one of SEQ ID NOS: 2238, 2241, 2244, 2248, 2249, or 2259-2280. In some embodiments, a gRNA variant comprises a sequence of any one of SEQ ID NOS: 2238, 2241, 2244, 2248, 2249, or 2259-2280. In some embodiments, a gRNA variant comprises a sequence of any one of SEQ ID NOS: 2281-2331. In some embodiments, a gRNA variant comprises a sequence of any one of SEQ ID NOS: 57544-57589 and 59352. In some embodiments, a gRNA variant comprises one or more chemical modifications to the sequence.

Additional representative gRNA variant scaffold sequences for use with the gene repressor systems of the instant disclosure are included as SEQ ID NOS: 2101-2237.

e. gRNA 316

Guide scaffolds can be made by several methods, including recombinantly or by solid-phase RNA synthesis. However, the length of the scaffold can affect the manufacturability when using solid-phase RNA synthesis, with longer lengths resulting in increased manufacturing costs, decreased purity and yield, and higher rates of synthesis failures. For use in lipid nanoparticle (LNP) formulations, solid-phase RNA synthesis of the scaffold is preferred in order to generate the quantities needed for commercial development. While previous experiments had identified gRNA scaffold 235 (SEQ ID NO: 2292) as having enhanced properties relative to gRNA scaffold 174 (SEQ ID NO: 2238) its increased length rendered its use for LNP formulations problematic. Accordingly, alternative sequences were sought. In some embodiments, the disclosure provides gRNA wherein the gRNA and linked targeting sequence has a sequence less than about 120 nucleotides, less than about 110 nucleotides, or less than about 100 nucleotides.

In one embodiment, a scaffold was designed wherein the scaffold 235 sequence was modified by a domain swap in which the extended stem loop of scaffold 174 replaced the extended stem loop of the 235 scaffold, resulting in the chimeric RNA scaffold 316 having the sequence ACUGGCGCUUCUAUCUGAUUACUCUGAGCGCCAUCACCAGCGACUAUGUCGUAGU GGGUAAAGCUCCCUCUUCGGAGGGAGCAUCAGAG (SEQ ID NO: 59352), having 89 nucleotides, compared with the 99 nucleotides of gRNA scaffold 235. In addition to improvements in manufacturability, the 316 scaffold was determined to perform comparably or more favorably than gRNA scaffold 174 in editing assays, as described in the Examples. The resulting 316 scaffold had the further advantage in that the extended stem loop did not contain CpG motifs; an enhanced property described more fully, below.

f. Chemically-Modified Scaffolds

In another aspect, the present disclosure relates to gRNAs having chemical modifications. In some embodiments, the chemical modification is addition of a 2'O-methyl group to one or more nucleotides of the sequence. In some embodiments, the chemical modification is substitution of a phosphorothioate bond between two or more nucleotides of the sequence.

g. Stem Loop Modifications

In some embodiments, the gRNA variant of the gene repressor systems comprises an exogenous extended stem loop, with such differences from a reference gRNA described as follows. In some embodiments, an exogenous extended stem loop has little or no identity to the reference stem loop regions disclosed herein (e.g., SEQ ID NO: 15). In some embodiments, an exogenous stem loop is at least 10 bp, at least 20 bp, at least 30 bp, at least 40 bp, at least 50 bp, at least 60 bp, at least 70 bp, at least 80 bp, at least 90 bp, at least 100 bp, at least 200 bp, at least 300 bp, at least 400 bp, at least 500 bp, at least 600 bp, at least 700 bp, at least 800 bp, at least 900 bp, or at least 1,000 bp. In some embodiments, the gRNA variant comprises an extended stem loop region comprising at least 10, at least 100, at least 500, or at least 1000 nucleotides. In some embodiments, the heterologous stem loop increases the stability of the gRNA. In some embodiments, the heterologous RNA stem loop is capable of binding a protein, an RNA structure, a DNA sequence, or a small molecule. In some embodiments, an exogenous stem loop region comprises one or more RNA stem loops or hairpins, for example a thermostable RNA such as MS2 binding (or tagging) sequence (ACAUGAGGAUCACCCAUGU (SEQ ID NO: 33276), Qβ hairpin (AUGCAUGUCUAAGACAGCAU (SEQ ID NO: 33277)), U1 hairpin II (GGAAUCCAUUGCACUCCGGAUUUCACUAG (SEQ ID NO: 33278)), Uvsx (CCUCUUCGGAGG (SEQ ID NO: 33279)), PP7 (AAGGAGUUUAUAUGGAAACCCUU (SEQ ID NO: 33280)), Phage replication loop (AGGUGGGACGACCUCUCGGUCGUCCUAUCU (SEQ ID NO: 33281)), Kissing loop. a (UGCUCGCUCCGUUCGAGCA (SEQ ID NO: 33282)), Kissing loop_b1 (UGCUCGACGCGUCCUCGAGCA (SEQ ID NO: 33283)), Kissing loop_b2 (UGCUCGUUUGCGGCUACGAGCA (SEQ ID NO: 33284)), G quadriplex M3q (AGGGAGGGAGGGAGAGG (SEQ ID NO: 33285)), G quadriplex telomere basket (GGUUAGGGUUAGGGUUAGG (SEQ ID NO: 33286)), Sarcin-ricin loop (CUGCUCAGUACGAGAGGAACCGCAG (SEQ ID NO: 33287)), Pseudoknots (UACACUGGGAUCGCUGAAUUAGAGAUCGGCGUCCUUUCAUUCUAUAUACUUUGG AGUUUUAAAAUGUCUCUAAGUACA (SEQ ID NO: 33288)), transactivation response element (TAR) (GGCUCGUGUAGCU- CAUUAGCUCCGAGCC (SEQ ID NO: 57741)), iron responsive element (IRE) CCGUGUGCAUCCGCAGUGUCGGAUCCACGG (SEQ ID NO: 57742)), transactivation response element (TAR) GGCUCGUGUAGCUCAUUAGCUCCGAGCC (SEQ ID NO: 57743)), phage GA hairpin (AAAACAUAAGGAAAACCUAUGUU (SEQ ID NO: 57744)), phage AN hairpin (GCCCUGAAGAAGGGC (SEQ ID NO: 57745)), or sequence variants thereof. In some embodiments, one of the foregoing hairpin sequences is incorporated into the stem loop to help traffic the incorporation of the gRNA (and an associated CasX in an RNP complex) into a budding XDP (described more fully, below).

In some embodiments, a sgRNA variant of the gene repressor systems of the disclosure comprises one or more additional changes to a previously generated variant, the previously generated variant itself serving as the reference sequence. In some embodiments, a sgRNA variant comprises one or more additional changes to a sequence of SEQ ID NO: 2238, SEQ ID NO: 2239, SEQ ID NO: 2240, SEQ ID NO: 2241, SEQ ID NO: 2241, SEQ ID NO: 2274, SEQ ID NO: 2275, SEQ ID NO: 2279, or SEQ ID NO: 59352.

In exemplary embodiments, a sgRNA variant comprises one or more additional changes to a sequence of SEQ ID NO: 2238 (Variant Scaffold 174, referencing Table 2).

In exemplary embodiments, a sgRNA variant comprises one or more additional changes to a sequence of SEQ ID NO: 2239 (Variant Scaffold 175, referencing Table 2).

In exemplary embodiments, a sgRNA variant comprises one or more additional changes to a sequence of SEQ ID NO: 2275 (Variant Scaffold 215, referencing Table 2).

In exemplary embodiments, a sgRNA variant comprises one or more additional changes to a sequence of SEQ ID NO: 2292 (Variant Scaffold 235, referencing Table 2).

In exemplary embodiments, a sgRNA variant comprises one or more additional changes to a sequence of SEQ ID NO: 59352 (Variant Scaffold 316, referencing Table 2).

h. Complex Formation with dCasX Protein

In some embodiments, a gRNA variant of the disclosure has an improved affinity for a dCasX and linked repressor domain(s) when compared to a reference gRNA, thereby improving its ability to form a ribonucleoprotein (RNP) complex with the dCasX protein and linked repressor domain(s). Improving ribonucleoprotein complex formation may, in some embodiments, improve the efficiency with which functional RNPs are assembled. In some embodiments, greater than 90%, greater than 93%, greater than 95%, greater than 96%, greater than 97%, greater than 98% or greater than 99% of RNPs comprising a gRNA variant and a spacer are competent for binding to a target nucleic acid.

Exemplary nucleotide changes that can improve the ability of gRNA variants to form a complex with dXR may, in some embodiments, include replacing the scaffold stem with a thermostable stem loop. Without wishing to be bound by any theory, replacing the scaffold stem with a thermostable stem loop could increase the overall binding stability of the gRNA variant with the dXR. Alternatively, or in addition, removing a large section of the stem loop could change the gRNA variant folding kinetics and make a functional folded gRNA easier and quicker to structurally-assemble, for example by lessening the degree to which the gRNA variant can get "tangled" in itself. In some embodiments, choice of scaffold stem loop sequence could change with different spacers that are utilized for the gRNA. In some embodiments, scaffold sequence can be tailored to the spacer and therefore the target sequence. Biochemical assays can be used to evaluate the binding affinity of dXR for the gRNA variant to form the RNP, including the assays of the Examples. For example, a person of ordinary skill can measure changes in the amount of a fluorescently tagged gRNA that is bound to an immobilized dXR, as a response to increasing concentrations of an additional unlabeled "cold competitor" gRNA. Alternatively, or in addition, fluorescence signal can be monitored to or seeing how it changes as different amounts of fluorescently-labeled gRNA are flowed over immobilized dXR. Alternatively, the ability to form an RNP can be assessed using in vitro assays against a defined target nucleic acid sequence.

i. Adding or Changing gRNA Function

In some embodiments, gRNA variants of the system can comprise larger structural changes that change the topology of the gRNA variant with respect to the reference gRNA, thereby allowing for different gRNA functionality. For example, in some embodiments a gRNA variant has swapped an endogenous stem loop of the reference gRNA scaffold with a previously identified stable RNA structure or a stem loop that can interact with a protein or RNA binding partner to recruit additional moieties to the dCasX variant or to recruit dCasX variant to a specific location, such as the inside of a XDP capsid, that has the binding partner to the said RNA structure. The RNA binding domain can be a retroviral Psi packaging element inserted into the gRNA or is a stem loop or hairpin (e.g., MS2 hairpin, Qβ hairpin, U1 hairpin II, Uvsx, or PP7 hairpin) with affinity to a protein selected from the group consisting of MS2 coat protein, PP7 coat protein, Qβ coat protein, U1A protein, or phage R-loop, which can facilitate the binding of gRNA to the dCasX variant. Similar RNA components with affinity to protein structures incorporated into the dCasX variant include kissing loop, a, kissing loop_b1, kissing loop_b2, G quadriplex M3q, G quadriplex telomere basket, sarcin-ricin loop, and pseudoknots. In some embodiments, the gRNA variants of the disclosure comprise multiple components of the foregoing, or multiple copies of the same component.

V. CRISPR Proteins of the Gene Repressor Systems

Provided herein are gene repressor systems comprising fusion proteins comprising catalytically dead CRISPR proteins. In some embodiments, the catalytically-dead CRISPR protein is a catalytically-dead class 2 CRISPR protein. Class 2 systems are distinguished from Class 1 systems in that they have a single multi-domain effector protein and are further divided into a Type II, Type V, or Type VI system, described in Makarova, et al. Evolutionary classification of CRISPR-Cas systems: a burst of class 2 and derived variants. *Nature Rev. Microbiol.* 18:67 (2020), incorporated herein by reference. In some embodiments, the catalytically-dead CRISPR protein is a Class 2, Type II CRISPR/Cas nucleases such as Cas9. In other cases, the catalytically-dead CRISPR is a Class 2, Type V CRISPR/Cas nucleases such as a Cas12a (Cpf1), Cas12b (C2c1), Cas12c (C2c3), Cas12d (CasY), Cas12e (CasX), Cas12f, Cas12g, Cas12h, Cas12i, Cas12j, Cas12k, Cas12l, Cas14, and/or CasΦ.

The nucleases of Type V systems differ from Type II effectors (e.g., Cas9), which contain two nuclear domains that are each responsible for the cleavage of one strand of the target DNA, with the HNH nuclease inserted inside the Ruv-C like nuclease domain sequence. The Type V nucleases possess a single RNA-guided RuvC domain-containing effector but no HNH domain, and they recognize a T-rich protospacer adjacent motif (PAM) 5' upstream to the target region on the non-targeted strand, which is different from Cas9 systems which rely on G-rich PAM at 3'side of target sequences. Type V nucleases generate staggered double-stranded breaks distal to the PAM sequence, unlike Cas9, which generates a blunt end in the proximal site close to the PAM. In addition, Type V nucleases degrade ssDNA in trans when activated by target dsDNA or ssDNA binding in cis. In some embodiments, the Type V nucleases utilized in the XDP embodiments recognize a 5' TC PAM motif and produce staggered ends cleaved by the RuvC domain. The Type V systems (e.g., Cas12) only contain a RuvC-like nuclease domain that cleaves both strands. Type VI (Cas13) are unrelated to the effectors of Type II and V systems and contain two HEPN domains and target RNA.

The term "CasX protein", as used herein, refers to a family of proteins, and encompasses all naturally occurring CasX proteins ("reference CasX"), as well as CasX variants possessing one or more improved characteristics relative to a naturally-occurring reference CasX protein. In the context of the present disclosure, catalytically-dead CasX variants are prepared from reference CasX and CasX variant proteins, and exemplary dCasX variant sequences are presented in SEQ ID NOS: 17-36 and 59353-59358 as set forth in Table 4. The CasX and dCasX proteins of the disclosure comprise at least one of the following domains: a non-target strand binding (NTSB) domain, a target strand loading (TSL) domain, a helical I domain, a helical II domain, an oligonucleotide binding domain (OBD), and a RuvC domain (the last of which may be modified or deleted to create the catalytically dead CasX variant), described more fully, below.

a. Reference CasX Proteins

The disclosure provides reference CasX proteins that are naturally-occurring and that were the starting material for the aforementioned protocols for introducing sequence modifications for generation of the dCasX variants. For example, reference CasX proteins can be isolated from naturally occurring prokaryotes, such as Deltaproteobacteria, Planctomycetes, or *Candidatus Sungbacteria* species. A reference CasX protein (sometimes referred to herein as a reference CasX polypeptide) is a type II CRISPR/Cas endonuclease belonging to the CasX (sometimes referred to as Cas12e) family of proteins that is capable of interacting with a guide RNA to form a ribonucleoprotein (RNP) complex.

In some cases, a reference CasX protein is isolated or derived from Deltaproteobacteria having a sequence of:

```
                                                     (SEQ ID NO: 1)
  1 MEKRINKIRK KLSADNATKP VSRSGPMKTL LVRVMTDDLK KRLEKRRKKP EVMPQVISNN

 61 AANNLRMLLD DYTKMKEAIL QVYWQEFKDD HVGLMCKFAQ PASKKIDQNK LKPEMDEKGN

121 LTTAGFACSQ CGQPLFVYKL EQVSEKGKAY TNYFGRCNVA EHEKLILLAQ LKPEKDSDEA

181 VTYSLGKFGQ RALDFYSIHV TKESTHPVKP LAQIAGNRYA SGPVGKALSD ACMGTIASFL

241 SKYQDIIIEH QKVVKGNQKR LESLRELAGK ENLEYPSVTL PPQPHTKEGV DAYNEVIARV

301 RMWVNLNLWQ KLKLSRDDAK PLLRLKGFPS FPVVERRENE VDWWNTINEV KKLIDAKRDM

361 GRVFWSGVTA EKRNTILEGY NYLPNENDHK KREGSLENPK KPAKRQFGDL LLYLEKKYAG

421 DWGKVFDEAW ERIDKKIAGL TSHIEREEAR NAEDAQSKAV LTDWLRAKAS FVLERLKEMD

481 EKEFYACEIQ LQKWYGDLRG NPFAVEAENR VVDISGFSIG SDGHSIQYRN LLAWKYLENG

541 KREFYLLMNY GKKGRIRFTD GTDIKKSGKW QGLLYGGGKA KVIDLTFDPD DEQLIILPLA

601 FGTRQGREFI WNDLLSLETG LIKLANGRVI EKTIYNKKIG RDEPALFVAL TFERREVVDP

661 SNIKPVNLIG VDRGENIPAV IALTDPEGCP LPEFKDSSGG PTDILRIGEG YKEKQRAIQA

721 AKEVEQRRAG GYSRKFASKS RNLADDMVRN SARDLFYHAV THDAVLVFEN LSRGFGRQGK

781 RTFMTERQYT KMEDWLTAKL AYEGLTSKTY LSKTLAQYTS KTCSNCGFTI TTADYDGMLV

841 RLKKTSDGWA TTLNNKELKA EGQITYYNRY KRQTVEKELS AELDRLSEES GNNDISKWTK

901 GRRDEALFLL KKRFSHRPVQ EQFVCLDCGH EVHADEQAAL NIARSWLFLN SNSTEFKSYK

961 SGKQPFVGAW QAFYKRRLKE VWKPNA.
```

In some cases, a reference CasX protein is isolated or derived from Planctomycetes having a sequence of:

```
                                                     (SEQ ID NO: 2)
  1 MQEIKRINKI RRRLVKDSNT KKAGKTGPMK TLLVRVMTPD LRERLENLRK KPENIPQPIS

 61 NTSRANLNKL LTDYTEMKKA ILHVYWEEFQ KDPVGLMSRV AQPAPKNIDQ RKLIPVKDGN

121 ERLTSSGFAC SQCCQPLYVY KLEQVNDKGK PHTNYFGRCN VSEHERLILL SPHKPEANDE

181 LVTYSLGKFG QRALDFYSIH VTRESNHPVK PLEQIGGNSC ASGPVGKALS DACMGAVASF

241 LTKYQDIILE HQKVIKKNEK RLANLKDIAS ANGLAFPKIT LPPQPHTKEG IEAYNNVVAQ

301 IVIWVNLNLW QKLKIGRDEA KPLQRLKGFP SFPLVERQAN EVDWWDMVCN VKKLINEKKE
```

-continued

```
361 DGKVFWQNLA GYKRQEALLP YLSSEEDRKK GKKFARYQFG DLLLHLEKKH GEDWGKVYDE

421 AWERIDKKVE GLSKHIKLEE ERRSEDAQSK AALTDWLRAK ASFVIEGLKE ADKDEFCRCE

481 LKLQKWYGDL RGKPFAIEAE NSILDISGFS KQYNCAFIWQ KDGVKKLNLY LIINYFKGGK

541 LRFKKIKPEA FEANRFYTVI NKKSGEIVPM EVNENFDDPN LIILPLAFGK RQGREFIWND

601 LLSLETGSLK LANGRVIEKT LYNRRTRQDE PALFVALTFE RREVLDSSNI KPMNLIGIDR

661 GENIPAVIAL TDPEGCPLSR FKDSLGNPTH ILRIGESYKE KQRTIQAAKE VEQRRAGGYS

721 RKYASKAKNL ADDMVRNTAR DLLYYAVTQD AMLIFENLSR GFGRQGKRTF MAERQYTRME

781 DWLTAKLAYE GLPSKTYLSK TLAQYTSKTC SNCGFTITSA DYDRVLEKLK KTATGWMTTI

841 NGKELKVEGQ ITYYNRYKRQ NVVKDLSVEL DRLSEESVNN DISSWTKGRS GEALSLLKKR

901 FSHRPVQEKF VCLNCGFETH ADEQAALNIA RSWLFLRSQE YKKYQTNKTT GNTDKRAFVE

961 TWQSFYRKKL KEVWKPAV.
```

In some cases, a reference CasX protein is isolated or derived from *Candidatus Sungbacteria* having a sequence of

```
                                                  (SEQ ID NO: 3)
  1 MDNANKPSTK SLVNTTRISD HFGVTPGQVT RVFSFGIIPT KRQYAIIERW FAAVEAARER

 61 LYGMLYAHFQ ENPPAYLKEK FSYETFFKGR PVLNGLRDID PTIMTSAVFT ALRHKAEGAM

121 AAFHTNHRRL FEEARKKMRE YAECLKANEA LLRGAADIDW DKIVNALRTR LNTCLAPEYD

181 AVIADFGALC AFRALIAETN ALKGAYNHAL NQMLPALVKV DEPEEAEESP RLRFFNGRIN

241 DLPKFPVAER ETPPDTETII RQLEDMARVI PDTAEILGYI HRIRHKAARR KPGSAVPLPQ

301 RVALYCAIRM ERNPEEDPST VAGHFLGEID RVCEKRRQGL VRTPFDSQIR ARYMDIISFR

361 ATLAHPDRWT EIQFLRSNAA SRRVRAETIS APFEGFSWTS NRINPAPQYG MALAKDANAP

421 ADAPELCICL SPSSAAFSVR EKGGDLIYMR PTGGRRGKDN PGKEITWVPG SFDEYPASGV

481 ALKLRLYFGR SQARRMLINK TWGLLSDNPR VFAANAELVG KKRNPQDRWK LFFHMVISGP

541 PPVEYLDFSS DVRSRARTVI GINRGEVNPL AYAVVSVEDG QVLEEGLLGK KEYIDQLIET

601 RRRISEYQSR EQTPPRDLRQ RVRHLQDTVL GSARAKIHSL IAFWKGILAI ERLDDQFHGR

661 EQKIIPKKTY LANKTGFMNA LSFSGAVRVD KKGNPWGGMI EIYPGGISRT CTQCGTVWLA

721 RRPKNPGHRD AMVVIPDIVD DAAATGFDNV DCDAGTVDYG ELFTLSREWV RLTPRYSRVM

781 RGTLGDLERA IRQGDDRKSR QMLELALEPQ PQWGQFFCHR CGFNGQSDVL AATNLARRAI

841 SLIRRLPDID TPPTP.
```

b. Catalytically-Dead CasX Variant Proteins (dCasX Variant)

In the gene repressor systems, the CasX protein is catalytically dead (dCasX) but retains the ability to bind a target nucleic acid. The present disclosure provides catalytically-dead variants (interchangeably referred to herein as "dCasX variant" or "dCasX variant protein"), wherein the catalytically-dead CasX variants comprise at least one modification in at least one domain relative to the catalytically-dead versions of sequences of SEQ ID NOS:1-3 (described, supra). An exemplary catalytically dead CasX protein comprises one or more mutations in the active site of the RuvC domain of the CasX protein. In some embodiments, a catalytically dead reference CasX protein comprises substitutions at residues 672, 769 and/or 935 with reference to SEQ ID NO: 1. In one embodiment, a catalytically-dead reference CasX protein comprises substitutions of D672A, E769A and/or D935A with reference to SEQ ID NO: 1. In other embodiments, a catalytically-dead reference CasX protein comprises substitutions at amino acids 659, 756 and/or 922 with reference to SEQ ID NO: 2. In some embodiments, a catalytically-dead reference CasX protein comprises D659A, E756A and/or D922A substitutions with reference to of SEQ ID NO: 2. An exemplary RuvC domain of the dCasX of the disclosure comprises amino acids 661-824 and 935-986 of SEQ ID NO: 1, or amino acids 648-812 and 922-978 of SEQ ID NO: 2, with one or more amino acid modifications relative to said RuvC cleavage domain sequence, wherein the dCasX variant exhibits one or more improved characteristics compared to the reference dCasX. In further embodiments, a catalytically-dead CasX variant protein comprises deletions of all or part of the RuvC domain of the reference CasX protein. It will be understood that the same foregoing substitutions or deletions can similarly be introduced into any of the CasX variants of SEQ ID NOS: 33352-33624 or 57647-57735 of the disclosure, relative to the corresponding positions (allowing for any insertions or deletions) of the starting variant, resulting in a dCasX variant (see, e.g., Table 4 for exemplary sequences).

In some embodiments, the dCasX variant with linked repressor domain exhibits at least one improved characteristic compared to the reference dCasX protein with linked repressor domain configured in a comparable fashion, e.g. a catalytically dead version of a CasX variant of any one of SEQ ID NOS: 33352-33624 or 57647-57735. All variants that improve one or more functions or characteristics of the dCasX variant protein when with linked repressor domain compared to a reference dCasX protein with linked repressor domain described herein are envisaged as being within the scope of the disclosure. In some embodiments, the modification is a mutation in one or more amino acids of the reference dCasX. In some embodiments, the modification is a mutation in one or more amino acids of a dCasX variant that has been subjected to additional mutations or alterations in the sequence. In other embodiments, the modification is a substitution of one or more domains of the reference dCasX with one or more domains from a different CasX. In some embodiments, insertion includes the insertion of a part or all of a domain from a different CasX protein. Mutations can occur in any one or more domains of the reference dCasX protein or dCasX variant, and may include, for example, deletion of part or all of one or more domains, or one or more amino acid substitutions, deletions, or insertions in any domain. The domains of CasX proteins include the non-target strand binding (NTSB) domain, the target strand loading (TSL) domain, the helical I domain, the helical II domain, the oligonucleotide binding domain (OBD), and the RuvC DNA cleavage domain, which can further comprise subdomains, described below. Any change in amino acid sequence of a reference dCasX protein that leads to an improved characteristic of the protein is considered a dCasX variant protein of the disclosure. For example, dCasX variants can comprise one or more amino acid substitutions, insertions, deletions, or swapped domains, or any combinations thereof, relative to a reference dCasX protein sequence.

Suitable mutagenesis methods for generating dCasX variant proteins of the disclosure may include, for example, Deep Mutational Evolution (DME), deep mutational scanning (DMS), error prone PCR, cassette mutagenesis, random mutagenesis, staggered extension PCR, gene shuffling, or domain swapping. In some embodiments, the dCasX variants are designed, for example by selecting one or more desired mutations in a reference dCasX. In certain embodiments, the activity of a reference dCasX protein is used as a benchmark against which the activity of one or more dCasX variants are compared, thereby measuring improvements in function of the dCasX variants.

In some embodiments of the dCasX variants described herein, the at least one modification comprises: (a) a substitution of 1 to 100 consecutive or non-consecutive amino acids in the dCasX variant; (b) a deletion of 1 to 100 consecutive or non-consecutive amino acids in the dCasX variant; (c) an insertion of 1 to 100 consecutive or non-consecutive amino acids in the dCasX; or (d) any combination of (a)-(c). In some embodiments, the at least one modification comprises: (a) a substitution of 5-10 consecutive or non-consecutive amino acids in the dCasX variant; (b) a deletion of 1-5 consecutive or non-consecutive amino acids in the dCasX variant; (c) an insertion of 1-5 consecutive or non-consecutive amino acids in the dCasX; or (d) any combination of (a)-(c).

Any amino acid can be substituted for any other amino acid in the substitutions described herein. The substitution can be a conservative substitution (e.g., a basic amino acid is substituted for another basic amino acid). The substitution can be a non-conservative substitution (e.g., a basic amino acid is substituted for an acidic amino acid or vice versa). For example, a proline in a reference dCasX protein can be substituted for any of arginine, histidine, lysine, aspartic acid, glutamic acid, serine, threonine, asparagine, glutamine, cysteine, glycine, alanine, isoleucine, leucine, methionine, phenylalanine, tryptophan, tyrosine or valine to generate a dCasX variant protein of the disclosure.

Any permutation of the substitution, insertion and deletion embodiments described herein can be combined to generate a dCasX variant protein of the disclosure. For example, a dCasX variant protein can comprise at least one substitution and at least one deletion relative to a reference dCasX protein sequence, at least one substitution and at least one insertion relative to a reference dCasX protein sequence, at least one insertion and at least one deletion relative to a reference dCasX protein sequence, or at least one substitution, one insertion and one deletion relative to a reference dCasX protein sequence.

In some embodiments, the dCasX variant protein comprises between 700 and 1200 amino acids, between 800 and 1100 amino acids or between 900 and 1000 amino acids.

The dCasX and linked repressor domains of the disclosure have an enhanced ability to efficiently bind target nucleic acid, when complexed with a gRNA as an RNP, utilizing PAM TC motif, including PAM sequences selected from TTC, ATC, GTC, or CTC, compared to an RNP of a reference dCasX protein and reference gRNA. In the foregoing, the PAM sequence is located at least 1 nucleotide 5' to the non-target strand of the protospacer having identity with the targeting sequence of the gRNA in an assay system compared to the binding of an RNP comprising a reference dCasX protein and reference gRNA in a comparable assay system.

In some embodiments, an RNP comprising the dCasX variant protein with linked repressor domains and a gRNA of the disclosure, at a concentration of 20 pM or less, is capable of binding a double stranded DNA target with an efficiency of at least 70%, at least 80%, at least 85%, at least 90% or at least 95%. In one embodiment, an RNP of a dCasX variant with linked repressor domains and a gRNA variant exhibits greater binding of a target sequence in the target nucleic acid compared to an RNP comprising a reference dCasX protein with linked repressor domains and a reference gRNA in a comparable assay system, wherein the PAM sequence of the target nucleic acid is TTC. In another embodiment, an RNP of a dCasX variant with linked repressor domains and gRNA variant exhibits greater binding affinity of a target sequence in the target nucleic acid compared to an RNP comprising a reference dCasX protein with linked repressor domains and a reference gRNA in a comparable assay system, wherein the PAM sequence of the target nucleic acid is ATC. In another embodiment, an RNP of a dCasX variant with linked repressor domains and gRNA variant exhibits greater binding affinity of a target sequence in the target nucleic acid compared to an RNP comprising a reference dCasX protein with linked repressor domains and a reference gRNA in a comparable assay system, wherein the PAM sequence of the target nucleic acid is CTC. In another embodiment, an RNP of a dCasX variant with linked repressor domains and gRNA variant exhibits greater binding affinity of a target sequence in the target nucleic acid compared to an RNP comprising a reference dCasX protein with linked repressor domains and a reference gRNA in a comparable assay system, wherein the PAM sequence of the target nucleic acid is GTC. In the foregoing embodiments, the increased binding affinity for the one or more PAM sequences is at least 1.5-fold greater or more compared to the binding affinity of an RNP of any one of the reference dCasX proteins (modified from SEQ ID NOS:1-3) with linked repressor domains and the gRNA of Table 1 for the PAM sequences.

c. dCasX Variant Proteins with Domains from Multiple Source Proteins

In certain embodiments, the disclosure provides a chimeric dCasX variant protein for use in the dXR systems comprising protein domains from two or more different CasX proteins, such as two or more naturally occurring CasX proteins, or two or more CasX variant protein sequences as described herein. As used herein, a "chimeric dCasX protein" refers to a catalytically-dead CasX containing at least two domains isolated or derived from different sources, such as two naturally occurring proteins, which may, in some embodiments, be isolated from different species. For example, in some embodiments, a chimeric dCasX variant protein comprises a first domain from a first CasX protein and a second domain from a second, different CasX protein. In some embodiments, the first domain can be selected from the group consisting of the NTSB, TSL, helical I-I, helical I-II, helical II, OBD-I, OBD-II, RuvC-I and RuvC-II domains. In some embodiments, the second domain is selected from the group consisting of the NTSB, TSL, helical I-I, helical I-II, helical II, OBD-I, OBD-II, RuvC-I and RuvC-II domains with the second domain being different from the foregoing first domain. A chimeric dCasX variant protein may comprise an NTSB, TSL, helical I-I, helical I-II, helical II, OBD-I, and OBD-II domains from a CasX protein of SEQ ID NO: 2, and a RuvC-I and/or RuvC-II domain from a CasX protein of SEQ ID NO: 1, or vice versa, in which mutations or other sequence alterations are introduced to create the catalytically dead variant with improved properties of the variant, relative to the reference dCasX protein. As an example of the foregoing, the chimeric RuvC domain comprises amino acids 661 to 824 of SEQ ID NO: 1 and amino acids 922 to 978 of SEQ ID NO: 2. As an alternative example of the foregoing, a chimeric RuvC domain comprises amino acids 648 to 812 of SEQ ID NO: 2 and amino acids 935 to 986 of SEQ ID NO: 1. In a particular embodiment, a dCasX for use in the dXR comprises an NTSB domain and helical I-II domain from SEQ ID NO: 1 and a helical I-I domain from SEQ ID NO:2; the latter being a chimeric domain. Coordinates of CasX domains in the reference CasX proteins of SEQ ID NO: 1 and SEQ ID NO: 2 are provided in Table 3 below.

TABLE 3

Domain coordinates in Reference CasX proteins

| Domain Name | Coordinates in SEQ ID NO: 1 | Coordinates in SEQ ID NO: 2 |
|---|---|---|
| OBD-I | 1-55 | 1-57 |
| helical I-I | 56-99 | 58-101 |
| NTSB | 100-190 | 102-191 |
| helical I-II | 191-331 | 192-332 |
| helical II | 332-508 | 333-500 |
| OBD-II | 509-659 | 501-646 |
| RuvC-I | 660-823 | 647-810 |
| TSL | 824-933 | 811-920 |
| RuvC-II | 934-986 | 921-978 |

TABLE 3-continued

*OBD I and II, helical I-I and I-II, and RuvC I and II are also sometimes referred to as OBD a and b, helical I a and b, and RuvC a and b.

In some embodiments, an improved characteristic of the dCasX variant is at least about 1.1 to about 100,000-fold improved relative to the reference dCasX protein. In some embodiments, an improved characteristic of the CasX variant is at least about 1.1 to about 10,000-fold improved, at least about 1.1 to about 1,000-fold improved, at least about 1.1 to about 500-fold improved, at least about 1.1 to about 400-fold improved, at least about 1.1 to about 300-fold improved, at least about 1.1 to about 200-fold improved, at least about 1.1 to about 100-fold improved, at least about 1.1 to about 50-fold improved, at least about 1.1 to about 40-fold improved, at least about 1.1 to about 30-fold improved, at least about 1.1 to about 20-fold improved, at least about 1.1 to about 10-fold improved, at least about 1.1 to about 9-fold improved, at least about 1.1 to about 8-fold improved, at least about 1.1 to about 7-fold improved, at least about 1.1 to about 6-fold improved, at least about 1.1 to about 5-fold improved, at least about 1.1 to about 4-fold improved, at least about 1.1 to about 3-fold improved, at least about 1.1 to about 2-fold improved, at least about 1.1 to about 1.5-fold improved, at least about 1.5 to about 3-fold improved, at least about 1.5 to about 4-fold improved, at least about 1.5 to about 5-fold improved, at least about 1.5 to about 10-fold improved, at least about 5 to about 10-fold improved, at least about 10 to about 20-fold improved, at least 10 to about 30-fold improved, at least 10 to about 50-fold improved or at least 10 to about 100-fold improved than the reference CasX protein. In some embodiments, an improved characteristic of the dCasX variant is at least about 10 to about 1000-fold improved relative to the reference dCasX protein.

In some embodiments, a dCasX variant protein utilized in the gene repressor systems of the disclosure comprises a sequence of SEQ ID NOS: 33352-33624 or 57647-57735 and one or more insertions, substitutions or deletions thereto as described supra that inactivate the catalytic domain of the CasX variant to produce a dCasX variant. In some embodiments, a dCasX variant protein utilized in the gene repressor systems of the disclosure comprises a sequence of SEQ ID NOS: 17-36 and 59353-59358 as set forth in Table 4. In some embodiments, a dCasX variant protein consists of a sequence of SEQ ID NOS: 17-36 and 59353-59358 as set forth in Table 4. In other embodiments, a dCasX variant protein comprises a sequence at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical to a sequence of SEQ ID NOS: 17-36 and 59353-59358 as set forth in Table 4.

TABLE 4 dCasX Variant Sequences

| SEQ ID NO | dCasX | Amino Acid Sequence |
| --- | --- | --- |
| 17 | dCasX533 | QEIKRINKIRRRLVKDSNTKKAGKTRGPMKTLLVRVMTPDLRERLENLRKKPENIPQPI<br>SNTSRANLNKLLTDYTEMKKAILHVYWEEFQKDPVGLMSRVAQPASKKIDQNKLKPEMD<br>EKGNLTTAGFACSQCGQPLFVYKLEQVSEKGKAYTNYFGRCNVAEHEKLILLAQLKPEK<br>DSDEAVTYSLGKFGQRALDFYSIHVTKESTHPVKPLAQIAGNRYASYPVGKALSDACMG<br>TIASFLSKYQDIIIEHQKVVKGNQKRLESLRELAGKENLEYPSVTLPPQPHTKEGVDAY<br>NEVIARVRMWVNLNLWQKLKLSRDDAKPLLRLKGFPSFPLVERQANEVDWWDMVCNVKK<br>LINEKKEDGKVFWQNLAGYKRQEALRPYLSSEEDRKKGKKFARYQLGDLLLHLEKKHGE<br>DWGKVYDEAWERIDKKVEGLSKHIKLEEERRSEDAQSKAALTDWLRAKASFVIEGLKEA<br>DKDEFCRCELKLQKWYGDLRGKPFAIEAENSILDISGFSKQYNCAFIWQKDGVKKLNLY<br>LIINYFKGGKLRFKKIKPEAFEANRFYTVINKKSGEIVPMEVNFNFDDPNLIILPLAFG<br>KRQGREFIWNDLLSLETGSLKLANGRVIEKTLYNRRTRQDEPALFVALTFERREVLDSS<br>NIKPMNLIGVARGENIPAVIALTDPEGCPLSRFKDSLGNPTHILRIGESYKEKQRTIQA<br>KKEVEQRRAGGYSRKYASKAKNLADDMVRNTARDLLYYAVTQDAMLIFANLSRGFGRQG<br>KRTFMAERQYTRMEDWLTAKLAYEGLPSKTYLSKTLAQYTSKTCSNCGFTITSADYDRV<br>LEKLKKTATGWMTTINGKELKVEGQITYYNRYKRQNVVKDLSVELDRLSEESVNNDISS<br>WTKGRSGEALSLLKKRFSHRPVQEKFVCLNCGFETHAAEQAALNIARSWLFLRSQEYKK<br>YQTNKTTGNTDKRAFVETWQSFYRKKLKEVWKPAV |
| 18 | dCasX491 | QEIKRINKIRRRLVKDSNTKKAGKTGPMKTLLVRVMTPDLRERLENLRKKPENIPQPIS<br>NTSRANLNKLLTDYTEMKKAILHVYWEEFQKDPVGLMSRVAQPASKKIDQNKLKPEMDE<br>KGNLTTAGFACSQCGQPLFVYKLEQVSEKGKAYTNYFGRCNVAEHEKLILLAQLKPEKD<br>SDEAVTYSLGKFGQRALDFYSIHVTKESTHPVKPLAQIAGNRYASGPVGKALSDACMGT<br>IASFLSKYQDIIIEHQKVVKGNQKRLESLRELAGKENLEYPSVTLPPQPHTKEGVDAYN<br>EVIARVRMWVNLNLWQKLKLSRDDAKPLLRLKGFPSFPLVERQANEVDWWDMVCNVKKL<br>INEKKEDGKVFWQNLAGYKRQEALRPYLSSEEDRKKGKKFARYQLGDLLLHLEKKHGED<br>WGKVYDEAWERIDKKVEGLSKHIKLEEERRSEDAQSKAALTDWLRAKASFVIEGLKEAD<br>KDEFCRCELKLQKWYGDLRGKPFAIEAENSILDISGFSKQYNCAFIWQKDGVKKLNLYL<br>IINYFKGGKLRFKKIKPEAFEANRFYTVINKKSGEIVPMEVNENFDDPNLIILPLAFGK<br>RQGREFIWNDLLSLETGSLKLANGRVIEKTLYNRRTRQDEPALFVALTFERREVLDSSN<br>IKPMNLIGVARGENIPAVIALTDPEGCPLSRFKDSLGNPTHILRIGESYKEKQRTIQAK<br>KEVEQRRAGGYSRKYASKAKNLADDMVRNTARDLLYYAVTQDAMLIFANLSRGFGRQGK<br>RTFMAERQYTRMEDWLTAKLAYEGLSKTYLSKTLAQYTSKTCSNCGFTITSADYDRVLE<br>KLKKTATGWMTTINGKELKVEGQITYYNRYKRQNVVKDLSVELDRLSEESVNNDISSWT<br>KGRSGEALSLLKKRFSHRPVQEKFVCLNCGFETHAAEQAALNIARSWLFLRSQEYKKYQ<br>TNKTTGNTDKRAFVETWQSFYRKKLKEVWKPAV |
| 19 | dCasX532 | QEIKRINKIRRRLVKDSNTKKAGKTRGPMKTLLVRVMTPDLRERLENLRKKPENIPQPI<br>SNTSRANLNKLLTDYTEMKKAILHVYWEEFQKDPVGLMSRVAQPASKKIDQNKLKPEMD<br>EKGNLTTAGFACSQCGQPLFVYKLEQVSEKGKAYTNYFGRCNVAEHEKLILLAQLKPEK<br>DSDEAVTYSLGKFGQRALDFYSIHVTKESTHPVKPLAQIAGNRYASGPVGKALSDACMG<br>TIASFLSKYQDIIIEHQKVVKGNQKRLESLRELAGKENLEYPSVTLPPQPHTKEGVDAY<br>NEVIARVRMWVNLNLWQKLKLSRDDAKPLLRLKGFPSFPLVERQANEVDWWDMVCNVKK<br>LINEKKEDGKVFWQNLAGYKRQEALRPYLSSEEDRKKGKKFARYQLGDLLLHLEKKHGE<br>DWGKVYDEAWERIDKKVEGLSKHIKLEEERRSEDAQSKAALTDWLRAKASFVIEGLKEA<br>DKDEFCRCELKLQKWYGDLRGKPFAIEAENSILDISGFSKQYNCAFIWQKDGVKKLNLY<br>LIINYFKGGKLRFKKIKPEAFEANRFYTVINKKSGEIVPMEVNFNFDDPNLIILPLAFG<br>KRQGREFIWNDLLSLETGSLKLANGRVIEKTLYNRRTRQDEPALFVALTFERREVLDSS<br>NIKPMNLIGVARGENIPAVIALTDPEGCPLSRFKDSLGNPTHILRIGESYKEKQRTIQA<br>KKEVEQRRAGGYSRKYASKAKNLADDMVRNTARDLLYYAVTQDAMLIFANLSRGFGRQG<br>KRTEMAERQYTRMEDWLTAKLAYEGLPSKTYLSKTLAQYTSKTCSNCGFTITSADYDRV<br>LEKLKKTATGWMTTINGKELKVEGQITYYNRYKRQNVVKDLSVELDRLSEESVNNDISS<br>WTKGRSGEALSLLKKRFSHRPVQEKFVCLNCGFETHAAEQAALNIARSWLFLRSQEYKK<br>YQTNKTTGNTDKRAFVETWQSFYRKKLKEVWKPAV |
| 20 | dCasX529 | QEIKRINKIRRRLVKDSNTKKAGKTGPMKTLLVRVMTPDLRERLENLRKKPENIPQPIS<br>NTSRANLNKLLTDYTEMKKAILHVYWEEFQKDPVGLMSRVAQPASKKIDQNKLKPEMDE<br>KGNLTTAGFACSQCGQPLFVYKLEQVSEKGKAYTNYFGRCNVAEHEKLILLAQLKPEKD<br>SDEAVTYSLGKFGQRALDFYSIHVTKESTHPVKPLAQIAGNRYASNPVGKALSDACMGT<br>IASFLSKYQDIIIEHQKVVKGNQKRLESLRELAGKENLEYPSVTLPPQPHTKEGVDAYN<br>EVIARVRMWVNLNLWQKLKLSRDDAKPLLRLKGFPSFPLVERQANEVDWWDMVCNVKKL<br>INEKKEDGKVFWQNLAGYKRQEALRPYLSSEEDRKKGKKFARYQLGDLLLHLEKKHGED<br>WGKVYDEAWERIDKKVEGLSKHIKLEEERRSEDAQSKAALTDWLRAKASFVIEGLKEAD<br>KDEFCRCELKLQKWYGDLRGKPFAIEAENSILDISGFSKQYNCAFIWQKDGVKKLNLYL<br>IINYFKGGKLRFKKIKPEAFEANRFYTVINKKSGEIVPMEVNFNFDDPNLIILPLAFGK<br>RQGREFIWNDLLSLETGSLKLANGRVIEKTLYNRRTRQDEPALFVALTFERREVLDSSN<br>IKPMNLIGVARGENIPAVIALTDPEGCPLSRFKDSLGNPTHILRIGESYKEKQRTIQAK<br>KEVEQRRAGGYSRKYASKAKNLADDMVRNTARDLLYYAVTQDAMLIFANLSRGFGRQGK<br>RTFMAERQYTRMEDWLTAKLAYEGLPSKTYLSKTLAQYTSKTCSNCGFTITSADYDRVL<br>EKLKKTATGWMTTINGKELKVEGQITYYNRYKRQNVVKDLSVELDRLSEESVNNDISSW<br>TKGRSGEALSLLKKRFSHRPVQEKFVCLNCGFETHAAEQAALNIARSWLFLRSQEYKKY<br>QTNKTTGNTDKRAFVETWQSFYRKKLKEVWKPAV |
| 21 | dCasX531 | QEIKRINKIRRRLVKDSNTKKAGKTGPMKTLLVRVMTPDLRERLENLRKKPENIPQPIS<br>NTSRANLNKLLTDYTEMKKAILHVYWEEFQKDPVGLMSRVAQPASKKIDQNKLKPEMDE |

TABLE 4-continued dCasX Variant Sequences

| SEQ ID NO | dCasX | Amino Acid Sequence |
|---|---|---|
| | | KGNLTTAGFACSQCGQPLFVYKLEQVSEKGKAYTNYFGRCNVAEHEKLILLAQLKPEKD<br>SDEAVTYSLGKFGQRALDFYSIHVTKESTHPVKPLAQIAGNRYASGPVGKALSDACMGT<br>IASFLSKYQDIIIEHQKVVKGNQKRLESLRELAGKENLEYPSVTLPPQPHTKEGVDAYN<br>EVIARVRMWVNLNLWQKLKLSRDDAKPLLRLKGFPSFPLVERQANEVDWWDMVCNVKKL<br>INEKKEDGKVFWQNLAGYKRQEALRPYLSSEEDRKKGKKFARYQLGDLLLHLEKKHGED<br>WGKVYDEAWERIDKKVEGLSKHIKLEEERRSEDAQSKAALTDWLRAKASFVIEGLKEAD<br>KDEFCRCELKLQKWYGDLRGKPFAIEAENSILDISGFSKQYNCAFIWQKDGVKKLNLYL<br>IINYFKGYGKLRFKKIKPEAFEANRFYTVINKKSGEIVPMEVNFNFDDPNLIILPLAFG<br>KRQGREFIWNDLLSLETGSLKLANGRVIEKTLYNRRTRQDEPALFVALTFERREVLDSS<br>NIKPMNLIGVARGENIPAVIALTDPEGCPLSRFKDSLGNPTHILRIGESYKEKQRTIQA<br>KKEVEQRRAGGYSRKYASKAKNLADDMVRNTARDLLYYAVTQDAMLIFANLSRGFGRQG<br>KRTFMAERQYTRMEDWLTAKLAYEGLPSKTYLSKTLAQYTSKTCSNCGFTITSADYDRV<br>LEKLKKTATGWMTTINGKELKVEGQITYYNRYKRQNVVKDLSVELDRLSEESVNNDISS<br>WTKGRSGEALSLLKKRFSHRPVQEKFVCLNCGFETHAAEQAALNIARSWLFLRSQEYKK<br>YQTNKTTGNTDKRAFVETWQSFYRKKLKEVWKPAV |
| 22 | dCasX530 | QEIKRINKIRRRLVKDSNTKKAGKTGPMKTLLVRVMTPDLRERLENLRKKPENIPQPIS<br>NTSRANLNKLLTDYTEMKKAILHVYWEEFQKDPVGLMSRVAQPASKKIDQNKLKPEMDE<br>KGNLTTAGFACSQCGQPLFVYKLEQVSEKGKAYTNYFGRCNVAEHEKLILLAQLKPEKD<br>SDEAVTYSLGKFGQRALDFYSIHVTKESTHPVKPLAQIAGNRYASGPVGKALSDACMGT<br>IASFLSKYQDIIIEHQKVVKGNQKRLESLRELAGKENLEYPSVTLPPQPHTKEGVDAYN<br>EVIARVRMWVNLNLWQKLKLSRDDAKPLLRLKGFPSFPLVERQANEVDWWDMVCNVKKL<br>INEKKEDGKVFWQNLAGYKRQEALRPYLSSEEDRKKGKKFARYQLGDLLLHLEKKHGED<br>WGKVYDEAWERIDKKVEGLSKHIKLEEERRSEDAQSKAALTDWLRAKASFVIEGLKEAD<br>KDEFCRCELKLQKWYGDLRGKPFAIEAENSILDISGFSKQYNCAFIWQKDGVKKLNLYL<br>IINYFKGWGKLRFKKIKPEAFEANRFYTVINKKSGEIVPMEVNENFDDPNLIILPLAFG<br>KRQGREFIWNDLLSLETGSLKLANGRVIEKTLYNRRTRQDEPALFVALTFERREVLDSS<br>NIKPMNLIGVARGENIPAVIALTDPEGCPLSRFKDSLGNPTHILRIGESYKEKQRTIQA<br>KKEVEQRRAGGYSRKYASKAKNLADDMVRNTARDLLYYAVTQDAMLIFANLSRGFGRQG<br>KRTFMAERQYTRMEDWLTAKLAYEGLPSKTYLSKTLAQYTSKTCSNCGFTITSADYDRV<br>LEKLKKTATGWMTTINGKELKVEGQITYYNRYKRQNVVKDLSVELDRLSEESVNNDISS<br>WTKGRSGEALSLLKKRFSHRPVQEKFVCLNCGFETHAAEQAALNIARSWLFLRSQEYKK<br>YQTNKTTGNTDKRAFVETWQSFYRKKLKEVWKPAV |
| 23 | dCasX528 | QEIKRINKIRRRLVKDSNTKKAGKTGPMKTLLVRVMTPDLRERLENLRKKPENIPQPIS<br>NTSRANLNKLLTDYTEMKKAILHVYWEEFQKDPVGLMSRVAQPASKKIDQNKLKPEMDE<br>KGNLTTAGFACSQCGQPLFVYKLEQVSEKGKAYTNYFGRCNVAEHEKLILLAQLKPEKD<br>SDEAVTYSLGKFGQRALDFYSIHVTKESTHPVKPLAQIAGNRYASYPVGKALSDACMGT<br>IASFLSKYQDIIIEHQKVVKGNQKRLESLRELAGKENLEYPSVTLPPQPHTKEGVDAYN<br>EVIARVRMWVNLNLWQKLKLSRDDAKPLLRLKGFPSFPLVERQANEVDWWDMVCNVKKL<br>INEKKEDGKVFWQNLAGYKRQEALRPYLSSEEDRKKGKKFARYQLGDLLLHLEKKHGED<br>WGKVYDEAWERIDKKVEGLSKHIKLEEERRSEDAQSKAALTDWLRAKASFVIEGLKEAD<br>KDEFCRCELKLQKWYGDLRGKPFAIEAENSILDISGFSKQYNCAFIWQKDGVKKLNLYL<br>IINYFKGGKLRFKKIKPEAFEANRFYTVINKKSGEIVPMEVNENFDDPNLIILPLAFGK<br>RQGREFIWNDLLSLETGSLKLANGRVIEKTLYNRRTRQDEPALFVALTFERREVLDSSN<br>IKPMNLIGVARGENIPAVIALTDPEGCPLSRFKDSLGNPTHILRIGESYKEKQRTIQAK<br>KEVEQRRAGGYSRKYASKAKNLADDMVRNTARDLLYYAVTQDAMLIFANLSRGFGRQGK<br>RTFMAERQYTRMEDWLTAKLAYEGLPSKTYLSKTLAQYTSKTCSNCGFTITSADYDRVL<br>EKLKKTATGWMTTINGKELKVEGQITYYNRYKRQNVVKDLSVELDRLSEESVNNDISSW<br>TKGRSGEALSLLKKRFSHRPVQEKFVCLNCGFETHAAEQAALNIARSWLFLRSQEYKKY<br>QTNKTTGNTDKRAFVETWQSFYRKKLKEVWKPAV |
| 24 | dCasX527 | QEIKRINKIRRRLVKDSNTKKAGKTRGPMKTLLVRVMTPDLRERLENLRKKPENIPQPI<br>SNTSRANLNKLLTDYTEMKKAILHVYWEEFQKDPVGLMSRVAQPASKKIDQNKLKPEMD<br>EKGNLTTAGFACSQCGQPLFVYKLEQVSEKGKAYTNYFGRCNVAEHEKLILLAQLKPEK<br>DSDEAVTYSLGKFGQRALDFYSIHVTKESTHPVKPLAQIAGNRYASGPVGKALSDACMG<br>TIASFLSKYQDIIIEHQKVVKGNQKRLESLRELAGKENLEYPSVTLPPQPHTKEGVDAY<br>NEVIARVRMWVNLNLWQKLKLSRDDAKPLLRLKGFPSFPLVERQANEVDWWDMVCNVKK<br>LINEKKEDGKVFWQNLAGYKRQEALRPYLSSEEDRKKGKKFARYQLGDLLLHLEKKHGE<br>DWGKVYDEAWERIDKKVEGLSKHIKLEEERRSEDAQSKAALTDWLRAKASFVIEGLKEA<br>DKDEFCRCELKLQKWYGDLRGKPFAIEAENSILDISGFSKQYNCAFIWQKDGVKKLNLY<br>LIINYFKGGKLRFKKIKPEAFEANRFYTVINKKSGEIVPMEVNFNFDDPNLIILPLAFG<br>KRQGREFIWNDLLSLETGSLKLANGRVIEKTLYNRRTRQDEPALFVALTFERREVLDSS<br>NIKPMNLIGVARGENIPAVIALTDPEGCPLSRFKDSLGNPTHILRIGESYKEKQRTIQA<br>KKEVEQRRAGGYSRKYASKAKNLADDMVRNTARDLLYYAVTQDAMLIFANLSRGFGRQG<br>KRTEMAERQYTRMEDWLTAKLAYEGLSKTYLSKTLAQYTSKTCSNCGFTITSADYDRVL<br>EKLKKTATGWMTTINGKELKVEGQITYYNRYKRQNVVKDLSVELDRLSEESVNNDISSW<br>TKGRSGEALSLLKKRFSHRPVQEKFVCLNCGFETHAAEQAALNIARSWLFLRSQEYKKY<br>QTNKTTGNTDKRAFVETWQSFYRKKLKEVWKPAV |
| 25 | dCasX515 | QEIKRINKIRRRLVKDSNTKKAGKTGPMKTLLVRVMTPDLRERLENLRKKPENIPQPIS<br>NTSRANLNKLLTDYTEMKKAILHVYWEEFQKDPVGLMSRVAQPASKKIDQNKLKPEMDE<br>KGNLTTAGFACSQCGQPLFVYKLEQVSEKGKAYTNYFGRCNVAEHEKLILLAQLKPEKD<br>SDEAVTYSLGKFGQRALDFYSIHVTKESTHPVKPLAQIAGNRYASGPVGKALSDACMGT |

TABLE 4-continued dCasX Variant Sequences

| SEQ ID NO | dCasX | Amino Acid Sequence |
|---|---|---|
| | | IASFLSKYQDIIIEHQKVVKGNQKRLESLRELAGKENLEYPSVTLPPQPHTKEGVDAYN |
| | | EVIARVRMWVNLNLWQKLKLSRDDAKPLLRLKGFPSFPLVERQANEVDWWDMVCNVKKL |
| | | INEKKEDGKVFWQNLAGYKRQEALRPYLSSEEDRKKGKKFARYQLGDLLLHLEKKHGED |
| | | WGKVYDEAWERIDKKVEGLSKHIKLEEERRSEDAQSKAALTDWLRAKASFVIEGLKEAD |
| | | KDEFCRCELKLQKWYGDLRGKPFAIEAENSILDISGFSKQYNCAFIWQKDGVKKLNLYL |
| | | IINYFKGGKLRFKKIKPEAFEANRFYTVINKKSGEIVPMEVNFNFDDPNLIILPLAFGK |
| | | RQGREFIWNDLLSLETGSLKLANGRVIEKTLYNRRTRQDEPALFVALTFERREVLDSSN |
| | | IKPMNLIGVARGENIPAVIALTDPEGCPLSRFKDSLGNPTHILRIGESYKEKQRTIQAK |
| | | KEVEQRRAGGYSRKYASKAKNLADDMVRNTARDLLYYAVTQDAMLIFANLSRGFGRQGK |
| | | RTFMAERQYTRMEDWLTAKLAYEGLPSKTYLSKTLAQYTSKTCSNCGFTITSADYDRVL |
| | | EKLKKTATGWMTTINGKELKVEGQITYYNRYKRQNVVKDLSVELDRLSEESVNNDISSW |
| | | TKGRSGEALSLLKKRFSHRPVQEKFVCLNCGFETHAAEQAALNIARSWLFLRSQEYKKY |
| | | QTNKTTGNTDKRAFVETWQSFYRKKLKEVWKPAV |
| 26 | dCasX514 | QEIKRINKIRRRLVKDSNTKKAGKTGPMKTLLVRVMTPDLRERLENLRKKPENIPQPIS |
| | | NTSRANLNKLLTDYTEMKKAILHVYWEEFQKDPVGLMSRVAQPASKKIDQNKLKPEMDE |
| | | KGNLTTAGFACSQCGQPLFVYKLEQVSEKGKAYTNYFGRCNVAEHEKLILLAQLKPEKD |
| | | SDEAVTYSLGKFGQRALDFYSIHVTKESTHPVKPLAQIAGNRYASGPVGKALSDACMGT |
| | | IASFLSKYQDIIIEHQKVVKGNQKRLESLRELAGKENLEYPSVTLPPQPHTKEGVDAYN |
| | | EVIARVRMWVNLNLWQKLKLSRDDAKPLLRLKGFPSFPLVERQANEVDWWDMVCNVKKL |
| | | INEKKEDGKVFWQNLAGYKRQEALRPYLSSEEDRKKGKKFARYQLGDLLLHLEKKHGED |
| | | WGKVYDEAWERIDKKVEGLSKHIKLEEERRSEDAQSKAALTDWLRAKASFVIEGLKEAD |
| | | KDEFCRCELKLQKWYGDLRGKPFAIEAENSILDISGFSKQYNCAFIWQKDGVKKLNLYL |
| | | IINYFKGGKLRFKKIKPEAFEANRFYTVINKKSGEIVPMEVNFNFDDPNLIILPLAFGK |
| | | RQGREFIWNDLLSLETGSLKLANGRVIEKTLYNRRTRQDEPALFVALTFERREVLDSSN |
| | | IKPMNLIGVARGENIPAVIALTDPEGCPLSRFKDSLGNPTHILRIGESYKEKQRTIQAK |
| | | KEVEQRRAGGYSRKYASKAKNLADDMVRNTARDLLYYAVTQDAMLIFANLSRGFGRQGK |
| | | RTFMAERQYTRMEDWLTAKLAYEGLSKTYLSKTLAQYTSKTCSNCGFTIHTSADYDRVL |
| | | EKLKKTATGWMTTINGKELKVEGQITYYNRYKRQNVVKDLSVELDRLSEESVNNDISSW |
| | | TKGRSGEALSLLKKRFSHRPVQEKFVCLNCGFETHAAEQAALNIARSWLFLRSQEYKKY |
| | | QTNKTTGNTDKRAFVETWQSFYRKKLKEVWKPAV |
| 27 | dCasX516 | QEIKRINKIRRRLVKDSNTKKAGKTGPMKTLLVRVMTPDLRERLENLRKKPENIPQPIS |
| | | NTSRANLNKLLTDYTEMKKAILHVYWEEFQKDPVGLMSRVAQPASKKIDQNKLKPEMDE |
| | | KGNLTTAGFACSQCGQPLFVYKLEQVSEKGKAYTNYFGRCNVAEHEKLILLAQLKPEKD |
| | | SDEAVTYSLGKFGQRALDFYSIHVTKESTHPVKPLAQIAGNRYASGPVGKALSDACMGT |
| | | IASFLSKYQDIIIEHQKVVKGNQKRLESLRELAGKENLEYPSVTLPPQPHTKEGVDAYN |
| | | EVIARVRMWVNHNLWQKLKLSRDDAKPLLRLKGFPSFPLVERQANEVDWWDMVCNVKKL |
| | | INEKKEDGKVFWQNLAGYKRQEALRPYLSSEEDRKKGKKFARYQLGDLLLHLEKKHGED |
| | | WGKVYDEAWERIDKKVEGLSKHIKLEEERRSEDAQSKAALTDWLRAKASFVIEGLKEAD |
| | | KDEFCRCELKLQKWYGDLRGKPFAIEAENSILDISGFSKQYNCAFIWQKDGVKKLNLYL |
| | | IINYFKGGKLRFKKIKPEAFEANRFYTVINKKSGEIVPMEVNENFDDPNLIILPLAFGK |
| | | RQGREFIWNDLLSLETGSLKLANGRVIEKTLYNRRTRQDEPALFVALTFERREVLDSSN |
| | | IKPMNLIGVARGENIPAVIALTDPEGCPLSRFKDSLGNPTHILRIGESYKEKQRTIQAK |
| | | KEVEQRRAGGYSRKYASKAKNLADDMVRNTARDLLYYAVTQDAMLIFANLSRGFGRQGK |
| | | RTFMAERQYTRMEDWLTAKLAYEGLSKTYLSKTLAQYTSKTCSNCGFTITSADYDRVLE |
| | | KLKKTATGWMTTINGKELKVEGQITYYNRYKRQNVVKDLSVELDRLSEESVNNDISSWT |
| | | KGRSGEALSLLKKRFSHRPVQEKFVCLNCGFETHAAEQAALNIARSWLFLRSQEYKKYQ |
| | | TNKTTGNTDKRAFVETWQSFYRKKLKEVWKPAV |
| 28 | dCasX517 | QEIKRINKIRRRLVKDSNTKKAGKTGPMKTLLVRVMTPDLRERLENLRKKPENIPQPIS |
| | | NTSRANLNKLLTDYTEMKKAILHVYWEEFQKDPVGLMSRVAQPASKKIDQNKLKPEMDE |
| | | KGNLTTAGFACSQCGQPLFVYKLEQVSEKGKAYTNYFGRCNVAEHEKLILLAQLKPEKD |
| | | SDEAVTYSLGKFGQRALDFYSIHVTKESTHPVKPLAQIAGNRYASGAPVGKALSDACMG |
| | | TIASFLSKYQDIIIEHQKVVKGNQKRLESLRELAGKENLEYPSVTLPPQPHTKEGVDAY |
| | | NEVIARVRMWVNLNLWQKLKLSRDDAKPLLRLKGFPSFPLVERQANEVDWWDMVCNVKK |
| | | LINEKKEDGKVFWQNLAGYKRQEALRPYLSSEEDRKKGKKFARYQLGDLLLHLEKKHGE |
| | | DWGKVYDEAWERIDKKVEGLSKHIKLEEERRSEDAQSKAALTDWLRAKASFVIEGLKEA |
| | | DKDEFCRCELKLQKWYGDLRGKPFAIEAENSILDISGFSKQYNCAFIWQKDGVKKLNLY |
| | | LIINYFKGGKLRFKKIKPEAFEANRFYTVINKKSGEIVPMEVNFNFDDPNLIILPLAFG |
| | | KRQGREFIWNDLLSLETGSLKLANGRVIEKTLYNRRTRQDEPALFVALTFERREVLDSS |
| | | NIKPMNLIGVARGENIPAVIALTDPEGCPLSRFKDSLGNPTHILRIGESYKEKQRTIQA |
| | | KKEVEQRRAGGYSRKYASKAKNLADDMVRNTARDLLYYAVTQDAMLIFANLSRGFGRQG |
| | | KRTFMAERQYTRMEDWLTAKLAYEGLSKTYLSKTLAQYTSKTCSNCGFTITSADYDRVL |
| | | EKLKKTATGWMTTINGKELKVEGQITYYNRYKRQNVVKDLSVELDRLSEESVNNDISSW |
| | | TKGRSGEALSLLKKRFSHRPVQEKFVCLNCGFETHAAEQAALNIARSWLFLRSQEYKKY |
| | | QTNKTTGNTDKRAFVETWQSFYRKKLKEVWKPAV |
| 29 | dCasX518 | RQEIKRINKIRRRLVKDSNTKKAGKTGPMKTLLVRVMTPDLRERLENLRKKPENIPQPI |
| | | SNTSRANLNKLLTDYTEMKKAILHVYWEEFQKDPVGLMSRVAQPASKKIDQNKLKPEMD |
| | | EKGNLTTAGFACSQCGQPLFVYKLEQVSEKGKAYTNYFGRCNVAEHEKLILLAQLKPEK |
| | | DSDEAVTYSLGKFGQRALDFYSIHVTKESTHPVKPLAQIAGNRYASGPVGKALSDACMG |
| | | TIASFLSKYQDIIIEHQKVVKGNQKRLESLRELAGKENLEYPSVTLPPQPHTKEGVDAY |
| | | NEVIARVRMWVNLNLWQKLKLSRDDAKPLLRLKGFPSFPLVERQANEVDWWDMVCNVKK |

TABLE 4-continued dCasX Variant Sequences

| SEQ ID NO | dCasX | Amino Acid Sequence |
|---|---|---|
| | | LINEKKEDGKVFWQNLAGYKRQEALRPYLSSEEDRKKGKKFARYQLGDLLLHLEKKHGE<br>DWGKVYDEAWERIDKKVEGLSKHIKLEEERRSEDAQSKAALTDWLRAKASFVIEGLKEA<br>DKDEFCRCELKLQKWYGDLRGKPFAIEAENSILDISGFSKQYNCAFIWQKDGVKKLNLY<br>LIINYFKGGKLRFKKIKPEAFEANRFYTVINKKSGEIVPMEVNENFDDPNLIILPLAFG<br>KRQGREFIWNDLLSLETGSLKLANGRVIEKTLYNRRTRQDEPALFVALTFERREVLDSS<br>NIKPMNLIGVARGENIPAVIALTDPEGCPLSRFKDSLGNPTHILRIGESYKEKQRTIQA<br>KKEVEQRRAGGYSRKYASKAKNLADDMVRNTARDLLYYAVTQDAMLIFANLSRGFGRQG<br>KRTEMAERQYTRMEDWLTAKLAYEGLSKTYLSKTLAQYTSKTCSNCGFTITSADYDRVL<br>EKLKKTATGWMTTINGKELKVEGQITYYNRYKRQNVVKDLSVELDRLSEESVNNDISSW<br>TKGRSGEALSLLKKRFSHRPVQEKFVCLNCGFETHAAEQAALNIARSWLFLRSQEYKKY<br>QTNKTTGNTDKRAFVETWQSFYRKKLKEVWKPAV |
| 30 | dCasX519 | QEIKRINKIRRRLVKDSNTKKAGKTGPMKTLLVRVMTPDLRERLENLRKKPENIPQPIS<br>NTSRANLNKLLTDYTEMKKAILHVYWEEFQKDPVGLMSRVAQPASKKIDQNKLKPEMDE<br>KGNLTTAGFACSQCGQPLFVYKLEQVSEKGKAYTNYFGRCNVAEHEKLILLAQLKPEKD<br>SDEAVTYSLGKFGQRALDFYSIHVTKESTHPVKPLAQIAGNRYASGPVGKALSDACMGT<br>IASFLSKYQDIIIEHQKVVKGNQKRLESLRELAGKENLEYPSVTLPPQPHTKEGVDAYN<br>EVIARVRMWVNLNLWQKLKLSRDDAKPLLRLKGFPSFPLVERQANEVDWWDMVCNVKKL<br>INEKKEDGKVFWQNLAGYKRQEALRPYLSSEEDRKKGKKFARYQLGDLLLHLEKKHGED<br>WGKVYDEAWERIDKKVEGLSKHIKLEEERRSEDAQSKAALTDWLRAKASFVIEGLKEAD<br>KDEFCRCELKLQKWYGDLRGKPFAIEAENSILDISGFSKQYNCAFIWQKDGVKKLNLYL<br>IINYFKGGKLRFKKIKPEAFEANRFYTVINKKSGEIVPMEVNENFDDPNLIILPLAFGK<br>RQGREFIWNDLLSLETGSLKLANGRVIEKTLYNRRTRQDEPALFVALTFERREVLDSSN<br>IKPMNLIGVARGENIPAVIALTDPEGCPLSRFKDSLGNPTHIQLRIGESYKEKQRTIQA<br>KKEVEQRRAGGYSRKYASKAKNLADDMVRNTARDLLYYAVTQDAMLIFANLSRGFGRQG<br>KRTFMAERQYTRMEDWLTAKLAYEGLSKTYLSKTLAQYTSKTCSNCGFTITSADYDRVL<br>EKLKKTATGWMTTINGKELKVEGQITYYNRYKRQNVVKDLSVELDRLSEESVNNDISSW<br>TKGRSGEALSLLKKRFSHRPVQEKFVCLNCGFETHAAEQAALNIARSWLFLRSQEYKKY<br>QTNKTTGNTDKRAFVETWQSFYRKKLKEVWKPAV |
| 31 | dCasX520 | QEIKRINKIRRRLVKDSNTKKAGKTGPMKTLLVRVMTPDLRERLENLRKKPENIPQPIS<br>NTSRANLNKLLTDYTEMKKAILHVYWEEFQKDPVGLMSRVAQPASKKIDQNKLKPEMDE<br>KGNLTTAGFACSQCGQPLFVYKLEQVSEKGKAYTNYFGRCNVAEHEKLILLAQLKPEKD<br>SDEAVTYSLGKFGQRALDFYSIHVTKESTHPVKPLAQIAGNRYASGPVGKALSDACMGT<br>IASFLSKYQDIIIEHQKVVKGNQKRLESLRELAGKENLEYPSVTLPPQPHTKEGVDAYN<br>EVIARVRMWVNLNLWQKLKLSRDDAKPLLRLKGFPSFPLVERQANEVDWWDMVCNVKKL<br>INEKKEDGKVFWQNLAGYKRQEALRPYLSSEEDRKKGKKFARYQLGDLLLHLEKKHGED<br>WGKVYDEAWERIDKKVEGLSKHIKLEEERRSEDAQSKAALTDWLRAKASFVIEGLKEAD<br>KDEFCRCELKLQKWYGDLRGKPFAIEAENSILDISGFSKQYNCAFIWQKDGVKKLNLYL<br>IINYFKGGKLRFKKIKPEAFEANRFYTVINKKSGEIVPMEVNENFDDPNLIILPLAFGK<br>RQGREFIWNDLLSLETGSLKLANGRVIEKTLYNRRTRQDEPALFVALTFERREVLDSSN<br>IKPMNLIGVARGENIPAVIALTDPEGCPLSRFKDSLGNPTHILRIGESYKEKQRTTQAK<br>KEVEQRRAGGYSRKYASKAKNLADDMVRNTARDLLYYAVTQDAMLIFANLSRGFGRQGK<br>RTFMAERQYTRMEDWLTAKLAYEGLSKTYLSKTLAQYTSKTCSNCGFTITSADYDRVLE<br>KLKKTATGWMTTINGKELKVEGQITYYNRYKRQNVVKDLSVELDRLSEESVNNDISSWT<br>KGRSGEALSLLKKRFSHRPVQEKFVCLNCGFETHAAEQAALNIARSWLFLRSQEYKKYQ<br>TNKTTGNTDKRAFVETWQSFYRKKLKEVWKPAV |
| 32 | dCasX522 | QEIKRINKIRRRLVKDSNTKKAGKTGPMKTLLVRVMTPDLRERLENLRKKPENIPQPIS<br>NTSRANLNKLLTDYTEMKKAILHVYWEEFQKDPVGLMSRVAQPASKKIDQNKLKPEMDE<br>KGNLTTAGFACSQCGQPLFVYKLEQVSEKGKAYTNYFGRCNVAEHEKLILLAQLKPEKD<br>SDEAVTYSLGKFGQRALDFYSIHVTKESTHPVKPLAQIAGNRYASGPVGKALSDACMGT<br>IASFLSKYQDIIIEHQKVVKGNQKRLESLRELAGKENLEYPSVTLPPQPHTKEGVDAYN<br>EVIARVRMWVNLNLWQKLKLSRDDAKPLLRLKGFPSFPLVERQANEVDWWDMVCNVKKL<br>INEKKEDGKVFWQNLAGYKRQEALRPYLSSEEDRKKGKKFARYQLGDLLLHLEKKHGED<br>WGKVYDEAWERIDKKVEGLSKHIKLEEERRSEDAQSKAALTDWLRAKASFVIEGLKEAD<br>KDEFCRCELKLQKWYGDLRGKPFAIEAENSILDISGFSKQYNCAFIWQKDGVKKLNLYL<br>IINYFKGGKLRFKKIKPEAFEANRFYTVINKKSGEIVPMEVNENFDDPNLIILPLAFGK<br>RQGREFIWNDLLSLETGSLKLANGRVIEKTLYNRRTRQDEPALFVALTFERREVLDSSN<br>IKPMNLIGVARGENIPAVIALTDPEGCPLSRFKRSLGNPTHILRIGESYKEKQRTIQAK<br>KEVEQRRAGGYSRKYASKAKNLADDMVRNTARDLLYYAVTQDAMLIFANLSRGFGRQGK<br>RTFMAERQYTRMEDWLTAKLAYEGLSKTYLSKTLAQYTSKTCSNCGFTITSADYDRVLE<br>KLKKTATGWMTTINGKELKVEGQITYYNRYKRQNVVKDLSVELDRLSEESVNNDISSWT<br>KGRSGEALSLLKKRFSHRPVQEKFVCLNCGFETHAAEQAALNIARSWLFLRSQEYKKYQ<br>TNKTTGNTDKRAFVETWQSFYRKKLKEVWKPAV |
| 33 | dCasX523 | QEIKRINKIRRRLVKDSNTKKAGKTYPMKTLLVRVMTPDLRERLENLRKKPENIPQPIS<br>NTSRANLNKLLTDYTEMKKAILHVYWEEFQKDPVGLMSRVAQPASKKIDQNKLKPEMDE<br>KGNLTTAGFACSQCGQPLFVYKLEQVSEKGKAYTNYFGRCNVAEHEKLILLAQLKPEKD<br>SDEAVTYSLGKFGQRALDFYSIHVTKESTHPVKPLAQIAGNRYASGPVGKALSDACMGT<br>IASFLSKYQDIIIEHQKVVKGNQKRLESLRELAGKENLEYPSVTLPPQPHTKEGVDAYN<br>EVIARVRMWVNLNLWQKLKLSRDDAKPLLRLKGFPSFPLVERQANEVDWWDMVCNVKKL<br>INEKKEDGKVFWQNLAGYKRQEALRPYLSSEEDRKKGKKFARYQLGDLLLHLEKKHGED<br>WGKVYDEAWERIDKKVEGLSKHIKLEEERRSEDAQSKAALTDWLRAKASFVIEGLKEAD |

TABLE 4-continued dCasX Variant Sequences

| SEQ ID NO | dCasX | Amino Acid Sequence |
|---|---|---|
| | | KDEFCRCELKLQKWYGDLRGKPFAIEAENSILDISGFSKQYNCAFIWQKDGVKKLNLYL |
| | | IINYFKGGKLRFKKIKPEAFEANRFYTVINKKSGEIVPMEVNENFDDPNLIILPLAFGK |
| | | RQGREFIWNDLLSLETGSLKLANGRVIEKTLYNRRTRQDEPALFVALTFERREVLDSSN |
| | | IKPMNLIGVARGENIPAVIALTDPEGCPLSRFKDSLGNPTHILRIGESYKEKQRTIQAK |
| | | KEVEQRRAGGYSRKYASKAKNLADDMVRNTARDLLYYAVTQDAMLIFANLSRGFGRQGK |
| | | RTFMAERQYTRMEDWLTAKLAYEGLSKTYLSKTLAQYTSKTCSNCGFTITSADYDRVLE |
| | | KLKKTATGWMTTINGKELKVEGQITYYNRYKRQNVVKDLSVELDRLSEESVNNDISSWT |
| | | KGRSGEALSLLKKRFSHRPVQEKFVCLNCGFETHAAEQAALNIARSWLFLRSQEYKKYQ |
| | | TNKTTGNTDKRAFVETWQSFYRKKLKEVWKPAV |
| 34 | dCasX524 | QEIKRINKIRRRLVKDSNTKKAGKTGPMKTLLVRVMTPDLRERLENLRKKPENIPQPIS |
| | | NTSRANLNKLLTDYTEMKKAILHVYWEEFQKDPVGLMSRVAQPASKKIDQNKLKPEMDE |
| | | KGNLTTAGFACSQCGQPLFVYKLEQVSEKGKAYTNYFGRCNVAEHEKLILLAQLKPEKD |
| | | SDEAVTYSLGKFGQRALDFYSIHVTKESTHPVKPLAQIAGNRYASGPVGKALSDACMGT |
| | | IASFLSKYQDIIIEHQKVVKGNQKRLESLRELAGKENLEYPSVTLPPQPHTKEGVDAYN |
| | | EVIARVRMWVNLNLWQKLKLSRDDAKPLLRLKGFPSFPLVERQANEVDWWDMVCNVKKL |
| | | INEKKEDGKVFWQNLAGYKRQEALRPYLSSEEDRKKGKKFARYQLGDLLLHLEKKHGED |
| | | WGKVYDEAWERIDKKVEGLSKHIKLEEERRSEDAQSKAALTDWLRAKASFVIEGLKEAD |
| | | KDEFCRCELKLQKWYGDLRGKPFAIEAENSILDISGFSKQYNCAFIWQKDGVKKLNLYL |
| | | IINYFKGGKLRFKKIKPEAFEANRFYTVINKKSGEIVPMEVNFNFDDPNLIILPLAFGK |
| | | RQGREFIWNDLLSLETGSLKLANGRVIEKTLYNRRTRQDEPALFVALTFERREVLDSSN |
| | | IKPMNLIGVARGENIPAVIALTDPEGCPLSRFKDSLGNPTHILRIGESYKEKQRTIQAK |
| | | KEVEQRRAGGYSRKYASKAKNLADDMVRNTARDLLYYAVTQDAMLIFANLSRGFGRQGK |
| | | RTFMAERQYTRMEDWLTAKLAYEGLSKTYLSKTLAQYTSKTCSNCGFTIHSADYDRVLE |
| | | KLKKTATGWMTTINGKELKVEGQITYYNRYKRQNVVKDLSVELDRLSEESVNNDISSWT |
| | | KGRSGEALSLLKKRFSHRPVQEKFVCLNCGFETHAAEQAALNIARSWLFLRSQEYKKYQ |
| | | TNKTTGNTDKRAFVETWQSFYRKKLKEVWKPAV |
| 35 | dCasX525 | QEIKRINKIRRRLVKDSNTKKAGKTGPMKTLLVRVMTPDLRERLENLRKKPENIPQPIS |
| | | NTSRANLNKLLTDYTEMKKAILHVYWEEFQKDPVGLMSRVAQPASKKIDQNKLKPEMDE |
| | | KGNLTTAGFACSQCGQPLFVYKLEQVSEKGKAYTNYFGRCNVAEHEKLILLAQLKPEKD |
| | | SDEAVTYSLGKFGQRALDFYSIHVTKESTHPVKPLAQIAGNRYASGPVGKALSDACMGT |
| | | IASFLSKYQDIIIEHQKVVKGNQKRLESLRELAGKENLEYPSVTLPPQPHTKEGVDAYN |
| | | EVIARVRMWVNLNLWQKLKLSRDDAKPLLRLKGFPSFPLVERQANEVDWWDMVCNVKKL |
| | | INEKKEDGKVFWQNLAGYKRQEALRPYLSSEEDRKKGKKFARYQLGDLLLHLEKKHGED |
| | | WGKVYDEAWERIDKKVEGLSKHIKLEEERRSEDAQSKAALTDWLRAKASFVIEGLKEAD |
| | | KDEFCRCELKLQKWYGDLRGKPFAIEAENSILDISGFSKQYNCAFIWQKDGVKKLNLYL |
| | | IINYFKGGKLRFKKIKPEAFEANRFYTVINKKSGEIVPMEVNENFDDPNLIILPLAFGK |
| | | RQGREFIWNDLLSLETGSLKLANGRVIEKTLYNRRTRQDEPALFVALTFERREVLDSSN |
| | | IKPMNLIGVARGENIPAVIALTDPEGCPLSRFKDSLGNPTHILRIGESYKEKQRTIQAK |
| | | KEVEQRRAGGYSRKYASKAKNLADDMVRNTARDLLYYAATQDAMLIFANLSRGFGRQGK |
| | | RTFMAERQYTRMEDWLTAKLAYEGLSKTYLSKTLAQYTSKTCSNCGFTITSADYDRVLE |
| | | KLKKTATGWMTTINGKELKVEGQITYYNRYKRQNVVKDLSVELDRLSEESVNNDISSWT |
| | | KGRSGEALSLLKKRFSHRPVQEKFVCLNCGFETHAAEQAALNIARSWLFLRSQEYKKYQ |
| | | TNKTTGNTDKRAFVETWQSFYRKKLKEVWKPAV |
| 36 | dCasX526 | QEIKRINKIRRRLVKDSNTKKAGKTGPMKTLLVRVMTPDLRERLENLRKKPENIPQPIS |
| | | NTSRANLNKLLTDYTEMKKAILHVYWEEFQKDPVGLMSRVAQPASKKIDQNKLKPEMDE |
| | | KGNLTTAGFACSQCGQPLFVYKLEQVSEKGKAYTNYFGRCNVAEHEKLILLAQLKPEKD |
| | | SDEAVTYSLGKFGQRALDFYSIHVTKESTHPVKPLAQIAGNRYASGPVGKALSDACMGT |
| | | IASFLSKYQDIIIEHQKVVKGNQKRLESLRELAGKENLEYPSVTLPPQPHTKEGVDAYN |
| | | EVIARVRMWVNLNLWQKLKLSRDDAKPLLRLKGFPSFPLVERQANEVDWWDMVCNVKKL |
| | | INEKKEDGKVFWQNLAGYKRQEALRPYLSSEEDRKKGKKFARYQLGDLLLHLEKKHGED |
| | | WGKVYDEAWERIDKKVEGLSKHIKLEEERRSEDAQSKAALTDWLRAKASFVIEGLKEAD |
| | | KDEFCRCELKLQKWYGDLRGKPFAIEAENSILDISGFSKQYNCAFIWQKDGVKKLNLYL |
| | | IINYFKGGKLRFKKIKPEAFEANRFYTVINKKSGEIVPMEVNENFDDPNLIILPLAFGK |
| | | RQGREFIWNDLLSLETGSLKLANGRVIEKTLYNRRTRQDEPALFVALTFERREVLDSSN |
| | | IKPMNLIGVARGENIPAVIALTDPEGCPLSRFKDSLGNPTHILRIGESYKEKQRTIQAA |
| | | KEVEQRRAGGYSRKYASKAKNLADDMVRNTARDLLYYAVTQDAMLIFANLSRGFGRQGK |
| | | RTFMAERQYTRMEDWLTAKLAYEGLSKTYLSKTLAQYTSKTCSNCGFTITSADYDRVLE |
| | | KLKKTATGWMTTINGKELKVEGQITYYNRYKRQNVVKDLSVELDRLSEESVNNDISSWT |
| | | KGRSGEALSLLKKRFSHRPVQEKFVCLNCGFETHAAEQAALNIARSWLFLRSQEYKKYQ |
| | | TNKTTGNTDKRAFVETWQSFYRKKLKEVWKPAV |
| 59353 | dCasX535 | QEIKRINKIRRRLVKDSNTKKAGKTGPMKTLLVRVMTPDLRERLENLRKKPENIPQPIS |
| | | NTSRANLNKLLTDYTEMKKAILHVYWEEFQKDPVGLMSRVAQPASKKIDQNKLKPEMDE |
| | | KGNLTTAGFACSQCGQPLFVYKLEQVSEKGKAYTNYFGRCNVAEHEKLILLAQLKPEKD |
| | | SDEAVTYSLGKFGQRALDFYSIHVTKESTHPVKPLAQIAGNRYASSPVGKALSDACMGT |
| | | IASFLSKYQDIIIEHQKVVKGNQKRLESLRELAGKENLEYPSVTLPPQPHTKEGVDAYN |
| | | EVIARVRMWVNLNLWQKLKLSRDDAKPLLRLKGFPSFPLVERQANEVDWWDMVCNVKKL |
| | | INEKKEDGKVFWQNLAGYKRQEALRPYLSSEEDRKKGKKFARYQLGDLLLHLEKKHGED |
| | | WGKVYDEAWERIDKKVEGLSKHIKLEEERRSEDAQSKAALTDWLRAKASFVIEGLKEAD |
| | | KDEFCRCELKLQKWYGDLRGKPFAIEAENSILDISGFSKQYNCAFIWQKDGVKKLNLYL |
| | | IINYFKGGKLRFKKIKPEAFEANRFYTVINKKSGEIVPMEVNENFDDPNLIILPLAFGK |

TABLE 4-continued dCasX Variant Sequences

| SEQ ID NO | dCasX | Amino Acid Sequence |
|---|---|---|
| | | RQGREFIWNDLLSLETGSLKLANGRVIEKTLYNRRTRQDEPALFVALTFERREVLDSSNIKPMNLIGVARGENIPAVIALTDPEGCPLSRFKDSLGNPTHILRIGESYKEKQRTIQAKKEVEQRRAGGYSRKYASKAKNLADDMVRNTARDLLYYAVTQDAMLIFANLSRGFGRQGKRTFMAERQYTRMEDWLTAKLAYEGLPSKTYLSKTLAQYTSKTCSNCGFTITSADYDRVLEKLKKTATGWMTTINGKELKVEGQITYYNRYKRQNVVKDLSVELDRLSEESVNNDISSWTKGRSGEALSLLKKRFSHRPVQEKFVCLNCGFETHAAEQAALNIARSWLFLRSQEYKKYQTNKTTGNTDKRAFVETWQSFYRKKLKEVWKPAV |
| 59354 | dCasX593 | QEIKRINKIRRRLVKDSNTKKAGKTGPMKTLLVRVMTPDLRERLENLRKKPENIPQPISNTSRANLNKLLTDYTEMKKAILHVYWEEFQKDPVGLMSRVAQPASKKIDQNKLKPEMDEKGNLTTAGFACSQCGQPLFVYKLEQVSEKGKAYTNYFGRCNVAEHEKLILLAQLKPEKDSDEAVTYSLGKFGQRALDFYSIHVTKESTHPVKPLAQIAGNRYASGPVGKALSDACMGTIASFLSKYQDIIIEHQKVVKGNQKRLESLRELAGKENLEYPSVTLPPQPHTKEGVDAYNEVIARVRWWVNLNLWQKLKLSRDDAKPLLRLKGFPSFPLVERQANEVDWWDMVCNVKKLINEKKEDGKVFWQNLAGYKRQEALRPYLSSEEDRKKGKKFARYQLGDLLLHLEKKHGEDWGKVYDEAWERIDKKVEGLSKHIKLEEERRSEDAQSKAALTDWLRAKASFVIEGLKEADKDEFCRCELKLQKWYGDLRGKPFAIEAENSILDISGFSKQYNCAFIWQKDGVKKLNLYLIINYFKGGKLRFKKIKPEAFEANRFYTVINKKSGEIVPMEVNFNFDDPNLIILPLAFGKRQGREFIWNDLLSLETGSLKLANGRVIEKTLYNRRTRQDEPALFVALTFERREVLDSSNIKPMNLIGVARGENIPAVIALTDPEGCPLSRFKDSLGNPTHILRIGESYKEKQRTIQAKKEVEQRRAGGYSRKYASKAKNLADDMVRNTARDLLYYAVTQDAMLIFANLSRGFGRQGKRTFMAERQYTRMEDWLTAKLAYEGLPSKTYLSKTLAQYTSKTCSNCGFTITSADYDRVLEKLKKTATGWMTTINGKELKVEGQITYYNRYKRQNVVKDLSVELDRLSEESVNNDISSWTKGRSGEALSLLKKRFSHRPVQEKFVCLNCGFETHAAEQAALNIARSWLFLRSQEYKKYQTNKTTGNTDKRAFVETWQSFYRKKLKEVWKPAV |
| 59355 | dCasX668 | QEIKRINKIRRRLVKDSNTKKAGKTRGPMKTLLVRVMTPDLRERLENLRKKPENIPQPISNTSRANLNKLLTDYTEMKKAILHVYWEEFQKDPVGLMSRVAQPASKKIDQNKLKPEMDEKGNLTTAGFACSQCGQPLFVYKLEQVSEKGKAYTNYFGRCNVAEHEKLILLAQLKPEKDSDEAVTYSLGKFGQRALDFYSIHVTKESTHPVKPLAQIAGNRYASSPVGKALSDACMGTIASFLSKYQDIIIEHQKVVKGNQKRLESLRELAGKENLEYPSVTLPPQPHTKEGVDAYNEVIARVRMWVNLNLWQKLKLSRDDAKPLLRLKGFPSFPLVERQANEVDWWDMVCNVKKLINEKKEDGKVFWQNLAGYKRQEALRPYLSSEEDRKKGKKFARYQLGDLLLHLEKKHGEDWGKVYDEAWERIDKKVEGLSKHIKLEEERRSEDAQSKAALTDWLRAKASFVIEGLKEADKDEFCRCELKLQKWYGDLRGKPFAIEAENSILDISGFSKQYNCAFIWQKDGVKKLNLYLIINYFKGGKLRFKKIKPEAFEANRFYTVINKKSGEIVPMEVNENFDDPNLIILPLAFGKRQGREFIWNDLLSLETGSLKLANGRVIEKTLYNRRTRQDEPALFVALTFERREVLDSSNIKPMNLIGVARGENIPAVIALTDPEGCPLSRFKDSLGNPTHILRIGESYKEKQRTIQAKKEVEQRRAGGYSRKYASKAKNLADDMVRNTARDLLYYAVTQDAMLIFANLSRGFGRQGKRTFMAERQYTRMEDWLTAKLAYEGLPSKTYLSKTLAQYTSKTCSNCGFTITSADYDRVLEKLKKTATGWMTTINGKELKVEGQITYYNRYKRQNVVKDLSVELDRLSEESVNNDISSWTKGRSGEALSLLKKRFSHRPVQEKFVCLNCGFETHAAEQAALNIARSWLFLRSQEYKKYQTNKTTGNTDKRAFVETWQSFYRKKLKEVWKPAV |
| 59356 | dCasX672 | QEIKRINKIRRRLVKDSNTKKAGKTGPMKTLLVRVMTPDLRERLENLRKKPENIPQPISNTSRANLNKLLTDYTEMKKAILHVYWEEFQKDPVGLMSRVAQPASKKIDQNKLKPEMDEKGNLTTAGFACSQCGQPLFVYKLEQVSEKGKAYTNYFGRCNVAEHEKLIKLAQLKPEKDSDEAVTYSLGKFGQRALDFYSIHVTKESTHPVKPLAQIAGNRYASSPVGKALSDACMGTIASFLSKYQDIIIEHQKVVKGNQKRLESLRELAGKENLEYPSVTLPPQPHTKEGVDAYNEVIARVRMWVNLNLWQKLKLSRDDAKPLLRLKGFPSFPLVERQANEVDWWDMVCNVKKLINEKKEDGKVFWQNLAGYKRQEALRPYLSSEEDRKKGKKFARYQLGDLLLHLEKKHGEDWGKVYDEAWERIDKKVEGLSKHIKLEEERRSEDAQSKAALTDWLRAKASFVIEGLKEADKDEFCRCELKLQKWYGDLRGKPFAIEAENSILDISGFSKQYNCAFIWQKDGVKKLNLYLIINYFKGGKLRFKKIKPEAFEANRFYTVINKKSGEIVPMEVNFNFDDPNLIILPLAFGKRQGREFIWNDLLSLETGSLKLANGRVIEKTLYNRRTRQDEPALFVALTFERREVLDSSNIKPMNLIGVARGENIPAVIALTDPEGCPLSRFKDSLGNPTHILRIGESYKEKQRTIQAKKEVEQRRAGGYSRKYASKAKNLADDMVRNTARDLLYYAVTQDAMLIFANLSRGFGRQGKRTFMAERQYTRMEDWLTAKLAYEGLPSKTYLSKTLAQYTSKTCSNCGFTITSADYDRVLEKLKKTATGWMTTINGKELKVEGQITYYNRYKRQNVVKDLSVELDRLSEESVNNDISSWTKGRSGEALSLLKKRFSHRPVQEKFVCLNCGFETHAAEQAALNIARSWLFLRSQEYKKYQTNKTTGNTDKRAFVETWQSFYRKKLKEVWKPAV |
| 59357 | dCasX676 | QEIKRINKIRRRLVKDSNTKKAGKTRGPMKTLLVRVMTPDLRERLENLRKKPENIPQPISNTSRANLNKLLTDYTEMKKAILHVYWEEFQKDPVGLMSRVAQPASKKIDQNKLKPEMDEKGNLTTAGFACSQCGQPLFVYKLEQVSEKGKAYTNYFGRCNVAEHEKLIKLAQLKPEKDSDEAVTYSLGKFGQRALDFYSIHVTKESTHPVKPLAQIAGNRYASSPVGKALSDACMGTIASFLSKYQDIIIEHQKVVKGNQKRLESLRELAGKENLEYPSVTLPPQPHTKEGVDAYNEVIARVRMWVNLNLWQKLKLSRDDAKPLLRLKGFPSFPLVERQANEVDWWDMVCNVKKLINEKKEDGKVFWQNLAGYKRQEALRPYLSSEEDRKKGKKFARYQLGDLLLHLEKKHGEDWGKVYDEAWERIDKKVEGLSKHIKLEEERRSEDAQSKAALTDWLRAKASFVIEGLKEADKDEFCRCELKLQKWYGDLRGKPFAIEAENSILDISGFSKQYNCAFIWQKDGVKKLNLYLIINYFKGGKLRFKKIKPEAFEANRFYTVINKKSGEIVPMEVNENFDDPNLIILPLAFGKRQGREFIWNDLLSLETGSLKLANGRVIEKTLYNRRTRQDEPALFVALTFERREVLDSSNIKPMNLIGVARGENIPAVIALTDPEGCPLSRFKDSLGNPTHILRIGESYKEKQRTIQA |

TABLE 4-continued dCasX Variant Sequences

| SEQ ID NO | dCasX | Amino Acid Sequence |
|---|---|---|
| | | KKEVEQRRAGGYSRKYASKAKNLADDMVRNTARDLLYYAVTQDAMLIFANLSRGFGRQG<br>KRTFMAERQYTRMEDWLTAKLAYEGLPSKTYLSKTLAQYTSKTCSNCGFTITSADYDRV<br>LEKLKKTATGWMTTINGKELKVEGQITYYNRYKRQNVVKDLSVELDRLSEESVNNDISS<br>WTKGRSGEALSLLKKRFSHRPVQEKFVCLNCGFETHAAEQAALNIARSWLFLRSQEYKK<br>YQTNKTTGNTDKRAFVETWQSFYRKKLKEVWKPAV |
| 59358 | dCasX812 | QEIKRINKIRRRLVKDSNTKKAGKTGPMKTLLVRVMTPDLRERLENLRKKPENIPQPIS<br>NTSRANLNKLLTDYTEMKKAILHVYWEEFQKDPVGLMSRVAQPASKKIDQNKLKPEMDE<br>KGNLTTAGFACSQCGQPLFVYKLEQVSEKGKAYTNYFGRCNVAEHEKLILLAQLKPEKD<br>SDEAVTYSLGKFGQRALDFYSIHVTKESTHPVKPLAQIAGNRYASGPVGKALSDACMGT<br>IASFLSKYQDIIIEHQKVVKGNQKRLESLRELAGKENLEYPSVTLPPQPHTKEGVDAYN<br>EVIARVRMWVNLNLWQKLKLSRDDAKPLLRLKKFPSFPLVERQANEVDWWDMVCNVKKL<br>INEKKEDGKVFWQNLAGYKRQEALRPYLSSEEDRKKGKKFARYQLGDLLLHLEKKHGED<br>WGKVYDEAWERIDKKVEGLSKHIKLEEERRSEDAQSKAALTDWLRAKASFVIEGLKEAD<br>KDEFCRCELKLQKWYGDLRGKPFAIEAENSILDISGFSKQYNCAFIWQKDGVKKLNLYL<br>IINYFKGGKLRFKKIKPEAFEANRFYTVINKKSGEIVPMEVNENFDDPNLIILPLAFGK<br>RQGREFIWNDLLSLETGSLKLANGRVIEKTLYNRRTRQDEPALFVALTFERREVLDSSN<br>IKPMNLIGVARGENIPAVIALTDPEGCPLSRFKDSLGNPTHILRIGESYKEKQRTIQAK<br>KEVEQRRAGGYSRKYASKAKNLADDMVRNTARDLLYYAVTQDAMLIFANLSRGFGRQGK<br>RTFMAERQYTRMEDWLTAKLAYEGLPSKTYLSKTLAQYTSKTCSNCGFTITSADYDRVL<br>EKLKKTATGWMTTINGKELKVEGQITYYNRYKRQNVVKDLSVELDRLSEESVNNDISSW<br>TKGRSGEALSLLKKRFSHRPVQEKFVCLNCGFETHAAEQAALNIARSWLFLRSQEYKKY<br>QTNKTTGNTDKRAFVETWQSFYRKKLKEVWKPAV |

d. Affinity for the gRNA

In some embodiments, a dCasX with linked repressor domains has improved affinity for the gRNA relative to a reference dCasX protein, leading to the formation of the ribonucleoprotein complex. Increased affinity of the dXR for the gRNA may, for example, result in a lower $K_d$ for the generation of a RNP complex, which can, in some cases, result in a more stable ribonucleoprotein complex formation. In some embodiments, the $K_d$ of a dXR for a gRNA is increased relative to a reference dCasX protein by a factor of at least about 1.1, at least about 1.2, at least about 1.3, at least about 1.4, at least about 1.5, at least about 1.6, at least about 1.7, at least about 1.8, at least about 1.9, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100. In some embodiments, the dCasX variant has about 1.1 to about 10-fold increased binding affinity to the gRNA compared to the catalytically-dead variant of reference CasX protein of SEQ ID NO: 2.

In some embodiments, increased affinity of the dCasX with linked repressor domains for the gRNA results in increased stability of the ribonucleoprotein complex when delivered to mammalian cells, including in vivo delivery to a subject. This increased stability can affect the function and utility of the complex in the cells of a subject, as well as result in improved pharmacokinetic properties in blood, when delivered to a subject. In some embodiments, increased affinity of the dXR, and the resulting increased stability of the ribonucleoprotein complex, allows for a lower dose of the dXR to be delivered to the subject or cells while still having the desired activity; for example in vivo or in vitro gene repression. The increased ability to form RNP and keep them in stable form can be assessed using in vitro assays known in the art.

In some embodiments, a higher affinity (tighter binding) of a dCasX variant protein and linked repressor domain to a gRNA allows for a greater amount of repression events when both the dCasX variant protein and the gRNA remain in an RNP complex. Increased repression events can be assessed using repression assays described herein.

Methods of measuring dXR fusion protein binding affinity for a gRNA include in vitro methods using purified dXR fusion protein and gRNA. The binding affinity for reference dXR can be measured by fluorescence polarization if the gRNA or dXR fusion protein is tagged with a fluorophore. Alternatively, or in addition, binding affinity can be measured by biolayer interferometry, electrophoretic mobility shift assays (EMSAs), or filter binding. Additional standard techniques to quantify absolute affinities of RNA binding proteins such as the reference dCasX and variant proteins of the disclosure for specific gRNAs such as reference gRNAs and variants thereof include, but are not limited to, isothermal calorimetry (ITC), and surface plasmon resonance (SPR), as well as the methods of the Examples.

e. Improved Specificity for a Target Site

In some embodiments, a dCasX variant protein with linked repressor domains has improved specificity for a target nucleic acid sequence relative to a reference dCasX protein with linked repressor domains. As used herein, "specificity," sometimes referred to as "target specificity," refers to the degree to which a CRISPR/Cas system ribonucleoprotein complex binds off-target sequences that are similar, but not identical to the target nucleic acid sequence; e.g., a dXR RNP with a higher degree of specificity would exhibit reduced off-target methylation of sequences relative to a reference dXR protein. The specificity, and the reduction of potentially deleterious off-target effects, of CRISPR/Cas system proteins can be vitally important in order to achieve an acceptable therapeutic index for use in mammalian subjects.

In some embodiments, a dCasX variant protein with linked repressor domains has improved specificity for a target site within the target sequence that is complementary to the targeting sequence of the gRNA. Without wishing to be bound by theory, it is possible that amino acid changes in the helical I and II domains that increase the specificity of the dXR for the target nucleic acid strand can increase the specificity of the dXR for the target nucleic acid overall. In some embodiments, amino acid changes that increase specificity of dXRs for target nucleic acid may also result in decreased affinity of dXRs for DNA.

f. Protospacer and PAM Sequences

Herein, the protospacer is defined as the DNA sequence complementary to the targeting sequence of the guide RNA and the DNA complementary to that sequence, referred to as the target strand and non-target strand, respectively. As used herein, the PAM is a nucleotide sequence proximal to the protospacer that, in conjunction with the targeting sequence of the gRNA, helps the orientation and positioning of the CasX on the DNA strand.

PAM sequences may be degenerate, and specific RNP constructs may have different preferred and tolerated PAM sequences that support different efficiencies of binding and, in the case of catalytically-active nucleases, cleavage. Following convention, unless stated otherwise, the disclosure refers to both the PAM and the protospacer sequence and their directionality according to the orientation of the non-target strand. This does not imply that the PAM sequence of the non-target strand, rather than the target strand, is determinative of cleavage or mechanistically involved in target recognition. For example, when reference is to a TTC PAM, it may in fact be the complementary GAA sequence that is required for target binding, or it may be some combination of nucleotides from both strands. In the case of the CasX proteins disclosed herein, the PAM is located 5' of the protospacer with a single nucleotide separating the PAM from the first nucleotide of the protospacer. Thus, in the case of reference CasX, a TTC PAM should be understood to mean a sequence following the formula 5'- . . . NNTTCN (protospacer)NNNNNN . . . 3' where 'N' is any DNA nucleotide and '(protospacer)' is a DNA sequence having identity with the targeting sequence of the guide RNA. In the case of a CasX variant with expanded PAM recognition, a TTC, CTC, GTC, or ATC PAM should be understood to mean a sequence following the formulae: 5'- . . . NNTTCN (protospacer)NNNNNN . . . 3'; 5'- . . . NNCTCN(protospacer)NNNNNN . . . 3'; 5'- . . . NNGTCN(protospacer) NNNNNN . . . 3'; or 5'- . . . NNATCN(protospacer) NNNNNN . . . 3'. Alternatively, a TC PAM should be understood to mean a sequence following the formula 5'- . . . NNNTCN(protospacer)NNNNNN . . . 3'.

In some embodiments, a dCasX variant exhibits greater repression efficiency and/or binding of a target sequence in the target nucleic acid when any one of the PAM sequences TTC, ATC, GTC, or CTC is located 1 nucleotide 5' to the non-target strand of the protospacer having identity with the targeting sequence of the gRNA in a cellular assay system compared to the repression efficiency and/or binding of an RNP comprising a reference dCasX protein in a comparable assay system. In some embodiments, the PAM sequence is TTC. In some embodiments, the PAM sequence is ATC. In some embodiments, the PAM sequence is CTC. In some embodiments, the PAM sequence is GTC.

g. dCasX Fusion Proteins

In some embodiments, the disclosure provides dXR fusion proteins comprising a heterologous protein.

In some cases, a heterologous polypeptide (a fusion partner) for use with a dXR provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like).

Figure 38:
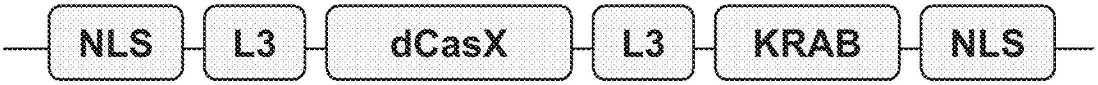
FIG. 38 illustrates the schematic of a generic dXR configuration as described in Example 1. NLS is the nuclear localization signal, L3 is linker 3 (see Table 24 for AA sequence).

In some cases, a dXR fusion protein includes (is fused to) a nuclear localization signal (NLS). In some cases, a dXR fusion protein is fused to 2 or more, 3 or more, 4 or more, or 5 or more 6 or more, 7 or more, 8 or more NLSs. In some cases, one or more NLSs (2 or more, 3 or more, 4 or more, or 5 or more NLSs) are positioned at or near (e.g., within 50 amino acids of) the N-terminus and/or the C-terminus of the dXR fusion protein. In some cases, one or more NLSs (2 or more, 3 or more, 4 or more, or 5 or more NLSs) are positioned at or near (e.g., within 50 amino acids of) the N-terminus of the dXR fusion protein. In some cases, one or more NLSs (2 or more, 3 or more, 4 or more, or 5 or more NLSs) are positioned at or near (e.g., within 50 amino acids of) the C-terminus of the dXR fusion protein. In some cases, one or more NLSs (3 or more, 4 or more, or 5 or more NLSs) are positioned at or near (e.g., within 50 amino acids of) both the N-terminus and the C-terminus of the dXR fusion protein. In some cases, an NLS is positioned at the N-terminus and an NLS is positioned at the C-terminus of the dXR fusion protein. Representative configurations of dXR with NLS are shown in FIGS. 7, 38, and 45.

In some cases, non-limiting examples of NLSs suitable for use with a dXR include sequences having at least about 80%, at least about 90%, or at least about 95% identity or are identical to sequences derived from: the NLS of the SV40 virus large T-antigen, having the amino acid sequence PKKKRKV (SEQ ID NO: 33289); the NLS from nucleoplasmin (e.g., the nucleoplasmin bipartite NLS with the sequence KRPAATKKAGQAKKKK (SEQ ID NO: 33290); the c-myc NLS having the amino acid sequence PAAKRVKLD (SEQ ID NO: 33291) or RQRRNELKRSP (SEQ ID NO: 33292); the hRNPAI M9 NLS having the sequence NQSSNFGPMKGGNFGGRSSGPYGGGGQYFAKPRNQGGY (SEQ ID NO: 33293); the sequence RMRIZFKNKGKDTAELRRRRVEVSVELRKAKKDEQILKRRNV (SEQ ID NO: 33294) of the IBB domain from importin-alpha; the sequences VSRKRPRP (SEQ ID NO: 33295) and PPKKARED (SEQ ID NO: 33296) of the myoma T protein; the sequence PQPKKKPL (SEQ ID NO: 33297) of human p53; the sequence SALIKKKKKMAP (SEQ ID NO: 33298) of mouse c-abl IV; the sequences DRLRR (SEQ ID NO: 33299) and PKQKKRK (SEQ ID NO: 33300) of the influenza virus NS1; the sequence RKLKKKIKKL (SEQ ID NO: 33301) of the Hepatitis virus delta antigen; the sequence REKKKFLKRR (SEQ ID NO: 33302) of the mouse Mxl protein; the sequence KRKGDEVDGVDEVAKKKSKK (SEQ ID NO: 33303) of the human poly(ADP-ribose) polymerase; the sequence RKCLQAGMNLEARKTKK (SEQ ID NO: 33304) of the steroid hormone receptors (human) glucocorticoid; the sequence PRPRKIPR (SEQ ID NO: 33305) of Boma disease virus P protein (BDV-P1); the sequence PPRKKRTVV (SEQ ID NO: 33306) of hepatitis C virus nonstructural protein (HCV-NS5A); the sequence NLSKKKKRKREK (SEQ ID NO: 33307) of LEF1; the sequence RRPSRPFRKP (SEQ ID NO: 33308) of ORF57 simirae; the sequence KRPRSPSS (SEQ ID NO: 33309) of EBV LANA; the sequence KRGINDRNFWRGENERKTR (SEQ ID NO: 33310) of Influenza A protein; the sequence PRPPKMARYDN (SEQ ID NO: 33311) of human RNA helicase A (RHA); the sequence KRSFSKAF (SEQ ID NO: 33312) of nucleolar RNA helicase II; the sequence KLKIKRPVK (SEQ ID NO: 33313) of TUS-protein; the sequence PKKKRKVPPPPAAKRVKLD (SEQ ID NO: 33314) associated with importin-alpha; the sequence PKTRRRPRRSQRKRPPT (SEQ ID NO: 33315) from the Rex protein in HTLV-1; the sequence SRRRKANPTKLSENAKKLAKEVEN (SEQ ID NO: 33316) from the EGL-13 protein of *Caenorhabditis elegans*; and the sequences KTRRRPRRSQRKRPPT (SEQ ID NO: 33317), RRKKRRPRRKKRR (SEQ ID NO: 33318), PKKKSRKPKKKSRK (SEQ ID NO: 33319), HKKKHPDASVNFSEFSK (SEQ ID NO: 33320), QRPGPYDRPQRPGPYDRP (SEQ ID NO: 33321), LSPSLSPLLSPSLSPL (SEQ ID NO: 33322), RGKGGKGLGKGGAKRHRK (SEQ ID NO: 33323), PKRGRGRPKRGRGR (SEQ ID NO: 33324), PKKKRKVPPPPAAKRVKLD (SEQ ID NO: 33325), PKKKRKVPPPPKKKRKV (SEQ ID NO: 33326), PAKRARRGYKC (SEQ ID NO: 33327), KLGPRKATGRW (SEQ ID NO: 33328), PRRKREE (SEQ ID NO: 33329), PYRGRKE (SEQ ID NO: 33330), PLRKRPRR (SEQ ID NO: 33331), PLRKRPRRGSPLRKRPRR (SEQ ID NO: 33332), PAAKRVKLDGGKRTADGSEFESPKKKRKV (SEQ ID NO: 33333), PAAKRVKLDGGKRTADGSEFESPKKKRKVGIHGVPAA (SEQ ID NO: 33334), PAAKRVKLDGGKRTADGSEFESPKKKRKVAEAAAKEAAAKEAAAKA (SEQ ID NO: 33335), PAAKRVKLDGGKRTADGSEFESPKKKRKVPG (SEQ ID NO: 33336), KRKGSPERGERKRHW (SEQ ID NO: 33337), KRTADSQHSTPPKTKRKVEFEPKKKRKV (SEQ ID NO: 33338), and PKKKRKVGGSKRTADSQHSTPPKTKRKVEFEPKKKRKV (SEQ ID NO: 33339). In some embodiments, the one or more NLS are linked to the dXR or to adjacent NLS with a linker peptide wherein the linker peptide is selected from the group consisting of RS, (G)n (SEQ ID NO: 33240), (GS)n (SEQ ID NO: 33241), (GGS)n (SEQ ID NO: 33242), (GSGGS)n (SEQ ID NO: 33243), (GGSGGS)n (SEQ ID NO: 33244), (GGGS)n (SEQ ID NO: 33245), GGSG (SEQ ID NO: 33246), GGSGG (SEQ ID NO: 33247), GSGSG (SEQ ID NO: 33248), GSGGG (SEQ ID NO: 33249), GGGSG (SEQ ID NO: 33250), GSSSG (SEQ ID NO: 33251), (GP)n (SEQ ID NO: 33252), GPGP (SEQ ID NO: 33253), GGSGGGS (SEQ ID NO: 33254), GSGSGGG (SEQ ID NO: 57628), GGCGGTTCCGGCGGAGGAAGC (SEQ ID NO: 57624), GGCGGTTCCGGCGGAGGTTCC (SEQ ID NO: 57625), GGATCAGGCTCTGGAGGTGGA (SEQ ID NO: 57627), GGAGGGCCGAGCTCTGGCGCACCCCCACCAAGTGGAGGGTCTCCTGCCGGGTCCCC AACATCTACTGAAGAAGGCACCAGCGAATCCGCAACGCCCGAGTCAGGCCCTGGTA CCTCCACAGAACCATCTGAAGGTAGTGCGCCTGGTTCCCCAGCTGGAAGCCCTACTT CCACCGAAGAAGGCACGTCAACCGAACCAAGTGAAGGATCTGCCCCTGGGACCAGC ACTGAACCATCTGAG (SEQ ID NO: 57620), SSGNSNANSRGPSFSSGLVPLSLRGSH (SEQ ID NO: 57623), GGPSSGAPPPSGGSPAGSPTSTEEGTSESATPESGPGTSTEPSEGSAPGSPAGSPTSTEEGT STEPSEGSAPGTSTEPSE (SEQ ID NO: 57621), TCTAGCGGCAATAGTAACGCTAACAGCCGCGGGCCGAGCTTCAGCAGCGGCCTGGT GCCGTTAAGCTTGCGCGGCAGCCAT (SEQ ID NO: 57622), GGP, PPP, PPAPPA (SEQ ID NO: 33255), PPPGPPP (SEQ ID NO: 33256), PPPG (SEQ ID NO: 33257), PPP(GGGS)n (SEQ ID NO: 33258), (GGGS)nPPP (SEQ ID NO: 33259), AEAAAKEAAAKEAAAKA (SEQ ID NO:33260), AEAAAKEAAAKA (SEQ ID NO: 33261), SGSETPGTSESATPES (SEQ ID NO: 33262), and TPPKTKRKVEFE (SEQ ID NO: 33263), wherein n is an integer of 1 to 5.

In general, NLS (or multiple NLSs) are of sufficient strength to drive accumulation of a reference or dCasX variant fusion protein in the nucleus of a eukaryotic cell. Detection of accumulation in the nucleus may be performed by any suitable technique. For example, a detectable marker may be fused to a reference or dCasX variant fusion protein such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

In some embodiments, a dXR comprising an N-terminal NLS comprises a sequence of any one of SEQ ID NOS: 37-112 as set forth in Tables 5 and 6 and SEQ ID NOS: 59359-59432 as set forth in Table 7.

TABLE 5

N-terminal NLS sequences

| NLS Amino Acid Sequence* | NLS ID | SEQ ID NO |
|---|---|---|
| **PKKKRKV**SR | 1 | 37 |
| **PKKKRKV**GGS**PKKKRKV**GGS**PKKKRKV**GGS**PKKKRKV**SR | 2 | 38 |
| **PKKKRKV**GGS**PKKKRKV**GGS**PKKKRKV**GGS**PKKKRKV**GGS**PKKKRKV**GGS**PKKKRKV**SR | 3 | 39 |
| **PAAKRVKLD**SR | 4 | 40 |
| **PAAKRVKLD**GGS**PAAKRVKLD**SR | 5 | 41 |
| **PAAKRVKLD**GGS**PAAKRVKLD**GGS**PAAKRVKLD**GGS**PAAKRVKLD**SR | 6 | 42 |
| **PAAKRVKLD**GGS**PAAKRVKLD**GGS**PAAKRVKLD**GGS**PAAKRVKLD**GGS**PAAKRVKLD**GGS**PAAKRVKLD**SR | 7 | 43 |
| **KRPAATKKAGQAKKKK**SR | 8 | 44 |
| **KRPAATKKAGQAKKKK**GGS**KRPAATKKAGQAKKKK**SR | 9 | 45 |

TABLE 5-continued

| N-terminal NLS sequences | | |
|---|---|---|
| NLS Amino Acid Sequence* | NLS ID | SEQ ID NO |
| **PAAKRVKLD**GGS**PKKKRKV**SR | 10 | 46 |
| **PAAKKKKLD**GGS**PKKKRKV**SR | 11 | 47 |
| **PAAKKKKLD**SR | 12 | 48 |
| **PAAKKKKLD**GGS**PAAKKKKLD**GGS**PAAKKKKLD**SR | 13 | 49 |
| **PAAKKKKLD**GGS**PAAKKKKLD**GGS**PAAKKKKLD**GGS**PAAKKKKLD**SR | 14 | 50 |
| **PAKRARRGYKC**SR | 15 | 51 |
| **PAKRARRGYKC**GS**PAKRARRGYKC**SR | 16 | 52 |
| **PRRKREE**SR | 17 | 53 |
| **PYRGRKE**SR | 18 | 54 |
| **PLRKRPRR**SR | 19 | 55 |
| **PLRKRPRR**GS**PLRKRPRR**SR | 20 | 56 |
| **PAAKRVKLD**GG**KRTADGSEFESPKKKRKV**GGS | 21 | 57 |
| **PAAKRVKLD**GG**KRTADGSEFESPKKKRKV**PPPPG | 22 | 58 |
| **PAAKRVKLD**GG**KRTADGSEFESPKKKRKV**GIHGVPAAPG | 23 | 59 |
| **PAAKRVKLD**GG**KRTADGSEFESPKKKRKV**GGGSGGGSPG | 24 | 60 |
| **PAAKRVKLD**GG**KRTADGSEFESPKKKRKV**PGGGSGGGSPG | 25 | 61 |
| **PAAKRVKLD**GG**KRTADGSEFESPKKKRKV**AEAAAKEAAAKEAAAKAPG | 26 | 62 |
| **PAAKRVKLD**GG**KRTADGSEFESPKKKRKV**PG | 27 | 63 |
| **PAAKRVKLD**GGS**PKKKRKV**GGS | 28 | 64 |
| **PAAKRVKLD**PPPPKKKRKVPG | 29 | 65 |
| **PAAKRVKLD**PG | 30 | 66 |
| **PAAKRVKLD**GGGSGGGSGGGS | 31 | 67 |
| **PAAKRVKLD**PPP | 32 | 68 |
| **PAAKRVKLD**GGGSGGGSGGGSPPP | 33 | 69 |
| **PKKKRKV**PPP | 34 | 70 |
| **PKKKRKV**GGS | 35 | 71 |

*Sequences in bold are NLS, while unbolded sequences are linkers.

TABLE 6

| C-terminal NLS sequences | | |
|---|---|---|
| NLS Amino Acid Sequence | NLS ID | SEQ ID NO |
| GS**PKKKRKV** | 1 | 72 |
| GS**PKKKRKV**GGS**PKKKRKV**GGS**PKKKRKV**GGS**PKKKRKV** | 2 | 73 |
| GS**PKKKRKV**GGS**PKKKRKV**GGS**PKKKRKV**GGS**PKKKRKV**GGS**PKKKRKV**GGS**PKKKRKV** | 3 | 74 |
| GS**PAAKRVKLD** | 4 | 75 |
| GS**PAAKRVKLD**GGS**PAAKRVKLD** | 5 | 76 |
| GS**PAAKRVKLD**GGS**PAAKRVKLD**GGS**PAAKRVKLD**GGS**PAAKRVKLD** | 6 | 77 |

TABLE 6-continued

| C-terminal NLS sequences | | |
|---|---|---|
| NLS Amino Acid Sequence | NLS ID | SEQ ID NO |
| GS**PAAKRVKLD**GGS**PAAKRVKLD**GGS**PAAKRVKLD**GGS**PAAKRVKLD**GGS**PAAKRVKLD** GGS**PAAKRVKLD** | 7 | 78 |
| GS**KRPAATKKAGQAKKKK** | 8 | 79 |
| **KRPAATKKAGQAKKKK**GGS**KRPAATKKAGQAKKKK** | 9 | 80 |
| GSPAAKRVKLGGSPAAKRVKLGGS**PKKKRKV**GGS**PKKKRKV** | 10 | 81 |
| GS**KLGPRKATGRW**GS | 11 | 82 |
| GS**KRKGSPERGERKRHW**GS | 12 | 83 |
| GS**PKKKRKV**GSGS**KRPAATKKAGQAKKKK**LE | 13 | 84 |
| GP**KRTADSQHSTPPKTKRKV**EFE**PKKKRKV** | 14 | 85 |
| GGGSGGGS**KRTADSQHSTPPKTKRKV**EFE**PKKKRKV** | 15 | 86 |
| AEAAAKEAAAKEAAAKA**KRTADSQHSTPPKTKRKV**EFE**PKKKRKV** | 16 | 87 |
| GPPKKKRKVGGS**KRTADSQHSTPPKTKRKV**EFE**PKKKRKV** | 17 | 88 |
| GPAEAAAKEAAAKEAAAKA**PAAKRVKLD** | 18 | 89 |
| GPGGGSGGGSGGGS**PAAKRVKLD** | 19 | 90 |
| GP**PKKKREV**PPP**PAAKRVKLD** | 20 | 91 |
| GP**PAAKRVKLD** | 21 | 92 |
| VGS**KRPAATKKAGQAKKKK** | 24 | 95 |
| TGGGPGGGAAAGSGS**PKKKRKV**GSGS**KRPAATKKAGQAKKKK**LE | 25 | 96 |
| TGGGPGGGAAAGSGS**PKKKRKV**GSGS | 27 | 98 |
| PPP**PKKKRKV**PPP | 28 | 99 |
| GGS**PKKKRKV**PPP | 29 | 100 |
| PPP**PKKKRKV** | 30 | 101 |
| GGS**PKKKRKV** | 31 | 102 |
| GGS**PKKKRKV**GGSGGSGGS | 32 | 103 |
| GGS**PKKKRKV**GGS**PKKKRKV** | 33 | 104 |
| GGSGGSGGS**PKKKRKV**GGS**PKKKRKV** | 34 | 105 |
| VGGGSGGGSGGGS**PAAKRVKLD** | 35 | 106 |
| VPPP**PAAKRVKLD** | 36 | 107 |
| VPPPGGGSGGGSGGGS**PAAKRVKLD** | 37 | 108 |
| VGS**PAAKRVKLD** | 41 | 112 |

* Sequences in bold are NLS, while unbolded sequences are linkers.

TABLE 7

| Additional NLS sequences | | | |
|---|---|---|---|
| N-terminal NLS Sequences | SEQ ID NO | C-terminal NLS Sequences | SEQ ID NO |
| PKKKRKVGGSPKKKRKVSRQEIKRINKI RRRLVKDSNTKKAGKTGP | 59359 | TLESPAAKRVKLDGGSPAAKRVKLD GGSPAAKRVKLDGGSPAAKRVKLDG GSPAAKRVKLDGGSPAAKRVKLDTL | 59396 |

TABLE 7-continued

| Additional NLS sequences | | | |
|---|---|---|---|
| N-terminal NLS Sequences | SEQ ID NO | C-terminal NLS Sequences | SEQ ID NO |
| | | ESKRPAATKKAGQAKKKKGGSKRPAATKKAGQAKKKKGGSKRPAATKKAGQAKKKKGGSKRPAATKKAGQAKKKK | |
| PKKKRKVGGSPKKKRKVGGSPKKKRKVGGSPKKKRKVSRQEIKRINKIRRRLVKDSNTKKAGKTGP | 59360 | TLESKRPAATKKAGQAKKKKTLESKRPAATKKAGQAKKKKGGSKRPAATKKAGQAKKKKGGSKRPAATKKAGQAKKKKGGSKRPAATKKAGQAKKKKGGSKRPAATKKAGQAKKKKGGSKRPAATKKAGQAKKKK | 59397 |
| PKKKRKVGGSPKKKRKVGGSPKKKRKVGGSPKKKRKVGGSPKKKRKVGGSPKKKRKVSRQEIKRINKIRRRLVKDSNTKKAGKTGP | 59361 | TLESKRPAATKKAGQAKKKKGGSKRPAATKKAGQAKKKKTLESPKKKRKVGGSPKKKRKVGGSPKKKRKVGGSPKKKRKV | 59398 |
| PAAKRVKLDGGSPAAKRVKLDSRQEIKRINKIRRRLVKDSNTKKAGKTGP | 59362 | TLEGGSPKKKRKVTLESPKKKRKVGGSPKKKRKVGGSPKKKRKVGGSPKKKRKV | 59399 |
| PAAKRVKLDGGSPAAKRVKLDGGSPAAKRVKLDGGSPAAKRVKLDSRQEIKRINKIRRRLVKDSNTKKAGKTGP | 59363 | TLEGGSPKKKRKVTLESPAAKRVKLDGGSPAAKRVKLDGGSPAAKRVKLDGGSPAAKRVKLD | 59400 |
| PAAKRVKLDGGSPAAKRVKLDGGSPAAKRVKLDGGSPAAKRVKLDGGSPAAKRVKLDGGSPAAKRVKLDSRQEIKRINKIRRRLVKDSNTKKAGKTGP | 59364 | TLEGGSPKKKRKVTLESPAAKRVKLDGGSPAAKRVKLDGGSPAAKRVKLDGGSPAAKRVKLDGGSPAAKRVKLDGGSPAAKRVKLD | 59401 |
| KRPAATKKAGQAKKKKSRDISRQEIKRINKIRRRLVKDSNTKKAGKTGP | 59365 | TLEGGSPKKKRKVTLESKRPAATKKAGQAKKKK | 59402 |
| KRPAATKKAGQAKKKKSRQEIKRINKIRRRLVKDSNTKKAGKTGP | 59366 | TLEGGSPKKKRKVTLESKRPAATKKAGQAKKKKGGSKRPAATKKAGQAKKKK | 59403 |
| KRPAATKKAGQAKKKKGGSKRPAATKKAGQAKKKKSRDISRQEIKRINKIRRRLVKDSNTKKAGKTGP | 59367 | TLEGGSPKKKRKVTLEGGSPKKKRKV | 59404 |
| KRPAATKKAGQAKKKKGGSKRPAATKKAGQAKKKKGGSKRPAATKKAGQAKKKKGGSKRPAATKKAGQAKKKKSRDISRQEIKRINKIRRRLVKDSNTKKAGKTGP | 59368 | TLEVGPKRTADSQHSTPPKTKRKVEFEPKKKRKVTLEGGSPKKKRKV | 59405 |
| KRPAATKKAGQAKKKKGGSKRPAATKKAGQAKKKKGGSKRPAATKKAGQAKKKKGGSKRPAATKKAGQAKKKKGGSKRPAATKKAGQAKKKKSRDISRQEIKRINKIRRRLVKDSNTKKAGKTGP | 59369 | TLEVGGGSGGGSKRTADSQHSTPPKTKRKVEFEPKKKRKVTLEGGSPKKKRKV | 59406 |
| PKKKRKVGGSPKKKRKVGGSPKKKRKVGGSPKKKRKVSRDISRQEIKRINKIRRRLVKDSNTKKAGKTGP | 59370 | TLEVAEAAAKEAAAKEAAAKAKRTADSQHSTPPKTKRKVEFEPKKKRKVTLEGGSPKKKRKV | 59407 |
| PAAKRVKLDGGSPAAKRVKLDGGSPAAKRVKLDGGSPAAKRVKLDSRDISRQEIKRINKIRRRLVKDSNTKKAGKTGP | 59371 | TLEVGPPKKKRKVGGSKRTADSQHSTPPKTKRKVEFEPKKKRKVTLEGGSPKKKRKV | 59408 |
| PAAKRVKLDGGSPAAKRVKLDGGSPAAKRVKLDGGSPAAKRVKLDGGSPAAKRVKLDGGSPAAKRVKLDSRDISRQEIKRINKIRRRLVKDSNTKKAGKTGP | 59372 | TLEVGPAEAAAKEAAAKEAAAKAPAAKRVKLDTLEGGSPKKKRKV | 59409 |
| PAAKRVKLDGGKRTADGSEFESPKKKRKVGGSSRDISRQEIKRINKIRRRLVKDSNTKKAGKTGP | 59373 | TLEVGPGGGSGGGSGGGSPAAKRVKLDTLEVGPKRTADSQHSTPPKTKRKVEFEPKKKRKV | 59410 |
| PAAKRVKLDGGKRTADGSEFESPKKKRKVPPPPGSRDISRQEIKRINKIRRRLVKDSNTKKAGKTGP | 59374 | TLEVGPPKKKRKVPPPPAAKRVKLDTLEVGGGSGGGSKRTADSQHSTPPKTKRKVEFEPKKKRKV | 59411 |

TABLE 7-continued

Additional NLS sequences

| N-terminal NLS Sequences | SEQ ID NO | C-terminal NLS Sequences | SEQ ID NO |
|---|---|---|---|
| PAAKRVKLDGGKRTADGSEFESPKKKRKVGIHGVPAAPGSRDISRQEIKRINKIRRRLVKDSNTKKAGKTGP | 59375 | TLEVGPPAAKRVKLDTLEVAEAAAKEAAAKEAAAKAKRTADSQHSTPPKTKRKVEFEPKKKRKV | 59412 |
| PAAKRVKLDGGKRTADGSEFESPKKKRKVGGGSGGGSPGSRDISRQEIKRINKIRRRLVKDSNTKKAGKTGP | 59376 | TLEVGP KRTADSQHSTPPKTKRKVEFEPKKKRKVTLEVGPPKKKRKVGGSKRTADSQHSTPPKTKRKVEFEPKKKRKV | 59413 |
| PAAKRVKLDGGKRTADGSEFESPKKKRKVPGGGSGGGSPGSRDISRQEIKRINKIRRRLVKDSNTKKAGKTGP | 59377 | TLEVGGGSGGGSKRTADSQHSTPPKTKRKVEFEPKKKRKVTLEVGPAEAAAKEAAAKEAAAKAPAAKRVKLD | 59414 |
| PAAKRVKLDGGKRTADGSEFESPKKKRKVAEAAAKEAAAKEAAAKAPGSRDISRQEIKRINKIRRRLVKDSNTKKAGKTGP | 59378 | GSKRPAATKKAGQAKKKKTLEVGPGGGSGGGSGGGSPAAKRVKLD | 59415 |
| PAAKRVKLDGGKRTADGSEFESPKKKRKVPGSRDISRQEIKRINKIRRRLVKDSNTKKAGKTGP | 59379 | GSKRPAATKKAGQAKKKKTLEVGPPKKKRKVPPPPAAKRVKLD | 59416 |
| PAAKRVKLDGGSPKKKRKVGGSSRDISRQEIKRINKIRRRLVKDSNTKKAGKTGP | 59380 | GSKRPAATKKAGQAKKKKTLEVGPPAAKRVKLD | 59417 |
| PAAKRVKLDPPPPKKKRKVPGSRDISRQEIKRINKIRRRLVKDSNTKKAGKTGP | 59381 | GSPKKKRKVTLEVGPKRTADSQHSTPPKTKRKVEFEPKKKRKV | 59418 |
| PAAKRVKLDPGRSRDISRQEIKRINKIRRRLVKDSNTKKAGKTGP | 59382 | GSKRPAATKKAGQAKKKKTLEVGGGSGGGSKRTADSQHSTPPKTKRKVEFEPKKKRKV | 59419 |
| PKKKRKVSRDISRQEIKRINKIRRRLVKDSNTKKAGKTGP | 59383 | GSKRPAATKKAGQAKKKKGSKRPAATKKAGQAKKKK | 59420 |
| PKKKRKVSRQEIKRINKIRRRLVKDSNTKKAGKTGP | 59384 | GSPKKKRKVGSPKKKRKV | 59421 |
| PAAKRVKLDSRQEIKRINKIRRRLVKDSNTKKAGKTGP | 59385 | GGGSGGGSKRTADSQHSTPPKTKRKVEFEPKKKRKVGSKRPAATKKAGQAKKKK | 59422 |
| TSPKKKRKVALEYPYDVPDYA | 59386 | GPPKKKRKVGGSKRTADSQHSTPPKTKRKVEFEPKKKRKVGSKRPAATKKAGQAKKKK | 59423 |
| TLESKRPAATKKAGQAKKKKAPGEYPYDVPDYA | 59387 | TGGGPGGGAAAGSGSPKKKRKVGSGSGSKRPAATKKAGQAKKKK | 59424 |
| GSKRPAATKKAGQAKKKKYPYDVPDYA | 59388 | GPKRTADSQHSTPPKTKRKVEFEPKKKRKVGSKRPAATKKAGQAKKKK | 59425 |
| TLESKRPAATKKAGQAKKKKGGSKRPAATKKAGQAKKKKAPGEYPYDVPDYATSPKKKRKVALEYPYDVPDYA | 59389 | AEAAAKEAAAKEAAAKAKRTADSQHSTPPKTKRKVEFEPKKKRKVGSPKKKRKV | 59426 |
| TLESKRPAATKKAGQAKKKKGGSKRPAATKKAGQAKKKKGGSKRPAATKKAGQAKKKKTSPKKKRKVALEYPYDVPDYA | 59390 | GPPKKKRKVPPPPAAKRVKLDGGGSGGGSKRTADSQHSTPPKTKRKVEFEPKKKRKV | 59427 |
| TLESKRPAATKKAGQAKKKKGGSKRPAATKKAGQAKKKKGGSKRPAATKKAGQAKKKKGGSKRPAATKKAGQAKKKKGGSKRPAATKKAGQAKKKKTSPKKKRKVALEYPYDVPDYA | 59391 | GSPAAKRVKLDGGSPAAKRVKLDGGSPAAKRVKLDGGSPAAKRVKLDGGSPAAKRVKLDGGSPAAKRVKLDGPPKKKKRKVGGSKRTADSQHSTPPKTKRKVEFEPKKKRKV | 59428 |
| TLESPKKKRKVGGSPKKKRKVGGSPKKKRKVGGSPKKKRKVTLESKRPAATKKAGQAKKKKAPGEYPYDVPDYA | 59392 | GSPAAKRVKLGGSPAAKRVKLGGSPKKKRKVGGSPKKKRKVTGGGPGGGAAAGSGSPKKKRKVGSGS | 59429 |
| APAAKRVKLDSR | 59393 | GSKRPAATKKAGQAKKKKGGSKRPAATKKAGQAKKKKGPKRTADSQHSTPPKTKRKVEFEPKKKRKV | 59430 |

TABLE 7-continued

| Additional NLS sequences | | | |
|---|---|---|---|
| N-terminal NLS Sequences | SEQ ID NO | C-terminal NLS Sequences | SEQ ID NO |
| MAPKKKRKVSR | 59394 | GSKRPAATKKAGQAKKKKGGSKRPAATKKAGQAKKKKAEAAAKEAAAKEAAAKAKRTADSQHSTPPKTKRKVEFEPKKKRKV | 59431 |
| GSPKKKRKV | 59395 | | NO |

In some cases, a dXR fusion protein includes a "Protein Transduction Domain" or PTD (also known as a CPP—cell penetrating peptide), which refers to a protein, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from an extracellular space to an intracellular space, or from the cytosol to within an organelle. In some embodiments, a PTD is covalently linked to the amino terminus of a dXR fusion protein. In some embodiments, a PTD is covalently linked to the carboxyl terminus of a dXR fusion protein. Examples of PTDs include but are not limited to peptide transduction domain of HIV TAT comprising YGRKKRRQRRR (SEQ ID NO: 33340), RKKRRQRR (SEQ ID NO: 33341); YARAAARQARA (SEQ ID NO: 33342); THRLPRRRRRR (SEQ ID NO: 33343); and GGRRARRRRRR (SEQ ID NO: 33344); a polyarginine sequence comprising a number of arginines sufficient to direct entry into a cell (e.g., 3, 4, 5, 6, 7, 8, 9, 10, or 10-50 arginines (SEQ ID NO: 33345)); a VP22 domain (Zender et al. (2002) Cancer Gene Ther. 9(6):489-96); an *Drosophila* Antennapedia protein transduction domain (Noguchi et al. (2003) Diabetes 52(7): 1732-1737); a truncated human calcitonin peptide (Trehin et al. (2004) Pharm. Research 21: 1248-1256); polylysine (Wender et al. (2000) Proc. Natl. Acad. Sci. USA 97: 13003-13008); RRQRRTSKLMKR (SEQ ID NO: 33346); Transportan GWTLNSAGYLLGKINLKALAALAKKIL (SEQ ID NO: 33347); KALAWEAKLAKALAKALAKHLAKALAKALKCEA (SEQ ID NO: 33348); and RQIKIWFQNRRMKWKK (SEQ ID NO: 33349).

In some embodiments, the individual components of the dXR may be linked via a linker polypeptide (e.g., one or more linker polypeptides). The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers are generally produced by using synthetic, linker-encoding oligonucleotides to couple the proteins. Peptide linkers with a degree of flexibility can be used. The linking peptides may have virtually any amino acid sequence, bearing in mind that the preferred linkers will have a sequence that results in a generally flexible peptide. The use of small amino acids, such as glycine, serine, proline and alanine, are of use in creating a flexible peptide. The creation of such sequences is routine to those of skill in the art. A variety of different linkers are commercially available and are considered suitable for use. Example linker polypeptides include one or more linkers selected from the group consisting of RS, (G)n (SEQ ID NO: 33240), (GS)n (SEQ ID NO: 33241), (GGS)n (SEQ ID NO: 33242), (GSGGS)n (SEQ ID NO: 33243), (GGSGGS)n (SEQ ID NO: 33244), (GGGS)n (SEQ ID NO: 33245), GGSG (SEQ ID NO: 33246), GGSGG (SEQ ID NO: 33247), GSGSG (SEQ ID NO: 33248), GSGGG (SEQ ID NO: 33249), GGGSG (SEQ ID NO: 33250), GSSSG (SEQ ID NO: 33251), (GP)n (SEQ ID NO: 33252), GPGP (SEQ ID NO: 33253), GGSGGGS (SEQ ID NO: 33254), GGP, PPP, PPAPPA (SEQ ID NO: 33255), PPPGPPP (SEQ ID NO: 33256), PPPG (SEQ ID NO: 33257), PPP(GGGS)n (SEQ ID NO: 33258), (GGGS)nPPP (SEQ ID NO: 33259), AEAAAKEAAAKEAAAKA (SEQ ID NO: 33260), AEAAAKEAAAKA (SEQ ID NO: 33261), SGSETPGTSESATPES (SEQ ID NO: 33262), TPPKTKRKVEFE (SEQ ID NO: 33263), GSGSGGG (SEQ ID NO: 57628), GGCGGTTCCGGCGGAGGAAGC (SEQ ID NO: 57624), GGCGGTTCCGGCGGAGGTTCC (SEQ ID NO: 57625), GGATCAGGCTCTGGAGGTGGA (SEQ ID NO: 57627), GGAGGGCCGAGCTCTGGCGCACCCCCACCAAGTGGAGGGTCTCCTGCCGGGTCCCC AACATCTACTGAAGAAGGCACCAGCGAATCCGCAACGCCCGAGTCAGGCCCTGGTA CCTCCACAGAACCATCTGAAGGTAGTGCGCCTGGTTCCCCAGCTGGAAGCCCTACTT CCACCGAAGAAGGCACGTCAACCGAACCAAGTGAAGGATCTGCCCCTGGGACCAGC ACTGAACCATCTGAG (SEQ ID NO: 57620), SSGNSNANSRGPSFSSGLVPLSLRGSH (SEQ ID NO: 57623), GGPSSGAPPPSGGSPAGSPTSTEEGTSESATPESGPGTSTEPSEGSAPGSPAGSPTSTEEGT STEPSEGSAPGTSTEPSE (SEQ ID NO: 57621), and TCTAGCGGCAATAGTAACGCTAACAGCCGCGGGCCGAGCTTCAGCAGCGGCCTGGT GCCGTTAAGCTTGCGCGGCAGCCAT (SEQ ID NO: 57622), wherein n is an integer of 1 to 5. The ordinarily skilled artisan will recognize that design of a peptide conjugated to any elements described above can include linkers that are all or partially flexible, such that the linker can include a flexible linker as well as one or more portions that confer less flexible structure.

VI. gRNA and dCRISPR Protein-Repressor Domain Gene Repression Pairs

In another aspect, provided herein are compositions comprising a gene repression pair, the gene repression pair comprising a catalytically-dead CRISPR protein with one or more linked repressor domains and a guide RNA. In some embodiments, the gene repressor pair comprises a catalytically-dead Class 2 CRISPR-Cas with one or more linked repressor domains. In some embodiments, the gene repressor pair comprises a catalytically-dead Class 2, Type II, Type V, or Type VI CRISPR protein. In some embodiments, the gene repression pair includes Class 2, Type II CRISPR/Cas proteins such as a catalytically-dead Cas9. In other cases, the gene repression pair include Class 2, Type V CRISPR/Cas nucleases such as catalytically-dead Cas12a (Cpf1), Cas12b (C2c1), Cas12c (C2c3), Cas12d (CasY), Cas12e (CasX), Cas12f, Cas12g, Cas12h, Cas12i, Cas12j, Cas12k, Cas12l, Cas14, and/or CasΦ proteins.

In certain embodiments, the gene repression pair comprises a dCasX variant protein as described herein (e.g., any one of the sequences set forth in Table 4) linked to one or more repressor domains (e.g., any one of the sequences of SEQ ID NOS: 889-2100, 2332-33239, 33625-57543, and 59450, while the guide RNA is a gRNA variant as described herein (e.g., SEQ ID NOS: 2238-2331, 57544-57589 and 59352 or a sequence as set forth in Table 2), or sequence variants having at least 60%, or at least 70%, at least about 80%, or at least about 90%, or at least about 95%, or at least about 96%, or at least about 97%, or at least about 98%, or at least about 99% sequence identity thereto, wherein the gRNA comprises a targeting sequence complementary to the target nucleic acid. In some embodiments, the gene repression pair comprises a dCasX selected from any one of SEQ ID NOS: 17-36 and 59353-59358 as set forth in Table 4, one or more repressor domains linked to the dCasX selected from any one of the sequences of SEQ ID NOS: 889-2100, 2332-33239, 33625-57543 and 59450, and a gRNA selected from any one of SEQ ID NOS: 2238, 2239, and 2292. In some embodiments, the gene repression pair comprises a dCasX selected from any one of SEQ ID NOS: 17-36 and 59353-59358 as set forth in Table 4, one or more repressor domains linked to the dCasX selected from any one of the sequences of SEQ ID NOS: 355-888, 33625-57543, and 59450, and a gRNA selected from any one of SEQ ID NOS: 2238, 2239, and 2292, wherein the gRNA comprises a targeting sequence complementary to the target nucleic acid. In some embodiments, the gene repression pair comprises a dCasX selected from any one of SEQ ID NOS: 17-36 and 59353-59358, one or more repressor domains linked to the dCasX selected from any one of the sequences of SEQ ID NOS: 355-888, 33625-57543, and 59450, and a gRNA selected from any one of SEQ ID NOS: 2238-2331, 57544-57589 and 59352, wherein the gRNA comprises a targeting sequence complementary to the target nucleic acid.

In some embodiments, the gene repression pair comprises a dXR comprising a dCasX of SEQ ID NO:18, a KRAB domain sequence of SEQ ID NOS: 57746-57755, a DNMT3A catalytic domain of SEQ ID NOS: 33625-57543 and 59450, a DNMT3L interaction domain of SEQ ID NO: 59625, and an ADD domain of SEQ ID NO: 59452, wherein the dXR has the configuration of configurations 1, 4 or 5 of FIG. 45, and a gRNA of SEQ ID NOS: 2292 or 59352, wherein the gRNA comprises a targeting sequence complementary to the target nucleic acid.

In other embodiments, a gene repression pair comprises the dCasX protein selected from any one of SEQ ID NOS: 17-36 and 59353-59358 as set forth in Table 4 and one or more repressor domains linked to the dCasX, a first gRNA (a gRNA variant as described herein (e.g., SEQ ID NOS: 2238-2331, 57544-57589 and 59352, or a sequence as set forth in Table 2) with a targeting sequence, and a second gRNA variant and dXR, wherein the second gRNA variant has a targeting sequence complementary to a different or overlapping portion of the target nucleic acid compared to the targeting sequence of the first gRNA.

In some embodiments, wherein the gene repression pair comprises both a dCasX variant protein and the linked repressor domain and a gRNA variant as described herein, the one or more characteristics of the gene repression pair is improved beyond what can be achieved by varying the dCasX protein or the gRNA alone. In some embodiments, the dCasX variant protein and the gRNA variant act additively to improve one or more characteristics of the gene repression pair. In some embodiments, the dCasX variant protein and the gRNA variant act synergistically to improve one or more characteristics of the gene repression pair. In the foregoing embodiments, the improvement is at least about 2-fold, at least about 5-fold, at least about 10-fold, at least about 50-fold, at least about 100-fold, at least about 500-fold, at least about 1000-fold, at least about 5000-fold, at least about 10,000-fold, or at least about 100,000-fold compared to the characteristic of a reference dCasX protein and reference gRNA pair.

VII. Vectors

In some embodiments, provided herein are vectors comprising polynucleotides encoding the catalytically-dead CRISPR protein and linked repressor domains and gRNA variants described herein. In some cases, the vectors are utilized for the expression and recovery of the catalytically-dead CRISPR protein (e.g., dXR) and the gRNA components of the gene repression pair or the RNP. In other cases, the vectors are utilized for the delivery of the encoding polynucleotides to target cells for the repression of the target nucleic acid, as described more fully, below.

In some embodiments, provided herein are polynucleotides encoding the gRNA variants described herein. In some embodiments, said polynucleotides are DNA. In other embodiments, said polynucleotides are RNA. In other embodiments, said polynucleotides are mRNA. In some embodiments, provided herein are vectors comprising the polynucleotides sequences encoding the gRNA variants described herein. In some embodiments, the vectors comprising the polynucleotides include bacterial plasmids, viral vectors, and the like. In some embodiments, a dXR and a gRNA variant are encoded on the same vector. In some embodiments, a dXR and a gRNA variant are encoded on different vectors.

In some embodiments, the disclosure provides a vector comprising a nucleotide sequence encoding the components of the dXR:gRNA system. For example, in some embodiments provided herein is a recombinant expression vector comprising a) a nucleotide sequence encoding a dXR fusion protein; and b) a nucleotide sequence encoding a gRNA variant described herein. In some cases, the nucleotide sequence encoding the dXR fusion protein and/or the nucleotide sequence encoding the gRNA variant are operably linked to a promoter that is operable in a cell type of choice (e.g., a prokaryotic cell, a eukaryotic cell, a plant cell, an animal cell, a mammalian cell, a primate cell, a rodent cell, a human cell). Suitable promoters for inclusion in the vectors are described herein, below.

In some embodiments, the nucleotide sequence encoding the dXR fusion protein is codon optimized. This type of optimization can entail a mutation of a dCasX-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized dCasX variant-encoding nucleotide sequence could be used. As another non-limiting example, if the intended host cell were a mouse cell, then a mouse codon-optimized dCasX variant-encoding nucleotide sequence could be generated. As another non-limiting example, if the intended host cell were a bacterial cell, then a bacterial codon-optimized dXR fusion protein-encoding nucleotide sequence could be generated.

In some embodiments, a nucleotide sequence encoding a dXR fusion protein is mRNA, designed for incorporation into an LNP. In some embodiments, an mRNA encoding a dXR fusion protein of the disclosure is chemically modified, wherein the chemical modification is substitution of N1-methyl-pseudouridine for one or more uridine nucleotides of the sequence. In some embodiments, an mRNA encoding a dXR fusion protein of the disclosure is codon optimized. In some embodiments, an mRNA encoding a dXR fusion protein of the disclosure comprises one or more sequences selected from the group consisting of SEQ ID NOS: 59584, 59585, 59610, 59611, 59622 and 59623. In some embodiments, an mRNA encoding a dXR fusion protein of the disclosure comprises one or more sequences encoded by a sequence selected from the group consisting of 59444-59449, 59455-59456, 59488-59497, 59568-59583, 59595-59609, and 59612-59621.

In some embodiments, provided herein are one or more recombinant expression vectors such as (i) a nucleotide sequence that encodes a gRNA as described herein (e.g., operably linked to a promoter that is operable in a target cell such as a eukaryotic cell); and (ii) a nucleotide sequence encoding a dXR fusion protein (e.g., operably linked to a promoter that is operable in a target cell such as a eukaryotic cell). In some embodiments, the sequences encoding the gRNA and dXR fusion proteins are in different recombinant expression vectors, and in other embodiments the gRNA and dXR fusion proteins are in the same recombinant expression vector. In some embodiments, either the gRNA in the recombinant expression vector, the dXR fusion protein encoded by the recombinant expression vector, or both, are variants of a reference dCasX protein or gRNAs as described herein. In the case of the nucleotide sequence encoding the gRNA, the recombinant expression vector can be transcribed in vitro, for example using T7 promoter regulatory sequences and T7 polymerase in order to produce the gRNA, which can then be recovered by conventional methods; e.g., purification via gel electrophoresis. Once synthesized, the gRNA may be utilized in the gene repression pair to directly contact a target nucleic acid or may be introduced into a cell by any of the well-known techniques for introducing nucleic acids into cells (e.g., microinjection, electroporation, transfection, etc.).

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a dXR and/or gRNA is operably linked to a control element; e.g., a transcriptional control element, such as a promoter. In some embodiments, a nucleotide sequence encoding a dXR fusion protein is operably linked to a control element; e.g., a transcriptional control element, such as a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34(+) cell, bone marrow (BM) CD34(+) cell, etc.). By transcriptional activation, it is intended that transcription will be increased above basal levels in the target cell by 10-fold, by 100-fold, more usually by 1000-fold.

Non-limiting examples of Pol II promoters include, but are not limited to EF-1alpha, EF-1alpha core promoter, Jens Tornoe (JeT), promoters from cytomegalovirus (CMV), CMV immediate early (CMVIE), CMV enhancer, herpes simplex virus (HSV) thymidine kinase, early and late simian virus 40 (SV40), the SV40 enhancer, long terminal repeats (LTRs) from retrovirus, mouse metallothionein-I, adenovirus major late promoter (Ad MLP), CMV promoter full-length promoter, the minimal CMV promoter, the chicken β-actin promoter (CBA), CBA hybrid (CBh), chicken β-actin promoter with cytomegalovirus enhancer (CB7), chicken beta-Actin promoter and rabbit beta-Globin splice acceptor site fusion (CAG), the rous sarcoma virus (RSV) promoter, the HIV-Ltr promoter, the hPGK promoter, the HSV TK promoter, a 7SK promoter, the Mini-TK promoter, the human synapsin I (SYN) promoter which confers neuron-specific expression, beta-actin promoter, super core promoter 1 (SCP1), the Mecp2 promoter for selective expression in neurons, the minimal IL-2 promoter, the Rous sarcoma virus enhancer/promoter (single), the spleen focus-forming virus long terminal repeat (LTR) promoter, the TBG promoter, promoter from the human thyroxine-binding globulin gene (Liver specific), the PGK promoter, the human ubiquitin C promoter (UBC), the UCOE promoter (Promoter of HNRPA2B1-CBX3), the synthetic CAG promoter, the Histone H2 promoter, the Histone H3 promoter, the U1a1 small nuclear RNA promoter (226 nt), the U1a1 small nuclear RNA promoter (226 nt), the U1b2 small nuclear RNA promoter (246 nt) 26, the GUSB promoter, the CBh promoter, rhodopsin (Rho) promoter, silencing-prone spleen focus forming virus (SFFV) promoter, a human H1 promoter (H1), a POL1 promoter, the TTR minimal enhancer/promoter, the b-kinesin promoter, mouse mammary tumor virus long terminal repeat (LTR) promoter, the human eukaryotic initiation factor 4A (EIF4A1) promoter, the ROSA26 promoter, the glyceraldehyde 3-phosphate dehydrogenase (GAPDH) promoter, tRNA promoters, and truncated versions and sequence variants of the foregoing. In a particular embodiment, the Pol II promoter is EF-1alpha, wherein the promoter enhances transfection efficiency, the transgene transcription or expression of the CRISPR nuclease, the proportion of expression-positive clones and the copy number of the episomal vector in long-term culture. Non-limiting examples of Pol III promoters include, but are not limited to U6, mini U6, U6 truncated promoters, BiH1 (Bidirectional H1 promoter), BiU6, Bi7SK, BiH1 (Bidirectional U6, 7SK, and H1 promoters), gorilla U6, rhesus U6, human 7SK, human H1 promoter, and truncated versions and sequence variants thereof. In the foregoing embodiment, the Pol III promoter enhances the transcription of the gRNA.

Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, fluorescent protein, etc.) that can be fused to the dXR fusion protein, thus resulting in a chimeric CasX variant polypeptide.

Recombinant expression vectors of the disclosure can also comprise elements that facilitate robust expression of dXR and/or variant gRNAs of the disclosure. For example, recombinant expression vectors can include one or more of a polyadenylation signal (poly(A), an intronic sequence or a post-transcriptional regulatory element such as a woodchuck hepatitis post-transcriptional regulatory element (WPRE). Exemplary poly(A) sequences include hGH poly(A) signal (short), HSV TK poly(A) signal, synthetic polyadenylation signals, SV40 poly(A) signal, β-globin poly(A) signal and the like. In addition, vectors used for providing a nucleic acid encoding a gRNA and/or a dXR protein to a cell may include nucleic acid sequences that encode for selectable markers in the target cells, so as to identify cells that have taken up the gRNA and/or dXR protein. A person of ordinary skill in the art will be able to select suitable elements to include in the recombinant expression vectors described herein.

A recombinant expression vector sequence can be packaged into a virus or virus-like particle (also referred to herein as a "particle" or "virion") for subsequent infection and transformation of a cell, ex vivo, in vitro or in vivo. Such particles or virions will typically include proteins that encapsidate or package the vector genome. In some embodiments, a recombinant expression vector of the present disclosure is a recombinant adeno-associated virus (AAV) vector. In some embodiments, a recombinant expression vector of the present disclosure is a recombinant lentivirus vector. In some embodiments, a recombinant expression vector of the present disclosure is a recombinant retroviral vector.

a. Recombinant AAV for Delivery of dXR:rRNA

Adeno-associated virus (AAV) is a small (20 nm), non-pathogenic virus that is useful in treating human diseases in situations that employ a viral vector for delivery to a cell such as a eukaryotic cell, either in vivo or ex vivo for cells to be prepared for administering to a subject. A construct is generated, for example a construct encoding a fusion protein and gRNA embodiments as described herein, and is flanked with AAV inverted terminal repeat (ITR) sequences, thereby enabling packaging of the AAV vector into an AAV viral particle, with the assistance of the AAV cap coding region sequences, described below.

An "AAV" vector may refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are many known serotypes of primate AAVs. In some embodiments, the AAV vector is selected from AAV1, AAV2, AAV3, AAV4, AAV5, AAV6, AAV7, AAV8, AAV9, AAV 10, AAV11, AAV12, AAV 44.9, AAV 9.45, AAV 9.61, AAV-Rh74 (Rhesus macaque-derived AAV), and AAVRh10, and modified capsids of these serotypes. For example, serotype AAV-2 is used to refer to an AAV which contains capsid proteins encoded from the cap gene of AAV-2 and a genome containing 5' and 3' ITR sequences from the same AAV-2 serotype. Pseudotyped AAV refers to an AAV that contains capsid proteins from one serotype and a viral genome including 5'-3' ITRs of a second serotype. Pseudotyped rAAV would be expected to have cell surface binding properties of the capsid serotype and genetic properties consistent with the ITR serotype. Pseudotyped recombinant AAV (rAAV) are produced using standard techniques described in the art. As used herein, for example, rAAV1 may be used to refer an AAV having both capsid proteins and 5'-3' ITRs from the same serotype or it may refer to an AAV having capsid proteins from serotype 1 and 5'-3' ITRs from a different AAV serotype, e.g., AAV serotype 2. For each example illustrated herein the description of the vector design and production describes the serotype of the capsid and 5'-3' ITR sequences.

An "AAV virus" or "AAV viral particle" refers to a viral particle composed of at least one AAV capsid protein (preferably by all of the capsid proteins of a wild-type AAV) and an encapsidated polynucleotide. If the particle additionally comprises a heterologous polynucleotide (i.e., a polynucleotide other than a wild-type AAV genome to be delivered to a mammalian cell, termed a "transgene"), it is typically referred to as "rAAV". An exemplary heterologous polynucleotide is a polynucleotide comprising a dXR protein and/or sgRNA of any of the embodiments described herein. Being naturally replication-defective and capable of transducing nearly every cell type in the human body, AAV represents a suitable vector for therapeutic use in gene therapy or vaccine delivery. Typically, when producing a recombinant AAV vector, the sequence between the two ITRs is replaced with one or more sequences of interest (e.g., a transgene), and the Rep and Cap sequences are provided in trans, making the ITRs the only viral DNA that remains in the vector. The resulting recombinant AAV vector genome construct comprises two cis-acting 130 to 145-nucleotide ITRs flanking an expression cassette encoding the transgene sequences of interest, providing at least 4.7 kb or more for packaging of foreign DNA that can include a transgene, one or more promoters and accessory elements, such that the total size of the vector is below 5 to 5.2 kb, which is compatible with packaging within the AAV capsid (it being understood that as the size of the construct exceeds this threshold, the packaging efficiency of the vector decreases). The transgene may be used, in the context of the present disclosure to repress transcription of a defective gene in the cells of a subject. In the context of CRISPR-mediated gene repression, however, the size limitation of the expression cassette is a challenge for most CRISPR systems (e.g., Cas9), given the large size of the nucleases. It has been discovered, however, that the small size of the dCasX and gRNA permits the creation of "all in one" constructs that can deliver dXR:gRNA capable of gene repression in cells.

By "adeno-associated virus inverted terminal repeats" or "AAV ITRs" is meant the art recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome. The nucleotide sequences of AAV ITR regions are known. See, for example Kotin, R. M. (1994) Human Gene Therapy 5:793-801; Berns, K. I. "Parvoviridae and their Replication" in Fundamental Virology, $2^{nd}$ Edition, (B. N. Fields and D. M. Knipe, eds.). As used herein, an AAV ITR need not have the wild-type nucleotide sequence depicted, but may be altered, e.g., by the insertion, deletion or substitution of nucleotides. Additionally, the AAV ITR may be derived from any of several AAV serotypes, including without limitation, AAV1, AAV2, AAV3, AAV4, AAV5, AAV6, AAV7, AAV8, AAV9, AAV10, AAV-Rh74, and AAVRh10, and modified capsids of these serotypes. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell. Use of AAV serotypes for integration of heterologous sequences into a host cell is known in the art (see, e.g., WO2018195555A1 and US20180258424A1, incorporated by reference herein). In one particular embodiment, the ITRs are derived from serotype AAV1. In another particular embodiment of the AAV of the disclosure, the ITRs are derived from serotype AAV2, the 5' ITR having sequence CCTGCAGGCAGCTGCGCGCTCGCTCGCT-CACTGAGGCCGCCCGGGCGTCGGGCGAC CTTTGGTCGCCCGGCCTCAGT-GAGCGAGCGAGCGCGCAGAGAGGGAGTGGC-CAACT CCATCACTAGGGGTTCCT (SEQ ID NO: 33350) and the 3' ITR having sequence AGGAACCCCTAGTGATGGAGTTGGC-CACTCCCTCTCTGCGCGCTCGCTCGCTCACTG AGGCCGGGCGAC-CAAAGGTCGCCCGACGCCCGGGCTTTGCCCGG-GCGGCCTCAGTG AGCGAGCGAGCGCGCAGCTGCCTGCAGG (SEQ ID NO: 33351).

By "AAV rep coding region" is meant the region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome.

By "AAV cap coding region" is meant the region of the AAV genome which encodes the capsid proteins VP1, VP2, and VP3, or functional homologues thereof. These Cap expression products supply the packaging functions which are collectively required for packaging the viral genome.

In some embodiments, AAV capsids utilized for delivery of a transgene comprising the encoding sequences for the dXR and gRNA of the disclosure to a host cell can be derived from any of several AAV serotypes, including without limitation, AAV1, AAV2, AAV3, AAV4, AAV5, AAV6, AAV7, AAV8, AAV9, AAV10, AAV11, AAV12, AAV 44.9, AAV-Rh74 (Rhesus macaque-derived AAV), and AAVRh10, and the AAV ITRs are derived from AAV serotype 1 or serotype 2.

In order to produce rAAV viral particles, an AAV expression vector is introduced into a suitable host cell using known techniques, such as by transfection. Packaging cells are typically used to form virus particles; such cells include HEK293 cells (and other cells known in the art), which package adenovirus. A number of transfection techniques are generally known in the art; see, e.g., Sambrook et al. (1989) Molecular Cloning, a laboratory manual, Cold Spring Harbor Laboratories, New York. Particularly suitable transfection methods include calcium phosphate co-precipitation, direct microinjection into cultured cells, electroporation, liposome mediated gene transfer, lipid-mediated transduction, and nucleic acid delivery using high-velocity microprojectiles.

In some embodiments, host cells transfected with the above-described AAV expression vectors are rendered capable of providing AAV helper functions in order to replicate and encapsidate the nucleotide sequences flanked by the AAV ITRs to produce rAAV viral particles. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs (open reading frames), encoding the rep and cap coding regions, or functional homologues thereof. Accessory functions can be introduced into and then expressed in host cells using methods known to those of skill in the art. Commonly, accessory functions are provided by infection of the host cells with an unrelated helper virus. In some embodiments, accessory functions are provided using an accessory function vector. Depending on the host/vector system utilized, any of a number of suitable transcription and translation control elements, including constitutive and inducible promoters, transcription enhancer elements, transcription terminators, etc., may be used in the expression vector.

The present disclosure provides AAV comprising a transgene encoding a dXR and a gRNA, wherein the dXR comprises a dCasX and a KRAB domain as the single repressor, given the size limitations of the transgene. In some embodiments, the transgene encodes a dXR fusion protein of the systems comprising a single KRAB domain operably linked to the dCasX selected from the group of sequences of SEQ ID NOS: 17-36 and 59353-59358 as set forth in Table 4, wherein the KRAB domain is selected from the group of sequences consisting of SEQ ID NOS: 57746-59342, or a sequence having at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In some embodiments, the transgene encodes a dXR fusion protein of the systems comprising a single KRAB domain operably linked to the dCasX selected from the group of sequences of SEQ ID NOS: 17-36 and 59353-59358 as set forth in Table 4, wherein the KRAB domain is selected from the group of sequences consisting of SEQ ID NOS: 57746-57840, or a sequence having at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In some embodiments, the transgene encodes a dXR fusion protein of the systems comprising a single KRAB domain operably linked to the dCasX selected from the group of sequences of SEQ ID NOS: 17-36 and 59353-59358 as set forth in Table 4, wherein the KRAB domain is selected from the group of sequences consisting of SEQ ID NOS: 57746-57755, or a sequence having at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In a particular embodiment, the transgene encodes a dXR fusion protein of the systems comprising a single KRAB domain operably linked to the dCasX of SEQ ID NOS: 18 as set forth in Table 4, wherein the KRAB domain is selected from the group of sequences consisting of SEQ ID NOS: 57746-57755, or a sequence having at least about 70%, at least about 75%, at least about 80%, at least about 85%, at least about 90% at least about 91%, at least about 92%, at least about 93% at least about 94% at least about 95%, at least about 96%, at least about 97%, at least about 98%, or at least about 99% identity thereto. The transgene of the foregoing embodiments further encodes a gRNA having a scaffold comprising a sequence of SEQ ID NO: 2292 or 59352, or a sequence having at least about 70%, at least about 80%, at least about 95%, at least about 96%, at least about 97%, at least about 98%, or at least about 99% sequence identity thereto, wherein the gRNA comprises a targeting sequence complementary to a target nucleic acid sequence of a gene targeted for repression. In the foregoing embodiments, the dXR and gRNA are each operably linked to a promoter, embodiments of which are described herein.

b. VLP and XDP for Delivery of dXR:gRNA

In other embodiments, retroviruses, for example, lentiviruses, may be suitable for use as vectors for delivery of the encoding nucleic acids of the gene repressor systems of the present disclosure. Commonly used retroviral vectors are "defective"; e.g. unable to produce viral proteins required for productive infection, and may be referred to a virus-like particles (VLP) or as a delivery particle (XDP), depending on the components utilized. Rather, replication of the vector requires growth in a packaging cell line. To generate viral particles comprising nucleic acids of interest, the retroviral nucleic acids comprising the nucleic acid are packaged into VLP or XDP capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art.

In some embodiments, the disclosure provides vectors encoding or comprising a gene repressor system comprising a dXR fusion protein, wherein the dXR fusion protein comprises a first transcriptional repressor domain, and wherein the dXR comprises a catalytically-dead CasX of any of the embodiments described herein linked to a KRAB domain of any of the embodiments described herein as the first repressor domain.

In other embodiments, the disclosure provides vectors encoding or comprising a gene repressor system comprising a fusion protein, wherein the fusion protein comprises a catalytically-dead CasX of any of the embodiments described herein linked to a first, a second, and a third transcriptional repressor domain, wherein first transcriptional repressor domain is a KRAB domain of any of the embodiments described herein, the second domain is a DNMT3A catalytic domain of any of the embodiments described herein, the third transcriptional repressor domain is a DNMT3L interaction domain, and the fusion protein comprises one or more NLS and linker peptides. In some embodiments, the fusion protein is configured, from N-terminus to C-terminus: NLS-Linker4-DNMT3A CD-Linker2-DNMT3L ID-Linker 1-Linker3-dCasX-Linker3-KRAB-NLS; NLS-Linker3-dCasX-Linker3-KRAB-NLS-Linker1-DNMT3A CD-Linker2-DNMT3L ID; NLS-Linker3-dCasX-Linker1-DNMT3A CD-Linker2-DNMT3L ID-Linker3-KRAB-NLS; NLS-KRAB-Linker3-DNMT3A CD-Linker2-DNMT3L ID-Linker1-dCasX-Linker3-NLS, or NLS-DNMT3A CD-Linker2-DNMT3L ID-Linker3-KRAB-Linker1-dCasX-Linker3-NLS.

In other embodiments, the disclosure provides vectors encoding or comprising a gene repressor system comprising a fusion protein, wherein the fusion protein comprises a catalytically-dead CasX of any of the embodiments described herein linked to a first, a second, a third, and a fourth transcriptional repressor domain, wherein first transcriptional repressor domain is a KRAB domain of any of the embodiments described herein, the second domain is a DNMT3A catalytic domain of any of the embodiments described herein, the third transcriptional repressor domain a DNMT3L interaction domain, and the fourth transcriptional repressor domain is a ATRX-DNMT3-DNMT3L (ADD) domain linked N-terminal to the DNMT3A catalytic domain and the fusion protein comprises one or more NLS and linker peptides. In some embodiments, the fusion protein is configured, from N-terminus to C-terminus: NLS-Linker4-ADD-DNMT3A CD-Linker2-DNMT3L ID-Linker 1-Linker3-dCasX-Linker3-KRAB-NLS; NLS-Linker3-dCasX-Linker3-KRAB-NLS-Linker1-ADD-DNMT3A CD-Linker2-DNMT3L ID; NLS-Linker3-dCasX-Linker1-DNMT3A CD-Linker2-DNMT3L ID-Linker3-KRAB-NLS; NLS-KRAB-Linker3-ADD-DNMT3A CD-Linker2-DNMT3L ID-Linker1-dCasX-Linker3-NLS, or NLS-ADD-DNMT3A CD-Linker2-DNMT3L ID-Linker3-KRAB-Linker1-dCasX-Linker3-NLS.

In some embodiments, the present disclosure provides XDP comprising components selected from all or a portion of a retroviral gag polyprotein, a gag-poly polyprotein, dXR:gRNA RNPs, RNA trafficking components, and one or more tropism factors having binding affinity for a cell surface marker of a target cell to facilitates entry of the XDP into the target cell.

In some embodiments, the retroviral components of the XDP system are derived from a Orthretrovirinae virus or a Spumaretrovirinae virus wherein the Orthretrovirinae virus is selected from the group consisting of Alpharetrovirus, Betaretrovirus, Deltaretrovirus, Epsilonretrovirus, Gammaretrovirus, and Lentivirus, and the Spumaretrovirinae virus is selected from the group consisting of Bovispumavirus, Equispumavirus, Felispumavirus, Prosimiispumavirus, Simiispumavirus, and Spumavirus.

XDP for use with the dXR:gRNA system can be constructed in different configurations based on the components utilized. In some embodiments, XDP comprise one or more retroviral components selected from a Gag polyprotein, a Gag-transframe region-pol protease polyprotein (Gag-TFR-PR), matrix protein (MA), a nucleocapsid protein (NC), a capsid protein (CA), a p1 peptide, a p6 peptide, a p2A peptide, a p2B peptide, a p10 peptide, a p12 peptide, a p21/24 peptide, a p12/p3/p8 peptide, a p20 peptide, a protease cleavage site, and a protease capable of cleaving the protease cleavage sites, which can be encoded on one or more nucleic acids for the production of the XDP in the packaging cell. The remaining components, such as the encapsidated payload of dXR and the gRNA (complexed as RNPs), RNA trafficking components (described below) used to increase the incorporation of RNP into the XDP, and the tropism factor, can be incorporated into the nucleic acid encoding the retroviral components or can be encoded on separate nucleic acids. In some embodiments, the components of the XDP system are encoded on a single nucleic acid, on two nucleic acids, on three nucleic acids, on four nucleic acids, or on five nucleic acids which, in turn, are incorporated into plasmids used in the transfection to create the XDP in packaging cells. Representative, non-limiting configurations of plasmids used to make XDP in the packaging cells are presented in FIGS. 4 and 5. In a particular embodiment of the configuration of FIG. 4, the Gag polyprotein of plasmid 1 and the Gag-TFR-PR polyprotein of plasmid 2 are derived from Lentivirus (with an HIV-1 protease), the encoded MS2 of plasmid 1 comprises the sequence of SEQ ID NO: 33276, the encoded dXR fusion protein of plasmid 3 comprises any of the dXR embodiments described herein, the VSV-G plasmid encodes the VSV-G sequence of SEQ ID NO: 113, and the gRNA plasmid encodes a scaffold of SEQ ID NO: 2292 or 59352. In some embodiments, the components of the XDP system are capable of self-assembling into an XDP with the incorporated RNP of the dXR:gRNA when the one or more nucleic acids are introduced into a eukaryotic host cell and are expressed. In the foregoing embodiment, the dXR:gRNA RNP is encapsidated within the XDP upon self-assembly of the XDP. In a particular embodiment, the tropism factor is incorporated on the XDP surface upon self-assembly of the XDP. XDP compositions and methods of making XDP are described in WO2021113772A1 and PCT/US22/32579, incorporated by reference herein.

The polynucleotides encoding the Gag, dXR and gRNA of any of the embodiments described herein can further comprise paired components designed to assist the trafficking of the components out of the nucleus of the host cell and facilitate recruitment of the complexed CasX:gRNA into the budding XDP. Non-limiting examples of such non-covalent trafficking components include hairpin RNA or loops such as MS2 hairpin, PP7 hairpin, Qβ hairpin, boxB, transactivation response element (TAR), Rev response element, phage GA hairpin, and U1 hairpin II that have binding affinity for MS2 coat protein, PP7 coat protein, Q$ coat protein, protein N, protein Tat, Rev, phage GA coat protein, and U1A signal recognition particle, respectively, that are fused to the Gag polyprotein. It has been discovered that the incorporation of the binding partner inserted into the guide RNA and the packaging recruiter into the nucleic acid comprising the Gag polypeptide facilitates the packaging of the XDP particle due, in part, to the affinity of the CasX for the gRNA, resulting in an RNP, such that both the gRNA and CasX are associated with Gag during the encapsidation process of the XDP, increasing the proportion of XDP comprising RNP compared to a construct lacking the binding partner and packaging recruiter. In other embodiments, the gRNA can comprise Rev response element (RRE) or portions thereof that have binding affinity to Rev, which can be linked to the Gag polyprotein. In other embodiments, the gRNA can comprise one or more RRE and one or more MS2 hairpin sequences. The RRE can be selected from the group consisting of Stem IIB of Rev response element (RRE), Stem II-V of RRE, Stem II of RRE, Rev-binding element (RBE) of Stem IIB, and full-length RRE. In the foregoing embodiment, the components include sequences of UGGGCGCAGCGUCAAUGACGCUGACGGUACA (Stem IIB, SEQ ID NO: 57736), GCACUAUGGGCGCAGCGUCAAUGACGCUGACGGUACAGGCCAGACAAUUAUUGU CUGGUAUAGUGC (Stem II, SEQ ID NO: 57737), CAGGAAGCACUAUGGGCGCAGCGUCAAUGACGCUGACGGUACAGGCCAGACAAU UAUUGUCUGGUAUAGUGCAGCAGCAGAACAAUUUGCUGAGGGCUAUUGAGGCGC AACAGCAUCUGUUGCAACUCACAGUCUGGGGCAUCAAGCAGCUCCAGGCAAGAA UCCUG (Stem II-V, SEQ ID NO: 57738), GCUGACGGUACAGGC (RBE, SEQ ID NO: 57739), and AGGAGCUUUGUUCCUUGGGUUCUUGGGAGCAGCAGGAAGCACUAUGGGCGCAGC GUCAAUGACGCUGACGGUACAGGCCAGACAAUUAUUGUCUGGUAUAGUGCAGCA GCAGAACAAUUUGCUGAGGGCUAUUGAGGCGCAACAGCAUCUGUUGCAACUCAC AGUCUGGGGCAUCAAGCAGCUCCAGGCAAGAAUCCUGGCUGUGGAAAGAUACCU AAAGGAUCAACAGCUCCU (full-length RRE, SEQ ID NO: 57740). In other embodiments, the gRNA can comprise one or more RRE and one or more MS2 hairpin sequences. In a particular embodiment, the gRNA comprises an MS2 hairpin variant that is optimized to increase the binding affinity to the MS2 coat protein, thereby enhancing the incorporation of the gRNA and associated CasX into the budding XDP.

In some embodiments, the tropism factor incorporated on the XDP surface is selected from the group consisting of a glycoprotein, an antibody fragment, a receptor, and a ligand to a target cell marker. In one embodiment ofthe foregoing, the tropism factor is a glycoprotein having a sequence selected from the group consisting ofthe sequences set forth in Table 8, or a sequence having at least about 85%, at least about 90%, at least about 91%, at least about 92%, at least about 93%, at least about 94%, at least about 95%, at least about 96%, at least about 97%, at least about 98%, or at least about 99% sequence identity thereto. In a particular embodiment, the glycoprotein is VSV-G.

TABLE 8

Glycoproteins for XDP

| SEQ ID NO | Virus | Plasmid |
|---|---|---|
| 113 | Vesicular Stomatitis Virus | pGP2 |
| 114 | Human Immunodeficiency Virus | pGP3 |
| 115 | Avian leukosis virus | pGP4 |
| 116 | Rous Sarcoma Virus | pGP5 |
| 117 | Mouse mammary tumor virus | pGP6 |
| 118 | Human T-lymphotropic virus 1 | pGP7 |
| 119 | RD114 Endogenous Feline Retrovirus | pGP8 |
| 120 | Gibbon ape leukemia virus | pGP9 |
| 121 | Moloney Murine leukemia virus | pGP10 |
| 122 | Baboon Endogenous Virus | pGP11 |
| 123 | Human Foamy Virus | pGP12 |
| 124 | Pseudorabies virus | pGP13.1 |
| 125 | Pseudorabies virus | pGP13.2 |
| 126 | Pseudorabies virus | pGP13.3 |
| 127 | Pseudorabies virus | pGP13.4 |
| 128 | Herpes simplex virus 1 (HHV1) | pGP14.1 |
| 129 | Herpes simplex virus 1 (HHV1) | pGP14.2 |
| 130 | Herpes simplex virus 1 (HHV1) | pGP14.3 |
| 131 | Herpes simplex virus 1 (HHV1) | pGP14.4 |
| 132 | Hepatitis C Virus | pGP23 |

TABLE 8-continued

| SEQ ID NO | Virus | Plasmid |
|---|---|---|
| | Glycoproteins for XDP | |
| 133 | Rabies Virus | pGP29 |
| 134 | Mokola Virus | pGP30 |
| 135 | Measles Virus | pGP32.1 |
| 136 | Measles Virus | pGP32.2 |
| 137 | Ebola Zaire Virus | pGP41 |
| 138 | Dengue | pGP25 |
| 139 | Zika virus | pGP26 |
| 140 | West Nile Virus | pGP27 |
| 141 | Japanese Encephalitis Virus | pGP28 |
| 142 | Hepatitis G Virus | pGP24 |
| 143 | Mumps Virus F | pGP31.1 |
| 144 | Mumps Virus HN | pGP31.2 |
| 145 | Sendai Virus F | pGP33.1 |
| 146 | Sendai Virus HN | pGP33.2 |
| 147 | AcMNPV gp64 | pGP59 |
| 148 | Ross River Virus | pGP54 |
| 149 | Codon optimized rabies virus | pGP29.2 |
| 150 | Rabies virus (strain Nishigahara RCEH) (RABV) | pGP29.3 |
| 151 | Rabies virus (strain India) (RABV) | pGP29.4 |
| 152 | Rabies virus (strain CVS-11) (RABV) | pGP29.5 |
| 153 | Rabies virus (strain ERA) (RABV) | pGP29.6 |
| 154 | Rabies virus (strain SAD B19) (RABV) | pGP29.7 |
| 155 | Rabies virus (strain Vnukovo-32) (RABV) | pGP29.8 |
| 156 | Rabies virus (strain Pasteur vaccins/PV) (RABV) | pGP29.9 |
| 157 | Rabies virus (strain PM1503/AVO1) (RABV) | pGP29.1 |
| 158 | Rabies virus (strain China/DRV) (RABV) | pGP29.11 |
| 159 | Rabies virus (strain China/MRV) (RABV) | pGP29.12 |
| 160 | Rabies virus (isolate Human/Algeria/1991) (RABV) | pGP29.13 |
| 161 | Rabies virus (strain HEP-Flury) (RABV) | pGP29.14 |
| 162 | Rabies virus (strain silver-haired bat-associated) (RABV) (SHBRV) | pGP29.15 |
| 163 | HSV2 gB | pGP15.1 |
| 164 | HSV2 gD | pGP15.2 |
| 165 | HSV2 gH | pGP15.3 |
| 166 | HSV2 gL | pGP15.4 |
| 167 | Varicella gB | pGP16.1 |
| 168 | Varicella gK | pGP16.2 |
| 169 | Varicella gH | pGP16.3 |
| 170 | Varicella gL | pGP16.4 |
| 171 | Hepatitis B gL | pGP22.1 |
| 172 | Hepatitis B gM | pGP22.2 |
| 173 | Hepatitis B gS | pGP22.3 |
| 174 | Eastern equine encephalitis virus (EEEV) | pGP65 |
| 175 | Venezuelan equine encephalitis viruses (VEEV) | pGP66 |
| 176 | Western equine encephalitis virus (WEEV) | pGP67 |
| 177 | Semliki Forest virus | pGP68 |
| 178 | Sindbis virus | pGP69 |
| 179 | Chikungunya virus (CHIKV) | pGP70 |
| 180 | Bornavirus BoDV-1 | pGP58 |
| 181 | Tick-borne encephalitis virus (TBEV) | pGP71 |
| 182 | Usutu virus | pGP72 |
| 183 | St. Louis encephalitis virus | pGP73 |
| 184 | Yellow fever virus | pGP74 |
| 185 | Dengue virus 2 | pGP75 |
| 186 | Dengue virus 3 | pGP76 |
| 187 | Dengue virus 4 | pGP77 |
| 188 | Murray Valley encephalitis virus (MVEV) | pGP78 |
| 189 | Powassan virus | pGP79 |
| 190 | H5 Hemagglutinin | pGP80 |
| 191 | H7 Hemagglutinin | pGP81 |
| 192 | N1 Neuraminidase | pGP82 |
| 193 | Canine Distemper Virus | pGP83 |
| 194 | VSAV | pGP92 |
| 195 | ABVV | pGP99 |
| 196 | CARV | pGP98 |
| 197 | CHPV | pGP97 |
| 198 | COCV | pGP100 |
| 199 | VSIV | pGP91 |
| 200 | ISFV | pGP90 |
| 201 | JURV | pGP87 |
| 202 | MSPV | pGP89 |
| 203 | MARV | pGP88 |
| 204 | MORV | pGP101 |
| 205 | VSNJV | pGP84 |
| 206 | PERV | pGP85 |

TABLE 8-continued

| Glycoproteins for XDP | | |
|---|---|---|
| SEQ ID NO | Virus | Plasmid |
| 207 | PIRYV | pGP94 |
| 208 | RADV | pGP96 |
| 209 | YBV | pGP86 |
| 210 | VSV CEN AM - 94GUB | pGP93 |
| 211 | VSV South America 85CLB | pGP95 |
| 212 | Nipah Virus | pGP34.1 |
| 213 | Nipah Virus | pGP34.2 |
| 214 | Hendra Virus | pGP35.1 |
| 215 | Hendra Virus | pGP35.2 |
| 216 | Newcastle disease virus | pGP37.1 |
| 217 | Newcastle disease virus | pGP37.2 |
| 218 | RSV f0 | pGP55.1 |
| 219 | RSV G | pGP55.2 |
| 220 | Bovine respiratory syncytial virus (strain Rb94) (BRS) | pGP102 |
| 221 | Murine pneumonia virus (strain 15) (MPV) | pGP103 |
| 222 | Measles virus (strain Edmonston) (MeV) (Subacute sclerose panencephalitis virus) | pGP104 |
| 223 | Measles virus (strain Edmonston B) (MeV) (Subacute sclerose panencephalitis virus) | pGP105 |
| 224 | Human respiratory syncytial virus B (strain B1) | pGP106 |
| 225 | Rinderpest virus (strain RBOK) (RDV) | pGP107 |
| 226 | Simian virus 41 (SV41) | pGP108 |
| 227 | Mumps virus (strain Miyahara vaccine) (MuV) | pGP109 |
| 228 | Canine distemper virus (strain Onderstepoort) (CDV) | pGP110 |
| 229 | Human respiratory syncytial virus A (strain Long) | pGP111 |
| 230 | Sendai virus (strain Fushimi) (SeV) | pGP112 |
| 231 | Human respiratory syncytial virus A (strain RSS-2) | pGP113 |
| 232 | Rinderpest virus (strain RBT1) (RDV) | pGP114 |
| 233 | Measles virus (strain Leningrad-16) (MeV) (Subacute sclerose panencephalitis virus) | pGP115 |
| 234 | Human parainfluenza 2 virus (HPIV-2) | pGP116 |
| 235 | Avian metapneumovirus (isolate Canada goose/Minnesota/15a/2001) (AMPV) | pGP117 |
| 236 | Phocine distemper virus (PDV) | pGP118 |
| 237 | Sendai virus (strain Harris) (SeV) | pGP119 |
| 238 | Bovine parainfluenza 3 virus (BPIV-3) | pGP120 |
| 239 | Measles virus (strain Ichinose-B95a) (MeV) (Subacute sclerose panencephalitis virus) | pGP121 |
| 240 | Human parainfluenza 2 virus (strain Toshiba) (HPIV-2) | pGP122 |
| 241 | Newcastle disease virus (strain B1-Hitchner/47) (NDV) | pGP123 |
| 242 | Measles virus (strain Yamagata-1) (MeV) (Subacute sclerose panencephalitis virus) | pGP124 |
| 243 | Measles virus (strain IP-3-Ca) (MeV) (Subacute sclerose panencephalitis virus) | pGP125 |
| 244 | Measles virus (strain Edmonston-AIK-C vaccine) (MeV) (Subacute sclerose panencephalitis virus) | pGP126 |
| 245 | Turkey rhinotracheitis virus (TRTV) | pGP127 |
| 246 | Human parainfluenza 2 virus (strain Greer) (HPIV-2) | pGP128 |
| 247 | Hendra virus (isolate Horse/Autralia/Hendra/1994) | pGP129 |
| 248 | Human metapneumovirus (strain CAN97-83) (HMPV) | pGP130 |
| 249 | Bovine respiratory syncytial virus (strain Copenhagen) (BRS) | pGP131 |
| 250 | Sendai virus (strain Z) (SeV) (Sendai virus (strain HVJ)) | pGP132 |
| 251 | Human parainfluenza 3 virus (strain Wash/47885/57) (HPIV-3) (Human parainfluenza 3 virus (strain NIH 47885)) | pGP133 |
| 252 | Mumps virus (strain SBL-1) (MuV) | pGP134 |
| 253 | Measles virus (strain Edmonston-Zagreb vaccine) (MeV) (Subacute sclerose panencephalitis virus) | pGP135 |
| 254 | Human parainfluenza 1 virus (strain C39) (HPIV-1) | pGP136 |
| 255 | Sendai virus (strain Hamamatsu) (SeV) | pGP137 |
| 256 | Mumps virus (strain RW) (MuV) | pGP138 |
| 257 | Infectious hematopoietic necrosis virus (strain Oregon69) (IHNV) | pGP139 |
| 258 | Drosophila melanogaster sigma virus (isolate Drosophila/USA/AP30/2005) (DMelSV) | pGP140 |
| 259 | Hirame rhabdovirus (strain Korea/CA 9703/1997) (HIRRV) | pGP141 |
| 260 | Sonchus yellow net virus (SYNV) | pGP142 |
| 261 | European bat lyssavirus 1 (strain Bat/Germany/RV9/1968) (EBLV1) | pGP143 |
| 262 | Lagos bat virus (LBV) | pGP144 |
| 263 | Duvenhage virus (DUVV) | pGP145 |
| 264 | West Caucasian bat virus (WCBV) | pGP146 |
| 265 | European bat lyssavirus 2 (strain Human/Scotland/RV1333/2002) (EBLV2) | pGP147 |
| 266 | Irkut virus (IRKV) | pGP148 |
| 267 | Tupaia virus (isolate Tupaia/Thailand/—/1986) (TUPV) | pGP149 |

TABLE 8-continued

Glycoproteins for XDP

| SEQ ID NO | Virus | Plasmid |
|---|---|---|
| 268 | Rabies virus (strain ERA) (RABV) | pGP150 |
| 269 | Ovine respiratory syncytial virus (strain WSU 83-1578) (ORSV) | pGP151 |
| 270 | Human respiratory syncytial virus A (strain rsb5857) | pGP152 |
| 271 | Piry virus (PIRYV) | pGP153 |
| 272 | Human respiratory syncytial virus A (strain rsb6190) | pGP154 |
| 273 | Rabies virus (strain SAD B19) (RABV) | pGP155 |
| 274 | Australian bat lyssavirus (isolate Human/AUS/1998) (ABLV) | pGP156 |
| 275 | Rabies virus (strain Vnukovo-32) (RABV) | pGP157 |
| 276 | Aravan virus (ARAV) | pGP158 |
| 277 | Sigma virus | pGP159 |
| 278 | Viral hemorrhagic septicemia virus (strain 07-71) (VHSV) | pGP160 |
| 279 | Rabies virus (strain Pasteur vaccins/PV) (RABV) | pGP161 |
| 280 | Bovine respiratory syncytial virus (strain Rb94) (BRS) | pGP162 |
| 281 | Tibrogargan virus (strain CS132) (TIBV) | pGP163 |
| 282 | Infectious hematopoietic necrosis virus (strain Round Butte) (IHNV) | pGP164 |
| 283 | Human respiratory syncytial virus B (strain 18537) | pGP165 |
| 284 | Adelaide River virus (ARV) | pGP166 |
| 285 | Australian bat lyssavirus (isolate Bat/AUS/1996) (ABLV) | pGP167 |
| 286 | Bovine ephemeral fever virus (strain BB7721) (BEFV) | pGP168 |
| 287 | Isfahan virus (ISFV) | pGP169 |
| 288 | Rabies virus (strain silver-haired bat-associated) (RABV) (SHBRV) | pGP170 |
| 289 | Snakehead rhabdovirus (SHRV) | pGP171 |
| 290 | Infectious hematopoietic necrosis virus (strain WRAC) (IHNV) | pGP172 |
| 291 | Zaire ebolavirus (strain Kikwit-95) (ZEBOV) (Zaire Ebola virus) | pGP173 |
| 292 | Sudan ebolavirus (strain Maleo-79) (SEBOV) (Sudan Ebola virus) | pGP174 |
| 293 | Tai Forest ebolavirus (strain Cote d'Ivoire-94) (TAFV) (Cote d'Ivoire Ebola virus) | pGP175 |
| 294 | Reston ebolavirus (strain Philippines-96) (REBOV) (Reston Ebola virus) | pGP176 |
| 295 | Lake Victoria marburgvirus (strain Angola/2005) (MARV) | pGP177 |
| 296 | Zaire ebolavirus (strain Eckron-76) (ZEBOV) (Zaire Ebola virus) | pGP178 |
| 297 | Reston ebolavirus (strain Reston-89) (REBOV) (Reston Ebola virus) | pGP179 |
| 298 | Tai Forest ebolavirus (strain Cote d'Ivoire-94) (TAFV) (Cote d'Ivoire Ebola virus) | pGP180 |
| 299 | Lake Victoria marburgvirus (strain Ozolin-75) (MARV) (Marburg virus (strain South Africa/Ozolin/1975)) | pGP181 |
| 300 | Zaire ebolavirus (strain Mayinga-76) (ZEBOV) (Zaire Ebola virus) | pGP182 |
| 301 | Lake Victoria marburgvirus (strain Popp-67) (MARV) (Marburg virus (strain West Germany/Popp/1967)) | pGP183 |
| 302 | Sudan ebolavirus (strain Boniface-76) (SEBOV) (Sudan Ebola virus) | pGP184 |
| 303 | Reston ebolavirus (strain Reston-89) (REBOV) (Reston Ebola virus) | pGP185 |
| 304 | Sudan ebolavirus (strain Human/Uganda/Gulu/2000) (SEBOV) (Sudan Ebola virus) | pGP186 |
| 305 | Zaire ebolavirus (strain Gabon-94) (ZEBOV) (Zaire Ebola virus) | pGP187 |
| 306 | Reston ebolavirus (strain Reston-89) (REBOV) (Reston Ebola virus) | pGP188 |
| 307 | Simian virus 41 (SV41) | pGP189 |
| 308 | Newcastle disease virus (strain D26/76) (NDV) | pGP190 |
| 309 | Xenotropic MuLV-related virus (isolate VP42) (XMRV) | pGP191 |
| 310 | Xenotropic MuLV-related virus (isolate VP62) (XMRV) | pGP192 |
| 311 | Simian immunodeficiency virus (isolate F236/smH4) (SIV-sm) (Simian immunodeficiency virus sooty mangabey monkey) | pGP193 |
| 312 | Simian immunodeficiency virus (isolate Mm251) (SIV-mac) (Simian immunodeficiency virus rhesus monkey) | pGP194 |
| 313 | Simian immunodeficiency virus (isolate GB1) (SIV-mnd) (Simian immunodeficiency virus mandrill) | pGP195 |
| 314 | Simian immunodeficiency virus (isolate Mm142-83) (SIV-mac) (Simian immunodeficiency virus rhesus monkey) | pGP196 |

TABLE 8-continued

Glycoproteins for XDP

| SEQ ID NO | Virus | Plasmid |
|---|---|---|
| 315 | Simian immunodeficiency virus (isolate MB66) (SIV-cpz) (Chimpanzee immunodeficiency virus) | pGP197 |
| 316 | Simian immunodeficiency virus (isolate EK505) (SIV-cpz) (Chimpanzee immunodeficiency virus) | pGP198 |
| 317 | Feline immunodeficiency virus (strain UK2) (FIV) | pGP199 |
| 318 | Feline immunodeficiency virus (strain San Diego) (FIV) | pGP200 |
| 319 | Feline immunodeficiency virus (isolate Wo) (FIV) | pGP201 |
| 320 | Feline immunodeficiency virus (isolate Petaluma) (FIV) | pGP202 |
| 321 | Feline immunodeficiency virus (strain UK8) (FIV) | pGP203 |
| 322 | Feline immunodeficiency virus (strain UT-113) (FIV) | pGP204 |
| 323 | Mayoro Virus | pGP205 |
| 324 | Barmah Forest Virus | pGP206 |
| 325 | Aura virus | pGP207 |
| 326 | Bebaru Virus | pGP208 |
| 327 | Middleburg virus | pGP209 |
| 328 | Mucambo virus | pGP210 |
| 329 | Ndumu Virus | pGP211 |
| 330 | O'nyong-nyong virus | pGP212 |
| 331 | Pixuna virus | pGP213 |
| 332 | Tonate Virus | pGP214 |
| 333 | Trocara virus | pGP215 |
| 334 | Whataroa virus | pGP216 |
| 335 | Bussuquara virus | pGP217 |
| 336 | Jugra virus | pGP218 |

In some embodiments, the protease encoded in the nucleic acids utilized in the XDP system is selected from the group consisting of HIV-1 protease, tobacco etch virus protease (TEV), potyvirus HC protease, potyvirus P1 protease, PreScission (HRV3C protease), b virus NIa protease, B virus RNA-2-encoded protease, aphthovirus L protease, enterovirus 2A protease, rhinovirus 2A protease, picorna 3C protease, comovirus 24K protease, nepovirus 24K protease, RTSV (rice tungro spherical virus) 3C-like protease, parsnip yellow fleck virus protease, 3C-like protease, heparin, cathepsin, thrombin, factor Xa, metalloproteinase, and enterokinase.

In some embodiments, the present disclosure provides eukaryotic cells transfected with the plasmids encoding the XDP system of any one of the foregoing embodiments, wherein the cell is a packaging cell capable of facilitating the expression of the encoded dXR:gRNA and XDP components and the assembly of the XDP particles that encapsidate RNP of the dXR and gRNA. In some embodiments, the eukaryotic cell is selected from the group consisting of HEK293 cells, HEK293T cells, Lenti-X 293T cells, BHK cells, HepG2, Saos-2, HuH7, NS0 cells, SP2/0 cells, YO myeloma cells, A549 cells, P3X63 mouse myeloma cells, PER cells, PER.C6 cells, hybridoma cells, VERO, NIH3T3 cells, COS, WI38, MRC5, A549, HeLa cells, CHO cells, and HT1080 cells. In some embodiments, the packaging host cell can be modified to reduce or eliminate cell surface markers or receptors that would otherwise be incorporated into the XDP, thereby reducing an immune response to the cell surface markers or receptors by the subject receiving an administration of the XDP. Such markers can include receptors or proteins capable of being bound by MHC receptors or that would otherwise trigger an immune response in a subject. In some embodiments, the packaging host cell is modified to reduce or eliminate the expression of a cell surface marker selected from the group consisting of B2M, CIITA, PD1, and HLA-E KI, wherein the incorporation of the marker is reduced on the surface of the XDP. In some embodiments, the packaging host cell is modified to express one or more cell surface markers selected from the group consisting of CD46, CD47, CD55, CD59, CD24, CD58, SLAMF4, and SLAMF3 (serving as "don't eat me" signals), wherein the cell surface marker is incorporated onto the surface of the XDP, wherein said incorporation disables XDP engulfment and phagocytosis by host surveillance cells such as macrophages and monocytes.

For non-viral delivery, vectors can also be delivered wherein the vector or vectors encoding and/or comprising the dXR and gRNA are formulated in nanoparticles, wherein the nanoparticles contemplated include, but are not limited to nanospheres, liposomes, quantum dots, polyethylene glycol particles, hydrogels, and micelles. As described more fully, below, lipid nanoparticles are generally composed of an ionizable cationic lipid and three or more additional components, such as cholesterol, DOPE, polylactic acid-co-glycolic acid, and a polyethylene glycol (PEG) containing lipid. In some embodiments, mRNA encoding the dXR variants of the embodiments disclosed herein are formulated in a lipid nanoparticle. In some embodiments, the nanoparticle comprises the gRNA of the embodiments disclosed herein. In some embodiments, the nanoparticle comprises mRNA encoding the dXR and the gRNA. In some embodiments, the components of the dXR:gRNA system are formulated in separate nanoparticles for delivery to cells or for administration to a subject in need thereof.

c. Lipid Nanoparticles (LNP)

In another aspect, the present disclosure provides lipid nanoparticles (LNP) for delivery of a gRNA and an mRNA encoding a fusion protein of any of the system embodiments disclosed herein. In certain embodiments, a composition described herein comprises LNP encapsidating a gene repressor system of the disclosure (i.e., an mRNA encoding a fusion protein (e.g., a dXR) and a gRNA with a targeting sequence to the target nucleic acid) which represses transcription of a target gene.

In some embodiments, the LNP of the disclosure are tissue- or organ-specific, have excellent biocompatibility, and can deliver the systems comprising mRNA encoding the dXR and a gRNA with a targeting sequence to the target nucleic acid with high efficiency, and thus can be usefully used for the repression or silencing of the target nucleic acid of a gene in cells of a subject having a disease or disorder.

In their native forms, nucleic acid polymers are unstable in biological fluids and cannot penetrate the membrane of target cells to be delivered to the cytoplasm, thus requiring delivery systems capable of entering a cell. Lipid nanoparticles (LNP) have proven useful for both the protection and delivery of nucleic acids to tissues and cells. Furthermore, the use of mRNA in LNP to encode the CRISPR nuclease eliminates the possibility of undesirable genome integration compared to DNA vectors. Moreover, mRNA efficiently transfects both mitotic and non-mitotic cells, as it does not require entry into the nucleus since it exerts its function in the cytoplasmic compartment. LNP as a delivery platform offers the additional advantage of being able to co-formulate both the mRNA encoding the CRISPR nuclease and the gRNA into single LNP particles.

Accordingly, in various embodiments, the disclosure encompasses LNP and compositions that may be used for a variety of purposes, including the delivery of encapsulated dXR:gRNA systems to cells, both in vitro and in vivo. In some embodiments, the gRNA for use in the LNP is the sequence of SEQ ID NO: 59352. In some embodiments, the gRNA for use in the LNP comprises one or more chemical modifications to the sequence. In some embodiments, the mRNA for incorporation into the LNP of the disclosure encode any of the dXR embodiments described herein. In some embodiments, the mRNA for incorporation into the LNP of the disclosure are codon optimized. In some embodiments, an mRNA encoding a dXR fusion protein of the disclosure is chemically modified, wherein the chemical modification is substitution of N1-methyl-pseudouridine for one or more uridine nucleotides of the sequence. In some embodiments, an mRNA for incorporation into the LNP of the disclosure comprises one or more sequences selected from the group consisting of SEQ ID NOS: 59584-59585, 59610, 59611, 59622 and 59623. In some embodiments, In some embodiments, an mRNA for incorporation into the LNP of the disclosure comprises one or more sequences encoded by a sequence selected from the group consisting of 59444-59449, 59455-59456, 59488-59497, 59568-59583, 59595-59609, and 59612-59621.

In some embodiments, the disclosure encompasses LNP encapsidating a gRNA and an mRNA encoding a fusion protein of a dCasX linked to a first repressor domain, wherein the repressor domain is a KRAB domain of any of the embodiments described herein. In some embodiments, the disclosure encompasses LNP encapsidating a gRNA and an mRNA encoding a fusion protein of a dCasX linked to a first and a second repressor domain, wherein the first repressor domain is a KRAB domain and the second repressor domain is a DNMT3A catalytic domain. In some embodiments, the disclosure encompasses LNP encapsidating a gRNA and an mRNA encoding a fusion protein of a dCasX linked to a first, a second, and a third repressor domain, wherein the first repressor domain is a KRAB domain, the second repressor domain is a DNMT3A catalytic domain, and the third domain is a DNMT3L interaction domain. In some embodiments, the disclosure encompasses LNP encapsidating a gRNA and an mRNA encoding a fusion protein of a dCasX linked to a first, a second, a third, and a fourth repressor domain, wherein the first repressor domain is a KRAB domain, the second repressor domain is a DNMT3A catalytic domain, the third domain is a DNMT3L interaction domain, and the fourth domain is a DNMT3A ADD domain. In the foregoing embodiments, the components of the fusion protein can be arrayed in alternate configurations, as portrayed in FIG. 7 and FIG. 45. In certain embodiments, the disclosure encompasses methods of treating or preventing diseases or disorders in a subject in need thereof by contacting the subject with an LNP that encapsulates the dXR:gRNA systems of the embodiments described herein, wherein the dXR is an encoding mRNA and the gRNA comprises a targeting sequence complementary to a target nucleic acid in cells of the subject.

In some embodiments, the present disclosure provides LNP in which the gRNA and mRNA encoding the dXR are incorporated into single LNP particles. In certain embodiments, the LNP composition includes a ratio of gRNA to dXR mRNA of the embodiments described herein from about 25:1 to about 1:25, as measured by weight. In certain embodiments, the LNP formulation includes a ratio of gRNA to dXR mRNA, such as dXR mRNA from about 10:1 to about 1:10. In certain embodiments, the LNP formulation includes a ratio of gRNA to dXR mRNA from about 8:1 to about 1:8. In some embodiments, the LNP formulation includes a ratio of gRNA to dXR mRNA, from about 5:1 to about 1:5. In some embodiments, ratio range is about 3:1 to 1:3, about 2:1 to 1:2, about 5:1 to 1:2, about 5:1 to 1:1, about 3:1 to 1:2, about 3:1 to 1:1, about 3:1, about 2:1 to 1:1. In some embodiments, the gRNA to mRNA ratio is about 3:1 or about 2:1. In some embodiments the ratio of gRNA to dXR mRNA is about 1:1. The ratio may be about 25:1, 10:1, 5:1, 3:1, 1:1, 1:3, 1:5, 1:10, or 1:25.

In other embodiments, the present disclosure provides LNP in which the gRNA and mRNA encoding the dXR are incorporated into separate LNP particles, which can be formulated together in varying ratios for administration.

In some embodiments, the optimized mRNA of the disclosure encoding the CasX protein may be provided in a solution to be mixed with a lipid solution such that the mRNA may be encapsulated in the LNP. A suitable mRNA solution may be any aqueous solution containing mRNA to be encapsulated at various concentrations. For example, a suitable mRNA solution may contain an mRNA at a concentration of or greater than about 0.01 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.25 mg/ml, 1.5 mg/ml, 1.75 mg/ml, or 2.0 mg/ml. In some embodiments, a suitable mRNA solution may contain an mRNA at a concentration ranging from about 0.01-2.0 mg/ml, 0.01-1.5 mg/ml, 0.01-1.25 mg/ml, 0.01-1.0 mg/ml, 0.01-0.9 mg/ml, 0.01-0.8 mg/ml, 0.01-0.7 mg/ml, 0.01-0.6 mg/ml, 0.01-0.5 mg/ml, 0.01-0.4 mg/ml, 0.01-0.3 mg/ml, 0.01-0.2 mg/ml, 0.01-0.1 mg/ml, 0.05-1.0 mg/ml, 0.05-0.9 mg/ml, 0.05-0.8 mg/ml, 0.05-0.7 mg/ml, 0.05-0.6 mg/ml, 0.05-0.5 mg/ml, 0.05-0.4 mg/ml, 0.05-0.3 mg/ml, 0.05-0.2 mg/ml, 0.05-0.1 mg/ml, 0.1-1.0 mg/ml, 0.2-0.9 mg/ml, 0.3-0.8 mg/ml, 0.4-0.7 mg/ml, or 0.5-0.6 mg/ml. In some embodiments, a suitable mRNA solution may contain an mRNA at a concentration up to about 5.0 mg/ml, 4.0 mg/ml, 3.0 mg/ml, 2.0 mg/ml, 1.0 mg/ml, 0.9 mg/ml, 0.8 mg/ml, 0.7 mg/ml, 0.6 mg/ml, 0.5 mg/ml, 0.4 mg/ml, 0.3 mg/ml, 0.2 mg/ml, 0.1 mg/ml, 0.05 mg/ml, 0.04 mg/ml, 0.03 mg/ml, 0.02 mg/ml, 0.01 mg/ml, or 0.05 mg/ml.

In some embodiments, the gRNA of the disclosure may be provided in a solution to be mixed with a lipid solution such that the gRNA may be encapsulated in the LNP. A suitable gRNA solution may be any aqueous solution containing gRNA to be encapsulated at various concentrations. For example, a suitable gRNA solution may contain a gRNA at a concentration of or greater than about 0.01 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.25 mg/ml, 1.5 mg/ml, 1.75 mg/ml, or 2.0 mg/ml. In some embodiments, a suitable gRNA solution may contain an gRNA at a concentration ranging from about 0.01-2.0 mg/ml, 0.01-1.5 mg/ml, 0.01-1.25 mg/ml, 0.01-1.0 mg/ml, 0.01-0.9 mg/ml, 0.01-0.8 mg/ml, 0.01-0.7 mg/ml, 0.01-0.6 mg/ml, 0.01-0.5 mg/ml, 0.01-0.4 mg/ml, 0.01-0.3 mg/ml, 0.01-0.2 mg/ml, 0.01-0.1 mg/ml, 0.05-1.0 mg/ml, 0.05-0.9 mg/ml, 0.05-0.8 mg/ml, 0.05-0.7 mg/ml, 0.05-0.6 mg/ml, 0.05-0.5 mg/ml, 0.05-0.4 mg/ml, 0.05-0.3 mg/ml, 0.05-0.2 mg/ml, 0.05-0.1 mg/ml, 0.1-1.0 mg/ml, 0.2-0.9 mg/ml, 0.3-0.8 mg/ml, 0.4-0.7 mg/ml, or 0.5-0.6 mg/ml.

In some embodiments, a suitable gRNA solution may contain a gRNA at a concentration up to about 5.0 mg/ml, 4.0 mg/ml, 3.0 mg/ml, 2.0 mg/ml, 1.0 mg/ml, 0.9 mg/ml, 0.8 mg/ml, 0.7 mg/ml, 0.6 mg/ml, 0.5 mg/ml, 0.4 mg/ml, 0.3 mg/ml, 0.2 mg/ml, 0.1 mg/ml, 0.05 mg/ml, 0.04 mg/ml, 0.03 mg/ml, 0.02 mg/ml, 0.01 mg/ml, or 0.05 mg/ml.

Early formulations of LNP utilizing permanently cationic lipids resulted in LNPs with positive surface charge that proved toxic in vivo, plus were rapidly cleared by phagocytic cells. By changing to ionizable cationic lipids bearing tertiary or quaternary amines, especially those with pKa<7, resulting LNP achieve efficient encapsulation of nucleic acid polymers at low pH by interacting electrostatically with the negative charges of the phosphate backbone of mRNA or gRNA, that also result in largely neutral systems at physiological pH values, thus alleviating problems associated with permanently-charged cationic lipids. Herein, "ionizable lipid" means an amine-containing lipid which can be easily protonated, and for example, it may be a lipid of which charge state changes depending on the surrounding pH. The ionizable lipid may be protonated (positively charged) at a pH below the pKa of a cationic lipid, and it may be substantially neutral at a pH over the pKa. In one example, the LNP may comprise a protonated ionizable lipid and/or an ionizable lipid showing neutrality. In some embodiments, the LNP has a pKa of 5 to 8, 5.5 to 7.5, 6 to 7, or 6.5 to 7. The pKa of the LNP is important for in vivo stability and release of the nucleic acid payload of the LNP. In some embodiments, the LNP having the foregoing pKa ranges may be safely delivered to a target organ (for example, the liver, lung, heart, spleen, as well as to tumors) and/or target cell (hepatocyte, LSEC, cardiac cell, cancer cell, etc.) in vivo, and after endocytosis, exhibit a positive charge to release the encapsulated payload through electrostatic interaction with an anionic protein of the endosome membrane.

The ionizable lipid is an ionizable compound having characteristics similar to lipids generally, and through electrostatic interaction with a nucleic acid (for example, an mRNA or gRNA of the disclosure), may play a role of encapsulating the nucleic acid within the LNP with high efficiency.

According to the type of the amine comprised in the ionizable lipid, (i) the nucleic acid encapsulation efficiency, (ii) PDI (polydispersity index) and/or (iii) the nucleic acid delivery efficiency to tissue and/or cells constituting an organ (for example, hepatocytes or liver sinusoidal endothelial cells in the liver) of the LNP may be different. In certain embodiments, the ionizable cationic lipid comprises from about 46 mol % to about 66 mol % of the total lipid present in the particle.

The LNP comprising an ionizable lipid comprising an amine may have one or more kinds of the following characteristics: (1) encapsulating a drug or biologic with high efficiency; (2) uniform size of prepared particles (or having a low PDI value); and/or (3) superior nucleic acid delivery efficiency to organs such as liver, lung, heart, spleen, as well as to tumors, and/or cells constituting such organs (for example, hepatocytes, LSEC, cardiac cells, cancer cells, etc.).

The lipid composition of lipid nanoparticles usually consists of an ionizable amino lipid, a helper lipid (usually a phospholipid), cholesterol, and a polyethylene glycol-lipid conjugate (PEG-lipid) to improve the colloidal stability in biological environments by reducing a specific absorption of plasma proteins and forming a hydration layer over the nanoparticles, and are formulated at typical mole ratios of 50:10:37-39:1.5-2.5, with variations made to adjust individual properties. As the PEG-lipid forms the surface lipid, the size of the LNP can be readily varied by varying the proportion of surface (PEG) lipid to the core (ionizable cationic) lipids. In some embodiments, the PEG-lipid can be varied from ~1 to 5 mol % to modify particle properties such as size, stability, and circulation time. In particular, the cationic lipid form plays a crucial role both in nucleic acid encapsulation through electrostatic interactions and intracellular release by disrupting endosomal membranes. The mRNA and gRNA (with targeting sequences) are encapsulated within the LNP by the ionic interactions they form with the positively charged cationic (or ionizable) lipid. Non-limiting examples of ionizable cationic lipid components utilized in the LNP of the disclosure are selected from DLin-MC3-DMA (heptatriaconta-6,9,28,31-tetraen-19-yl4-(dimethylamino)butanoate), DLin-KC2-DMA (2,2-dilinoleyl-4-(2-dimethylaminoethyl)-[1,3]-dioxolane), and TNT (1,3,5-triazinane-2,4,6-trione) and TT (N1,N3,N5-tris(2-aminoethyl)benzene-1,3,5-tricarboxamide). Non-limiting examples of helper lipids utilized in the LNP of the disclosure are selected from DSPC (1,2-distearoyl-sn-glycero-3-phosphocholine), POPC (2-Oleoyl-1-palmitoyl-sn-glycero-3-phosphocholine) and DOPE (1,2-Dioleoyl-sn-glycero-3-phosphoethanolamine). Cholesterol and PEG-DMG ((R)-2,3-bis(octadecyloxy)propyl-1-(methoxy polyethylene glycol 2000) carbamate) or PEG-DSG (1,2-Distearoyl-rac-glycero-3-methylpolyoxyethylene glycol 2000) are components utilized for the stability, circulation, and size of the LNP.

In other embodiments, the ionizable cationic lipid in the nucleic acid-lipid particles of the disclosure may comprise, for example, one or more ionizable cationic lipids wherein the ionizable cationic lipid is a dialkyl lipid. In another embodiment, the ionizable cationic lipid is a trialkyl lipid. In one particular embodiment, the ionizable cationic lipid is selected from the group consisting of 1,2-dilinoleyloxy-N,N-dimethylaminopropane (DLinDMA), 1,2-dilinolenyloxy-N,N-dimethylaminopropane (DLinDMA), 1,2-di-.gamma.-linolenyloxy-N,N-dimethylaminopropane (gamma.-DLinDMA), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), dilinoleylmethyl-3-dimethylaminopropionate (DLin-M-C2-DMA), or salts thereof and mixtures thereof. In a particular embodiment, the ionizable cationic lipid is selected from the group consisting of 1,2-dilinoleyloxy-N,N-dimethylaminopropane (DLinDMA), 1,2-dilinolenyloxy-N,N-dimethylaminopropane (DLenDMA), 1,2-di-.gamma.-linolenyloxy-N,N-dimethylaminopropane (.gamma.-DLenDMA; a salt thereof, or a mixture thereof. In some embodiments, the N/P ratio (nitrogen from the cationic/ionizable lipid and phosphate from the nucleic acid) is in the range of is about 3:1 to 7:1, or about 4:1 to 6:1, or is 3:1, or is 4:1, or is 5:1, or is 6:1, or is 7:1.

The phospholipid of the elements of the LNP according to one example plays a role of covering and protecting a core formed by interaction of the ionizable lipid and nucleic acid in the LNP, and may facilitate cell membrane permeation and endosomal escape during intracellular delivery of the nucleic acid by binding to the phospholipid bilayer of a target cell.

For the phospholipid, a phospholipid which can promote fusion of the LNP according to one example may be used without limitation, and for example, it may be one or more kinds selected from the group consisting of dioleoylphosphatidylethanolamine (DOPE), distearoylphosphatidylcholine (DSPC), palmitoyloleoylphosphatidylcholine (POPC), egg phosphatidylcholine (EPC), dioleoylphosphatidylcholine (DOPC), dipalmitoylphosphatidylcholine (DPPC), dioleoylphosphatidylglycerol (DOPG), dipalmitoylphosphatidylglycerol (DPPG), distearoylphosphatidylethanolamine (DSPE), phosphatidylethanolamine (PE), dipalmitoylphosphatidylethanolamine, 1,2-dioleoyl-sn-glycero-3-phosphoethanolamine, 1-palmitoyl-2-oleoyl-sn-glycero-3-phosphoethanolamine(POPE), 1-palmitoyl-2-dioleoyl-sn-glycero-3-phosphocholine(POPC), 1,2-dioleoyl-sn-glycero-3-[phospho-L-serine](DOPS), 1,2-dioleoyl-sn-glycero-3-[phospho-L-serine] and the like. In one example, the LNP comprising DOPE may be effective in mRNA delivery (excellent delivery efficacy).

The cholesterol of the elements of the LNP according to one example may provide morphological rigidity to lipid filling in the LNP and be dispersed in the core and surface of the nanoparticle to improve the stability of the nanoparticle.

Herein, "lipid-PEG (polyethyleneglycol) conjugate", "lipid-PEG", "PEG-lipid", "PEG-lipid", or "lipid-PEG" refers to a form in which lipid and PEG are conjugated, and means a lipid in which a polyethylene glycol (PEG) polymer which is a hydrophilic polymer is bound to one end. The lipid-PEG conjugate contributes to the particle stability in serum of the nanoparticle within the LNP, and plays a role of preventing aggregation between nanoparticles. In addition, the lipid-PEG conjugate may protect nucleic acids from degrading enzyme during in vivo delivery of the nucleic acids and enhance the stability of nucleic acids in vivo and increase the half-life of the drug or biologic encapsulated in the nanoparticle. Examples of PEG-lipid conjugates include, but are not limited to, PEG-DAG conjugates, PEG-DAA conjugates, and mixtures thereof. In certain embodiments, the PEG-lipid conjugate is selected from the group consisting of a PEG-diacylglycerol (PEG-DAG) conjugate, a PEG-dialkyloxypropyl (PEG-DAA) conjugate, a PEG-phospholipid conjugate, a PEG-ceramide (PEG-Cer) conjugate, and a mixture thereof. In certain embodiments, the PEG-lipid conjugate is a PEG-DAA conjugate. In certain embodiments, the PEG-DAA conjugate in the lipid particle may comprise a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl (Cis) conjugate, or mixtures thereof. In certain embodiments, wherein the PEG-DAA conjugate is a PEG-dimyristyloxypropyl ($C_{14}$) conjugate. In other embodiments, the lipid-PEG conjugate may be PEG bound to phospholipid such as phosphatidylethanolamine (PEG-PE), PEG conjugated to ceramide (PEG-CER, ceramide-PEG conjugate, ceramide-PEG, cholesterol or PEG conjugated to derivative thereof, PEG-c-DOMG, PEG-DMG, PEG-DLPE, PEG-DMPE, PEG-DPPC, PEG-DSPE(DSPE-PEG), and a mixture thereof, and for example, may be C16-PEG2000 ceramide (N-palmitoyl-sphingosine-1-{succinyl[methoxy(polyethylene glycol)2000]}), DMG-PEG 2000, 14:0 PEG2000 PE.

In certain embodiments, the conjugated lipid that inhibits aggregation of particles comprises from about 0.5 mol % to about 3 mol % of the total lipid present in the particle.

In one example, the average molecular weight of the lipid-PEG conjugate may be 100 daltons to 10,000 daltons, 200 daltons to 8,000 daltons, 500 daltons to 5,000 daltons, 1,000 daltons to 3,000 daltons, 1,000 daltons to 2,600 daltons, 1,500 daltons to 2,600 daltons, 1,500 daltons to 2,500 daltons, 2,000 daltons to 2,600 daltons, 2,000 daltons to 2,500 daltons, or 2,000 daltons.

For the lipid in the lipid-PEG conjugate, any lipid capable of binding to polyethyleneglycol may be used without limitation, and the phospholipid and/or cholesterol which are other elements of the LNP may be also used. Specifically, the lipid in the lipid-PEG conjugate may be ceramide, dimyristoylglycerol (DMG), succinoyl-diacylglycerol (s-DAG), distearoylphosphatidylcholine (DSPC), distearoylphosphatidylethanolamine (DSPE), or cholesterol, but not limited thereto.

In the lipid-PEG conjugate, the PEG may be directly conjugated to the lipid or linked to the lipid via a linker moiety. Any linker moiety suitable for binding PEG to the lipid may be used, and for example, includes an ester-free linker moiety and an ester-containing linker moiety. The ester-free linker moiety includes not only amido (—C(O)NH—), amino (—NR—), carbonyl (—C(O)—), carbamate (—NHC(O)O—), urea (—NHC(O)NH—), disulfide (—S—S—), ether (—O—), succinyl (—(O)CCH2CH2C(O)—), succinamidyl (—NHC(O)CH2CH2C(O)NH—), ether, disulfide but also combinations thereof (for example, a linker containing both a carbamate linker moiety and an amido linker moiety), but not limited thereto. The ester-containing linker moiety includes for example, carbonate (—OC(O)O—), succinoyl, phosphate ester (—O—(O)POH—O—), sulfonate ester, and combinations thereof, but not limited thereto.

In certain embodiments, the nucleic acid-lipid particle has a total lipid:gRNA mass ratio of from about 5:1 to about 15:1. In some embodiments, the weight ratio of the ionizable lipid and nucleic acid comprised in the LNP may be 1 to 20:1, 1 to 15:1, 1 to 10:1, 5 to 20:1, 5 to 15:1, 5 to 10:1, 7.5 to 20:1, 7.5 to 15:1, or 7.5 to 10:1.

In some embodiments, the LNP may comprise the ionizable lipid of 20 to 50 parts by weight, phospholipid of 10 to 30 parts by weight, cholesterol of 20 to 60 parts by weight (or 20 to 60 parts by weight), and lipid-PEG conjugate of 0.1 to 10 parts by weight (or 0.25 to 10 parts by weight, 0.5 to 5 parts by weight). The LNP may comprise the ionizable lipid of 20 to 50% by weight, phospholipid of 10 to 30% by weight, cholesterol of 20 to 60% by weight (or 30 to 60% by weight), and lipid-PEG conjugate of 0.1 to 10% by weight (or 0.25 to 10% by weight, 0.5 to 5% by weight) based on the total nanoparticle weight. In other example, the LNP may comprise the ionizable lipid of 25 to 50% by weight, phospholipid of 10 to 20% by weight, cholesterol of 35 to 55% by weight, and lipid-PEG conjugate of 0.1 to 10% by weight (or 0.25 to 10% by weight, 0.5 to 5% by weight), based on the total nanoparticle weight.

In some embodiments, the approach to formulating the LNP of the disclosure (described more fully in the examples) is to dissolve lipids in an organic solvent such as ethanol, which is then mixed through a micromixer with the nucleic acid dissolved in an acidic buffer (usually pH 4). At this pH the ionizable cationic lipid is positively charged and interacts with the negatively-charged nucleic acid polymers. The resulting nanostructures containing the nucleic acids are then converted to neutral LNP when dialyzed against a neutral buffer during the ethanol removal step. The LNP formed by this have a distinct electron-dense nanostructured core where the ionizable cationic lipids are organized into inverted micelles around the encapsulated mRNA molecules, as opposed to the traditional bilayer liposomal structures.

In some embodiments, the LNP may have an average diameter of 20 nm to 200 nm, 20 nm to 180 nm, 20 nm to 170 nm, 20 nm to 150 nm, 20 nm to 120 nm, 20 nm to 100 nm, 20 nm to 90 nm, 30 nm to 200 nm, 30 to 180 nm, 30 nm to 170 nm, 30 nm to 150 nm, 30 nm to 120 nm, 30 nm to 100 nm, 30 nm to 90 nm, 40 nm to 200 nm, 40 to 180 nm, 40 nm to 170 nm, 40 nm to 150 nm, 40 nm to 120 nm, 40 nm to 100 nm, 40 nm to 90 nm, 40 nm to 80 nm, 40 nm to 70 nm, 50 nm to 200 nm, 50 to 180 nm, 50 nm to 170 nm, 50 nm to 150 nm, 50 nm to 120 nm, 50 nm to 100 nm, 50 nm to 90 nm, 60 nm to 200 nm, 60 to 180 nm, 60 nm to 170 nm, 60 nm to 150 nm, 60 nm to 120 nm, 60 nm to 100 nm, 60 nm to 90 nm, 70 nm to 200 nm, 70 to 180 nm, 70 nm to 170 nm, 70 nm to 150 nm, 70 nm to 120 nm, 70 nm to 100 nm, 70 nm to 90 nm, 80 nm to 200 nm, 80 to 180 nm, 80 nm to 170 nm, 80 nm to 150 nm, 80 nm to 120 nm, 80 nm to 100 nm, 80 nm to 90 nm, 90 nm to 200 nm, 90 to 180 nm, 90 nm to 170 nm, 90 nm to 150 nm, 90 nm to 120 nm, or 90 nm to 100 nm. The LNP may be sized for easy introduction into organs or tissues, including but not limited to liver, lung, heart, spleen, as well as to tumors. When the size of the LNP is smaller than the above range, it is difficult to maintain stability as the surface area of the LNP is excessively increased, and thus delivery to the target tissue and/or therapeutic effect may be reduced. The LNP may specifically target liver tissue. The LNP may imitate metabolic behaviors of natural lipoproteins very similarly, and may be usefully applied for the lipid metabolism process by the liver and therapeutic mechanism through this. During the drug or biologic delivery to hepatocytes or and/or LSEC (liver sinusoidal endothelial cells), the diameter of the fenestrae leading from the sinusoidal lumen to the hepatocytes and LSEC is about 140 nm in mammals and about 100 nm in humans, so LNPs having a diameter in the above ranges may have superior delivery efficiency to hepatocytes and LSEC compared to LNP having the diameter outside the above range.

According to some embodiments, the LNP comprised in the composition for nucleic acid delivery into target cells may comprise the ionizable lipid:phospholipid:cholesterol: lipid-PEG conjugate in the range described above or at a molar ratio of 20 to 50:10 to 30:30 to 60:0.5 to 5, at a molar ratio of 25 to 45:10 to 25:40 to 50:0.5 to 3, at a molar ratio of 25 to 45:10 to 20:40 to 55:0.5 to 3, or at a molar ratio of 25 to 45:10 to 20:40 to 55:1.0 to 1.5. The LNP comprising components at a molar ratio in the above range may have excellent delivery efficiency specific to cells of target organs.

The LNP according to some embodiments exhibits a positive charge under the acidic pH condition by showing a pKa of 5 to 8, 5.5 to 7.5, 6 to 7, or 6.5 to 7, and may encapsulate a nucleic acid with high efficiency by easily forming a complex with a nucleic acid through electrostatic interaction with a therapeutic agent such as a nucleic acid showing a negative charge, and it may be usefully used as a composition for intracellular or in vivo delivery of a drug or biologic (for example, nucleic acid or protein). Herein, "encapsulation" refers to encapsulating a delivery substance for surrounding and embedding it in vivo efficiently, and the encapsulation efficiency (encapsulation efficiency) mean the content of the drug or biologic encapsulated in the LNP for the total drug or biologic content used for preparation.

The encapsulation efficiency of the nucleic acids of the composition in the LNP may be 70% or more, 75% or more, 80% or more, 85% or more, 90% or more, 91% or more, 92% or more, 94% or more, or 95% or more. In other embodiments, the encapsulation efficiency of the nucleic acids of the composition in the LNP is over 80% to 99% or less, over 80% to 97% or less, over 80% to 95% or less, 85% or more to 95% or less, 87% or more to 95% or less, 90% or more to 95% or less, 91% or more to 95% or less, 91% or more to 94% or less, over 91% to 95% or less, 92% or more to 99% or less, 92% or more to 97% or less, or 92% or more to 95% or less. As used herein, "encapsulation efficiency" means the percentage of LNP particles containing the nucleic acids to be incorporated within the LNP. In some embodiments, the mRNA encoding the dXR and a gRNA with a targeting sequence to the target nucleic acid of the disclosure are fully encapsulated in the nucleic acid-lipid particle.

The target organs to which a nucleic acid is delivered by the LNP include, but are not limited to the liver, lung, heart, spleen, as well as to tumors. The LNP according to one embodiment is liver tissue-specific and has excellent biocompatibility and can deliver the nucleic acids of a dXR: gRNA system composition with high efficiency, and thus it can be usefully used in related technical fields such as lipid nanoparticle-mediated gene therapy. In a particular embodiment, the target cell to which the nucleic acids of the dXR:gRNA system are delivered by the LNP according to one example may be a hepatocyte and/or LSEC in vivo. In other embodiments, the disclosure provides LNP formulated for delivery of the nucleic acids of the embodiments to cells ex vivo.

Accordingly, in certain embodiments, the disclosure encompasses gRNA molecules that target the expression of one or more target nucleic acids, nucleic acid-lipid particles comprising an mRNA encoding a dXR fusion protein of the disclosure and one or more of the gRNAs that target the expression of one or more target nucleic acids, nucleic acid-lipid particles comprising one or more (e.g., a cocktail) of the gRNAs, and methods of delivering and/or administering the nucleic acid-lipid particles. The gRNA molecules may be delivered concurrently with or sequentially with a mRNA molecule that encodes the dXR fusion protein, thereby delivering components to utilize the system to treat disease in a human in need of such treatment, for example, a human in need of treatment or prevention of a disorder. In certain embodiments the mRNA that encodes the dXR fusion protein and gRNA may be present in the same nucleic acid-lipid particle, or they may be present in different nucleic acid-lipid particles.

The disclosure also provides a pharmaceutical composition comprising one or more (e.g., a cocktail) of the gRNA targeting different sequences, together with one or more of the dXR described herein, and a pharmaceutically acceptable carrier. With respect to formulations comprising an dXR:gRNA cocktail, the different types of gRNA species present in the cocktail (e.g., gRNA with different targeting sequences) may be co-encapsulated in the same particle, or each type of gRNA species present in the cocktail may be encapsulated in a separate particle. The LNP cocktail may be formulated in the particles described herein using a mixture of two, three or more individual gRNA (each having a unique targeting sequence) at identical, similar, or different concentrations or molar ratios.

In one embodiment, a cocktail of mRNA encoding the fusion protein and two or more gRNA with different targeting sequences to the target nucleic acid is formulated using identical, similar, or different concentrations or molar ratios of each gRNA species, and the different types of gRNA are co-encapsulated in the same particle. In another embodiment, each type of gRNA species present in the cocktail is encapsulated in different particles at identical, similar, or different gRNA concentrations or molar ratios, and the particles thus formed (each containing a different gRNA payload) are administered separately (e.g., at different times in accordance with a therapeutic regimen), or are combined and administered together as a single unit dose (e.g., with a pharmaceutically acceptable carrier). The particles described herein are serum-stable, are resistant to nuclease degradation, and are substantially non-toxic to mammals such as humans.

In certain embodiments, the nucleic acid-lipid particle has an electron dense core.

In some embodiments, the disclosure provides nucleic acid-lipid particles comprising: (a) one or more (e.g., a cocktail) of mRNA encoding the dXR and a gRNA with a targeting sequence to the target nucleic acid described herein; (b) one or more ionizable cationic lipids or salts thereof comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle.

In one embodiment, the nucleic acid-lipid particle comprises: (a) one or more (e.g., a cocktail) mRNA encoding the dXR and a gRNA with a targeting sequence to the target nucleic acid described herein; (b) a ionizable cationic lipid or a salt thereof comprising from about 52 mol % to about 62 mol % of the total lipid present in the particle; (c) a mixture of a phospholipid and cholesterol or a derivative thereof comprising from about 36 mol % to about 47 mol % of the total lipid present in the particle; and (d) a PEG-lipid conjugate comprising from about 1 mol % to about 2 mol % of the total lipid present in the particle. In one particular embodiment, the formulation is a four-component system comprising about 1.4 mol % PEG-lipid conjugate (e.g., PEG2000-C-DMA), about 57.1 mol % ionizable cationic lipid (e.g., DLin-K-C2-DMA) or a salt thereof, about 7.1 mol % DPPC (or DSPC), and about 34.3 mol % cholesterol (or derivative thereof).

In another embodiment, the nucleic acid-lipid particle comprises: (a) one or more (e.g., a cocktail) mRNA encoding the dXR and a gRNA with a targeting sequence to the target nucleic acid described herein; (b) a ionizable cationic lipid or a salt thereof comprising from about 46.5 mol % to about 66.5 mol % of the total lipid present in the particle; (c) cholesterol or a derivative thereof comprising from about 31.5 mol % to about 42.5 mol % of the total lipid present in the particle; and (d) a PEG-lipid conjugate comprising from about 1 mol % to about 2 mol % of the total lipid present in the particle. In one particular embodiment, the formulation is a three-component system which is phospholipid-free and comprises about 1.5 mol % PEG-lipid conjugate (e.g., PEG2000-C-DMA), about 61.5 mol % ionizable cationic lipid (e.g., DLin-K-C2-DMA) or a salt thereof, and about 36.9 mol % cholesterol (or derivative thereof).

Additional formulations are described in PCT Publication No. WO 09/127060 and published US patent application publication numbers US 2011/0071208 A1 and US 2011/0076335 A1, the disclosures of which are herein incorporated by reference in their entirety.

In other embodiments, the present disclosure provides nucleic acid-lipid particles comprising: (a) one or more (e.g., a cocktail) gRNA molecules described herein; (b) one or more ionizable lipids or salts thereof comprising from about 2 mol % to about 50 mol % of the total lipid present in the particle; (c) one or more non-cationic lipids comprising from about 5 mol % to about 90 mol % of the total lipid present in the particle; and (d) one or more conjugated lipids that inhibit aggregation of particles comprising from about 0.5 mol % to about 20 mol % of the total lipid present in the particle.

In one aspect of this embodiment, the nucleic acid-lipid particle comprises: (a) one or more (e.g., a cocktail) mRNA encoding the dXR and a gRNA with a targeting sequence to the target nucleic acid described herein; (b) a ionizable cationic lipid or a salt thereof comprising from about 30 mol % to about 50 mol % of the total lipid present in the particle; (c) a mixture of a phospholipid and cholesterol or a derivative thereof comprising from about 47 mol % to about 69 mol % of the total lipid present in the particle; and (d) a PEG-lipid conjugate comprising from about 1 mol % to about 3 mol % of the total lipid present in the particle. In one particular embodiment, the formulation is a four-component system which comprises about 2 mol % PEG-lipid conjugate (e.g., PEG2000-C-DMA), about 40 mol % ionizable cationic lipid (e.g., DLin-K-C2-DMA) or a salt thereof, about 10 mol % DPPC (or DSPC), and about 48 mol % cholesterol (or derivative thereof).

In further embodiments, the present disclosure provides nucleic acid-lipid particles comprising: (a) one or more (e.g., a cocktail) mRNA encoding the dXR and a gRNA with a targeting sequence to the target nucleic acid described herein; (b) one or more ionizable cationic lipids or salts thereof comprising from about 50 mol % to about 65 mol % of the total lipid present in the particle; (c) one or more non-cationic lipids comprising from about 25 mol % to about 45 mol % of the total lipid present in the particle; and (d) one or more conjugated lipids that inhibit aggregation of particles comprising from about 5 mol % to about 10 mol % of the total lipid present in the particle.

In another embodiment, the nucleic acid-lipid particle comprises: (a) one or more (e.g., a cocktail) mRNA encoding the dXR and a gRNA with a targeting sequence to the target nucleic acid described herein; (b) a ionizable cationic lipid or a salt thereof comprising from about 50 mol % to about 60 mol % of the total lipid present in the particle; (c) a mixture of a phospholipid and cholesterol or a derivative thereof comprising from about 35 mol % to about 45 mol % of the total lipid present in the particle; and (d) a PEG-lipid conjugate comprising from about 5 mol % to about 10 mol % of the total lipid present in the particle.

In certain embodiments, the non-cationic lipid mixture in the formulation comprises: (i) a phospholipid of from about 5 mol % to about 10 mol % of the total lipid present in the particle; and (ii) cholesterol or a derivative thereof of from about 25 mol % to about 35 mol % of the total lipid present in the particle. In one particular embodiment, the formulation is a four-component system which comprises about 7 mol % PEG-lipid conjugate (e.g., PEG750-C-DMA), about 54 mol % ionizable cationic lipid (e.g., DLin-K-C2-DMA) or a salt thereof, about 7 mol % DPPC (or DSPC), and about 32 mol % cholesterol (or derivative thereof).

In another embodiment, the nucleic acid-lipid particle comprises: (a) one or more (e.g., a cocktail) mRNA encoding the dXR and a gRNA with a targeting sequence to the target nucleic acid described herein; (b) a ionizable cationic lipid or a salt thereof comprising from about 55 mol % to about 65 mol % of the total lipid present in the particle; (c) cholesterol or a derivative thereof comprising from about 30 mol % to about 40 mol % of the total lipid present in the particle; and (d) a PEG-lipid conjugate comprising from about 5 mol % to about 10 mol % of the total lipid present in the particle. In one particular embodiment, the formulation is a three-component system which is phospholipid-free and comprises about 7 mol % PEG-lipid conjugate (e.g., PEG750-C-DMA), about 58 mol % ionizable cationic lipid (e.g., DLin-K-C2-DMA) or a salt thereof, and about 35 mol % cholesterol (or derivative thereof).

In certain embodiments of the disclosure, the nucleic acid-lipid particle comprises: (a) one or more (e.g., a cocktail) mRNA encoding the dXR and a gRNA with a targeting sequence to the target nucleic acid described herein; (b) a ionizable cationic lipid or a salt thereof comprising from about 48 mol % to about 62 mol % of the total lipid present in the particle; (c) a mixture of a phospholipid and cholesterol or a derivative thereof, wherein the phospholipid comprises about 7 mol % to about 17 mol % of the total lipid present in the particle, and wherein the cholesterol or derivative thereof comprises about 25 mol % to about 40 mol % of the total lipid present in the particle; and (d) a PEG-lipid conjugate comprising from about 0.5 mol % to about 3.0 mol % of the total lipid present in the particle.

VIII. Applications

The fusion proteins, gRNA, nucleic acids encoding the fusion proteins and variants thereof provided herein, as well as vectors encoding such components, particle systems for the delivery of the gene repressor systems, or LNP comprising nucleic acids are useful for various applications, including therapeutics, diagnostics, and research.

Provided herein are methods of repression of transcription of a target gene encoded by a target nucleic acid in a cell, comprising contacting the target nucleic acid with a dXR and a gRNA with a targeting sequence that is complementary to the target nucleic acid. In some embodiments of the method, the repressor system is provided to the cells as a dXR:gRNA RNP complex, embodiments of which have been described supra, wherein the contacting results in repression or silencing of transcription. In other embodiments of the method, the repressor system is provided to the cells as a nucleic acid or a vector comprising the nucleic acids encoding the dXR and gRNA, or as a lipid nanoparticle (LNP) comprising mRNA encoding the dXR and gRNA components, wherein the contacting results in repression or silencing of transcription of the target nucleic acid upon expression of the dXR and gRNA and binding of the resulting RNP complex to the target nucleic acid. In some embodiments, the vector is an AAV encoding the dXR and gRNA components. In other embodiments of the method, the vector is a virus-like particle, an XDP comprising multiple dXR:gRNA RNPs, wherein the contacting of the target nucleic acid results in repression or silencing of transcription of the gene proximal to the binding location of the RNP of the target nucleic acid.

In some embodiments of the method of repressing expression of a target nucleic acid in a cell, the repressor system is provided to the cells encapsidated in a population of lipid nanoparticles (LNP), described more fully, above. An LNP represents a particle made from lipids, wherein the nucleic acids of the system are fully encapsulated within the lipid. In certain instances, LNP are extremely useful for systemic applications, as they can exhibit extended circulation lifetimes following intravenous (i.v.) injection, they can accumulate at distal sites within the subject, and when used to encapsidate the dXR:gRNA systems of the embodiments, they can mediate repression or silencing of target gene expression at these distal sites. Preferably, these LNP compositions would encapsulate the nucleic acids of the system with high-efficiency, have high drug:lipid ratios, protect the encapsulated nucleic acid from degradation and clearance in serum, be suitable for systemic delivery, and provide intracellular delivery of the encapsulated nucleic acid. In some embodiments of the method, the repressor system is provided to the cells as a first and a second lipid nanoparticle (LNP) wherein the first LNP encapsidates mRNA encoding the dXR fusion protein of any of the embodiments described herein and the second LNP encapsidates the gRNA of any of the embodiments described herein, wherein the contacting of the cell and uptake of the LNP results in expression of the dXR fusion protein and complexing of the dXR and gRNA as an RNP, wherein upon binding of the resulting RNP complex to the target nucleic acid, repression or silencing of transcription of the target nucleic acid occurs. In other embodiments, the repressor system is provided to the cells as a population of LNPs wherein the LNP encapsidates both the mRNA encoding the dXR fusion protein of any of the embodiments described herein and a gRNA of any of the embodiments described herein, wherein the contacting of the cells and the uptake of the LNP results in expression of the dXR fusion protein and complexing of the RNP repression, wherein upon binding of the resulting RNP complex to the target nucleic acid, repression or silencing of transcription of the target nucleic occurs.

In some embodiments of the method, upon binding of the dXR:gRNA RNP to the target nucleic acid, transcription of the gene in the population of cells is repressed by at least about 10%, at least about 20%, at least about 30%, at least about 40%, at least about 50%, at least about 60%, at least about 70%, at least about 75%, at least about 80%, at least about 85%, at least about 90%, at least about 95%, or at least 99% greater compared to the repression effected by an RNP comprising a comparable guide RNA and a catalytically dead CasX variant without a repressor domain, when assessed in an in vitro assay. In other embodiments, transcription of the gene in the population of cells is repressed by at least about 10% to about 90%, or at least 20% to about 80%, or at least about 30% to about 60% compared to the repression effected by an RNP comprising a comparable guide RNA and a catalytically dead CasX variant without a repressor domain, when assessed in an in vitro assay. In some embodiments of the method, the repression of transcription in the populations of cells is sustained for at least about 8 hours, at least about 1 day, at least about 1 week, at least about 2 weeks, at least about 3 weeks, at least about 1 month, at least about 2 months, or at least about 6 months or longer. Exemplary assays to measure repression are described herein, including the Examples, below.

In some cases, off-target methylation or off-target transcription repression by the dXR:gRNA RNP is less than about 10%, less than about 9%, less than about 8%, less than about 7%, less than about 6%, less than about 5%, less than about 4%, less than about 3%, less than about 2%, or less than about 1% in the cells genome-wide.

In some embodiments of the method of repressing a target nucleic acid in a cell, the gRNA scaffold utilized in the dXR:gRNA systems of the disclosure is selected from the group of sequences consisting of SEQ ID NOS: 2238-2331, 57544-57589, and 59352, set forth in Table 2, or a sequence having at least about 80%, at least about 90%, at least about 95%, at least about 95%, at least about 96%, at least about 97%, at least about 98%, at least about 99% sequence identity thereto, and the gRNA further comprises a targeting sequence that is complementary to the target nucleic acid to be repressed. In some embodiments of the method, the gRNA scaffold utilized in the dXR:gRNA systems of the disclosure comprises one or more chemical modifications. In some embodiments of the method, the dCasX variant is a sequence of SEQ ID NOS: 17-36 and 59353-59358 as set forth in Table 4, or a sequence having at least about 80%, at least about 90%, at least about 95%, at least about 95%, at least about 96%, at least about 97%, at least about 98%, at least about 99% sequence identity thereto, and is linked to a first repressor domain, a first and a second repressor domain, a first, second and third repressor domain, or a first, second, third, and fourth repressor domains. In some embodiments of the method, the first domain linked to the dCasX as a fusion protein (or encoded to be expressed as a fusion protein) is a KRAB domain of any of the embodiments described herein. In some embodiments of the method, the first domain linked to the dCasX as a fusion protein is a KRAB domain sequence and the second repressor domain is a DNMT3A catalytic domain sequence. In some embodiments of the method, the first domain linked to the dCasX as a fusion protein is a KRAB domain sequence, the second repressor domain is a DNMT3A catalytic domain sequence, and the third repressor is a DNMT3L interaction domain sequence. In some embodiments of the method, the first domain linked to the dCasX as a fusion protein is a KRAB domain sequence, the second repressor domain is a DNMT3A catalytic domain sequence, the third repressor is a DNMT3L interaction domain sequence, and the fourth domain in a DNMT3A ADD domain. In some embodiments of the foregoing, KRAB domain is selected from the group consisting of SEQ ID NOS: 889-2100 and 2332-33239, or a sequence having at least about 80%, at least about 90%, at least about 95%, at least about 95%, at least about 96%, at least about 97%, at least about 98%, at least about 99% sequence identity thereto. In some embodiments of the method of repressing a target nucleic acid in a cell, the KRAB domain comprises one or more motifs selected from the group consisting of a) $PX_1X_2X_3X_4X_5X_6EX_7$, wherein $X_1$ is A, D, E, or N, $X_2$ is L or V, $X_3$ is I or V, $X_4$ is S, T, or F, $X_5$ is H, K, L, Q, R or W, $X_6$ is L or M, and $X_7$ is G, K, Q, or R; b) $X_1X_2X_3X_4GX_5X_6X_7X_8X_9$, wherein $X_1$ is L or V, $X_2$ is A, G, L, T or V, $X_3$ is A, F, or S, $X_4$ is L or V, $X_5$ is C, F, H, I, L or Y, $X_6$ is A, C, P, Q, or S, $X_7$ is A, F, G, I, S, or V, $X_8$ is A, P, S, or T, and $X_9$ is K or R; c) $QX_1X_2LYRX_3VMX_4$ (SEQ ID NO: 59345), wherein $X_1$ is K or R, $X_2$ is A, D, E, G, N, S, or T, $X_3$ is D, E, or S, and $X_4$ is L or R; d) $X_1X_2X_3FX_4DVX_5X_6X_7FX_8X_9X_{10}X_{11}$ (SEQ ID NO: 59346), wherein $X_1$ is A, L, P, or S, $X_2$ is L or V, $X_3$ is S or T, $X_4$ is A, E, G, K, or R, $X_5$ is A or T, $X_6$ is I or V, $X_7$ is D, E, N, or Y, $X_8$ is S or T, $X_9$ is E, P, Q, R, or W, $X_{10}$ is E or N, and $X_{11}$ is E or Q; e) $X_1X_2X_3PX_4X_5X_6X_7X_8X_9X_{10}$, wherein $X_1$ is E, G, or R, $X_2$ is E or K, $X_3$ is A, D, or E, $X_4$ is C or W, $X_5$ is I, K, L, M, T, or V, $X_6$ is I, L, P, or V, $X_7$ is D, E, K, or V, $X_8$ is E, G, K, P, or R, $X_9$ is A, D, R, G, K, Q, or V, and $X_{10}$ is D, E, G, I, L, R, S, or V; f) $LYX_1X_2VMX_3EX_4X_5X_6X_7X_8X_9X_{10}$ (SEQ ID NO: 59348), wherein $X_1$ is K or R, $X_2$ is D or E, $X_3$ is L, Q, or R, $X_4$ is N or T, $X_5$ is F or Y, $X_6$ is A, E, G, Q, R, or S, $X_7$ is H, L, or N, $X_8$ is L or V, $X_9$ is A, G, I, L, T, or V, and $X_{10}$ is A, F, or S; g) $FX_1DVX_2X_3X_4FX_5X_6X_7EWX_8$ (SEQ ID NO: 59349), wherein $X_1$ is A, E, G, K, or R, $X_2$ is A, S, or T, $X_3$ is I or V, $X_4$ is D, E, N, or Y, $X_5$ is S or T, $X_6$ is E, L, P, Q, R, or W, $X_7$ is D or E, and $X_8$ is A, E, G, Q, or R; h) $X_1PX_2X_3X_4X_5$ $X_6LEX_7X_8X_9X_{10}X_{11}X_{12}$, wherein $X_1$ is K or R, $X_2$ is A, D, E, or N, $X_3$ is I, L, M, or V, $X_4$ is I or V, $X_5$ is F, S, or T, $X_6$ is H, K, L, Q, R, or W, $X_7$ is K, Q, or R, $X_8$ is E, G, or R, $X_9$ is D, E, or K, $X_{10}$ is A, D, or E, $X_{11}$ is L or P, and $X_{12}$ is C or W; or i) $X_1LX_2X_3X_4QX_5X_6$, wherein $X_1$ is C, H, L, Q, or W, $X_2$ is D, G, N, R, or S, $X_3$ is L, P, S, or T, $X_4$ is A, S, or T, $X_5$ is K or R, and $X_6$ is A, D, E, K, N, S, or T, and the KRAB domain comprises a sequence selected from the group consisting of SEQ ID NOS: 57746-59342, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In some embodiments of the method, the DNMT3A catalytic domain comprises a sequence selected from the group consisting of SEQ ID NOS: 33625-57543 and 59450, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In some embodiments of the method, the DNMT3L interaction domain comprises a sequence of SEQ ID NO: 59625, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto. In some embodiments of the method, the DNMT3A ADD domain comprises a sequence of SEQ ID NO: 59452, or a sequence having at least about 70%, at least about 80%, at least about 85%, at least about 90% at least about 91%, at least about 92%, at least about 93% at least about 94% at least about 95%, at least about 96%, at least about 97%, at least about 98%, or at least about 99% identity thereto.

In some embodiments of the method of repressing a target nucleic acid in a cell, the method further comprises inclusion of a second gRNA, or a nucleic acid encoding the second gNA, wherein the second gNA has a targeting sequence complementary to a different portion of the target nucleic acid sequence and is capable of forming a ribonuclear protein complex (RNP) with the dXR fusion protein.

In some embodiments of the method of repressing a target nucleic acid in a cell, the repression occurs in vitro, outside of a cell, in a cell-free system. In some embodiments, the repression occurs in vitro, inside of a cell, for example in a cell culture system. In some embodiments, the repression occurs in vivo inside of a cell, for example in a cell in an organism. In some embodiments, the cell is a eukaryotic cell. Exemplary eukaryotic cells may include a mammalian cell, a rodent cell, a mouse cell, a rat cell, a pig cell, a dog cell, a primate cell, and a non-human primate cell. In some embodiments, the cell is a human cell. In some embodiments, the cell is an embryonic stem cell, an induced pluripotent stem cell, a germ cell, a fibroblast, an oligodendrocyte, a glial cell, a hematopoietic stem cell, a neuron progenitor cell, a neuron, an astrocyte, a muscle cell, a bone cell, a hepatocyte, a pancreatic cell, a retinal cell, a cancer cell, a T-cell, a B-cell, an NK cell, a fetal cardiomyocyte, a myofibroblast, a mesenchymal stem cell, an autotransplanted expanded cardiomyocyte, an adipocyte, a totipotent cell, a pluripotent cell, a blood stem cell, a myoblast, a bone marrow cell, a mesenchymal cell, a parenchymal cell, an epithelial cell, an endothelial cell, a mesothelial cell, fibroblasts, osteoblasts, chondrocytes, a hematopoietic stem cell, a bone-marrow derived progenitor cell, a myocardial cell, a skeletal cell, a fetal cell, an undifferentiated cell, a multipotent progenitor cell, a unipotent progenitor cell, a monocyte, a cardiac myoblast, a skeletal myoblast, a macrophage, a capillary endothelial cell, a xenogeneic cell, an allogenic cell, or a post-natal stem cell. The cell can be in a subject. In some embodiments, repression occurs in the subject having a mutation in an allele of a gene wherein the mutation causes a disease or disorder in the subject. In some embodiments, repression reduces or silence transcription of an allele of a gene causing a disease or disorder in the subject, wherein the subject is selected from the group consisting of mouse, rat, pig, non-human primate, and human. In some embodiments, repression occurs in vitro inside of the cell prior to introducing the cell into a subject. In some embodiments, the cell is autologous or allogeneic with respect to the subject.

Methods of introducing a nucleic acid (e.g., nucleic acids encoding a dXR:gRNA system, or variants thereof as described herein) into a cell in vitro are known in the art, and any convenient method can be used to introduce a nucleic acid into a cell. Suitable methods include viral infection, transfection, lipofection, electroporation, calcium phosphate precipitation, polyethyleneimine (PEI)-mediated transfection, DEAE-dextran mediated transfection, liposome-mediated transfection, particle gun technology, nucleofection, electroporation, LNP transfection, direct addition by cell penetrating dXR proteins that are fused to or recruit donor DNA, cell squeezing, calcium phosphate precipitation, direct microinjection, nanoparticle-mediated nucleic acid delivery, and the like. Nucleic acids may be provided to the cells using well-developed transfection techniques, and the commercially available TransMessenger® reagents from Qiagen, Stemfect™ RNA Transfection Kit from Stemgent, and TransIT®-mRNA Transfection Kit from Mirus Bio LLC, Lonza nucleofection, Maxagen electroporation and the like. In some embodiments, vectors may be provided directly to a target host cell such that the vectors are taken up by the cells. Introducing recombinant expression vectors into cells can occur in any suitable culture media and under any suitable culture conditions that promote the survival of the cells.

A dXR protein or an mRNA encoding the dXR of the disclosure may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids or nucleotides (as applicable) may be substituted with unnatural amino acids or nucleotides. The particular sequence and the manner of preparation will be determined by convenience, economics, purity required, and the like.

The dXR fusion protein may also be prepared by recombinantly producing a polynucleotide sequence coding for the dXR of any of the embodiments described herein and incorporating the encoding gene into an expression vector appropriate for a host cell. For production of the encoded dXR of any of the embodiments described herein, the methods include transforming an appropriate host cell with an expression vector comprising the encoding polynucleotide, and culturing the host cell under conditions causing or permitting the resulting dXR of any of the embodiments described herein to be expressed or transcribed in the transformed host cell, thereby producing the dXR, which are recovered by methods described herein or by standard purification methods known in the art or as described in the Examples. Standard recombinant techniques in molecular biology are used to make the polynucleotides and expression vectors of the present disclosure.

A dXR protein of the disclosure may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 50% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a dXR polypeptide, or a dXR fusion polypeptide, of the present disclosure is at least 80% pure, at least 85% pure, at least 90% pure, at least 95% pure, at least 98% pure, or at least 99% pure (e.g., free of contaminants, non-dXR proteins or other macromolecules, etc.).

In some embodiments, to induce repression of transcription of a target nucleic acid (e.g., genomic DNA) in an in vitro cell, the dXR and gRNA of the present disclosure, whether they be introduced as nucleic acids (including encapsidated within an LNP or within an AAV) or an RNP, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 7 days, e.g., every 1.5 days, every 2 days, every 3 days, or any other frequency from about every day to about every 7 days. In some embodiments, to induce repression of transcription of a target nucleic acid in a subject, the dXR and gRNA of the present disclosure may be provided to the subject cells one or more times; e.g., one time, twice, three times, or more than three times, and the cells allowed to incubate with the agent(s) for some amount of time following each contacting event; e.g., 16-24 hours, after which time the media is replaced with fresh media and the cells are cultured further.

In some embodiments, the present disclosure provides a method of treating a subject with a disorder caused by a genetic mutation, comprising administering a therapeutically-effective dose of: (i) an AAV vector encoding the dXR:gRNA systems of any of the embodiments described herein, (ii) an XDP comprising RNP of the dXR:gRNA systems of any of the embodiments described herein, (iii) LNP comprising gRNA and mRNA encoding the dXR (which may be a single LNP, or are formulated as a first and second LNP encapsidating the mRNA encoding the dXR fusion protein and gRNA, respectively), or (iv) combinations of (i)-(iii), wherein upon binding of the RNP of the gene repressor system to the target nucleic acid of a gene in cells of the subject represses transcription of the gene proximal to the binding location of the RNP. In some embodiments, the gRNA target nucleic acid sequence complementary to the targeting sequence is within 1 kb of a transcription start site (TSS) in the gene, wherein upon binding of the RNP transcription is repressed. In some embodiments, the gRNA target nucleic acid sequence complementary to the targeting sequence is within 500 bps upstream to 500 bps downstream of a TSS of the gene, wherein upon binding of the RNP transcription is repressed.

In some embodiments, the gRNA target nucleic acid sequence complementary to the targeting sequence is within 300 bps upstream to 300 bps downstream of a TSS of the gene, wherein upon binding of the RNP transcription is repressed. In some embodiments, the gRNA target nucleic acid sequence complementary to the targeting sequence is within 1 kb of an enhancer of the gene, wherein upon binding of the RNP transcription is repressed. In some embodiments, the gRNA target nucleic acid sequence complementary to the targeting sequence is within the 3' untranslated region of the gene, wherein upon binding of the RNP transcription is repressed. In some embodiments, the gRNA target nucleic acid sequence complementary to the targeting sequence is within an exon of the gene, wherein upon binding of the RNP transcription is repressed. In some embodiments, the gRNA target nucleic acid sequence complementary to the targeting sequence is within exon 1 of the gene, wherein upon binding of the RNP transcription is repressed.

In some embodiments of the methods of treating a subject with a therapeutically-effective dose of the dXR:gRNA systems, transcription of the targeted gene in the cells of the subject is repressed by at least about 10%, at least about 20%, at least about 30%, at least about 40%, at least about 50%, at least about 60%, at least about 70%, at least about 75%, at least about 80%, at least about 85%, at least about 90%, at least about 95%, or at least 99%. In some embodiments of the methods of treating a subject with the dXR:gRNA systems with a therapeutically-effective dose of the foregoing dXR systems, the repression of transcription of the gene in the targeted cells of the subject is sustained for at least about 8 hours, at least about 1 day, at least about 7 days, at least about 2 weeks, at least about 3 weeks, at least about 1 month, at least about 2 months, or at least about 6 months or longer.

In some embodiments, the present disclosure provides a method of treating a subject with a disorder caused by a genetic mutation, comprising administering a therapeutically-effective amount of an AAV vector of any of the embodiments described herein, wherein upon the contacting of the targeted cell, the dXR:gRNA is expressed and complexes as an RNP, and upon binding of the RNP to the target nucleic acid in cells of the subject, transcription of the gene proximal to the binding location of the RNP is repressed wherein the treatment results in improvement in at least one clinically-relevant endpoint associated with the disorder. In some embodiments of the method, the AAV vector is administered at a dose of at least about $1\times10^{5}$ viral genomes (vg)/kg, at least about $1\times10^{6}$ vg/kg, at least about $1\times10^{7}$ vg/kg, at least about $1\times10^{8}$ vg/kg, at least about $1\times10^{9}$ vg/kg, at least about $1\times10^{10}$ vg/kg, at least about $1\times10^{11}$ vg/kg, at least about $1\times10^{12}$ vg/kg, at least about $1\times10^{13}$ vg/kg, at least about $1\times10^{14}$ vg/kg, at least about $1\times10^{15}$ vg/kg, at least about $1\times10^{6}$ vg/kg. In other embodiments, the AAV vector is administered to the subject at a dose of at least about $1\times10^{5}$ vg/kg to about $1\times10^{16}$ vg/kg, at least about $1\times10^{6}$ vg/kg to about $1\times10^{15}$ vg/kg, or at least about $1\times10^{7}$ vg/kg to about $1\times10^{14}$ vg/kg. In one embodiment of the foregoing, transcription of the gene in the targeted cells is repressed by at least about 10%, at least about 20%, at least about 30%, at least about 40%, at least about 50%, at least about 60%, at least about 70%, at least about 75%, at least about 80%, at least about 85%, at least about 90%, at least about 95%, or at least 99%. In another embodiment of the foregoing, transcription of the gene in the cells is repressed by at least about 10% to about 99%, or at least 20% to about 90%, at least about 30% to about 80%, or at least about 40% to about 60%.

In some embodiments, the present disclosure provides a method of treating a subject with a disorder caused by a genetic mutation, comprising administering a therapeutically-effective amount of an XDP of any of the embodiments described herein, wherein upon the contacting of the targeted cell and the binding of the RNP of the XDP to the target nucleic acid in cells of the subject, transcription of the gene proximal to the binding location of the RNP is repressed wherein the treatment results in improvement in at least one clinically-relevant endpoint associated with the disorder. In some embodiments of the method, the XDP is administered at a dose of at least about $1\times10^{5}$ particles/kg, at least about $1\times10^{6}$ particles/kg, at least about $1\times10^{7}$ particles/kg, at least about $1\times10^{8}$ particles/kg, at least about $1\times10^{9}$ particles/kg, at least about $1\times10^{10}$ particles/kg, at least about $1\times10^{11}$ particles/kg, at least about $1\times10^{12}$ particles/kg, at least about $1\times10^{13}$ particles/kg, at least about $1\times10^{14}$ particles/kg, at least about $1\times10^{15}$ particles/kg, at least about $1\times10^{6}$ particles/kg. In other embodiments, the XDP is administered to the subject at a dose of at least about $1\times10^{5}$ particles/kg to about $1\times10^{16}$ particles/kg, or at least about $1\times10^{6}$ particles/kg to about $1\times10^{15}$ particles/kg, or at least about $1\times10^{7}$ particles/kg to about $1\times10^{14}$ particles/kg. In one embodiment of the foregoing, transcription of the gene in the targeted cells is repressed by at least about 10%, at least about 20%, at least about 30%, at least about 40%, at least about 50%, at least about 60%, at least about 70%, at least about 75%, at least about 80%, at least about 85%, at least about 90%, at least about 95%, or at least 99%. In another embodiment of the foregoing, transcription of the gene in the cells is repressed by at least about 10% to about 99%, or at least 20% to about 90%, at least about 30% to about 80%, or at least about 40% to about 60%.

In some embodiments, the present disclosure provides a method of treating a subject with a disorder caused by a genetic mutation, comprising administering a therapeutically-effective amount of an LNP comprising mRNA encoding the dXR fusion protein and a gRNA (which may be a single LNP, or are formulated as a first and second LNP encapsidating the mRNA encoding the dXR fusion protein and gRNA, respectively), of any of the embodiments described herein, wherein upon the contacting of the targeted cell the dXR fusion protein is expressed and complexed with the gRNA to form an RNP, and upon the binding of the RNP to the target nucleic acid in cells of the subject, transcription of the gene proximal to the binding location of the RNP is repressed wherein the treatment results in improvement in at least one clinically-relevant endpoint associated with the disorder. In some embodiments of the method, the LNP are administered at a dose of at least about $1\times10^{5}$ particles/kg, at least about $1\times10^{6}$ particles/kg, at least about $1\times10^{7}$ particles/kg, at least about $1\times10^{8}$ particles/kg, at least about $1\times10^{9}$ particles/kg, at least about $1\times10^{10}$ particles/kg, at least about $1\times10^{11}$ particles/kg, at least about $1\times10^{12}$ particles/kg, at least about $1\times10^{13}$ particles/kg, at least about $1\times10^{14}$ particles/kg, at least about $1\times10^{15}$ particles/kg, at least about $1\times10^{6}$ particles/kg. In other embodiments, the LNP are administered to the subject at a dose of at least about $1\times10^{5}$ particles/kg to about $1\times10^{16}$ particles/kg, or at least about $1\times10^{6}$ particles/kg to about $1\times10^{15}$ particles/kg, or at least about $1\times10^{7}$ particles/kg to about $1\times10^{14}$ particles/kg. In one embodiment of the foregoing, transcription of the gene in the targeted cells is repressed by at least about 10%, at least about 20%, at least about 30%, at least about 40%, at least about 50%, at least about 60%, at least about 70%, at least about 75%, at least about 80%, at least about 85%, at least about 90%, at least about 95%, or at least 99%. In another embodiment of the foregoing, transcription of the gene in the cells is repressed by at least about 10% to about 99%, or at least 20% to about 90%, at least about 30% to about 80%, or at least about 40% to about 60%.

In the embodiments of the method of treatment, the AAV vector, the XDP, or the LNP is administered to the subject by a route of administration selected from subcutaneous, intradermal, intraneural, intranodal, intramedullary, intramuscular, intralumbar, intrathecal, subarachnoid, intraventricular, intracapsular, intravenous, intralymphatical, or intraperitoneal routes, wherein the administering method is injection, transfusion, or implantation, or combinations thereof. In some embodiments, the subject is selected from the group consisting of mouse, rat, pig, non-human primate, and human.

A number of therapeutic strategies have been used to design the compositions for use in the methods of treatment of a subject with a disease. In some embodiments, the invention provides a method of treatment of a subject having a disease, the method comprising administering to the subject a dXR:gRNA composition, an AAV vector, an XDP, of an LNP of any of the embodiments disclosed herein according to a treatment regimen comprising one or more consecutive doses using a therapeutically effective dose. In some embodiments of the treatment regimen, the therapeutically effective dose of the composition or vector is administered as a single dose. In other embodiments of the treatment regimen, the therapeutically effective dose is administered to the subject as two or more doses over a period of at least two weeks, or at least one month, or at least two months, or at least three months, or at least four months, or at least five months, or at least six months. In some embodiments of the treatment regimen, the effective doses are administered by a route selected from the group consisting of subcutaneous, intradermal, intraneural, intranodal, intramedullary, intramuscular, intralumbar, intrathecal, subarachnoid, intraventricular, intracapsular, intravenous, intralymphatical, intravitreal, subretinal, or intraperitoneal routes, wherein the administering method is injection, transfusion, or implantation. In some embodiments of the treatment regimen, the subject is selected from the group consisting of mouse, rat, pig, non-human primate, and human.

In some embodiments, the administering of the therapeutically effective amount of a dXR:gRNA modality, including a vector or an LNP comprising a polynucleotide encoding a dXR protein and a guide ribonucleic acid composition disclosed herein, to repress expression of a gene product to a subject with a disease leads to the prevention or amelioration of the underlying disease such that an improvement is observed in at least one clinically-relevant endpoint associated with the disease, notwithstanding that the subject may still be afflicted with the underlying disease. In some embodiments, the administration of the therapeutically effective amount of the dXR:gRNA modality leads to an improvement in at least two clinically-relevant parameters associated with the disease.

In embodiments in which two or more different targeting complexes are provided to the cell (e.g., two dXR:gRNA comprising two or more different targeting sequences that are complementary to different sequences within the same or different target nucleic acid), the complexes may be provided simultaneously or they may be provided consecutively; e.g. the first dXR:gRNA targeted complex being provided first, followed by the second targeted complex.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle, a liposome, or a lipid nanoparticle, embodiments of which have been described more fully, above. There are four types of lipids, anionic (negatively-charged), neutral, cationic (positively-charged), or ionizable cationic employed in LNP. Cationic lipids (or ionizable lipids at the appropriate pH) of LNP, due to their positive charge, naturally complex with the negatively charged DNA. Also, as a result of their charge, they interact with the cell membrane. Endocytosis of the LNP then occurs, and the DNA is released into the cytoplasm. The cationic lipids also protect against degradation of the DNA by the cell.

In another aspect, the present disclosure provides compositions of gene repressor systems of any of the embodiments described herein for use as a medicament in the treatment of a disease in a subject. In some embodiments, the subject the subject is selected from the group consisting of mouse, rat, pig, non-human primate, and human.

IX. Kits and Articles of Manufacture

In another aspect, provided herein are kits comprising a fusion protein and one or a plurality of gRNA of any of the embodiments of the disclosure formulated in a pharmaceutically acceptable excipient and contained in a suitable container (for example a tube, vial or plate). In some embodiments, the kit comprises a gRNA variant of the disclosure. Exemplary gRNA variants that can be included comprise a sequence of any one of SEQ ID NOS: 2238-2331, 57544-57589, and 59352, or a sequence of Table 2, together with a targeting sequence appropriate for the gene to be repressed linked to the 3' end of the scaffold. In some embodiments, the kit comprises a dCasX variant protein of the disclosure (e.g., a sequence of SEQ ID NOS: 17-36 and 59353-59358 as set forth in Table 4) linked to one or more repressor domains of the embodiments described herein; e.g, DNMT3A catalytic domain, DNMT3L interaction domain, and DNMT3A ADD domain.

In some embodiments, the kit comprises a vector encoding a dXR:gRNA of any of the embodiments described herein, formulated in a pharmaceutically acceptable excipient and contained in a suitable container.

In certain embodiments, provided herein are kits comprising an LNP comprising an mRNA encoding a dXR as described herein, formulated in a pharmaceutically acceptable excipient and contained in a suitable container.

In some embodiments, the kit further comprises a buffer, a nuclease inhibitor, a protease inhibitor, a liposome, a therapeutic agent, a label, instructions for use, a label visualization reagent, or any combination of the foregoing.

The present description sets forth numerous exemplary configurations, methods, parameters, and the like. It should be recognized, however, that such description is not intended as a limitation on the scope of the present disclosure, but is instead provided as a description of exemplary embodiments. Embodiments of the present subject matter described above may be beneficial alone or in combination, with one or more other aspects or embodiments. Without limiting the foregoing description, certain non-limiting embodiments of the disclosure are provided below. As will be apparent to those of skill in the art upon reading this disclosure, each of the individually numbered embodiments may be used or combined with any of the preceding or following individually numbered embodiments. This is intended to provide support for all such combinations of embodiments and is not limited to combinations of embodiments explicitly provided below:

The following Examples are merely illustrative and are not meant to limit any aspects of the present disclosure in any way.

ENUMERATED EMBODIMENTS

The disclosure can be understood with respect to the following illustrated, enumerated embodiments:

SET 1.

1. A gene repressor system comprising:

(a) a catalytically-dead Class 2, Type V CRISPR protein;

(b) one or more transcription repressor domains; and (c) a guide ribonucleic acid (gRNA)

wherein:

i) the one or more transcription repressor domains are linked to the catalytically-dead Class 2, Type V CRISPR protein as a fusion protein;

ii) the gRNA comprises a targeting sequence complementary to a target nucleic acid sequence of a gene; and iii) the fusion protein is capable of forming a ribonuclear protein complex (RNP) with the gRNA.

2. The gene repressor system of embodiment 1, wherein the gene encodes mRNA, rRNA, tRNA, structural RNA, or protein.

3. The gene repressor system of embodiment 1, wherein the one or more transcription repressor domains are selected from the group consisting of Krüppel-associated box (KRAB), methyl-CpG (mCpG) binding domain 2 (MeCP2), DNMT3A, DNMT3L, FOG, EZH2, SID4X, SID, NcoR, NuE, methyl-CpG (mCpG) binding domain 2 (meCP2), Switch independent 3 transcription regulator family member A (SIN3A), histone deacetylase HDT1 (HDT1), n-terminal truncation of methyl-CpG-binding domain containing protein 2 (MBD2B), nuclear inhibitor of protein phosphatase-1 (NIPP1), and heterochromatin protein 1 (HP1A).

4. The gene repressor system of embodiment 3, wherein the KRAB transcriptional repressor domain is selected from the group consisting of ZNF343, ZNF337, ZNF334, ZNF215, ZNF519, ZNF485, ZNF214, ZNF33B, ZNF287, ZNF705A, ZNF37A, KRBOX4, ZKSCAN3, ZKSCAN4, ZNF57, ZNF557, ZNF705B, ZNF662, ZNF77, ZNF500, ZNF558, ZNF620, ZNF713, ZNF823, ZNF440, ZNF441, ZNF136, SNRPB, ZNF735, ZKSCAN2, ZNF619, ZNF627, ZNF333, ABCA11P, PLD5P1, ZNF25, ZNF727, ZNF595, ZNF14, ZNF33A, ZNF101, ZNF253, ZNF56, ZNF720, ZNF85, ZNF66, ZNF722P, ZNF486, ZNF682, ZNF626, ZNF100, ZNF93, ZKSCAN1, ZNF257, ZNF729, ZNF208, ZNF90, ZNF430, ZNF676, ZNF91, ZNF429, ZNF675, ZNF681, ZNF99, ZNF431, ZNF98, ZNF708, ZNF732, SSX2, ZNF721, ZNF726, ZNF730, ZNF506, ZNF728, ZNF141, ZNF723, ZNF302, ZNF484, LINC00960, SSX2B, ZNF718, ZNF74, ZNF157, ZNF790, ZNF565, ZNF705G, VN1R107P, SLC27A5, ZNF737, SSX4, ZNF850, ZNF717, ZNF155, ZNF283, ZNF404, ZNF114, ZNF716, ZNF230, ZNF45, ZNF222, ZNF286A, ZNF624, ZNF223, ZNF284, ZNF790-AS1, ZNF382, ZNF749, ZNF615, ZFP90, ZNF225, ZNF234, ZNF568, ZNF614, ZNF584, ZNF432, ZNF461, ZNF182, ZNF630, ZNF630-AS1, ZNF132, ZNF420, ZNF324B, ZNF616, ZNF471, ZNF227, ZNF324, ZNF860, ZFP28, ZNF470, ZNF586, ZNF235, ZNF274, ZNF446, ZFP1, ZIM3, ZNF212, ZNF766, ZNF264, ZNF480, ZNF667, ZNF805, ZNF610, ZNF783, ZNF621, ZNF8-DT, ZNF880, ZNF213-AS1, ZNF213, ZNF263, ZSCAN32, ZIM2, ZNF597, ZNF786, KRBA1, ZNF460, ZNF8, ZNF875, ZNF543, ZNF133, ZNF229, ZNF528, SSX1, ZNF81, ZNF578, ZNF862, ZNF777, ZNF425, ZNF548, ZNF746, ZNF282, ZNF398, ZNF599, ZNF251, ZNF195, ZNF181, RBAK-RBAKDN, ZFP37, RN7SL526P, ZNF879, ZNF26, ZSCAN21, ZNF3, ZNF354C, ZNF10, ZNF75D, ZNF426, ZNF561, ZNF562, ZNF846, ZNF782, ZNF552, ZNF587B, ZNF814, ZNF587, ZNF92, ZNF417, ZNF256, ZNF473, ZFP14, ZFP82, ZNF529, ZNF605, ZFP57, ZNF724, ZNF43, ZNF354A, ZNF547, SSX4B, ZNF585A, ZNF585B, ZNF792, ZNF789, ZNF394, ZNF655, ZFP92, ZNF41, ZNF674, ZNF546, ZNF780B, ZNF699, ZNF177, ZNF560, ZNF583, ZNF707, ZNF808, ZKSCAN5, ZNF137P, ZNF611, ZNF600, ZNF28, ZNF773, ZNF549, ZNF550, ZNF416, ZIK1, ZNF211, ZNF527, ZNF569, ZNF793, ZNF571-AS1, ZNF540, ZNF571, ZNF607, ZNF75A, ZNF205, ZNF175, ZNF268, ZNF354B, ZNF135, ZNF221, ZNF285, ZNF419, ZNF30, ZNF304, ZNF254, ZNF701, ZNF418, ZNF71, ZNF570, ZNF705E, KRBOX1, ZNF510, ZNF778, PRDM9, ZNF248, ZNF845, ZNF525, ZNF765, ZNF813, ZNF747, ZNF764, ZNF785, ZNF689, ZNF311, ZNF169, ZNF483, ZNF493, ZNF189, ZNF658, ZNF564, ZNF490, ZNF791, ZNF678, ZNF454, ZNF34, ZNF7, ZNF250, ZNF705D, ZNF641, ZNF2, ZNF554, ZNF555, ZNF556, ZNF596, ZNF517, ZNF331, ZNF18, ZNF829, ZNF772, ZNF17, ZNF112, ZNF514, ZNF688, PRDM7, ZNF695, ZNF670-ZNF695, ZNF138, ZNF670, ZNF19, ZNF316, ZNF12, ZNF202, RBAK, ZNF83, ZNF468, ZNF479, ZNF679, ZNF736, ZNF680, ZNF273, ZNF107, ZNF267, ZKSCAN8, ZNF84, ZNF573, ZNF23, ZNF559, ZNF44, ZNF563, ZNF442, ZNF799, ZNF443, ZNF709, ZNF566, ZNF69, ZNF700, ZNF763, ZNF433-AS1, ZNF433, ZNF878, ZNF844, ZNF788P, ZNF20, ZNF625-ZNF20, ZNF625, ZNF606, ZNF530, ZNF577, ZNF649, ZNF613, ZNF350, ZNF317, ZNF300, ZNF180, ZNF415, VN1R1, ZNF266, ZNF738, ZNF445, ZNF852, ZKSCAN7, ZNF660, MPRIPP1, ZNF197, ZNF567, ZNF582, ZNF439, ZFP30, ZNF559-ZNF177, ZNF226, ZNF841, ZNF544, ZNF233, ZNF534, ZNF836, ZNF320, KRBA2, ZNF761, ZNF383, ZNF224, ZNF551, ZNF154, ZNF671, ZNF776, ZNF780A, ZNF888, ZNF816-ZNF321P, ZNF321P, ZNF816, ZNF347, ZNF665, ZNF677, ZNF160, ZNF184, ZNF140, ZNF589, ZNF891, ZFP69B, ZNF436, POGK, ZNF669, ZFP69, ZNF684, ZNF124, and ZNF496.

5. The gene repressor system of embodiment 1, wherein the one or more transcription repressor domains are selected from the group of sequences consisting of SEQ ID NOS: 889-2100 and 2332-33239, or a sequence having at least about 85%, at least about 90%, at least about 91%, at least about 92%, at least about 93% at least about 94% at least about 95%, at least about 96%, at least about 97%, at least about 98%, or at least about 99% identity thereto.

6. The gene repressor system of embodiment 1, wherein the one or more transcription repressor domains are selected from the group of sequences consisting of SEQ ID NOS: 889-2100 and 2332-33239.

7. The gene repressor complex of any one of the preceding embodiments, wherein the fusion protein comprises two transcriptional repressor domains, wherein the first transcriptional repressor domain is different from the second transcriptional repressor domain.

8. The gene repressor complex of embodiment 7, wherein the first transcriptional repressor domain is KRAB and the second transcriptional repressor domain is selected from the group consisting of methyl-CpG (mCpG) binding domain 2 (MeCP2), DNMT3A, DNMT3L, FOG, EZH2, SID4X, SID, NcoR, NuE, methyl-CpG (mCpG) binding domain 2 (meCP2), Switch independent 3 transcription regulator family member A (SIN3A), histone deacetylase HDT1 (HDT1), n-terminal truncation of methyl-CpG-binding domain containing protein 2 (MBD2B), nuclear inhibitor of protein phosphatase-1 (NIPP1), heterochromatin protein 1 (HP1A), mixed lineage leukemia protein-1 (MLL1), MLL2, MLL3, MLL4, MLL5, SET Domain Containing 1A (SETD1A), SETD1B, SETD2, Suppressor Of Variegation 3-9 Homolog 1 (SUV39H1), SUV39H2, euchromatic histone lysine methyltransferase 1 (EHMT1), histone-lysine N-methyltransferase EZH1 (EZH1), nuclear receptor binding SET domain protein 1 (NSD1), NSD2, NSD3, ASH1 like histone lysine methyltransferase (ASH1L), tripartite motif containing 28 (TRIM28), Methyltransferase Like 3 (METTL3), METTL4, family with sequence similarity 208 member A (FAM208A), M-Phase Phosphoprotein 8 (MPHOSPH8), and Periphilin 1 (PPHLN1).

9. The gene repressor complex of embodiment 7 or embodiment 8, wherein the fusion protein comprises a third transcriptional repressor domain, wherein the third transcriptional repressor domain is different from the first and the second transcriptional repressor domains.

10. The gene repressor complex of embodiment 9, wherein the first transcriptional repressor domain is KRAB and the second and third transcriptional repressor domains are selected from the group consisting of methyl-CpG (mCpG) binding domain 2 (MeCP2), DNMT3A, DNMT3L, FOG, EZH2, SID4X, SID, NcoR, NuE, methyl-CpG (mCpG) binding domain 2 (meCP2), Switch independent 3 transcription regulator family member A (SIN3A), histone deacetylase HDT1 (HDT1), n-terminal truncation of methyl-CpG-binding domain containing protein 2 (MBD2B), nuclear inhibitor of protein phosphatase-1 (NIPP1), heterochromatin protein 1 (HP1A), mixed lineage leukemia protein-1 (MLL1), MLL2, MLL3, MLL4, MLL5, SET Domain Containing 1A (SETD1A), SETD1B, SETD2, Suppressor Of Variegation 3-9 Homolog 1 (SUV39H1), SUV39H2, euchromatic histone lysine methyltransferase 1 (EHMT1), histone-lysine N-methyltransferase EZH1 (EZH1), nuclear receptor binding SET domain protein 1 (NSD1), NSD2, NSD3, ASH1 like histone lysine methyltransferase (ASH1L), tripartite motif containing 28 (TRIM28), Methyltransferase Like 3 (METTL3), METTL4, family with sequence similarity 208 member A (FAM208A), M-Phase Phosphoprotein 8 (MPHOSPH8), and Periphilin 1 (PPHLN1).

11. The gene repressor complex of any one of embodiments 7-10, wherein the transcriptional repressor domains are linked by linker peptide sequences.

12. The gene repressor complex of any one of the preceding embodiments, wherein the one or more transcriptional repressor domains are linked at or near the C-terminus of the catalytically-dead Class 2, Type V CRISPR protein by linker peptide sequences.

13. The gene repressor complex of embodiments 1-11, wherein the one or more transcriptional repressor domains are linked at or near the N-terminus of the catalytically-dead Class 2, Type V CRISPR protein by linker peptide sequences.

14. The gene repressor complex of any one of embodiments 11-13, wherein the linker peptide is selected from the group consisting of RS, (G)n (SEQ ID NO: 33240), (GS)n (SEQ ID NO: 33241), (GGS)n (SEQ ID NO: 33242), (GSGGS)n (SEQ ID NO: 33243), (GGSGGS)n (SEQ ID NO: 33244), (GGGS)n (SEQ ID NO: 33245), GGSG (SEQ ID NO: 33246), GGSGG (SEQ ID NO: 33247), GSGSG (SEQ ID NO: 33248), GSGGG (SEQ ID NO: 33249), GGGSG (SEQ ID NO: 33250), GSSSG (SEQ ID NO: 33251), (GP)n (SEQ ID NO: 33252), GPGP (SEQ ID NO: 33253), GGSGGGS (SEQ ID NO: 33254), GGP, PPP, PPAPPA (SEQ ID NO: 33255), PPPGPPP (SEQ ID NO: 33256), PPPG (SEQ ID NO: 33257), PPP(GGGS)n (SEQ ID NO: 33258), (GGGS)nPPP (SEQ ID NO: 33259), AEAAAKEAAAKEAAAKA (SEQ ID NO:33260), AEAAAKEAAAKA (SEQ ID NO: 33261), SGSETPGTSESATPES (SEQ ID NO: 33262), and TPPKTKRKVEFE (SEQ ID NO: 33263), wherein n is an integer of 1 to 5.

15. The gene repressor system of any one of the preceding embodiments, wherein the catalytically-dead Class 2, Type V CRISPR protein comprises a catalytically-dead CasX variant protein (dCasX) comprising a sequence selected from the group consisting of SEQ ID NOS: 17-36 as set forth in Table 4, or a sequence having at least about 85%, at least about 90%, at least about 95%, at least about 96%, at least about 97%, at least about 98%, or at least about 99% sequence identity thereto.

16. The gene repressor system of any one of embodiments 1-14, wherein the catalytically-dead Class 2, Type V CRISPR protein comprises a catalytically-dead CasX variant protein (dCasX) comprising a sequence selected from the group consisting of the sequences SEQ ID NOS: 17-36 as set forth in Table 4.

17. The gene repressor system of embodiment 15 or embodiment 16, comprising a sequence selected from the group consisting of the sequences as set forth in SEQ ID NOS: 889-2100 and 2332-33239, or a sequence having at least about 85%, at least about 90%, at least about 95%, at least about 96%, at least about 97%, at least about 98%, or at least about 99% sequence identity thereto.

18. The gene repressor system of embodiment 15 or embodiment 16, comprising a sequence selected from the group consisting of the sequences as set forth in SEQ ID NOS: 889-2100 and 2332-33239.

19. The gene repressor system of any one of embodiments 15-18, wherein the fusion protein further comprises one or more nuclear localization signals (NLS).

20. The gene repressor system of embodiment 19, wherein the one or more NLS are selected from the group of sequences consisting of PKKKRKV (SEQ ID NO: 33289), KRPAATKKAGQAKKKK (SEQ ID NO: 33290), PAAKRVKLD (SEQ ID NO: 33291), RQRRNELKRSP (SEQ ID NO: 33292), NQSSNFGPMKGGNFGGRSSGPYGGGGQYFAKPRNQGGY (SEQ ID NO: 33293), RMRIZFKNKGKDTAELRRRRVEVSVELRKAKKDEQILKRRNV (SEQ ID NO: 33294), VSRKRPRP (SEQ ID NO: 33295), PPKKARED (SEQ ID NO: 33296), PQPKKKPL (SEQ ID NO: 166), SALIKKKKKMAP (SEQ ID NO: 33298), DRLRR (SEQ ID NO: 33299), PKQKKRK (SEQ ID NO: 33300), RKLKKKIKKL (SEQ ID NO: 33301), REKKKFLKRR (SEQ ID NO: 33302), KRKGDEVDGVDEVAKKKSKK (SEQ ID NO: 33303), RKCLQAGMNLEARKTKK (SEQ ID NO: 33304), PRPRKIPR (SEQ ID NO: 33305), PPRKKRTVV (SEQ ID NO: 33306), NLSKKKKRKREK (SEQ ID NO: 33307), RRPSRPFRKP (SEQ ID NO: 33308), KRPRSPSS (SEQ ID NO: 33309), KRGINDRNFWRGENERKTR (SEQ ID NO: 33310), PRPPKMARYDN (SEQ ID NO: 33311), KRSFSKAF (SEQ ID NO: 33312), KLKIKRPVK (SEQ ID NO: 33313), PKKKRKVPPPPAAKRVKLD (SEQ ID NO: 33314), PKTRRRPRRSQRKRPPT (SEQ ID NO: 33315), SRRRKANPTKLSENAKKLAKEVEN (SEQ ID NO:

33316), KTRRRPRRSQRKRPPT (SEQ ID NO: 33317), RRKKRRPRRKKRR (SEQ ID NO: 33318), PKKKSRKPKKKSRK (SEQ ID NO: 33319), HKKKHP-DASVNFSEFSK (SEQ ID NO: 33320), QRPGPY-DRPQRPGPYDRP (SEQ ID NO: 33321), LSPSLSPLL-SPSLSPL (SEQ ID NO: 33322), RGKGGKGLGKGGAKRHRK (SEQ ID NO: 33323), PKRGRGRPKRGRGR (SEQ ID NO: 33324), PKKKRKVPPPPAAKRVKLD (SEQ ID NO: 33325), PKKKRKVPPPPKKKRKV (SEQ ID NO: 33326), PAKRARRGYKC (SEQ ID NO: 33327), KLGPRKAT-GRW (SEQ ID NO: 33328), PRRKREE (SEQ ID NO: 33329), PYRGRKE (SEQ ID NO: 33330), PLRKRPRR (SEQ ID NO: 33331), PLRKRPRRGSPLRKRPRR (SEQ ID NO: 33332), PAAKRVKLDGGKRTADGSEF-ESPKKKRKV (SEQ ID NO: 33333), PAAKRVKLDGGKRTADGSEF-ESPKKKRKVGIHGVPAA (SEQ ID NO: 33334), PAAKRVKLDGGKRTADGSEFESPKKKRK-VAEAAAKEAAAKEAAAKA (SEQ ID NO: 33335), PAAKRVKLDGGKRTADGSEFESPKKKRKVPG (SEQ ID NO: 33336), KRKGSPERGERKRHW (SEQ ID NO: 33337), KRTADSQHSTPPKTKRKVEFEPKKKRKV (SEQ ID NO: 33338).

21. The gene repressor system of embodiment 19 or embodiment 20, wherein the one or more NLS are linked at or near the C-terminus of the dCasX or the repressor domain.

22. The gene repressor system of embodiment 19 or embodiment 20, wherein the one or more NLS are linked at or near the N-terminus of the dCasX or the repressor domain.

23. The gene repressor system of embodiment 19 or embodiment 20, wherein the one or more NLS are linked at or near both the N-terminus and the C-terminus of the dCasX or the repressor domain.

24. The gene repressor system of embodiment 19, wherein the one or more NLS are selected from the group of sequences as set forth in Table 5 and are linked at or near the N-terminus of the dCasX or the repressor domain.

25. The gene repressor system of embodiment 19, wherein the one or more NLS are selected from the group of SEQ ID NOS: 72-112 as set forth in Table 6 and are linked at or near the C-terminus of the dCasX or the repressor domain.

26. The gene repressor system of embodiment 19, wherein one or more NLS are selected from the group of SEQ ID NOS: 37-71 as set forth in Table 5 and are linked at or near the N-terminus of the dCasX or the repressor domain and one or more NLS are selected from the group of sequences as set forth in Table 6 and are linked at or near the C-terminus of the dCasX or the repressor domain.

27. The gene repressor system of any one of embodiments 19-26, wherein the one or more NLS are linked to the dCasX variant protein, the repressor domain, or to adjacent NLS with one or more linker peptides wherein the linker peptides are selected from the group consisting of RS, (G)n (SEQ ID NO: 33240), (GS)n (SEQ ID NO: 33241), (GGS)n (SEQ ID NO: 33242), (GSGGS)n (SEQ ID NO: 33243), (GGSGGS)n (SEQ ID NO: 33244), (GGGS)n (SEQ ID NO: 33245), GGSG (SEQ ID NO: 33246), GGSGG (SEQ ID NO: 33247), GSGSG (SEQ ID NO: 33248), GSGGG (SEQ ID NO: 33249), GGGSG (SEQ ID NO: 33250), GSSSG (SEQ ID NO: 33251), (GP)n (SEQ ID NO: 33252), GPGP (SEQ ID NO: 33253), GGSGGGS (SEQ ID NO: 33254), GGP, PPP, PPAPPA (SEQ ID NO: 33255), PPPGPPP (SEQ ID NO: 33256), PPPG (SEQ ID NO: 33257), PPP(GGGS)n (SEQ ID NO: 33258), (GGGS)nPPP (SEQ ID NO: 33259), AEAAAKEAAAKEAAAKA (SEQ ID NO: 33260), AEAAAKEAAAKA (SEQ ID NO: 33261), SGSETPGTS-ESATPES (SEQ ID NO: 33262), and TPPKTKRKVEFE (SEQ ID NO: 33263), wherein n is an integer of 1 to 5.

28. The gene repressor system of any one of the preceding embodiments, wherein the gRNA has a scaffold comprising a sequence selected from the group consisting of SEQ ID NOS: 2101-2331 as set forth in Table 2, or a sequence having at least about 85%, at least about 90%, at least about 95%, at least about 96%, at least about 97%, at least about 98%, or at least about 99% sequence identity thereto.

29. The gene repressor system of any one of embodiments 1-28, wherein the gRNA has a scaffold comprising a sequence selected from the group consisting of SEQ ID NOS: 2101-2331, as set forth in Table 2.

30. The gene repressor system of any one of the preceding embodiments, wherein the gRNA comprises a targeting sequence having 15, 16, 17, 18, 19, 20, or 21 nucleotides.

31. The gene repressor system of embodiment 30, wherein the target nucleic acid sequence complementary to the targeting sequence is within 1 kb of a transcription start site (TSS) in the gene.

32. The gene repressor system of embodiment 30, wherein the target nucleic acid sequence complementary to the targeting sequence is within 500 bps upstream to 500 bps downstream of a TSS of the gene.

33. The gene repressor system of embodiment 30, wherein the target nucleic acid sequence complementary to the targeting sequence is within 1 kb 3' or 5' to an untranslated region of the gene.

34. The gene repressor system of embodiment 30, wherein the target nucleic acid sequence complementary to the targeting sequence is within the open reading frame of the gene.

35. The gene repressor system of embodiment 30, wherein the target nucleic acid sequence complementary to the targeting sequence is within an exon of the gene.

36. The gene repressor system of embodiment 35, wherein the target nucleic acid sequence complementary to the targeting sequence is within exon 1 of the gene.

37. The gene repressor system of any one of the preceding embodiments, wherein the RNP is capable of binding the target nucleic acid but is not capable of cleaving the target nucleic acid.

38. A nucleic acid encoding the fusion protein of the gene repressor system of any one of the preceding embodiments.

39. A nucleic acid encoding the gRNA of any one of the preceding embodiments.

40. The nucleic acid of embodiment 38 or embodiment 39, wherein the nucleic acid sequence is codon optimized for expression in a eukaryotic cell.

41. A vector comprising the nucleic acids of embodiments 38-40.

42. The vector of embodiment 41, wherein the vector is selected from the group consisting of a retroviral vector, a lentiviral vector, an adenoviral vector, an adeno-associated viral (AAV) vector, a herpes simplex virus (HSV) vector, a virus-like particle (VLP) vector, a delivery particle system (XDP) vector, a plasmid, a minicircle, a nanoplasmid, and an RNA vector.

43. The vector of embodiment 42, wherein the vector is an AAV vector.

44. The vector of embodiment 43, wherein the AAV vector is selected from AAV1, AAV2, AAV3, AAV4, AAV5, AAV6, AAV7, AAV8, AAV9, AAV10, AAV11, AAV12, AAV 44.9, AAV-Rh74, or AAVRh10.

45. The vector of embodiment 43 or embodiment 44, wherein the nucleic acid encoding the fusion protein and the gRNA are incorporated as a transgene between a 5' and a 3' inverted terminal repeat (ITR) sequence within the AAV.

46. The vector of embodiment 42, wherein the vector is a XDP vector comprising a nucleic acid encoding one or more components of a retroviral gag polyprotein or a gag-pol polyprotein.

47. The vector of embodiment 46, wherein the nucleic acid encodes one or more components are selected from the group consisting of a gag-transframe region-pol protease polyprotein (gag-TFR-PR), a matrix protein (MA), a nucleocapsid protein (NC), a capsid protein (CA), a p1 peptide, a p6 peptide, a P2A peptide, a P2B peptide, a P10 peptide, a p12 peptide, a PP21/24 peptide, a P12/P3/P8 peptide, a P20 peptide, an MS2 coat protein, a protease, and a protease cleavage site.

48. The vector of embodiment 46 or embodiment 47, wherein the nucleic acid further encodes the fusion protein of embodiment 38.

49. The vector of embodiment 46 or embodiment 47, wherein the vector comprises a first nucleic acid encoding the fusion protein and a second nucleic acid encoding the one or more components of the gag polyprotein.

50. The vector of embodiment 48 or embodiment 49, further comprising a nucleic acid encoding a pseudotyping viral envelope glycoprotein or antibody fragment that provides for binding and fusion of the XDP to a target cell.

51. The vector of any one of embodiments 47-50, wherein the encoded gRNA further comprises an MS2 hairpin sequence.

52. The vector of any one of embodiments 47-51, further comprising a nucleic acid encoding a Gag-transframe region-Pol protease polyprotein (Gag-TFR-PR) and intervening protease cleavage sites between each component of the Gag-TFR-PR.

Figure 4:
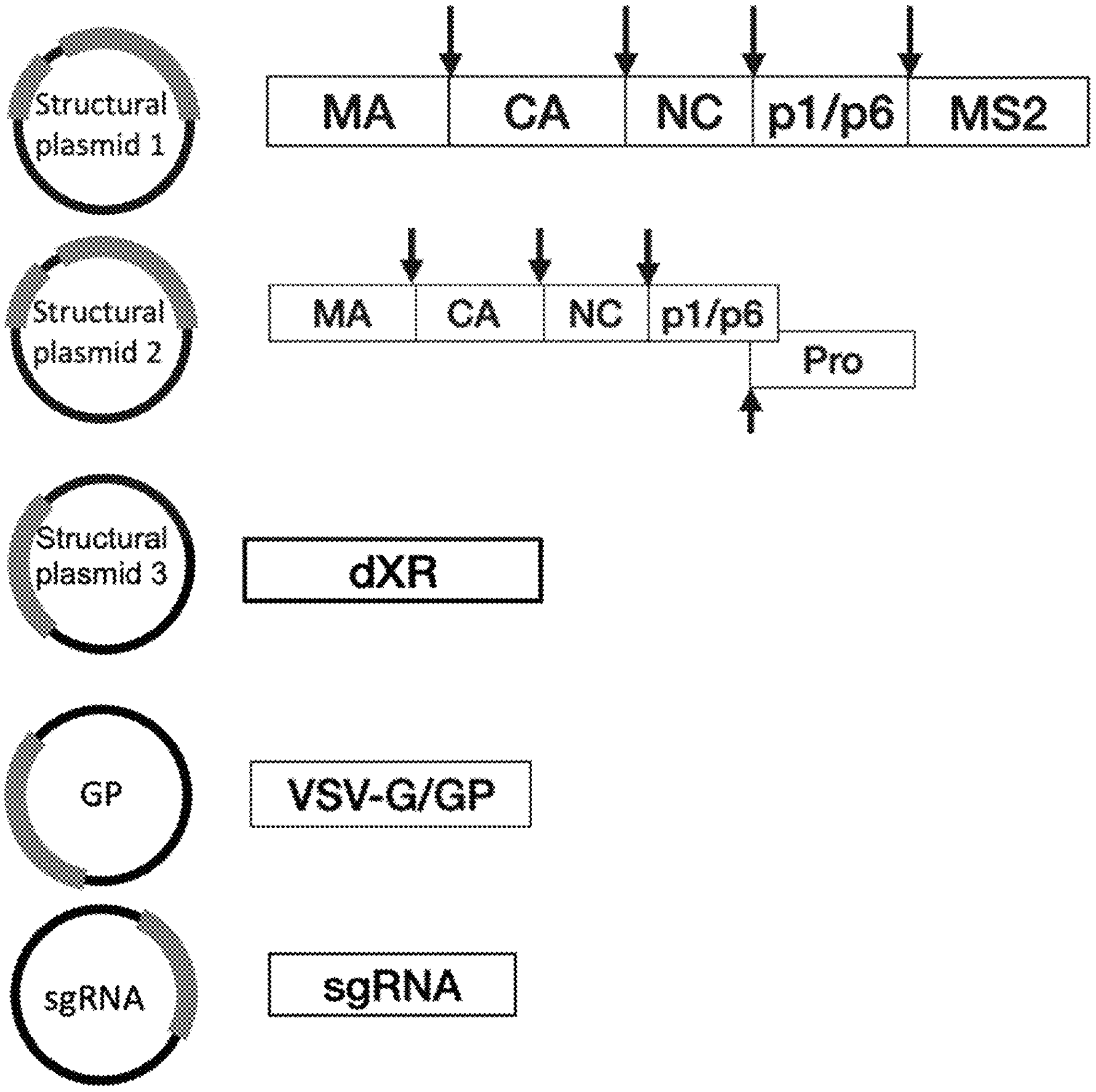
FIG. 4 shows the schematics that depict the plasmids utilized in the creation of an XDP construct in which the dXR is encoded on a separate plasmid and the plasmid encoding Gag components also encodes an MS2 coat protein, with protease cleavage sequence sites indicated by arrows.
Figure 5:
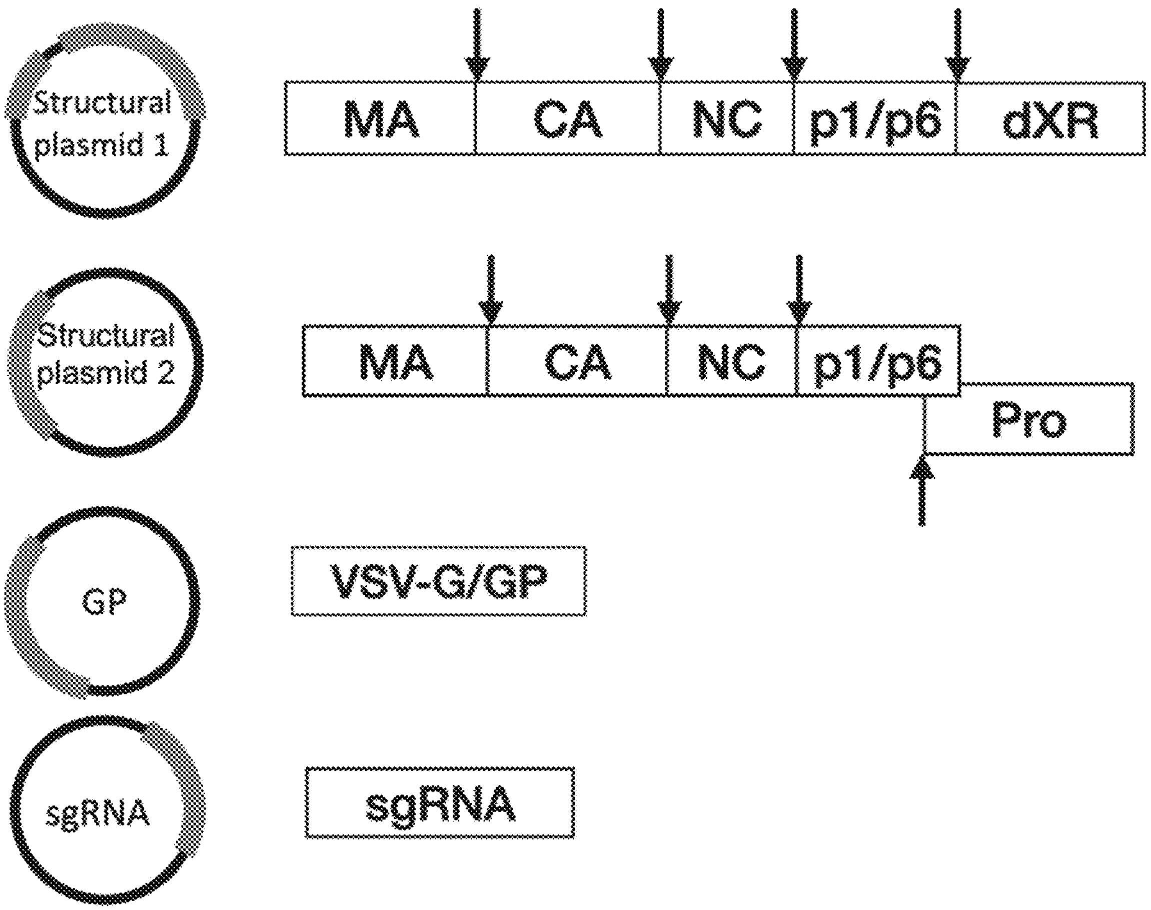
FIG. 5 shows the schematics that depict the plasmids utilized in the creation of an XDP construct in which the dXR is encoded on the plasmid encoding Gag components, with protease cleavage sequence sites indicated by arrows.

53. The vector of embodiment 52, wherein the nucleic acids are configured as depicted in FIG. 4 or FIG. 5.

54. A host cell comprising the vector of any one of embodiments 41-53.

55. The host cell of embodiment 54, wherein the host cell is selected from the group consisting of BHK, HEK293, HEK293T, NS0, SP2/0, YO myeloma cells, P3X63 mouse myeloma cells, PER, PER.C6, NIH3T3, COS, HeLa, CHO, and yeast cells.

56. An XDP comprising:

(a) one or more components of selected from the group consisting of a matrix protein (MA), a nucleocapsid protein (NC), a capsid protein (CA), a p1 peptide, a p6 peptide, a P2A peptide, a P2B peptide, a P10 peptide, a p12 peptide, a PP21/24 peptide, a P12/P3/P8 peptide, a P20 peptide, an MS2 coat protein, a protease, and a protease cleavage site;

(b) an RNP comprising the gene repressor system of any one of embodiments 1-37 wherein the RNP is encapsidated within the XDP upon self-assembly of the XDP;

(c) a pseudotyping viral envelope glycoprotein or antibody fragment incorporated on the XDP capsid surface that provides for binding and fusion of the XDP to a target cell.

57. A method of repressing transcription of a target nucleic acid sequence in a population of cells, the method comprising introducing into cells:

(a) RNP comprising the gene repressor system of any one of embodiments 1-37;

(b) the nucleic acid of any one of embodiments 38-40;

(c) the vector as in any one of embodiments 41-52;

(e) the XDP of embodiment 56; or (f) combinations thereof, wherein upon binding of the RNP to the target nucleic acid, transcription of the gene proximal to the binding location of the RNP is repressed in the cells.

58. The method of embodiment 57, wherein transcription of the gene in the population of cells is repressed by at least about 10%, at least about 20%, at least about 30%, at least about 40%, at least about 50%, at least about 60%, at least about 70%, at least about 75%, at least about 80%, at least about 85%, at least about 90%, at least about 95%, or at least 99% greater compared to the repression effected by an RNP comprising a comparable guide RNA and a catalytically dead CasX variant without a repressor domain, when assessed in an in vitro assay.

59. The method of embodiment 57 or embodiment 58, wherein off-target binding or off-target transcription repression is less than about 5%, less than about 4%, less than about 3%, less than about 2%, or less than about 1% in the cells.

60. The method of any one of embodiments 57-59, wherein the repression of transcription in the cells is sustained for at least about 8 hours, at least about 1 day, at least about 1 week, or at least about 1 month.

61. The method of any one of embodiments 57-60, further comprising a second gRNA or a nucleic acid encoding the second gNA, wherein the second gNA has a targeting sequence complementary to a different portion of the target nucleic acid sequence and is capable of forming a ribonuclear protein complex (RNP) with the catalytically-dead Class 2, Type V CRISPR protein.

62. A method of treating a subject with a disorder caused by a genetic mutation, comprising administering a therapeutically-effective amount of:

(a) the AAV vector of embodiment 43 or embodiment 44; or (b) the XDP of embodiment 56, wherein upon binding of the RNP to the target nucleic acid in cells of the subject contacted by the AAV vector or XDP, transcription of the gene proximal to the binding location of the RNP is repressed.

63. The method of embodiment 62, wherein transcription of the gene in the targeted cells is repressed by at least about 10%, at least about 20%, at least about 30%, at least about 40%, at least about 50%, at least about 60%, at least about 70%, at least about 75%, at least about 80%, at least about 85%, at least about 90%, at least about 95%, or at least 99%.

64. The method of embodiment 62 or embodiment 63, wherein the treating results in improvement in at least one clinically-relevant endpoint associated with the disease or disorder.

65. The method of any one of embodiments 62-64, wherein the AAV vector or XDP is administered to the subject by a route of administration selected from subcutaneous, intradermal, intraneural, intranodal, intramedullary, intramuscular, intralumbar, intrathecal, subarachnoid, intraventricular, intracapsular, intravenous, intralymphatical, or intraperitoneal routes, wherein the administering method is injection, transfusion, or implantation, or combinations thereof.

66. The method of embodiment 65, wherein the XDP is administered at a dose of at least about $1\times10^5$ particles/kg, or at least about $1\times10^6$ particles/kg, or at least about $1\times10^7$ particles/kg, or at least about $1\times10^8$ particles/kg, or at least about $1\times10^9$ particles/kg, or at least about $1\times10^{10}$ particles/kg, or at least about $1\times10^{11}$ particles/kg, or at least about $1\times10^{12}$ particles/kg, or at least about $1\times10^{13}$ particles/kg, or at least about $1\times10^{14}$ particles/kg, or at least about $1\times10^{15}$ particles/kg, or at least about $1\times10^{16}$ particles/kg.

67. The method of embodiment 65, wherein the XDP is administered to the subject at a dose of at least about $1\times10^5$ particles/kg to about $1\times10^{16}$ particles/kg, or at least about $1\times10^6$ particles/kg to about $1\times10^{15}$ particles/kg, or at least about $1\times10^7$ particles/kg to about $1\times10^{14}$ particles/kg.

68. The method of embodiment 65, wherein the AAV vector is administered to the subject at a dose of at least about $1\times10^8$ vector genomes (vg), at least about $1\times10^5$ vector genomes/kg (vg/kg), at least about $1\times10^6$ vg/kg, at least about $1\times10^7$ vg/kg, at least about $1\times10^8$ vg/kg, at least about $1\times10^9$ vg/kg, at least about $1\times10^{10}$ vg/kg, at least about $1\times10^{11}$ vg/kg, at least about $1\times10^{12}$ vg/kg, at least about $1\times10^{13}$ vg/kg, at least about $1\times10^{14}$ vg/kg, at least about $1\times10^{15}$ vg/kg, or at least about $1\times10^{16}$ vg/kg.

69. The method of embodiment 65, wherein the AAV vector is administered to the subject at a dose of at least about $1\times10^5$ vg/kg to about $1\times10^{16}$ vg/kg, at least about $1\times10^6$ vg/kg to about $1\times10^{15}$ vg/kg, or at least about $1\times10^7$ vg/kg to about $1\times10^{14}$ vg/kg.

70. The method of any one of embodiments 62-69, wherein the XDP or AAV vector is administered to the subject according to a treatment regimen comprising one or more consecutive doses of the XDP or AAV.

71. The method of embodiment 70, wherein the therapeutically effective dose is administered to the subject as two or more doses over a period of at least two weeks, or at least one month, or at least two months, or at least three months, or at least four months, or at least five months, or at least six months, or once a year.

72. The method of any one of embodiments 62-71, wherein the subject is selected from the group consisting of mouse, rat, pig, and non-human primate.

73. The method of any one of embodiments 62-71, wherein the subject is human.

74. A pharmaceutical composition comprising the gene repressor system of any one of embodiments 1-37 and a pharmaceutically acceptable excipient.

75. The gene repressor system of any one of embodiments 1-37 for use as a medicament in the treatment of a subject a disorder caused by a genetic mutation.

76. The gene repressor system of any one of embodiments 1-37, wherein the targeting sequence of the gRNA is complementary to a non-target strand sequence located 1 nucleotide 3' of a protospacer adjacent motif (PAM) sequence.

77. The composition of embodiment 76, wherein the PAM sequence comprises a TC motif.

78. The composition of embodiment 77, wherein the PAM sequence comprises ATC, GTC, CTC or TTC.

SET 2.

1. A gene repressor system comprising:

(a) a catalytically-dead Class 2, Type V CRISPR protein;

(b) one or more transcription repressor domains; and (c) a guide ribonucleic acid (gRNA) wherein:

i) the one or more transcription repressor domains are linked to the catalytically-dead Class 2, Type V CRISPR protein as a fusion protein;

ii) the gRNA comprises a targeting sequence complementary to a target nucleic acid sequence of a gene targeted for repression, silencing, or downregulation; iii) the fusion protein is capable of forming a ribonuclear protein complex (RNP) with the gRNA; and iv) the RNP is capable of binding to the target nucleic acid.

2. The gene repressor system of embodiment 1, wherein the gene encodes mRNA, rRNA, tRNA, or structural RNA.

3. The gene repressor system of embodiment 1, wherein the one or more transcription repressor domains are selected from the group consisting of a Krüppel-associated box (KRAB), DNA methyltransferase 3 alpha (DNMT3A), DNMT3A-like protein (DNMT3L), DNA methyltransferase 3 beta (DNMT3B), DNA methyltransferase 1 (DNMT1), Friend of GATA-1 (FOG), Mad mSIN3 interaction domain (SID), enhanced SID (SID4X), nuclear receptor corepressor (NcoR), nuclear effector protein (NuE), KOX1 repression domain, the ERF repressor domain (ERD), the SRDX repression domain, histone lysine methyltransferases such as PR/SET domain containing protein (Pr-SET)7/8, lysine methyltransferase 5B (SUV4-20H1), PR/SET domain 2 (RIZ1), histone lysine demethylases such as lysine demethylase 4A (JMJD2A/JHDM3A), lysine demethylase 4B (JMJD2B), lysine demethylase 4C (JMJD2C/GASC1), lysine demethylase 4D (JMJD2D), lysine demethylase 5A (JARID1A/RBP2), lysine demethylase 5B (JARID1B/PLU-1), lysine demethylase 5C (JARID 1C/SMCX), lysine demethylase 5D (JARID1D/SMCY), sirtuin 1 (SIRT1), SIRT2, DNA methylases such as HhaI DNA m5c-methyltransferase (M.HhaI), methyltransferase 1 (MET1), histone H3 lysine 9 methyltransferase G9a (G9a), S-adenosyl-L-methionine-dependent methyltransferases superfamily protein (DRM3), DNA cytosine methyltransferase MET2a (ZMET2), methyl-CpG (mCpG) binding domain 2 (meCP2), Switch independent 3 transcription regulator family member A (SIN3A), histone deacetylase HDT1 (HDT1), n-terminal truncation of methyl-CpG-binding domain containing protein 2 (MBD2B), nuclear inhibitor of protein phosphatase-1 (NIPP1), GLP, chromomethylase 1 (CMT1), chromomethylase 2 (CMT2), heterochromatin protein 1 (HP1A), mixed lineage leukemia protein-5 (MLL5), histone-lysine N-methyltransferase SETDB1 (SETB1), Suppressor Of Variegation 3-9 Homolog 1 (SUV39H1), SUV39H2, euchromatic histone lysine methyltransferase 1 (EHMT1), histone-lysine N-methyltransferase EZH1 (EZH1), EZH2, nuclear receptor binding SET domain protein 1 (NSD1), NSD2, NSD3, ASH1 like histone lysine methyltransferase (ASH1L), tripartite motif containing 28 (TRIM28), Methyltransferase Like 3 (METTL3), METTL4, family with sequence similarity 208 member A (FAM208A), M-Phase Phosphoprotein 8 (MPHOSPH8), SET domain containing 2 (SETD2), histone deacetylase 1 (HDAC1), HDAC2, HDAC3, HDAC8, HDAC4, HDAC5, HDAC7, HDAC9, and Periphilin 1 (PPHLN1) domain.

4. The gene repressor system of embodiment 3, wherein the transcription repressor domain is a KRAB domain.

5. The gene repressor system of embodiment 4, wherein the KRAB transcriptional repressor domain is selected from the group consisting of ZNF343, ZNF337, ZNF334, ZNF215, ZNF519, ZNF485, ZNF214, ZNF33B, ZNF287, ZNF705A, ZNF37A, KRBOX4, ZKSCAN3, ZKSCAN4, ZNF57, ZNF557, ZNF705B, ZNF662, ZNF77, ZNF500, ZNF558, ZNF620, ZNF713, ZNF823, ZNF440, ZNF441, ZNF136, SNRPB, ZNF735, ZKSCAN2, ZNF619, ZNF627, ZNF333, ABCA11P, PLD5P1, ZNF25, ZNF727, ZNF595, ZNF14, ZNF33A, ZNF101, ZNF253, ZNF56, ZNF720, ZNF85, ZNF66, ZNF722P, ZNF486, ZNF682, ZNF626, ZNF100, ZNF93, ZKSCAN1, ZNF257, ZNF729, ZNF208, ZNF90, ZNF430, ZNF676, ZNF91, ZNF429, ZNF675, ZNF681, ZNF99, ZNF431, ZNF98, ZNF708, ZNF732, SSX2, ZNF721, ZNF726, ZNF730, ZNF506, ZNF728, ZNF141, ZNF723, ZNF302, ZNF484, LINC00960, SSX2B, ZNF718, ZNF74, ZNF157, ZNF790, ZNF565, ZNF705G, VN1R107P, SLC27A5, ZNF737, SSX4, ZNF850, ZNF717, ZNF155, ZNF283, ZNF404, ZNF114, ZNF716, ZNF230, ZNF45, ZNF222, ZNF286A, ZNF624, ZNF223, ZNF284, ZNF790-AS1, ZNF382, ZNF749, ZNF615, ZFP90, ZNF225, ZNF234, ZNF568, ZNF614, ZNF584, ZNF432, ZNF461, ZNF182, ZNF630, ZNF630-AS1, ZNF132, ZNF420, ZNF324B, ZNF616, ZNF471, ZNF227, ZNF324, ZNF860, ZFP28, ZNF470, ZNF586, ZNF235, ZNF274, ZNF446, ZFP1, ZIM3, ZNF212, ZNF766, ZNF264, ZNF480, ZNF667, ZNF805, ZNF610, ZNF783, ZNF621, ZNF8-DT, ZNF880, ZNF213-AS1, ZNF213, ZNF263, ZSCAN32, ZIM2, ZNF597, ZNF786, KRBA1, ZNF460, ZNF8, ZNF875, ZNF543, ZNF133, ZNF229, ZNF528, SSX1, ZNF81, ZNF578, ZNF862, ZNF777, ZNF425, ZNF548, ZNF746, ZNF282, ZNF398, ZNF599, ZNF251, ZNF195, ZNF181, RBAK-RBAKDN, ZFP37, RN7SL526P, ZNF879, ZNF26, ZSCAN21, ZNF3, ZNF354C, ZNF10, ZNF75D, ZNF426, ZNF561, ZNF562, ZNF846, ZNF782, ZNF552, ZNF587B, ZNF814, ZNF587, ZNF92, ZNF417, ZNF256, ZNF473, ZFP14, ZFP82, ZNF529, ZNF605, ZFP57, ZNF724, ZNF43, ZNF354A, ZNF547, SSX4B, ZNF585A, ZNF585B, ZNF792, ZNF789, ZNF394, ZNF655, ZFP92, ZNF41, ZNF674, ZNF546, ZNF780B, ZNF699, ZNF177, ZNF560, ZNF583, ZNF707, ZNF808, ZKSCAN5, ZNF137P, ZNF611, ZNF600, ZNF28, ZNF773, ZNF549, ZNF550, ZNF416, ZIK1, ZNF211, ZNF527, ZNF569, ZNF793, ZNF571-AS1, ZNF540, ZNF571, ZNF607, ZNF75A, ZNF205, ZNF175, ZNF268, ZNF354B, ZNF135, ZNF221, ZNF285, ZNF419, ZNF30, ZNF304, ZNF254, ZNF701, ZNF418, ZNF71, ZNF570, ZNF705E, KRBOX1, ZNF510, ZNF778, PRDM9, ZNF248, ZNF845, ZNF525, ZNF765, ZNF813, ZNF747, ZNF764, ZNF785, ZNF689, ZNF311, ZNF169, ZNF483, ZNF493, ZNF189, ZNF658, ZNF564, ZNF490, ZNF791, ZNF678, ZNF454, ZNF34, ZNF7, ZNF250, ZNF705D, ZNF641, ZNF2, ZNF554, ZNF555, ZNF556, ZNF596, ZNF517, ZNF331, ZNF18, ZNF829, ZNF772, ZNF17, ZNF112, ZNF514, ZNF688, PRDM7, ZNF695, ZNF670-ZNF695, ZNF138, ZNF670, ZNF19, ZNF316, ZNF12, ZNF202, RBAK, ZNF83, ZNF468, ZNF479, ZNF679, ZNF736, ZNF680, ZNF273, ZNF107, ZNF267, ZKSCAN8, ZNF84, ZNF573, ZNF23, ZNF559, ZNF44, ZNF563, ZNF442, ZNF799, ZNF443, ZNF709, ZNF566, ZNF69, ZNF700, ZNF763, ZNF433-AS1, ZNF433, ZNF878, ZNF844, ZNF788P, ZNF20, ZNF625-ZNF20, ZNF625, ZNF606, ZNF530, ZNF577, ZNF649, ZNF613, ZNF350, ZNF317, ZNF300, ZNF180, ZNF415, VN1R1, ZNF266, ZNF738, ZNF445, ZNF852, ZKSCAN7, ZNF660, MPRIPP1, ZNF197, ZNF567, ZNF582, ZNF439, ZFP30, ZNF559-ZNF177, ZNF226, ZNF841, ZNF544, ZNF233, ZNF534, ZNF836, ZNF320, KRBA2, ZNF761, ZNF383, ZNF224, ZNF551, ZNF154, ZNF671, ZNF776, ZNF780A, ZNF888, ZNF816-ZNF321P, ZNF321P, ZNF816, ZNF347, ZNF665, ZNF677, ZNF160, ZNF184, ZNF140, ZNF589, ZNF891, ZFP69B, ZNF436, POGK, ZNF669, ZFP69, ZNF684, ZNF124, ZNF496, and sequence variants thereof.

6. The gene repressor system of embodiment 4 or embodiment 5, wherein the KRAB domain is selected from the group of sequences consisting of SEQ ID NOS: 889-2100 and 2332-33239, or a sequence having at least about 85%, at least about 90%, at least about 91%, at least about 92%, at least about 93% at least about 94% at least about 95%, at least about 96%, at least about 97%, at least about 98%, or at least about 99% identity thereto.

7. The gene repressor system of embodiment 4 or embodiment 5, wherein the KRAB domain is selected from the group of sequences consisting of SEQ ID NOS: 889-2100 and 2332-33239.

8. The gene repressor complex of any one of embodiments 1-7, wherein the one or more transcriptional repressor domains are linked at or near the C-terminus of the catalytically-dead Class 2, Type V CRISPR protein by linker peptide sequences.

9. The gene repressor complex of embodiments 1-7, wherein the one or more transcriptional repressor domains are linked at or near the N-terminus of the catalytically-dead Class 2, Type V CRISPR protein by linker peptide sequences.

10. The gene repressor complex of any one of embodiments 1-9, wherein the fusion protein comprises two transcriptional repressor domains, wherein the first transcriptional repressor domain is different from the second transcriptional repressor domain.

11. The gene repressor complex of embodiment 10, wherein the first transcriptional repressor domain is KRAB and the second transcriptional repressor domain is selected from the group consisting of DNMT3A, DNMT3L, DNMT3B, DNMT1, FOG, SID, SID4X, NcoR, NuE, KOX1, ERD, Pr-SET 7/8, SUV4-20H1, RIZ1, JMJD2A/JHDM3A, JMJD2B, JMJD2C/GASC1, JMJD2D, JARID1A/RBP2, JARID1B/PLU-1, JARID 1C/SMCX, JARID1D/SMCY, SIRT1, SIRT2, M.HhaI, MET1, G9a, DRM3, ZMET2, meCP2, SIN3A, HDT1, MBD2B, NIPP1, GLP, CMT1, CMT2, HP1A, MLL5, SETB1, SUV39H1, SUV39H2, EHMT1, EZH1, EZH2, NSD1, NSD2, NSD3, ASH1L, TRIM28, METTL3, METTL4, FAM208A, MPHOSPH8, SETD2, HDAC1, HDAC2, HDAC3, HDAC8, HDAC4, HDAC5, HDAC7, HDAC9, and PPHLN1.

12. The gene repressor complex of embodiment 11, wherein the second transcriptional repressor domain is a DNMT3A domain, or a sequence variant thereof.

13. The gene repressor complex of embodiment 12, wherein the DNMT3A domain is selected from the group consisting of SEQ ID NOS: 33625-57543.

14. The gene repressor complex of any one of embodiments 10-13, wherein the fusion protein comprises a third transcriptional repressor domain, wherein the third transcriptional repressor domain is different from the first and the second transcriptional repressor domains.

15. The gene repressor complex of embodiment 14, wherein the third transcriptional repressor domain is selected from the group consisting of DNMT3L, DNMT3B, DNMT1, FOG, SID, SID4X, NcoR, NuE, KOX1, ERD, Pr-SET 7/8, SUV4-20H1, RIZ1, JMJD2A/JHDM3A, JMJD2B, JMJD2C/GASC1, JMJD2D, JARID1A/RBP2, JARID1B/PLU-1, JARID 1C/SMCX, JARID1D/SMCY, SIRT1, SIRT2, M.HhaI, MET1, G9a, DRM3, ZMET2, meCP2, SIN3A, HDT1, MBD2B, NIPP1, GLP, CMT1, CMT2, HP1A, MLL5, SETB1, SUV39H1, SUV39H2, EHMT1, EZH1, EZH2, NSD1, NSD2, NSD3, ASH1L, TRIM28, METTL3, METTL4, FAM208A, MPHOSPH8, SETD2, HDAC1, HDAC2, HDAC3, HDAC8, HDAC4, HDAC5, HDAC7, HDAC9, and PPHLN1.

16. The gene repressor complex of embodiment 14 or embodiment 15, wherein the third transcriptional repressor domain is DMNT3L, or a sequence variant thereof.

17. The gene repressor complex of any one of embodiments 1-16, wherein the second and/or third transcriptional repressor domains are linked to the catalytically-dead Class 2, Type V CRISPR protein or to a transcriptional repressor domain by a linker peptide sequence.

18. The gene repressor complex of any one of embodiments 8-17, wherein the linker peptide is selected from the group consisting of RS, (G)n (SEQ ID NO: 33240), (GS)n (SEQ ID NO: 33241), (GGS)n (SEQ ID NO: 33242), (GSGGS)n (SEQ ID NO: 33243), (GGSGGS)n (SEQ ID NO: 33244), (GGGS)n (SEQ ID NO: 33245), GGSG (SEQ ID NO: 33246), GGSGG (SEQ ID NO: 33247), GSGSG (SEQ ID NO: 33248), GSGGG (SEQ ID NO: 33249), GGGSG (SEQ ID NO: 33250), GSSSG (SEQ ID NO: 33251), (GP)n (SEQ ID NO: 33252), GPGP (SEQ ID NO: 33253), GGSGGGS (SEQ ID NO: 33254), GSGSGGG (SEQ ID NO: 57628), GGP, PPP, PPAPPA (SEQ ID NO: 33255), PPPGPPP (SEQ ID NO: 33256), PPPG (SEQ ID NO: 33257), PPP(GGGS)n (SEQ ID NO: 33258), (GGGS)nPPP (SEQ ID NO: 33259), AEAAAKEAAAKEAAAKA (SEQ ID NO:33260), AEAAAKEAAAKA (SEQ ID NO: 33261), SGSETPGTSESATPES (SEQ ID NO: 33262), and TPPKTKRKVEFE (SEQ ID NO: 33263), wherein n is an integer of 1 to 5.

19. The gene repressor system of any one of embodiments 1-18, wherein the catalytically-dead Class 2, Type V CRISPR protein comprises a catalytically-dead CasX variant protein (dCasX) comprising a sequence selected from the group consisting of SEQ ID NOS: 17-36 as set forth in Table 4, or a sequence having at least about 85%, at least about 90%, at least about 95%, at least about 96%, at least about 97%, at least about 98%, or at least about 99% sequence identity thereto.

20. The gene repressor system of any one of embodiments 1-18, wherein the catalytically-dead Class 2, Type V CRISPR protein comprises a catalytically-dead CasX variant protein (dCasX) comprising a sequence selected from the group consisting of the sequences SEQ ID NOS: 17-36 as set forth in Table 4.

21. The gene repressor system of any one of embodiments 1-20, wherein the fusion protein further comprises one or more nuclear localization signals (NLS).

22. The gene repressor system of embodiment 21, wherein the one or more NLS are selected from the group of sequences consisting of PKKKRKV (SEQ ID NO: 33289), KRPAATKKAGQAKKKK (SEQ ID NO: 33290), PAAKRVKLD (SEQ ID NO: 33291), RQRRNELKRSP (SEQ ID NO: 33292), NQSSNFGPMKGGNFGGRSSGPYGGGGQYFAKPRNQGGY (SEQ ID NO: 33293), RMRIZFKNKGKDTAELRRRRVEVSVELRKAKKDEQILKRRNV (SEQ ID NO: 33294), VSRKRPRP (SEQ ID NO: 33295), PPKKARED (SEQ ID NO: 33296), PQPKKKPL (SEQ ID NO: 166), SALIKKKKKMAP (SEQ ID NO: 33298), DRLRR (SEQ ID NO: 33299), PKQKKRK (SEQ ID NO: 33300), RKLKKKIKKL (SEQ ID NO: 33301), REKKKFLKRR (SEQ ID NO: 33302), KRKGDEVDGVDEVAKKKSKK (SEQ ID NO: 33303), RKCLQAGMNLEARKTKK (SEQ ID NO: 33304), PRPRKIPR (SEQ ID NO: 33305), PPRKKRTVV (SEQ ID NO: 33306), NLSKKKKRKREK (SEQ ID NO: 33307), RRPSRPFRKP (SEQ ID NO: 33308), KRPRSPSS (SEQ ID NO: 33309), KRGINDRNFWRGENERKTR (SEQ ID NO: 33310), PRPPKMARYDN (SEQ ID NO: 33311), KRSFSKAF (SEQ ID NO: 33312), KLKIKRPVK (SEQ ID NO: 33313), PKKKRKVPPPPAAKRVKLD (SEQ ID NO: 33314), PKTRRRPRRSQRKRPPT (SEQ ID NO: 33315), SRRRKANPTKLSENAKKLAKEVEN (SEQ ID NO: 33316), KTRRRPRRSQRKRPPT (SEQ ID NO: 33317), RRKKRRPRRKKRR (SEQ ID NO: 33318), PKKKSRKPKKKSRK (SEQ ID NO: 33319), HKKKHPDASVNFSEFSK (SEQ ID NO: 33320), QRPGPYDRPQRPGPYDRP (SEQ ID NO: 33321), LSPSLSPLLSPSLSPL (SEQ ID NO: 33322), RGKGGKGLGKGGAKRHRK (SEQ ID NO: 33323), PKRGRGRPKRGRGR (SEQ ID NO: 33324), PKKKRKVPPPPAAKRVKLD (SEQ ID NO: 33325), PKKKRKVPPPPKKKRKV (SEQ ID NO: 33326), PAKRARRGYKC (SEQ ID NO: 33327), KLGPRKATGRW (SEQ ID NO: 33328), PRRKREE (SEQ ID NO: 33329), PYRGRKE (SEQ ID NO: 33330), PLRKRPRR (SEQ ID NO: 33331), PLRKRPRRGSPLRKRPRR (SEQ ID NO: 33332), PAAKRVKLDGGKRTADGSEFESPKKKRKV (SEQ ID NO: 33333), PAAKRVKLDGGKRTADGSEFESPKKKRKVGIHGVPAA (SEQ ID NO: 33334), PAAKRVKLDGGKRTADGSEFESPKKKRKVAEAAAKEAAAKEAAAKA (SEQ ID NO: 33335), PAAKRVKLDGGKRTADGSEFESPKKKRKVPG (SEQ ID NO: 33336), KRKGSPERGERKRHW (SEQ ID NO: 33337), KRTADSQHSTPPKTKRKVEFEPKKKRKV (SEQ ID NO: 33338), and SEQ ID NOS: 37-112.

23. The gene repressor system of embodiment 21 or embodiment 22, wherein the one or more NLS are linked at or near the C-terminus of the dCasX or the repressor domain.

24. The gene repressor system of embodiment 21 or embodiment 22, wherein the one or more NLS are linked at or near the N-terminus of the dCasX or the repressor domain.

25. The gene repressor system of embodiment 21 or embodiment 22, wherein the one or more NLS are linked at or near both the N-terminus and the C-terminus of the dCasX or the repressor domain.

26. The gene repressor system of embodiment 21, wherein the one or more NLS are selected from the group of SEQ ID NOS: 37-71 as set forth in Table 5 and are linked at or near the N-terminus of the dCasX or the repressor domain.

27. The gene repressor system of embodiment 21, wherein the one or more NLS are selected from the group of SEQ ID NOS: 72-112 as set forth in Table 6 and are linked at or near the C-terminus of the dCasX or the repressor domain.

28. The gene repressor system of embodiment 21, wherein one or more NLS comprise an NLS selected from the group consisting of SEQ ID NOS: 37-71 as set forth in Table 5 and are linked at or near the N-terminus of the dCasX or the repressor domain, and an NLS selected from the group consisting of SEQ ID NOS: 72-112 as set forth in Table 6 and are linked at or near the C-terminus of the dCasX or the repressor domain.

29. The gene repressor system of any one of embodiments 21-28, wherein the one or more NLS are linked to the dCasX variant protein, the repressor domain, or to adjacent NLS with one or more linker peptides wherein the linker peptides are selected from the group consisting of RS, (G)n (SEQ ID NO: 33240), (GS)n (SEQ ID NO: 33241), (GGS)n (SEQ ID NO: 33242), (GSGGS)n (SEQ ID NO: 33243), (GGSGGS)n (SEQ ID NO: 33244), (GGGS)n (SEQ ID NO: 33245), GGSG (SEQ ID NO: 33246), GGSGG (SEQ ID NO: 33247), GSGSG (SEQ ID NO: 33248), GSGGG (SEQ ID NO: 33249), GGGSG (SEQ ID NO: 33250), GSSSG (SEQ ID NO: 33251), (GP)n (SEQ ID NO: 33252), GPGP (SEQ ID NO: 33253), GGSGGGS (SEQ ID NO: 33254), GGP, PPP, PPAPPA (SEQ ID NO: 33255), PPPGPPP (SEQ ID NO: 33256), PPPG (SEQ ID NO: 33257), PPP(GGGS)n (SEQ ID NO: 33258), (GGGS)nPPP (SEQ ID NO: 33259), AEAAAKEAAAKEAAAKA (SEQ ID NO: 33260), AEAAAKEAAAKA (SEQ ID NO: 33261), SGSETPGTS-ESATPES (SEQ ID NO: 33262), and TPPKTKRKVEFE (SEQ ID NO: 33263), wherein n is an integer of 1 to 5.

30. The gene repressor complex of any one of embodiments 21-29, wherein the fusion protein is configured according to a configuration as portrayed in FIG. 7.

31. The gene repressor system of any one of embodiments 1-30, wherein the gRNA has a scaffold comprising a sequence selected from the group consisting of SEQ ID NOS: 2238-2331 and 57544-57589 as set forth in Table 2, or a sequence having at least about 85%, at least about 90%, at least about 95%, at least about 96%, at least about 97%, at least about 98%, or at least about 99% sequence identity thereto.

32. The gene repressor system of any one of embodiments 1-31, wherein the gRNA has a scaffold comprising a sequence selected from the group consisting of SEQ ID NOS: 2238-2331 and 57544-57589, as set forth in Table 2.

33. The gene repressor system of any one of embodiments 1-32, wherein the gRNA comprises a targeting sequence having 15, 16, 17, 18, 19, 20, or 21 nucleotides.

34. The gene repressor system of embodiment 33, wherein the target nucleic acid sequence complementary to the targeting sequence is within 1 kb of a transcription start site (TSS) in the gene.

35. The gene repressor system of embodiment 33, wherein the target nucleic acid sequence complementary to the targeting sequence is within 500 bps upstream to 500 bps downstream of a TSS of the gene.

36. The gene repressor system of embodiment 33, wherein the target nucleic acid sequence complementary to the targeting sequence is within 300 bps upstream to 300 bps downstream of a TSS of the gene.

37. The gene repressor system of embodiment 33, wherein the target nucleic acid sequence complementary to the targeting sequence is within 1 kb of an enhancer of the gene.

38. The gene repressor system of embodiment 33, wherein the target nucleic acid sequence complementary to the targeting sequence is within the 3' untranslated region of the gene.

39. The gene repressor system of embodiment 33, wherein the target nucleic acid sequence complementary to the targeting sequence is within an exon of the gene.

40. The gene repressor system of embodiment 39, wherein the target nucleic acid sequence complementary to the targeting sequence is within exon 1 of the gene.

41. The gene repressor system of any one of embodiments 1-40, wherein the RNP is capable of binding to the target nucleic acid but is not capable of cleaving the target nucleic acid.

42. A nucleic acid encoding the fusion protein of the gene repressor system of any one of embodiments 1-41.

43. A nucleic acid encoding the gRNA of the gene repressor system of any one of embodiments 1-41.

44. The nucleic acid of embodiment 42, wherein the nucleic acid sequence is codon optimized for expression in a eukaryotic cell.

45. A lipid nanoparticle comprising the nucleic acid of embodiment 42.

46. A lipid nanoparticle comprising the nucleic acid of embodiment 43.

47. A lipid nanoparticle comprising a first nucleic acid encoding the fusion protein and a second nucleic acid comprising the gRNA of the repressor system of any one of embodiments 1-41.

48. A lipid nanoparticle composition comprising a first population of lipid nanoparticles and a second population of lipid nanoparticles, and nucleic acids encoding the gene repressor system of any one of embodiments 1-41, wherein the first population comprises lipid nanoparticles that encapsidate a first nucleic acid encoding the fusion protein and the second population of lipid nanoparticles comprises nanoparticles that encapsidate a second nucleic acid encoding the gRNA or that comprises the gRNA.

49. A vector comprising the nucleic acid of any one of embodiments 42-44.

50. The vector of embodiment 49, wherein the vector is selected from the group consisting of a retroviral vector, a lentiviral vector, an adenoviral vector, an adeno-associated viral (AAV) vector, a herpes simplex virus (HSV) vector, a virus-like particle (VLP) vector, a plasmid, a minicircle, a nanoplasmid, and an RNA vector.

51. The vector of embodiment 50, wherein the vector is an AAV vector.

52. The vector of embodiment 51, wherein the AAV vector is selected from AAV1, AAV2, AAV3, AAV4, AAV5, AAV6, AAV7, AAV8, AAV9, AAV10, AAV11, AAV12, AAV 44.9, AAV-Rh74, or AAVRh10.

53. The vector of embodiment 51 or embodiment 52, wherein the nucleic acid encoding the fusion protein and the gRNA are incorporated as a transgene between a 5' and a 3' inverted terminal repeat (ITR) sequence within the AAV.

54. A delivery particle system (XDP) comprising:

(a) one or more components of selected from the group consisting of a matrix protein (MA), a nucleocapsid protein (NC), a capsid protein (CA), a p1 peptide, a p6 peptide, a p2A peptide, a p2B peptide, a p10 peptide, a p12 peptide, a pp21/24 peptide, a p12/p3/p8 peptide, a p20 peptide, an MS2 coat protein, PP7 coat protein, Q coat protein, U1A signal recognition particle, phage R-loop, Rev protein, and Psi packaging element;

(b) an RNP comprising the gene repressor system of any one of embodiments 1-41 wherein the RNP is encapsidated within the XDP;

(c) a tropism factor incorporated on the XDP surface that provides for binding and fusion of the XDP to a target cell.

55. The XDP of embodiment 54, wherein the tropism factor is selected from the group consisting of a pseudotyping viral envelope glycoprotein, an antibody fragment, or a cell receptor fragment.

56. A method of repressing transcription of a target nucleic acid sequence of a gene in a population of cells, the method comprising introducing into the cells:

(a) an RNP comprising the gene repressor system of any one of embodiments 1-41;

(b) the nucleic acid of any one of embodiments 42-44;

(c) the vector of any one of embodiments 49-53;

(d) the XDP of embodiment 54 or 55;

(e) the lipid nanoparticle of any one of embodiments 45-47; or (f) the lipid nanoparticle composition of embodiment 48, wherein upon binding of the RNP of the gene repressor system to the target nucleic acid, transcription of the gene proximal to the binding location of the RNP is repressed in the cells.

57. The method of embodiment 56, wherein the binding location of the RNP is selected from the group consisting of:

(a) a sequence within 300 to 1,000 base pairs 5' to a transcription start site (TSS) in the gene;

(b) a sequence within 300 to 1,000 base pairs 3' to a TSS in the gene;

(c) a sequence within 300 to 1,000 base pairs to an enhancer of the gene;

(d) a sequence within the open reading frame of the gene;

(e) a sequence within an exon of the gene; or (f) a sequence in the 3' untranslated region (UTR) of the gene.

58. The method of embodiment 56 or embodiment 57, wherein transcription of the gene is repressed 5' to the binding location of the RNP.

59. The method of embodiment 56 or embodiment 57, wherein transcription of the gene is repressed 3' to the binding location of the RNP.

60. The method of any one of embodiments 56-59, wherein transcription of the gene in the population of cells is repressed by at least about 10%, at least about 20%, at least about 30%, at least about 40%, at least about 50%, at least about 60%, at least about 70%, at least about 75%, at least about 80%, at least about 85%, at least about 90%, at least about 95%, or at least 99% greater compared to untreated cells, when assessed in an in vitro assay.

61. The method of any one of embodiments 56-60, wherein off-target methylation or off-target transcription repression is less than about 10%, less than about 9%, less than about 8%, less than about 7%, less than about 6%, less than about 5%, less than about 4%, less than about 3%, less than about 2%, or less than about 1% in the cells, when assessed in an in vitro assay.

62. The method of any one of embodiments 56-61, wherein the repression of transcription in the cells is sustained for at least about 8 hours, at least about 1 day, at least about 7 days, at least about 1 month, or at least about 2 months.

63. The method of any one of embodiments 56-62, further comprising a second gRNA or a nucleic acid encoding the second gNA, wherein the second gNA has a targeting sequence complementary to a different portion of the target nucleic acid sequence and is capable of forming a ribonuclear protein complex (RNP) with the fusion protein comprising the catalytically-dead Class 2, Type V CRISPR protein and the one or more transcription repressor domains.

64. The method of any one of embodiments 56-63, wherein the method mediates a heritable epigenetic change in the gene of the cells.

65. A method of treating a subject with a disorder caused by a genetic mutation, comprising administering a therapeutically-effective dose of:

(a) the AAV vector of any one of embodiments 51-53;

(b) the XDP of embodiment 54 or embodiment 55;

(c) the lipid nanoparticle of any one of embodiments 45-47; or (d) the lipid nanoparticle composition of embodiment 48;

wherein upon binding of the RNP of the gene repressor system to the target nucleic acid of a gene in cells of the subject transcription of the gene proximal to the binding location of the RNP is repressed.

66. The method of embodiment 65, wherein transcription of the gene is repressed 5' to the binding location of the RNP.

67. The method of embodiment 65, wherein transcription of the gene is repressed 3' to the binding location of the RNP.

68. The method of any one of embodiments 65, wherein transcription of the gene in the cells is repressed by at least about 10%, at least about 20%, at least about 30%, at least about 40%, at least about 50%, at least about 60%, at least about 70%, at least about 75%, at least about 80%, at least about 85%, at least about 90%, at least about 95%, or at least 99%.

69. The method of any one of embodiments 65, wherein the repression of transcription of the gene in the cells is sustained for at least about 8 hours, at least about 1 day, at least about 7 days, at least about 1 month, or at least about 2 months.

70. The method of any one of embodiments 65-69, wherein the method mediates a heritable epigenetic change in the gene of the cells of the subject.

71. The method of any one of embodiments 65-70, wherein the AAV vector, XDP, or the lipid nanoparticles are administered to the subject by a route of administration selected from subcutaneous, intradermal, intraneural, intranodal, intramedullary, intramuscular, intralumbar, intrathecal, subarachnoid, intraventricular, intracapsular, intravenous, intralymphatical, or intraperitoneal routes, wherein the administering method is injection, transfusion, or implantation, or combinations thereof.

72. The method of embodiment 71, wherein the XDP or the lipid nanoparticles are administered at a dose of at least about $1\times10^5$ particles/kg, or at least about $1\times10^6$ particles/kg, or at least about $1\times10^7$ particles/kg, or at least about $1\times10^8$ particles/kg, or at least about $1\times10^9$ particles/kg, or at least about $1\times10^{10}$ particles/kg, or at least about $1\times10^{11}$ particles/kg, or at least about $1\times10^{12}$ particles/kg, or at least about $1\times10^{13}$ particles/kg, or at least about $1\times10^{14}$ particles/kg, or at least about $1\times10^{15}$ particles/kg, or at least about $1\times10^{16}$ particles/kg.

73. The method of embodiment 71, wherein the XDP or the lipid nanoparticles are administered to the subject at a dose of at least about $1\times10^5$ particles/kg to about $1\times10^{16}$ particles/kg, or at least about $1\times10^6$ particles/kg to about $1\times10^{15}$ particles/kg, or at least about $1\times10^7$ particles/kg to about $1\times10^{14}$ particles/kg.

74. The method of embodiment 71, wherein the AAV vector is administered to the subject at a dose of at least about $1\times10^8$ vector genomes (vg), at least about $1\times10^5$ vector genomes/kg (vg/kg), at least about $1\times10^6$ vg/kg, at least about $1\times10^7$ vg/kg, at least about $1\times10^8$ vg/kg, at least about $1\times10^9$ vg/kg, at least about $1\times10^{10}$ vg/kg, at least about $1\times10^{11}$ vg/kg, at least about $1\times10^{12}$ vg/kg, at least about $1\times10^{13}$ vg/kg, at least about $1\times10^{14}$ vg/kg, at least about $1\times10^{15}$ vg/kg, or at least about $1\times10^{16}$ vg/kg.

75. The method of embodiment 71, wherein the AAV vector is administered to the subject at a dose of at least about $1\times10^5$ vg/kg to about $1\times10^{16}$ vg/kg, at least about $1\times10^6$ vg/kg to about $1\times10^{15}$ vg/kg, or at least about $1\times10^7$ vg/kg to about $1\times10^{14}$ vg/kg.

76. The method of embodiment 71, wherein the first and second lipid nanoparticles are each administered at a dose of at least about $1\times10^5$ particles/kg, or at least about $1\times10^6$ particles/kg, or at least about $1\times10^7$ particles/kg, or at least about $1\times10^8$ particles/kg, or at least about $1\times10^9$ particles/kg, or at least about $1\times10^{10}$ particles/kg, or at least about $1\times10^{11}$ particles/kg, or at least about $1\times10^{12}$ particles/kg, or at least about $1\times10^{13}$ particles/kg, or at least about $1\times10^{14}$ particles/kg, or at least about $1\times10^{15}$ particles/kg, or at least about $1\times10^{16}$ particles/kg.

77. The method of embodiment 71, wherein the first and the second lipid nanoparticles are each administered to the subject at a dose of at least about $1\times10^5$ particles/kg to about $1\times10^{16}$ particles/kg, or at least about $1\times10^6$ particles/kg to about $1\times10^{15}$ particles/kg, or at least about $1\times10^7$ particles/kg to about $1\times10^{14}$ particles/kg.

78. The method of any one of embodiments 65-77, wherein the XDP, the AAV vector, or the first and second lipid nanoparticles are administered to the subject according to a treatment regimen comprising one or more consecutive doses.

79. The method of any one of embodiments 65-78, wherein the therapeutically effective dose is administered to the subject as two or more doses over a period of at least two weeks, or at least one month, or at least two months, or at least three months, or at least four months, or at least five months, or at least six months, or once a year.

80. The method of any one of embodiments 65-79, wherein the treating results in improvement in at least one clinically-relevant endpoint associated with the disorder in the subject.

81. The method of any one of embodiments 65-79, wherein the subject is selected from the group consisting of mouse, rat, pig, and non-human primate.

82. The method of any one of embodiments 65-79, wherein the subject is human.

83. A pharmaceutical composition comprising the gene repressor system of any one of embodiments 1-41 and a pharmaceutically acceptable excipient.

84. The gene repressor system of any one of embodiments 1-41 for use as a medicament in the treatment of a subject a disorder caused by a genetic mutation.

85. The gene repressor system of any one of embodiments 1-41, wherein the targeting sequence of the gRNA is complementary to a non-target strand sequence located 1 nucleotide 3' of a protospacer adjacent motif (PAM) sequence.

86. The composition of embodiment 85, wherein the PAM sequence comprises a TC motif.

87. The composition of embodiment 85 or embodiment 86, wherein the PAM sequence comprises ATC, GTC, CTC or TTC.

88. The composition of embodiment 85, wherein the PAM sequence comprises a TC motif.

89. The composition of embodiment 85 or embodiment 86, wherein the PAM sequence comprises ATC, GTC, CTC or TTC.

EXAMPLES

Example 1: Demonstration of a Catalytically-Dead CasX Repressor (dXR) System on Repression of B2M at RNA and Protein Levels Experiments were performed to determine if various catalytically-dead CasX repressor (dXR) constructs can act as transcriptional repressors in mammalian cells.

Materials and Methods:

dXR variant plasmids encoding constructs having the configuration of U6-gRNA+Ef1α-NLS-GGS-dCasX491-GGS-KRAB variant-NLS (dCasX491 refers to catalytically-dead CasX 491), were transiently transfected into HEK293T cells in an arrayed 96-well format. These constructs also contained a 2× FLAG sequence, as well as sequences encoding either a gRNA scaffold 174 (SEQ ID NO: 2238) having a spacer (spacer 7.37) targeting the endogenous B2M (beta-2-microglobulin) gene or a non-targeting control (spacer 0.0), which were all cloned upstream of a P2A-puromycin element on the plasmid. Four different effector domains were tested in addition to the "naked" dCasX491 (KRAB variant domains listed in Table 9; spacer sequences listed in Table 10; sequences of additional elements listed in Table 11). The sequences encoding the full dXR molecule are listed in Table 12. The corresponding protein sequences of the dXR molecule are listed in Table 13, and the generic configuration of the dXR molecule is illustrated in FIG. 38. Positive and negative controls based on a catalytically-dead Cas9 nuclease (with or without a ZNF10 repressor) with a B2M-targeting gRNA (spacer 7.14) or a non-targeting gRNA control (spacer 0.0) were included, along with a catalytically-active CasX 491 and gRNA with the same 7.37 and 0.0 spacers. Two days after transfection, total RNA was harvested, and reverse transcribed to generate a cDNA library. Changes in gene expression were calculated by performing qPCR on the targeted gene and a housekeeping gene as reference. Relative gene expression represents the amount of target-specific RNA relative to a reference gene normalized to the non-targeting guide condition for two biological replicates. In addition to the wells used for RNA measurements, a separate set of wells was harvested seven days post-transfection and analyzed for B2M protein expression. Expression of B2M protein was determined by using an antibody that detects the B2M-dependent HLA protein complex on the cell surface. Cells that expressed B2M (B2M+) were measured using flow cytometry, and the relevant data are shown in Table 14.

TABLE 9

Sequences of KRAB domains tested fused to CasX.

| Domain Name | KRAB domain sequence | Construct name | SEQ ID NO |
|---|---|---|---|
| ZIM3 | MNNSQGRVTFEDVTVNFTQGEWQRLNPEQRNLYRDVMLE-NYSNLVSVG QGETTKPDVILRLEQGKEPWLEEEEVLGSGRAEKNG-DIGGQIWKPKDV KESL | dXR1 | 337 |
| ZNF10 | MDAKSLTAWSRTLVTFKDVFVDFTREEWKLLDTAQQIVYRNVMLE-NYK NLVSLGYQLTKPDVILRLEKGEEP | dXR2 | 338 |
| ZNF10- | MDAKSLTAWSRTLVTFKDVFVDFTREEWKLLDTAQQIVYRNVMLE-NYK | dXR3 | 339 |

TABLE 9-continued

| Sequences of KRAB domains tested fused to CasX. | | | |
|---|---|---|---|
| Domain Name | KRAB domain sequence | Construct name | SEQ ID NO |
| MeCP2 | NLVSLGYQLTKPDVILR-LEKGEEPWLVSGGGSGGSGSSPKKKRKVEAS VQVKRVLEKSPGKLLVKMPFQASPGGKGEGGGATTSAQVM-VIKRPGRK RKAEADPQAIPKKRGRKPGSVVAAAAAEAKKKAVKES-SIRSVQETVLP IKKRKTRETVSIEVKEVVKPLLVSTLGEKSGKGLKTCKSPGRK-SKESS PKGRSSSASSPPKKEHHHHHHHAESPKAPMPLLPPPPP-PEPQSSEDPI SPPEPQDLSSSICKEEKMPRAGSLESDGCPKEPAKTQP | | |
| ZNF334 | KMKKFQIPVSFQDLTVNFTQEEWQQLDPAQRLLYRDVMLE-NYSNLVSV GYHVSKPDVIFKLEQGEEPWIVEEFSNQNYPD | dXR4 | 340 |

TABLE 10

| Sequences of spacers tested. | | | | |
|---|---|---|---|---|
| Spacer ID | DNA sequence | SEQ ID NO | RNA sequence | SEQ ID NO |
| 7.37 | GGCCGAGATGTC TCGCTCCG | 341 | GGCCGAGAUGUC UCGCUCCG | 59628 |
| 7.148 | CGCGAGCACAGC TAAGGCCA | 342 | CGCGAGCACAGC UAAGGCCA | 59629 |
| 0.0 | CGAGACGTAATT ACGTCTCG | 343 | CGAGACGUAAUU ACGUCUCG | 59630 |

TABLE 11

Sequences of additional key dXR elements to generate the dXR construct having the configuration illustrated in FIG. 38. Note that buffer sequences are not listed.

| Key component | SEQ ID NO (DNA) | SEQ ID NO (Protein) |
|---|---|---|
| dCasX491 | 57618 | 57619 |
| Linker 3A | 57624 | 57626 |
| Linker 3B | 57625 | |
| NLS A | 57629 | 57631 |
| NLS B | 57630 | |

TABLE 12

DNA sequences of dXR constructs.

| dXR ID | KRAB domain | SEQ ID NO (DNA sequence of dXR encoding construct) |
|---|---|---|
| dXR1 | ZIM3 | 59434 |
| dXR2 | ZNF10 | 59435 |
| dXR3 | ZNF10-MeCP2 | 59436 |
| dXR4 | ZNF334 | 59437 |

TABLE 13

Protein sequences of the dXR molecules.

| dXR ID | KRAB domain | SEQ ID NO (Amino Acid Sequence of dXR Molecule) |
|---|---|---|
| dXR1 | ZIM3 | 59438 |
| dXR2 | ZNF10 | 59439 |
| dXR3 | ZNF10-MeCP2 | 59440 |
| dXR4 | ZNF334 | 59441 |

Results

All conditions with a guide RNA targeting the gene resulted in repression, although the strength of repression varied by the choice of domain (FIG. 1). Catalytically-dead CasX molecules with effector domains depleted most of the targeted RNA in 48 hours (~81% of the RNA is depleted on average) comparable to dCas9-KRAB (~82% of RNA depleted). On the protein level, dCasX confers slight repression on its own (~10% of cells negative at the protein level), but addition of any KRAB domain considerably contributed to further repression (a range of 80-89% of cells were negative for the B2M protein (Table 14). Furthermore, most CasX constructs compared favorably in depleting protein compared to the dCas9 controls (22% of cells negative for dCas9 and 81% of cells negative for dCas9-KRAB) (Table 14).

TABLE 14

Repression of B2M protein levels by CasX and Cas9 molecules and repressor constructs. Data represent biological triplicates.

| Molecule | Spacer | % cells expressing B2M protein* | std deviation |
|---|---|---|---|
| dCas9 | 0.0 | 97.34 | 0.16 |
| dCas9-KRAB | 0.0 | 98.54 | 0.19 |
| CasX | 0.0 | 98.62 | 0.66 |
| dCasX | 0.0 | 95.90 | 0.50 |
| dXR1 | 0.0 | 98.09 | 0.18 |
| dXR2 | 0.0 | 98.01 | 0.11 |
| dXR3 | 0.0 | 97.51 | 0.28 |
| dXR4 | 0.0 | 98.23 | 0.11 |
| dCas9 | 7.14 | 77.87 | 0.15 |
| dCas9-KRAB | 7.14 | 18.83 | 0.45 |
| CasX | 7.37 | 21.60 | 0.56 |
| dCasX | 7.37 | 85.70 | 0.00 |

TABLE 14-continued

Repression of B2M protein levels by CasX and Cas9 molecules and repressor constructs. Data represent biological triplicates.

| Molecule | Spacer | % cells expressing B2M protein* | std deviation |
|---|---|---|---|
| dXR1 | 7.37 | 13.50 | 0.66 |
| dXR2 | 7.37 | 16.90 | 0.96 |
| dXR3 | 7.37 | 10.20 | 0.46 |
| dXR4 | 7.37 | 19.80 | 1.64 |

*Data represent % of cells counted that were positive

In Table 14, dCasX refers to catalytically-dead CasX 491, dXR1-4 refer to dCasX491 fused to the KRAB domains indicated in Table 9, in the following orientation: U6-gRNA+Ef1α-NLS-GGS-dCasX-GGS-KRAB variant-NLS, and CasX refers to catalytically active CasX 491. dCas9-KRAB refers to dCas9 fused to a ZNF10-KRAB domain.

The results demonstrate that dXR can transcriptionally repress an endogenous locus (B2M) resulting in loss of target protein. Furthermore, the addition and choice of transcriptional effector domains affects the overall potency of the molecule.

Example 2: Demonstration of dXR Effectiveness on HBEGF for High-Throughput Screening Experiments were performed to determine the feasibility of using dXR constructs for high-throughput screening of molecules in mammalian cells.

Materials and Methods:

HEK293T cells were seeded in a 6-well plate at 300,000 cells/well and lipofected with 1 μg of plasmid encoding either a CasX molecule (491), a catalytically-dead CasX 491 with the ZNF10-KRAB repressor domain (dXR) and a guide scaffold 174 (SEQ ID NO: 2238) with a spacer targeting the HBEGF gene or a non-targeting spacer. Five combinations of CasX-based molecules and gRNAs with the indicated spacers (Table 15) were transfected into five separate wells. HBEGF is the receptor that mediates entry of diphtheria toxin that, when added to the cells, inhibits translation and leads to cell death. Targeting of the HBEGF gene with a CasX or dXR molecule and targeting gRNA should prevent toxin entry and allow survival of the cells, whereas cells treated with CasX and dXR molecules and a non-targeting gRNA should not survive. One day post-transfection, cells in each transfected well were split into 12 different wells in a 96-well plate and selected with puromycin. Over three days, cells were treated with six different concentrations of diphtheria toxin (0, 0.2, 2, 20, 200, and 2000 ng/mL), and biological duplicates were performed. After another two days, cells were split into fresh media, and total cell counts were measured on an ImageXpress Pico Automated Cell Imaging System.

TABLE 15

Sequences of spacers tested.

| Spacer ID | DNA sequence | SEQ ID NO | RNA sequence | SEQ ID NO | Molecule |
|---|---|---|---|---|---|
| 34.19 | ACTGGGAGGCTCAGCCCATG | 344 | ACUGGGAGGCUCAGCCCAUG | 59631 | CasX |
| 34.21 | TGTTCTGTCTTGAACTAGCT | 345 | UGUUCUGUCUUGAACUAGCU | 59632 | CasX |
| 34.28 | TGAGTGTCTTGTCTTGCTCA | 346 | UGAGUGUCUUGUCUUGCUCA | 59633 | dXR |
| 0.0 | CGAGACGTAATTACGTCTCG | 343 | CGAGACGUAAUUACGUCUCG | 59630 | CasX & dXR |

Results

Figure 2:
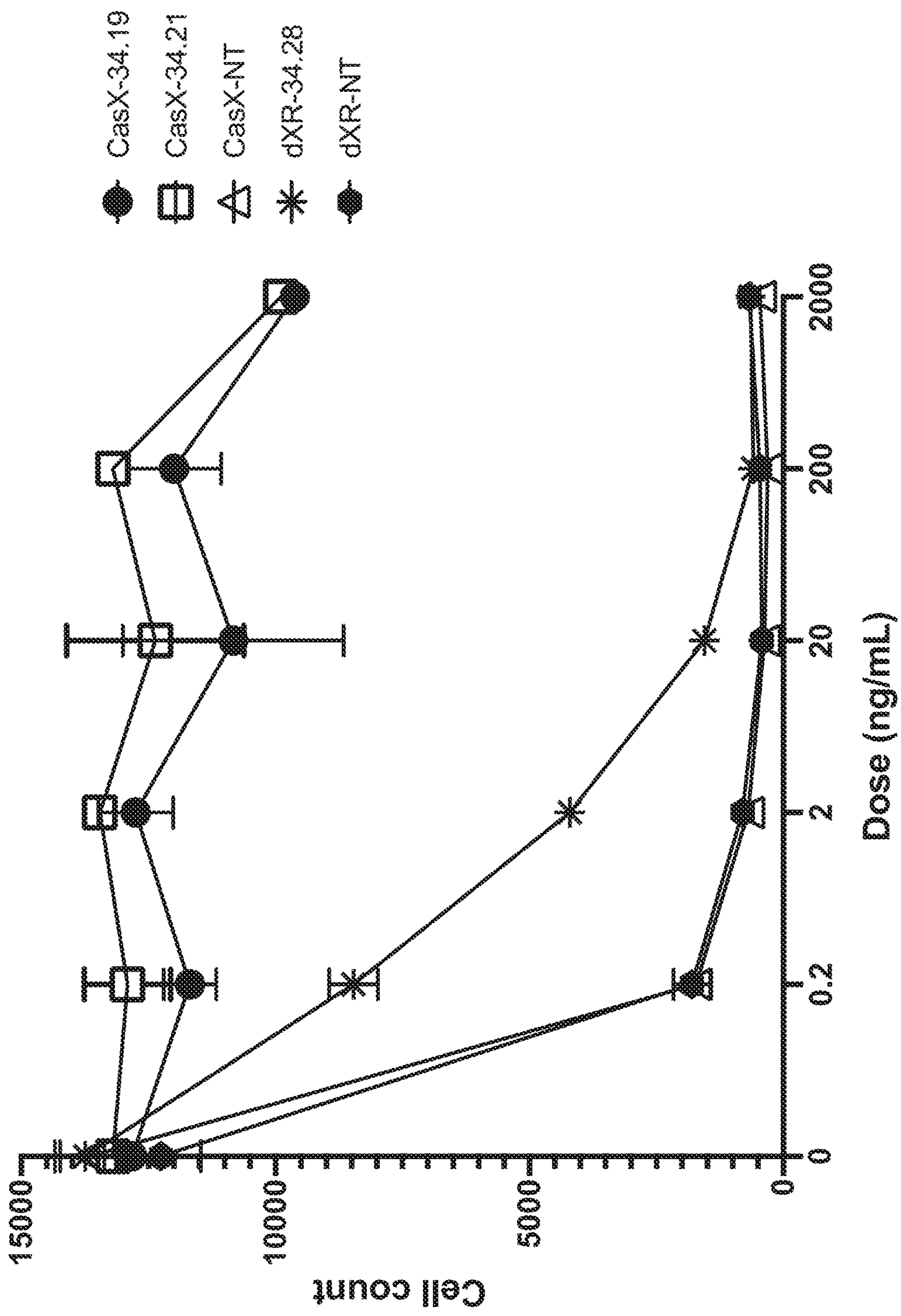
FIG. 2 shows the dose response results of the diphtheria toxin titration for cells transduced with either catalytically active CasX editors with gRNAs targeting the gene encoding the Heparin Binding EGF-like Growth Factor (HBEGF), i.e., CasX-34.19 and CasX-34.21; a catalytically-dead CasX (dCasX) protein linked to a repressor domain as a fusion protein targeted to HBEGF (dXR fusion proteins, i.e., dXR1-34.28); or a non-targeting dXR molecule (CasX-NT or dXR-NT), as described in Example 2. Data represent the mean and standard deviation of two biological replicates.

The results of the diphtheria toxin assay are illustrated in the plot in FIG. 2. dXR-mediated repression of the HBEGF gene resulted in survival of cells, but only at low doses of toxin (0.2-20 ng/mL). However, those same doses led to complete cell death in the control cells treated with non-targeting constructs. High doses (>20 ng/mL) of toxin led to cell death in both the dXR and control samples, suggesting that the basal level of transcription permitted by dXR allows sufficient toxin to enter and trigger cell death. The results show that CasX-edited cells remained protected as editing of the locus leads to complete loss of functional protein. The non-targeting controls died at all doses, demonstrating the efficacy of the toxin when HBEGF is not repressed or edited.

The results show that dXR protects at low doses of toxin, demonstrating that this molecule can be screened in a range of 0.2-20 ng/mL diphtheria toxin, with highest fold-enrichment between dXR and control observed at 0.2 ng/mL. Note that while CasX protects at all doses, repression by dXR still induces low basal expression of the target that leads to toxicity of the cells at high doses of the toxin.

Example 3: Demonstration of the Ability of Catalytically Dead CasX-Based Repressor (dXR) to Repress C9orf72

Experiments were performed to determine if dCasX-based repressors can induce transcriptional silencing of a reporter constructed with the 5'UTR of the C9orf72 gene. This system will allow studying the efficacy of dXR-gRNA combinations in cell types in which C9orf72 is not endogenously expressed and, furthermore, allow high-throughput screening of additional dXR molecules using a gRNA with spacers known to be active in editing systems.

Materials and Methods:

A clonal reporter cell line was constructed by nucleofecting K562 (a human myelogenous leukemia cell line) cells with a plasmid reporter containing the CMV promoter, the C9orf72 complete 5'UTR (Exon1a-Exon1b-Exon2 with all potential ATG start codons mutated and two artificial PAMs added at the 5' and 3' ends), and a coding sequence of TurboGFP-PEST-p2A-HSV_TK. The CMV promoter allows constitutive expression of the reporter, the C9orf72 5'UTR provides a sequence to target with dCasX constructs, and the GFP and TK (Herpes Simplex Virus-1 Thymidine Kinase) proteins provide markers for selection and counter-selection. Specifically, TK metabolizes the typically inert pro-drug ganciclovir into a toxic thymidine analog that leads to cell death. The nucleofected cells were selected in hygromycin for 1 month, sorted to single cells and characterized for ganciclovir sensitivity. A single clone (GFP-TK-c10)

was selected that displayed complete cell death within 5 days at a ganciclovir concentration of 5 μg/mL.

GFP-TK-c10 cells were transduced (250,000 cells; 6-well format) with lentiviruses encoding dXR molecule containing the ZNF10-KRAB domain and gRNA with scaffold 174 (SEQ ID NO: 2238) and spacers targeting the 5'UTR sequence of the C9orf72 locus present in the GFP-TK reporter (Table 16). Transductions were carried out in an arrayed fashion in which one lentivirus was applied to one well of cells. 48 hours after transduction, cells were treated with 5 μg/mL ganciclovir for 5 days and then stained with trypan blue and counted on an automated cell counter.

TABLE 16

Spacers tested in arrayed transductions.

| Spacer ID | DNA sequence | SEQ ID NO | RNA sequence | SEQ ID NO |
|---|---|---|---|---|
| 29.2000 | CGTAACCTACGG TGTCCCGC | 347 | CGUAACCUACGG UGUCCCGC | 59670 |
| 29.168 | TAGCGGGACACC GTAGGTTA | 348 | UAGCGGGACACC GUAGGUUA | 59671 |
| 29.163 | CTTTTGGGGGCG GGGTCTAG | 349 | CUUUUGGGGGCG GGGUCUAG | 59672 |
| 0.0 | CGAGACGTAATT ACGTCTCG | 343 | CGAGACGUAAUU ACGUCUCG | 59630 |

Separately, cells were transduced (250,000 cells; 6-well format) with multiple virus combinations at defined ratios (Table 17). 48 hours post-transduction, half of the cells in each well were harvested and frozen as cell pellets, and the other half were selected in the same manner (5 days; 5 μg/mL ganciclovir). After ganciclovir selection the remaining cells were harvested and gDNA was extracted from both pre- and post-ganciclovir treatment samples. Primers flanking the region containing the spacer sequence in the lentivirus constructs were used to generate amplicons for next generation sequencing analysis in which the ratios of the spacers in each well were compared pre- and post-selection. These ratios were used to calculate spacer fitness scores for each competition by taking the log 2 of the fold change in the spacer frequency from pre-selection to post-selection. Fitness was determined by the following equation:

$$\text{Fitness} = \log_2(\text{spacer frequency post-selection}/\text{spacer frequency pre-selection})$$

TABLE 17

Matrix of competition experiments (each virus present at equal ratio).

| Experiment | 29.2000 (1) | 29.168 (2) | 29.163 (3) | 0.0 (NT) |
|---|---|---|---|---|
| 1 | + | − | − | + |
| 2 | − | + | − | + |
| 3 | − | − | + | + |
| 4 | + | + | − | + |
| 5 | + | − | + | + |
| 6 | − | + | + | + |
| 7 | + | + | + | + |

Results

Figure 3:
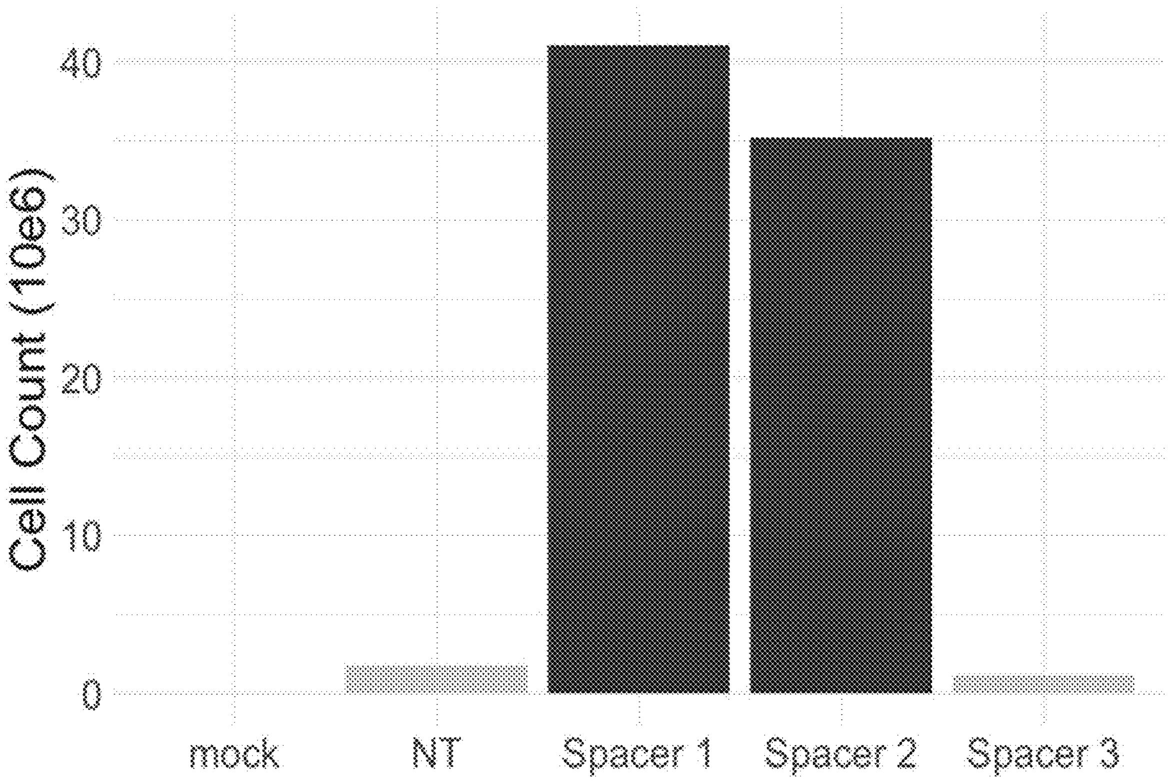
FIG. 3 shows cell counts from arrayed testing of dXR and three spacers targeting the 5'UTR sequence of the C9orf72 locus in a TK-GFP cell line after ganciclovir treatment, as described in Example 3. Data represent single point cell counts after treatment with ganciclovir. NT: non-targeting spacer.

Treatment with dXR containing the ZNF10-KRAB domain and guide 174 with Spacers 1 (29.2000) and 2 (29.168) permitted cell survival (FIG. 3), while mock, NT (0.0) and Spacer 3 (29.163) conditions all resulted in cell death. The results of constructs utilizing Spacers 1 and 2 demonstrate that the combination of a dXR molecule and a C9orf72-targeting spacer can induce potent transcriptional repression, establishing this system as a platform by which to measure dXR and spacer potency at a therapeutically-relevant locus.

Furthermore, measurements of spacer fitness in Table 18 demonstrate the quantitative and reproducible nature of this assay as constructs utilizing Spacers 1 and 2 both permitted cell survival, with Spacer 2 measurably more potent than Spacer 1 in all competitions. Furthermore, constructs with Spacer 3 were ineffective in almost all competitions, demonstrating the utility of this system in screening for effective spacers.

The results demonstrate that dXR molecules can transcriptionally repress therapeutically-relevant sequences and distinguish between functional and non-functional spacers.

TABLE 18

Spacer fitness calculated from lentivirus competition experiments.

| Experiment | Spacer | Fitness* |
|---|---|---|
| 1 | 1 | 0.65 |
| 1 | NT | −3.38 |
| 2 | 2 | 0.88 |
| 2 | NT | −3.10 |
| 3 | 3 | 0.12 |
| 3 | NT | −0.38 |
| 4 | 1 | −0.09 |
| 4 | 2 | 0.83 |
| 5 | 1 | 0.90 |
| 5 | 2 | 0.98 |
| 5 | 3 | −4.40 |
| 5 | NT | −3.44 |

*Data represent the log2 fold change in frequency of spacer counts as measured by next generation sequencing; a positive score indicates a spacer is more fit than the other spacers present in the competition.

Example 4: Development of a Selection to Identify Improved Repressors for Inclusion in dXR Compositions To develop better dXR molecules, a library of transcriptional effector domains from many species was tested in a selection assay. As KRAB domains are one of the largest and most rapidly-evolved domains in vertebrates, domains from species not previously evaluated were anticipated to provide improved strength and permanence of repression.

Materials and Methods:

Identification of Candidate KRAB Domains:

KRAB domains were identified by downloading all sequences annotated with Prosite accession ps50805 (the accession number for KRAB domains). All domains were extended by 100 amino acids (with the annotation centered in the middle) to include potential unannotated functional sequence. In addition, HMMER, a tool to identify domains, was run on a set of high-quality primate annotations from recently completed alignments of long-read primate genome assemblies described (Warren, W C, et al. Sequence diversity analyses of an improved rhesus macaque genome enhance its biomedical utility. Science 370, Issue 6523, eabc6617in (2020); Fiddes, I T, et al. Comparative Annotation Toolkit (CAT)-simultaneous clade and personal genome annotation. Genome Res. 28(7):1029 (2018); Mao, Y, et al. A high-quality bonobo genome refines the analysis of hominid evolution. Nature 594:77 (2021)), to identify KRAB domains in these assemblies most of which were not present in UniProt. The search resulted in 32,120 unique sequences from 159 different organisms that will be tested for their potency in repression. The complete list of sequences is listed as SEQ ID NOS: 355-2100 and 2332-33239. Additionally, 580 random amino acid sequence 80 residues in length were included in the library as negative controls, and 304 human KRAB domains were included based on work by Tycko, J. et al. (*Cell.* 2020 Dec. 23; 183(7):2020-2035).

Screening Methods:

The KRAB domains described above were synthesized as DNA oligos, amplified, and cloned into a dCasX491 C-terminal GS linker lentiviral construct along with guide scaffold 174 (SEQ ID NO: 2238) with either Spacer 34.28 or Spacer 29.168, both of which repress their respective targets (i.e., HBEGF and GFP-TK) and confer survival in the assays described in the above Examples. For each KRAB domain, the C-terminal GS linker was synonymously substituted to produce unique DNA barcodes that could be differentiated by NGS allowing internal technical replicates to be assessed in each pooled experiment. These plasmids were used to generate the lentiviral constructs of the library. The lentiviral library with 29,168 plasmids were used to transduce GFP-TK cells, which were treated with 1 μg/mL puromycin to remove untransduced cells, then 5 μg/mL ganciclovir for 5 days. After selection, gDNA was extracted, and gDNA containing the KRAB domain in the surviving cells was amplified and sequenced.

An analogous assay was performed with the lentiviral library with spacer 34.28 targeting HBEGF. HEK293T cells were transduced, treated with 1 μg/mL puromycin to remove untransduced cells, and selection was carried out at 2 ng/mL diphtheria toxin for 48 hours. gDNA was extracted, amplified, and sequenced as described above. gDNA samples were also extracted, amplified, and sequenced from the cells before selection with ganciclovir or diphtheria toxin, as a control. Two independent replicates were performed for both the diphtheria toxin and GFP-TK selections.

Assessment of B2M Repression:

Representative KRAB domains were cloned into a dCasX491 C-terminal GS linker lentiviral construct along with guide scaffold 316 (SEQ ID NO: 59352) with spacer 7.15 (GGAAUGCCCGCCAGCGCGAC; SEQ ID NO: 59634), targeting the B2M locus. Separately, representative KRAB domains were cloned into a dCasX491 C-terminal GS linker lentiviral construct along with guide scaffold 174 (SEQ ID NO: 2238) with spacer 7.37 (SEQ ID NO: 57644), targeting the B2M locus. The lentiviral plasmid constructs encoding dXRs with various KRAB domains were generated using standard molecular cloning techniques. These constructs included sequences encoding dCasX491, and a KRAB domain from ZNF10, ZIM3, or one of the KRAB domains tested in the library. Cloned and sequence-validated constructs were midi-prepped and subjected to quality assessment prior to transfection in HEK293T cells.

HEK293T cells were seeded at a density of 30,000 cells in each well of a 96-well plate. The next day, each well was transiently transfected using lipofectamine with 100 ng of dXR plasmids, each containing a dXR construct with a different KRAB domain and a gRNA having a targeting spacer to the B2M locus. Experimental controls included dXR constructs with KRAB domains from ZNF10 or ZIM3, KRAB domains that were in the library but not in the top 95 or 1597 KRAB domains, or dCas9-ZNF10, each with a corresponding B2M-targeting gRNA. Each construct was tested in triplicate. 24 hours post-transfection, cells were selected with 1p g/mL puromycin for two days. Seven or ten days after transfection, cells were harvested for editing repression analysis by analyzing B2M protein expression via HLA immunostaining followed by flow cytometry. B2M expression was determined by using an antibody that would detect the B2M-dependent HLA protein expressed on the cell surface. HLA+ cells were measured using the Attune™ NxT flow cytometer.

Data Analysis:

To understand the diversity of protein sequences in the tested KRAB library, an evolutionary scale modeling (ESM) transformer (ESM-1b) was applied to the initial library of 32,120 KRAB domain amino acid sequences to generate a high dimensional representation of the sequences (Rives, A. et al. *Proc Natl Acad Sci USA.* 2021 Apr. 13; 118(15)). Next, Uniform Manifold Approximation and Projection (UMAP) was applied to reduce the data set to a two-dimensional representation of the sequence diversity (McInnes, L., Healy, J., ArXiv e-prints 1802.03426, 2018). Using this technique, 75 clusters of KRAB domain sequences were identified.

Protein sequence motifs were generated using the STREME algorithm (Bailey, T., *Bioinformatics.* 2021 Mar. 24; 37(18):2834-2840) to identify motifs enriched in strong repressors.

Results

Selections were performed to identify the KRAB domains out of a library of 32,120 unique sequences that were the most potent transcriptional repressors. The diphtheria toxin selections produced higher quality NGS libraries and were therefore selected for further analysis. The fold change in the abundance of each KRAB domain in the library before and after selection was calculated for each barcode-KRAB pair such that together the two independent replicates of the experiment represent 12 measurements of each KRAB domain's fitness.

Figure 16:
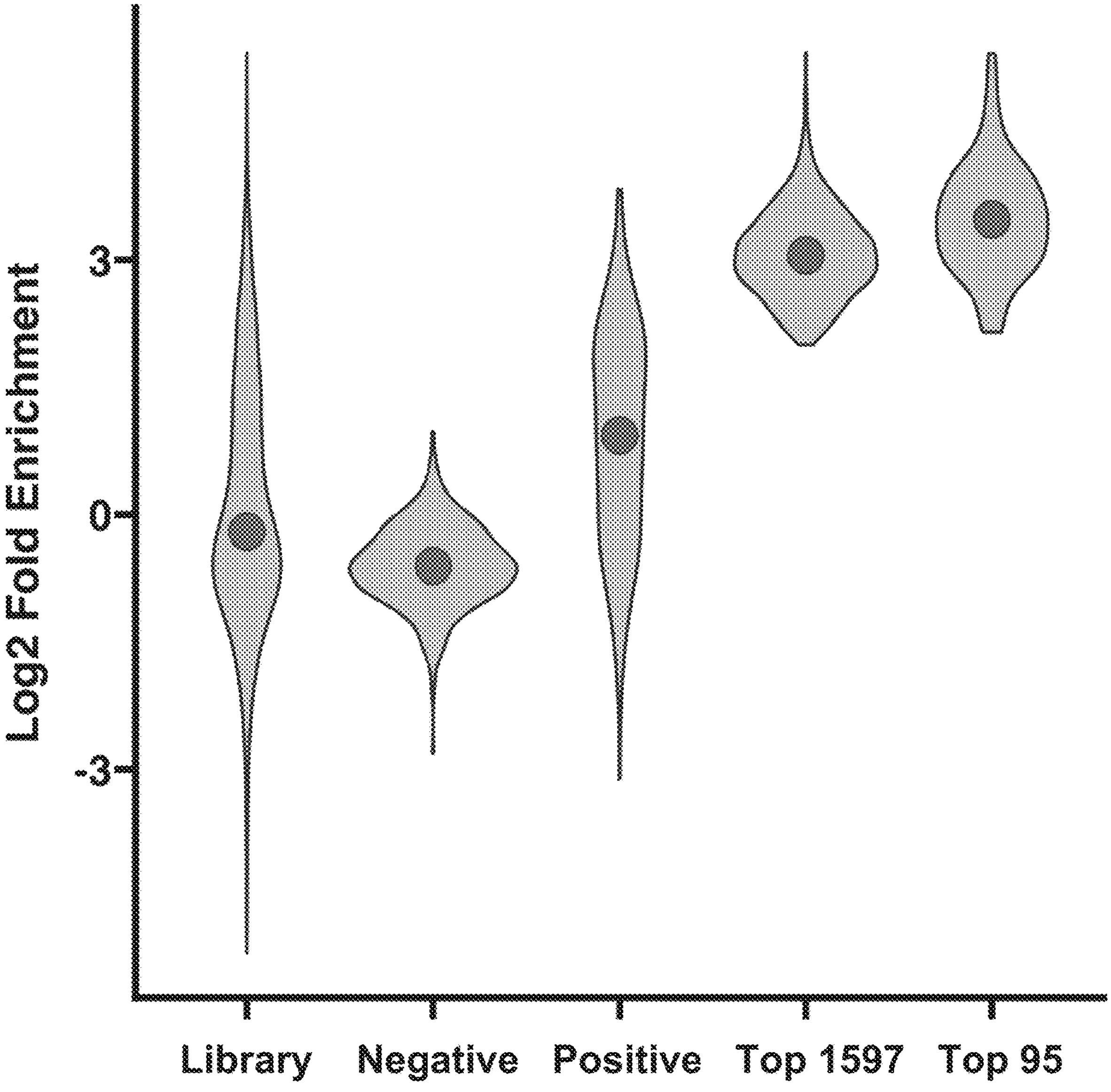
FIG. 16 provides violin plots showing the log 2 (fold change) of sequences before and after selection for their ability to support dXR repression of the HBEGF locus, as described in Example 4. The plots show the results for the entire KRAB domain library, a negative control set of sequences, a positive control set of known KRAB repressors, the top 1597 KRAB domains tested with log 2(fold change)>2 and p-values<0.01, and the top 95 KRAB domains tested.

FIG. 16 shows the range of $\log_2$(fold change) values for the entire library, the randomized sequences that served as negative controls, a positive control set of KRAB domains that were shown to have a $\log_2$(fold change) greater than 1 on day 5 of the HT-recruit experiment performed by Tycko et al. (Cell. 2020 Dec. 23; 183(7):2020-2035). As shown in FIG. 16, the diphtheria toxin selection successfully enriched for KRAB domains that were more potent repressors. The negative control sequences were de-enriched from the library following selection.

To identify the KRAB domains that were reproducibly enriched in the post-selection library, a p-value threshold of less than 0.01 and a log 2(fold change) threshold of greater than 2 was set. 1597 KRAB domains met these criteria. P-values were calculated via the MAGeCK algorithm which uses a permutation test and false discovery rate adjustment for multiple testing (Wei, L. et al. *Genome Biol.* 2014; 15(12):554). The $\log_2$(fold change) values of these top 1597 KRAB domains are shown in FIG. 16, and the amino acid sequences, p-values, and log 2(fold change) values are provided in Table 19, below. In contrast, Zim3 had a log 2(fold change) of 1.7787, standard Znf10 had a $\log_2$(fold change) of 1.3637, and an alternate Znf10 corresponding to the Znf10 KRAB domain used in Tycko, J. et al. (Cell. 2020 Dec. 23; 183(7):2020-2035) had a $\log_2$(fold change) of 1.6182. Therefore, the 1597 top KRAB domains were substantially superior repressors to Znf10 and Zim3. Many of these top KRAB repressors contained amino acids with residues that are predicted to stabilize interactions with the Trim28 protein when compared to Zim3 and Znf10 (Stoll, G. A. et al., bioRxiv 2022.03.17.484746)

To further narrow down the list of KRAB domains while maintaining a breadth of amino acid sequence diversity, a set of 95 lead domains was chosen from within the 1597 by selecting the best domains from each cluster, as well as the top 25 best repressors of the 1597. These top 95 KRAB domains were further narrowed to a top 10 based on by choosing the top domains by log 2(fold change), p-value, and performance in independent repression assays, as described below. The top 10 KRAB domains identified were DOMAIN_737, DOMAIN_10331, DOMAIN_10948, DOMAIN_11029, DOMAIN_17358, DOMAIN_17759, DOMAIN_18258, DOMAIN_19804, DOMAIN_20505, and DOMAIN_26749.

TABLE 19

List of 1,597 KRAB domain candidates identified from the high throughput screen assessing dXR repression of the HBEGF gene and subsequent application of the following criteria: p-value < 0.01 and $\log_2$(fold change) > 2.

| Domain ID | Species | SEQ ID NO | Log2 (fold change) | P-value |
|---|---|---|---|---|
| Top 10 KRAB domains | | | | |
| DOMAIN_737 | Bonobo | 57746 | 4.544 | 1.53E−07 |
| DOMAIN_10331 | *Colobus angolensis palliatus* | 57747 | 3.6796 | 1.53E−07 |
| DOMAIN_10948 | *Colobus angolensis palliatus* | 57748 | 3.2959 | 2.30E−06 |
| DOMAIN_11029 | *Mandrillus leucophaeus* | 57749 | 3.5748 | 1.53E−07 |
| DOMAIN_17358 | *Bos indicus × Bos taurus* | 57750 | 4.9878 | 1.53E−07 |
| DOMAIN_17759 | *Felis catus* | 57751 | 3.3159 | 1.38E−06 |
| DOMAIN_18258 | *Physeter macrocephalus* | 57752 | 3.75 | 3.42E−04 |
| DOMAIN_19804 | *Callorhinus ursinus* | 57753 | 3.8217 | 1.53E−07 |
| DOMAIN_20505 | *Chlorocebus sabaeus* | 57754 | 3.4989 | 2.91E−06 |
| DOMAIN_26749 | *Ophiophagus hannah* | 57755 | 5.4323 | 1.53E−07 |
| Remaining KRAB domains in the top 95 KRAB domains | | | | |
| DOMAIN_221 | Bonobo | 57756 | 3.5533 | 3.06E−06 |
| DOMAIN_881 | Bonobo | 57757 | 4.3546 | 4.59E−07 |
| DOMAIN_2380 | Orangutan | 57758 | 3.2024 | 1.74E−04 |
| DOMAIN_2942 | Gibbon | 57759 | 3.3658 | 1.38E−06 |
| DOMAIN_4687 | Marmoset | 57760 | 5.2288 | 3.22E−06 |
| DOMAIN_4806 | Marmoset | 57761 | 3.3896 | 1.58E−04 |
| DOMAIN_4968 | Marmoset | 57762 | 3.0315 | 0.0022262 |
| DOMAIN_5066 | Marmoset | 57763 | 2.9062 | 0.0067409 |
| DOMAIN_5290 | Owl Monkey | 57764 | 3.0993 | 5.16E−05 |
| DOMAIN_5463 | Owl Monkey | 57765 | 3.2102 | 0.0022788 |
| DOMAIN_6248 | *Saimiri boliviensis boliviensis* | 57766 | 2.4415 | 0.0056883 |
| DOMAIN_6445 | *Alligator sinensis* | 57767 | 3.1151 | 4.51E−04 |
| DOMAIN_6802 | *Pantherophis guttatus* | 57768 | 3.0403 | 5.18E−04 |
| DOMAIN_6807 | *Xenopus laevis* | 57769 | 3.1615 | 5.16E−05 |
| DOMAIN_7255 | *Microcaecilia unicolor* | 57770 | 4.5265 | 1.38E−06 |
| DOMAIN_7694 | *Columba livia* | 57771 | 3.7111 | 1.13E−04 |
| DOMAIN_8503 | *Mus caroli* | 57772 | 2.8193 | 0.003503 |
| DOMAIN_8790 | *Marmota monax* | 57773 | 2.7436 | 2.06E−04 |
| DOMAIN_8853 | *Mesocricetus auratus* | 57774 | 4.6199 | 1.53E−07 |
| DOMAIN_9114 | *Peromyscus maniculatus bairdii* | 57775 | 2.2058 | 0.0048423 |
| DOMAIN_9331 | *Peromyscus maniculatus bairdii* | 57776 | 4.1063 | 4.59E−07 |
| DOMAIN_9538 | *Mus musculus* | 57777 | 3.5443 | 1.20E−04 |
| DOMAIN_9960 | *Octodon degus* | 57778 | 3.4751 | 1.07E−06 |
| DOMAIN_10123 | *Rattus norvegicus* | 57779 | 3.6356 | 8.11E−06 |
| DOMAIN_10277 | *Dipodomys ordii* | 57780 | 2.8257 | 4.16E−04 |
| DOMAIN_10577 | *Colobus angolensis palliatus* | 57781 | 4.1248 | 1.53E−07 |
| DOMAIN_11348 | *Chlorocebus sabaeus* | 57782 | 3.3651 | 2.95E−05 |
| DOMAIN_11386 | *Capra hircus* | 57783 | 3.7637 | 4.75E−06 |
| DOMAIN_11486 | *Bos mutus* | 57784 | 4.8326 | 1.53E−07 |
| DOMAIN_11683 | *Nomascus leucogenys* | 57785 | 2.9249 | 0.0015672 |
| DOMAIN_12292 | *Sus scrofa* | 57786 | 4.3194 | 1.53E−07 |
| DOMAIN_12452 | *Neophocaena asiaeorientalis asiaeorientalis* | 57787 | 3.8774 | 5.05E−06 |
| DOMAIN_12631 | *Macaca fascicularis* | 57788 | 3.6926 | 1.53E−07 |
| DOMAIN_13331 | *Macaca fascicularis* | 57789 | 3.5154 | 2.15E−04 |
| DOMAIN_13468 | *Phascolarctos cinereus* | 57790 | 4.1548 | 1.38E−06 |
| DOMAIN_13539 | Gorilla | 57791 | 3.4924 | 1.79E−05 |
| DOMAIN_14659 | *Acinonyx jubatus* | 57792 | 4.0495 | 1.06E−05 |
| DOMAIN_14755 | *Cebus imitator* | 57793 | 3.1667 | 1.88E−04 |
| DOMAIN_15126 | *Callithrix jacchus* | 57794 | 2.9781 | 4.08E−04 |

TABLE 19-continued

List of 1,597 KRAB domain candidates identified from the high throughput screen assessing dXR repression of the HBEGF gene and subsequent application of the following criteria: p-value < 0.01 and $\log_2$(fold change) > 2.

| Domain ID | Species | SEQ ID NO | Log2 (fold change) | P-value |
|---|---|---|---|---|
| DOMAIN_15507 | *Cebus imitator* | 57795 | 3.8531 | 1.53E−07 |
| DOMAIN_16444 | *Acinonyx jubatus* | 57796 | 3.2246 | 2.30E−06 |
| DOMAIN_16688 | *Lipotes vexillifer* | 57797 | 3.5601 | 4.26E−05 |
| DOMAIN_16806 | *Sapajus apella* | 57798 | 3.9386 | 1.53E−07 |
| DOMAIN_17317 | *Otolemur garnettii* | 57799 | 3.4551 | 1.81E−04 |
| DOMAIN_17432 | *Otolemur garnettii* | 57800 | 3.11 | 1.36E−05 |
| DOMAIN_17905 | Chimp | 57801 | 2.5038 | 5.60E−04 |
| DOMAIN_18137 | *Monodelphis domestica* | 57802 | 3.292 | 3.51E−05 |
| DOMAIN_18216 | *Physeter macrocephalus* | 57803 | 3.0602 | 9.40E−04 |
| DOMAIN_18563 | OwlMonkey | 57804 | 3.0406 | 0.0034849 |
| DOMAIN_19229 | *Enhydra lutris kenyoni* | 57805 | 4.0294 | 5.01E−05 |
| DOMAIN_19460 | *Monodelphis domestica* | 57806 | 3.995 | 1.97E−05 |
| DOMAIN_19476 | OwlMonkey | 57807 | 4.1343 | 1.53E−07 |
| DOMAIN_19821 | *Rhinopithecus roxellana* | 57808 | 3.583 | 1.53E−07 |
| DOMAIN_19892 | *Ursus maritimus* | 57809 | 3.1396 | 5.21E−04 |
| DOMAIN_19896 | *Ovis aries* | 57810 | 2.2228 | 1.58E−04 |
| DOMAIN_19949 | *Callorhinus ursinus* | 57811 | 3.2903 | 2.62E−04 |
| DOMAIN_21247 | *Neovison vison* | 57812 | 2.741 | 0.0043129 |
| DOMAIN_21317 | *Pteropus vampyrus* | 57813 | 4.0893 | 1.18E−05 |
| DOMAIN_21336 | *Equus caballus* | 57814 | 2.738 | 0.005135 |
| DOMAIN_21603 | *Lipotes vexillifer* | 57815 | 2.8535 | 4.35E−04 |
| DOMAIN_21755 | *Equus caballus* | 57816 | 3.1889 | 0.0028238 |
| DOMAIN_22153 | *Zalophus californianus* | 57817 | 3.6967 | 3.52E−06 |
| DOMAIN_22270 | Bonobo | 57818 | 2.3813 | 0.0030391 |
| DOMAIN_23394 | *Vicugna pacos* | 57819 | 4.0769 | 3.06E−07 |
| DOMAIN_23723 | *Carlito syrichta* | 57820 | 3.5301 | 8.71E−05 |
| DOMAIN_24125 | *Saimiri boliviensis boliviensis* | 57821 | 3.9692 | 1.53E−07 |
| DOMAIN_24458 | *Lynx pardinus* | 57822 | 3.4012 | 9.66E−05 |
| DOMAIN_24663 | *Myotis brandtii* | 57823 | 2.9806 | 1.49E−04 |
| DOMAIN_25289 | *Ursus maritimus* | 57824 | 3.4113 | 7.70E−05 |
| DOMAIN_25379 | *Sapajus apella* | 57825 | 3.5892 | 1.53E−07 |
| DOMAIN_25405 | *Desmodus rotundus* | 57826 | 3.8846 | 3.20E−05 |
| DOMAIN_26070 | *Geotrypetes seraphini* | 57827 | 3.7958 | 1.53E−07 |
| DOMAIN_26322 | *Geotrypetes seraphini* | 57828 | 2.9265 | 7.13E−04 |
| DOMAIN_26732 | *Meleagris gallopavo* | 57829 | 2.7548 | 0.0057183 |
| DOMAIN_27060 | *Gopherus agassizii* | 57830 | 2.7943 | 0.0029172 |
| DOMAIN_27385 | *Octodon degus* | 57831 | 4.1339 | 2.77E−05 |
| DOMAIN_27506 | *Bos mutus* | 57832 | 3.8121 | 4.29E−06 |
| DOMAIN_27604 | *Ailuropoda melanoleuca* | 57833 | 2.8198 | 6.05E−05 |
| DOMAIN_27811 | *Callithrix jacchus* | 57834 | 2.9728 | 8.34E−05 |
| DOMAIN_28640 | *Colinus virginianus* | 57835 | 3.624 | 4.13E−06 |
| DOMAIN_28803 | *Monodelphis domestica* | 57836 | 3.0697 | 2.07E−05 |
| DOMAIN_29304 | *Peromyscus maniculatus bairdii* | 57837 | 4.0496 | 1.53E−07 |
| DOMAIN_30173 | *Phyllostomus discolor* | 57838 | 2.2538 | 5.41E−04 |
| DOMAIN_30661 | *Physeter macrocephalus* | 57839 | 2.15 | 4.76E−05 |
| DOMAIN_31643 | *Micrurus lemniscatus lemniscatus* | 57840 | 3.8782 | 3.57E−04 |
| Remaining KRAB domains in the top 1597 KRAB domains | | | | |
| DOMAIN_10870 | *Vicugna pacos* | 57841 | 2.5964 | 0.004315 |
| DOMAIN_10918 | *Odobenus rosmarus divergens* | 57842 | 3.2079 | 9.21E−04 |
| DOMAIN_92 | Bonobo | 57843 | 2.1475 | 0.0021413 |
| DOMAIN_98 | Bonobo | 57844 | 2.7848 | 0.0055875 |
| DOMAIN_134 | Bonobo | 57845 | 2.9322 | 0.004676 |
| DOMAIN_143 | Bonobo | 57846 | 3.63 | 3.17E−05 |
| DOMAIN_145 | Bonobo | 57847 | 3.1497 | 4.09E−05 |
| DOMAIN_214 | Bonobo | 57848 | 2.1073 | 0.00941 |
| DOMAIN_225 | Bonobo | 57849 | 2.259 | 0.0013991 |
| DOMAIN_226 | Bonobo | 57850 | 3.0188 | 2.76E−04 |
| DOMAIN_235 | Bonobo | 57851 | 2.9615 | 0.0016622 |
| DOMAIN_302 | Bonobo | 57852 | 2.5092 | 0.0033327 |
| DOMAIN_313 | Bonobo | 57853 | 2.4558 | 0.0049862 |
| DOMAIN_344 | Bonobo | 57854 | 2.4948 | 0.0087725 |
| DOMAIN_362 | Bonobo | 57855 | 3.6736 | 2.38E−04 |
| DOMAIN_382 | Bonobo | 57856 | 3.1625 | 0.0019781 |
| DOMAIN_389 | Bonobo | 57857 | 3.011 | 3.42E−04 |
| DOMAIN_407 | Bonobo | 57858 | 3.8312 | 1.59E−04 |
| DOMAIN_418 | Bonobo | 57859 | 3.2429 | 1.37E−04 |
| DOMAIN_419 | Bonobo | 57860 | 3.5913 | 5.13E−05 |
| DOMAIN_421 | Bonobo | 57861 | 3.2969 | 1.06E−05 |

TABLE 19-continued

List of 1,597 KRAB domain candidates identified from the high throughput screen assessing dXR repression of the HBEGF gene and subsequent application of the following criteria: p-value < 0.01 and $\log_2$(fold change) > 2.

| Domain ID | Species | SEQ ID NO | Log2 (fold change) | P-value |
|---|---|---|---|---|
| DOMAIN_451 | Bonobo | 57862 | 3.0774 | 0.0018269 |
| DOMAIN_504 | Bonobo | 57863 | 3.2187 | 4.17E−04 |
| DOMAIN_516 | Bonobo | 57864 | 2.0448 | 0.0018554 |
| DOMAIN_621 | Bonobo | 57865 | 2.1025 | 0.0034678 |
| DOMAIN_623 | Bonobo | 57866 | 3.3299 | 6.50E−04 |
| DOMAIN_624 | Bonobo | 57867 | 2.8281 | 0.0031625 |
| DOMAIN_629 | Bonobo | 57868 | 3.6318 | 1.09E−05 |
| DOMAIN_668 | Bonobo | 57869 | 2.9256 | 6.60E−04 |
| DOMAIN_718 | Bonobo | 57870 | 3.9 | 8.73E−06 |
| DOMAIN_731 | Bonobo | 57871 | 2.1318 | 0.0058273 |
| DOMAIN_749 | Bonobo | 57872 | 3.1162 | 0.0060655 |
| DOMAIN_759 | Bonobo | 57873 | 3.3019 | 0.0046077 |
| DOMAIN_761 | Bonobo | 57874 | 3.181 | 9.64E−04 |
| DOMAIN_784 | Bonobo | 57875 | 2.4886 | 0.0083818 |
| DOMAIN_801 | Bonobo | 57876 | 2.4863 | 0.0040602 |
| DOMAIN_802 | Bonobo | 57877 | 2.6563 | 5.66E−04 |
| DOMAIN_811 | Bonobo | 57878 | 2.4706 | 0.0035997 |
| DOMAIN_812 | Bonobo | 57879 | 2.8201 | 0.0013526 |
| DOMAIN_888 | Bonobo | 57880 | 2.8951 | 0.0033756 |
| DOMAIN_893 | Bonobo | 57881 | 2.7511 | 5.41E−04 |
| DOMAIN_938 | Bonobo | 57882 | 2.2926 | 0.0040367 |
| DOMAIN_966 | Chimp | 57883 | 3.3535 | 5.49E−04 |
| DOMAIN_972 | Chimp | 57884 | 3.7627 | 5.59E−05 |
| DOMAIN_980 | Chimp | 57885 | 2.9297 | 0.0011707 |
| DOMAIN_987 | Chimp | 57886 | 2.6881 | 5.48E−04 |
| DOMAIN_999 | Chimp | 57887 | 2.7361 | 0.0038248 |
| DOMAIN_1006 | Chimp | 57888 | 3.2119 | 1.28E−04 |
| DOMAIN_1079 | Chimp | 57889 | 3.7915 | 3.90E−05 |
| DOMAIN_1137 | Chimp | 57890 | 3.1719 | 4.58E−04 |
| DOMAIN_1153 | Chimp | 57891 | 3.7928 | 5.16E−04 |
| DOMAIN_1184 | Chimp | 57892 | 3.2772 | 5.47E−04 |
| DOMAIN_1237 | Chimp | 57893 | 2.1795 | 0.0059151 |
| DOMAIN_1242 | Chimp | 57894 | 2.7144 | 0.0037672 |
| DOMAIN_1247 | Chimp | 57895 | 2.9622 | 4.18E−04 |
| DOMAIN_1378 | Gorilla | 57896 | 3.2279 | 0.0022191 |
| DOMAIN_1381 | Gorilla | 57897 | 4.1424 | 3.35E−05 |
| DOMAIN_1382 | Gorilla | 57898 | 3.0579 | 1.91E−04 |
| DOMAIN_1457 | Gorilla | 57899 | 2.6896 | 0.0026956 |
| DOMAIN_1523 | Gorilla | 57900 | 2.8607 | 0.0042127 |
| DOMAIN_1539 | Gorilla | 57901 | 2.9337 | 0.0028055 |
| DOMAIN_1561 | Gorilla | 57902 | 2.8783 | 0.0011557 |
| DOMAIN_1565 | Gorilla | 57903 | 2.771 | 3.04E−04 |
| DOMAIN_1578 | Gorilla | 57904 | 3.4875 | 5.97E−04 |
| DOMAIN_1621 | Gorilla | 57905 | 3.3004 | 1.20E−04 |
| DOMAIN_1790 | Gorilla | 57906 | 3.0669 | 0.0038707 |
| DOMAIN_1816 | Gorilla | 57907 | 3.108 | 0.0011178 |
| DOMAIN_1818 | Gorilla | 57908 | 3.2866 | 6.15E−04 |
| DOMAIN_1822 | Gorilla | 57909 | 2.4697 | 1.04E−04 |
| DOMAIN_1870 | Gorilla | 57910 | 2.215 | 0.0044522 |
| DOMAIN_1875 | Gorilla | 57911 | 2.5576 | 0.0043383 |
| DOMAIN_1893 | Gorilla | 57912 | 2.3898 | 0.0043422 |
| DOMAIN_1946 | Orangutan | 57913 | 3.1449 | 9.41E−04 |
| DOMAIN_1952 | Orangutan | 57914 | 3.0762 | 5.53E−04 |
| DOMAIN_1964 | Orangutan | 57915 | 2.3009 | 0.0099771 |
| DOMAIN_1978 | Orangutan | 57916 | 3.2215 | 0.0029968 |
| DOMAIN_2014 | Orangutan | 57917 | 2.7323 | 3.95E−04 |
| DOMAIN_2034 | Orangutan | 57918 | 3.7415 | 1.38E−06 |
| DOMAIN_2119 | Orangutan | 57919 | 2.2117 | 0.0054271 |
| DOMAIN_2208 | Orangutan | 57920 | 2.3044 | 0.009903 |
| DOMAIN_2223 | Orangutan | 57921 | 2.6106 | 0.0087315 |
| DOMAIN_2229 | Orangutan | 57922 | 2.9337 | 0.0032308 |
| DOMAIN_2245 | Orangutan | 57923 | 3.2712 | 0.0012727 |
| DOMAIN_2255 | Orangutan | 57924 | 3.1952 | 0.002815 |
| DOMAIN_2295 | Orangutan | 57925 | 3.2816 | 6.61E−04 |
| DOMAIN_2299 | Orangutan | 57926 | 2.5125 | 0.0042678 |
| DOMAIN_2376 | Orangutan | 57927 | 2.1539 | 9.52E−04 |
| DOMAIN_2391 | Orangutan | 57928 | 2.4608 | 0.0045936 |
| DOMAIN_2398 | Orangutan | 57929 | 3.3125 | 3.44E−04 |
| DOMAIN_2470 | Orangutan | 57930 | 2.3815 | 0.0031273 |
| DOMAIN_2499 | Orangutan | 57931 | 3.114 | 0.0050479 |
| DOMAIN_2563 | Orangutan | 57932 | 2.8105 | 0.003781 |
| DOMAIN_2576 | Orangutan | 57933 | 3.1733 | 2.56E−04 |
| DOMAIN_2590 | Orangutan | 57934 | 2.8348 | 0.0091663 |

TABLE 19-continued

List of 1,597 KRAB domain candidates identified from the high throughput screen assessing dXR repression of the HBEGF gene and subsequent application of the following criteria: p-value < 0.01 and $log_2$(fold change) > 2.

| Domain ID | Species | SEQ ID NO | Log2 (fold change) | P-value |
|---|---|---|---|---|
| DOMAIN_2629 | Orangutan | 57935 | 3.092 | 0.0015715 |
| DOMAIN_2652 | Orangutan | 57936 | 4.3981 | 4.59E−07 |
| DOMAIN_2744 | Gibbon | 57937 | 2.863 | 0.003897 |
| DOMAIN_2754 | Gibbon | 57938 | 3.7601 | 1.17E−04 |
| DOMAIN_2786 | Gibbon | 57939 | 2.5449 | 0.0037666 |
| DOMAIN_2806 | Gibbon | 57940 | 3.1649 | 0.0083733 |
| DOMAIN_2808 | Gibbon | 57941 | 2.6227 | 0.0079231 |
| DOMAIN_2813 | Gibbon | 57942 | 2.9522 | 4.12E−04 |
| DOMAIN_2851 | Gibbon | 57943 | 3.3945 | 3.80E−04 |
| DOMAIN_2867 | Gibbon | 57944 | 3.0591 | 4.79E−04 |
| DOMAIN_2888 | Gibbon | 57945 | 2.4267 | 0.0043214 |
| DOMAIN_2891 | Gibbon | 57946 | 2.7489 | 0.0082897 |
| DOMAIN_2896 | Gibbon | 57947 | 2.7253 | 0.0094587 |
| DOMAIN_2904 | Gibbon | 57948 | 2.8035 | 0.0019408 |
| DOMAIN_2908 | Gibbon | 57949 | 2.6452 | 0.0062379 |
| DOMAIN_2943 | Gibbon | 57950 | 2.9574 | 9.75E−04 |
| DOMAIN_2962 | Gibbon | 57951 | 2.1784 | 6.34E−04 |
| DOMAIN_2992 | Gibbon | 57952 | 2.6341 | 0.0045667 |
| DOMAIN_2994 | Gibbon | 57953 | 3.1921 | 0.0022412 |
| DOMAIN_2997 | Gibbon | 57954 | 2.9911 | 0.0016588 |
| DOMAIN_3000 | Gibbon | 57955 | 2.9522 | 5.36E−04 |
| DOMAIN_3062 | Gibbon | 57956 | 2.6076 | 0.0035414 |
| DOMAIN_3087 | Gibbon | 57957 | 2.7999 | 5.44E−04 |
| DOMAIN_3092 | Gibbon | 57958 | 3.1954 | 2.80E−05 |
| DOMAIN_3094 | Gibbon | 57959 | 3.7195 | 2.83E−05 |
| DOMAIN_3096 | Gibbon | 57960 | 3.3962 | 2.16E−04 |
| DOMAIN_3123 | Gibbon | 57961 | 3.1293 | 1.88E−05 |
| DOMAIN_3137 | Gibbon | 57962 | 2.8303 | 0.0038836 |
| DOMAIN_3300 | Gibbon | 57963 | 3.0127 | 2.76E−04 |
| DOMAIN_3328 | Gibbon | 57964 | 2.3718 | 0.0015893 |
| DOMAIN_3332 | Gibbon | 57965 | 2.8786 | 0.0036582 |
| DOMAIN_3335 | Gibbon | 57966 | 4.0001 | 4.75E−06 |
| DOMAIN_3336 | Gibbon | 57967 | 3.5946 | 4.75E−06 |
| DOMAIN_3337 | Gibbon | 57968 | 2.9398 | 0.0053162 |
| DOMAIN_3344 | Gibbon | 57969 | 3.2218 | 4.60E−04 |
| DOMAIN_3373 | Gibbon | 57970 | 3.0768 | 0.0030033 |
| DOMAIN_3434 | Gibbon | 57971 | 2.4767 | 0.0035835 |
| DOMAIN_3463 | Gibbon | 57972 | 3.5462 | 5.96E−04 |
| DOMAIN_3557 | Rhesus | 57973 | 2.4416 | 0.0024889 |
| DOMAIN_3575 | Rhesus | 57974 | 3.7842 | 1.53E−07 |
| DOMAIN_3585 | Rhesus | 57975 | 2.4981 | 0.0036466 |
| DOMAIN_3586 | Rhesus | 57976 | 2.365 | 0.0033728 |
| DOMAIN_3602 | Rhesus | 57977 | 2.0444 | 0.0061662 |
| DOMAIN_3661 | Rhesus | 57978 | 2.4083 | 0.0088114 |
| DOMAIN_3691 | Rhesus | 57979 | 2.8393 | 0.0018244 |
| DOMAIN_3759 | Rhesus | 57980 | 2.5324 | 0.004454 |
| DOMAIN_3760 | Rhesus | 57981 | 2.7025 | 0.0017399 |
| DOMAIN_3781 | Rhesus | 57982 | 2.9317 | 0.0024892 |
| DOMAIN_3782 | Rhesus | 57983 | 2.3058 | 0.0048669 |
| DOMAIN_3803 | Rhesus | 57984 | 3.0165 | 0.0083941 |
| DOMAIN_3832 | Rhesus | 57985 | 2.7334 | 0.0026058 |
| DOMAIN_4030 | Rhesus | 57986 | 2.5274 | 0.0038526 |
| DOMAIN_4036 | Rhesus | 57987 | 2.7725 | 0.001577 |
| DOMAIN_4046 | Rhesus | 57988 | 2.7847 | 0.0088564 |
| DOMAIN_4120 | Rhesus | 57989 | 3.3237 | 4.55E−05 |
| DOMAIN_4121 | Rhesus | 57990 | 3.3195 | 1.53E−07 |
| DOMAIN_4126 | Rhesus | 57991 | 3.529 | 1.65E−04 |
| DOMAIN_4129 | Rhesus | 57992 | 3.7382 | 9.33E−04 |
| DOMAIN_4184 | Rhesus | 57993 | 3.2397 | 9.40E−04 |
| DOMAIN_4185 | Rhesus | 57994 | 2.9116 | 0.0032623 |
| DOMAIN_4199 | Rhesus | 57995 | 2.6844 | 0.0058444 |
| DOMAIN_4239 | Rhesus | 57996 | 4.4187 | 9.19E−07 |
| DOMAIN_4394 | Marmoset | 57997 | 3.8103 | 4.09E−05 |
| DOMAIN_4425 | Marmoset | 57998 | 2.9741 | 0.0087646 |
| DOMAIN_4461 | Marmoset | 57999 | 3.0094 | 0.0076595 |
| DOMAIN_4463 | Marmoset | 58000 | 2.9717 | 0.008252 |
| DOMAIN_4515 | Marmoset | 58001 | 4.2166 | 1.21E−05 |
| DOMAIN_4516 | Marmoset | 58002 | 2.7603 | 0.0027577 |
| DOMAIN_4534 | Marmoset | 58003 | 2.6242 | 0.0034292 |
| DOMAIN_4574 | Marmoset | 58004 | 2.7135 | 9.16E−04 |
| DOMAIN_4580 | Marmoset | 58005 | 2.9618 | 3.22E−06 |
| DOMAIN_4589 | Marmoset | 58006 | 2.507 | 0.0070104 |
| DOMAIN_4665 | Marmoset | 58007 | 3.2985 | 0.0011116 |

TABLE 19-continued

List of 1,597 KRAB domain candidates identified from the high throughput screen assessing dXR repression of the HBEGF gene and subsequent application of the following criteria: p-value < 0.01 and $log_2$(fold change) > 2.

| Domain ID | Species | SEQ ID NO | Log2 (fold change) | P-value |
|---|---|---|---|---|
| DOMAIN_4705 | Marmoset | 58008 | 3.5232 | 5.02E−04 |
| DOMAIN_4722 | Marmoset | 58009 | 4.8639 | 1.53E−07 |
| DOMAIN_4748 | Marmoset | 58010 | 3.0477 | 5.73E−04 |
| DOMAIN_4749 | Marmoset | 58011 | 3.5545 | 2.83E−05 |
| DOMAIN_4751 | Marmoset | 58012 | 3.238 | 4.91E−05 |
| DOMAIN_4774 | Marmoset | 58013 | 2.8894 | 0.0029528 |
| DOMAIN_4823 | Marmoset | 58014 | 2.7527 | 0.0083334 |
| DOMAIN_4913 | Marmoset | 58015 | 2.8878 | 0.0028098 |
| DOMAIN_4921 | Marmoset | 58016 | 3.5291 | 4.44E−06 |
| DOMAIN_4922 | Marmoset | 58017 | 4.0258 | 1.82E−05 |
| DOMAIN_4978 | Marmoset | 58018 | 2.7787 | 0.0025526 |
| DOMAIN_5005 | Marmoset | 58019 | 2.8406 | 0.00183 |
| DOMAIN_5006 | Marmoset | 58020 | 3.8614 | 1.38E−06 |
| DOMAIN_5029 | Marmoset | 58021 | 2.2642 | 0.0022609 |
| DOMAIN_5031 | Marmoset | 58022 | 2.8605 | 0.0025559 |
| DOMAIN_5060 | Marmoset | 58023 | 2.6043 | 8.74E−04 |
| DOMAIN_5096 | Marmoset | 58024 | 2.456 | 0.008963 |
| DOMAIN_5099 | Marmoset | 58025 | 3.1407 | 0.0021138 |
| DOMAIN_5102 | Marmoset | 58026 | 2.7241 | 0.0024099 |
| DOMAIN_5103 | Marmoset | 58027 | 2.1016 | 0.0093552 |
| DOMAIN_5125 | Marmoset | 58028 | 2.911 | 0.0015369 |
| DOMAIN_5188 | OwlMonkey | 58029 | 2.1842 | 0.0046295 |
| DOMAIN_5201 | OwlMonkey | 58030 | 3.3658 | 1.53E−07 |
| DOMAIN_5217 | OwlMonkey | 58031 | 2.4689 | 0.0031316 |
| DOMAIN_5235 | OwlMonkey | 58032 | 3.437 | 4.62E−04 |
| DOMAIN_5246 | OwlMonkey | 58033 | 2.7473 | 0.0042075 |
| DOMAIN_5248 | OwlMonkey | 58034 | 4.1052 | 1.53E−07 |
| DOMAIN_5267 | OwlMonkey | 58035 | 3.1247 | 0.0016383 |
| DOMAIN_5273 | OwlMonkey | 58036 | 2.4023 | 0.0069063 |
| DOMAIN_5299 | OwlMonkey | 58037 | 2.7399 | 0.0093892 |
| DOMAIN_5337 | OwlMonkey | 58038 | 3.7616 | 4.52E−05 |
| DOMAIN_5370 | OwlMonkey | 58039 | 3.0452 | 0.0088803 |
| DOMAIN_5440 | OwlMonkey | 58040 | 2.7871 | 0.0048658 |
| DOMAIN_5485 | OwlMonkey | 58041 | 2.7826 | 0.0080202 |
| DOMAIN_5489 | OwlMonkey | 58042 | 2.6774 | 0.0021808 |
| DOMAIN_5518 | OwlMonkey | 58043 | 2.8542 | 0.0030235 |
| DOMAIN_5527 | OwlMonkey | 58044 | 3.1092 | 0.0016793 |
| DOMAIN_5603 | OwlMonkey | 58045 | 3.2806 | 0.0015418 |
| DOMAIN_5716 | OwlMonkey | 58046 | 3.0606 | 5.36E−04 |
| DOMAIN_5742 | *Homo sapiens* | 58047 | 2.8617 | 0.0029913 |
| DOMAIN_5765 | *Rattus norvegicus* | 58048 | 4.2973 | 1.53E−07 |
| DOMAIN_5774 | *Homo sapiens* | 58049 | 2.9608 | 3.75E−05 |
| DOMAIN_5782 | *Homo sapiens* | 58050 | 2.9086 | 4.56E−04 |
| DOMAIN_5791 | *Homo sapiens* | 58051 | 2.6823 | 0.0051494 |
| DOMAIN_5792 | *Homo sapiens* | 58052 | 3.0218 | 8.56E−04 |
| DOMAIN_5806 | *Homo sapiens* | 58053 | 2.866 | 0.0037801 |
| DOMAIN_5822 | *Homo sapiens* | 58054 | 2.9335 | 0.0074467 |
| DOMAIN_5843 | *Homo sapiens* | 58055 | 3.1821 | 2.83E−05 |
| DOMAIN_5866 | *Homo sapiens* | 58056 | 2.6362 | 0.0080677 |
| DOMAIN_5883 | *Homo sapiens* | 58057 | 3.0097 | 5.52E−04 |
| DOMAIN_5896 | *Bos taurus* | 58058 | 2.9429 | 0.0023166 |
| DOMAIN_5901 | *Homo sapiens* | 58059 | 3.2935 | 0.0012981 |
| DOMAIN_5914 | *Homo sapiens* | 58060 | 2.5527 | 0.0029099 |
| DOMAIN_5921 | *Homo sapiens* | 58061 | 2.4715 | 0.00101 |
| DOMAIN_5943 | *Mus musculus* | 58062 | 2.501 | 0.0027917 |
| DOMAIN_5946 | *Homo sapiens* | 58063 | 3.2998 | 1.38E−06 |
| DOMAIN_5968 | *Bos taurus* | 58064 | 3.2856 | 3.86E−04 |
| DOMAIN_5984 | *Homo sapiens* | 58065 | 2.9852 | 2.37E−04 |
| DOMAIN_5989 | *Mus musculus* | 58066 | 3.6632 | 9.30E−04 |
| DOMAIN_5994 | Orangutan | 58067 | 2.9214 | 5.04E−04 |
| DOMAIN_6038 | *Homo sapiens* | 58068 | 3.3315 | 2.59E−04 |
| DOMAIN_6053 | Orangutan | 58069 | 3.2566 | 1.21E−04 |
| DOMAIN_6063 | *Homo sapiens* | 58070 | 3.5653 | 0.0019059 |
| DOMAIN_6078 | *Homo sapiens* | 58071 | 2.6246 | 0.0075453 |
| DOMAIN_6134 | *Homo sapiens* | 58072 | 2.7081 | 0.0034203 |
| DOMAIN_6169 | *Homo sapiens* | 58073 | 3.3909 | 1.68E−06 |
| DOMAIN_6172 | *Homo sapiens* | 58074 | 3.883 | 1.07E−06 |
| DOMAIN_6249 | *Saimiri boliviensis boliviensis* | 58075 | 3.5469 | 4.44E−06 |

TABLE 19-continued

List of 1,597 KRAB domain candidates identified from the high throughput screen assessing dXR repression of the HBEGF gene and subsequent application of the following criteria: p-value < 0.01 and $log_2$(fold change) > 2.

| Domain ID | Species | SEQ ID NO | Log2 (fold change) | P-value |
|---|---|---|---|---|
| DOMAIN_6293 | *Rattus norvegicus* | 58076 | 2.6707 | 0.0034812 |
| DOMAIN_6354 | *Terrapene carolina triunguis* | 58077 | 2.4812 | 0.0095055 |
| DOMAIN_6356 | *Terrapene carolina triunguis* | 58078 | 2.9197 | 0.0031965 |
| DOMAIN_6382 | *Gopherus agassizii* | 58079 | 3.2875 | 1.66E−04 |
| DOMAIN_6398 | *Gopherus agassizii* | 58080 | 2.8238 | 0.0059966 |
| DOMAIN_6410 | *Podarcis muralis* | 58081 | 2.7633 | 0.0034243 |
| DOMAIN_6433 | *Podarcis muralis* | 58082 | 3.0313 | 1.16E−04 |
| DOMAIN_6458 | *Gopherus agassizii* | 58083 | 2.8973 | 0.0048435 |
| DOMAIN_6472 | *Alligator sinensis* | 58084 | 2.9259 | 0.0052565 |
| DOMAIN_6482 | *Paroedura picta* | 58085 | 3.3106 | 0.0019705 |
| DOMAIN_6501 | *Paroedura picta* | 58086 | 3.4172 | 0.0010204 |
| DOMAIN_6539 | *Paroedura picta* | 58087 | 3.2371 | 0.0025654 |
| DOMAIN_6555 | *Paroedura picta* | 58088 | 3.534 | 4.92E−04 |
| DOMAIN_6577 | *Terrapene carolina triunguis* | 58089 | 3.3168 | 3.95E−04 |
| DOMAIN_6595 | *Terrapene carolina triunguis* | 58090 | 2.2407 | 0.0027133 |
| DOMAIN_6599 | *Terrapene carolina triunguis* | 58091 | 3.3653 | 4.49E−05 |
| DOMAIN_6697 | *Podarcis muralis* | 58092 | 2.6712 | 7.35E−04 |
| DOMAIN_6737 | *Microcaecilia unicolor* | 58093 | 2.4861 | 0.0065704 |
| DOMAIN_6738 | *Microcaecilia unicolor* | 58094 | 2.9275 | 7.79E−04 |
| DOMAIN_6741 | *Microcaecilia unicolor* | 58095 | 3.5726 | 2.50E−04 |
| DOMAIN_6866 | *Alligator mississippiensis* | 58096 | 3.5825 | 1.02E−04 |
| DOMAIN_6936 | *Callipepla squamata* | 58097 | 3.5294 | 9.07E−04 |
| DOMAIN_6938 | *Alligator mississippiensis* | 58098 | 2.6093 | 0.0020584 |
| DOMAIN_6952 | *Alligator mississippiensis* | 58099 | 2.3403 | 0.0084774 |
| DOMAIN_6970 | *Phasianus colchicus* | 58100 | 3.343 | 3.02E−04 |
| DOMAIN_7000 | *Phasianus colchicus* | 58101 | 2.8279 | 0.0039843 |
| DOMAIN_7098 | *Microcaecilia unicolor* | 58102 | 2.7074 | 0.0030553 |
| DOMAIN_7109 | *Microcaecilia unicolor* | 58103 | 2.9932 | 0.0077318 |
| DOMAIN_7123 | *Microcaecilia unicolor* | 58104 | 2.9074 | 0.0043723 |
| DOMAIN_7166 | *Microcaecilia unicolor* | 58105 | 3.1419 | 5.72E−04 |
| DOMAIN_7183 | *Microcaecilia unicolor* | 58106 | 2.4918 | 1.27E−04 |
| DOMAIN_7184 | *Microcaecilia unicolor* | 58107 | 2.2019 | 0.0099168 |
| DOMAIN_7328 | *Terrapene carolina triunguis* | 58108 | 3.1808 | 5.04E−05 |
| DOMAIN_7353 | *Microcaecilia unicolor* | 58109 | 2.6649 | 0.0042219 |
| DOMAIN_7365 | *Microcaecilia unicolor* | 58110 | 2.597 | 0.0042403 |
| DOMAIN_7480 | *Gopherus agassizii* | 58111 | 3.1707 | 5.44E−04 |
| DOMAIN_7510 | *Gopherus agassizii* | 58112 | 3.0452 | 6.73E−04 |
| DOMAIN_7534 | *Gopherus agassizii* | 58113 | 3.4086 | 2.50E−04 |
| DOMAIN_7553 | *Gopherus agassizii* | 58114 | 2.9036 | 0.0088341 |
| DOMAIN_7605 | *Alligator sinensis* | 58115 | 2.8444 | 0.0018789 |
| DOMAIN_7607 | *Alligator sinensis* | 58116 | 2.7102 | 0.0018612 |
| DOMAIN_7641 | *Gallus gallus* | 58117 | 3.6727 | 4.51E−04 |
| DOMAIN_7653 | *Gallus gallus* | 58118 | 3.3772 | 0.0028364 |
| DOMAIN_7678 | *Chelonia mydas* | 58119 | 2.7348 | 0.0039197 |
| DOMAIN_7711 | *Columba livia* | 58120 | 3.7965 | 1.67E−05 |
| DOMAIN_7716 | *Pogona vitticeps* | 58121 | 3.1171 | 0.0011931 |
| DOMAIN_7745 | *Meleagris gallopavo* | 58122 | 3.4946 | 0.0016126 |
| DOMAIN_7750 | *Columba livia* | 58123 | 2.8111 | 0.0012249 |
| DOMAIN_7774 | *Pogona vitticeps* | 58124 | 3.427 | 8.09E−04 |
| DOMAIN_7796 | *Chelonia mydas* | 58125 | 2.9513 | 1.04E−04 |
| DOMAIN_7813 | *Columba livia* | 58126 | 3.4645 | 7.95E−04 |
| DOMAIN_7824 | *Columba livia* | 58127 | 2.9383 | 5.45E−04 |
| DOMAIN_7850 | *Terrapene carolina triunguis* | 58128 | 3.124 | 5.15E−04 |
| DOMAIN_7895 | *Patagioenas fasciata monilis* | 58129 | 3.2254 | 0.0013863 |
| DOMAIN_7925 | *Gallus gallus* | 58130 | 3.3919 | 0.0025195 |
| DOMAIN_8012 | *Callipepla squamata* | 58131 | 3.2046 | 0.0023734 |
| DOMAIN_8013 | *Callipepla squamata* | 58132 | 3.9783 | 2.13E−05 |
| DOMAIN_8014 | *Callipepla squamata* | 58133 | 3.7425 | 6.23E−05 |
| DOMAIN_8036 | *Alligator mississippiensis* | 58134 | 2.3504 | 0.0094483 |
| DOMAIN_8041 | *Dipodomys ordii* | 58135 | 3.6568 | 3.47E−04 |
| DOMAIN_8054 | *Cavia porcellus* | 58136 | 3.5889 | 4.15E−05 |
| DOMAIN_8148 | *Cricetulus griseus* | 58137 | 3.6904 | 4.82E−05 |
| DOMAIN_8151 | *Cricetulus griseus* | 58138 | 3.1527 | 0.0034782 |
| DOMAIN_8154 | *Cricetulus griseus* | 58139 | 2.8774 | 0.0027807 |
| DOMAIN_8167 | *Mus musculus* | 58140 | 3.9362 | 1.04E−04 |

TABLE 19-continued

List of 1,597 KRAB domain candidates identified from the high throughput screen assessing dXR repression of the HBEGF gene and subsequent application of the following criteria: p-value < 0.01 and $\log_2$(fold change) > 2.

| Domain ID | Species | SEQ ID NO | Log2 (fold change) | P-value |
|---|---|---|---|---|
| DOMAIN_8179 | *Mesocricetus auratus* | 58141 | 3.0623 | 0.0026242 |
| DOMAIN_8182 | *Mus caroli* | 58142 | 2.2411 | 0.0018051 |
| DOMAIN_8216 | *Cricetulus griseus* | 58143 | 3.1747 | 9.05E−05 |
| DOMAIN_8226 | *Rattus norvegicus* | 58144 | 2.4602 | 0.0090772 |
| DOMAIN_8235 | *Mus caroli* | 58145 | 2.8965 | 0.0012522 |
| DOMAIN_8282 | *Peromyscus maniculatus bairdii* | 58146 | 3.9882 | 1.07E−06 |
| DOMAIN_8289 | *Peromyscus maniculatus bairdii* | 58147 | 3.3026 | 2.94E−04 |
| DOMAIN_8301 | *Mesocricetus auratus* | 58148 | 3.1084 | 0.0017647 |
| DOMAIN_8303 | *Ictidomys tridecemlineatus* | 58149 | 3.6843 | 1.34E−04 |
| DOMAIN_8305 | *Ictidomys tridecemlineatus* | 58150 | 2.5554 | 0.0084633 |
| DOMAIN_8308 | *Marmota monax* | 58151 | 2.6564 | 3.69E−04 |
| DOMAIN_8317 | *Mus caroli* | 58152 | 3.3091 | 2.40E−05 |
| DOMAIN_8340 | *Peromyscus maniculatus bairdii* | 58153 | 2.2764 | 0.0086378 |
| DOMAIN_8353 | *Peromyscus maniculatus bairdii* | 58154 | 2.7989 | 4.14E−04 |
| DOMAIN_8370 | *Cavia porcellus* | 58155 | 3.5737 | 2.58E−04 |
| DOMAIN_8412 | *Mus musculus* | 58156 | 2.4486 | 0.0077639 |
| DOMAIN_8418 | *Cricetulus griseus* | 58157 | 2.4014 | 0.001307 |
| DOMAIN_8424 | *Peromyscus maniculatus bairdii* | 58158 | 2.7945 | 0.0019818 |
| DOMAIN_8425 | *Peromyscus maniculatus bairdii* | 58159 | 2.8391 | 0.004804 |
| DOMAIN_8460 | *Peromyscus maniculatus bairdii* | 58160 | 3.1352 | 6.66E−05 |
| DOMAIN_8467 | *Mesocricetus auratus* | 58161 | 3.8156 | 7.15E−05 |
| DOMAIN_8489 | *Mus caroli* | 58162 | 2.8336 | 0.0042299 |
| DOMAIN_8492 | *Mus musculus* | 58163 | 3.3107 | 0.0032374 |
| DOMAIN_8502 | *Cricetulus griseus* | 58164 | 2.1429 | 4.22E−04 |
| DOMAIN_8545 | *Rattus norvegicus* | 58165 | 3.1044 | 0.0011282 |
| DOMAIN_8546 | *Mus musculus* | 58166 | 2.9439 | 0.0033958 |
| DOMAIN_8547 | *Mus caroli* | 58167 | 3.3997 | 0.0022286 |
| DOMAIN_8549 | *Mus caroli* | 58168 | 2.8508 | 0.0052033 |
| DOMAIN_8555 | *Cricetulus griseus* | 58169 | 3.2852 | 5.62E−05 |
| DOMAIN_8618 | *Mesocricetus auratus* | 58170 | 2.6363 | 0.008293 |
| DOMAIN_8688 | *Mus musculus* | 58171 | 2.4409 | 2.00E−04 |
| DOMAIN_8689 | *Mus musculus* | 58172 | 2.8548 | 6.62E−04 |
| DOMAIN_8712 | *Mesocricetus auratus* | 58173 | 2.7776 | 0.0028768 |
| DOMAIN_8742 | *Peromyscus maniculatus bairdii* | 58174 | 2.3354 | 0.002149 |
| DOMAIN_8746 | *Mesocricetus auratus* | 58175 | 3.317 | 1.64E−04 |
| DOMAIN_8789 | *Marmota monax* | 58176 | 3.1756 | 0.0021937 |
| DOMAIN_8793 | *Mus caroli* | 58177 | 2.6774 | 9.60E−05 |
| DOMAIN_8816 | *Peromyscus maniculatus bairdii* | 58178 | 2.4156 | 2.32E−04 |
| DOMAIN_8830 | *Cavia porcellus* | 58179 | 3.0644 | 0.0025588 |
| DOMAIN_8839 | *Peromyscus maniculatus bairdii* | 58180 | 3.0637 | 0.0036542 |
| DOMAIN_8844 | *Peromyscus maniculatus bairdii* | 58181 | 4.1629 | 7.81E−06 |
| DOMAIN_8850 | *Peromyscus maniculatus bairdii* | 58182 | 2.695 | 0.0040575 |
| DOMAIN_8862 | *Marmota monax* | 58183 | 2.3521 | 0.0061537 |
| DOMAIN_8881 | *Cricetulus griseus* | 58184 | 3.743 | 1.49E−05 |
| DOMAIN_8886 | *Cricetulus griseus* | 58185 | 3.5727 | 1.94E−05 |
| DOMAIN_8899 | *Mesocricetus auratus* | 58186 | 3.2182 | 9.45E−05 |
| DOMAIN_8931 | *Cricetulus griseus* | 58187 | 2.9497 | 8.73E−04 |
| DOMAIN_8936 | *Cricetulus griseus* | 58188 | 4.3486 | 1.07E−06 |
| DOMAIN_8953 | *Mus caroli* | 58189 | 2.5941 | 0.0032969 |
| DOMAIN_8982 | *Mesocricetus auratus* | 58190 | 3.1585 | 3.54E−05 |
| DOMAIN_8989 | *Marmota monax* | 58191 | 2.2309 | 0.0094553 |
| DOMAIN_9012 | *Mus musculus* | 58192 | 2.3905 | 0.0070058 |
| DOMAIN_9042 | *Mus caroli* | 58193 | 2.5894 | 0.0033885 |
| DOMAIN_9060 | *Cricetulus griseus* | 58194 | 2.5974 | 0.0027286 |
| DOMAIN_9119 | *Mesocricetus auratus* | 58195 | 2.2985 | 0.0052412 |
| DOMAIN_9141 | *Mus caroli* | 58196 | 3.035 | 2.62E−05 |
| DOMAIN_9159 | *Dipodomys ordii* | 58197 | 3.0141 | 0.0023052 |
| DOMAIN_9174 | *Peromyscus maniculatus bairdii* | 58198 | 2.5194 | 0.0035749 |
| DOMAIN_9175 | *Peromyscus maniculatus bairdii* | 58199 | 2.4231 | 0.0042293 |

TABLE 19-continued

List of 1,597 KRAB domain candidates identified from the high throughput screen assessing dXR repression of the HBEGF gene and subsequent application of the following criteria: p-value < 0.01 and $\log_2$(fold change) > 2.

| Domain ID | Species | SEQ ID NO | Log2 (fold change) | P-value |
|---|---|---|---|---|
| DOMAIN_9189 | *Heterocephalus glaber* | 58200 | 3.3801 | 1.76E−04 |
| DOMAIN_9192 | *Mus caroli* | 58201 | 2.7981 | 0.008526 |
| DOMAIN_9217 | *Mesocricetus auratus* | 58202 | 3.8919 | 5.43E−05 |
| DOMAIN_9235 | *Mus musculus* | 58203 | 2.7307 | 0.0035899 |
| DOMAIN_9250 | *Marmota monax* | 58204 | 3.466 | 0.0012007 |
| DOMAIN_9265 | *Mus musculus* | 58205 | 2.1221 | 0.0021172 |
| DOMAIN_9290 | *Peromyscus maniculatus bairdii* | 58206 | 4.256 | 1.07E−06 |
| DOMAIN_9303 | *Marmota monax* | 58207 | 2.5344 | 0.0051732 |
| DOMAIN_9313 | *Mus musculus* | 58208 | 2.7692 | 0.0061916 |
| DOMAIN_9324 | *Peromyscus maniculatus bairdii* | 58209 | 3.1782 | 0.0020198 |
| DOMAIN_9329 | *Peromyscus maniculatus bairdii* | 58210 | 4.263 | 7.81E−06 |
| DOMAIN_9332 | *Peromyscus maniculatus bairdii* | 58211 | 3.9002 | 1.38E−06 |
| DOMAIN_9356 | *Ictidomys tridecemlineatus* | 58212 | 2.9297 | 0.0037302 |
| DOMAIN_9389 | *Marmota monax* | 58213 | 3.1785 | 2.65E−05 |
| DOMAIN_9424 | *Dipodomys ordii* | 58214 | 3.771 | 1.53E−07 |
| DOMAIN_9435 | *Fukomys damarensis* | 58215 | 3.1672 | 3.01E−04 |
| DOMAIN_9446 | *Marmota monax* | 58216 | 2.8722 | 3.80E−04 |
| DOMAIN_9489 | *Dipodomys ordii* | 58217 | 3.0215 | 0.0074336 |
| DOMAIN_9503 | *Ictidomys tridecemlineatus* | 58218 | 2.9864 | 0.0021536 |
| DOMAIN_9526 | *Mesocricetus auratus* | 58219 | 2.9435 | 0.0042492 |
| DOMAIN_9530 | *Mesocricetus auratus* | 58220 | 2.7003 | 0.0026178 |
| DOMAIN_9541 | *Dipodomys ordii* | 58221 | 2.8442 | 0.0028404 |
| DOMAIN_9542 | *Octodon degus* | 58222 | 2.6734 | 0.0036809 |
| DOMAIN_9544 | *Octodon degus* | 58223 | 2.9143 | 0.0054966 |
| DOMAIN_9559 | *Mus caroli* | 58224 | 3.327 | 0.001653 |
| DOMAIN_9563 | *Mus musculus* | 58225 | 3.7261 | 3.81E−05 |
| DOMAIN_9576 | *Octodon degus* | 58226 | 2.1952 | 0.0094564 |
| DOMAIN_9617 | *Mesocricetus auratus* | 58227 | 2.4034 | 0.0040152 |
| DOMAIN_9643 | *Dipodomys ordii* | 58228 | 3.4306 | 0.0023603 |
| DOMAIN_9697 | *Octodon degus* | 58229 | 2.7566 | 0.0063579 |
| DOMAIN_9704 | *Dipodomys ordii* | 58230 | 3.1674 | 0.0013462 |
| DOMAIN_9706 | *Octodon degus* | 58231 | 2.821 | 0.0041809 |
| DOMAIN_9713 | *Cricetulus griseus* | 58232 | 3.0323 | 0.002243 |
| DOMAIN_9716 | *Mus caroli* | 58233 | 2.9009 | 0.0040762 |
| DOMAIN_9723 | *Mus caroli* | 58234 | 2.1903 | 0.0058971 |
| DOMAIN_9725 | *Mus caroli* | 58235 | 2.9654 | 0.0028095 |
| DOMAIN_9776 | *Marmota monax* | 58236 | 2.6258 | 0.0084697 |
| DOMAIN_9787 | *Mus caroli* | 58237 | 3.2962 | 8.37E−05 |
| DOMAIN_9789 | *Mus musculus* | 58238 | 2.5801 | 0.0012534 |
| DOMAIN_9822 | *Ictidomys tridecemlineatus* | 58239 | 2.9382 | 0.0065879 |
| DOMAIN_9824 | *Heterocephalus glaber* | 58240 | 3.1306 | 8.34E−05 |
| DOMAIN_9827 | *Mus caroli* | 58241 | 2.1904 | 0.0077554 |
| DOMAIN_9843 | *Mus musculus* | 58242 | 2.3385 | 0.0035982 |
| DOMAIN_9846 | *Cricetulus griseus* | 58243 | 2.7865 | 0.0025033 |
| DOMAIN_9857 | *Mesocricetus auratus* | 58244 | 3.3666 | 8.92E−04 |
| DOMAIN_9858 | *Mesocricetus auratus* | 58245 | 3.0047 | 1.33E−04 |
| DOMAIN_9878 | *Marmota monax* | 58246 | 3.7349 | 2.61E−04 |
| DOMAIN_9891 | *Mus caroli* | 58247 | 2.8116 | 3.13E−04 |
| DOMAIN_9915 | *Mus caroli* | 58248 | 3.4011 | 3.45E−04 |
| DOMAIN_9962 | *Rattus norvegicus* | 58249 | 2.7249 | 0.004063 |
| DOMAIN_9993 | *Rattus norvegicus* | 58250 | 2.7601 | 0.0035973 |
| DOMAIN_10018 | *Octodon degus* | 58251 | 3.3372 | 4.27E−04 |
| DOMAIN_10041 | *Mus caroli* | 58252 | 2.8662 | 0.0062437 |
| DOMAIN_10044 | *Mus musculus* | 58253 | 2.826 | 0.0043095 |
| DOMAIN_10050 | *Octodon degus* | 58254 | 3.3147 | 0.0020066 |
| DOMAIN_10057 | *Mus musculus* | 58255 | 2.2961 | 0.0026799 |
| DOMAIN_10091 | *Fukomys damarensis* | 58256 | 2.1679 | 4.36E−04 |
| DOMAIN_10127 | *Peromyscus maniculatus bairdii* | 58257 | 3.6912 | 3.83E−06 |
| DOMAIN_10160 | *Ictidomys tridecemlineatus* | 58258 | 2.9333 | 4.23E−04 |
| DOMAIN_10184 | *Mus caroli* | 58259 | 4.2854 | 1.53E−07 |
| DOMAIN_10241 | *Octodon degus* | 58260 | 3.5766 | 8.19E−05 |
| DOMAIN_10257 | *Octodon degus* | 58261 | 3.1757 | 5.20E−04 |
| DOMAIN_10294 | *Mus musculus* | 58262 | 2.689 | 0.0067073 |
| DOMAIN_10334 | *Mustela putorius furo* | 58263 | 3.3529 | 5.07E−05 |

TABLE 19-continued

List of 1,597 KRAB domain candidates identified from the high throughput screen assessing dXR repression of the HBEGF gene and subsequent application of the following criteria: p-value < 0.01 and $\log_2$(fold change) > 2.

| Domain ID | Species | SEQ ID NO | Log2 (fold change) | P-value |
|---|---|---|---|---|
| DOMAIN_10351 | *Delphinapterus leucas* | 58264 | 3.3309 | 3.78E−04 |
| DOMAIN_10359 | *Delphinapterus leucas* | 58265 | 2.9199 | 0.0036842 |
| DOMAIN_10381 | *Vicugna pacos* | 58266 | 2.215 | 0.0057838 |
| DOMAIN_10386 | *Odobenus rosmarus divergens* | 58267 | 2.8337 | 0.0028753 |
| DOMAIN_10403 | *Vicugna pacos* | 58268 | 3.3993 | 0.0016441 |
| DOMAIN_10420 | *Odobenus rosmarus divergens* | 58269 | 3.7185 | 1.01E−04 |
| DOMAIN_10425 | *Delphinapterus leucas* | 58270 | 2.8616 | 0.0041775 |
| DOMAIN_10427 | *Carlito syrichta* | 58271 | 2.3719 | 0.0078328 |
| DOMAIN_10491 | *Vicugna pacos* | 58272 | 3.7199 | 0.0012761 |
| DOMAIN_10495 | *Delphinapterus leucas* | 58273 | 3.4705 | 5.27E−04 |
| DOMAIN_10526 | *Delphinapterus leucas* | 58274 | 2.4499 | 0.0033355 |
| DOMAIN_10573 | *Cervus elaphus hippelaphus* | 58275 | 2.4077 | 5.02E−04 |
| DOMAIN_10612 | *Vicugna pacos* | 58276 | 2.4997 | 0.0035134 |
| DOMAIN_10613 | *Odobenus rosmarus divergens* | 58277 | 2.9148 | 5.62E−05 |
| DOMAIN_10623 | *Carlito syrichta* | 58278 | 3.2233 | 0.0018333 |
| DOMAIN_10646 | *Delphinapterus leucas* | 58279 | 2.9354 | 0.0036496 |
| DOMAIN_10647 | *Delphinapterus leucas* | 58280 | 2.9514 | 7.60E−04 |
| DOMAIN_10675 | *Ornithorhynchus anatinus* | 58281 | 3.2777 | 5.13E−05 |
| DOMAIN_10684 | *Odobenus rosmarus divergens* | 58282 | 4.531 | 1.64E−05 |
| DOMAIN_10704 | *Colobus angolensis palliatus* | 58283 | 3.1582 | 0.004292 |
| DOMAIN_10705 | *Colobus angolensis palliatus* | 58284 | 3.6392 | 4.09E−05 |
| DOMAIN_10733 | *Odobenus rosmarus divergens* | 58285 | 3.315 | 0.0028523 |
| DOMAIN_10762 | *Erinaceus europaeus* | 58286 | 3.9254 | 4.55E−05 |
| DOMAIN_10763 | *Mustela putorius furo* | 58287 | 2.5924 | 0.0073193 |
| DOMAIN_10765 | *Mustela putorius furo* | 58288 | 2.5661 | 0.0076445 |
| DOMAIN_10807 | *Erinaceus europaeus* | 58289 | 3.5237 | 1.54E−04 |
| DOMAIN_10882 | *Vicugna pacos* | 58290 | 3.6289 | 2.93E−04 |
| DOMAIN_10902 | *Vicugna pacos* | 58291 | 3.1052 | 0.0096752 |
| DOMAIN_10917 | *Odobenus rosmarus divergens* | 58292 | 3.7871 | 1.53E−07 |
| DOMAIN_10943 | *Cervus elaphus hippelaphus* | 58293 | 2.5554 | 0.0037715 |
| DOMAIN_10974 | *Chelonia mydas* | 58294 | 2.6444 | 0.0091318 |
| DOMAIN_11006 | *Loxodonta africana* | 58295 | 2.6669 | 6.71E−04 |
| DOMAIN_11024 | *Suricata suricatta* | 58296 | 3.2397 | 2.77E−04 |
| DOMAIN_11031 | *Mandrillus leucophaeus* | 58297 | 2.5516 | 0.005857 |
| DOMAIN_11034 | *Mandrillus leucophaeus* | 58298 | 2.2541 | 0.0042161 |
| DOMAIN_11040 | *Sus scrofa* | 58299 | 3.5161 | 3.39E−04 |
| DOMAIN_11049 | *Neophocaena asiaeorientalis asiaeorientalis* | 58300 | 2.7072 | 0.0015299 |
| DOMAIN_11053 | *Nomascus leucogenys* | 58301 | 3.677 | 4.44E−06 |
| DOMAIN_11069 | *Capra hircus* | 58302 | 3.2745 | 0.0036948 |
| DOMAIN_11071 | *Chrysochloris asiatica* | 58303 | 3.1268 | 0.0012421 |
| DOMAIN_11097 | *Mandrillus leucophaeus* | 58304 | 3.239 | 0.0011508 |
| DOMAIN_11110 | *Sus scrofa* | 58305 | 3.6632 | 4.76E−04 |
| DOMAIN_11129 | *Nomascus leucogenys* | 58306 | 2.3864 | 1.88E−04 |
| DOMAIN_11130 | *Nomascus leucogenys* | 58307 | 2.3487 | 6.64E−04 |
| DOMAIN_11132 | *Bos indicus* | 58308 | 3.5671 | 3.08E−05 |
| DOMAIN_11157 | *Suricata suricatta* | 58309 | 3.6671 | 8.22E−05 |
| DOMAIN_11158 | *Chrysochloris asiatica* | 58310 | 2.6889 | 0.0035388 |
| DOMAIN_11162 | *Mandrillus leucophaeus* | 58311 | 3.2804 | 2.65E−04 |
| DOMAIN_11178 | *Sus scrofa* | 58312 | 2.4845 | 0.0043413 |
| DOMAIN_11192 | *Neophocaena asiaeorientalis asiaeorientalis* | 58313 | 2.8798 | 2.10E−04 |
| DOMAIN_11202 | *Nomascus leucogenys* | 58314 | 3.5851 | 4.18E−05 |
| DOMAIN_11204 | *Nomascus leucogenys* | 58315 | 3.5793 | 5.22E−05 |
| DOMAIN_11225 | *Capra hircus* | 58316 | 3.606 | 0.0011566 |
| DOMAIN_11227 | *Capra hircus* | 58317 | 2.7556 | 0.0032733 |
| DOMAIN_11264 | *Sus scrofa* | 58318 | 3.5019 | 5.64E−04 |
| DOMAIN_11265 | *Sus scrofa* | 58319 | 4.2521 | 1.53E−07 |
| DOMAIN_11282 | *Suricata suricatta* | 58320 | 3.536 | 1.53E−07 |
| DOMAIN_11289 | *Suricata suricatta* | 58321 | 2.69 | 2.48E−04 |
| DOMAIN_11291 | *Suricata suricatta* | 58322 | 4.0373 | 4.59E−07 |
| DOMAIN_11307 | *Mandrillus leucophaeus* | 58323 | 3.6383 | 1.07E−06 |
| DOMAIN_11312 | *Sus scrofa* | 58324 | 3.8532 | 9.26E−05 |

TABLE 19-continued

List of 1,597 KRAB domain candidates identified from the high throughput screen assessing dXR repression of the HBEGF gene and subsequent application of the following criteria: p-value < 0.01 and $\log_2$(fold change) > 2.

| Domain ID | Species | SEQ ID NO | Log2 (fold change) | P-value |
|---|---|---|---|---|
| DOMAIN_11314 | *Sus scrofa* | 58325 | 2.9575 | 0.0015357 |
| DOMAIN_11321 | *Nomascus leucogenys* | 58326 | 2.9718 | 0.0086853 |
| DOMAIN_11331 | *Capra hircus* | 58327 | 3.0611 | 4.37E−04 |
| DOMAIN_11332 | *Capra hircus* | 58328 | 3.0468 | 2.19E−04 |
| DOMAIN_11356 | *Sus scrofa* | 58329 | 2.6549 | 0.0027629 |
| DOMAIN_11359 | *Sus scrofa* | 58330 | 3.1036 | 0.0092232 |
| DOMAIN_11381 | *Nomascus leucogenys* | 58331 | 3.1705 | 4.83E−04 |
| DOMAIN_11393 | *Suricata suricatta* | 58332 | 3.4256 | 1.65E−04 |
| DOMAIN_11401 | *Suricata suricatta* | 58333 | 2.6345 | 0.0077459 |
| DOMAIN_11403 | *Suricata suricatta* | 58334 | 3.4222 | 2.27E−04 |
| DOMAIN_11413 | *Sus scrofa* | 58335 | 2.1814 | 0.0084919 |
| DOMAIN_11433 | *Neophocaena asiaeorientalis asiaeorientalis* | 58336 | 3.3986 | 1.91E−05 |
| DOMAIN_11446 | *Nomascus leucogenys* | 58337 | 2.6971 | 3.26E−04 |
| DOMAIN_11461 | *Equus caballus* | 58338 | 2.508 | 0.0090515 |
| DOMAIN_11466 | *Suricata suricatta* | 58339 | 3.4716 | 0.0027896 |
| DOMAIN_11470 | *Mandrillus leucophaeus* | 58340 | 3.1038 | 0.0012895 |
| DOMAIN_11502 | *Trichechus manatus latirostris* | 58341 | 3.601 | 4.21E−05 |
| DOMAIN_11505 | *Trichechus manatus latirostris* | 58342 | 3.0969 | 9.19E−07 |
| DOMAIN_11534 | *Sus scrofa* | 58343 | 3.8118 | 1.91E−05 |
| DOMAIN_11554 | *Nomascus leucogenys* | 58344 | 3.0498 | 4.11E−04 |
| DOMAIN_11567 | *Zalophus californianus* | 58345 | 3.4239 | 0.0010611 |
| DOMAIN_11581 | *Equus caballus* | 58346 | 3.1882 | 4.10E−04 |
| DOMAIN_11612 | *Loxodonta africana* | 58347 | 3.3006 | 0.0040119 |
| DOMAIN_11621 | *Chrysochloris asiatica* | 58348 | 3.2074 | 5.42E−04 |
| DOMAIN_11643 | *Nomascus leucogenys* | 58349 | 2.3544 | 0.0020207 |
| DOMAIN_11662 | *Capra hircus* | 58350 | 3.7889 | 2.36E−04 |
| DOMAIN_11672 | *Suricata suricatta* | 58351 | 3.318 | 0.0022931 |
| DOMAIN_11701 | *Capra hircus* | 58352 | 2.5282 | 0.0084694 |
| DOMAIN_11726 | *Sus scrofa* | 58353 | 3.4183 | 1.09E−05 |
| DOMAIN_11749 | *Chlorocebus sabaeus* | 58354 | 3.2721 | 0.0023817 |
| DOMAIN_11753 | *Mandrillus leucophaeus* | 58355 | 2.6119 | 0.0062269 |
| DOMAIN_11760 | *Neophocaena asiaeorientalis asiaeorientalis* | 58356 | 2.8102 | 0.0039794 |
| DOMAIN_11796 | *Sus scrofa* | 58357 | 2.2811 | 0.0010219 |
| DOMAIN_11813 | *Canis lupus familiaris* | 58358 | 3.5195 | 7.62E−04 |
| DOMAIN_11825 | *Mandrillus leucophaeus* | 58359 | 3.9893 | 1.53E−07 |
| DOMAIN_11851 | *Nomascus leucogenys* | 58360 | 3.0241 | 1.32E−04 |
| DOMAIN_11858 | *Canis lupus familiaris* | 58361 | 3.6419 | 1.53E−07 |
| DOMAIN_11862 | *Canis lupus familiaris* | 58362 | 2.8817 | 0.0032412 |
| DOMAIN_11865 | *Muntiacus muntjak* | 58363 | 3.0474 | 0.0026931 |
| DOMAIN_11868 | *Mandrillus leucophaeus* | 58364 | 3.5158 | 4.44E−06 |
| DOMAIN_11908 | *Canis lupus familiaris* | 58365 | 2.894 | 0.0035529 |
| DOMAIN_11923 | *Sus scrofa* | 58366 | 3.2271 | 0.0018734 |
| DOMAIN_11925 | *Mandrillus leucophaeus* | 58367 | 3.5582 | 3.04E−04 |
| DOMAIN_11928 | *Neophocaena asiaeorientalis asiaeorientalis* | 58368 | 3.751 | 7.59E−04 |
| DOMAIN_11933 | *Neophocaena asiaeorientalis asiaeorientalis* | 58369 | 4.1135 | 1.52E−05 |
| DOMAIN_11944 | *Bos indicus* | 58370 | 3.2762 | 0.0022727 |
| DOMAIN_11950 | *Canis lupus familiaris* | 58371 | 4.3869 | 2.91E−06 |
| DOMAIN_11988 | *Muntiacus muntjak* | 58372 | 3.5916 | 3.83E−06 |
| DOMAIN_11996 | *Canis lupus familiaris* | 58373 | 3.0831 | 0.0015161 |
| DOMAIN_11999 | *Canis lupus familiaris* | 58374 | 3.7891 | 5.04E−05 |
| DOMAIN_12001 | *Mandrillus leucophaeus* | 58375 | 2.4384 | 0.0057376 |
| DOMAIN_12021 | *Canis lupus familiaris* | 58376 | 2.4637 | 0.0018489 |
| DOMAIN_12051 | *Muntiacus muntjak* | 58377 | 2.7925 | 0.0039375 |
| DOMAIN_12057 | *Muntiacus muntjak* | 58378 | 2.0631 | 0.0086017 |
| DOMAIN_12079 | *Muntiacus muntjak* | 58379 | 2.4029 | 0.0095567 |
| DOMAIN_12092 | *Bos mutus* | 58380 | 3.1752 | 1.82E−05 |
| DOMAIN_12114 | *Neophocaena asiaeorientalis asiaeorientalis* | 58381 | 3.3227 | 6.62E−04 |
| DOMAIN_12133 | *Canis lupus familiaris* | 58382 | 3.0204 | 0.0034751 |
| DOMAIN_12139 | *Canis lupus familiaris* | 58383 | 2.8097 | 0.0066678 |

TABLE 19-continued

List of 1,597 KRAB domain candidates identified from the high throughput screen assessing dXR repression of the HBEGF gene and subsequent application of the following criteria: p-value < 0.01 and $\log_2$(fold change) > 2.

| Domain ID | Species | SEQ ID NO | Log2 (fold change) | P-value |
|---|---|---|---|---|
| DOMAIN_12147 | *Neophocaena asiaeorientalis asiaeorientalis* | 58384 | 2.6974 | 9.14E-04 |
| DOMAIN_12158 | *Nomascus leucogenys* | 58385 | 3.0332 | 0.006631 |
| DOMAIN_12187 | *Canis lupus familiaris* | 58386 | 3.6477 | 5.13E-05 |
| DOMAIN_12191 | *Muntiacus muntjak* | 58387 | 3.6138 | 8.18E-04 |
| DOMAIN_12195 | *Canis lupus familiaris* | 58388 | 2.9023 | 1.11E-04 |
| DOMAIN_12206 | *Bos mutus* | 58389 | 2.9101 | 5.13E-04 |
| DOMAIN_12210 | *Bos indicus* | 58390 | 3.6136 | 0.0018284 |
| DOMAIN_12214 | *Muntiacus muntjak* | 58391 | 2.613 | 9.76E-04 |
| DOMAIN_12231 | *Nomascus leucogenys* | 58392 | 2.6703 | 0.00421 |
| DOMAIN_12261 | *Neophocaena asiaeorientalis asiaeorientalis* | 58393 | 2.7989 | 0.0029785 |
| DOMAIN_12285 | Gorilla | 58394 | 2.2573 | 0.0091023 |
| DOMAIN_12313 | *Bos indicus* | 58395 | 2.6903 | 0.0012684 |
| DOMAIN_12320 | *Muntiacus muntjak* | 58396 | 2.5075 | 0.0023021 |
| DOMAIN_12365 | *Nomascus leucogenys* | 58397 | 3.5626 | 7.78E-04 |
| DOMAIN_12395 | *Ailuropoda melanoleuca* | 58398 | 3.1504 | 3.56E-04 |
| DOMAIN_12459 | *Bos indicus* | 58399 | 4.0425 | 3.06E-06 |
| DOMAIN_12463 | *Ailuropoda melanoleuca* | 58400 | 3.2567 | 0.009339 |
| DOMAIN_12467 | Gorilla | 58401 | 2.9575 | 4.85E-04 |
| DOMAIN_12498 | *Muntiacus muntjak* | 58402 | 2.8947 | 0.0075569 |
| DOMAIN_12499 | *Muntiacus muntjak* | 58403 | 2.2932 | 0.0064341 |
| DOMAIN_12508 | Gorilla | 58404 | 3.0173 | 0.0024497 |
| DOMAIN_12511 | Gorilla | 58405 | 3.0694 | 0.0023557 |
| DOMAIN_12517 | *Lynx canadensis* | 58406 | 2.6983 | 0.0017522 |
| DOMAIN_12544 | Gorilla | 58407 | 3.306 | 4.83E-04 |
| DOMAIN_12550 | *Ailuropoda melanoleuca* | 58408 | 3.0229 | 2.37E-04 |
| DOMAIN_12576 | Gorilla | 58409 | 3.04 | 0.0044151 |
| DOMAIN_12590 | *Bos indicus* | 58410 | 2.5531 | 0.0020023 |
| DOMAIN_12591 | *Bos indicus* | 58411 | 3.4169 | 0.0011553 |
| DOMAIN_12598 | *Muntiacus muntjak* | 58412 | 3.3709 | 4.18E-05 |
| DOMAIN_12599 | *Muntiacus muntjak* | 58413 | 2.2098 | 0.007064 |
| DOMAIN_12630 | *Macaca fascicularis* | 58414 | 3.6424 | 4.03E-05 |
| DOMAIN_12646 | *Myotis lucifugus* | 58415 | 3.487 | 0.0014708 |
| DOMAIN_12686 | *Phascolarctos cinereus* | 58416 | 2.76 | 0.0032103 |
| DOMAIN_12698 | *Phascolarctos cinereus* | 58417 | 2.8029 | 0.0066675 |
| DOMAIN_12704 | *Myotis lucifugus* | 58418 | 2.9127 | 0.0034078 |
| DOMAIN_12712 | *Puma concolor* | 58419 | 2.1195 | 0.008023 |
| DOMAIN_12728 | *Lynx canadensis* | 58420 | 3.1999 | 9.49E-04 |
| DOMAIN_12734 | *Phyllostomus discolor* | 58421 | 3.5207 | 1.38E-06 |
| DOMAIN_12755 | *Oryctolagus cuniculus* | 58422 | 2.8082 | 0.0061475 |
| DOMAIN_12764 | *Desmodus rotundus* | 58423 | 3.9505 | 1.53E-07 |
| DOMAIN_12769 | *Macaca fascicularis* | 58424 | 2.0555 | 0.0080928 |
| DOMAIN_12777 | *Phascolarctos cinereus* | 58425 | 2.1778 | 0.0057731 |
| DOMAIN_12780 | *Phascolarctos cinereus* | 58426 | 3.2671 | 1.01E-04 |
| DOMAIN_12801 | *Sapajus apella* | 58427 | 2.0238 | 0.006988 |
| DOMAIN_12811 | *Macaca fascicularis* | 58428 | 2.4278 | 0.0068959 |
| DOMAIN_12815 | *Macaca fascicularis* | 58429 | 2.7296 | 0.0029445 |
| DOMAIN_12818 | *Macaca fascicularis* | 58430 | 3.6211 | 9.69E-05 |
| DOMAIN_12829 | *Phascolarctos cinereus* | 58431 | 3.3994 | 3.20E-04 |
| DOMAIN_12831 | *Phascolarctos cinereus* | 58432 | 2.9845 | 0.0029084 |
| DOMAIN_12839 | *Oryctolagus cuniculus* | 58433 | 3.4039 | 3.03E-04 |
| DOMAIN_12849 | *Muntiacus muntjak* | 58434 | 4.1042 | 1.53E-07 |
| DOMAIN_12896 | *Macaca fascicularis* | 58435 | 2.0413 | 0.0010397 |
| DOMAIN_12901 | *Macaca fascicularis* | 58436 | 3.5686 | 4.75E-06 |
| DOMAIN_12902 | *Macaca fascicularis* | 58437 | 3.3489 | 0.0016432 |
| DOMAIN_12912 | *Puma concolor* | 58438 | 2.7422 | 4.78E-04 |
| DOMAIN_12941 | *Phyllostomus discolor* | 58439 | 2.4012 | 0.0062382 |
| DOMAIN_12985 | *Phascolarctos cinereus* | 58440 | 3.7331 | 3.05E-05 |
| DOMAIN_13004 | *Macaca fascicularis* | 58441 | 3.2216 | 1.37E-04 |
| DOMAIN_13022 | *Phascolarctos cinereus* | 58442 | 3.0468 | 0.003082 |
| DOMAIN_13029 | *Myotis lucifugus* | 58443 | 3.1708 | 3.58E-04 |
| DOMAIN_13062 | *Ursus maritimus* | 58444 | 2.9752 | 2.10E-04 |
| DOMAIN_13068 | *Ailuropoda melanoleuca* | 58445 | 3.6132 | 2.43E-05 |
| DOMAIN_13089 | *Sapajus apella* | 58446 | 2.8761 | 0.0065934 |
| DOMAIN_13111 | *Ailuropoda melanoleuca* | 58447 | 2.6151 | 0.0090675 |
| DOMAIN_13121 | *Macaca fascicularis* | 58448 | 3.353 | 3.98E-04 |
| DOMAIN_13125 | *Macaca fascicularis* | 58449 | 3.2101 | 3.31E-04 |
| DOMAIN_13171 | *Phascolarctos cinereus* | 58450 | 3.0052 | 0.0061932 |
| DOMAIN_13193 | *Sapajus apella* | 58451 | 3.8948 | 1.53E-07 |
| DOMAIN_13227 | *Oryctolagus cuniculus* | 58452 | 2.3234 | 0.0034855 |

TABLE 19-continued

List of 1,597 KRAB domain candidates identified from the high throughput screen assessing dXR repression of the HBEGF gene and subsequent application of the following criteria: p-value < 0.01 and $log_2$(fold change) > 2.

| Domain ID | Species | SEQ ID NO | Log2 (fold change) | P-value |
|---|---|---|---|---|
| DOMAIN_13269 | *Desmodus rotundus* | 58453 | 2.7236 | 0.0010081 |
| DOMAIN_13277 | *Macaca fascicularis* | 58454 | 2.9151 | 4.66E−04 |
| DOMAIN_13282 | *Phascolarctos cinereus* | 58455 | 3.5504 | 8.75E−04 |
| DOMAIN_13284 | *Phascolarctos cinereus* | 58456 | 3.0903 | 0.0057642 |
| DOMAIN_13293 | *Myotis lucifugus* | 58457 | 2.5884 | 6.56E−04 |
| DOMAIN_13325 | *Macaca fascicularis* | 58458 | 2.4051 | 0.0085787 |
| DOMAIN_13332 | *Phascolarctos cinereus* | 58459 | 2.685 | 0.0052498 |
| DOMAIN_13333 | *Phascolarctos cinereus* | 58460 | 2.9787 | 0.0079948 |
| DOMAIN_13339 | *Puma concolor* | 58461 | 3.2731 | 5.64E−04 |
| DOMAIN_13346 | *Oryctolagus cuniculus* | 58462 | 2.9551 | 0.0031649 |
| DOMAIN_13363 | *Phyllostomus discolor* | 58463 | 2.2178 | 0.0041619 |
| DOMAIN_13364 | *Macaca fascicularis* | 58464 | 3.5606 | 2.40E−05 |
| DOMAIN_13379 | *Phascolarctos cinereus* | 58465 | 3.2967 | 0.0018734 |
| DOMAIN_13380 | *Myotis lucifugus* | 58466 | 3.6615 | 1.09E−05 |
| DOMAIN_13387 | *Sapajus apella* | 58467 | 2.8731 | 0.001777 |
| DOMAIN_13417 | *Ailuropoda melanoleuca* | 58468 | 3.7056 | 1.17E−04 |
| DOMAIN_13439 | *Sapajus apella* | 58469 | 2.5091 | 0.0050786 |
| DOMAIN_13470 | *Phascolarctos cinereus* | 58470 | 3.7598 | 2.40E−05 |
| DOMAIN_13486 | *Puma concolor* | 58471 | 3.4895 | 7.93E−04 |
| DOMAIN_13501 | *Macaca fascicularis* | 58472 | 2.8162 | 0.0083892 |
| DOMAIN_13509 | *Phascolarctos cinereus* | 58473 | 2.8053 | 0.00351 |
| DOMAIN_13516 | *Phascolarctos cinereus* | 58474 | 2.4421 | 0.0034809 |
| DOMAIN_13536 | Gorilla | 58475 | 3.3269 | 0.0064418 |
| DOMAIN_13537 | *Ailuropoda melanoleuca* | 58476 | 3.3265 | 8.83E−05 |
| DOMAIN_13562 | *Phascolarctos cinereus* | 58477 | 3.7608 | 4.71E−04 |
| DOMAIN_13565 | *Phascolarctos cinereus* | 58478 | 2.994 | 0.0032926 |
| DOMAIN_13574 | *Puma concolor* | 58479 | 3.1114 | 6.89E−04 |
| DOMAIN_13591 | *Lynx canadensis* | 58480 | 3.215 | 5.12E−04 |
| DOMAIN_13601 | *Macaca fascicularis* | 58481 | 2.4865 | 0.0065955 |
| DOMAIN_13609 | *Phascolarctos cinereus* | 58482 | 3.1787 | 0.002393 |
| DOMAIN_13610 | *Phascolarctos cinereus* | 58483 | 3.1925 | 0.0018707 |
| DOMAIN_13644 | *Phascolarctos cinereus* | 58484 | 3.2677 | 0.001927 |
| DOMAIN_13648 | *Oryctolagus cuniculus* | 58485 | 3.1393 | 0.0014022 |
| DOMAIN_13650 | *Ailuropoda melanoleuca* | 58486 | 3.8556 | 4.44E−06 |
| DOMAIN_13664 | *Macaca fascicularis* | 58487 | 2.7443 | 0.002582 |
| DOMAIN_13670 | *Phascolarctos cinereus* | 58488 | 3.154 | 4.21E−04 |
| DOMAIN_13690 | *Sapajus apella* | 58489 | 3.2587 | 0.0017001 |
| DOMAIN_13691 | *Sapajus apella* | 58490 | 2.6205 | 0.0033052 |
| DOMAIN_13703 | *Lynx canadensis* | 58491 | 3.7947 | 2.43E−05 |
| DOMAIN_13705 | *Phyllostomus discolor* | 58492 | 2.496 | 0.009207 |
| DOMAIN_13722 | *Phascolarctos cinereus* | 58493 | 2.4814 | 0.0058557 |
| DOMAIN_13723 | *Phascolarctos cinereus* | 58494 | 2.9677 | 0.0026349 |
| DOMAIN_13733 | *Sapajus apella* | 58495 | 3.3285 | 1.82E−04 |
| DOMAIN_13783 | *Macaca fascicularis* | 58496 | 2.5821 | 0.0093056 |
| DOMAIN_13805 | *Lynx canadensis* | 58497 | 3.1769 | 0.0088613 |
| DOMAIN_13823 | *Macaca fascicularis* | 58498 | 4.219 | 1.53E−07 |
| DOMAIN_13830 | *Phascolarctos cinereus* | 58499 | 2.6435 | 0.0033465 |
| DOMAIN_13832 | *Phascolarctos cinereus* | 58500 | 2.9705 | 0.0077505 |
| DOMAIN_13843 | *Phascolarctos cinereus* | 58501 | 3.6119 | 1.81E−04 |
| DOMAIN_13851 | *Canis lupus familiaris* | 58502 | 2.6472 | 0.0033845 |
| DOMAIN_13859 | *Macaca fascicularis* | 58503 | 2.2006 | 0.0086366 |
| DOMAIN_13878 | *Ailuropoda melanoleuca* | 58504 | 4.3232 | 4.75E−06 |
| DOMAIN_13880 | *Lynx canadensis* | 58505 | 3.0991 | 0.0013743 |
| DOMAIN_13907 | *Phascolarctos cinereus* | 58506 | 2.4263 | 0.0084749 |
| DOMAIN_13910 | *Bos mutus* | 58507 | 2.9556 | 0.0048664 |
| DOMAIN_13915 | *Muntiacus muntjak* | 58508 | 2.8554 | 0.0080147 |
| DOMAIN_13958 | *Phascolarctos cinereus* | 58509 | 3.2926 | 9.78E−05 |
| DOMAIN_13970 | *Lynx canadensis* | 58510 | 2.89 | 0.0058701 |
| DOMAIN_13979 | *Macaca fascicularis* | 58511 | 2.6188 | 0.0016793 |
| DOMAIN_13981 | *Phascolarctos cinereus* | 58512 | 2.8041 | 0.0024451 |
| DOMAIN_13984 | *Phascolarctos cinereus* | 58513 | 2.8513 | 0.0029797 |
| DOMAIN_13987 | *Myotis lucifugus* | 58514 | 3.0633 | 4.59E−04 |
| DOMAIN_13997 | *Puma concolor* | 58515 | 2.984 | 2.51E−04 |
| DOMAIN_14009 | *Ailuropoda melanoleuca* | 58516 | 2.9207 | 5.05E−05 |
| DOMAIN_14013 | *Ailuropoda melanoleuca* | 58517 | 2.4619 | 0.0082352 |
| DOMAIN_14031 | *Phyllostomus discolor* | 58518 | 3.0963 | 0.0045422 |
| DOMAIN_14040 | *Phascolarctos cinereus* | 58519 | 3.0933 | 0.0065673 |
| DOMAIN_14041 | *Phascolarctos cinereus* | 58520 | 2.9069 | 0.0077333 |
| DOMAIN_14049 | *Phascolarctos cinereus* | 58521 | 2.7761 | 0.0052936 |
| DOMAIN_14069 | *Lynx canadensis* | 58522 | 2.9182 | 0.0020008 |
| DOMAIN_14082 | *Phyllostomus discolor* | 58523 | 3.2495 | 2.19E−04 |
| DOMAIN_14083 | *Phyllostomus discolor* | 58524 | 2.7465 | 0.0042213 |
| DOMAIN_14108 | *Canis lupus familiaris* | 58525 | 3.0621 | 0.004127 |

TABLE 19-continued

List of 1,597 KRAB domain candidates identified from the high throughput screen assessing dXR repression of the HBEGF gene and subsequent application of the following criteria: p-value < 0.01 and $\log_2$(fold change) > 2.

| Domain ID | Species | SEQ ID NO | Log2 (fold change) | P-value |
|---|---|---|---|---|
| DOMAIN_14129 | *Lynx canadensis* | 58526 | 2.8195 | 0.0026925 |
| DOMAIN_14135 | *Bos mutus* | 58527 | 2.426 | 0.0033513 |
| DOMAIN_14147 | *Canis lupus familiaris* | 58528 | 3.3683 | 2.59E−04 |
| DOMAIN_14153 | *Muntiacus muntjak* | 58529 | 2.883 | 0.0011637 |
| DOMAIN_14197 | *Muntiacus muntjak* | 58530 | 2.9589 | 0.0041555 |
| DOMAIN_14219 | *Ailuropoda melanoleuca* | 58531 | 2.6653 | 0.0035657 |
| DOMAIN_14226 | *Lynx canadensis* | 58532 | 3.1176 | 0.0020645 |
| DOMAIN_14228 | *Lynx canadensis* | 58533 | 3.3445 | 7.54E−04 |
| DOMAIN_14256 | *Lynx canadensis* | 58534 | 2.4946 | 0.0066852 |
| DOMAIN_14287 | *Bos indicus* | 58535 | 3.6232 | 1.66E−04 |
| DOMAIN_14295 | *Muntiacus muntjak* | 58536 | 3.4018 | 7.22E−04 |
| DOMAIN_14322 | *Desmodus rotundus* | 58537 | 3.3716 | 1.94E−04 |
| DOMAIN_14337 | *Muntiacus muntjak* | 58538 | 3.2753 | 2.86E−05 |
| DOMAIN_14338 | *Ailuropoda melanoleuca* | 58539 | 3.1071 | 0.0022421 |
| DOMAIN_14358 | *Lynx canadensis* | 58540 | 2.7094 | 8.85E−04 |
| DOMAIN_14365 | *Desmodus rotundus* | 58541 | 3.0706 | 1.39E−04 |
| DOMAIN_14373 | *Macaca fascicularis* | 58542 | 2.5861 | 0.0069375 |
| DOMAIN_14382 | *Phascolarctos cinereus* | 58543 | 4.0523 | 7.52E−05 |
| DOMAIN_14444 | *Phyllostomus discolor* | 58544 | 2.4641 | 0.0037357 |
| DOMAIN_14487 | *Ailuropoda melanoleuca* | 58545 | 2.7981 | 0.0050538 |
| DOMAIN_14526 | *Ailuropoda melanoleuca* | 58546 | 3.2232 | 0.003818 |
| DOMAIN_14532 | *Lynx canadensis* | 58547 | 3.2071 | 2.43E−04 |
| DOMAIN_14534 | *Lynx canadensis* | 58548 | 2.8122 | 0.0039834 |
| DOMAIN_14546 | *Muntiacus muntjak* | 58549 | 3.5039 | 5.01E−05 |
| DOMAIN_14551 | *Ailuropoda melanoleuca* | 58550 | 3.6894 | 2.30E−06 |
| DOMAIN_14557 | *Lynx canadensis* | 58551 | 2.9876 | 2.85E−04 |
| DOMAIN_14574 | Gorilla | 58552 | 3.3356 | 7.83E−04 |
| DOMAIN_14576 | *Ailuropoda melanoleuca* | 58553 | 3.2158 | 0.0028459 |
| DOMAIN_14602 | Gorilla | 58554 | 3.2145 | 0.0037718 |
| DOMAIN_14627 | *Acinonyx jubatus* | 58555 | 2.9501 | 0.0033732 |
| DOMAIN_14639 | Rhesus | 58556 | 2.7046 | 0.0033915 |
| DOMAIN_14714 | *Odocoileus virginianus texanus* | 58557 | 3.2752 | 2.48E−04 |
| DOMAIN_14746 | *Odocoileus virginianus texanus* | 58558 | 2.605 | 0.0084645 |
| DOMAIN_14773 | *Sapajus apella* | 58559 | 3.5997 | 1.45E−05 |
| DOMAIN_14794 | *Acinonyx jubatus* | 58560 | 3.4295 | 4.09E−04 |
| DOMAIN_14795 | *Rhinopithecus roxellana* | 58561 | 2.8119 | 0.0024062 |
| DOMAIN_14800 | *Rhinopithecus roxellana* | 58562 | 2.274 | 0.0012494 |
| DOMAIN_14815 | *Cebus imitator* | 58563 | 3.3826 | 0.0075808 |
| DOMAIN_14820 | *Callithrix jacchus* | 58564 | 2.8836 | 0.0021743 |
| DOMAIN_14829 | *Rhinopithecus roxellana* | 58565 | 2.7188 | 4.08E−04 |
| DOMAIN_14845 | *Cebus imitator* | 58566 | 2.7224 | 0.0041993 |
| DOMAIN_14849 | *Cebus imitator* | 58567 | 2.3659 | 0.0093133 |
| DOMAIN_14862 | *Callithrix jacchus* | 58568 | 2.8116 | 0.0079314 |
| DOMAIN_14864 | Rhesus | 58569 | 3.3492 | 2.46E−04 |
| DOMAIN_14885 | *Cebus imitator* | 58570 | 3.5373 | 4.09E−05 |
| DOMAIN_14901 | *Bos taurus* | 58571 | 2.9774 | 0.0085175 |
| DOMAIN_14905 | *Rhinopithecus roxellana* | 58572 | 3.372 | 0.0034794 |
| DOMAIN_14928 | *Callithrix jacchus* | 58573 | 3.1547 | 2.58E−04 |
| DOMAIN_14939 | *Callorhinus ursinus* | 58574 | 2.3884 | 0.0071338 |
| DOMAIN_14946 | *Acinonyx jubatus* | 58575 | 3.2842 | 7.46E−04 |
| DOMAIN_14948 | *Acinonyx jubatus* | 58576 | 3.3727 | 1.73E−04 |
| DOMAIN_14974 | *Sapajus apella* | 58577 | 2.9963 | 0.0091608 |
| DOMAIN_14977 | *Sapajus apella* | 58578 | 3.0085 | 5.11E−04 |
| DOMAIN_14978 | *Acinonyx jubatus* | 58579 | 3.0358 | 0.0017363 |
| DOMAIN_14983 | *Rhinopithecus roxellana* | 58580 | 3.704 | 1.53E−07 |
| DOMAIN_14994 | *Bison bison bison* | 58581 | 2.4997 | 0.0054874 |
| DOMAIN_14995 | *Cebus imitator* | 58582 | 3.5057 | 4.13E−06 |
| DOMAIN_15042 | *Ovis aries* | 58583 | 3.0774 | 0.0045881 |
| DOMAIN_15070 | *Callithrix jacchus* | 58584 | 4.0108 | 2.60E−04 |
| DOMAIN_15083 | *Ovis aries* | 58585 | 2.7541 | 7.89E−04 |
| DOMAIN_15086 | *Ovis aries* | 58586 | 3.5994 | 2.56E−04 |
| DOMAIN_15089 | *Vulpes vulpes* | 58587 | 2.3585 | 0.0076298 |
| DOMAIN_15102 | *Acinonyx jubatus* | 58588 | 3.0929 | 0.0033921 |
| DOMAIN_15103 | *Bison bison bison* | 58589 | 2.652 | 0.0021839 |
| DOMAIN_15119 | *Callithrix jacchus* | 58590 | 3.3838 | 2.60E−06 |
| DOMAIN_15137 | *Ovis aries* | 58591 | 2.7071 | 0.0022528 |
| DOMAIN_15138 | *Vulpes vulpes* | 58592 | 3.1771 | 6.85E−04 |
| DOMAIN_15159 | *Ovis aries* | 58593 | 3.2135 | 0.0012084 |
| DOMAIN_15171 | *Vulpes vulpes* | 58594 | 3.2837 | 2.40E−05 |
| DOMAIN_15174 | *Vulpes vulpes* | 58595 | 3.1387 | 0.0033116 |
| DOMAIN_15184 | *Acinonyx jubatus* | 58596 | 3.0092 | 0.0021588 |

TABLE 19-continued

List of 1,597 KRAB domain candidates identified from the high throughput screen assessing dXR repression of the HBEGF gene and subsequent application of the following criteria: p-value < 0.01 and $\log_2$(fold change) > 2.

| Domain ID | Species | SEQ ID NO | Log2 (fold change) | P-value |
|---|---|---|---|---|
| DOMAIN_15197 | *Acinonyx jubatus* | 58597 | 3.0957 | 0.0012736 |
| DOMAIN_15227 | *Rhinopithecus roxellana* | 58598 | 3.5532 | 4.75E−06 |
| DOMAIN_15233 | *Rhinopithecus roxellana* | 58599 | 2.788 | 0.0046622 |
| DOMAIN_15234 | *Acinonyx jubatus* | 58600 | 3.546 | 0.0019916 |
| DOMAIN_15241 | *Odocoileus virginianus texanus* | 58601 | 3.3955 | 3.85E−04 |
| DOMAIN_15251 | *Callithrix jacchus* | 58602 | 2.2209 | 9.47E−04 |
| DOMAIN_15254 | *Callithrix jacchus* | 58603 | 3.5159 | 2.32E−04 |
| DOMAIN_15267 | *Ovis aries* | 58604 | 2.8528 | 0.0020149 |
| DOMAIN_15269 | *Ovis aries* | 58605 | 2.0839 | 0.0057336 |
| DOMAIN_15278 | *Callithrix jacchus* | 58606 | 3.2523 | 0.0089241 |
| DOMAIN_15279 | *Callithrix jacchus* | 58607 | 3.8574 | 6.87E−05 |
| DOMAIN_15352 | *Cebus imitator* | 58608 | 3.0832 | 0.0079363 |
| DOMAIN_15354 | *Tursiops truncatus* | 58609 | 3.5099 | 5.16E−05 |
| DOMAIN_15356 | *Acinonyx jubatus* | 58610 | 3.5466 | 0.0019099 |
| DOMAIN_15360 | *Neophocaena asiaeorientalis asiaeorientalis* | 58611 | 3.2575 | 3.95E−04 |
| DOMAIN_15363 | Orangutan | 58612 | 4.3121 | 1.53E−07 |
| DOMAIN_15391 | *Leptonychotes weddellii* | 58613 | 3.9053 | 1.53E−07 |
| DOMAIN_15406 | Chimp | 58614 | 3.4616 | 1.53E−07 |
| DOMAIN_15419 | *Rhinopithecus roxellana* | 58615 | 2.6943 | 0.0012439 |
| DOMAIN_15426 | *Odocoileus virginianus texanus* | 58616 | 2.9673 | 0.0024959 |
| DOMAIN_15447 | *Rhinopithecus roxellana* | 58617 | 3.1112 | 0.0031907 |
| DOMAIN_15451 | *Bison bison bison* | 58618 | 3.2905 | 0.0024601 |
| DOMAIN_15527 | *Balaenoptera acutorostrata scammoni* | 58619 | 3.0354 | 0.0023685 |
| DOMAIN_15536 | *Cebus imitator* | 58620 | 2.4515 | 0.0048713 |
| DOMAIN_15540 | *Callithrix jacchus* | 58621 | 3.124 | 0.0020464 |
| DOMAIN_15575 | *Callithrix jacchus* | 58622 | 2.594 | 0.0095671 |
| DOMAIN_15577 | *Callithrix jacchus* | 58623 | 2.4456 | 0.0010642 |
| DOMAIN_15581 | *Callorhinus ursinus* | 58624 | 3.2465 | 0.0031873 |
| DOMAIN_15586 | *Callorhinus ursinus* | 58625 | 2.6157 | 0.002815 |
| DOMAIN_15603 | *Cebus imitator* | 58626 | 3.5111 | 0.0027084 |
| DOMAIN_15605 | *Cebus imitator* | 58627 | 3.8196 | 2.50E−04 |
| DOMAIN_15634 | *Delphinapterus leucas* | 58628 | 3.3574 | 0.0025587 |
| DOMAIN_15636 | Chimp | 58629 | 2.2086 | 0.0062339 |
| DOMAIN_15638 | *Sapajus apella* | 58630 | 3.4277 | 1.53E−07 |
| DOMAIN_15669 | *Callorhinus ursinus* | 58631 | 2.8865 | 0.0027889 |
| DOMAIN_15687 | *Cebus imitator* | 58632 | 2.5362 | 0.0063187 |
| DOMAIN_15688 | *Cebus imitator* | 58633 | 3.2098 | 6.98E−04 |
| DOMAIN_15693 | Rhesus | 58634 | 3.8571 | 9.95E−06 |
| DOMAIN_15699 | *Bos taurus* | 58635 | 3.5255 | 7.09E−04 |
| DOMAIN_15753 | *Ovis aries* | 58636 | 3.1699 | 0.0035272 |
| DOMAIN_15759 | *Ovis aries* | 58637 | 3.1884 | 0.0011061 |
| DOMAIN_15764 | *Otolemur garnettii* | 58638 | 3.107 | 3.97E−04 |
| DOMAIN_15800 | *Otolemur garnettii* | 58639 | 3.4462 | 1.80E−04 |
| DOMAIN_15814 | Rhesus | 58640 | 3.9503 | 3.26E−05 |
| DOMAIN_15823 | *Ovis aries* | 58641 | 2.8458 | 0.0034405 |
| DOMAIN_15834 | *Otolemur garnettii* | 58642 | 3.7629 | 1.30E−05 |
| DOMAIN_15839 | *Callithrix jacchus* | 58643 | 2.3399 | 0.0090833 |
| DOMAIN_15863 | *Vulpes vulpes* | 58644 | 2.7434 | 0.0042734 |
| DOMAIN_15931 | *Ovis aries* | 58645 | 3.0861 | 0.0028731 |
| DOMAIN_15940 | *Enhydra lutris kenyoni* | 58646 | 2.8684 | 0.007571 |
| DOMAIN_15956 | *Bos taurus* | 58647 | 3.2271 | 4.36E−04 |
| DOMAIN_15972 | *Enhydra lutris kenyoni* | 58648 | 2.3299 | 1.05E−04 |
| DOMAIN_16009 | *Zalophus californianus* | 58649 | 3.2738 | 0.0020718 |
| DOMAIN_16011 | *Delphinapterus leucas* | 58650 | 4.3363 | 1.53E−07 |
| DOMAIN_16017 | *Ovis aries* | 58651 | 2.6715 | 0.0041604 |
| DOMAIN_16023 | *Rhinopithecus bieti* | 58652 | 2.2831 | 0.0064672 |
| DOMAIN_16050 | *Ovis aries* | 58653 | 2.7105 | 0.0086883 |
| DOMAIN_16063 | Rhesus | 58654 | 2.1603 | 0.0054023 |
| DOMAIN_16084 | *Enhydra lutris kenyoni* | 58655 | 3.0131 | 0.0022672 |
| DOMAIN_16115 | *Bos taurus* | 58656 | 2.9023 | 0.0027605 |
| DOMAIN_16123 | *Ovis aries* | 58657 | 2.3799 | 0.0079176 |
| DOMAIN_16147 | Orangutan | 58658 | 2.5699 | 4.83E−04 |
| DOMAIN_16184 | *Ovis aries* | 58659 | 3.7743 | 4.44E−06 |
| DOMAIN_16188 | *Otolemur garnettii* | 58660 | 2.5145 | 0.0014414 |
| DOMAIN_16238 | *Orangutan* | 58661 | 3.8734 | 2.87E−04 |
| DOMAIN_16246 | Rhesus | 58662 | 2.3971 | 3.89E−04 |
| DOMAIN_16253 | *Ovis aries* | 58663 | 4.488 | 1.53E−07 |
| DOMAIN_16266 | *Otolemur garnettii* | 58664 | 3.075 | 0.0019834 |

TABLE 19-continued

List of 1,597 KRAB domain candidates identified from the high throughput screen assessing dXR repression of the HBEGF gene and subsequent application of the following criteria: p-value < 0.01 and $\log_2$(fold change) > 2.

| Domain ID | Species | SEQ ID NO | Log2 (fold change) | P-value |
|---|---|---|---|---|
| DOMAIN_16274 | *Otolemur garnettii* | 58665 | 2.7655 | 0.0014904 |
| DOMAIN_16312 | *Vicugna pacos* | 58666 | 2.4302 | 0.0024702 |
| DOMAIN_16323 | *Trichechus manatus latirostris* | 58667 | 4.0053 | 2.15E−04 |
| DOMAIN_16340 | *Ovis aries* | 58668 | 2.778 | 0.0034068 |
| DOMAIN_16372 | *Odocoileus virginianus texanus* | 58669 | 4.2664 | 1.53E−07 |
| DOMAIN_16378 | *Callithrix jacchus* | 58670 | 2.9868 | 0.0037718 |
| DOMAIN_16399 | *Rhinopithecus roxellana* | 58671 | 4.0639 | 1.53E−07 |
| DOMAIN_16408 | *Cebus imitator* | 58672 | 2.0194 | 0.009233 |
| DOMAIN_16461 | *Cebus imitator* | 58673 | 3.1155 | 0.0020676 |
| DOMAIN_16471 | *Acinonyx jubatus* | 58674 | 3.3465 | 0.0021006 |
| DOMAIN_16478 | *Rhinopithecus roxellana* | 58675 | 2.8285 | 0.0023275 |
| DOMAIN_16516 | Rhesus | 58676 | 3.8473 | 1.94E−05 |
| DOMAIN_16517 | *Callithrix jacchus* | 58677 | 3.3189 | 2.60E−06 |
| DOMAIN_16534 | *Acinonyx jubatus* | 58678 | 2.7531 | 0.0057425 |
| DOMAIN_16556 | *Rhinopithecus roxellana* | 58679 | 2.4217 | 0.0084734 |
| DOMAIN_16566 | *Odocoileus virginianus texanus* | 58680 | 3.3903 | 7.82E−04 |
| DOMAIN_16576 | Chimp | 58681 | 2.6949 | 0.0021998 |
| DOMAIN_16597 | *Cebus imitator* | 58682 | 2.9869 | 0.0023416 |
| DOMAIN_16611 | *Papio anubis* | 58683 | 3.4786 | 1.53E−07 |
| DOMAIN_16618 | *Ursus maritimus* | 58684 | 3.1184 | 0.0015351 |
| DOMAIN_16629 | *Cebus imitator* | 58685 | 3.7569 | 1.57E−04 |
| DOMAIN_16630 | *Cebus imitator* | 58686 | 3.2435 | 1.36E−04 |
| DOMAIN_16638 | *Macaca nemestrina* | 58687 | 3.3871 | 0.0011337 |
| DOMAIN_16648 | *Physeter macrocephalus* | 58688 | 3.629 | 1.88E−05 |
| DOMAIN_16651 | *Delphinapterus leucas* | 58689 | 2.0926 | 0.0074143 |
| DOMAIN_16659 | *Leptonychotes weddellii* | 58690 | 3.8913 | 2.37E−05 |
| DOMAIN_16664 | *Leptonychotes weddellii* | 58691 | 3.4502 | 1.76E−05 |
| DOMAIN_16673 | *Phascolarctos cinereus* | 58692 | 3.0938 | 0.0039727 |
| DOMAIN_16677 | Orangutan | 58693 | 3.1577 | 0.0023254 |
| DOMAIN_16694 | *Callorhinus ursinus* | 58694 | 2.0979 | 0.0094743 |
| DOMAIN_16695 | *Callorhinus ursinus* | 58695 | 3.965 | 3.06E−07 |
| DOMAIN_16696 | *Tursiops truncatus* | 58696 | 3.0806 | 0.002705 |
| DOMAIN_16703 | *Phascolarctos cinereus* | 58697 | 3.3969 | 2.19E−04 |
| DOMAIN_16731 | *Ursus arctos horribilis* | 58698 | 2.849 | 1.30E−05 |
| DOMAIN_16734 | *Leptonychotes weddellii* | 58699 | 3.4791 | 2.57E−04 |
| DOMAIN_16738 | Chimp | 58700 | 3.5957 | 8.11E−06 |
| DOMAIN_16744 | *Enhydra lutris kenyoni* | 58701 | 3.637 | 6.38E−05 |
| DOMAIN_16763 | *Monodelphis domestica* | 58702 | 2.9244 | 0.0053031 |
| DOMAIN_16771 | *Saimiri boliviensis boliviensis* | 58703 | 3.3025 | 0.0027295 |
| DOMAIN_16773 | *Balaenoptera acutorostrata scammoni* | 58704 | 4.5309 | 1.38E−06 |
| DOMAIN_16776 | *Callorhinus ursinus* | 58705 | 3.0877 | 0.0024757 |
| DOMAIN_16809 | *Delphinapterus leucas* | 58706 | 2.4357 | 0.0068567 |
| DOMAIN_16811 | *Balaenoptera acutorostrata scammoni* | 58707 | 3.5141 | 3.08E−04 |
| DOMAIN_16856 | *Ursus maritimus* | 58708 | 2.7613 | 0.0040844 |
| DOMAIN_16865 | *Papio anubis* | 58709 | 3.9619 | 1.53E−07 |
| DOMAIN_16876 | *Callorhinus ursinus* | 58710 | 3.2183 | 4.66E−04 |
| DOMAIN_16877 | *Rhinolophus ferrumequinum* | 58711 | 3.3745 | 3.78E−05 |
| DOMAIN_16936 | *Rhinopithecus roxellana* | 58712 | 2.9808 | 0.0044295 |
| DOMAIN_16953 | *Callorhinus ursinus* | 58713 | 3.3286 | 1.62E−04 |
| DOMAIN_16973 | *Delphinapterus leucas* | 58714 | 3.0187 | 0.0041062 |
| DOMAIN_16994 | *Odocoileus virginianus texanus* | 58715 | 3.0575 | 0.0025431 |
| DOMAIN_17001 | *Rhinolophus ferrumequinum* | 58716 | 3.045 | 0.003661 |
| DOMAIN_17023 | *Sapajus apella* | 58717 | 2.5472 | 0.0041588 |
| DOMAIN_17027 | *Balaenoptera acutorostrata scammoni* | 58718 | 3.131 | 0.0028042 |
| DOMAIN_17041 | *Rhinopithecus roxellana* | 58719 | 2.7589 | 0.0074146 |
| DOMAIN_17062 | *Rhinopithecus roxellana* | 58720 | 3.2594 | 7.33E−05 |
| DOMAIN_17105 | Rhesus | 58721 | 2.637 | 0.0054256 |
| DOMAIN_17108 | *Phyllostomus discolor* | 58722 | 2.4499 | 0.0018315 |
| DOMAIN_17134 | *Panthera pardus* | 58723 | 3.2502 | 0.0016926 |
| DOMAIN_17139 | *Ursus arctos horribilis* | 58724 | 4.0326 | 2.13E−05 |
| DOMAIN_17153 | *Ursus arctos horribilis* | 58725 | 2.1759 | 0.0043459 |
| DOMAIN_17167 | *Ursus maritimus* | 58726 | 4.1644 | 1.52E−05 |
| DOMAIN_17177 | *Physeter macrocephalus* | 58727 | 3.2446 | 0.002928 |

TABLE 19-continued

List of 1,597 KRAB domain candidates identified from the high throughput screen assessing dXR repression of the HBEGF gene and subsequent application of the following criteria: p-value < 0.01 and $\log_2$(fold change) > 2.

| Domain ID | Species | SEQ ID NO | Log2 (fold change) | P-value |
|---|---|---|---|---|
| DOMAIN_17180 | *Zalophus californianus* | 58728 | 2.945 | 0.0082198 |
| DOMAIN_17195 | *Ursus maritimus* | 58729 | 3.0566 | 0.0037464 |
| DOMAIN_17202 | *Ursus arctos horribilis* | 58730 | 2.6589 | 0.0072284 |
| DOMAIN_17206 | *Pteropus vampyrus* | 58731 | 3.7092 | 5.05E−06 |
| DOMAIN_17234 | *Delphinapterus leucas* | 58732 | 2.0152 | 0.0059669 |
| DOMAIN_17236 | *Rhinolophus ferrumequinum* | 58733 | 2.7166 | 0.0039056 |
| DOMAIN_17241 | *Muntiacus muntjak* | 58734 | 2.2217 | 0.003544 |
| DOMAIN_17264 | *Vicugna pacos* | 58735 | 3.0866 | 0.0021294 |
| DOMAIN_17278 | *Tursiops truncatus* | 58736 | 3.4898 | 4.12E−05 |
| DOMAIN_17279 | *Bison bison bison* | 58737 | 3.591 | 8.11E−06 |
| DOMAIN_17333 | *Camelus dromedarius* | 58738 | 2.8765 | 0.003642 |
| DOMAIN_17340 | *Leptonychotes weddellii* | 58739 | 3.1536 | 5.34E−05 |
| DOMAIN_17382 | *Leptonychotes weddellii* | 58740 | 3.075 | 0.0035284 |
| DOMAIN_17383 | *Leptonychotes weddellii* | 58741 | 2.953 | 0.0032519 |
| DOMAIN_17412 | *Ovis aries* | 58742 | 4.9319 | 1.53E−07 |
| DOMAIN_17421 | *Vulpes vulpes* | 58743 | 3.3129 | 2.83E−05 |
| DOMAIN_17474 | *Monodelphis domestica* | 58744 | 2.683 | 0.0036059 |
| DOMAIN_17483 | *Cercocebus atys* | 58745 | 3.5742 | 3.44E−05 |
| DOMAIN_17495 | *Neomonachus schauinslandi* | 58746 | 3.1828 | 5.59E−05 |
| DOMAIN_17497 | *Monodelphis domestica* | 58747 | 2.8088 | 5.07E−05 |
| DOMAIN_17509 | *Physeter macrocephalus* | 58748 | 3.438 | 8.07E−04 |
| DOMAIN_17516 | *Monodelphis domestica* | 58749 | 3.1523 | 4.18E−04 |
| DOMAIN_17525 | *Myotis davidii* | 58750 | 3.4986 | 7.28E−04 |
| DOMAIN_17534 | *Cercocebus atys* | 58751 | 2.9374 | 0.0033612 |
| DOMAIN_17547 | *Neomonachus schauinslandi* | 58752 | 3.2455 | 5.64E−04 |
| DOMAIN_17548 | *Neomonachus schauinslandi* | 58753 | 2.8002 | 5.08E−04 |
| DOMAIN_17574 | *Cercocebus atys* | 58754 | 3.4893 | 2.80E−05 |
| DOMAIN_17632 | *Monodelphis domestica* | 58755 | 3.3689 | 2.06E−04 |
| DOMAIN_17658 | *Monodelphis domestica* | 58756 | 3.8781 | 1.99E−06 |
| DOMAIN_17662 | *Monodelphis domestica* | 58757 | 2.7612 | 0.0040459 |
| DOMAIN_17666 | *Monodelphis domestica* | 58758 | 2.6895 | 0.002059 |
| DOMAIN_17671 | *Monodelphis domestica* | 58759 | 3.0937 | 0.008519 |
| DOMAIN_17689 | *Cercocebus atys* | 58760 | 3.6469 | 1.53E−07 |
| DOMAIN_17704 | *Neomonachus schauinslandi* | 58761 | 3.1047 | 0.0028404 |
| DOMAIN_17714 | *Monodelphis domestica* | 58762 | 2.2724 | 0.0043612 |
| DOMAIN_17717 | *Physeter macrocephalus* | 58763 | 2.9442 | 7.54E−04 |
| DOMAIN_17748 | *Leptonychotes weddellii* | 58764 | 3.0918 | 2.44E−04 |
| DOMAIN_17752 | *Leptonychotes weddellii* | 58765 | 3.2541 | 4.59E−04 |
| DOMAIN_17775 | *Camelus dromedarius* | 58766 | 2.6595 | 0.0033885 |
| DOMAIN_17798 | Orangutan | 58767 | 3.3458 | 5.16E−05 |
| DOMAIN_17801 | Orangutan | 58768 | 2.9733 | 0.0022819 |
| DOMAIN_17871 | *Leptonychotes weddellii* | 58769 | 3.1894 | 1.49E−05 |
| DOMAIN_17873 | *Leptonychotes weddellii* | 58770 | 3.4076 | 3.00E−04 |
| DOMAIN_17890 | *Cercocebus atys* | 58771 | 4.2356 | 2.80E−05 |
| DOMAIN_17898 | *Enhydra lutris kenyoni* | 58772 | 3.2117 | 0.0034476 |
| DOMAIN_17903 | Orangutan | 58773 | 2.4683 | 0.0030976 |
| DOMAIN_17925 | *Otolemur garnettii* | 58774 | 2.7982 | 0.0042639 |
| DOMAIN_18048 | OwlMonkey | 58775 | 2.5186 | 0.0087422 |
| DOMAIN_18083 | *Papio anubis* | 58776 | 2.9283 | 4.79E−04 |
| DOMAIN_18100 | *Neomonachus schauinslandi* | 58777 | 2.3606 | 0.0061598 |
| DOMAIN_18103 | *Monodelphis domestica* | 58778 | 2.7334 | 0.0056181 |
| DOMAIN_18136 | *Monodelphis domestica* | 58779 | 2.7288 | 6.75E−04 |
| DOMAIN_18155 | *Sarcophilus harrisii* | 58780 | 2.7528 | 0.0052222 |
| DOMAIN_18161 | *Cercocebus atys* | 58781 | 2.6663 | 0.0060803 |
| DOMAIN_18181 | *Physeter macrocephalus* | 58782 | 4.696 | 4.59E−07 |
| DOMAIN_18203 | *Monodelphis domestica* | 58783 | 3.7912 | 4.81E−04 |
| DOMAIN_18206 | *Monodelphis domestica* | 58784 | 2.3929 | 0.0046062 |
| DOMAIN_18214 | *Physeter macrocephalus* | 58785 | 2.6389 | 0.0094737 |
| DOMAIN_18227 | OwlMonkey | 58786 | 3.5267 | 5.66E−06 |
| DOMAIN_18241 | *Leptonychotes weddellii* | 58787 | 3.8187 | 9.60E−05 |
| DOMAIN_18243 | *Felis catus* | 58788 | 3.5331 | 6.96E−04 |
| DOMAIN_18244 | *Leptonychotes weddellii* | 58789 | 3.1726 | 0.0050817 |
| DOMAIN_18272 | *Neomonachus schauinslandi* | 58790 | 2.9141 | 0.0085916 |
| DOMAIN_18303 | *Monodelphis domestica* | 58791 | 2.9174 | 0.0018489 |
| DOMAIN_18312 | *Monodelphis domestica* | 58792 | 2.8473 | 8.20E−04 |
| DOMAIN_18323 | *Monodelphis domestica* | 58793 | 2.3956 | 0.0040336 |

TABLE 19-continued

List of 1,597 KRAB domain candidates identified from the high throughput screen assessing dXR repression of the HBEGF gene and subsequent application of the following criteria: p-value < 0.01 and $\log_2$(fold change) > 2.

| Domain ID | Species | SEQ ID NO | Log2 (fold change) | P-value |
|---|---|---|---|---|
| DOMAIN_18325 | *Monodelphis domestica* | 58794 | 2.7636 | 0.0038297 |
| DOMAIN_18332 | *Monodelphis domestica* | 58795 | 3.4328 | 4.68E−04 |
| DOMAIN_18345 | *Monodelphis domestica* | 58796 | 3.349 | 4.43E−04 |
| DOMAIN_18356 | *Monodelphis domestica* | 58797 | 3.1967 | 4.67E−04 |
| DOMAIN_18385 | *Neomonachus schauinslandi* | 58798 | 2.1472 | 0.0044932 |
| DOMAIN_18415 | *Neomonachus schauinslandi* | 58799 | 2.9768 | 4.55E−04 |
| DOMAIN_18424 | *Physeter macrocephalus* | 58800 | 3.7744 | 3.31E−04 |
| DOMAIN_18426 | *Physeter macrocephalus* | 58801 | 2.8011 | 0.0079672 |
| DOMAIN_18428 | *Physeter macrocephalus* | 58802 | 2.5903 | 0.0095383 |
| DOMAIN_18433 | OwlMonkey | 58803 | 3.4614 | 0.0022427 |
| DOMAIN_18441 | *Felis catus* | 58804 | 3.7534 | 1.77E−04 |
| DOMAIN_18458 | *Monodelphis domestica* | 58805 | 3.1061 | 0.0018603 |
| DOMAIN_18459 | *Monodelphis domestica* | 58806 | 3.1352 | 2.38E−04 |
| DOMAIN_18483 | *Monodelphis domestica* | 58807 | 2.8259 | 5.19E−04 |
| DOMAIN_18485 | *Monodelphis domestica* | 58808 | 2.8817 | 0.0011922 |
| DOMAIN_18498 | OwlMonkey | 58809 | 2.7354 | 0.0021141 |
| DOMAIN_18502 | *Myotis davidii* | 58810 | 3.4127 | 1.93E−04 |
| DOMAIN_18504 | *Cercocebus atys* | 58811 | 3.2213 | 5.38E−04 |
| DOMAIN_18536 | *Camelus dromedarius* | 58812 | 3.2028 | 0.0011217 |
| DOMAIN_18580 | *Cercocebus atys* | 58813 | 4.4477 | 3.22E−06 |
| DOMAIN_18589 | *Neomonachus schauinslandi* | 58814 | 3.039 | 0.0025063 |
| DOMAIN_18594 | *Monodelphis domestica* | 58815 | 3.2119 | 0.0036607 |
| DOMAIN_18618 | *Physeter macrocephalus* | 58816 | 2.6489 | 0.0072165 |
| DOMAIN_18646 | *Monodelphis domestica* | 58817 | 2.4678 | 0.007646 |
| DOMAIN_18670 | *Neomonachus schauinslandi* | 58818 | 3.1792 | 3.80E−04 |
| DOMAIN_18677 | *Monodelphis domestica* | 58819 | 2.2686 | 0.0068996 |
| DOMAIN_18693 | *Camelus dromedarius* | 58820 | 3.0179 | 0.0013759 |
| DOMAIN_18698 | *Felis catus* | 58821 | 3.3067 | 0.0093304 |
| DOMAIN_18711 | *Vulpes vulpes* | 58822 | 2.2749 | 0.0063986 |
| DOMAIN_18724 | Chimp | 58823 | 3.2062 | 5.16E−04 |
| DOMAIN_18726 | *Myotis davidii* | 58824 | 2.9362 | 0.0025771 |
| DOMAIN_18734 | *Monodelphis domestica* | 58825 | 2.8813 | 0.0092612 |
| DOMAIN_18752 | *Monodelphis domestica* | 58826 | 3.5544 | 4.85E−05 |
| DOMAIN_18753 | *Monodelphis domestica* | 58827 | 2.6101 | 3.54E−04 |
| DOMAIN_18760 | Chimp | 58828 | 3.1806 | 7.49E−05 |
| DOMAIN_18785 | *Leptonychotes weddellii* | 58829 | 2.9139 | 0.0019203 |
| DOMAIN_18817 | *Monodelphis domestica* | 58830 | 2.2496 | 0.0091589 |
| DOMAIN_18830 | *Monodelphis domestica* | 58831 | 3.2719 | 0.0032764 |
| DOMAIN_18835 | *Camelus dromedarius* | 58832 | 2.4878 | 8.56E−05 |
| DOMAIN_18873 | *Camelus dromedarius* | 58833 | 3.262 | 0.0049846 |
| DOMAIN_18891 | Orangutan | 58834 | 3.6429 | 1.38E−06 |
| DOMAIN_18923 | *Callithrix jacchus* | 58835 | 2.2053 | 0.0054504 |
| DOMAIN_18935 | *Ovis aries* | 58836 | 3.4507 | 3.14E−05 |
| DOMAIN_18947 | *Enhydra lutris kenyoni* | 58837 | 3.3167 | 7.58E−04 |
| DOMAIN_18971 | *Enhydra lutris kenyoni* | 58838 | 3.3941 | 5.05E−06 |
| DOMAIN_18977 | Orangutan | 58839 | 3.6262 | 9.03E−06 |
| DOMAIN_18979 | Orangutan | 58840 | 2.0034 | 0.0071822 |
| DOMAIN_19005 | *Enhydra lutris kenyoni* | 58841 | 3.4092 | 4.57E−04 |
| DOMAIN_19028 | *Orangutan* | 58842 | 2.3618 | 0.0022277 |
| DOMAIN_19056 | *Bos indicus* × *Bos taurus* | 58843 | 3.0542 | 0.001874 |
| DOMAIN_19072 | *Vulpes vulpes* | 58844 | 2.8133 | 0.0016331 |
| DOMAIN_19079 | *Otolemur garnettii* | 58845 | 4.0159 | 4.88E−05 |
| DOMAIN_19125 | *Otolemur garnettii* | 58846 | 2.9892 | 8.36E−04 |
| DOMAIN_19207 | *Enhydra lutris kenyoni* | 58847 | 2.655 | 0.0091617 |
| DOMAIN_19220 | *Camelus dromedarius* | 58848 | 3.1947 | 0.0088687 |
| DOMAIN_19221 | *Camelus dromedarius* | 58849 | 3.1733 | 4.21E−04 |
| DOMAIN_19299 | *Myotis davidii* | 58850 | 2.8882 | 0.0043533 |
| DOMAIN_19351 | Orangutan | 58851 | 3.1988 | 2.17E−04 |
| DOMAIN_19385 | *Monodelphis domestica* | 58852 | 2.9198 | 0.008105 |
| DOMAIN_19387 | *Monodelphis domestica* | 58853 | 3.4706 | 1.85E−04 |
| DOMAIN_19388 | *Physeter macrocephalus* | 58854 | 3.2831 | 7.71E−04 |
| DOMAIN_19404 | *Monodelphis domestica* | 58855 | 2.0125 | 0.0031965 |
| DOMAIN_19423 | *Monodelphis domestica* | 58856 | 3.49 | 0.002544 |
| DOMAIN_19424 | *Monodelphis domestica* | 58857 | 2.5838 | 0.0041846 |
| DOMAIN_19437 | OwlMonkey | 58858 | 2.826 | 0.001773 |
| DOMAIN_19445 | *Monodelphis domestica* | 58859 | 2.1105 | 0.0078325 |
| DOMAIN_19447 | *Monodelphis domestica* | 58860 | 3.4492 | 1.40E−04 |
| DOMAIN_19487 | *Monodelphis domestica* | 58861 | 3.4312 | 6.00E−04 |
| DOMAIN_19497 | *Monodelphis domestica* | 58862 | 3.466 | 2.80E−05 |

TABLE 19-continued

List of 1,597 KRAB domain candidates identified from the high throughput screen assessing dXR repression of the HBEGF gene and subsequent application of the following criteria: p-value < 0.01 and $\log_2$(fold change) > 2.

| Domain ID | Species | SEQ ID NO | Log2 (fold change) | P-value |
|---|---|---|---|---|
| DOMAIN_19517 | *Monodelphis domestica* | 58863 | 3.3361 | 1.04E-04 |
| DOMAIN_19533 | *Papio anubis* | 58864 | 2.5831 | 4.67E-04 |
| DOMAIN_19563 | *Papio anubis* | 58865 | 2.5522 | 0.0089134 |
| DOMAIN_19580 | *Monodelphis domestica* | 58866 | 3.5716 | 3.29E-05 |
| DOMAIN_19585 | *Monodelphis domestica* | 58867 | 3.0031 | 0.0032403 |
| DOMAIN_19596 | *Monodelphis domestica* | 58868 | 3.8583 | 8.18E-05 |
| DOMAIN_19597 | *Monodelphis domestica* | 58869 | 3.5081 | 4.46E-04 |
| DOMAIN_19600 | *Monodelphis domestica* | 58870 | 2.5854 | 0.0042185 |
| DOMAIN_19602 | *Physeter macrocephalus* | 58871 | 2.7219 | 0.0058524 |
| DOMAIN_19611 | *Lipotes vexillifer* | 58872 | 3.3901 | 4.24E-04 |
| DOMAIN_19629 | *Monodelphis domestica* | 58873 | 3.0535 | 0.0017954 |
| DOMAIN_19699 | *Otolemur garnettii* | 58874 | 2.8474 | 3.15E-04 |
| DOMAIN_19708 | *Bos indicus* × *Bos taurus* | 58875 | 3.6339 | 8.02E-04 |
| DOMAIN_19713 | Chimp | 58876 | 3.845 | 2.95E-05 |
| DOMAIN_19721 | *Otolemur garnettii* | 58877 | 2.6913 | 0.0089069 |
| DOMAIN_19776 | *Enhydra lutris kenyoni* | 58878 | 2.617 | 0.0093497 |
| DOMAIN_19777 | Orangutan | 58879 | 3.2427 | 0.0075444 |
| DOMAIN_19780 | Orangutan | 58880 | 3.0867 | 1.72E-04 |
| DOMAIN_19786 | Chimp | 58881 | 2.9155 | 5.94E-04 |
| DOMAIN_19788 | *Enhydra lutris kenyoni* | 58882 | 3.3393 | 4.71E-04 |
| DOMAIN_19800 | *Zalophus californianus* | 58883 | 2.368 | 0.009162 |
| DOMAIN_19805 | *Rhinolophus ferrumequinum* | 58884 | 2.6527 | 0.0030997 |
| DOMAIN_19818 | *Rhinopithecus roxellana* | 58885 | 2.3477 | 0.0022161 |
| DOMAIN_19883 | *Zalophus californianus* | 58886 | 3.5504 | 3.42E-04 |
| DOMAIN_19886 | *Panthera pardus* | 58887 | 2.8642 | 4.04E-05 |
| DOMAIN_19889 | *Vicugna pacos* | 58888 | 3.1963 | 4.15E-05 |
| DOMAIN_19891 | *Zalophus californianus* | 58889 | 3.2135 | 0.0010023 |
| DOMAIN_19921 | *Callorhinus ursinus* | 58890 | 2.0083 | 0.0055679 |
| DOMAIN_19944 | *Zalophus californianus* | 58891 | 3.8559 | 8.71E-05 |
| DOMAIN_19947 | Bonobo | 58892 | 2.2608 | 0.00818 |
| DOMAIN_19967 | *Tursiops truncatus* | 58893 | 2.9548 | 0.0027997 |
| DOMAIN_19968 | *Tursiops truncatus* | 58894 | 2.8089 | 0.004093 |
| DOMAIN_19990 | *Panthera pardus* | 58895 | 3.5329 | 0.0018768 |
| DOMAIN_19993 | *Tursiops truncatus* | 58896 | 3.4227 | 0.0047476 |
| DOMAIN_20012 | *Leptonychotes weddellii* | 58897 | 3.8253 | 3.41E-05 |
| DOMAIN_20023 | *Physeter macrocephalus* | 58898 | 3.6893 | 5.78E-04 |
| DOMAIN_20025 | *Carlito syrichta* | 58899 | 2.2451 | 0.002157 |
| DOMAIN_20030 | *Tursiops truncatus* | 58900 | 4.1273 | 3.22E-06 |
| DOMAIN_20089 | *Panthera pardus* | 58901 | 4.2275 | 8.99E-05 |
| DOMAIN_20095 | *Phascolarctos cinereus* | 58902 | 3.7141 | 1.55E-05 |
| DOMAIN_20115 | *Physeter macrocephalus* | 58903 | 3.1154 | 0.0030089 |
| DOMAIN_20134 | *Acinonyx jubatus* | 58904 | 3.2457 | 3.20E-04 |
| DOMAIN_20136 | *Sus scrofa* | 58905 | 3.3856 | 2.94E-04 |
| DOMAIN_20147 | *Odocoileus virginianus texanus* | 58906 | 3.7467 | 1.53E-07 |
| DOMAIN_20171 | *Trichechus manatus latirostris* | 58907 | 3.951 | 1.03E-05 |
| DOMAIN_20208 | *Pteropus vampyrus* | 58908 | 2.4805 | 0.0041634 |
| DOMAIN_20249 | *Vicugna pacos* | 58909 | 2.7041 | 0.0043741 |
| DOMAIN_20250 | *Phascolarctos cinereus* | 58910 | 3.5525 | 1.37E-04 |
| DOMAIN_20287 | *Cercocebus atys* | 58911 | 3.4486 | 5.29E-04 |
| DOMAIN_20318 | *Callithrix jacchus* | 58912 | 3.5311 | 3.52E-06 |
| DOMAIN_20332 | *Callithrix jacchus* | 58913 | 3.2855 | 0.0011689 |
| DOMAIN_20336 | *Panthera pardus* | 58914 | 2.3293 | 0.0076785 |
| DOMAIN_20345 | *Cebus imitator* | 58915 | 3.8132 | 1.53E-07 |
| DOMAIN_20352 | *Vicugna pacos* | 58916 | 2.9839 | 9.79E-04 |
| DOMAIN_20359 | *Pteropus vampyrus* | 58917 | 3.9594 | 4.06E-05 |
| DOMAIN_20371 | *Ursus arctos horribilis* | 58918 | 2.8418 | 0.0061393 |
| DOMAIN_20381 | *Saimiri boliviensis boliviensis* | 58919 | 2.0412 | 0.0013486 |
| DOMAIN_20398 | *Physeter macrocephalus* | 58920 | 3.1266 | 0.0039215 |
| DOMAIN_20436 | *Sus scrofa* | 58921 | 2.724 | 0.0058616 |
| DOMAIN_20455 | *Nomascus leucogenys* | 58922 | 3.112 | 2.94E-04 |
| DOMAIN_20462 | *Trichechus manatus latirostris* | 58923 | 5.4429 | 1.53E-07 |
| DOMAIN_20469 | *Equus caballus* | 58924 | 2.7506 | 0.0077201 |
| DOMAIN_20487 | *Mandrillus leucophaeus* | 58925 | 2.8325 | 0.0020982 |
| DOMAIN_20524 | *Nomascus leucogenys* | 58926 | 3.2893 | 0.0024993 |
| DOMAIN_20537 | *Chlorocebus sabaeus* | 58927 | 3.2762 | 0.0027249 |
| DOMAIN_20540 | *Mandrillus leucophaeus* | 58928 | 2.8477 | 0.0021931 |
| DOMAIN_20545 | *Sus scrofa* | 58929 | 2.711 | 0.0086718 |
| DOMAIN_20561 | *Chrysochloris asiatica* | 58930 | 3.8309 | 3.52E-05 |

TABLE 19-continued

List of 1,597 KRAB domain candidates identified from the high throughput screen assessing dXR repression of the HBEGF gene and subsequent application of the following criteria: p-value < 0.01 and $\log_2$(fold change) > 2.

| Domain ID | Species | SEQ ID NO | Log2 (fold change) | P-value |
|---|---|---|---|---|
| DOMAIN_20565 | *Suricata suricatta* | 58931 | 3.148 | 2.90E−04 |
| DOMAIN_20601 | *Sus scrofa* | 58932 | 2.9097 | 0.0037911 |
| DOMAIN_20652 | *Neophocaena asiaeorientalis asiaeorientalis* | 58933 | 2.7283 | 0.0038931 |
| DOMAIN_20667 | *Suricata suricatta* | 58934 | 3.7485 | 1.38E−06 |
| DOMAIN_20674 | *Mandrillus leucophaeus* | 58935 | 3.3115 | 1.53E−07 |
| DOMAIN_20716 | *Suricata suricatta* | 58936 | 3.6174 | 3.02E−05 |
| DOMAIN_20729 | *Mandrillus leucophaeus* | 58937 | 2.5535 | 0.0090894 |
| DOMAIN_20746 | *Chrysochloris asiatica* | 58938 | 3.4727 | 4.79E−04 |
| DOMAIN_20767 | *Sus scrofa* | 58939 | 3.1224 | 3.16E−04 |
| DOMAIN_20835 | *Suricata suricatta* | 58940 | 3.0025 | 0.0031432 |
| DOMAIN_20915 | *Mandrillus leucophaeus* | 58941 | 2.4373 | 0.0054586 |
| DOMAIN_20998 | Bonobo | 58942 | 2.6659 | 0.0044767 |
| DOMAIN_21010 | *Equus caballus* | 58943 | 2.2253 | 0.0040982 |
| DOMAIN_21023 | *Sarcophilus harrisii* | 58944 | 3.1196 | 0.0023342 |
| DOMAIN_21067 | *Zalophus californianus* | 58945 | 3.0246 | 0.0010917 |
| DOMAIN_21082 | *Loxodonta africana* | 58946 | 3.2032 | 0.0040056 |
| DOMAIN_21086 | *Pteropus vampyrus* | 58947 | 2.1339 | 0.0079029 |
| DOMAIN_21095 | *Trichechus manatus latirostris* | 58948 | 2.5003 | 0.0091721 |
| DOMAIN_21110 | *Neovison vison* | 58949 | 2.499 | 0.0065113 |
| DOMAIN_21123 | *Callorhinus ursinus* | 58950 | 3.237 | 4.13E−04 |
| DOMAIN_21133 | *Suricata suricatta* | 58951 | 3.1021 | 4.18E−04 |
| DOMAIN_21161 | *Sarcophilus harrisii* | 58952 | 3.2208 | 5.87E−04 |
| DOMAIN_21162 | *Sarcophilus harrisii* | 58953 | 2.885 | 6.85E−04 |
| DOMAIN_21175 | *Callorhinus ursinus* | 58954 | 3.3334 | 2.29E−04 |
| DOMAIN_21197 | *Tursiops truncatus* | 58955 | 2.214 | 0.0073288 |
| DOMAIN_21226 | *Sarcophilus harrisii* | 58956 | 2.6942 | 0.0033484 |
| DOMAIN_21260 | *Pteropus vampyrus* | 58957 | 3.1806 | 0.0039855 |
| DOMAIN_21276 | *Mandrillus leucophaeus* | 58958 | 3.0178 | 0.0029699 |
| DOMAIN_21277 | OwlMonkey | 58959 | 2.7115 | 0.0075352 |
| DOMAIN_21312 | *Lipotes vexillifer* | 58960 | 3.5287 | 4.75E−06 |
| DOMAIN_21333 | *Zalophus californianus* | 58961 | 3.5801 | 3.57E−05 |
| DOMAIN_21334 | *Equus caballus* | 58962 | 2.9508 | 8.67E−04 |
| DOMAIN_21335 | *Equus caballus* | 58963 | 2.518 | 0.0034809 |
| DOMAIN_21367 | *Equus caballus* | 58964 | 2.9921 | 0.0091001 |
| DOMAIN_21369 | *Equus caballus* | 58965 | 2.7947 | 0.0011824 |
| DOMAIN_21371 | *Physeter macrocephalus* | 58966 | 3.8804 | 4.44E−06 |
| DOMAIN_21421 | *Pteropus vampyrus* | 58967 | 2.7713 | 7.52E−05 |
| DOMAIN_21481 | Bonobo | 58968 | 2.7056 | 0.0012415 |
| DOMAIN_21494 | *Tursiops truncatus* | 58969 | 3.783 | 1.36E−04 |
| DOMAIN_21583 | *Sarcophilus harrisii* | 58970 | 3.1529 | 0.0026931 |
| DOMAIN_21588 | *Callorhinus ursinus* | 58971 | 3.4914 | 5.39E−04 |
| DOMAIN_21612 | OwlMonkey | 58972 | 3.2931 | 4.09E−05 |
| DOMAIN_21626 | *Monodelphis domestica* | 58973 | 3.5419 | 1.57E−04 |
| DOMAIN_21632 | *Monodelphis domestica* | 58974 | 2.6551 | 0.0071923 |
| DOMAIN_21658 | *Monodelphis domestica* | 58975 | 3.1325 | 2.50E−04 |
| DOMAIN_21786 | *Trichechus manatus latirostris* | 58976 | 3.2249 | 2.76E−04 |
| DOMAIN_21822 | *Equus caballus* | 58977 | 3.5647 | 3.22E−06 |
| DOMAIN_21823 | *Equus caballus* | 58978 | 3.2474 | 0.0072446 |
| DOMAIN_21844 | OwlMonkey | 58979 | 3.467 | 4.44E−06 |
| DOMAIN_21862 | *Chlorocebus sabaeus* | 58980 | 2.3797 | 0.0032299 |
| DOMAIN_21889 | *Equus caballus* | 58981 | 3.6563 | 4.18E−04 |
| DOMAIN_21896 | *Lipotes vexillifer* | 58982 | 2.8718 | 0.0093653 |
| DOMAIN_21900 | *Equus caballus* | 58983 | 2.7606 | 0.0041711 |
| DOMAIN_21909 | *Suricata suricatta* | 58984 | 3.2301 | 3.40E−04 |
| DOMAIN_21928 | *Callorhinus ursinus* | 58985 | 3.758 | 1.67E−05 |
| DOMAIN_21947 | *Trichechus manatus latirostris* | 58986 | 3.1204 | 0.003623 |
| DOMAIN_21951 | *Equus caballus* | 58987 | 2.8972 | 3.24E−04 |
| DOMAIN_21985 | *Suricata suricatta* | 58988 | 3.6273 | 1.99E−06 |
| DOMAIN_21988 | *Sarcophilus harrisii* | 58989 | 3.3393 | 0.0011817 |
| DOMAIN_21993 | *Lipotes vexillifer* | 58990 | 2.5494 | 0.0039206 |
| DOMAIN_22022 | *Tursiops truncatus* | 58991 | 3.9558 | 4.44E−06 |
| DOMAIN_22079 | *Trichechus manatus latirostris* | 58992 | 3.4511 | 6.43E−04 |
| DOMAIN_22117 | *Sarcophilus harrisii* | 58993 | 2.5969 | 0.0040801 |
| DOMAIN_22143 | *Pteropus vampyrus* | 58994 | 2.6595 | 9.36E−04 |
| DOMAIN_22151 | *Trichechus manatus latirostris* | 58995 | 3.1615 | 5.26E−04 |
| DOMAIN_22158 | *Lipotes vexillifer* | 58996 | 2.0562 | 0.0010562 |

TABLE 19-continued

List of 1,597 KRAB domain candidates identified from the high throughput screen assessing dXR repression of the HBEGF gene and subsequent application of the following criteria: p-value < 0.01 and $log_2$(fold change) > 2.

| Domain ID | Species | SEQ ID NO | Log2 (fold change) | P-value |
|---|---|---|---|---|
| DOMAIN_22166 | *Trichechus manatus latirostris* | 58997 | 4.2024 | 2.53E−05 |
| DOMAIN_22192 | *Trichechus manatus latirostris* | 58998 | 2.8134 | 0.0083622 |
| DOMAIN_22220 | Bonobo | 58999 | 2.8922 | 0.0013379 |
| DOMAIN_22268 | *Lipotes vexillifer* | 59000 | 2.6534 | 0.0053876 |
| DOMAIN_22278 | *Pteropus vampyrus* | 59001 | 3.3575 | 0.0037798 |
| DOMAIN_22280 | *Pteropus vampyrus* | 59002 | 3.1521 | 0.0017347 |
| DOMAIN_22285 | *Trichechus manatus latirostris* | 59003 | 3.0261 | 6.83E−04 |
| DOMAIN_22297 | *Sarcophilus harrisii* | 59004 | 2.4261 | 0.0066953 |
| DOMAIN_22311 | *Monodelphis domestica* | 59005 | 2.9903 | 0.0017115 |
| DOMAIN_22322 | *Tursiops truncatus* | 59006 | 3.4452 | 3.85E−04 |
| DOMAIN_22366 | OwlMonkey | 59007 | 4.848 | 3.06E−07 |
| DOMAIN_22375 | *Tursiops truncatus* | 59008 | 2.5484 | 0.0090894 |
| DOMAIN_22381 | *Tursiops truncatus* | 59009 | 3.8641 | 2.63E−04 |
| DOMAIN_22383 | *Pteropus vampyrus* | 59010 | 3.4752 | 2.48E−04 |
| DOMAIN_22407 | OwlMonkey | 59011 | 2.5308 | 0.0081831 |
| DOMAIN_22425 | OwlMonkey | 59012 | 3.0333 | 0.0032208 |
| DOMAIN_22430 | *Callorhinus ursinus* | 59013 | 2.982 | 0.0064761 |
| DOMAIN_22454 | *Monodelphis domestica* | 59014 | 2.6042 | 0.0022491 |
| DOMAIN_22458 | *Monodelphis domestica* | 59015 | 3.0003 | 0.0025373 |
| DOMAIN_22459 | *Monodelphis domestica* | 59016 | 2.9261 | 0.0013171 |
| DOMAIN_22462 | *Monodelphis domestica* | 59017 | 3.5597 | 2.34E−05 |
| DOMAIN_22471 | *Papio anubis* | 59018 | 3.6293 | 1.68E−06 |
| DOMAIN_22479 | OwlMonkey | 59019 | 3.9668 | 4.18E−05 |
| DOMAIN_22483 | OwlMonkey | 59020 | 2.1702 | 0.0013107 |
| DOMAIN_22495 | *Callorhinus ursinus* | 59021 | 2.2623 | 0.0043918 |
| DOMAIN_22512 | OwlMonkey | 59022 | 2.93 | 0.003255 |
| DOMAIN_22518 | *Lipotes vexillifer* | 59023 | 2.8869 | 0.0024472 |
| DOMAIN_22520 | *Callorhinus ursinus* | 59024 | 3.3586 | 2.83E−05 |
| DOMAIN_22527 | *Tursiops truncatus* | 59025 | 2.989 | 9.71E−04 |
| DOMAIN_22566 | *Papio anubis* | 59026 | 3.5278 | 6.63E−05 |
| DOMAIN_22586 | *Nomascus leucogenys* | 59027 | 2.1811 | 0.0021723 |
| DOMAIN_22615 | *Homo sapiens* | 59028 | 3.0957 | 4.43E−04 |
| DOMAIN_22654 | *Ursus arctos horribilis* | 59029 | 3.248 | 5.59E−05 |
| DOMAIN_22667 | *Saimiri boliviensis boliviensis* | 59030 | 3.4947 | 0.0037256 |
| DOMAIN_22669 | *Balaenoptera acutorostrata scammoni* | 59031 | 3.583 | 4.34E−04 |
| DOMAIN_22692 | *Propithecus coquereli* | 59032 | 3.2791 | 3.52E−04 |
| DOMAIN_22710 | *Propithecus coquereli* | 59033 | 3.4387 | 0.0032081 |
| DOMAIN_22740 | *Panthera pardus* | 59034 | 2.692 | 0.0027611 |
| DOMAIN_22742 | *Panthera pardus* | 59035 | 2.9133 | 0.0027938 |
| DOMAIN_22768 | *Ursus maritimus* | 59036 | 4.0609 | 7.81E−06 |
| DOMAIN_22771 | *Ursus americanus* | 59037 | 3.3498 | 2.83E−05 |
| DOMAIN_22776 | *Propithecus coquereli* | 59038 | 2.7757 | 2.88E−04 |
| DOMAIN_22778 | *Saimiri boliviensis boliviensis* | 59039 | 3.1251 | 4.93E−04 |
| DOMAIN_22782 | *Vombatus ursinus* | 59040 | 3.1663 | 4.24E−04 |
| DOMAIN_22917 | *Cervus elaphus hippelaphus* | 59041 | 3.8061 | 2.77E−05 |
| DOMAIN_22919 | *Colobus angolensis palliatus* | 59042 | 2.8609 | 0.003796 |
| DOMAIN_22928 | *Tupaia chinensis* | 59043 | 3.0141 | 0.0015348 |
| DOMAIN_22937 | *Ursus arctos horribilis* | 59044 | 3.0779 | 0.0032951 |
| DOMAIN_22939 | *Muntiacus reevesi* | 59045 | 3.6187 | 1.78E−04 |
| DOMAIN_22944 | *Muntiacus reevesi* | 59046 | 3.3908 | 5.28E−04 |
| DOMAIN_23007 | *Lynx pardinus* | 59047 | 3.7329 | 1.09E−04 |
| DOMAIN_23009 | *Saimiri boliviensis boliviensis* | 59048 | 3.1269 | 0.0062706 |
| DOMAIN_23011 | *Cervus elaphus hippelaphus* | 59049 | 3.6236 | 3.51E−05 |
| DOMAIN_23012 | *Cervus elaphus hippelaphus* | 59050 | 3.6131 | 2.50E−04 |
| DOMAIN_23013 | *Cervus elaphus hippelaphus* | 59051 | 3.4615 | 4.85E−04 |
| DOMAIN_23018 | *Colobus angolensis palliatus* | 59052 | 3.4177 | 2.30E−04 |
| DOMAIN_23039 | *Saimiri boliviensis boliviensis* | 59053 | 2.8829 | 5.70E−04 |
| DOMAIN_23040 | *Saimiri boliviensis boliviensis* | 59054 | 2.5742 | 0.0056531 |
| DOMAIN_23041 | *Vombatus ursinus* | 59055 | 3.6194 | 1.92E−04 |
| DOMAIN_23050 | *Balaenoptera acutorostrata scammoni* | 59056 | 2.9754 | 0.003318 |
| DOMAIN_23082 | *Mustela putorius furo* | 59057 | 3.9481 | 5.17E−05 |

TABLE 19-continued

List of 1,597 KRAB domain candidates identified from the high throughput screen assessing dXR repression of the HBEGF gene and subsequent application of the following criteria: p-value < 0.01 and $\log_2$(fold change) > 2.

| Domain ID | Species | SEQ ID NO | Log2 (fold change) | P-value |
|---|---|---|---|---|
| DOMAIN_23093 | *Propithecus coquereli* | 59058 | 3.2165 | 5.48E−04 |
| DOMAIN_23109 | *Mustela putorius furo* | 59059 | 2.9639 | 0.0019589 |
| DOMAIN_23113 | *Camelus ferus* | 59060 | 3.4612 | 3.52E−04 |
| DOMAIN_23136 | *Vicugna pacos* | 59061 | 3.285 | 2.16E−04 |
| DOMAIN_23181 | *Colobus angolensis palliatus* | 59062 | 2.7665 | 0.0021609 |
| DOMAIN_23196 | *Odobenus rosmarus divergens* | 59063 | 4.3363 | 3.22E−06 |
| DOMAIN_23200 | *Ursus americanus* | 59064 | 3.755 | 1.84E−06 |
| DOMAIN_23215 | *Vombatus ursinus* | 59065 | 3.0212 | 0.0035725 |
| DOMAIN_23217 | *Vombatus ursinus* | 59066 | 4.1674 | 2.76E−06 |
| DOMAIN_23239 | *Vicugna pacos* | 59067 | 3.0945 | 0.0090937 |
| DOMAIN_23250 | *Delphinapterus leucas* | 59068 | 2.71 | 3.14E−04 |
| DOMAIN_23260 | *Tupaia chinensis* | 59069 | 2.7567 | 0.0029622 |
| DOMAIN_23281 | *Colobus angolensis palliatus* | 59070 | 2.5048 | 0.0036625 |
| DOMAIN_23286 | *Mustela putorius furo* | 59071 | 3.3651 | 1.66E−04 |
| DOMAIN_23301 | *Gulo gulo* | 59072 | 2.6839 | 0.0035226 |
| DOMAIN_23323 | *Erinaceus europaeus* | 59073 | 3.2619 | 0.0031362 |
| DOMAIN_23331 | *Carlito syrichta* | 59074 | 2.8995 | 5.23E−04 |
| DOMAIN_23336 | *Carlito syrichta* | 59075 | 2.239 | 0.0065533 |
| DOMAIN_23341 | *Carlito syrichta* | 59076 | 2.656 | 0.0058992 |
| DOMAIN_23375 | *Vicugna pacos* | 59077 | 3.266 | 7.64E−04 |
| DOMAIN_23378 | *Odobenus rosmarus divergens* | 59078 | 3.0623 | 0.0016508 |
| DOMAIN_23419 | *Gulo gulo* | 59079 | 3.5213 | 7.41E−04 |
| DOMAIN_23453 | *Carlito syrichta* | 59080 | 2.2331 | 0.006161 |
| DOMAIN_23454 | *Carlito syrichta* | 59081 | 3.0632 | 7.96E−04 |
| DOMAIN_23458 | *Vicugna pacos* | 59082 | 2.4232 | 0.0045857 |
| DOMAIN_23480 | *Odobenus rosmarus divergens* | 59083 | 3.4432 | 3.38E−04 |
| DOMAIN_23494 | *Mustela putorius furo* | 59084 | 3.847 | 5.05E−06 |
| DOMAIN_23508 | *Mustela putorius furo* | 59085 | 2.3582 | 0.0047712 |
| DOMAIN_23513 | *Tupaia chinensis* | 59086 | 3.2927 | 5.31E−05 |
| DOMAIN_23514 | *Odobenus rosmarus divergens* | 59087 | 3.0166 | 4.77E−04 |
| DOMAIN_23561 | *Colobus angolensis palliatus* | 59088 | 3.2392 | 0.0021906 |
| DOMAIN_23574 | *Gulo gulo* | 59089 | 2.939 | 0.0083249 |
| DOMAIN_23575 | *Erinaceus europaeus* | 59090 | 3.4624 | 0.001589 |
| DOMAIN_23576 | *Erinaceus europaeus* | 59091 | 3.8014 | 2.89E−05 |
| DOMAIN_23590 | *Odobenus rosmarus divergens* | 59092 | 2.8653 | 0.0052881 |
| DOMAIN_23604 | *Vicugna pacos* | 59093 | 2.6984 | 0.0046123 |
| DOMAIN_23641 | *Carlito syrichta* | 59094 | 2.6942 | 0.0081075 |
| DOMAIN_23642 | *Delphinapterus leucas* | 59095 | 3.8829 | 2.28E−04 |
| DOMAIN_23654 | *Carlito syrichta* | 59096 | 2.337 | 0.0083622 |
| DOMAIN_23679 | *Tupaia chinensis* | 59097 | 3.7951 | 5.10E−05 |
| DOMAIN_23680 | *Vicugna pacos* | 59098 | 2.712 | 0.0034785 |
| DOMAIN_23709 | *Carlito syrichta* | 59099 | 4.545 | 1.53E−07 |
| DOMAIN_23711 | *Gulo gulo* | 59100 | 2.658 | 0.0016432 |
| DOMAIN_23721 | *Carlito syrichta* | 59101 | 2.972 | 0.0022972 |
| DOMAIN_23731 | *Colobus angolensis palliatus* | 59102 | 3.1609 | 2.35E−04 |
| DOMAIN_23745 | *Myotis brandtii* | 59103 | 3.4544 | 3.54E−04 |
| DOMAIN_23793 | *Odobenus rosmarus divergens* | 59104 | 2.7573 | 0.0081197 |
| DOMAIN_23804 | *Colobus angolensis palliatus* | 59105 | 2.3403 | 0.0086366 |
| DOMAIN_23827 | *Odobenus rosmarus divergens* | 59106 | 2.3013 | 0.009767 |
| DOMAIN_23854 | *Gulo gulo* | 59107 | 3.838 | 7.18E−05 |
| DOMAIN_23856 | *Erinaceus europaeus* | 59108 | 3.1072 | 0.0035694 |
| DOMAIN_23863 | *Mustela putorius furo* | 59109 | 2.8758 | 0.0085493 |
| DOMAIN_23885 | *Colobus angolensis palliatus* | 59110 | 3.033 | 0.0034316 |
| DOMAIN_23895 | *Mustela putorius furo* | 59111 | 2.6148 | 0.003318 |
| DOMAIN_23898 | *Mustela putorius furo* | 59112 | 2.7383 | 0.0035921 |
| DOMAIN_23916 | *Odobenus rosmarus divergens* | 59113 | 3.3232 | 1.63E−04 |
| DOMAIN_23931 | *Gulo gulo* | 59114 | 3.8077 | 1.49E−05 |
| DOMAIN_23940 | *Homo sapiens* | 59115 | 2.5087 | 0.0010424 |
| DOMAIN_23953 | *Muntiacus reevesi* | 59116 | 2.4156 | 0.0075055 |

TABLE 19-continued

List of 1,597 KRAB domain candidates identified from the high throughput screen assessing dXR repression of the HBEGF gene and subsequent application of the following criteria: p-value < 0.01 and $log_2$(fold change) > 2.

| Domain ID | Species | SEQ ID NO | Log2 (fold change) | P-value |
|---|---|---|---|---|
| DOMAIN_23979 | *Balaenoptera acutorostrata scammoni* | 59117 | 4.0461 | 5.77E−05 |
| DOMAIN_24020 | *Rhinolophus ferrumequinum* | 59118 | 3.1125 | 1.66E−04 |
| DOMAIN_24028 | *Ursus arctos horribilis* | 59119 | 3.8797 | 1.53E−07 |
| DOMAIN_24035 | *Propithecus coquereli* | 59120 | 3.2225 | 0.0017975 |
| DOMAIN_24042 | *Propithecus coquereli* | 59121 | 3.3038 | 4.75E−06 |
| DOMAIN_24083 | *Myotis brandtii* | 59122 | 3.9804 | 2.77E−05 |
| DOMAIN_24113 | *Propithecus coquereli* | 59123 | 3.3264 | 2.89E−04 |
| DOMAIN_24152 | *Vombatus ursinus* | 59124 | 3.3664 | 0.0022672 |
| DOMAIN_24204 | *Propithecus coquereli* | 59125 | 3.0779 | 4.60E−04 |
| DOMAIN_24212 | *Pteropus alecto* | 59126 | 2.498 | 0.0034998 |
| DOMAIN_24230 | *Muntiacus reevesi* | 59127 | 3.1832 | 1.53E−07 |
| DOMAIN_24256 | *Ursus arctos horribilis* | 59128 | 2.7933 | 0.0018808 |
| DOMAIN_24282 | *Muntiacus reevesi* | 59129 | 2.694 | 0.0052575 |
| DOMAIN_24306 | *Propithecus coquereli* | 59130 | 3.2084 | 0.0023952 |
| DOMAIN_24317 | *Myotis brandtii* | 59131 | 3.9767 | 3.17E−05 |
| DOMAIN_24379 | *Macaca nemestrina* | 59132 | 2.4643 | 0.0086804 |
| DOMAIN_24393 | *Propithecus coquereli* | 59133 | 3.8008 | 2.45E−06 |
| DOMAIN_24446 | *Propithecus coquereli* | 59134 | 3.6312 | 7.27E−05 |
| DOMAIN_24463 | *Balaenoptera acutorostrata scammoni* | 59135 | 2.5362 | 0.007147 |
| DOMAIN_24496 | *Ursus americanus* | 59136 | 3.6403 | 4.24E−04 |
| DOMAIN_24515 | *Balaenoptera acutorostrata scammoni* | 59137 | 3.7358 | 5.28E−05 |
| DOMAIN_24518 | *Balaenoptera acutorostrata scammoni* | 59138 | 3.4135 | 3.05E−05 |
| DOMAIN_24546 | *Ursus americanus* | 59139 | 3.4262 | 8.42E−06 |
| DOMAIN_24570 | *Saimiri boliviensis boliviensis* | 59140 | 3.6773 | 1.45E−05 |
| DOMAIN_24571 | *Balaenoptera acutorostrata scammoni* | 59141 | 2.6912 | 0.0038376 |
| DOMAIN_24600 | *Ursus americanus* | 59142 | 3.156 | 0.0012483 |
| DOMAIN_24614 | *Cervus elaphus hippelaphus* | 59143 | 2.6295 | 0.0046463 |
| DOMAIN_24615 | *Colobus angolensis palliatus* | 59144 | 2.4075 | 0.0069247 |
| DOMAIN_24653 | *Cervus elaphus hippelaphus* | 59145 | 2.9883 | 0.0083016 |
| DOMAIN_24677 | *Lynx pardinus* | 59146 | 2.3115 | 0.0094713 |
| DOMAIN_24719 | *Muntiacus reevesi* | 59147 | 2.7499 | 0.005142 |
| DOMAIN_24725 | *Ursus arctos horribilis* | 59148 | 3.4496 | 4.09E−05 |
| DOMAIN_24771 | *Myotis brandtii* | 59149 | 3.3701 | 0.0025351 |
| DOMAIN_24786 | *Vombatus ursinus* | 59150 | 2.9237 | 0.0078001 |
| DOMAIN_24788 | *Vombatus ursinus* | 59151 | 2.7694 | 0.0021557 |
| DOMAIN_24838 | *Pteropus alecto* | 59152 | 2.3323 | 0.0042954 |
| DOMAIN_24867 | *Nomascus leucogenys* | 59153 | 3.469 | 2.97E−04 |
| DOMAIN_24903 | *Ailuropoda melanoleuca* | 59154 | 3.0377 | 0.0030054 |
| DOMAIN_24939 | *Phascolarctos cinereus* | 59155 | 3.3066 | 6.08E−04 |
| DOMAIN_24947 | *Ursus maritimus* | 59156 | 2.9491 | 0.0055208 |
| DOMAIN_24975 | *Muntiacus muntjak* | 59157 | 3.2737 | 0.0069767 |
| DOMAIN_24993 | *Oryctolagus cuniculus* | 59158 | 3.3817 | 5.00E−04 |
| DOMAIN_25016 | *Oryctolagus cuniculus* | 59159 | 2.9822 | 0.0034776 |
| DOMAIN_25052 | *Pteropus alecto* | 59160 | 2.3634 | 0.0072024 |
| DOMAIN_25060 | *Ailuropoda melanoleuca* | 59161 | 3.6002 | 4.82E−04 |
| DOMAIN_25063 | *Phascolarctos cinereus* | 59162 | 2.9436 | 0.0042752 |
| DOMAIN_25070 | *Sapajus apella* | 59163 | 2.9649 | 0.0043634 |
| DOMAIN_25091 | *Phascolarctos cinereus* | 59164 | 2.9006 | 0.0039332 |
| DOMAIN_25094 | *Phascolarctos cinereus* | 59165 | 3.0413 | 0.0026876 |
| DOMAIN_25106 | *Canis lupus familiaris* | 59166 | 2.8622 | 0.0075508 |
| DOMAIN_25126 | *Puma concolor* | 59167 | 2.1478 | 0.005514 |
| DOMAIN_25128 | *Sapajus apella* | 59168 | 2.588 | 0.0029475 |
| DOMAIN_25131 | *Sapajus apella* | 59169 | 2.592 | 0.0051895 |
| DOMAIN_25146 | *Macaca nemestrina* | 59170 | 3.629 | 1.68E−06 |
| DOMAIN_25150 | *Muntiacus reevesi* | 59171 | 3.147 | 0.0018391 |
| DOMAIN_25157 | *Myotis brandtii* | 59172 | 3.0902 | 0.0012442 |
| DOMAIN_25194 | *Macaca nemestrina* | 59173 | 2.4613 | 0.003597 |
| DOMAIN_25204 | *Panthera pardus* | 59174 | 2.7595 | 0.0027917 |
| DOMAIN_25234 | *Saimiri boliviensis boliviensis* | 59175 | 2.743 | 0.0042296 |
| DOMAIN_25235 | *Oryctolagus cuniculus* | 59176 | 3.6965 | 1.76E−05 |
| DOMAIN_25334 | *Phascolarctos cinereus* | 59177 | 2.7501 | 0.0096299 |
| DOMAIN_25384 | *Rhinolophus ferrumequinum* | 59178 | 3.5139 | 8.10E−05 |
| DOMAIN_25389 | *Ursus maritimus* | 59179 | 3.0814 | 6.54E−04 |

TABLE 19-continued

List of 1,597 KRAB domain candidates identified from the high throughput screen assessing dXR repression of the HBEGF gene and subsequent application of the following criteria: p-value < 0.01 and $log_2$(fold change) > 2.

| Domain ID | Species | SEQ ID NO | Log2 (fold change) | P-value |
|---|---|---|---|---|
| DOMAIN_25400 | *Lynx canadensis* | 59180 | 2.2285 | 3.10E−04 |
| DOMAIN_25410 | *Puma concolor* | 59181 | 2.8699 | 0.0022843 |
| DOMAIN_25443 | *Muntiacus reevesi* | 59182 | 3.2531 | 0.0016615 |
| DOMAIN_25534 | *Ursus maritimus* | 59183 | 2.2698 | 0.0054246 |
| DOMAIN_25554 | *Panthera pardus* | 59184 | 3.0101 | 0.003898 |
| DOMAIN_25564 | *Muntiacus reevesi* | 59185 | 3.4378 | 6.04E−04 |
| DOMAIN_25565 | *Muntiacus reevesi* | 59186 | 2.6133 | 0.0011572 |
| DOMAIN_25623 | *Ursus maritimus* | 59187 | 3.4886 | 2.91E−06 |
| DOMAIN_25628 | *Rhinopithecus bieti* | 59188 | 2.8332 | 0.0022213 |
| DOMAIN_25649 | *Ursus arctos horribilis* | 59189 | 3.6884 | 5.62E−05 |
| DOMAIN_25654 | *Pteropus alecto* | 59190 | 2.2996 | 0.0031144 |
| DOMAIN_25671 | *Muntiacus reevesi* | 59191 | 3.5244 | 1.53E−07 |
| DOMAIN_25682 | *Rhinopithecus bieti* | 59192 | 2.5621 | 0.002108 |
| DOMAIN_25686 | *Panthera pardus* | 59193 | 2.8635 | 0.0031882 |
| DOMAIN_25726 | *Pteropus alecto* | 59194 | 2.8203 | 0.0039506 |
| DOMAIN_25741 | *Sapajus apella* | 59195 | 3.7244 | 1.32E−04 |
| DOMAIN_25780 | *Rhinopithecus bieti* | 59196 | 2.8383 | 0.0018385 |
| DOMAIN_25807 | *Puma concolor* | 59197 | 3.6511 | 0.0018679 |
| DOMAIN_25842 | *Rhinolophus ferrumequinum* | 59198 | 3.0942 | 2.44E−04 |
| DOMAIN_25844 | *Ursus maritimus* | 59199 | 2.5635 | 0.0037997 |
| DOMAIN_25857 | *Balaenoptera acutorostrata scammoni* | 59200 | 2.898 | 0.0026959 |
| DOMAIN_25865 | *Vombatus ursinus* | 59201 | 3.1027 | 0.0066133 |
| DOMAIN_25869 | *Vombatus ursinus* | 59202 | 2.3538 | 0.006932 |
| DOMAIN_25972 | *Geotrypetes seraphini* | 59203 | 3.2178 | 0.0036689 |
| DOMAIN_25973 | *Geotrypetes seraphini* | 59204 | 2.7804 | 0.001766 |
| DOMAIN_25996 | *Geotrypetes seraphini* | 59205 | 3.984 | 1.24E−05 |
| DOMAIN_26010 | *Geotrypetes seraphini* | 59206 | 2.1911 | 0.008383 |
| DOMAIN_26012 | *Geotrypetes seraphini* | 59207 | 2.3532 | 9.70E−04 |
| DOMAIN_26044 | *Geotrypetes seraphini* | 59208 | 2.8874 | 0.0068616 |
| DOMAIN_26103 | *Geotrypetes seraphini* | 59209 | 2.5308 | 0.0033422 |
| DOMAIN_26127 | *Geotrypetes seraphini* | 59210 | 2.5183 | 0.00586 |
| DOMAIN_26131 | *Geotrypetes seraphini* | 59211 | 2.4087 | 0.0068533 |
| DOMAIN_26134 | *Geotrypetes seraphini* | 59212 | 2.4433 | 0.0072939 |
| DOMAIN_26163 | *Geotrypetes seraphini* | 59213 | 2.4527 | 0.0041806 |
| DOMAIN_26177 | *Geotrypetes seraphini* | 59214 | 3.4467 | 1.27E−05 |
| DOMAIN_26180 | *Geotrypetes seraphini* | 59215 | 3.4522 | 1.35E−04 |
| DOMAIN_26194 | *Geotrypetes seraphini* | 59216 | 2.8857 | 0.0031518 |
| DOMAIN_26211 | *Pelodiscus sinensis* | 59217 | 2.6058 | 0.0064871 |
| DOMAIN_26233 | *Colinus virginianus* | 59218 | 3.6739 | 1.77E−04 |
| DOMAIN_26236 | *Pelodiscus sinensis* | 59219 | 2.7094 | 0.003991 |
| DOMAIN_26265 | *Geotrypetes seraphini* | 59220 | 2.5922 | 3.31E−04 |
| DOMAIN_26268 | *Geotrypetes seraphini* | 59221 | 2.1404 | 0.0020397 |
| DOMAIN_26292 | *Geotrypetes seraphini* | 59222 | 2.4722 | 0.0074388 |
| DOMAIN_26299 | *Geotrypetes seraphini* | 59223 | 2.3704 | 0.0058481 |
| DOMAIN_26305 | *Geotrypetes seraphini* | 59224 | 3.0107 | 0.0084216 |
| DOMAIN_26306 | *Geotrypetes seraphini* | 59225 | 2.6178 | 0.0051922 |
| DOMAIN_26335 | *Colinus virginianus* | 59226 | 4.0965 | 3.41E−04 |
| DOMAIN_26340 | *Pelodiscus sinensis* | 59227 | 3.1704 | 0.003352 |
| DOMAIN_26353 | *Pelodiscus sinensis* | 59228 | 3.5785 | 1.16E−04 |
| DOMAIN_26373 | *Pseudonaja textilis* | 59229 | 3.3204 | 5.13E−04 |
| DOMAIN_26407 | *Colinus virginianus* | 59230 | 2.9778 | 0.0049206 |
| DOMAIN_26414 | *Pelodiscus sinensis* | 59231 | 2.9544 | 0.0089308 |
| DOMAIN_26415 | *Pelodiscus sinensis* | 59232 | 2.5032 | 0.0035489 |
| DOMAIN_26416 | *Pelodiscus sinensis* | 59233 | 3.6321 | 4.36E−05 |
| DOMAIN_26417 | *Pelodiscus sinensis* | 59234 | 4.1057 | 4.46E−05 |
| DOMAIN_26423 | *Pelodiscus sinensis* | 59235 | 3.0169 | 0.0025697 |
| DOMAIN_26430 | *Pelodiscus sinensis* | 59236 | 2.6946 | 0.0051824 |
| DOMAIN_26439 | *Pelodiscus sinensis* | 59237 | 3.2468 | 0.0010568 |
| DOMAIN_26463 | *Pelodiscus sinensis* | 59238 | 2.8812 | 0.003427 |
| DOMAIN_26469 | *Pelodiscus sinensis* | 59239 | 3.021 | 5.08E−04 |
| DOMAIN_26496 | *Geotrypetes seraphini* | 59240 | 2.7991 | 0.0040994 |
| DOMAIN_26501 | *Geotrypetes seraphini* | 59241 | 2.6513 | 0.0041882 |
| DOMAIN_26518 | *Geotrypetes seraphini* | 59242 | 2.397 | 0.0087878 |
| DOMAIN_26577 | *Geotrypetes seraphini* | 59243 | 2.4722 | 0.0035247 |
| DOMAIN_26634 | *Gopherus agassizii* | 59244 | 2.8182 | 0.0079972 |
| DOMAIN_26636 | *Gopherus agassizii* | 59245 | 2.6934 | 0.0090052 |
| DOMAIN_26660 | *Phasianus colchicus* | 59246 | 3.201 | 4.90E−04 |
| DOMAIN_26679 | *Paroedura picta* | 59247 | 2.6033 | 0.001326 |
| DOMAIN_26780 | *Meleagris gallopavo* | 59248 | 3.1696 | 0.0031591 |
| DOMAIN_26783 | *Meleagris gallopavo* | 59249 | 3.2848 | 0.0020241 |
| DOMAIN_26795 | *Meleagris gallopavo* | 59250 | 3.3538 | 0.001228 |

TABLE 19-continued

List of 1,597 KRAB domain candidates identified from the high throughput screen assessing dXR repression of the HBEGF gene and subsequent application of the following criteria: p-value < 0.01 and $log_2$(fold change) > 2.

| Domain ID | Species | SEQ ID NO | Log2 (fold change) | P-value |
|---|---|---|---|---|
| DOMAIN_26800 | *Meleagris gallopavo* | 59251 | 3.8197 | 1.62E−04 |
| DOMAIN_26803 | *Aquila chrysaetos chrysaetos* | 59252 | 3.4265 | 0.001246 |
| DOMAIN_26852 | *Mus musculus* | 59253 | 2.8783 | 0.0025253 |
| DOMAIN_26853 | *Mus musculus* | 59254 | 3.6235 | 7.59E−04 |
| DOMAIN_26886 | *Homo sapiens* | 59255 | 3.3209 | 0.0016312 |
| DOMAIN_26925 | *Alligator sinensis* | 59256 | 3.2248 | 0.0036928 |
| DOMAIN_26999 | *Xenopus laevis* | 59257 | 3.4317 | 4.75E−06 |
| DOMAIN_27032 | *Alligator mississippiensis* | 59258 | 3.4805 | 0.0019423 |
| DOMAIN_27285 | *Peromyscus maniculatus bairdii* | 59259 | 3.092 | 5.16E−04 |
| DOMAIN_27498 | *Sus scrofa* | 59260 | 2.9278 | 0.0029754 |
| DOMAIN_27521 | *Suricata suricatta* | 59261 | 2.7447 | 0.0010703 |
| DOMAIN_27563 | *Muntiacus muntjak* | 59262 | 3.6292 | 6.63E−05 |
| DOMAIN_27566 | *Muntiacus muntjak* | 59263 | 2.7825 | 0.0020795 |
| DOMAIN_27579 | *Muntiacus muntjak* | 59264 | 3.8878 | 7.50E−06 |
| DOMAIN_27581 | *Canis lupus familiaris* | 59265 | 2.4582 | 0.0090172 |
| DOMAIN_27639 | *Macaca fascicularis* | 59266 | 2.452 | 0.0032574 |
| DOMAIN_27642 | *Puma concolor* | 59267 | 2.8615 | 0.0015287 |
| DOMAIN_27690 | *Myotis lucifugus* | 59268 | 3.1465 | 0.0012118 |
| DOMAIN_27705 | *Phascolarctos cinereus* | 59269 | 2.5921 | 0.0030483 |
| DOMAIN_27759 | *Bos taurus* | 59270 | 2.2124 | 0.0070756 |
| DOMAIN_27767 | *Callithrix jacchus* | 59271 | 2.2153 | 0.0023952 |
| DOMAIN_27777 | *Odocoileus virginianus texanus* | 59272 | 2.6766 | 0.0067364 |
| DOMAIN_27784 | *Ovis aries* | 59273 | 2.1631 | 0.0040915 |
| DOMAIN_27809 | *Cebus imitator* | 59274 | 2.8715 | 0.0025161 |
| DOMAIN_27827 | *Vulpes vulpes* | 59275 | 3.1318 | 2.13E−05 |
| DOMAIN_27833 | *Callithrix jacchus* | 59276 | 3.0164 | 4.27E−04 |
| DOMAIN_27866 | Orangutan | 59277 | 2.9226 | 0.0029981 |
| DOMAIN_27886 | *Bison bison bison* | 59278 | 2.735 | 0.0036356 |
| DOMAIN_27902 | *Vulpes vulpes* | 59279 | 2.9068 | 0.0039341 |
| DOMAIN_27988 | *Camelus dromedarius* | 59280 | 2.5381 | 0.0015476 |
| DOMAIN_28051 | *Neomonachus schauinslandi* | 59281 | 2.4353 | 0.0018581 |
| DOMAIN_28071 | *Enhydra lutris kenyoni* | 59282 | 3.2938 | 2.61E−04 |
| DOMAIN_28085 | *Enhydra lutris kenyoni* | 59283 | 2.2962 | 0.0029074 |
| DOMAIN_28103 | *Physeter macrocephalus* | 59284 | 2.4116 | 0.009594 |
| DOMAIN_28118 | OwlMonkey | 59285 | 3.1049 | 0.0027807 |
| DOMAIN_28158 | *Odocoileus virginianus texanus* | 59286 | 3.0762 | 0.0016156 |
| DOMAIN_28164 | *Callithrix jacchus* | 59287 | 2.7356 | 0.0064115 |
| DOMAIN_28299 | *Capra hircus* | 59288 | 3.5584 | 6.41E−05 |
| DOMAIN_28309 | *Pteropus vampyrus* | 59289 | 3.5338 | 3.28E−04 |
| DOMAIN_28335 | Bonobo | 59290 | 3.3013 | 2.50E−04 |
| DOMAIN_28341 | *Homo sapiens* | 59291 | 2.7008 | 5.14E−04 |
| DOMAIN_28417 | *Gulo gulo* | 59292 | 2.5366 | 5.02E−04 |
| DOMAIN_28421 | *Erinaceus europaeus* | 59293 | 3.0763 | 0.0038713 |
| DOMAIN_28507 | *Muntiacus reevesi* | 59294 | 3.2874 | 8.76E−04 |
| DOMAIN_28513 | *Propithecus coquereli* | 59295 | 2.3747 | 0.0050076 |
| DOMAIN_28533 | *Propithecus coquereli* | 59296 | 2.7575 | 0.0031303 |
| DOMAIN_28588 | *Rhinolophus ferrumequinum* | 59297 | 2.6131 | 0.0030648 |
| DOMAIN_28619 | *Rhinolophus ferrumequinum* | 59298 | 2.6504 | 0.0027237 |
| DOMAIN_28823 | *Microcaecilia unicolor* | 59299 | 2.331 | 0.0078575 |
| DOMAIN_28845 | *Camelus ferus* | 59300 | 3.0175 | 0.0017733 |
| DOMAIN_28929 | *Mus musculus* | 59301 | 3.1025 | 6.70E−04 |
| DOMAIN_29066 | *Xenopus tropicalis* | 59302 | 2.6393 | 3.67E−04 |
| DOMAIN_29164 | *Chelonia mydas* | 59303 | 2.1345 | 0.0029635 |
| DOMAIN_29260 | *Peromyscus maniculatus bairdii* | 59304 | 2.5127 | 0.0074146 |
| DOMAIN_29339 | *Mesocricetus auratus* | 59305 | 2.9581 | 0.0028165 |
| DOMAIN_29377 | *Mesocricetus auratus* | 59306 | 2.672 | 0.0070692 |
| DOMAIN_29426 | *Mus caroli* | 59307 | 2.0491 | 6.64E−04 |
| DOMAIN_29434 | *Mus caroli* | 59308 | 2.2707 | 0.005184 |
| DOMAIN_29467 | *Mus caroli* | 59309 | 3.4689 | 5.79E−05 |
| DOMAIN_29471 | *Cricetulus griseus* | 59310 | 3.1911 | 4.18E−05 |
| DOMAIN_29511 | *Peromyscus maniculatus bairdii* | 59311 | 3.4739 | 7.00E−05 |
| DOMAIN_29614 | *Peromyscus maniculatus bairdii* | 59312 | 3.4528 | 1.82E−04 |
| DOMAIN_29616 | *Mesocricetus auratus* | 59313 | 2.2807 | 0.0035376 |

TABLE 19-continued

List of 1,597 KRAB domain candidates identified from the high throughput screen assessing dXR repression of the HBEGF gene and subsequent application of the following criteria: p-value < 0.01 and $log_2$(fold change) > 2.

| Domain ID | Species | SEQ ID NO | Log2 (fold change) | P-value |
|---|---|---|---|---|
| DOMAIN_29765 | *Erinaceus europaeus* | 59314 | 3.3088 | 9.79E−04 |
| DOMAIN_29900 | *Nomascus leucogenys* | 59315 | 2.1583 | 0.0098463 |
| DOMAIN_30185 | *Rhinopithecus roxellana* | 59316 | 3.0766 | 5.83E−05 |
| DOMAIN_30211 | *Bison bison bison* | 59317 | 2.3322 | 0.0023122 |
| DOMAIN_30236 | *Callithrix jacchus* | 59318 | 2.7293 | 0.0021744 |
| DOMAIN_30329 | Rhesus | 59319 | 2.1216 | 0.0099018 |
| DOMAIN_30783 | Chimp | 59320 | 2.952 | 0.001698 |
| DOMAIN_31235 | *Vicugna pacos* | 59321 | 2.2828 | 0.0067045 |
| DOMAIN_31340 | *Homo sapiens* | 59322 | 2.8261 | 0.0021028 |
| DOMAIN_31383 | *Propithecus coquereli* | 59323 | 2.1919 | 0.0087058 |
| DOMAIN_31638 | *Balaenoptera acutorostrata scammoni* | 59324 | 2.0254 | 0.0036297 |
| DOMAIN_31798 | *Notechis scutatus* | 59325 | 4.8007 | 7.82E−04 |
| DOMAIN_31935 | *Rhinolophus ferrumequinum* | 59326 | 3.5544 | 0.0084786 |
| DOMAIN_32127 | Human | 59327 | 3.7547 | 2.62E−05 |
| DOMAIN_32145 | Human | 59328 | 3.1866 | 1.67E−05 |
| DOMAIN_32146 | Human | 59329 | 2.7628 | 0.0016129 |
| DOMAIN_32159 | Human | 59330 | 2.7874 | 0.0021753 |
| DOMAIN_32215 | Human | 59331 | 3.2653 | 0.001461 |
| DOMAIN_32223 | Human | 59332 | 2.8836 | 0.0068873 |
| DOMAIN_32255 | Human | 59333 | 3.8237 | 1.39E−05 |
| DOMAIN_32279 | Human | 59334 | 2.4917 | 0.0060199 |
| DOMAIN_32286 | Human | 59335 | 2.8921 | 0.0070992 |
| DOMAIN_32312 | Human | 59336 | 2.9151 | 0.0030308 |
| DOMAIN_32321 | Human | 59337 | 3.0441 | 0.0040854 |
| DOMAIN_32327 | Human | 59338 | 3.1024 | 0.0044212 |
| DOMAIN_32334 | Human | 59339 | 2.8117 | 0.0015241 |
| DOMAIN_32351 | Human | 59340 | 2.0727 | 0.0036362 |
| DOMAIN_32386 | Human | 59341 | 3.5521 | 3.87E−04 |
| DOMAIN_32390 | Human | 59342 | 3.757 | 4.30E−05 |

The KRAB domain with the highest $log_2$(fold change) was derived from the king cobra, *Ophiophagus hannah* (DOMAIN_26749; SEQ ID NO: 57755). Surprisingly, this sequence was highly divergent from human KRAB domains (with only 41% sequence identity) and was grouped in a sequence cluster of poor repressor domains.

Figure 17:
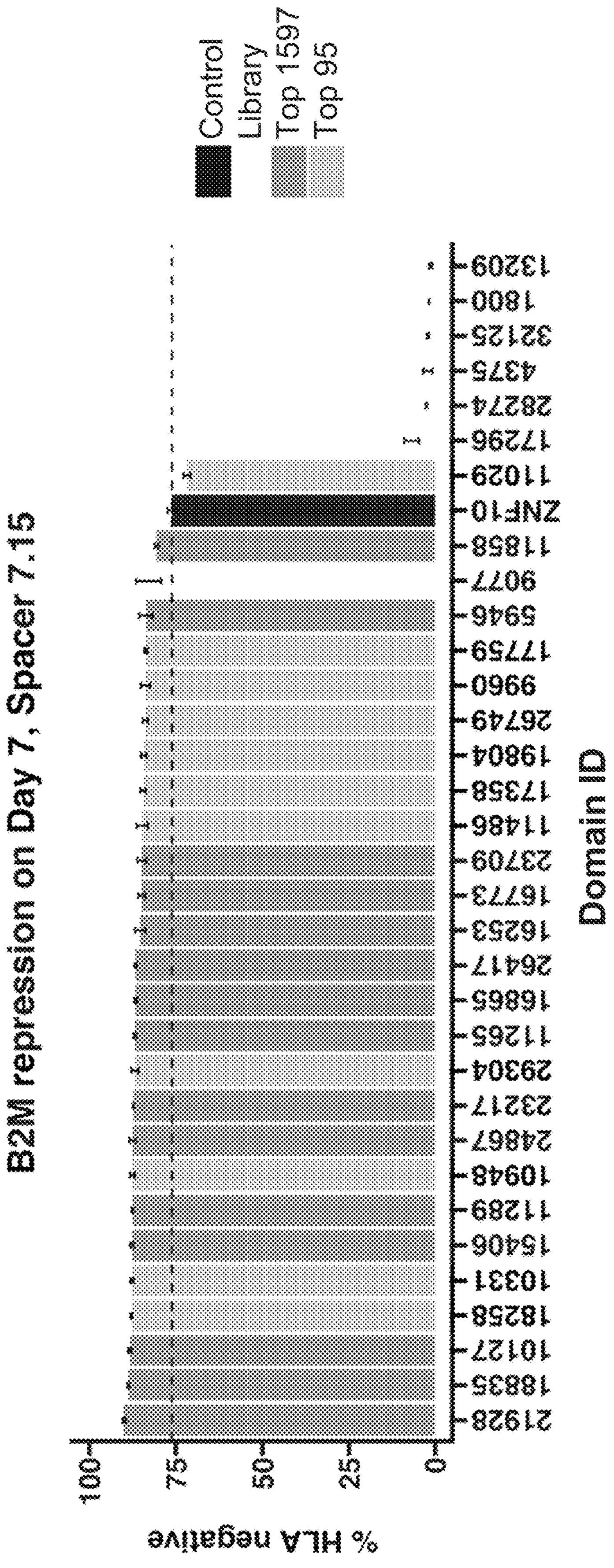
FIG. 17 shows B2M silencing activities (represented as percentage of HLA-negative cells) of dXR proteins with various KRAB domains, as described in Example 4. Data are presented as mean with standard deviation, N=3.
Figure 18:
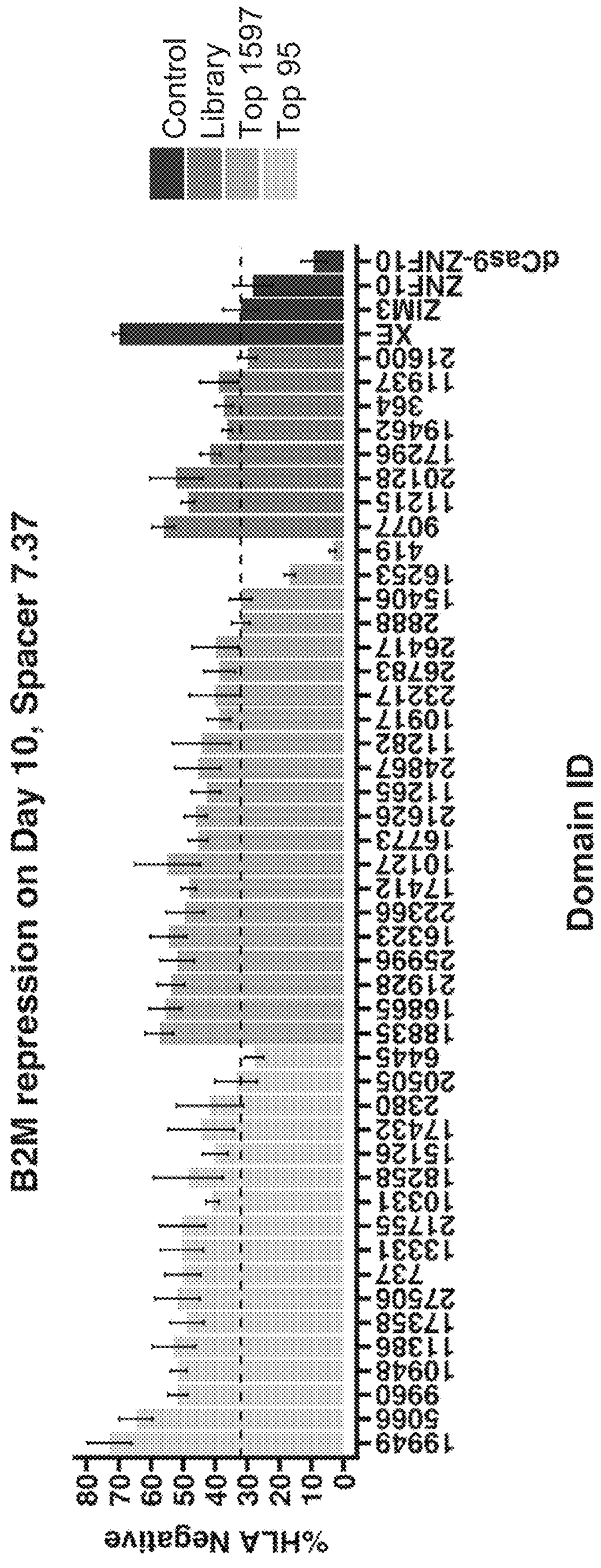
FIG. 18 shows B2M silencing activities (represented as percentage of HLA-negative cells) of dXR proteins with various KRAB domains, as described in Example 4. Data are presented as mean with standard deviation, N=3.
Figure 19A:
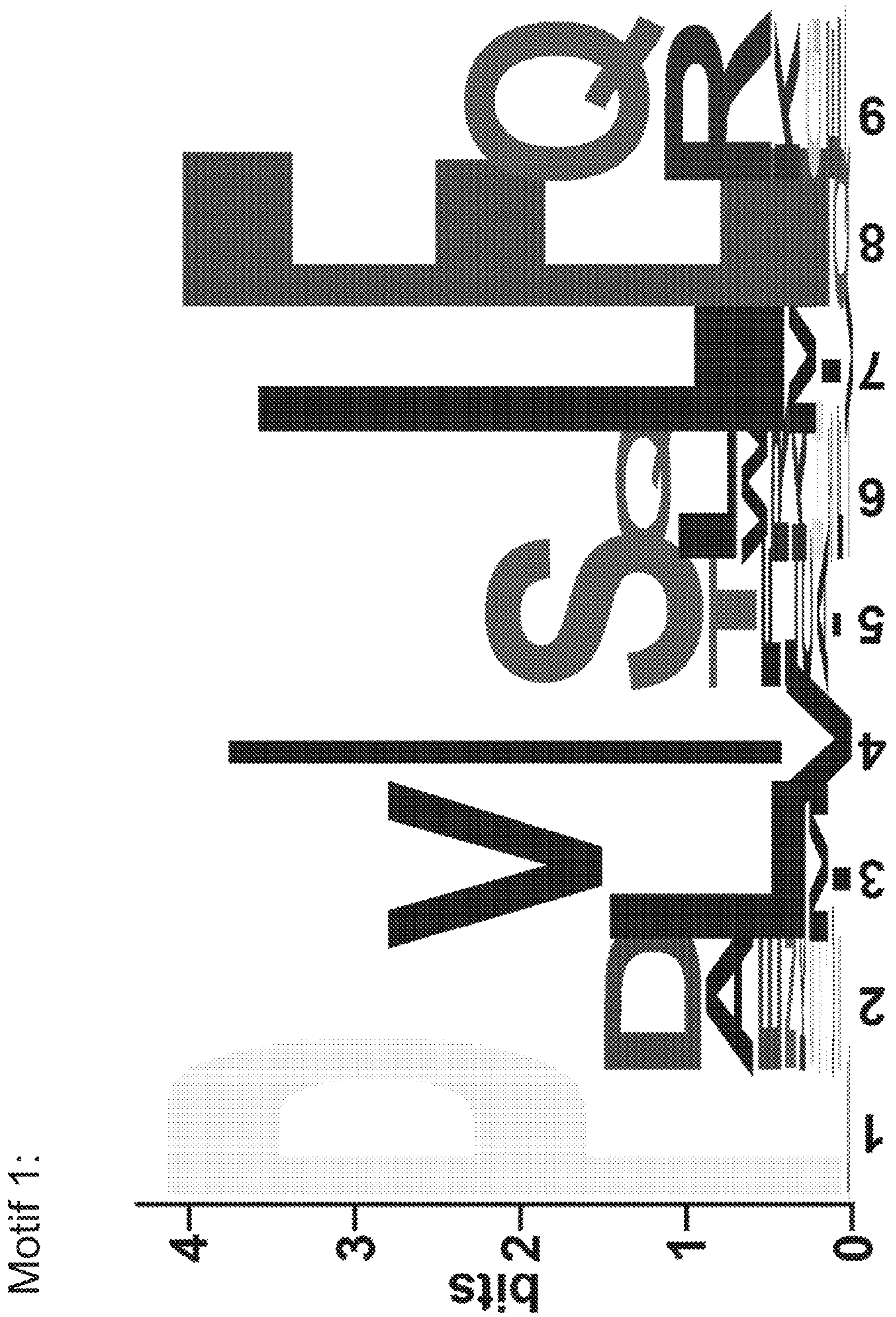
FIG. 19A provides the logo of KRAB domain motif 1, as described in Example 4.
Figure 19B:
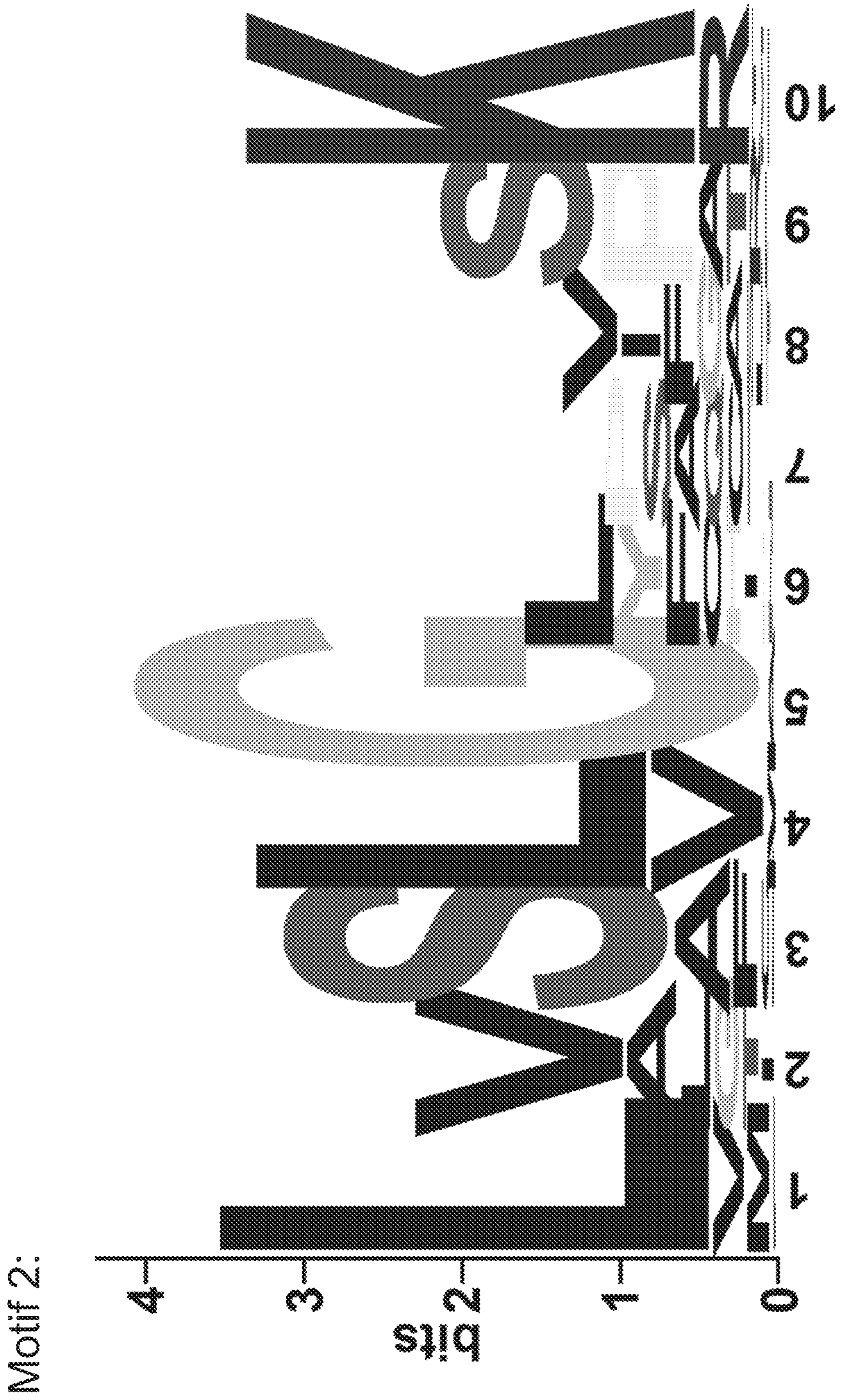
FIG. 19B provides the logo of KRAB domain motif 2, as described in Example 4.
Figure 19C:
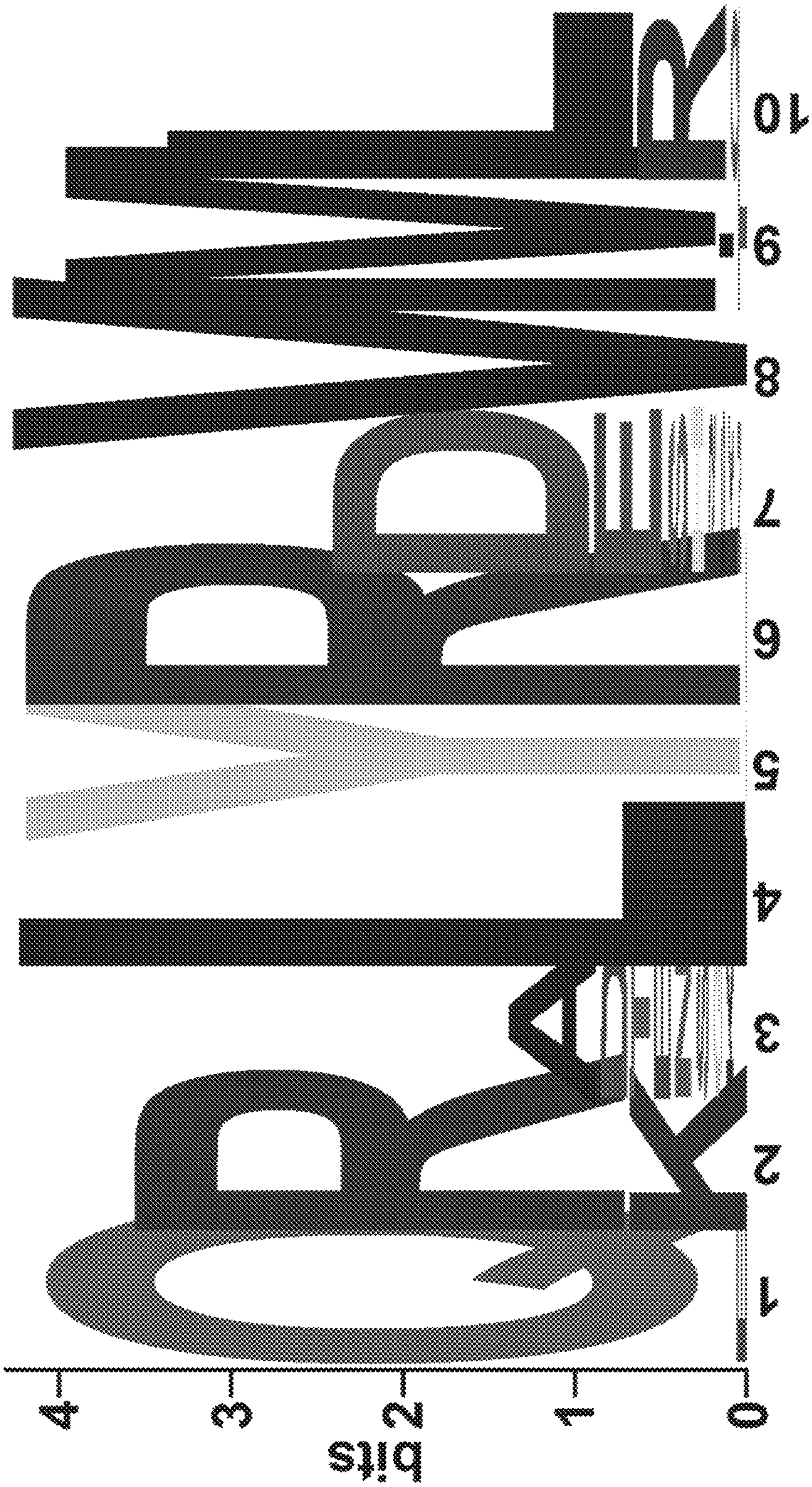
FIG. 19C provides the logo of KRAB domain motif 3 (SEQ ID NO: 59345), as described in Example 4.
Figure 19D:
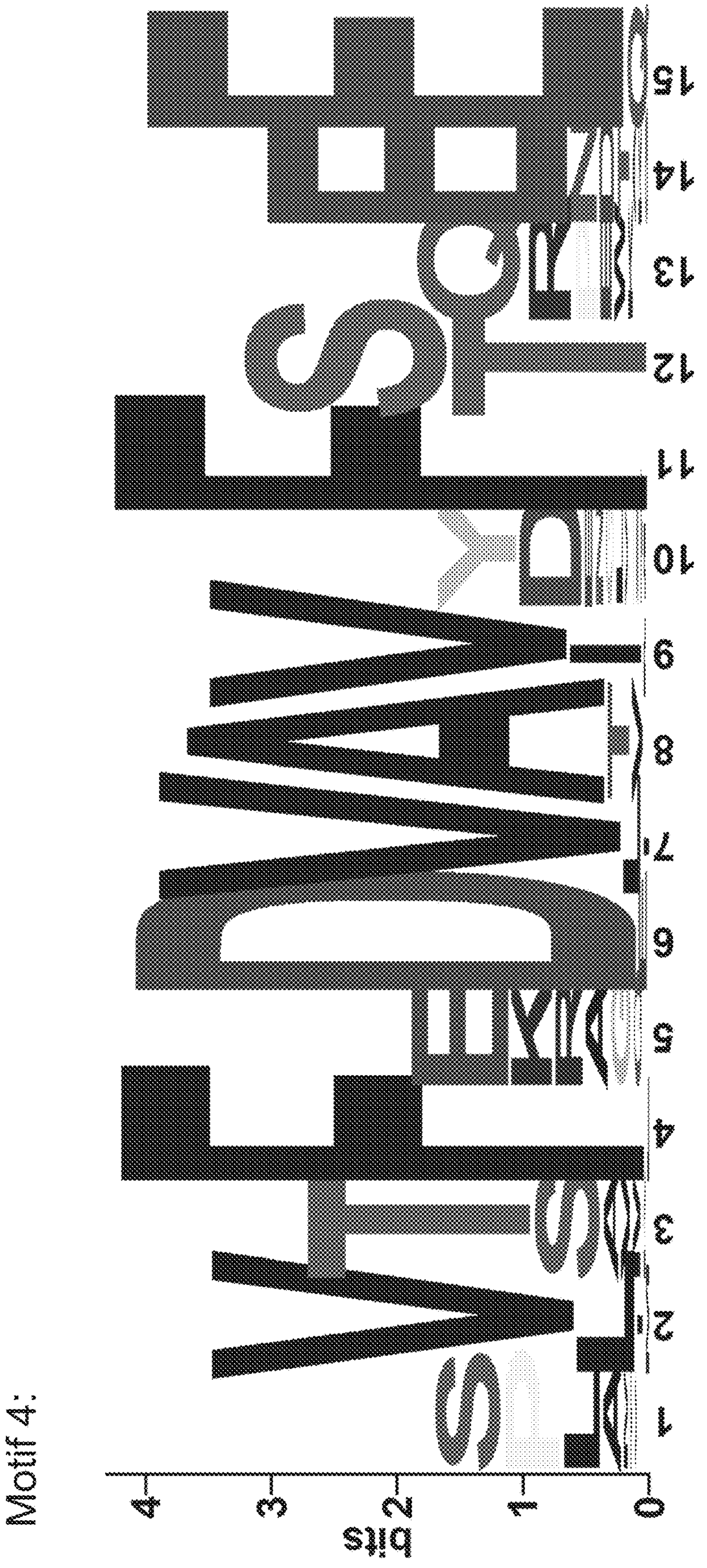
FIG. 19D provides the logo of KRAB domain motif 4 (SEQ ID NO: 59346), as described in Example 4.
Figure 19E:
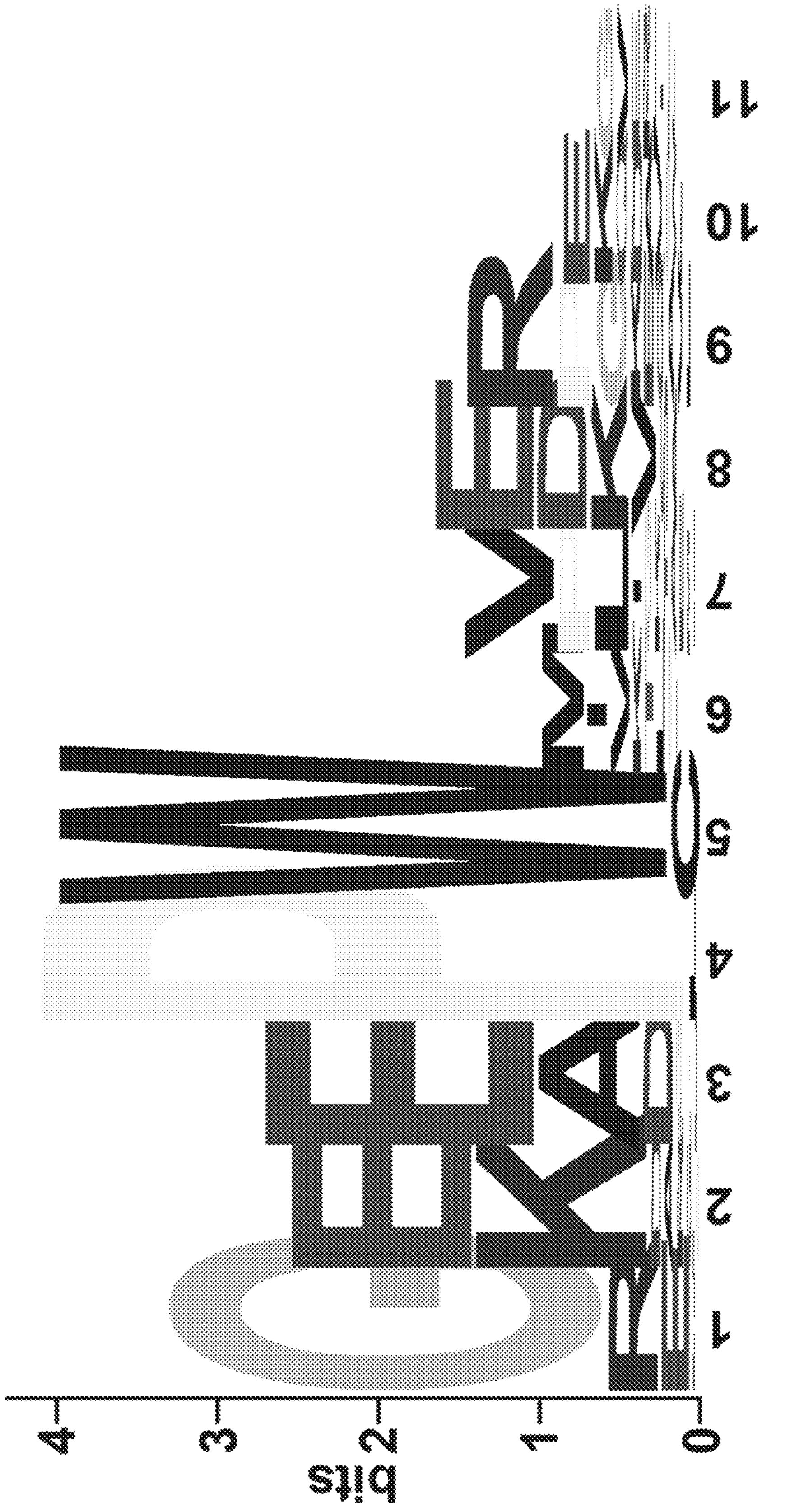
FIG. 19E provides the logo of KRAB domain motif 5 (SEQ ID NO: 59347), as described in Example 4.
Figure 19F:
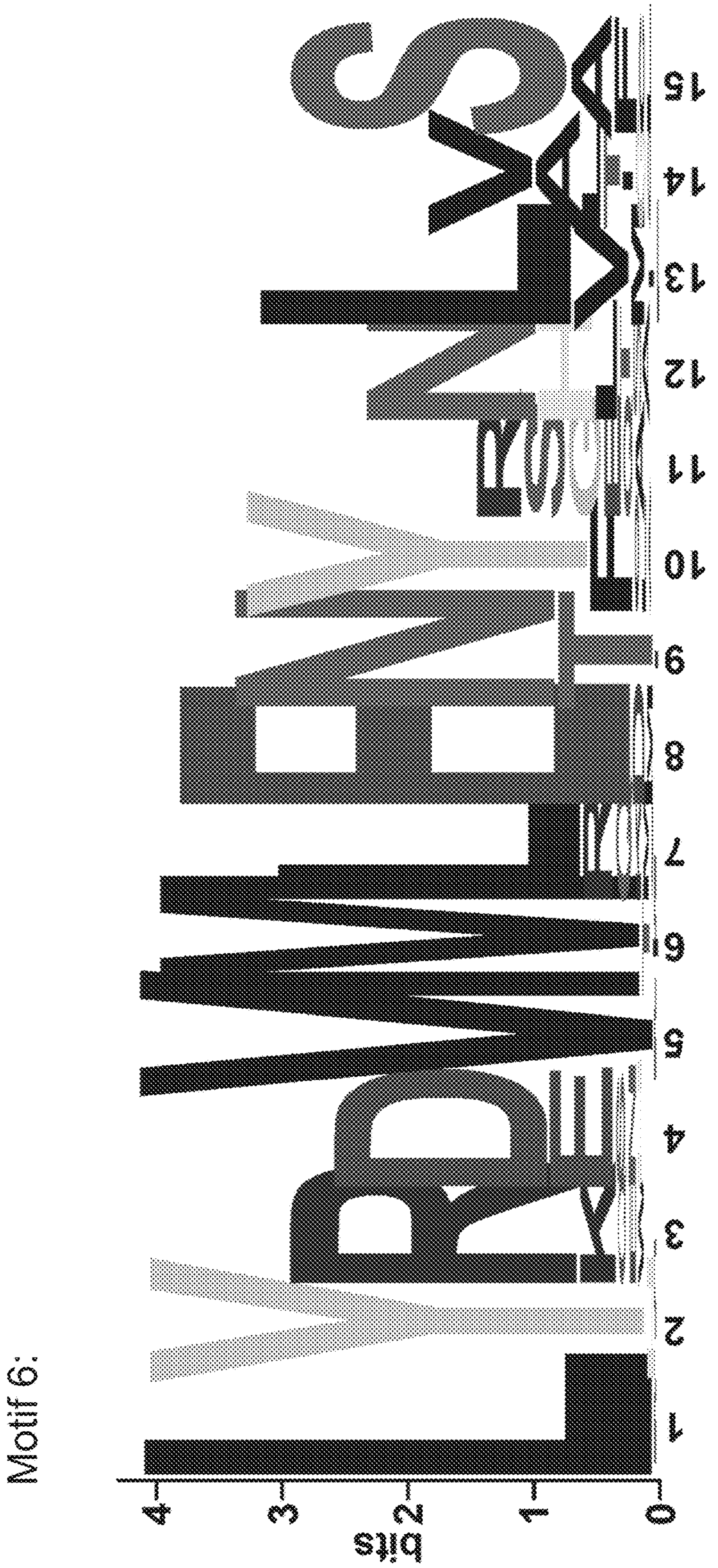
FIG. 19F provides the logo of KRAB domain motif 6 (SEQ ID NO: 59348), as described in Example 4.
Figure 19G:
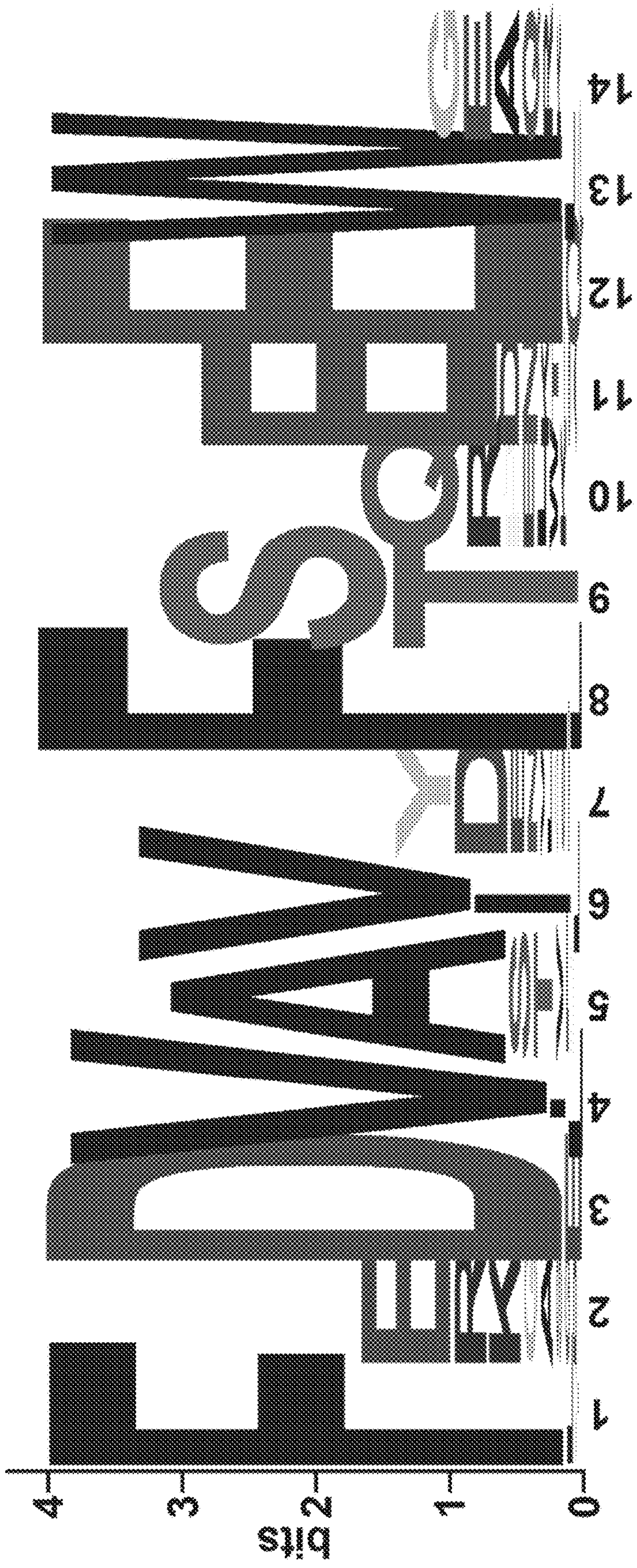
FIG. 19G provides the logo of KRAB domain motif 7 (SEQ ID NO: 59349), as described in Example 4.
Figure 19H:
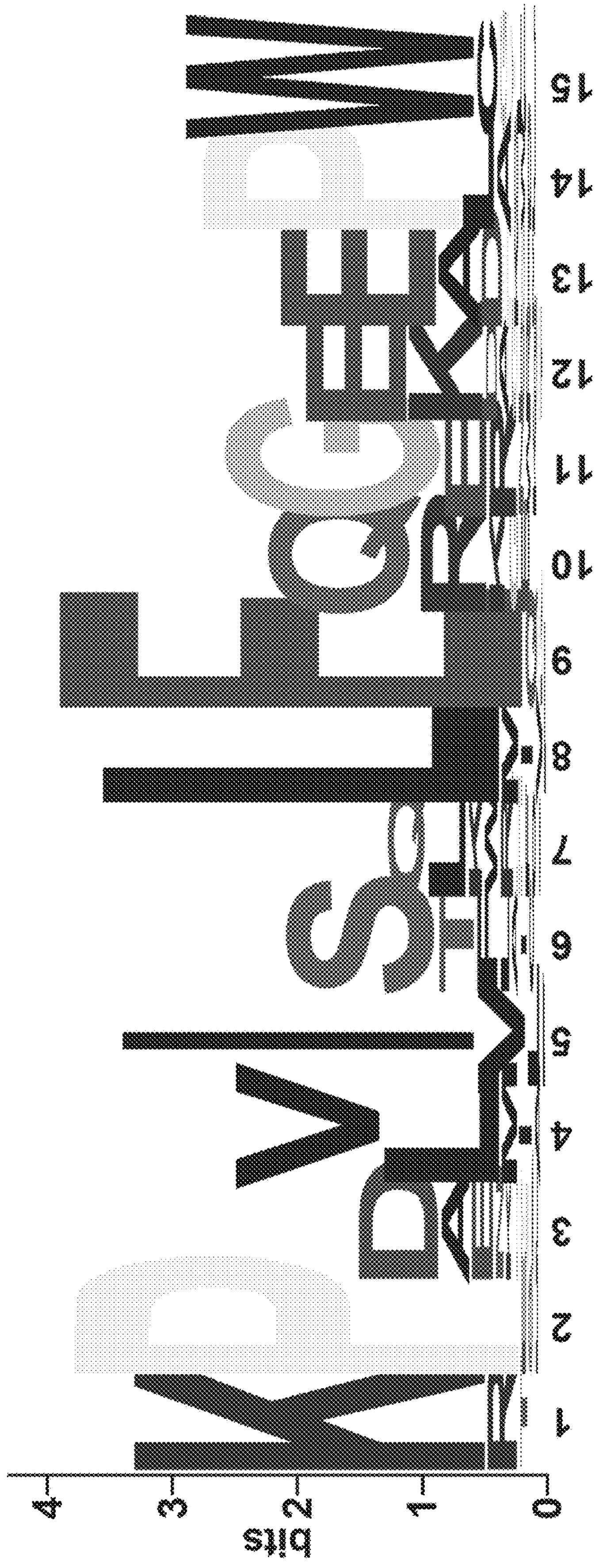
FIG. 19H provides the logo of KRAB domain motif 8, as described in Example 4.
Figure 19I:
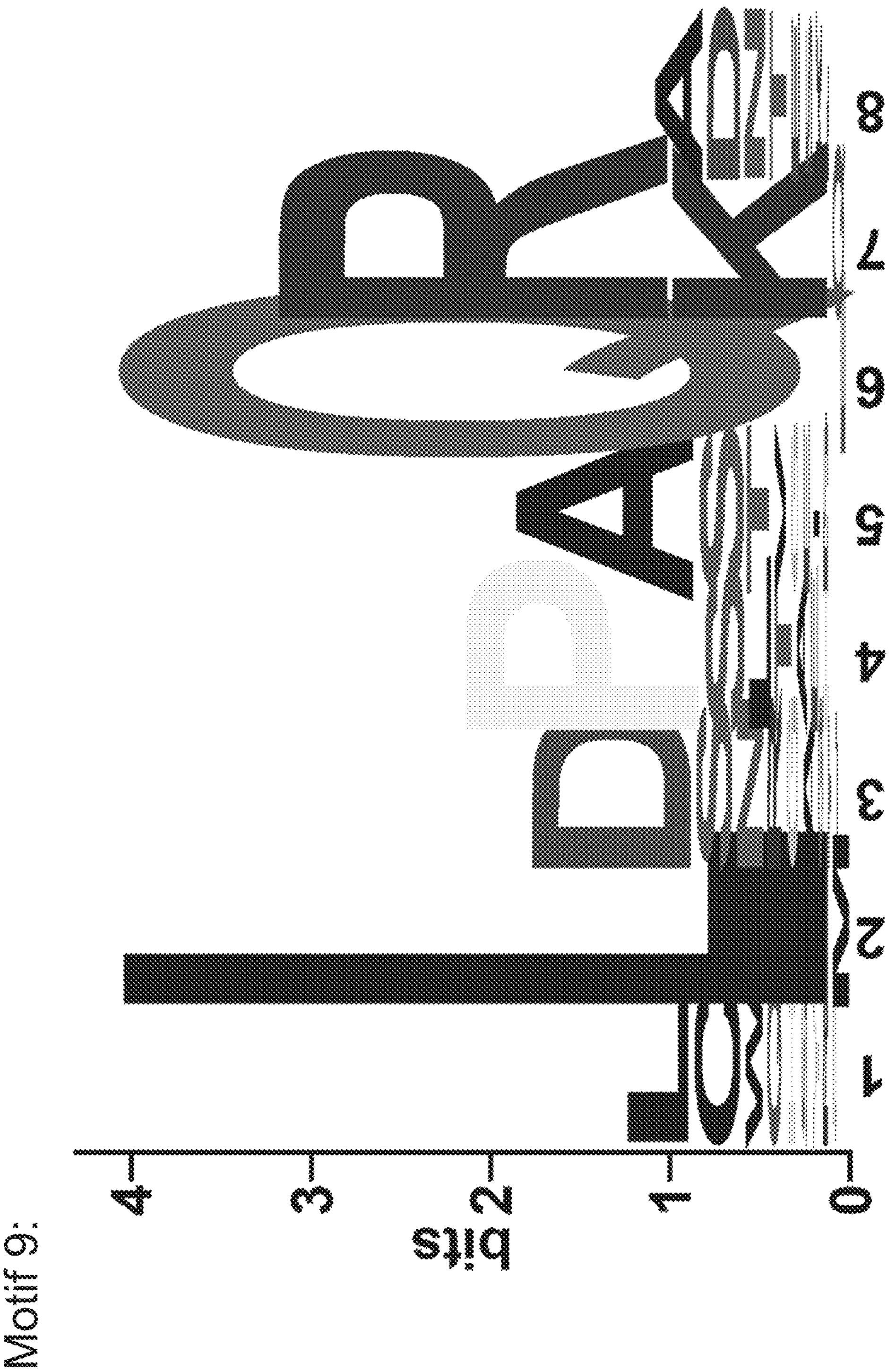
FIG. 19I provides the logo of KRAB domain motif 9, as described in Example 4.

To verify that the KRAB domains identified in the selection supported transcriptional repression in an independent assay, representative members of the top 95 and 1597 KRAB domains were used to generate dXR constructs, and their ability to repress transcription of the B2M locus was tested. As shown in FIG. 17, seven days after transduction, dXRs with all but one of the representative top 95 or 1597 KRAB domains tested repressed B2M to a greater extent than did the dXR with ZNF10. As shown in FIG. 18, ten days after transduction, the majority of the dXRs with representative top 95 or 1597 KRAB domains tested repressed B2M to a greater extent than did ZNF10 or ZIM3. dXR repression of a target locus tends to deteriorate over time, and ten days following transduction is believed to be a relatively late timepoint for measuring dXR repression. Therefore, it is particularly notable that many of the dXR constructs with KRAB domains in the top 95 and 1597 were able to repress B2M to a greater extent than dXR with KRAB domains derived from ZNF10 or ZIM3 as late as ten days following transduction.

To further understand the basis of the superior ability of the identified KRAB domains to repress transcription, protein sequence motifs were generated for the top 1597 KRAB domains using the STREME algorithm. Specifically, five motifs (motifs 1-5) were generated by comparing the amino acid sequences of the top 1597 KRAB domains to a negative training set of 1506 KRAB domains with p-values less than 0.01, and $log_2$(fold change) values less than 0. Logos of motifs 1-5 are provided in FIGS. 19A, 19B, 19C, 19D, and 19E. In addition, four motifs (motifs 6-9) were generated by comparing the top 1597 KRAB domains to shuffled sequences derived from the 1597 sequences. Logos of motifs 6-9 are provided in FIGS. 19F, 19G, 19H, and 19I.

Table 20, below, provides the p-value, E-value (a measure of statistical significance), and number and percentage of sequences matching the motif in the top 1597 KRAB domains for each of the nine motifs, as calculated by STREME. Table 21 provides the sequences of each motif, showing the amino acid residues present at each position within the motifs (from N- to C-terminus).

TABLE 20

Characteristics of protein sequence motifs of top 1597 KRAB domains.

| Motif ID | P-value | E-value | Number and percentage of sites matching motif in top 1597 KRAB domains |
|---|---|---|---|
| Motifs generated compared to a negative training set | | | |
| 1 | 3.7e−014 | 7.1e−013 | 1158 (72.5%) |
| 2 | 3.4e−012 | 6.4e−011 | 978 (61.2%) |
| 3 | 7.5e−010 | 1.4e−008 | 1017 (63.7%) |
| 4 | 7.0e−008 | 1.3e−006 | 987 (61.8%) |
| 5 | 1.7e−007 | 3.3e−006 | 678 (42.5%) |
| Motifs generated compared to shuffled sequences | | | |
| 6 | 1.2e−048 | 1.5e−047 | 1597 (100.0%) |
| 7 | 1.2e−048 | 1.5e−047 | 1597 (100.0%) |

TABLE 20-continued

| Characteristics of protein sequence motifs of top 1597 KRAB domains. | | | |
|---|---|---|---|
| Motif ID | P-value | E-value | Number and percentage of sites matching motif in top 1597 KRAB domains |
| 8 | 1.3e−042 | 1.6e−041 | 1377 (86.2%) |
| 9 | 2.1e−040 | 2.7e−039 | 1483 (92.9%) |

TABLE 21

Sequences of protein sequence motifs of top 1597 KRAB domains.

| Motif ID | Position in motif | Amino acid residues with >5% representation in motif |
|---|---|---|
| Motifs generated compared to a negative training set | | |
| 1 | 1 | P |
| | 2 | A, D, E, N |
| | 3 | L, V |
| | 4 | I, V |
| | 5 | S, T, F |
| | 6 | H, K, L, Q, R, W |
| | 7 | L, M |
| | 8 | E |
| | 9 | G, K, Q, R |
| 2 | 1 | L, V |
| | 2 | A, G, L, T, V |
| | 3 | A, F, S |
| | 4 | L, V |
| | 5 | G |
| | 6 | C, F, H, I, L, Y |
| | 7 | A, C, P, Q, S |
| | 8 | A, F, G, I, S, V |
| | 9 | A, P, S, T |
| | 10 | K, R |
| 3 | 1 | Q |
| | 2 | K, R |
| | 3 | A, D, E, G, N, S, T |
| | 4 | L |
| | 5 | Y |
| | 6 | R |
| | 7 | D, E, S |
| | 8 | V |
| | 9 | M |
| | 10 | L, R |
| 4 | 1 | A, L, P, S |
| | 2 | L, V |
| | 3 | S, T |
| | 4 | F |
| | 5 | A, E, G, K, R |
| | 6 | D |
| | 7 | V |
| | 8 | A, T |
| | 9 | I, V |
| | 10 | D, E, N, Y |
| | 11 | F |
| | 12 | S, T |
| | 13 | E, P, Q, R, W |
| | 14 | E, N |
| | 15 | E, Q |
| 5 | 1 | E, G, R |
| | 2 | E, K |
| | 3 | A, D, E |
| | 4 | P |
| | 5 | C, W |
| | 6 | I, K, L, M, T, V |
| | 7 | I, L, P, V |
| | 8 | D, E, K, V |

TABLE 21-continued

Sequences of protein sequence motifs of top 1597 KRAB domains.

| Motif ID | Position in motif | Amino acid residues with >5% representation in motif |
|---|---|---|
| | 9 | E, G, K, P, R |
| | 10 | A, D, R, G, K, Q, V |
| | 11 | D, E, G, I, L, R, S, V |
| Motifs generated compared to shuffled sequences | | |
| 6 | 1 | L |
| | 2 | Y |
| | 3 | K, R |
| | 4 | D, E |
| | 5 | V |
| | 6 | M |
| | 7 | L, Q, R |
| | 8 | E |
| | 9 | N, T |
| | 10 | F, Y |
| | 11 | A, E, G, Q, R, S |
| | 12 | H, L, N |
| | 13 | L, V |
| | 14 | A, G, I, L, T, V |
| | 15 | A, F, S |
| 7 | 1 | F |
| | 2 | A, E, G, K, R |
| | 3 | D |
| | 4 | V |
| | 5 | A, S, T |
| | 6 | I, V |
| | 7 | D, E, N, Y |
| | 8 | F |
| | 9 | S, T |
| | 10 | E, L, P, Q, R, W |
| | 11 | D, E |
| | 12 | E |
| | 13 | W |
| | 14 | A, E, G, Q, R |
| 8 | 1 | K, R |
| | 2 | P |
| | 3 | A, D, E, N |
| | 4 | I, L, M, V |
| | 5 | I, V |
| | 6 | F, S, T |
| | 7 | H, K, L, Q, R, W |
| | 8 | L |
| | 9 | E |
| | 10 | K, Q, R |
| | 11 | E, G, R |
| | 12 | D, E, K |
| | 13 | A, D, E |
| | 14 | L, P |
| | 15 | C, W |
| 9 | 1 | C, H, L, Q, W |
| | 2 | L |
| | 3 | D, G, N, R, S |
| | 4 | L, P, S, T |
| | 5 | A, S, T |
| | 6 | Q |
| | 7 | K, R |
| | 8 | A, D, E, K, N, S, T |

Notably, motifs 6 and 7 were present in 100% of the top 1597 KRAB domains. Many of the highly conserved positions in motif 6 (e.g., amino acid residues L1, Y2, V5, M6, and ES) are known to form an interface with Trim2S (also known as Kap1), which is responsible for recruiting transcriptional repressive machinery to a locus. Similarly, residues in motif 7 (D3, V4, E11, E12) all contribute to Trim2S recruitment. It is believed that many of the amino acid residues identified as enriched in the top KRAB domains strengthen Trim2S recruitment.

Notably, some of these residues are lacking in commonly used KRAB domains. Specifically, in the site in ZNF10 that matches motif 6, the residue at the first position is a valine instead of a leucine. In the site in ZIM3 that matches motif 7, the residue at position 11 is a glycine instead of a glutamic acid. Many of the other motifs described above that are not present in all KRAB domains may represent additional and novel mechanisms of repression that are specific to sequence clusters of KRABs.

Taken together, the experiments described herein have identified a suite of KRAB domains that are effective for promoting transcriptional repression in the context of a dXR molecule. These KRAB domains repressed transcription to a greater extent than ZNF10 and ZIM3. Finally, protein sequence motifs were identified that are associated with the KRAB domains that are the strongest transcriptional repressors.

Example 5: Demonstration of a Catalytically-Dead CasX Repressor (dXR) System on Repression of PTBP1 at the Protein Level Experiments were performed to demonstrate that various dXR constructs can act to repress the expression of the PTBP1 (Polypyrimidine Tract Binding Protein 1) protein in primary midbrain astrocyte cultures.

Materials and Methods:

Lentiviral Plasmid Cloning:

Lentiviral plasmid constructs coding for a dXR molecule were built using standard molecular cloning techniques. These constructs comprised of sequences coding for catalytically-dead CasX protein 491 (dCasX491; SEQ ID NO: 18) linked to the ZNF10 KRAB domain, along with guide RNA scaffold variant 174 (SEQ ID NO: 2238) and spacers targeting the PTBP1 locus (Table 23) or a non-targeting (NT; spacer 0.0) spacer. These spacers targeted either exon 1, 2, or 3 of the murine PTBP1 gene. Cloned and sequence-validated constructs were midi-prepped and subjected to quality assessment prior to transfection in HEK293T cells for production of lentiviral particles, which was performed using standard methods.

XDP (a CasX Delivery Particle) Construct Cloning and Production:

XDP plasmid constructs comprising sequences coding for CasX protein variant 491, guide scaffold 174, and a spacer targeting PTBP1 were cloned following standard methods and verified through Sanger sequencing.

XDPs containing ribonucleoproteins (RNPs) of CasX protein variant 491 and gRNA using scaffold 174 and a PTBP1-targeting spacer were produced using either suspension-adapted or adherent HEK293T Lenti-X cells. The methods to produce XDPs are described in WO2021113772A1, incorporated by reference in its entirety. Exemplary plasmids used to create these particles (and their configurations) are shown in FIGS. 4 and 5.

Transduction of Primary Midbrain Mouse Astrocytes and Western Blotting:

Primary midbrain mouse astrocytes were seeded at 150,000 cells per well in a 6-well plate format in NbAstro glial culture medium. Two days post-plating, cells were transduced with lentivirus-packaged dXR2 constructs encoding dCasX491 linked to the ZNF10 KRAB domain and guide scaffold 174 (SEQ ID NO: 2238) with spacers targeting PTBP1 (Table 22) or a non-targeting spacer. As a positive control, cells were transduced with XDP-28.10 containing RNPs of a catalytically-active CasX 491 and guide 174 with PTBP1-targeting spacer 28.10) in a separate well. 11 days post-transduction cells were harvested, pelleted, and lysed with RIPA buffer containing protease inhibitor for western blotting, which was performed following standard methods. Briefly, denatured protein samples were resolved by SDS-PAGE and transferred from gel onto PVDF membrane, which was immunoblotted for the PTBP1 protein. Protein quantification based on the western blot was quantified by densitometry using the Image Lab software. The ratio of PTBP1 protein/total protein for each experimental condition was normalized dXR relative to the ratio determined for the condition using dXR with the NT spacer, and the results were shown in FIG. 6 and Table 23.

TABLE 22

Sequences of mouse PTBP1-targeting spacers tested with dXR molecules in arrayed transductions.

| Spacer ID | Spacer DNA sequence | SEQ ID NO | Spacer RNA sequence | SEQ ID NO |
|---|---|---|---|---|
| 28.5 | CGCTGCGGTCTGTGGGCGTG | 350 | CGCUGCGGUCUGUGGGCGUG | 59635 |
| 28.9 | GTGTGCCATGGACGGGTAAG | 351 | GUGUGCCAUGGACGGGUAAG | 59636 |
| 28.10 | CAGCGGGGATCCGACGAGCT | 352 | CAGCGGGGAUCCGACGAGCU | 59637 |
| 28.11 | CCACGTGTGTCAGCAACGGC | 353 | CCACGUGUGUCAGCAACGGC | 59638 |
| 28.16 | ACAGCATCGTCCCAGACATA | 354 | ACAGCAUCGUCCCAGACAUA | 59639 |

Results

Figure 6:
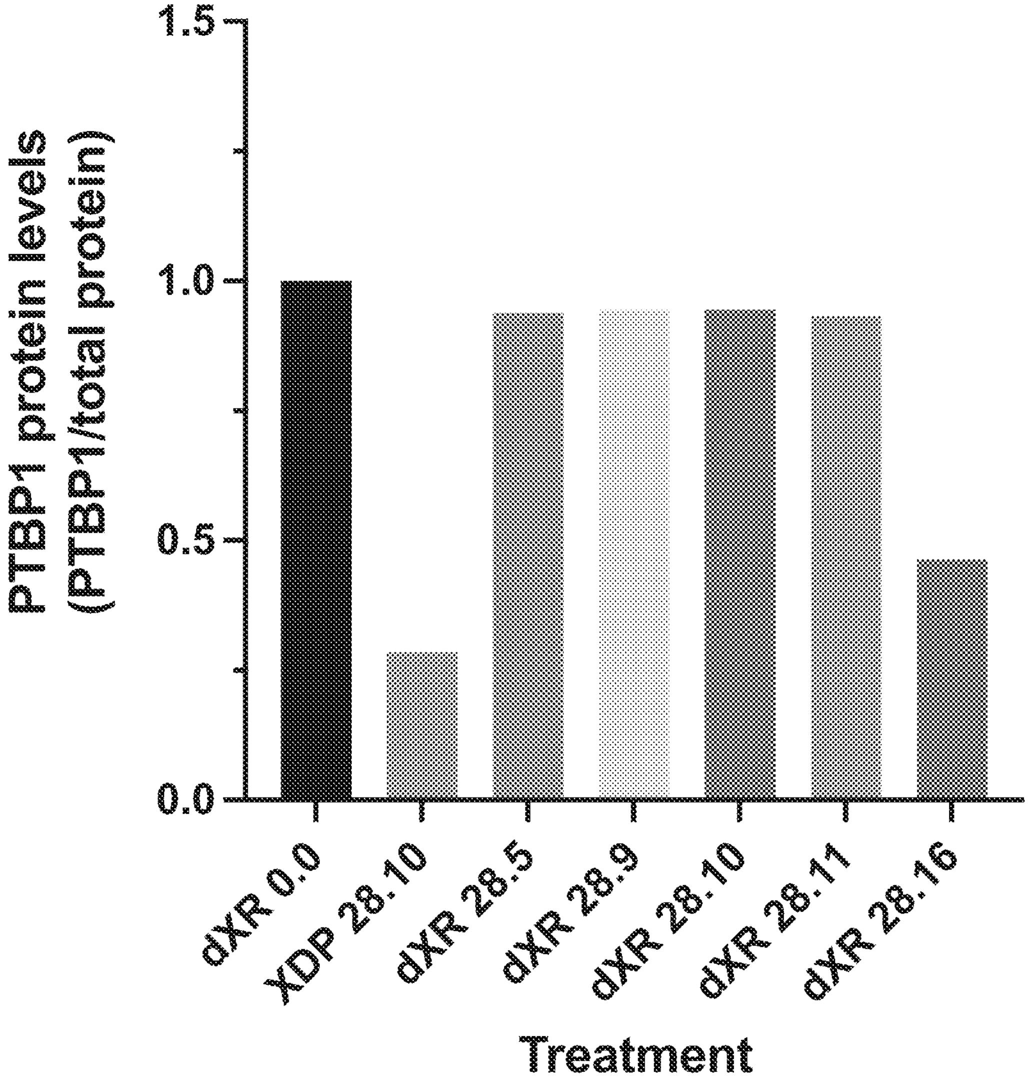
FIG. 6 is a bar graph showing the western blot quantification of PTBP1 protein levels in mouse astrocytes harvested 11 days post-transduction with lentiviral particles containing dXR with the indicated PTBP1-targeting spacer, as described in Example 5. Cells treated with XDPs containing CasX ribonuclear proteins (RNPs) using spacer 28.10 or lentiviral particles with the NT spacer served as experimental controls. The ratio of PTBP1 protein over total protein was normalized to that determined for the NT control in the graph.

Of the various dXR constructs with different PTBP1-targeting spacers delivered via lentiviral particles, treatment with the dXR and gRNA with spacer 28.16 construct showed reduced PTBP1 protein levels, while dXR constructs with guides having spacers 28.5, 28.9, 28.10 or 28.11 did not show any change in protein levels relative to protein levels determined in the NT spacer (dXR 0.0) condition (FIG. 6; Table 23). Specifically, use of spacer 28.16 resulted in nearly a 50% decrease in PTBP1 levels relative to the NT control (FIG. 6; Table 23). As expected, treatment with XDPs containing the catalytically-active CasX RNP showed the strongest decrease (>70%) in PTBP1 protein levels compared relative to the NT control (FIG. 6; Table 23). These data show that a dXR molecule and a guide having a PTBP1-targeting spacer can induce transcriptional repression, which results in decreased PTBP1 protein levels.

The results from these experiments demonstrate that dXR molecules with gRNAs targeting the PTBP1 locus were able to transcriptionally repress the therapeutically-relevant PTBP1 target efficiently in vitro, and the assay was able to distinguish between functional and non-functional spacers in the CasX repressor system.

TABLE 23

| Ratio of PTBP1 protein over total protein determined for each experimental condition and normalized relative to the ratio determined for the NT (dXR 0.0) condition. | |
|---|---|
| Experimental condition | Ratio of PTBP1 protein/total protein |
| dXR 0.0 | 1 |
| XDP 28.10 | 0.285 |
| dXR 28.5 | 0.939 |
| dXR 28.9 | 0.945 |
| dXR 28.10 | 0.945 |
| dXR 28.11 | 0.933 |
| dXR 28.16 | 0.464 |

Example 6: Use of a Catalytically-Dead CasX Repressor (dXR) System Fused with Additional Domains from DNMT3A and DNMT3L to Induce Durable Silencing of the B2M Locus Experiments were performed to determine whether rationally-designed epigenetic long-term CasX repressor (ELXR) molecules, with three repressor domains composed of a KRAB domain, the catalytic domain from DNMT3A and the interaction domain from DNMT3L fused to catalytically-dead CasX 491, would induce durable long-term repression of the endogenous B2M locus in vitro. In addition, multiple configurations of the ELXR molecules, which contain varying placements of the epigenetic domains relative to dCasX, were designed to assess how their arrangement would affect the duration of silencing of the B2M locus, as well as the specificity of their on-target methylation activity.

Materials and Methods:

Generation of ELXR Constructs and Lentiviral Plasmid Cloning:

Lentiviral plasmid constructs coding for an ELXR molecule were built using standard molecular cloning techniques. These constructs comprised of sequences coding for catalytically-dead CasX protein 491 (dCasX491), KRAB domain from ZNF10 or ZIM3, and the catalytic domain and interaction domain from DNMT3A (D3A) and DNMT3L (D3L) respectively. Briefly, constructs were ordered as oligonucleotides and assembled by overlap extension PCR followed by isothermal assembly. The resulting plasmids (sequences of key ELXR elements listed in Table 24 and select plasmid constructs in Table 25) contained constructs positioned in varying configurations to generate an ELXR molecule. The protein sequences for the ELXR molecules are listed in Table 26, and the ELXR configurations are illustrated in FIG. 7. Sequences encoding the ELXR molecules also contained a 2× FLAG tag. Plasmids also harbored sequences encoding gRNA scaffold variant 174 having either a spacer targeting the endogenous B2M locus or a non-targeting control (spacer sequences listed in Table 27). These constructs were all cloned upstream of a P2A-puromycin element on the lentiviral plasmid. Cloned and sequence-validated constructs were midi-prepped and subjected to quality assessment prior to transfection in HEK293T cells.

TABLE 24

Sequences of key ELXR elements (e.g., additional domains fused to CasX) to generate ELXR variant plasmids illustrated in FIG. 7.

| Key component | DNA SEQ ID NO | Protein sequence | Protein SEQ ID NO |
|---|---|---|---|
| ZNF10 KRAB domain | 57610 | MDAKSLTAWSRTLVTFKDVFVDFTREEWKLLDTAQQIV YRNVMLENYKNLVSLGYQLTKPDVILRLEKGEEP | 57611 |
| ZIM3 KRAB domain | 57612 | MNNSQGRVTFEDVTVNFTQGEWQRLNPEQRNLYRDVML ENYSNLVSVGQGETTKPDVILRLEQGKEPWLEEEEVLG SGRAEKNGDIGGQIWKPKDVKESL | 57613 |
| DNMT3A catalytic domain | 57614 | MNHDQEFDPPKVYPPVPAEKRKPIRVLSLFDGIATGLL VLKDLGIQVDRYIASEVCEDSITVGMVRHQGKIMYVGD VRSVTQKHIQEWGPFDLVIGGSPCNDLSIVNPARKGLY EGTGRLFFEFYRLLHDARPKEGDDRPFFWLFENVVAMG VSDKRDISRFLESNPVMIDAKEVSAAHRARYFWGNLPG MNRPLASTVNDKLELQECLEHGRIAKFSKVRTITTRSN SIKQGKDQHFPVFMNEKEDILWCTEMERVFGFPVHYTD VSNMSRLARQRLLGRSWSVPVIRHLFAPLKEYFACV | 57615 |
| DNMT3L interaction domain | 57616 | MGPMEIYKTVSAWKRQPVRVLSLFRNIDKVLKSLGFLE SGSGSGGGTLKYVEDVTNVVRRDVEKWGPFDLVYGSTQ PLGSSCDRCPGWYMFQFHRILQYALPRQESQRPFFWIF MDNLLLTEDDQETTTRFLQTEAVTLQDVRGRDYQNAMR VWSNIPGLKSKHAPLTPKEEEYLQAQVRSRSKLDAPKV DLLVKNCLLPLREYFKYFSQNSLPL | 57617 |
| dCasX491 | 57618 | QEIKRINKIRRRLVKDSNTKKAGKTGPMKTLLVRVMTP DLRERLENLRKKPENIPQPISNTSRANLNKLLTDYTEM KKAILHVYWEEFQKDPVGLMSRVAQPASKKIDQNKLKP EMDEKGNLTTAGFACSQCGQPLFVYKLEQVSEKGKAYT NYFGRCNVAEHEKLILLAQLKPEKDSDEAVTYSLGKFG QRALDFYSIHVTKESTHPVKPLAQIAGNRYASGPVGKA LSDACMGTIASFLSKYQDIIIEHQKVVKGNQKRLESLR ELAGKENLEYPSVTLPPQPHTKEGVDAYNEVIARVRMW VNLNLWQKLKLSRDDAKPLLRLKGFPSFPLVERQANEV | 57619 |

TABLE 24-continued

Sequences of key ELXR elements (e.g., additional domains fused to CasX) to generate ELXR variant plasmids illustrated in FIG. 7.

| Key component | DNA SEQ ID NO | Protein sequence | Protein SEQ ID NO |
|---|---|---|---|
| | | DWWDMVCNVKKLINEKKEDGKVFWQNLAGYKRQEALRPYLSSEEDRKKGKKFARYQLGDLLLHLEKKHGEDWGKVYDEAWERIDKKVEGLSKHIKLEEERRSEDAQSKAALTDWLRAKASFVIEGLKEADKDEFCRCELKLQKWYGDLRGKPFAIEAENSILDISGFSKQYNCAFIWQKDGVKKLNLYLIINYFKGGKLRFKKIKPEAFEANRFYTVINKKSGEIVPMEVNENFDDPNLIILPLAFGKRQGREFIWNDLLSLETGSLKLANGRVIEKTLYNRRTRQDEPALFVALTFERREVLDSSNIKPMNLIGVARGENIPAVIALTDPEGCPLSRFKDSLGNPTHILRIGESYKEKQRTIQAKKEVEQRRAGGYSRKYASKAKNLADDMVRNTARDLLYYAVTQDAMLIFANLSRGFGRQGKRTFMAERQYTRMEDWLTAKLAYEGLSKTYLSKTLAQYTSKTCSNCGFTITSADYDRVLEKLKKTATGWMTTINGKELKVEGQITYYNRYKRQNVVKDLSVELDRLSEESVNNDISSWTKGRSGEALSLLKKRFSHRPVQEKFVCLNCGFETHAAEQAALNIARSWLFLRSQEYKKYQTNKTTGNTDKRAFVETWQSFYRKKLKEVWKPAV | |
| Linker 1 | 57620 | GGPSSGAPPPSGGSPAGSPTSTEEGTSESATPESGPGTSTEPSEGSAPGSPAGSPTSTEEGTSTEPSEGSAPGTSTEPSE | 57621 |
| Linker 2 | 57622 | SSGNSNANSRGPSFSSGLVPLSLRGSH | 57623 |
| Linker 3A | 57624 | GGSGGGS | 57626 |
| Linker 3B | 57625 | | |
| Linker 4 | 57627 | GSGSGGG | 57628 |
| NLS A | 57629 | PKKKRKV | 57631 |
| NLS B | 57630 | | |

TABLE 25

DNA sequences of ELXR constructs*.

| ELXR ID | DNA sequence of ELXR molecule with the 2x FLAG (SEQ ID NO) |
|---|---|
| 1.A | 59477 |
| 1.B | 59478 |
| 2.A | 59479 |
| 2.B | 59480 |
| 3.A | 59481 |
| 3.B | 59482 |
| 4.A | 59483 |
| 4.B | 59484 |
| 5.A | 59485 |
| 5.B | 59486 |

*See Table 28 and 29 for construct ID.

TABLE 26

Protein sequences of ELXR molecules*.

| ELXR ID | Protein sequence of ELXR molecule (SEQ ID NO) |
|---|---|
| 1.A | 59467 |
| 1.B | 59468 |
| 2.A | 59469 |
| 2.B | 59470 |
| 3.A | 59471 |
| 3.B | 59472 |
| 4.A | 59473 |

TABLE 26-continued

Protein sequences of ELXR molecules*.

| ELXR ID | Protein sequence of ELXR molecule (SEQ ID NO) |
|---|---|
| 4.B | 59474 |
| 5.A | 59475 |
| 5.B | 59476 |

*See Tables 28 and 29 for ELXR construct ID.

TABLE 27

Sequences of spacers used in constructs.

| Spacer ID | Target gene | PAM | Sequence | SEQ ID NO |
|---|---|---|---|---|
| 7.37 | B2M | TTC | GGCCGAGAUGUCUCGCUCCG | 57644 |
| 7.148 | B2M | NGG | CGCGAGCACAGCUAAGGCCA | 57645 |
| 0.0 | Non-target | N/A | CGAGACGUAAUUACGUCUCG | 57646 |

Transfection of HEK293T Cells:

HEK293T cells were seeded at a density of 30,000 cells in each well of a 96-well plate. The next day, each well was transiently transfected using lipofectamine with 100 ng of ELXR variant plasmids, each containing a dCasX:gRNA construct encoding for a differently configured ELXR protein (FIG. 7), with the gRNA having either non-targeting spacer 0.0 or targeting spacer 7.37 to the B2M locus. Specifically, for one experiment, HEK293T cells were transfected with plasmids encoding ELXR proteins #1-3, and in a second experiment, cells were lipofected with plasmids encoding for ELXR protein #1, 4, and 5 (see Table 25 for sequences). In both experiments, ELXR molecules harbored a KRAB domain either from ZNF10 or ZIM3. Experimental controls included dCasX491 (with or without the ZNF10 repressor domain), catalytically-active CasX 491, and a catalytically-dead Cas9 fused to both the ZNF10-KRAB domain and DNMT3A/L domains, each with the same B2M-targeting or non-targeting gRNA. Each construct was tested in triplicate. 24 hours post-transfection, cells were selected with 1 μg/mL puromycin for two days. Six days after transfection, cells were harvested for repression analysis every 2-3 days by analyzing B2M protein expression via HLA immunostaining followed by flow cytometry. B2M expression was determined by using an antibody that would detect the B2M-dependent HLA protein expressed on the cell surface. HLA+ cells were measured using the Attune™ NxT flow cytometer. In addition, in a separate experiment, HEK293T cells transiently transfected with ELXR variant plasmids and the B2M-targeting gRNA or non-targeting gRNA were harvested at five days post-lipofection for genomic DNA (gDNA) extraction for bisulfite sequencing.

Bisulfite Sequencing to Assess ELXR Specificity Measured by Off-Target Methylation Levels at Target Locus:

To determine off-target methylation levels at the B2M locus, gDNA from harvested cells was extracted using the Zymo Quick-DNA Miniprep Plus kit following the manufacturer's instructions. The extracted gDNA was then subjected to bisulfite conversion using the EZ DNA Methylation™ Kit (Zymo) following the manufacturer's protocol, converting any non-methylated cytosine into uracil. The resulting bisulfite-treated DNA was subsequently sequenced using next-generation sequencing (NGS) to determine the levels of off-target methylation at the B2M and VEGFA loci.

NGS Processing and Analysis:

Target amplicons were amplified from 100 ng bisulfite-treated DNA via PCR with a set of primers specific to the bisulfite-converted target locations of interest (human B2M and VEGFA loci). These gene-specific primers contained an additional sequence at the 5' end to introduce an Illumina™ adapter. Amplified DNA products were purified with the Cytiva Sera-Mag Select DNA cleanup kit. Quality and quantification of the amplicon were assessed using a Fragment Analyzer DNA Analysis kit (Agilent, dsDNA 35-1500 bp). Amplicons were sequenced on the Illumina™ Miseq™ according to the manufacturer's instructions. Raw fastq files from sequencing were processed using Bismark Bisulfite Read Mapper and Methylation caller. PCR amplification of the bisulfite-treated DNA would convert all uracil nucleotides into thymine, and sequencing of the PCR product would determine the rate of cytosine-to-thymine conversion as a readout of the level of potential off-target methylation at the B2M and VEGFA loci mediated by each ELXR molecule.

Results

Figure 8A:
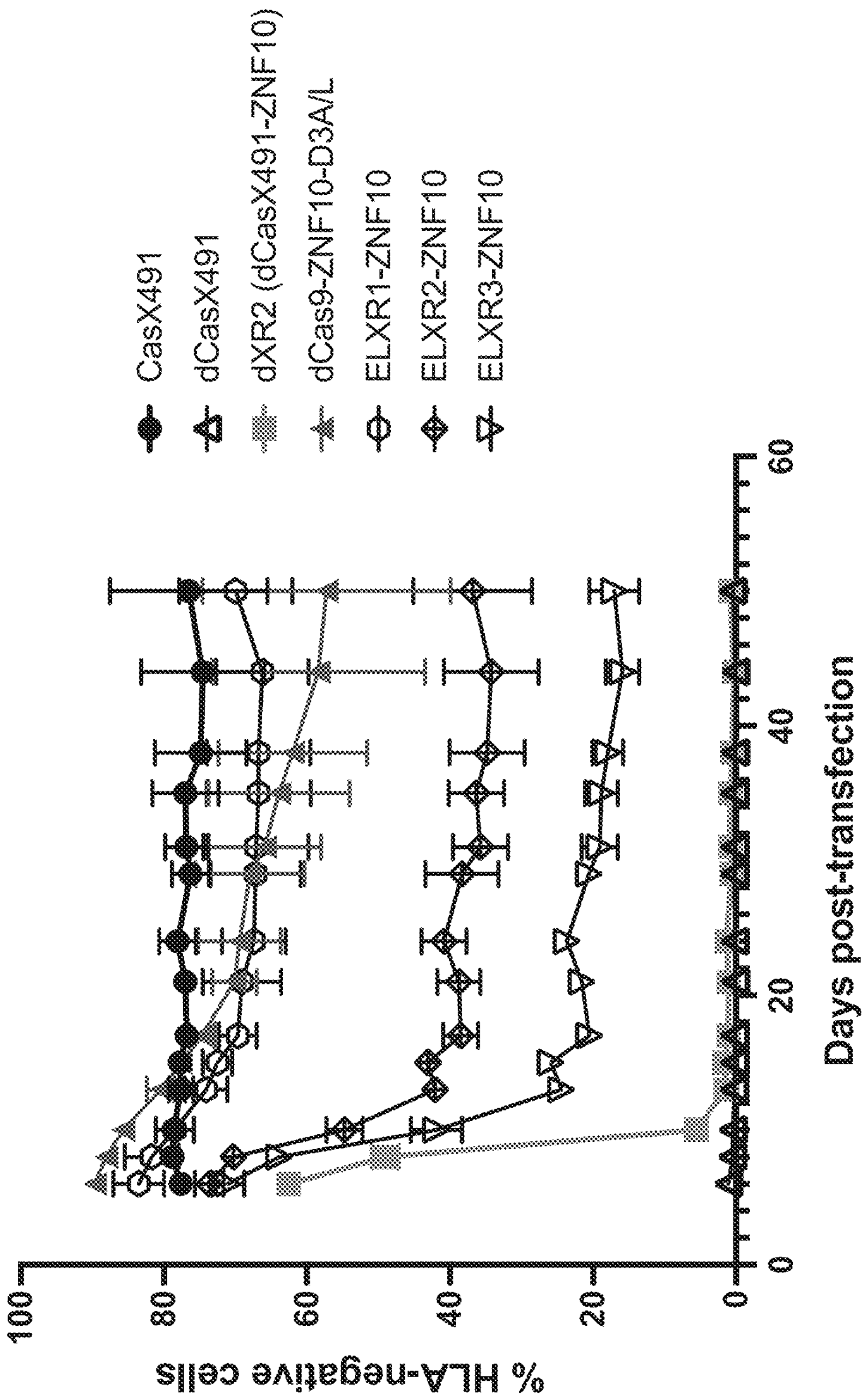
FIG. 8A presents the results of a time-course experiment comparing beta-2-microglobulin (B2M) repression activities (represented as percentage of HLA-negative cells) of ELXR proteins Nos. 1-3, as described in Example 6. Data are presented as mean with standard deviation, N=3.
Figure 8B:
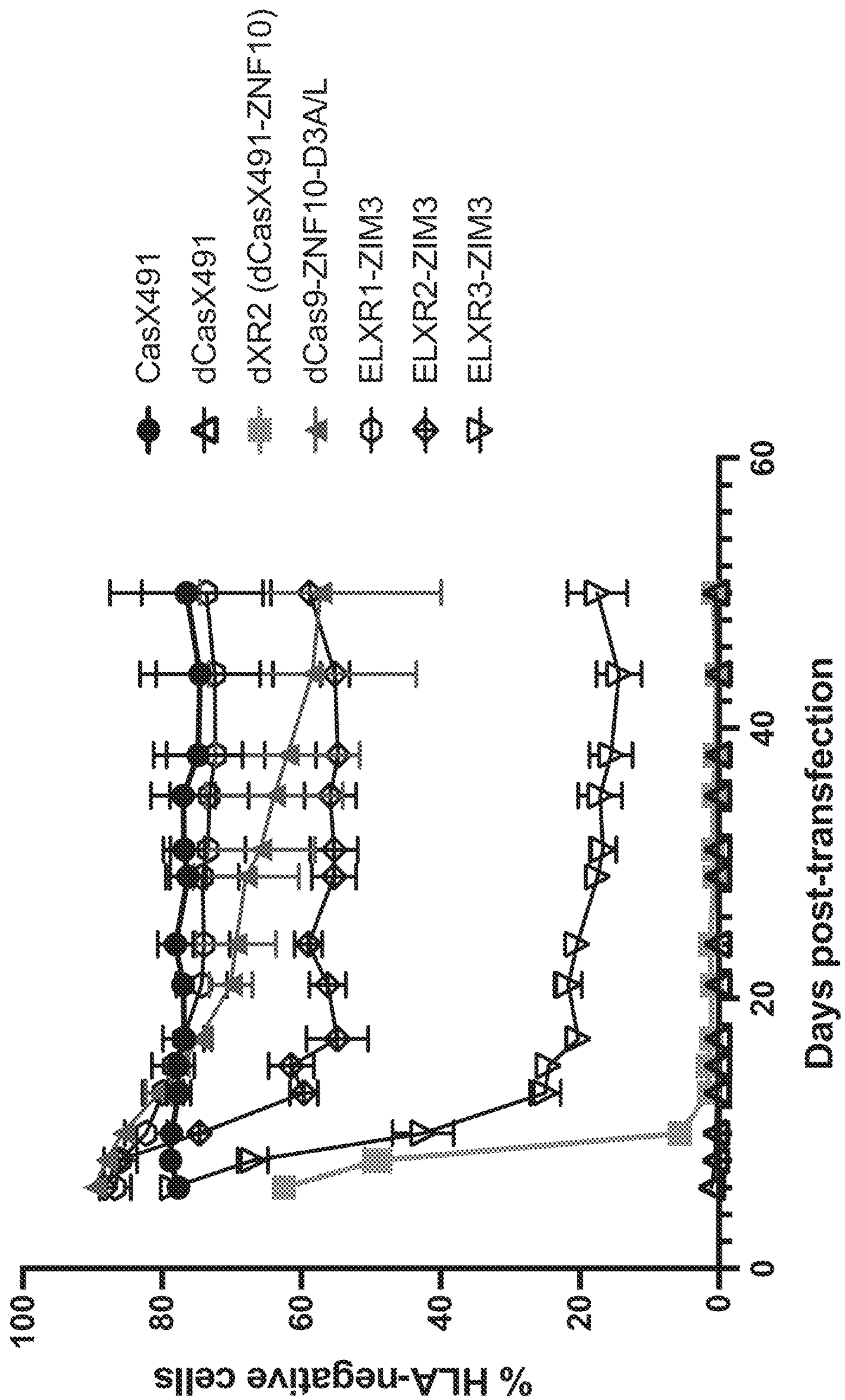
FIG. 8B presents the results of the same time-course experiment shown in FIG. 8A but illustrates the B2M repression activities of ELXR proteins Nos. 1-3 containing the ZIM3-KRAB domain, benchmarked against the same experimental controls, as described in Example 6. Data are presented as mean with standard deviation, N=3.

ELXR variant plasmids encoding for differently configured ELXR proteins (FIG. 7) were transiently transfected into HEK293T cells to determine whether the rationally-designed ELXR molecules could heritably silence gene expression of the target B2M locus in vitro. FIGS. 8A and 8B depict the results of a time-course experiment assessing B2M protein repression mediated by ELXR proteins #1-3, each of which harbored a KRAB domain from ZNF10 (FIG. 8A) or ZIM3 (FIG. 8B). Table 28 shows the average percentage of cells characterized as HLA-negative (indicative of depleted B2M expression) for each condition at 50 days post-transfection. The results illustrate that all ELXR molecules with a gRNA targeting the B2M locus were able to demonstrate sustained B2M repression for 50 days in vitro, although the potency of repression varied by the choice of KRAB domain and ELXR configuration. For instance, harboring a ZIM3-KRAB domain rendered the ELXR protein a more efficacious repressor than harboring a ZNF10-KRAB, and this effect was most prominently observed for ELXR #2 (compare FIG. 8A to FIG. 8B). Furthermore, positioning the DNMT3A/L domains at the N-terminus of dCasX491 (ELXR #1) resulted in more stable silencing of B2M expression compared to effects mediated by ELXRs with DNMT3A/L domains at the C-terminus of dCasX491 (ELXR #2 and #3; FIGS. 8A and 8B). These results also revealed that the relative positioning of the two types of repressor domains (i.e., dCasX491-KRAB-DNMT3A/L for ELXR #2 vs. dCasX491-DNMT3A/L-KRAB for ELXR #3) could also influence the overall potency of the ELXR molecule, despite both configurations being C-terminal fusions of dCasX491 (ELXR #2 and #3; FIGS. 8A and 8B).

Figure 9A:
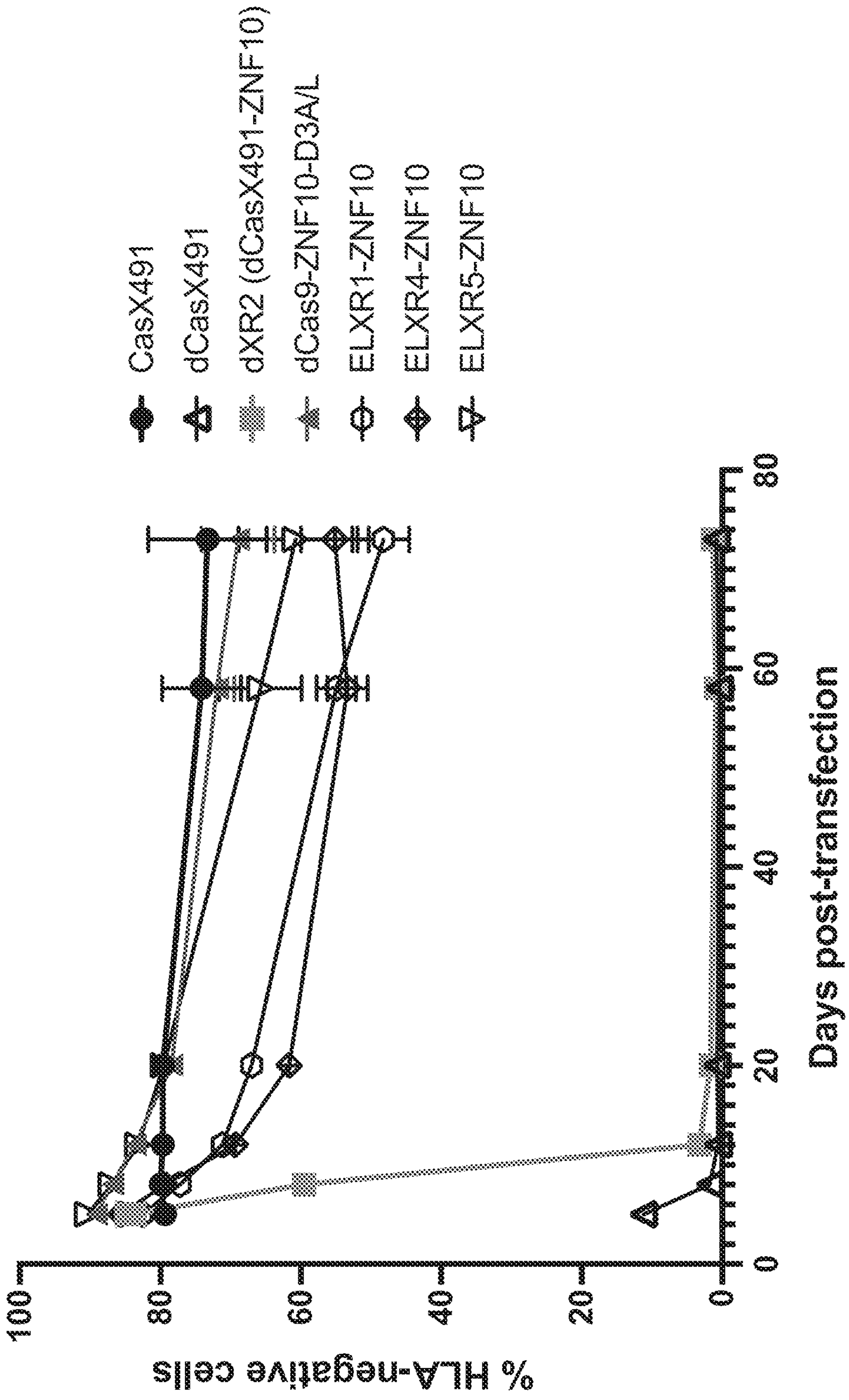
FIG. 9A presents the results of a time-course experiment comparing B2M silencing activities (represented as percentage of HLA-negative cells) of ELXR proteins #1, #4, and #5, as described in Example 6. Data are presented as mean with standard deviation, N=3.
Figure 9B:
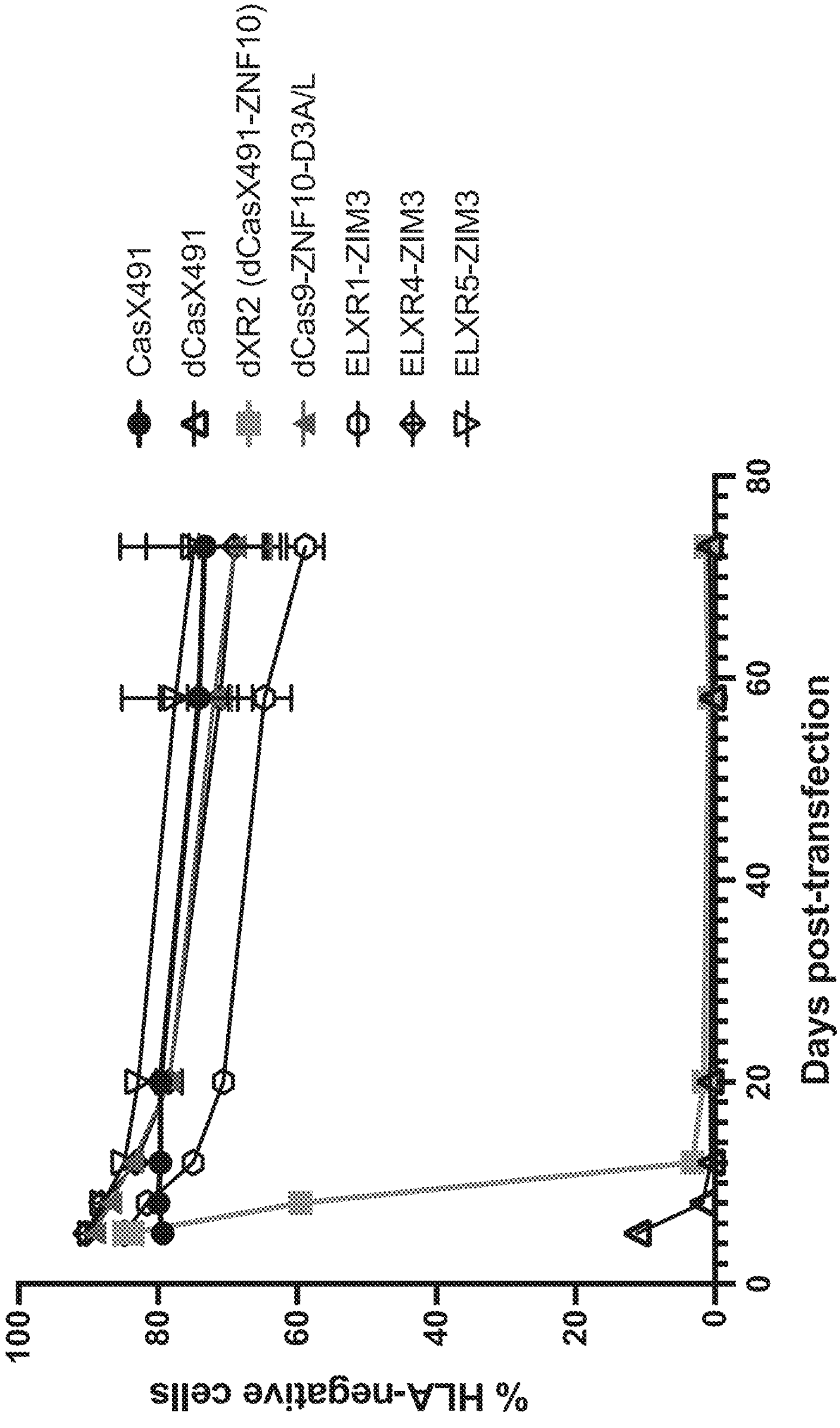
FIG. 9B presents the results of the same time-course experiment shown in FIG. 9A but illustrates the B2M silencing activities of ELXR proteins #1, #4, and #5 containing the ZIM3-KRAB domain, benchmarked against the same experimental controls, as described in Example 6. Data are presented as mean with standard deviation, N=3.

In a second time-course experiment, durable B2M repression was assessed for ELXR proteins #1, #4, and #5, where both the DNMT3A/L and KRAB domains were positioned at the N-terminus of dCasX491 for ELXR #4 and #5 (FIG. 7). Table 29 shows the average percentage of HLA-negative cells for each condition at 73 days post-lipofection. As similarly seen in the first time-course, all ELXR conditions with a B2M-targeting gRNA maintained durable silencing of the B2M locus (FIGS. 9A and 9B; Table 29). In fact, the results in this experiment demonstrate that ELXR #5 was able to achieve and sustain the highest level of B2M repression compared to that achieved by ELXR #1 or ELXR #4 for 73 days in vitro (FIGS. 9A and 9B). Furthermore, ELXR #4 containing the ZIM3-KRAB also appeared to outperform its ELXR #1 counterpart (FIG. 9B). For both time-course experiments discussed above, CasX 491-mediated editing resulted in durable silencing of the B2M expression, while an XR construct fusing only the KRAB domain to dCasx491 (dCasX491-ZNF10) only resulted in transient B2M knockdown.

TABLE 28

Levels of B2M repression mediated by CasX and Cas9 molecules and ELXR constructs #1-3 quantified at 50 days post-transfection.

| Molecule | Spacer | % HLA-negative cells (mean) | Standard deviation |
|---|---|---|---|
| CasX 491 | 0.0 | 0.29 | 0.09 |
| dCasX491 | 0.0 | N/A | N/A |
| dCasX491-ZNF10 | 0.0 | 0.40 | 0.18 |
| dCas9-ZNF10-D3A/L | 0.0 | 1.05 | 0.63 |
| ELXR1-ZNF10 | 0.0 | 0.99 | 0.35 |
| ELXR2-ZNF10 | 0.0 | 0.61 | 0.11 |
| ELXR3-ZNF10 | 0.0 | 0.79 | 0.29 |
| ELXR1-ZIM3 | 0.0 | 0.99 | 0.22 |
| ELXR2-ZIM3 | 0.0 | 0.78 | 0.27 |
| ELXR3-ZIM3 | 0.0 | 0.71 | 0.53 |
| CasX 491 | 7.37 | 76.57 | 11.03 |
| dCasX491 | 7.37 | 0.49 | 0.10 |
| dCasX491-ZNF10 | 7.148 | 0.89 | 0.19 |
| dCas9-ZNF10-D3A/L | 7.148 | 57.30 | 17.36 |
| ELXR1-ZNF10 (ELXR #1.B) | 7.37 | 69.97 | 7.89 |

TABLE 28-continued

Levels of B2M repression mediated by CasX and Cas9 molecules and ELXR constructs #1-3 quantified at 50 days post-transfection.

| Molecule | Spacer | % HLA-negative cells (mean) | Standard deviation |
|---|---|---|---|
| ELXR2-ZNF10 (ELXR #2.B) | 7.37 | 36.87 | 8.31 |
| ELXR3-ZNF10 (ELXR #3.B) | 7.37 | 17.07 | 3.50 |
| ELXR1-ZIM3 (ELXR #1.A) | 7.37 | 73.70 | 9.28 |
| ELXR2-ZIM3 (ELXR #2.A) | 7.37 | 58.83 | 0.87 |
| ELXR3-ZIM3 (ELXR #3.A) | 7.37 | 17.50 | 4.30 |

TABLE 29

Levels of B2M repression mediated by CasX and Cas9 molecules and ELXR constructs #1, #4, and #5 quantified at 73 days post-transfection.

| Molecule | Spacer | % HLA-negative cells (mean) | Standard deviation |
|---|---|---|---|
| CasX 491 | 0.0 | 0.71 | 0.05 |
| dCasX491 | 0.0 | N/A | N/A |
| dCasX491-ZNF10 | 0.0 | 0.76 | 0.12 |
| dCas9-ZNF10-D3A/L | 0.0 | 0.83 | 0.08 |
| ELXR1-ZNF10 | 0.0 | 1.04 | 0.44 |
| ELXR4-ZNF10 | 0.0 | 1.17 | 0.52 |
| ELXR5-ZNF10 | 0.0 | 1.94 | 1.27 |
| ELXR1-ZIM3 | 0.0 | 1.83 | 0.76 |
| ELXR4-ZIM3 | 0.0 | N/A | N/A |
| ELXR5-ZIM3 | 0.0 | 1.15 | 0.26 |
| CasX 491 | 7.37 | 73.30 | 8.43 |
| dCasX491 | 7.37 | 0.83 | 0.16 |
| dCasX491-ZNF10 | 7.148 | 1.37 | 0.37 |
| dCas9-ZNF10-D3A/L | 7.148 | 68.97 | 5.21 |
| ELXR1-ZNF10 (ELXR #1.B) | 7.37 | 48.27 | 3.66 |
| ELXR4-ZNF10 (ELXR #4.B) | 7.37 | 55.17 | 4.83 |
| ELXR5-ZNF10 (ELXR #5.B) | 7.37 | 60.77 | 8.12 |
| ELXR1-ZIM3 (ELXR #1.A) | 7.37 | 58.90 | 2.69 |
| ELXR4-ZIM3 (ELXR #4.A) | 7.37 | 69.00 | 6.58 |
| ELXR5-ZIM3 (ELXR #5.A) | 7.37 | 74.90 | 10.61 |

Figure 10:
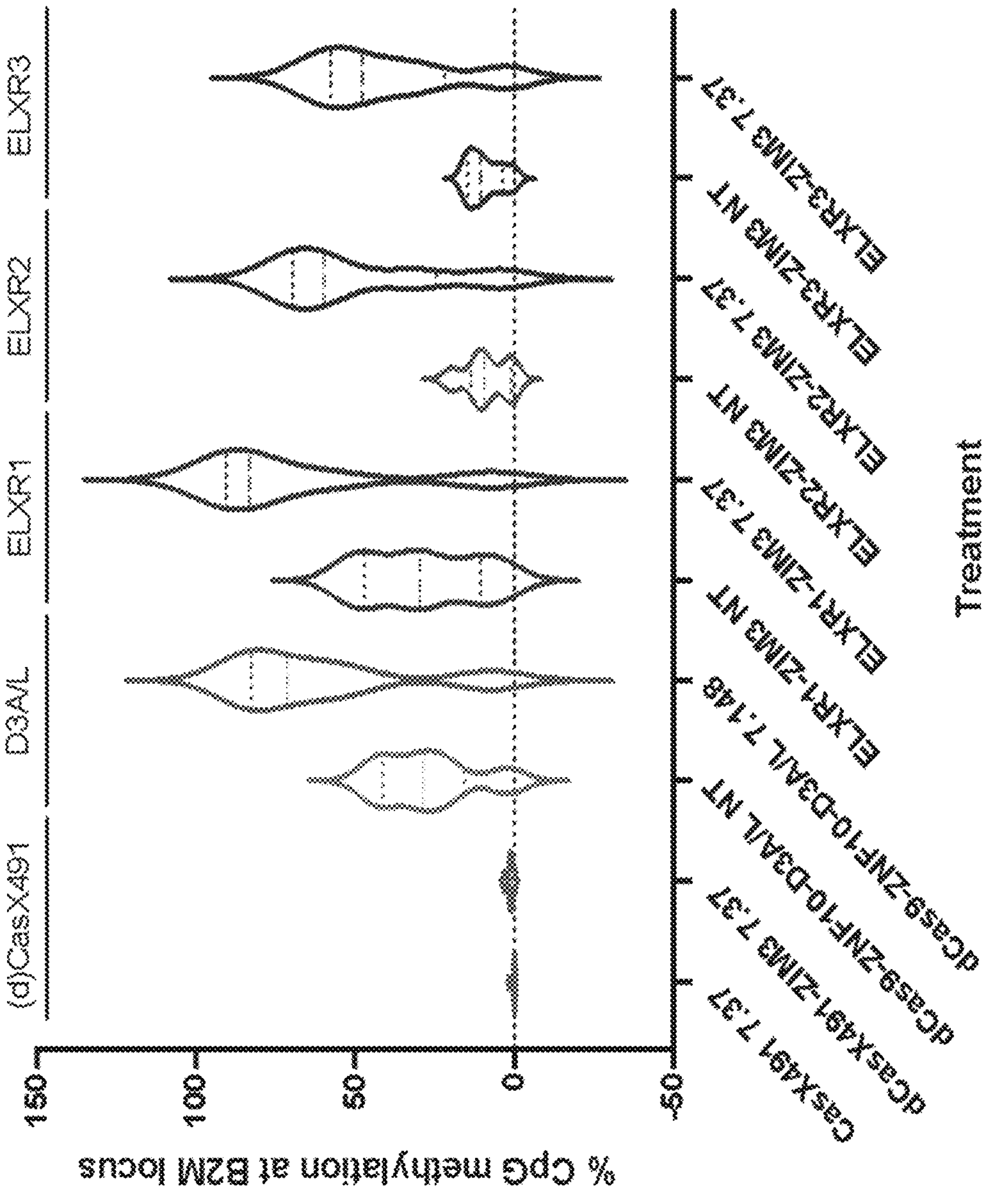
FIG. 10 is a violin plot of percent CpG methylation for CpG sites around the transcription start site of the B2M locus for each indicated experimental condition as described in Example 6.
Figure 11:
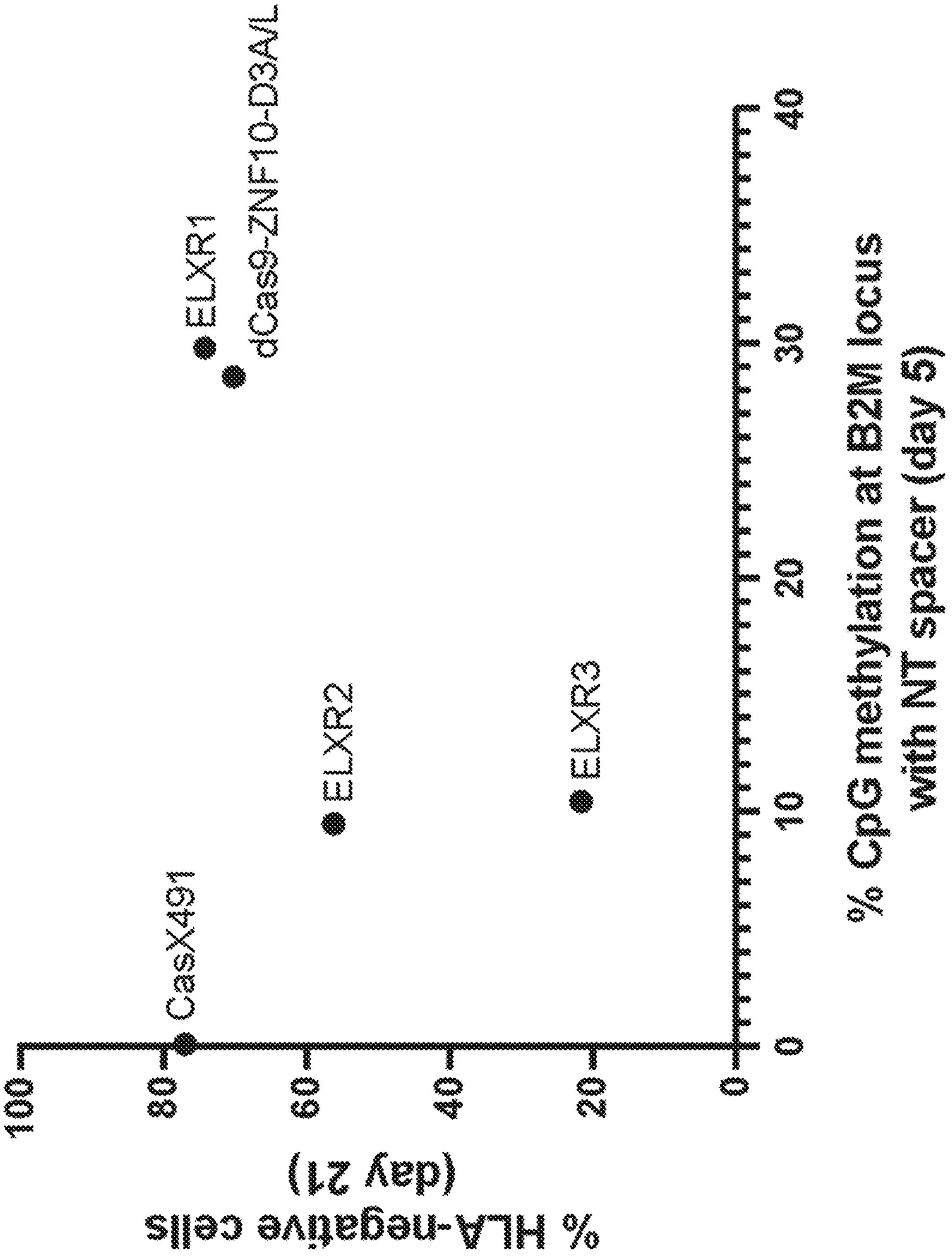
FIG. 11 is a dot plot showing the relative activity (average percentage of HLA-negative cells at day 21) versus specificity (percentage of off-target CpG methylation at the B2M locus quantified at day 5) for ELXR proteins #1-3, benchmarked against catalytically-active CasX 491 and dCas9-ZNF10-DNMT3A/L, as described in Example 6.

To evaluate the degree of off-target CpG methylation at the B2M locus mediated by the DNMT3A/L domains within the ELXR molecules, bisulfite sequencing was performed using genomic DNA extracted from HEK293T cells treated with ELXR proteins #1-3 containing the ZIM3-KRAB domain and harvested at five days post-lipofection. FIG. 10 illustrates the findings from bisulfite sequencing, specifically showing the distribution of the number of CpG sites around the transcription start site of the B2M locus that harbored a certain level of CpG methylation for each experimental condition. The results revealed that while ELXR #1 demonstrated the strongest on-target CpG-methylating activity (ELXR1-ZIM3 7.37), it induced the highest level of off-target CpG methylation (ELXR1-ZIM3 NT). ELXR #2 and ELXR #3 displayed weaker on-target CpG-methylating activity but relatively lower off-target methylation (FIG. 10). FIG. 11 is a scatterplot mapping the activity-specificity profiles for ELXR proteins #1-3 benchmarked against CasX 491 and dCas9-ZNF10-DNMT3A/L, where activity was measured as the average percentage of HLA-negative cells at day 21, and specificity was represented by the percentage of off-target CpG methylation at the B2M locus quantified at day 5.

Figure 12:
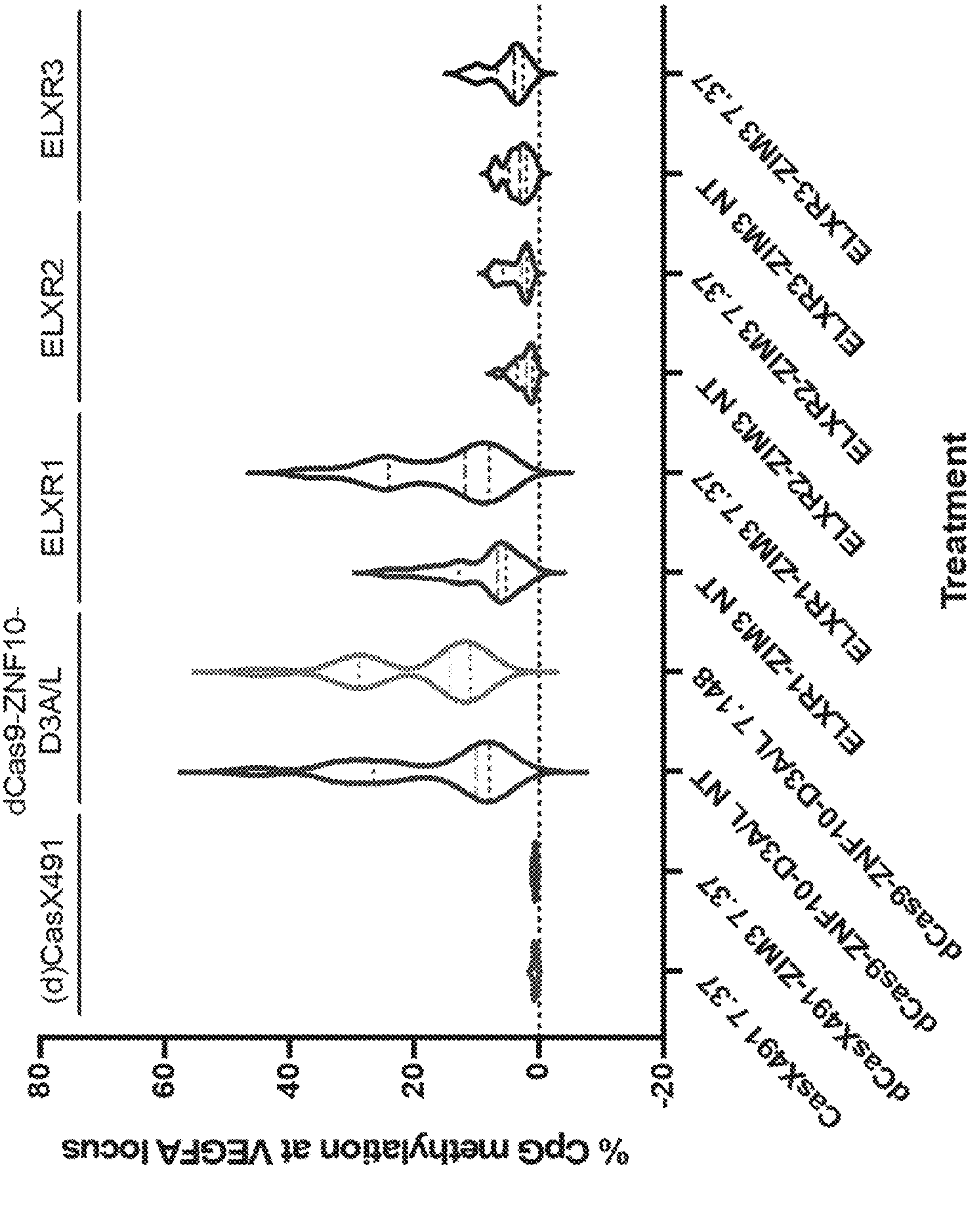
FIG. 12 is a violin plot of percent CpG methylation for CpG sites downstream of the transcription start site of the VEGFA locus for each indicated experimental condition as described in Example 6.

The degree of off-target CpG methylation mediated by the DNMT3A/L domain was further evaluated by assessing the level of CpG methylation at a different locus, i.e., VEGFA, by performing bisulfite sequencing using the same extracted gDNA as was used previously for FIG. 10. The violin plot in FIG. 12 illustrates the bisulfite sequencing results showing the distribution of CpG sites with CpG methylation at the VEGFA locus in cells treated with ELXR proteins #1-3 containing the ZIM3-KRAB domain and a B2M-targeting gRNA. The findings further demonstrate that use of ELXR #1 resulted in the highest level of off-target CpG methylation, supporting the data shown earlier in FIG. 10. In comparison, use of either ELXR #2 or ELXR #3 resulted in substantially lower off-target methylation at the −3 locus (FIG. 12).

Figure 13B:
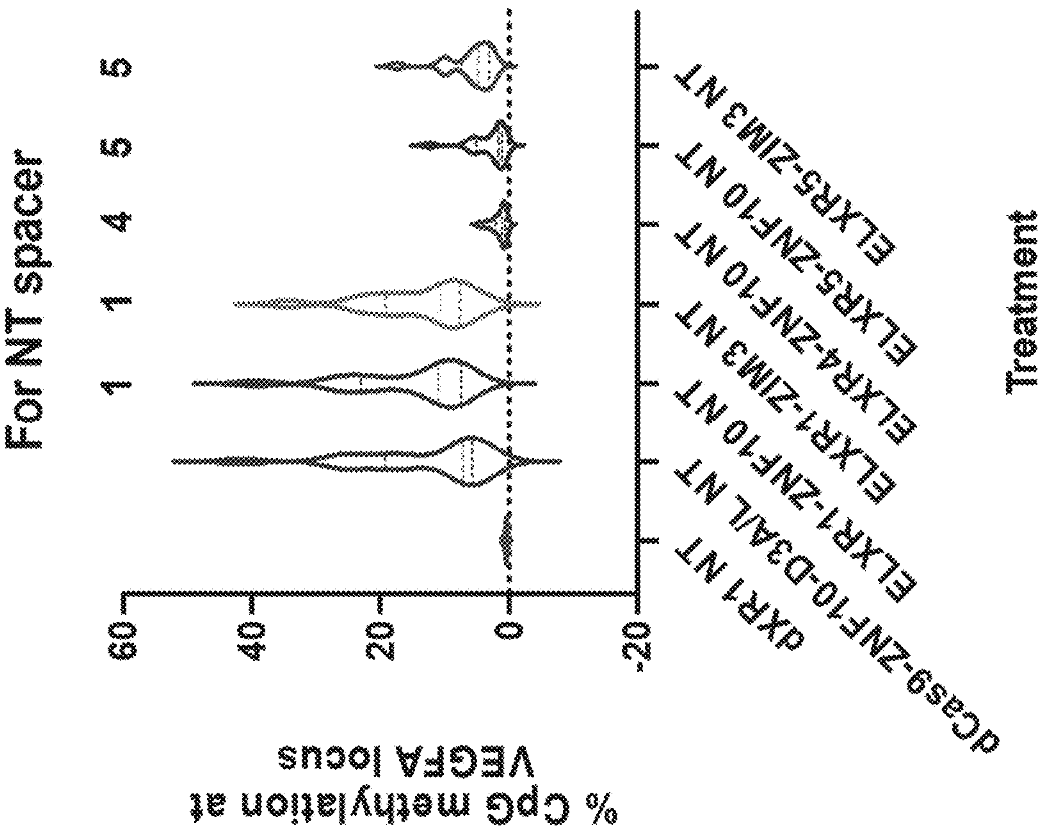
FIG. 13B is a violin plot of percent CpG methylation for CpG sites around the transcription start site of the VEGFA locus for each indicated experimental condition assessing ELXR #1, 4, and 5 with the non-targeting spacer as described in Example 6.
Figure 13A:
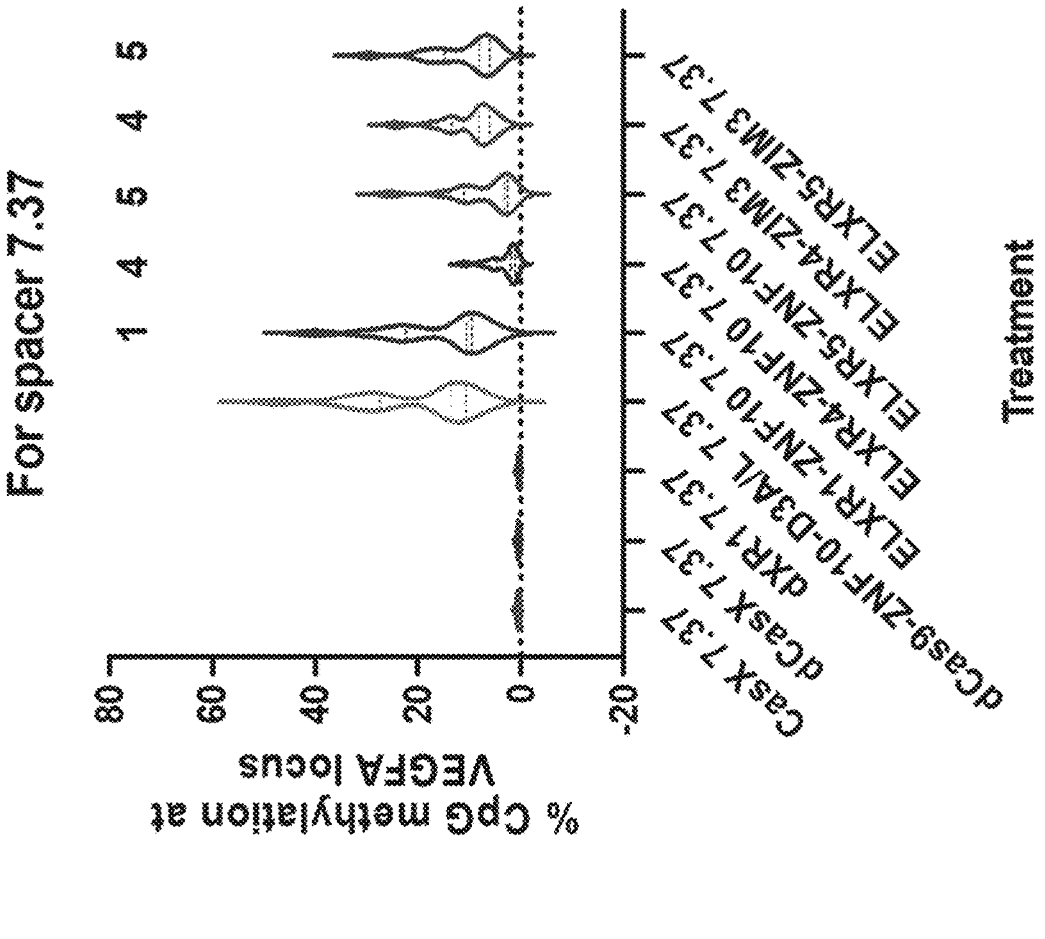
FIG. 13A is a violin plot of percent CpG methylation for CpG sites around the transcription start site of the VEGFA locus for each indicated experimental condition assessing ELXR #1, 4, and 5 with the B2M-targeting spacer as described in Example 6.

The extent of off-target CpG methylation at the VEGFA locus for ELXR molecules #1, #4, and #5 was also analyzed. The plots in FIGS. 13A-13B illustrate bisulfite sequencing results showing the distribution of CpG-methylated sites at the VEGFA locus in cells treated with ELXR #1, 4, and 5 containing a ZNF10 or ZIM3-KRAB domain and either a non-targeting gRNA (FIG. 13B) or a B2M-targeting gRNA (FIG. 13A). The data in FIG. 13B show that use of ELXR4-ZNF10, ELXR5-ZFN10, or ELXR5-ZIM3 resulted in markedly lower off-target CpG methylation at the VEGFA locus in comparison to use of ELXR1-ZNF10 or ELXR1-ZIM3. Similarly, the data in FIG. 13A show that use of ELXR #4 or ELXR #5 with either KRAB domain resulted in substantially lower levels of off-target CpG methylated sites compared to use with ELXR1-ZNF10. As exhibited in both FIGS. 13A and 13B, the level of non-specific CpG methylation demonstrated by ELXR #1 is comparable to that achieved by the dCas9-ZNF10-DNMT3A/L benchmark.

Figure 14:
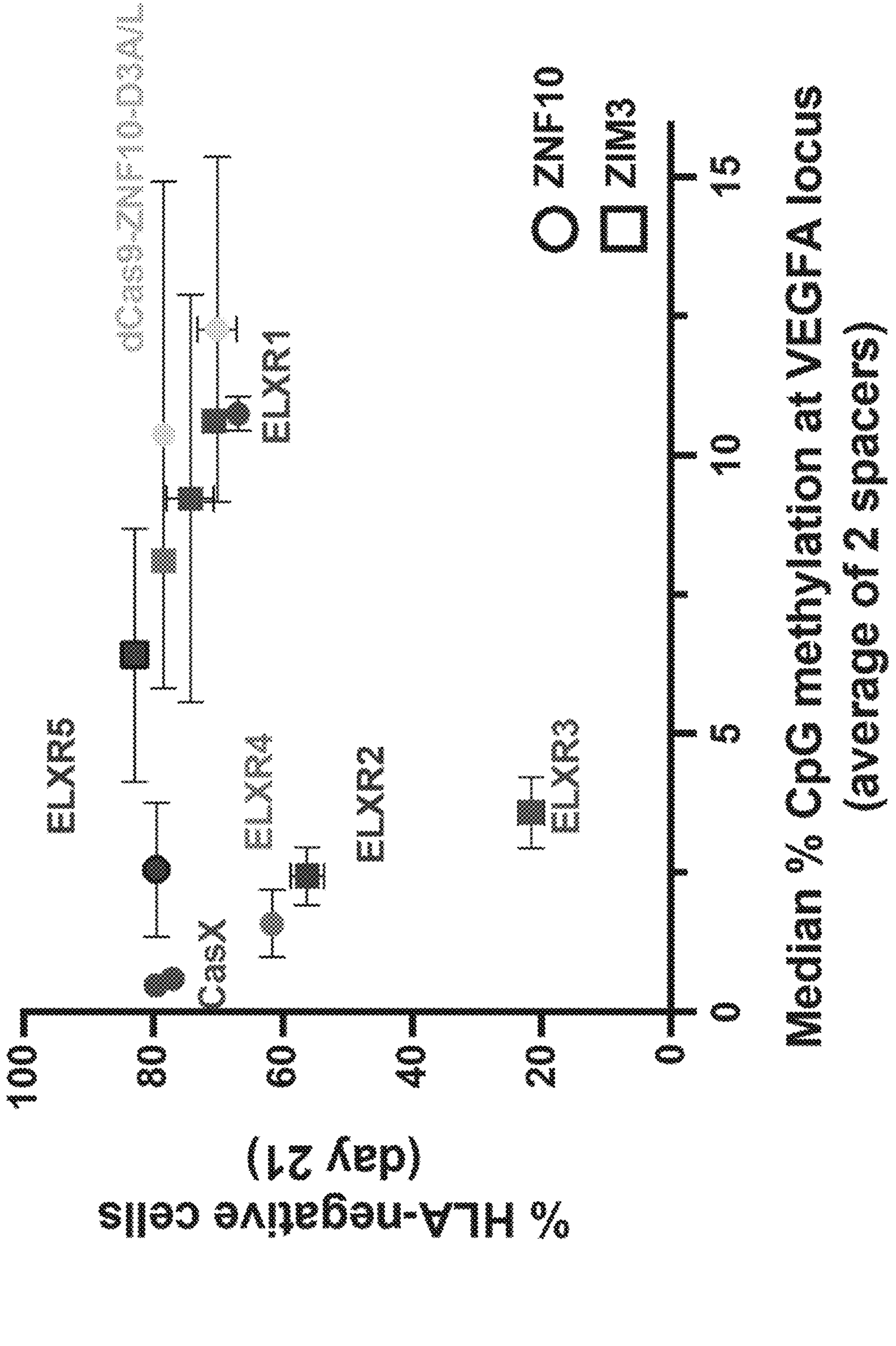
FIG. 14 is a scatterplot showing the relative activity (average percentage of HLA-negative cells at day 21) versus specificity (median percentage of off-target CpG methylation at the VEGFA locus quantified at day 5) for ELXR proteins #1-5 harboring either the ZNF10- or ZIM-KRAB domain, and the ELXR proteins were benchmarked against catalytically-active CasX 491 and dCas9-ZNF10-DNMT3A/L, as described in Example 6.

FIG. 14 is a scatterplot mapping the activity-specificity profiles for ELXR molecules #1-5, containing either ZNF10- or ZIM3-KRAB domain, benchmarked against CasX 491 and dCas9-ZNF10-DNMT3A/L, where activity was measured as the average percentage of HLA-negative cells at day 21, and specificity was represented by the median percentage of off-target CpG methylation at the VEGFA locus detected at day 5. The data show that of the five ELXR molecules assessed, use of ELXR #5 resulted in the highest level of repressive activity, while use of ELXR #4 resulted in the strongest level of specificity.

The experiments demonstrate that the rationally-engineered ELXR molecules were able to transcriptionally and heritably repress the endogenous B2M locus, resulting in sustained depletion of the target protein. The findings also show that the choice of KRAB domain and position and relative configuration of the DNMT3A/L domains could affect the overall potency and specificity of the ELXR molecule in durably silencing the target locus.

Example 7: Development of Functional Screens to Assess the Activity and Specificity of Rationally-Engineered Improved ELXR Variants To engineer ELXR variants with improved repression activity and target methylation specificity, a pooled screening assay will be developed. Briefly, systematic mutagenesis of the DNMT3A catalytic domain is performed to generate a library of DNMT3A variants (SEQ ID NOS: 33625-

57543) that will be tested in an ELXR molecule to screen for improved ELXR variants using various functional assays.

Materials and Methods:

Generation of a Library of DNMT3A Catalytic Domain Variants:

The following methods will be used to construct a DME library of the DNMT3A catalytic domain variants. A staging vector will be created to harbor the DNMT3A sequence flanked by restriction sites compatible with the destination vectors used for screening. The DNMT3A catalytic domain sequence will be divided into five ~200 bp fragments, and each fragment will be synthesized as an oligonucleotide pool. Each oligonucleotide pool will be constructed to contain three different types of modification libraries. First, a substitution oligonucleotide library that will result in each codon of the DNMT3A catalytic domain fragment being replaced with one of the 19 possible alternative codons coding for the 19 possible amino acid mutations. Second, a deletion oligonucleotide library will be prepared that will result in each codon of the fragment being systematically removed to delete that amino acid. Third, an insertion oligonucleotide library will be prepared that will insert one of the 20 possible codons at every position of the DNMT3A catalytic domain fragment. These oligonucleotide pools will be amplified and cloned into the staging vector using Golden Gate reactions and PCR-generated backbones. The pooled DNMT3A catalytic domain DME libraries will then be transferred into the lentiviral ELXR constructs coding for the ELXR molecule as described in Example 6 via restriction enzyme digestion and ligation prior to library amplification. To determine adequate library coverage, each fragment of the DNMT3A catalytic domain DME will be PCR amplified separately with gene specific primers, followed by NGS on the Illumina™ Miseq™ using overlapping paired end sequencing.

High-Throughput Screening of ELXR Variants Generated Using DNMT3A Catalytic Domain DME Libraries:

After following standard protocols for lentivirus production and titering, the resulting lentiviral library of ELXR variants will be subjected to different high-throughput functional screens. These functional screens are briefly described below.

A specificity-focused screen aims to identify DNMT3A catalytic domain variants that will yield ELXR molecules with decreased off-target methylation. For instance, an in vitro dropout assay could be used to identify DNMT3A catalytic domain variants that would not induce deleterious nonspecific methylation. Overexpression of DNMT3A leads to extraneous methylation which adversely affects cell growth, likely due to increased repression of genes critical for cell survival and proliferation. In this assay, HEK293T cells will be transduced with the lentiviral ELXR library at a low multiplicity of infection (MOI), and an initial population of transduced cells will be harvested prior to selection with puromycin for five days. After selection, multiple time point populations will be harvested at days 5, 7, 10 and 14, and gDNA will be extracted from all populations and subjected to PCR amplification and NGS sequencing of target amplicons containing the DNMT3A catalytic domain variants. Comparing the library composition readout between the initial and terminal populations will yield non-deleterious DNMT3A catalytic domain variants that confer cell survivability and growth. In parallel, methylation-sensitive promoters coupled to GFP have been developed in which overexpression of untargeted ELXR molecules lead to GFP repression due to off-target global methylation. An orthogonal screen will therefore be performed in which the DNMT3A catalytic domain DME libraries will be transduced in cell lines harboring these methylation-sensitive reporters, and quantification of GFP levels would allow assessment and identification of ELXR variants that cause off-target methylation over time.

An activity-focused screen aims to identify DNMT3A catalytic domain variants that will reveal ELXR molecules with increased on-target methylating activity. Here, the approach can leverage the spreading of DNA methylation to potentially repress the activity of a nearby promoter to identify ELXR-specific spacers and evaluate ELXR molecule activity at earlier time points. Briefly, HEK293T suspension cells will be transduced with the lentiviral ELXR library with the spacer targeting the B2M locus and selected with puromycin for five days. After selection, B2M protein expression will be measured by immunostaining, and cells that exhibit B2M repression (indicated by HLA-negative cells) will be sorted by FACS. Genomic DNA will be extracted from sorted HLA-negative cells for NGS analysis. Enrichment scores for each variant can be calculated by comparing the frequency of mutations in the sorted population relative to the naive cells to identify the DNMT3A catalytic domain variants that more potently repress B2M expression.

In addition to screening the library of DNMT3A catalytic domain variants, screening the library of KRAB repressor domains in parallel, which is described in Example 4 above, will help identify ELXR variants with improved activity and specificity profiles.

The experiments described in this example are expected to identify additional ELXR leads with improved durable repression activity and specificity. These improved ELXR molecules will be tested in various cell types against a therapeutic target of interest to further characterize and identify lead candidates for development.

Example 8: Demonstration that Catalytically-Dead CasX does not Edit at the Endogenous B2M Locus In Vitro Experiments were performed to demonstrate that catalytically-dead CasX is unable to edit the endogenous B2M gene in an in vitro assay.

Materials and Methods:

Generation of Catalytically-Dead CasX (dCasX) Constructs and Cloning:

CasX variants 491, 527, 668 and 676 with gRNA scaffold variant 174 were used in these experiments. To generate catalytically-dead CasX 491 (dCasX491; SEQ ID NO: 18) and catalytically-dead CasX 527 (dCasX527; SEQ ID NO: 24), the D659, E756, D921 catalytic residues of the RuvC domain of CasX variant 491, and D660, E757, and the D922 catalytic residue of the RuvC domain of CasX variant 527 were mutated to alanine to abolish the endonuclease activity. Similarly, D660, E757, D923-to-alanine mutations at catalytic residues within the RuvC domain of CasX variants 668 and 676 were designed to generate catalytically-dead CasX 668 (dCasX668; SEQ ID NO: 59355) and catalytically-dead CasX 676 (dCasX676; SEQ ID NO: 59357). The resulting plasmids contained constructs with the following configuration: Ef1α-SV40NLS-dCasX variant-SV40NLS. Plasmids also contained sequences encoding a gRNA scaffold variant 174 having a B2M-targeting spacer (spacer. 7.37; GGCCGAGAUGUCUCGCUCCG, SEQ ID NO: 59628) or a non-targeting spacer control (spacer 0.0; CGAGACGUAAUUACGUCUCG; SEQ ID NO: 59630).

Plasmids encoding for the catalytically-dead CasX variants (dCasX491, dCasX527, dCasX668, and dCasX676) were generated using standard molecular cloning methods and validated using Sanger-sequencing. Sequence-validated constructs were midi-prepped for subsequent transfection into HEK293T cells.

Plasmid Transfection into HEK293T Cells:

~30,000 HEK293T cells were seeded in each well of a 96-well plate; the next day, cells were transiently transfected with a plasmid containing a dCasX:gRNA construct encoding for dCasX491, dCasX527, dCasX668, or dCasX676 (sequences in Table 4), with the gRNA having either non-targeting spacer 0.0 or targeting spacer 7.37 to the B2M locus. Each construct was tested in triplicate. 24 hours post-transfection, cells were selected with puromycin, and six days after transfection, cells were harvested for editing analysis at the B2M locus by NGS. The following experimental controls were also included in this experiment: 1) catalytically-active CasX 491 with a B2M-targeting gRNA or a non-targeting gRNA; 2) catalytically-dead variant of Cas9 (dCas9) with the appropriate gRNAs; and 3) mock (no plasmid) transfection.

NGS Processing and Analysis:

Using the Zymo Quick-DNA Miniprep Plus kit following the manufacturer's instructions, gDNA was extracted from harvested cells. Target amplicons were amplified from extracted gDNA with a set of primers specific to the human B2M locus. These gene-specific primers contained an additional sequence at the 5' end to introduce an Illumina™ adapter and a 16-nucleotide unique molecule identifier. Amplified DNA products were purified with the Ampure XP DNA cleanup kit. Quality and quantification of the amplicon were assessed using a Fragment Analyzer DNA Analysis kit (Agilent, dsDNA 35-1500 bp). Amplicons were sequenced on the Illumina™ Miseq™ according to the manufacturer's instructions. Raw fastq files from sequencing were quality-controlled and processed using cutadapt v2.1, flash2 v2.2.00, and CRISPResso2 v2.0.29. Each sequence was quantified for containing an insertion or deletion (indel) relative to the reference sequence, in a window around the 3' end of the spacer (30 bp window centered at −3 bp from 3' end of spacer). CasX activity was quantified as the total percent of reads that contain insertions, substitutions, and/or deletions anywhere within this window for each sample.

Results

Figure 15:
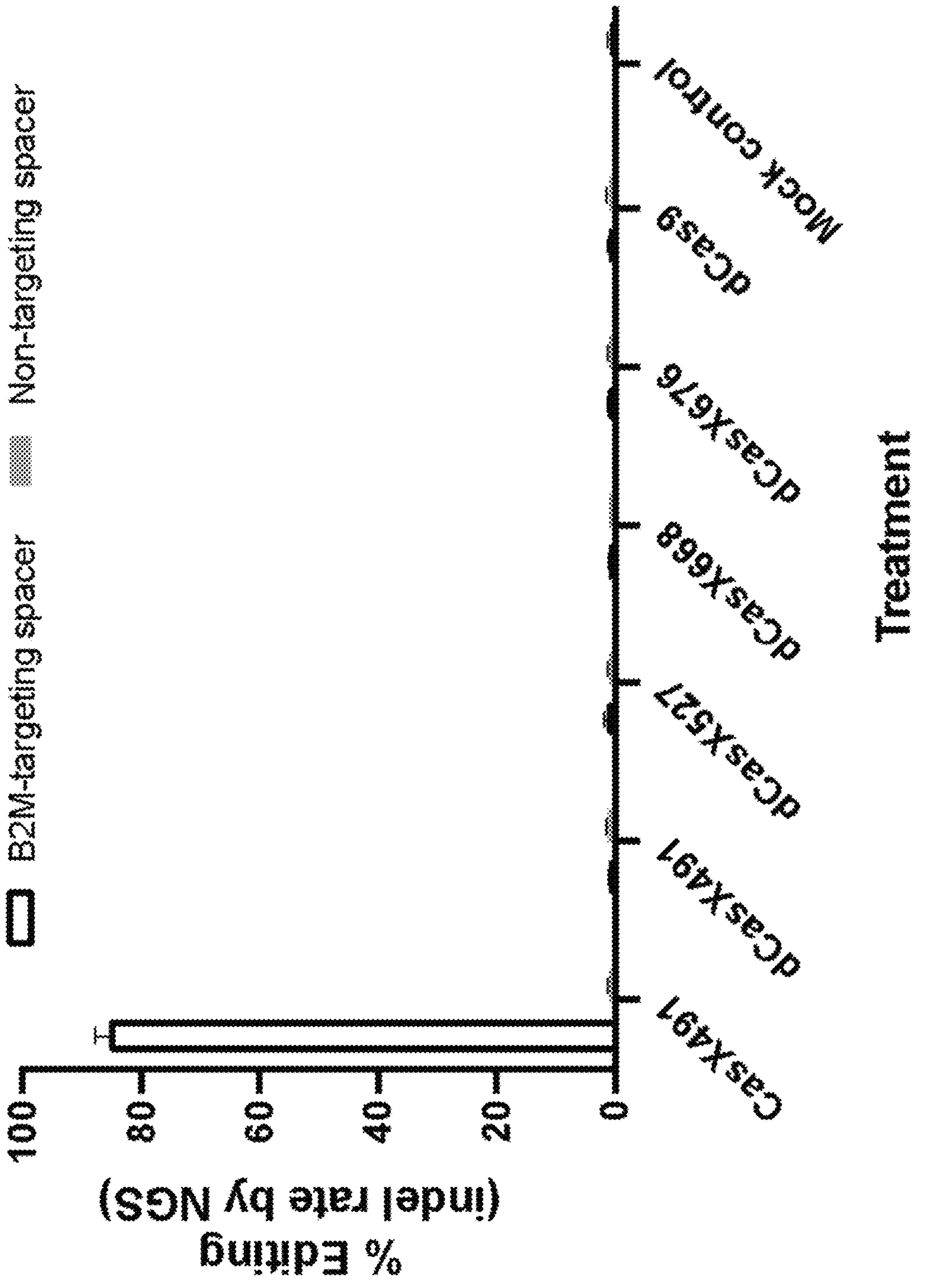
FIG. 15 is a quantification of percent editing measured as indel rate detected by NGS at the human B2M locus for each of the indicated catalytically-dead CasX variant with either a B2M-targeting spacer or a non-targeting spacer, as described in Example 8. Catalytically-active CasX 491, catalytically-inactive CasX9 (dCas9), and a mock transfection served as experimental controls.

The plot in FIG. 15 shows the results of the editing analysis, specifically the percent editing at the B2M locus measured as indel rate detected by NGS for each of the indicated treatment conditions. The data demonstrate that >80% editing was achieved at the B2M locus mediated by catalytically-active CasX 491. On the other hand, dCasX491, dCasX527, dCasX668, and dCasX676 did not exhibit editing at the B2M locus with the B2M-targeting spacer.

The results of this experiment demonstrate that catalytically-dead CasX does not edit at an endogenous target locus in vitro.

Example 9: Demonstration that Use of ELXR Molecules can Induce Durable Silencing of the Endogenous CD151 Gene Experiments were performed to demonstrate that ELXR molecules can induce long-term repression of an alternative endogenous locus, i.e., the CD151 gene, in a cell-based assay.

Materials and Methods:

ELXR molecules #1, #4, and #5 containing the ZIM3-KRAB domain (see FIG. 7 for specific configurations and Table 25 for encoding sequences) were assessed in this experiment.

Figure 20A:
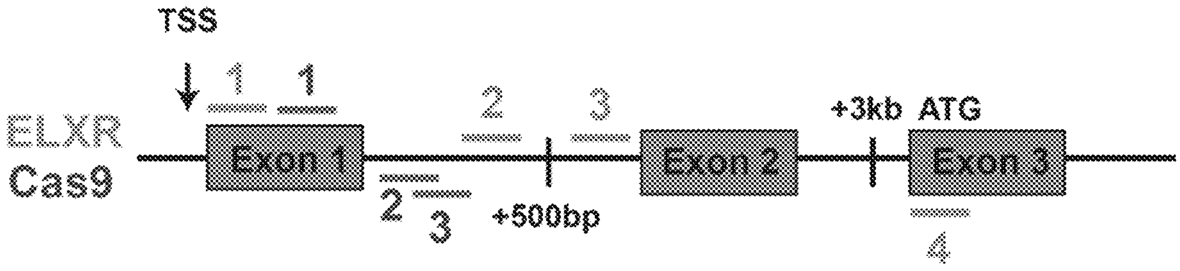
FIG. 20A is a schematic illustrating the relative positions of the CD151 sequences targeted by spacers for the assayed ELXR molecules and the dCas9-ZNF10-DNMT3A/L control, as described in Example 9. Positions targeted by gRNAs are indicated by light (paired with ELXRs) and dark gray (paired with dCas9-ZNF10-DNMT3A/L) bars.

Transfection of HEK293T Cells:

Seeded HEK293T cells were transiently transfected with 100 ng of ELXR variant plasmids, each containing an ELXR:gRNA construct encoding for ELXR molecule #1, #4, or #5, with four different gRNAs targeting the CD151 gene that encodes for an endogenous cell surface receptor (spacer sequences listed in Table 30). The next day, cells were selected with puromycin for four days. Cells were harvested for repression analysis at day 6, day 15, and day 22 after transfection. Repression analysis was performed by quantifying the level of CD151 protein expression via CD151 immunolabeling followed by flow cytometry using the Attune™ NxT flow cytometer. As experimental controls, HEK293T cells were also transfected with dCas9-ZNF10-DNMT3A/L with the appropriate CD151-targeting gRNAs (with targeting spacers 1-3 listed in Table 30). FIG. 20A is a schematic illustrating the relative positions of the targeting spacers listed in Table 30.

TABLE 30

Sequences of human CD151-targeting spacers used in constructs.

| Spacer ID | DNA sequence | SEQ ID NO | RNA sequence | SEQ ID NO |
|---|---|---|---|---|
| 39.1 | CAGCGCTGGGAGCCGCCGCC | 59640 | CAGCGCUGGGAGCCGCCGCC | 59647 |
| 39.2 | GCCCAGGGGTCCCGGGACGC | 59641 | GCCCAGGGGUCCCGGGACGC | 59648 |
| 39.3 | CTCCGCCCGCAGCAGCCCCC | 59642 | CUCCGCCCGCAGCAGCCCCC | 59649 |
| 39.4 | GACCTGCCGAGCGCCCGCCG | 59643 | GACCUGCCGAGCGCCCGCCG | 59650 |
| dCas9 spacer 1 | ACCACGCGTCCGAGTCCGG | 59644 | ACCACGCGUCCGAGUCCGG | 59651 |
| dCas9 spacer 2 | TGCTCATTGTCCCTGGACA | 59645 | UGCUCAUUGUCCCUGGACA | 59652 |
| dCas9 spacer 3 | GGACACCCTGCTCATTGTC | 59646 | GGACACCCUGCUCAUUGUC | 59653 |

Results

Figure 20B:
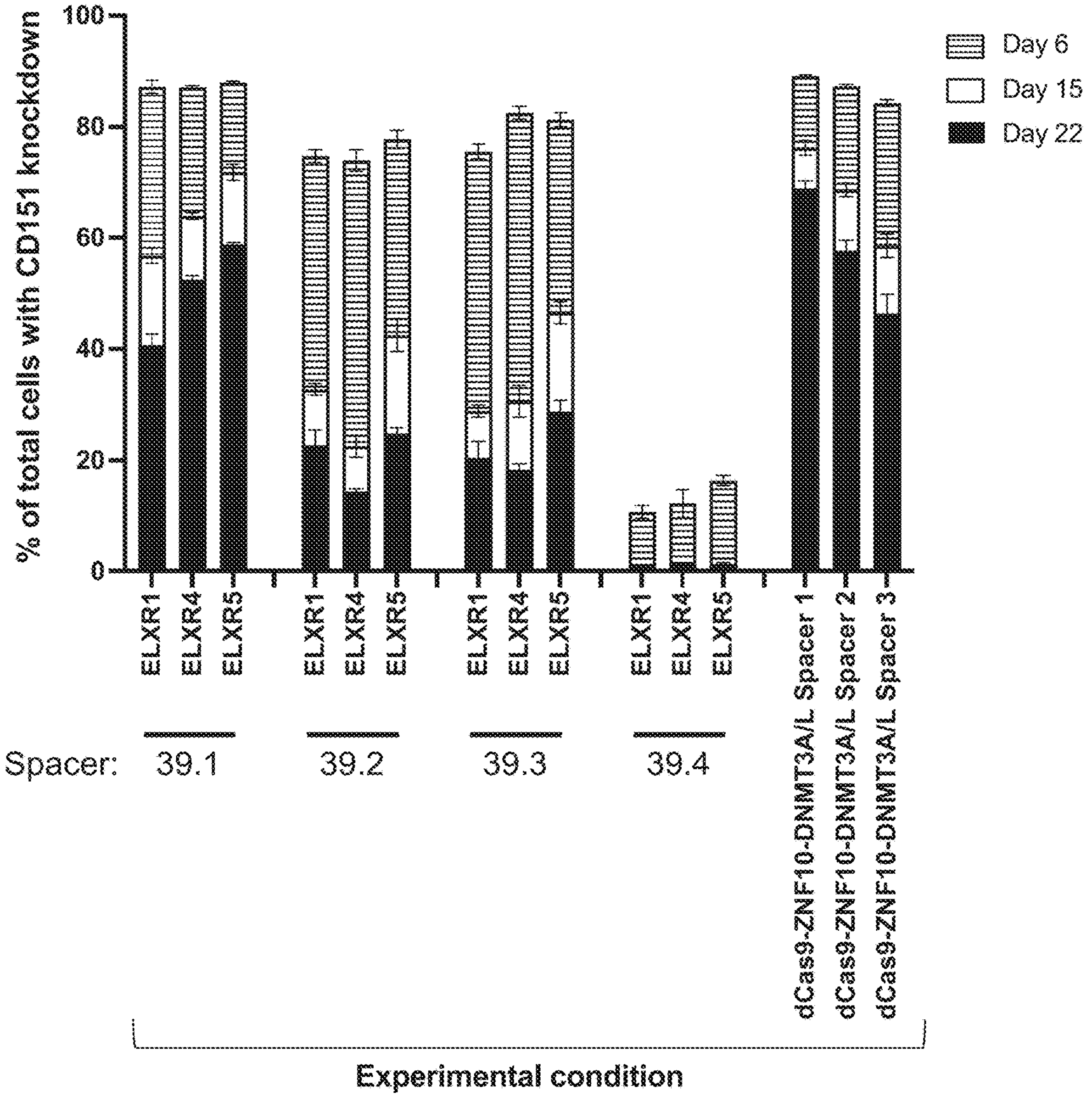
FIG. 20B is a bar graph that illustrates the results of a time-course experiment comparing CD151 repression activities (represented as percentage of total cells with CD151 knockdown) of ELXR proteins #1, #4, and #5 containing the ZIM3-KRAB domain with the indicated targeting spacers, as described in Example 9. Data for each timepoint (day 6, day 15, and day 22) are superimposed and are presented as mean with standard deviation, N=3.

ELXR variant plasmids encoding for ELXR #1, #4, and #5 harboring the ZIM3-KRAB domain were transiently transfected into HEK293T cells to determine whether these ELXR molecules could durably silence expression of the target CD151 gene in a cell-based assay. Quantification of the resulting CD151 knockdown by ELXRs is illustrated in FIG. 20B. The data demonstrate that use of three of the four tested targeting spacers resulted in durable silencing of the CD151 locus through 22 days post-transfection, albeit to varying levels of knockdown. Specifically, use of ELXR #1, #4, or #5 with targeting spacer 39.1 resulted in the strongest durable CD151 knockdown compared to that achieved when using other targeting spacers (FIG. 20B). The findings also show that use of ELXR #5 resulted in the strongest repressive activity, observable at Day 15 and Day 22 post-transfection across the tested spacers (FIG. 20B). Transfections with ELXR #5 and spacer pool or dCas9-ZNF10-DNMT3A/L and the appropriate gRNAs similarly resulted in durable silencing of the CD151 locus.

The results of this experiment demonstrate that ELXR molecules can induce heritable silencing of an alternative endogenous locus in vitro. Furthermore, the findings show that use of the ELXR #5 molecule resulted in the highest repression activity among the various ELXR configurations tested, indicating that position and relative arrangement of the DNMT3A/L domains affect overall activity of the ELXR molecule at the target locus.

Example 10: Demonstration that ELXRs have a Broader Targeting Window Compared to dXRs Experiments were performed to determine the targeting window of ELXR molecules at a gene promoter and to demonstrate that ELXRs have a wider targeting window compared to that of dXR molecules. As described in earlier examples, dXR is dCasX fused with a KRAB repressor domain, while ELXR is dCasX fused with a KRAB domain, DNMT3A catalytic domain, and a DNMT3L interaction domain.

Materials and Methods:

ELXR #1 containing the ZIM3-KRAB domain, as described in Example 6, and dXR1, as described in Example 1, were assessed in this experiment. Various gRNAs with scaffold 174 containing a B2M-targeting spacer were used in this experiment.

Figure 21A:
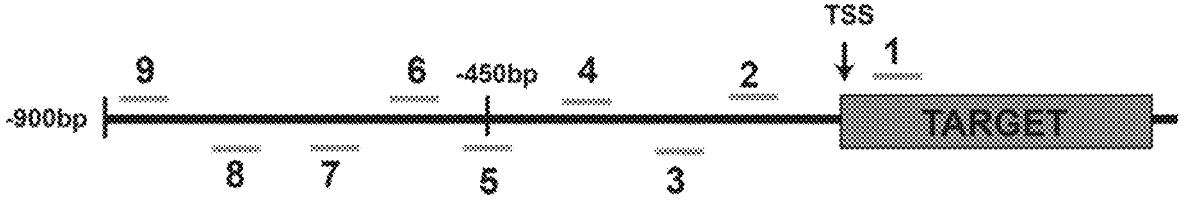
FIG. 21A is a schematic showing the positions of the various B2M-targeting gRNAs tiled across a ~1 KB window at the promoter region of the B2M gene, as described in Example 10. The numbers correspond to a particular B2M-targeting spacer shown in FIG. 21B. Targeting gRNAs are indicated by gray bars.

Transfection of HEK293T Cells:

Seeded HEK293T cells were lipofected with 100 ng of a plasmid containing a CasX:gRNA construct encoding for either XR1 or an ELXR #1 containing the ZIM3-KRAB domain, with nine different targeting gRNAs that tiled across ~1 KB region of the B2M promoter (spacer sequences listed in Table 31). The next day, cells were selected with puromycin for four additional days. Cells were harvested at six days after lipofection to determine B2M protein expression by flow cytometry as described in Example 6. HEK293T cells transfected with either ELXR #1 or dXR1 with a non-targeting gRNA was included as an experimental control. FIG. 21A is a schematic illustrating the tiling of the various B2M-targeting gRNAs (spacers listed in Table 31) within a ~1 KB window of the B2M promoter.

TABLE 31

Sequences of human B2M-targeting spacers used in constructs in this experiment.

| Spacer ID | DNA sequence | SEQ ID NO | RNA sequence | SEQ ID NO |
|---|---|---|---|---|
| 7.37 | GGCCGAGATGTCTCGCTCCG | 341 | GGCCGAGAUGUCUCGCUCCG | 59628 |
| 7.160 | TAAACATCACGAGACTCTAA | 59654 | UAAACAUCACGAGACUCUAA | 59662 |
| 7.161 | AGGACTTCAGGCTGGAGGCA | 59655 | AGGACUUCAGGCUGGAGGCA | 59663 |
| 7.162 | CGAATGAAAAATGCAGGTCC | 59656 | CGAAUGAAAAAUGCAGGUCC | 59664 |
| 7.163 | GITTATAACTACAGCTTGGG | 59657 | GUUUAUAACUACAGCUUGGG | 59665 |
| 7.164 | CTGAGCTGTCCTCAGGATGC | 59658 | CUGAGCUGUCCUCAGGAUGC | 59666 |
| 7.165 | TCCCTATGTCCTTGCTGTTT | 59659 | UCCCUAUGUCCUUGCUGUUU | 59667 |
| 7.166 | AGCGCCCTCTAGGTACATCA | 59660 | AGCGCCCUCUAGGUACAUCA | 59668 |
| 7.167 | GTTTACTGAGTACCTACTAT | 59661 | GUUUACUGAGUACCUACUAU | 59669 |

Results

Figure 21B:
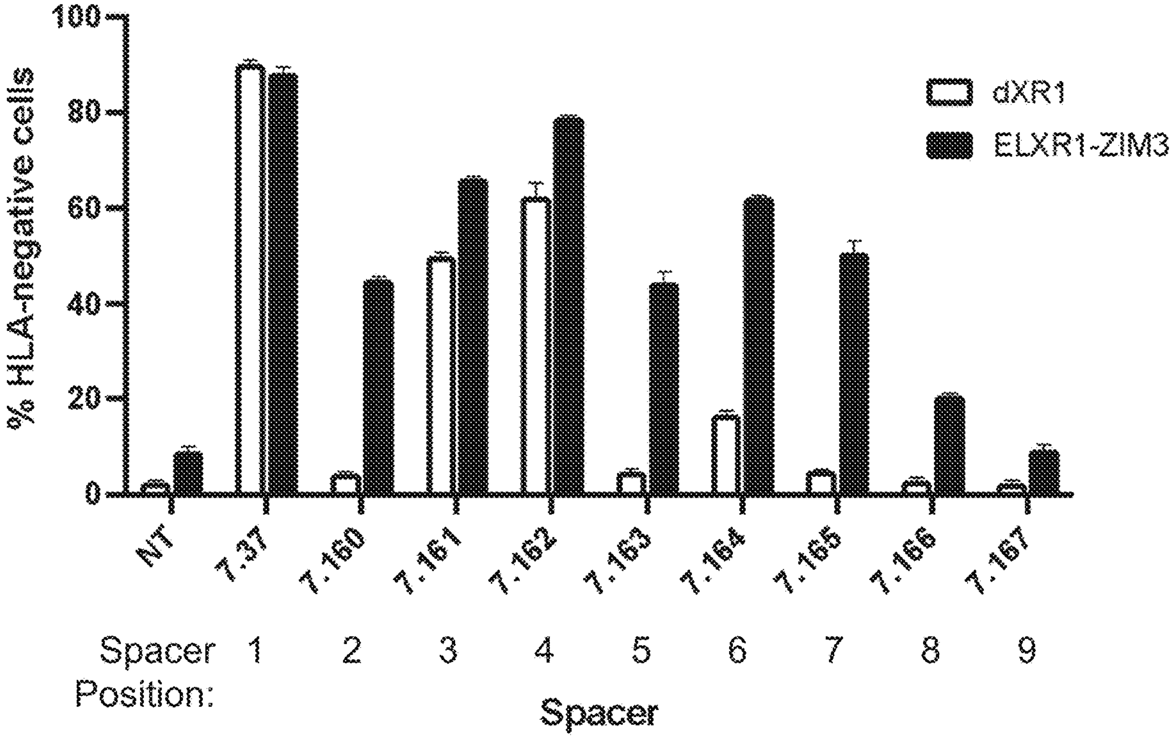
FIG. 21B is a bar graph that illustrates the quantification of B2M repression, represented as the average percentage of HLA-negative cells, mediated by either dXR1 or ELXR #1 with the indicated B2M-targeting spacers, as described in Example 10. Data are presented as mean with standard deviation, N=3. NT=non-targeting spacer.

To determine and compare the targeting window of ELXR molecules with that of dXR molecules, HEK293T cells were transfected with a plasmid encoding for either ELXR #1 or dXR1 with the various B2M-targeting gRNAs tiled across a ~1 KB region of the B2M promoter (Table 31). FIG. 21B is a plot depicting the results of the experiment assessing B2M protein repression (indicated by average percentage of cells characterized as HLA-negative) mediated by ELXR #1 compared with that mediated by dXR1 for the various B2M-targeting spacers. The data demonstrate that ELXR #1 was able to induce substantial B2M repression with more targeting spacers compared to that observed with dXR1 (FIG. 21B). Specifically, unlike the effects seen with dXR1, ELXR #1 was able to achieve meaningful B2M repression with spacers 7.160, 7.163, 7.164, and 7.165, suggesting that these four spacers are ELXR-specific spacers at the B2M locus. As anticipated, both ELXR #1 and dXR1 were able to induce a marked decrease in B2M protein expression with spacer 7.37 and a negligible decrease with a non-targeting spacer (FIG. 21B).

The results of this experiment demonstrate that ELXR molecules have a broader targeting window at the target locus compared to that of dXR molecules, and that ELXRs can function at longer distances from the gene promoter to induce repression of the target gene.

Example 11: Demonstration that Inclusion of the ADD Domain from DNMT3A Enhances Activity and Specificity of ELXR Molecules In addition to its C-terminal methyltransferase domain, DNMT3A contains two N-terminal domains that regulate its function and recruitment to chromatin: the ADD domain and the PWWP domain. The PWWP domain reportedly interacts with methylated histone tails, including H3K36me3. The ADD domain is known to have two key functions: 1) it allosterically regulates the catalytic activity of DNMT3A by serving as a methyltransferase auto-inhibitory domain, and 2) it recognizes unmethylated H3K4 (H3K4me0). The interaction of the ADD domain with the H3K4me0 mark unveils the catalytic site of DNMT3A, thereby recruiting an active DNMT3A to chromatin to implement de novo methylation at these sites.

Given these functions of the ADD domain, it is possible that including the ADD domain could enhance the activity and specificity of ELXR molecules. Here, experiments were performed to assess whether the incorporation of the ADD domain into the ELXR #5 molecule, described previously in Example 6, would result in improved long-term repression of the target locus and reduced off-target methylation. The effect of incorporating the PWWP domain along with the ADD domain on ELXR activity and specificity was also assessed.

Figure 36:
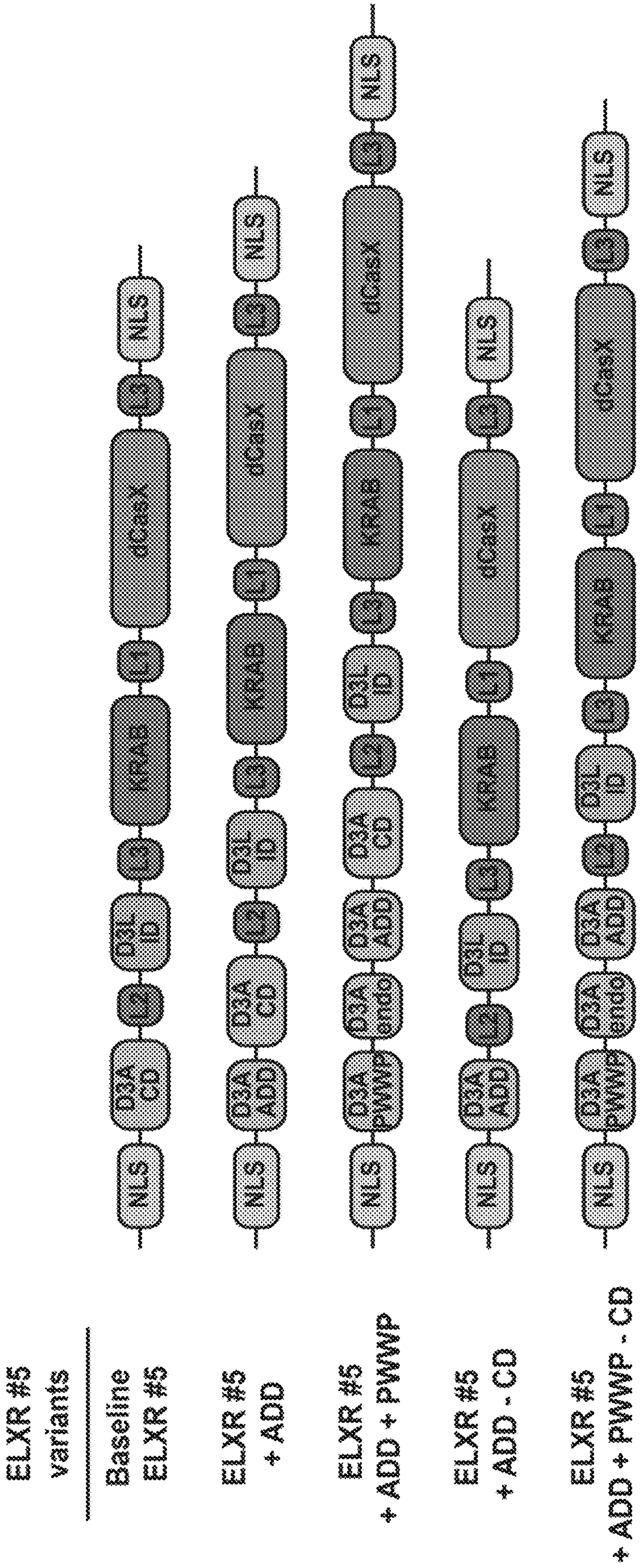
FIG. 36 illustrates the schematics of the various ELXR #5 architectures, where the additional DNMT3A domains were incorporated, as described in Example 11. The additional DNMT3A domains were the ADD domain of DNMT3A ("D3A ADD") and the PWWP domain of DNMT3A ("D3A PWWP"). "D3A endo" encodes for an endogenous sequence that occurs between DNMT3A PWWP and ADD domains. "D3A CD" and "D3L ID" denote the catalytic domain of DNMT3A and the interaction domain of DNMT3L respectively. "L1-L3" are linkers. "NLS" is the nuclear localization signal. See Table 33 for ELXR sequences.

Materials and Methods:

Generation of ELXR Constructs and Plasmid Cloning:

Plasmid constructs encoding for variants of the ELXR #5 construct with the ZIM3-KRAB domain (ELXR #5.A; see FIG. 7 for ELXR #5 configuration) were built using standard molecular cloning techniques. The resulting constructs comprised of sequences encoding for one of the following four alternative variations of ELXR5-ZIM3, where the additional DNMT3A domains were incorporated: 1) ELXR5-ZIM3+ADD; 2) ELXR5-ZIM3+ADD+PWWP; 3) ELXR5-ZIM3+ADD without the DNMT3A catalytic domain; and 4) ELXR5-ZIM3+ADD+PWWP without the DNMT3A catalytic domain. The sequences of key elements within the ELXR5-ZIM3 molecule and its variants are listed in Table 32, with the full encoding sequences for each ELXR5-ZIM3 and its variants listed in Table 33. FIG. 36 is a schematic that illustrates the various ELXR #5 architectures assayed in this example. Sequences encoding the ELXR molecules also contained a 2× FLAG tag. Plasmids also harbored constructs encoding for the gRNA scaffold variant 174 having either a spacer targeting the endogenous B2M locus or a non-targeting control (spacer sequences listed in Table 34).

TABLE 32

Sequences of key ELXR elements (e.g., additional domains fused to dCasX) to generate ELXR5 variant plasmids illustrated in FIG. 36.

| Key component | DNA Sequence (SEQ ID NO) | Protein sequence | SEQ ID NO |
|---|---|---|---|
| ZIM3 KRAB domain | 57612 | MNNSQGRVTFEDVTVNFTQGEWQRLNPEQRNLYRDVMLENYSNLVSVGQ GETTKPDVILRLEQGKEPWLEEEEVLGSGRAEKNGDIGGQIWKPKDVKE SL | 57613 |
| DNMT3A catalytic domain (CD) | 59444 | NHDQEFDPPKVYPPVPAEKRKPIRVLSLFDGIATGLLVLKDLGIQVDRY IASEVCEDSITVGMVRHQGKIMYVGDVRSVTQKHIQEWGPFDLVIGGSP CNDLSIVNPARKGLYEGTGRLFFEFYRLLHDARPKEGDDRPFFWLFENV VAMGVSDKRDISRFLESNPVMIDAKEVSAAHRARYFWGNLPGMNRPLAS TVNDKLELQECLEHGRIAKFSKVRTITTRSNSIKQGKDQHFPVFMNEKE DILWCTEMERVFGFPVHYTDVSNMSRLARQRLLGRSWSVPVIRHLFAPL KEYFACV | 59450 |
| DNMT3L interaction domain | 59445 | MGPMEIYKTVSAWKRQPVRVLSLFRNIDKVLKSLGFLESGSGSGGGTLK YVEDVTNVVRRDVEKWGPFDLVYGSTQPLGSSCDRCPGWYMFQFHRILQ YALPRQESQRPFFWIFMDNLLLTEDDQETTTRFLQTEAVTLQDVRGRDY QNAMRVWSNIPGLKSKHAPLTPKEEEYLQAQVRSRSKLDAPKVDLLVKN CLLPLREYFKYFSQNSLPL | 57617 |
| dCasX491 | 57618 | QEIKRINKIRRRLVKDSNTKKAGKTGPMKTLLVRVMTPDLRERLENLRK KPENIPQPISNTSRANLNKLLTDYTEMKKAILHVYWEEFQKDPVGLMSR VAQPASKKIDQNKLKPEMDEKGNLTTAGFACSQCGQPLFVYKLEQVSEK GKAYTNYFGRCNVAEHEKLILLAQLKPEKDSDEAVTYSLGKFGQRALDF YSIHVTKESTHPVKPLAQIAGNRYASGPVGKALSDACMGTIASFLSKYQ DIIIEHQKVVKGNQKRLESLRELAGKENLEYPSVTLPPQPHTKEGVDAY NEVIARVRMWVNLNLWQKLKLSRDDAKPLLRLKGFPSFPLVERQANEVD WWDMVCNVKKLINEKKEDGKVFWQNLAGYKRQEALRPYLSSEEDRKKGK KFARYQLGDLLLHLEKKHGEDWGKVYDEAWERIDKKVEGLSKHIKLEEE RRSEDAQSKAALTDWLRAKASFVIEGLKEADKDEFCRCELKLQKWYGDL RGKPFAIEAENSILDISGFSKQYNCAFIWQKDGVKKLNLYLIINYFKGG KLRFKKIKPEAFEANRFYTVINKKSGEIVPMEVNENFDDPNLIILPLAF GKRQGREFIWNDLLSLETGSLKLANGRVIEKTLYNRRTRQDEPALFVAL TFERREVLDSSNIKPMNLIGVARGENIPAVIALTDPEGCPLSRFKDSLG NPTHILRIGESYKEKQRTIQAKKEVEQRRAGGYSRKYASKAKNLADDMV RNTARDLLYYAVTQDAMLIFANLSRGFGRQGKRTFMAERQYTRMEDWLT AKLAYEGLSKTYLSKTLAQYTSKTCSNCGFTITSADYDRVLEKLKKTAT GWMTTINGKELKVEGQITYYNRYKRQNVVKDLSVELDRLSEESVNNDIS | 57619 |

TABLE 32-continued

| Sequences of key ELXR elements (e.g., additional domains fused to dCasX) to generate ELXR5 variant plasmids illustrated in FIG. 36. | | | |
|---|---|---|---|
| Key component | DNA Sequence (SEQ ID NO) | Protein sequence | SEQ ID NO |
| | | SWTKGRSGEALSLLKKRFSHRPVQEKFVCLNCGFETHAAEQAALNIARS WLFLRSQEYKKYQTNKTTGNTDKRAFVETWQSFYRKKLKEVWKPAV | |
| Linker 1 | 57620 | GGPSSGAPPPSGGSPAGSPTSTEEGTSESATPESGPGTSTEPSEGSAPG SPAGSPTSTEEGTSTEPSEGSAPGTSTEPSE | 57621 |
| Linker 2 | 57622 | SSGNSNANSRGPSFSSGLVPLSLRGSH | 57623 |
| Linker 3A' | 59446 | GGSGGG | 59451 |
| Linker 3B | 57625 | GGSGGGS | 57626 |
| Linker 4 | 57627 | GSGSGGG | 57628 |
| NLS A | 57629 | PKKKRKV | 57631 |
| NLS B | 57630 | | |
| DNMT3A ADD domain | 59447 | ERLVYEVRQKCRNIEDICISCGSLNVTLEHPLFIGGMCQNCKNCFLECA YQYDDDGYQSYCTICCGGREVLMCGNNNCCRCFCVECVDLLVGPGAAQA AIKEDPWNCYMCGHKGTYGLLRRREDWPSRLQMFFAN | 59452 |
| DNMT3A PWWP domain | 59448 | TKAADDEPEYEDGRGFGIGELVWGKLRGFSWWPGRIVSWWMTGRSRAAE GTRWVMWFGDGKFSVVCVEKLMPLSSFCSAFHQATYNKQPMYRKAIYEV LQVASSRAGKLFPACHDSDESDSGKAVEVQNKQMIEWALGGFQPSGPKG LEPPEEEKNPYKEV | 59453 |
| Endogenous sequence between DNMT3A PWWP and ADD domains (endo) | 59449 | YTDMWVEPEAAAYAPPPPAKKPRKSTTEKPKVKEIIDERTR | 59454 |

TABLE 33

| DNA sequences of constructs encoding ELXR5 variants assayed in this example, and protein sequences of ELXR5 variants. | | |
|---|---|---|
| ELXR ID | DNA Sequence (SEQ ID NO) | Protein SEQ ID NO |
| ELXR5-ZIM3 | 59455 | 59460 |
| ELXR5-ZIM3 + ADD | 59456 | 59461 |
| ELXR5-ZIM3 + ADD + PWWP | 59457 | 59462 |
| ELXR5-ZIM3 + ADD − CD | 59458 | 59463 |
| ELXR5-ZIM3 + ADD + PWWP − CD | 59459 | 59464 |

TABLE 34

| Sequences of spacers used in constructs. | | | |
|---|---|---|---|
| Spacer ID | Target gene | Sequence | SEQ ID NO |
| 0.0 | Non-target | CGAGACGUAAUUACGUCUCG | 57646 |
| 7.37 | B2M | GGCCGAGAUGUCUCGCUCCG | 57644 |
| 7.160 | B2M | UAAACAUCACGAGACUCUAA | 59662 |
| 7.165 | B2M | UCCCUAUGUCCUUGCUGUUU | 59667 |

Transfection of HEK293T Cells:

Seeded HEK293T cells were transiently transfected with 100 ng of ELXR5 variant plasmids, each containing an ELXR:gRNA construct encoding for ELXR5-ZIM3 or one of its alternative variations (FIG. 36; Table 33 for sequences), with the gRNA having either non-targeting spacer 0.0 or a B2M-targeting spacer (Table 34 for spacer sequences). The results in Example 10 identified spacers 7.160 and 7.165 to be ELXR-specific spacers. Each construct was tested in triplicate. 24 hours post-transfection, cells were selected with 1p g/mL puromycin for three days. Cells were harvested for repression analysis at day 5, day 12, day 21, and day 51 post-transfection. Briefly, repression analysis was conducted by analyzing B2M protein expression via HLA immunostaining followed by flow cytometry, as described in Example 6. In addition, HEK293T cells transiently transfected with ELXR5 variant plasmids and a B2M-targeting gRNA or non-targeting gRNA were harvested at seven days post-transfection for gDNA extraction for bisulfite sequencing to assess off-target methylation at the VEGFA locus, which was performed as described in Example 6.

Results

Figure 22:
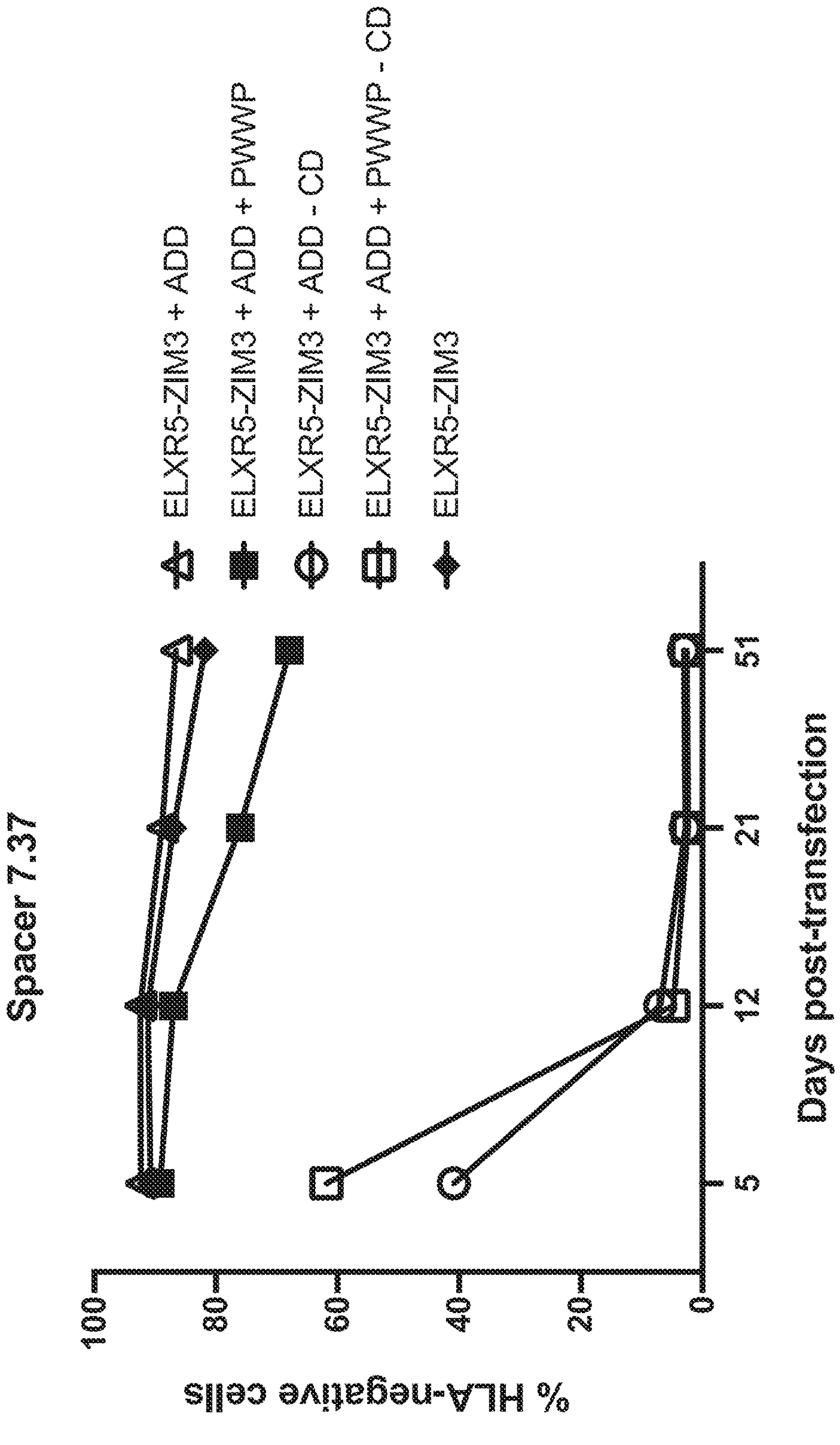
FIG. 22 presents the results of a time-course experiment comparing B2M repression activities (represented as percentage of HLA-negative cells) of the indicated ELXR5-ZIM3 and its variants with B2M-targeting gRNA using spacer 7.37, as described in Example 11. Data are presented as mean with standard deviation, N=3. CD=catalytic domain of DNMT3A.
Figure 23:
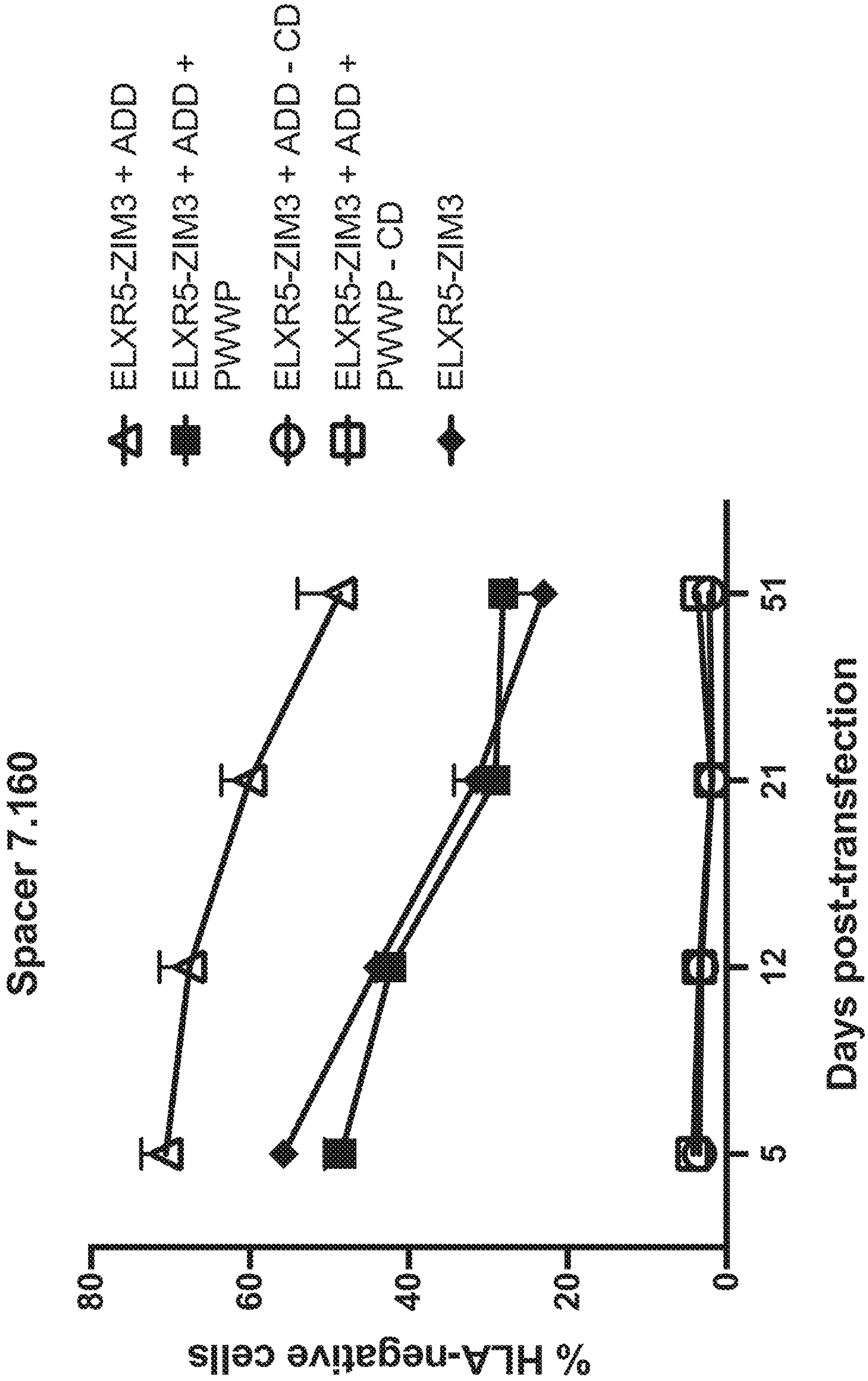
FIG. 23 presents the results of the same time-course experiment shown in FIG. 22 but shows B2M repression activities of the indicated ELXR5-ZIM3 variants with B2M-targeting gRNA using spacer 7.160, as described in Example 11. Data are presented as mean with standard deviation, N=3.
Figure 24:
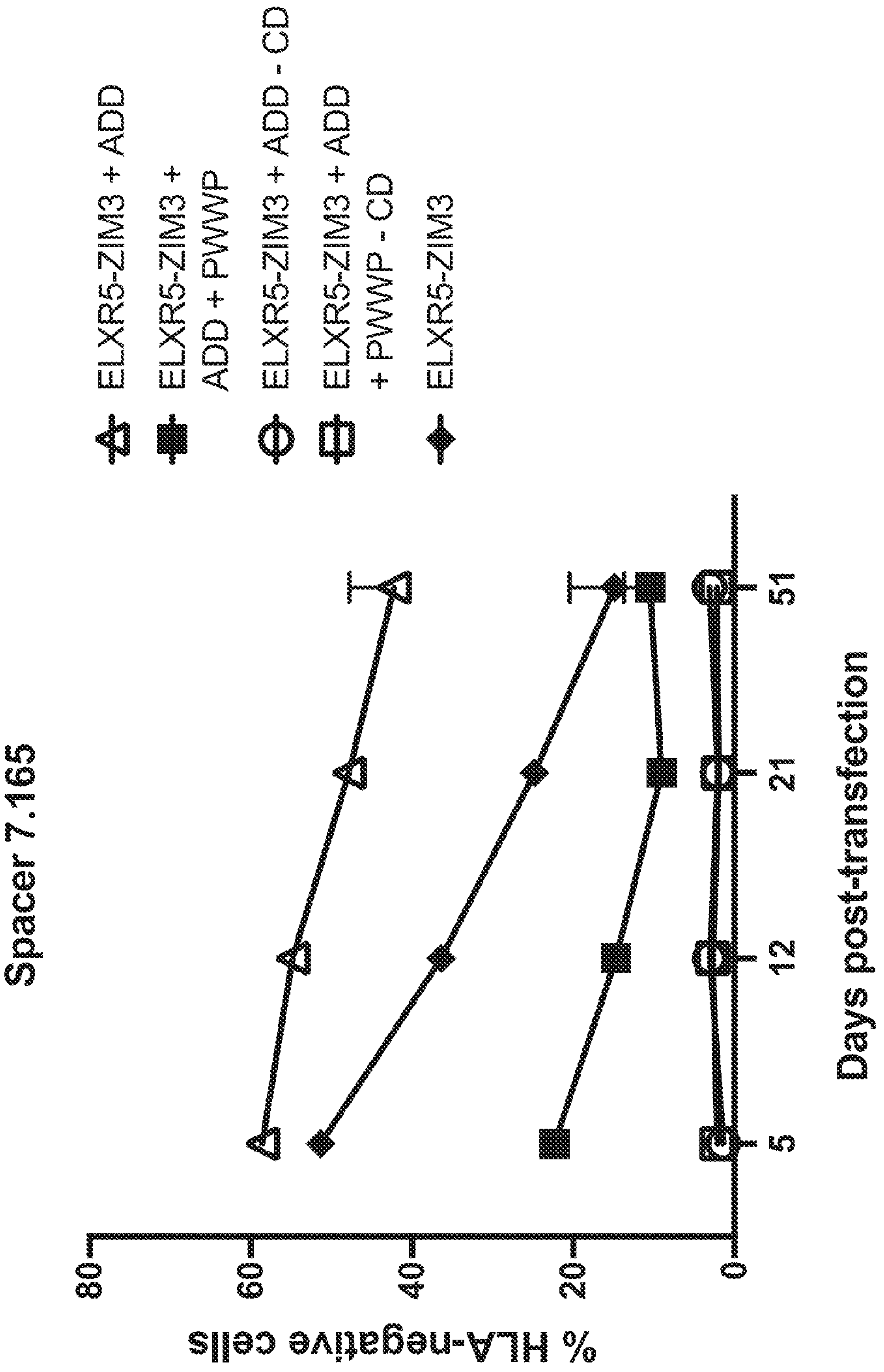
FIG. 24 presents the results of the same time-course experiment shown in FIG. 22 but shows B2M repression activities of the indicated ELXR5-ZIM3 variants with B2M-targeting gRNA using spacer 7.165, as described in Example 11. Data are presented as mean with standard deviation, N=3.
Figure 25:
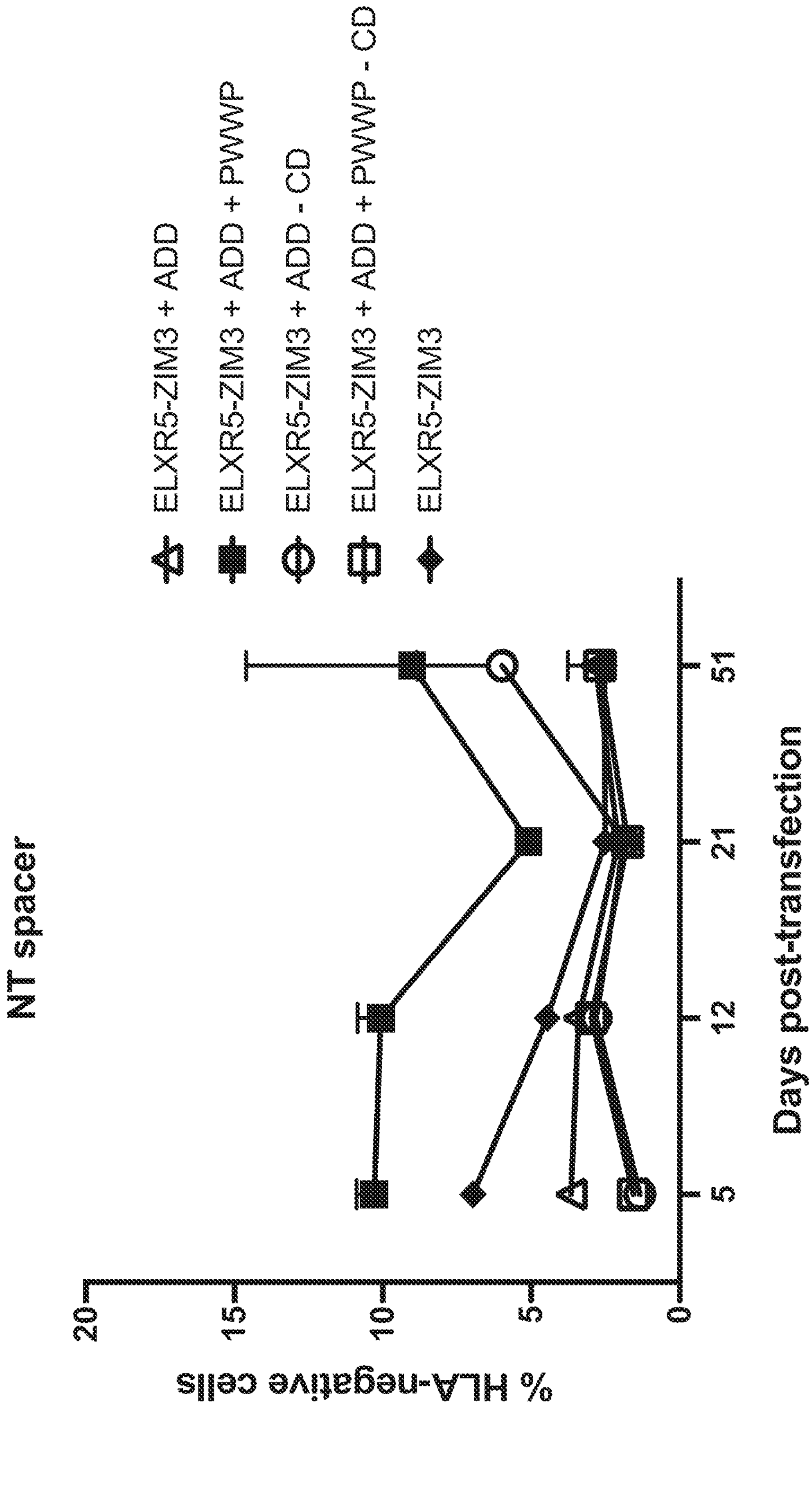
FIG. 25 presents the results of the same time-course experiment shown in FIG. 22 but shows B2M repression activities of the indicated ELXR5-ZIM3 variants with a non-targeting gRNA, as described in Example 11. Data are presented as mean with standard deviation, N=3.

The effects of incorporating the ADD domain with or without the PWWP domain into the ELXR5 molecule on increasing long-term repression of the target B2M locus and reducing off-target methylation were assessed. Variations of the ELXR5-ZIM3 molecule were evaluated with either a B2M-targeting gRNA (with spacer 7.37 and ELXR-specific spacers 7.160 and 7.165) or a non-targeting gRNA, and the results are depicted in the plots in FIGS. 22-25. FIG. 22 shows that use of spacer 7.37 resulted in saturating levels of repression activity when paired with ELXR5-ZIM3, ELXR5-ZIM3+ADD, and ELXR5-ZIM3+ADD+PWWP, rendering it more challenging to assess activity differences among the ELXR5 variants. However, the differences in repression activity among the ELXR5 variants were more pronounced when using spacers 7.160 and 7.165 (FIGS. 23 and 24). The data demonstrate that incorporation of the ADD domain resulted in a significant increase in long-term repression when paired with the two ELXR-specific spacers compared to the repression levels achieved with the other ELXR5-ZIM3 molecules. Meanwhile, incorporation of both ADD and PWWP domains did not result in improved repression of the B2M locus, especially compared to the baseline ELXR5-ZIM3 molecule. As anticipated, the two ELXR5 variants without the DNMT3A catalytic domain exhibited poor long-term repression. Furthermore, FIG. 25 indicates that addition of the ADD domain appeared to result in increased specificity, given the lower percentage of HLA-negative cells observed, relative to the baseline ELXR5-ZIM3 molecule.

Figure 26:
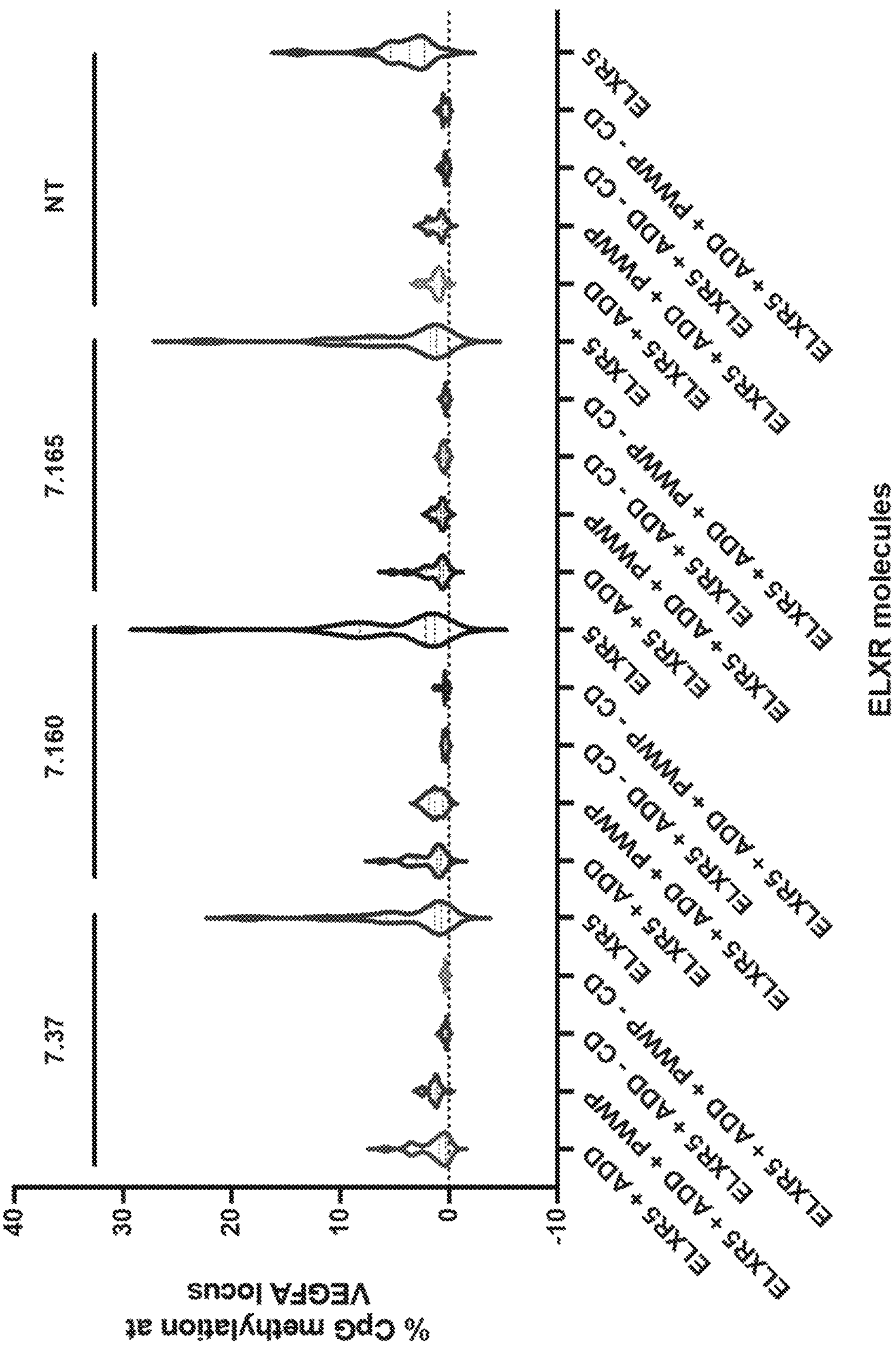
FIG. 26 is a violin plot of percent CpG methylation for CpG sites downstream of the transcription start site of the VEGFA locus for each indicated ELXR5-ZIM3 variant for the three B2M-targeting gRNA and non-targeting gRNA, as described in Example 11.
Figure 27:
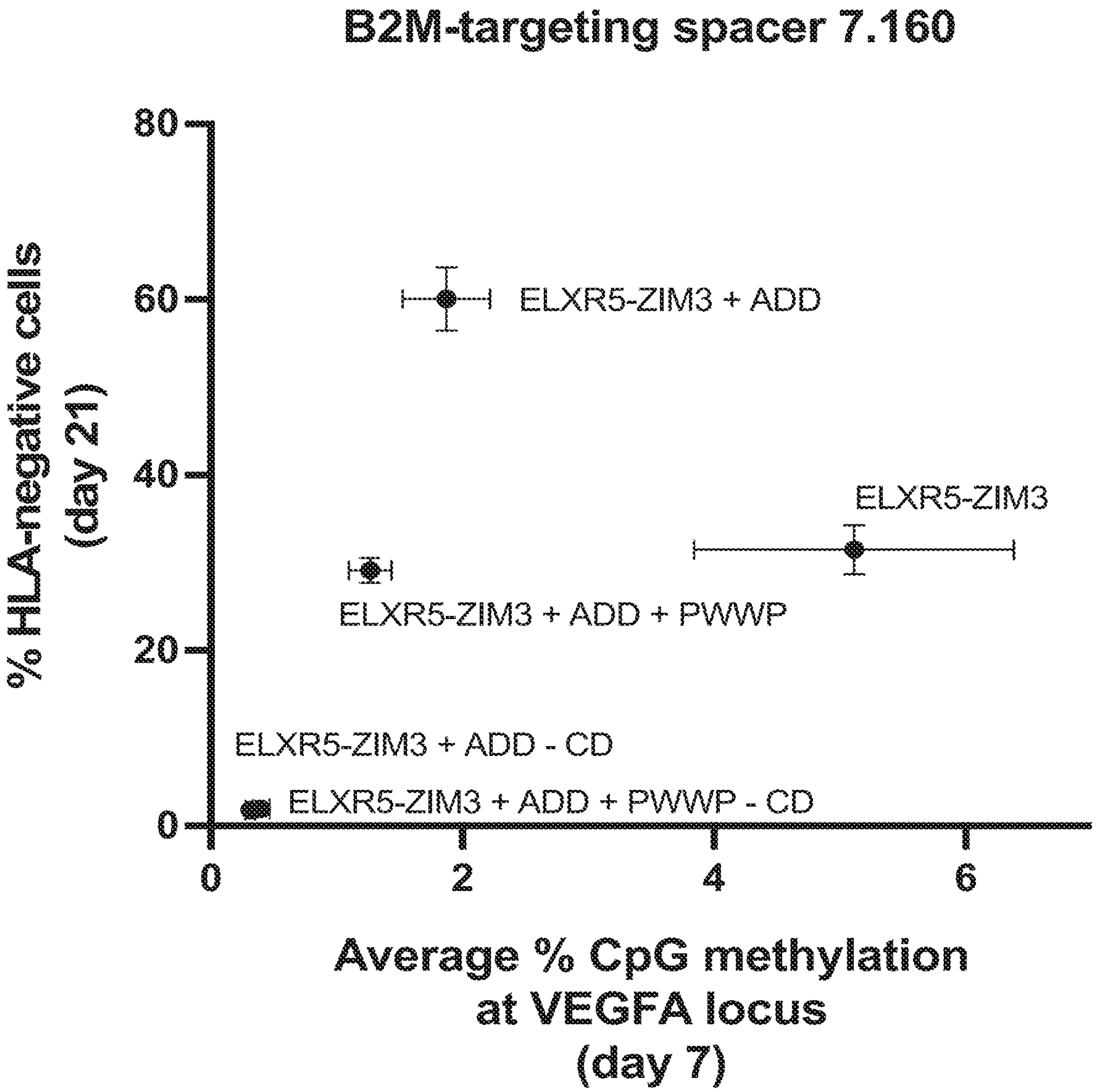
FIG. 27 is a scatterplot showing the relative activity (average percentage of HLA-negative cells at day 21 for spacer 7.160) versus specificity (percentage of off-target CpG methylation at the VEGFA locus quantified at day 7 for spacer 7.160) for the indicated ELXR5-ZIM3 variants, as described in Example 11.

Off-target CpG methylation at the VEGFA locus potentially mediated by the ELXR5 variants was assessed using bisulfite sequencing. FIG. 26 depicts the results from bisulfite sequencing, specifically showing the percentage of CpG methylation around the VEGFA locus. The results demonstrate that for all the B2M-targeting gRNAs, as well as the non-targeting gRNA, incorporation of the ADD domain into the ELXR5-ZIM3 molecule dramatically reduced the level of off-target methylation at the VEGFA locus (FIG. 26). FIG. 27 is a scatterplot mapping the activity-specificity profiles for the ELXR5-ZIM3 variants investigated in this example, where activity was measured as the average percentage of HLA-negative cells at day 21 when paired with spacer 7.160, and specificity was represented by the percentage of off-target CpG methylation at the VEGFA locus quantified at day 7 when paired with spacer 7.160. The scatterplot clearly shows that addition of the ADD domain significantly increases activity of the ELXR5 molecule relative to the baseline ELX5 molecule without the ADD domain (FIG. 27).

The experiments demonstrate that inclusion of the DNMT3A ADD domain, but not inclusion of both the ADD and PWWP domains, improves repression activity and specificity of ELXR molecules. This enhancement of activity and specificity is observed with multiple gRNAs, demonstrating the significance of the incorporation of the ADD domain into ELXRs.

Example 12: Demonstration that Silencing of a Target Locus Mediated by ELXR Molecules is Reversible Using a DNMT1 Inhibitor Experiments were performed to demonstrate that durable repression of a target locus mediated by ELXR molecules is reversible, such that treatment with a DNMT1 inhibitor would remove methyl marks to reactivate expression of the target gene.

Materials and Methods:

ELXR #5 containing the ZIM3-KRAB domain, which was generated as described in Example 6, and CasX variant 491 were used in this experiment. A B2M-targeting gRNA with scaffold 174 containing spacer 7.37 (SEQ ID NO: 57644) or a non-targeting gRNA containing spacer 0.0 (SEQ ID NO: 57646) were used in this experiment.

Transfection of HEK293T Cells:

HEK293T cells were transfected with 100 ng of a plasmid containing a construct encoding for either CasX 491 or ELXR #5 containing the ZIM3-KRAB domain with a B2M-targeting gRNA or non-targeting gRNA and cultured for 58 days. These transfected HEK293T cells were subsequently re-seeded at ~30,000 cells well of a 96-well plate and were treated with 5-aza-2'-deoxycytidine (5-azadC), a DNMT1 inhibitor, at concentrations ranging from 0 μM to 20 μM. Six days post-treatment with 5-azadC, cells were harvested for B2M silencing analysis at day 5, day 12, and day 21 post-transfection. Briefly, repression analysis was conducted by analyzing B2M protein expression via HLA immunostaining followed by flow cytometry, as described in Example 6. Treatments for each dose of 5-azadC for each experimental condition were performed in triplicates.

Results

Figure 34:
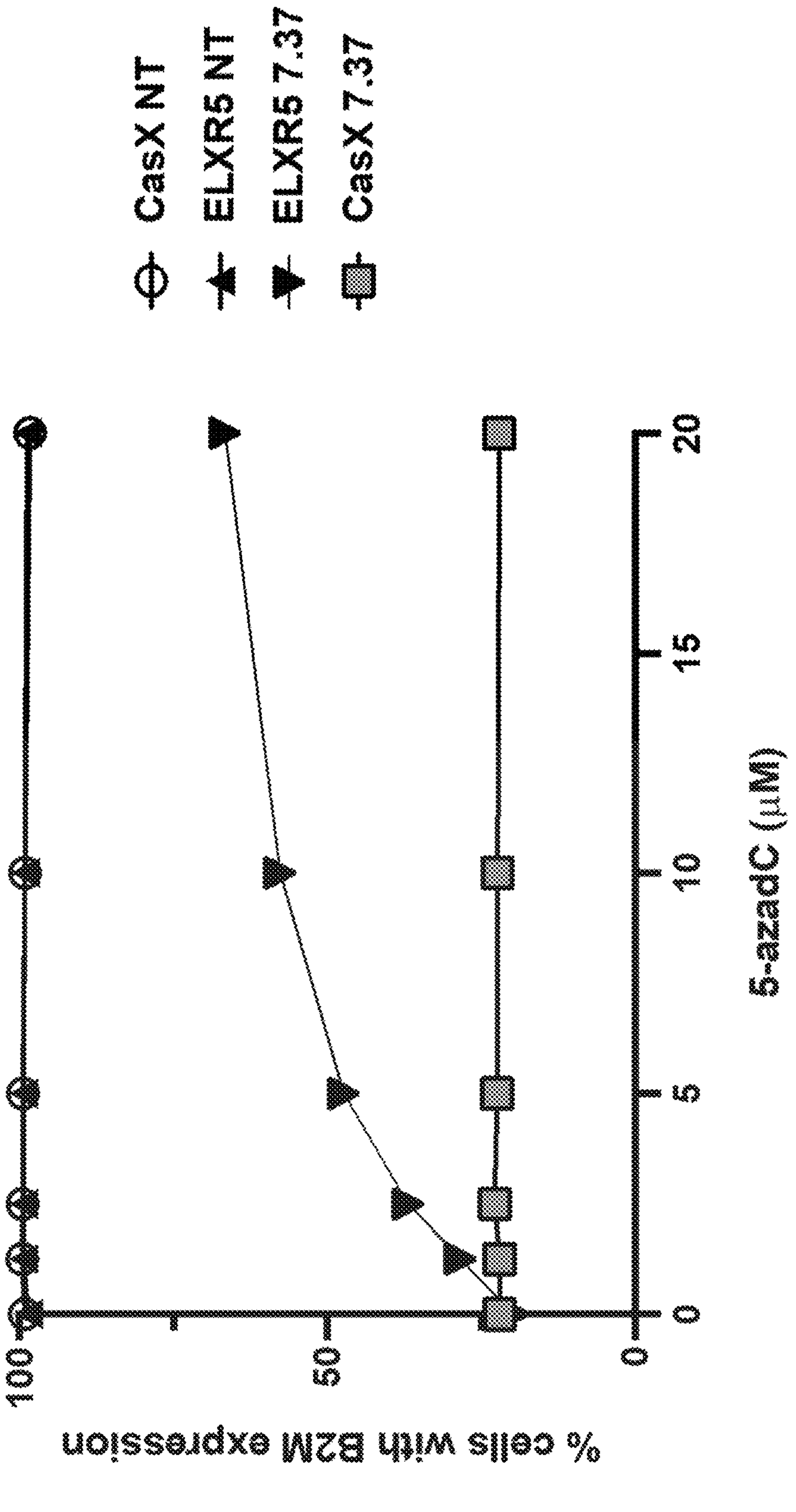
FIG. 34 is a plot illustrating percentage of HEK293T cells, transfected with a plasmid encoding the indicated CasX or ELXR:gRNA construct, that expressed B2M six days post-treatment with the DNMT1 inhibitor 5-azadC at varying concentrations, as described in Example 12.
Figure 35:
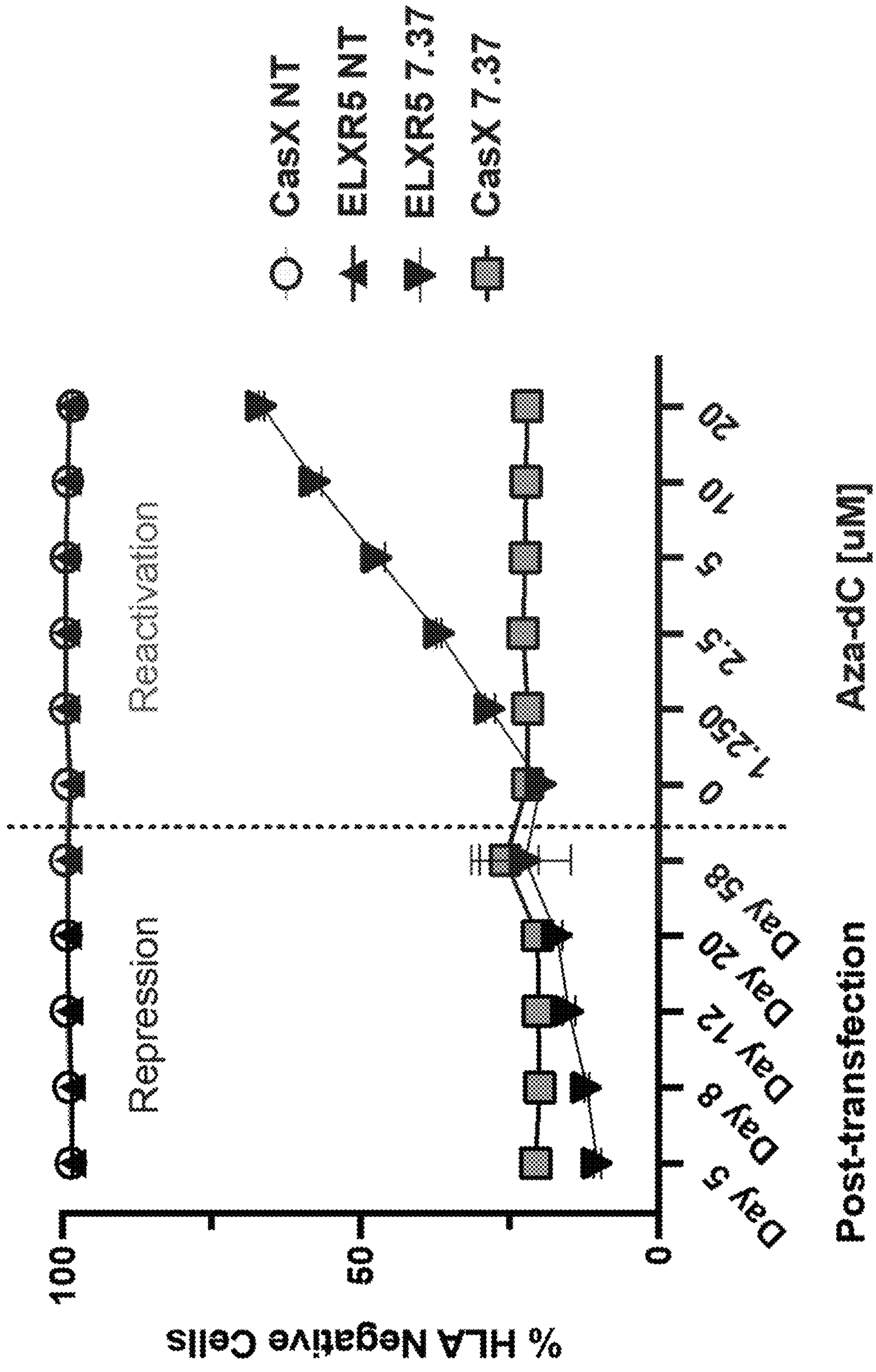
FIG. 35 is a plot that juxtaposes the quantification of B2M repression in HEK293T cells transfected with a plasmid encoding the indicated CasX or ELXR:gRNA construct and cultured for 58 days, with the quantification of B2M reactivation upon treatment of transfected cells with 5-azadC, as described in Example 12.

The plot in FIG. 34 shows the percentage of transfected HEK293T cells treated with the indicated concentrations of 5-azadC that expressed the B2M protein. The data demonstrate that 5-azadC treatment of cells transfected with a plasmid encoding ELXR5-ZIM3 with the B2M-targeting gRNA resulted in a reactivation of the B2M gene (FIG. 34). Specifically, ~75% of treated cells exhibited B2M expression with 20 μM 5-azadC, compared to the 25% of cells with B2M expression at 0 μM concentration (FIG. 34). Furthermore, 5-azadC treatment of cells transfected with a plasmid encoding CasX 491 with the B2M-targeting gRNA did not exhibit reactivation of the B2M gene. FIG. 35 is a plot that juxtaposes B2M repression activity with gene reactivation upon 5-azadC treatment. The data show B2M repression post-transfection with either CasX 491 or ELXR5-ZIM3 with the B2M-targeting gRNA, resulting in ~75% repression of B2M expression by day 58; however, B2M expression is increased upon 5-azadC treatment (FIG. 35). As anticipated, 5-azadC treatment of cells transfected with either CasX 491 or ELXR5-ZIM3 with the non-targeting gRNA did not demonstrate repression or reactivation (FIGS. 34-35).

The experiments demonstrate reversibility of ELXR-mediated repression of a target locus. By using a DNMT1 inhibitor to remove methyl marks implemented by ELXR molecules, the silenced target gene was reactivated to induce expression of the target protein.

Example 13: Demonstration that Inclusion of the ADD Domain from DNMT3A into ELXRs Enhances On-Target Activity and Decreases Off-Target Methylation Experiments were performed to assess the effects of incorporating the ADD domain into ELXR molecules having configurations #1, #4, and #5, described previously in Example 6, on long-term repression of the target locus and off-target methylation.

Figure 37:
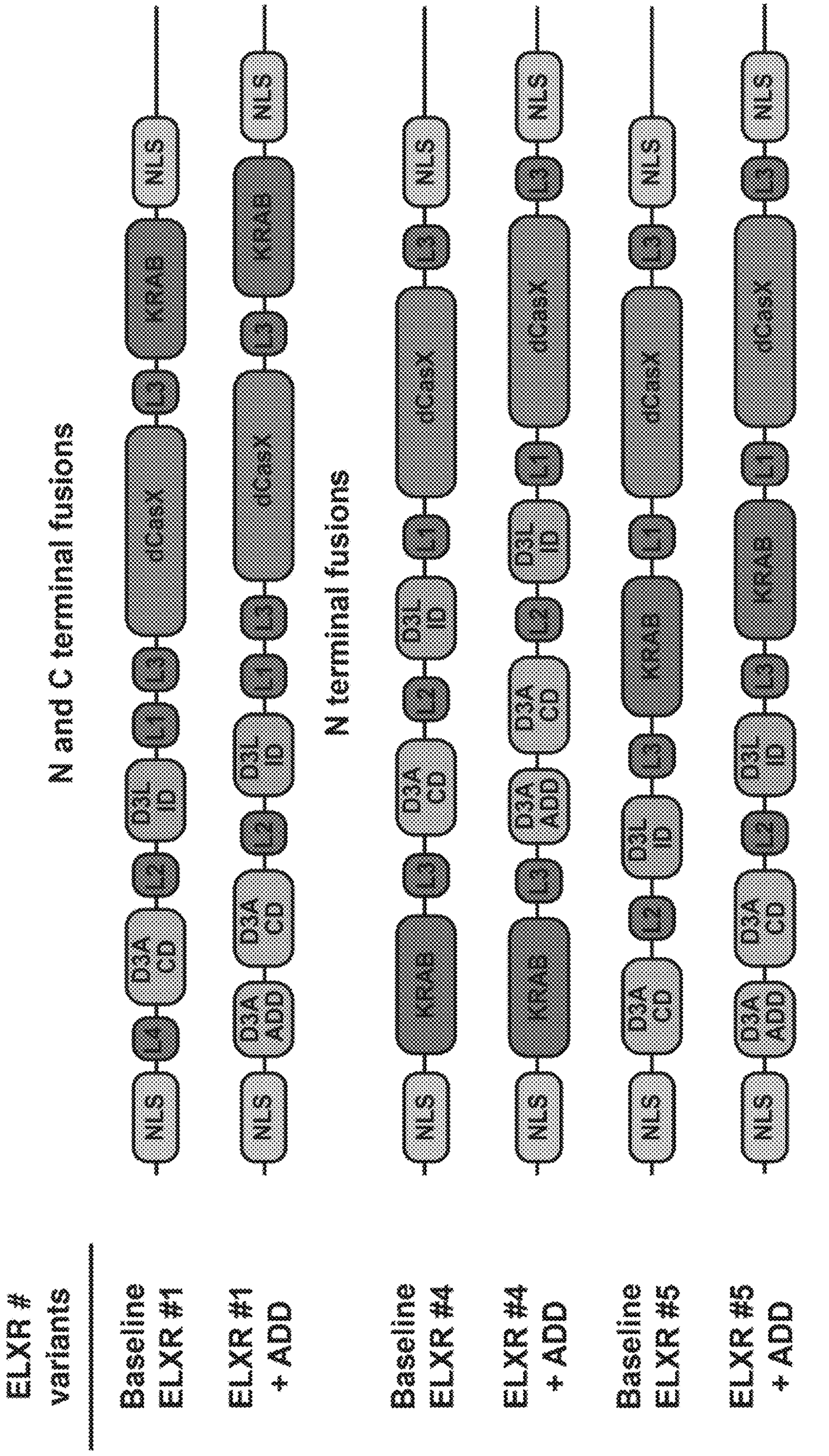
FIG. 37 illustrates the schematics of the general architectures of the ELXR molecules with the ADD domain for ELXR configuration #1, #4, and #5 tested in Example 13. "D3A ADD", "D3A CD" and "D3L ID" denote the ADD domain of DNMT3A, the catalytic domain of DNMT3A, and the interaction domain of DNMT3L respectively, as described in Example 13. "L1-L4" are linkers. "NLS" is the nuclear localization signal. See Table 35 for ELXR sequences.

Materials and Methods:

Generation of ELXR Constructs and Plasmid Cloning:

Plasmid constructs encoding for ELXR molecules having configurations #1, #4, and #5 with the ZNF10-KRAB or ZIM3-KRAB domain and the DNMT3A ADD domain were built using standard molecular cloning techniques. Sequences of the resulting ELXR molecules are listed in Table 35, which also shows the abbreviated construct names for a particular ELXR molecule (e.g., ELXR #1.A, #1.B). FIG. 37 is a schematic that illustrates the general architectures of ELXR molecules with the ADD domain incorporated for ELXR configuration #1, #4, and #5. Sequences encoding the ELXR molecules also contained a 2× FLAG tag. Plasmids also harbored sequences encoding gRNA scaffold 174 having either a spacer targeting the endogenous B2M locus or a non-targeting control (spacer sequences listed in Table 34).

Transfection of HEK293T Cells:

Seeded HEK293T cells were transiently transfected with 100 ng of ELXR variant plasmids, each containing an ELXR:gRNA construct encoding for an ELXR molecule (Table 35; FIG. 37), with the gRNA having either non-targeting spacer 0.0 or a B2M-targeting spacer (Table 34). Each construct was tested in triplicate. 24 hours post-transfection, cells were selected with 1 μg/mL puromycin for 3 days. Cells were harvested for repression analysis at day 8, day 13, day 20, and day 27 post-transfection. Briefly, repression analysis was conducted by analyzing B2M protein expression via HLA immunostaining followed by flow cytometry, as described in Example 6. In addition, cells were also harvested on day 5 post-transfection for gDNA extraction for bisulfite sequencing to assess off-target methylation at the non-targeted VEGFA locus, which was performed using similar methods as described in Example 6.

Results

The effects of incorporating the ADD domain into the ELXR molecules having configurations #1, #4, or #5, with either a ZNF10 or ZIM-KRAB, on long-term repression of the B2M locus and off-target methylation were evaluated. ELXR molecules were tested with either a B2M-targeting gRNA or a non-targeting gRNA, and the results are depicted in the plots in FIGS. 39A-42B. The data demonstrate that incorporation of the ADD domain into the ELXR molecules

TABLE 35

DNA and protein sequences of the various ELXR #1, #4, and #5 variants assayed in this example.

Figure 39A:
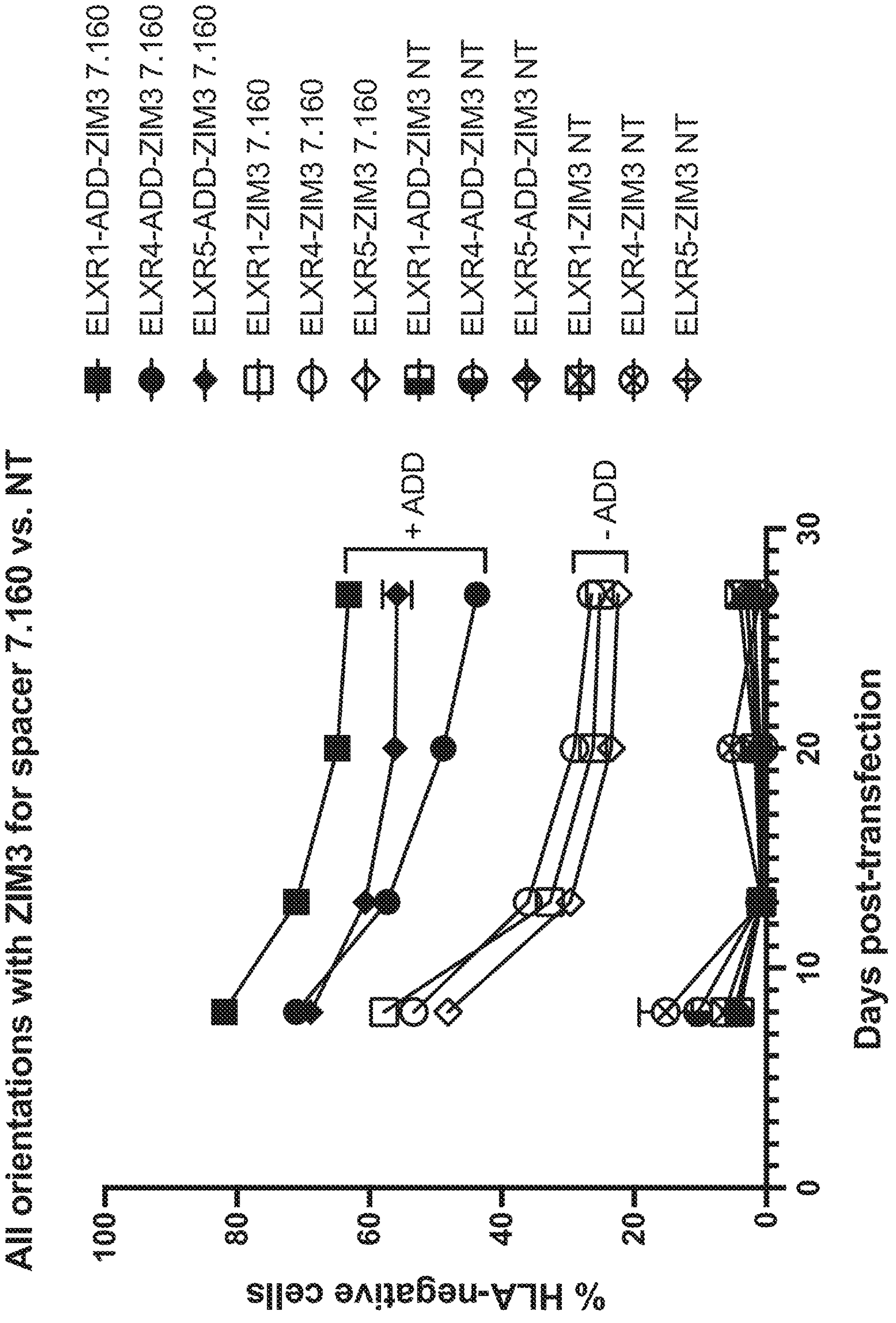
FIG. 39A presents the results of a time-course experiment comparing B2M repression activities (represented as percentage of HLA-negative cells) of ELXRs with the ZIM3-KRAB domain having configuration #1, #4, or #5 with or without the DNMT3A ADD domain when paired with the B2M-targeting gRNA with spacer 7.160, as described in Example 13. Data are presented as mean with standard deviation, N=3. "NT" is a gRNA with a non-targeting spacer.
Figure 39B:
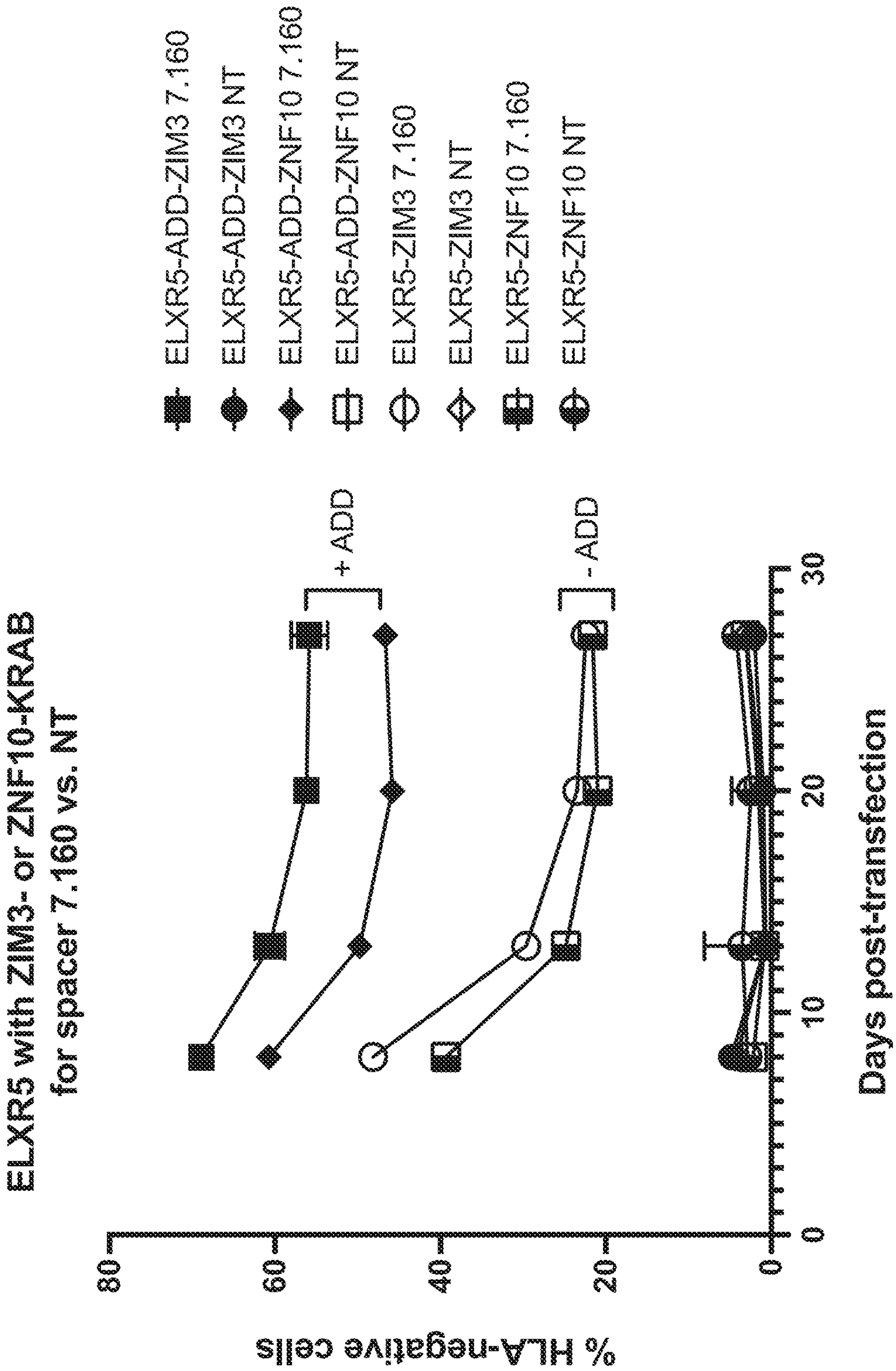
FIG. 39B is a plot showing the results of the same time-course experiment shown in FIG. 39A but illustrates B2M repression activities for ELXR #5 with the ZNF10 or ZIM3-KRAB domain, with or without the DNMT3A ADD domain, paired with the B2M-targeting gRNA with spacer 7.160, as described in Example 13. Data are presented as mean with standard deviation, N=3. "NT" is a gRNA with a non-targeting spacer.
Figure 39C:
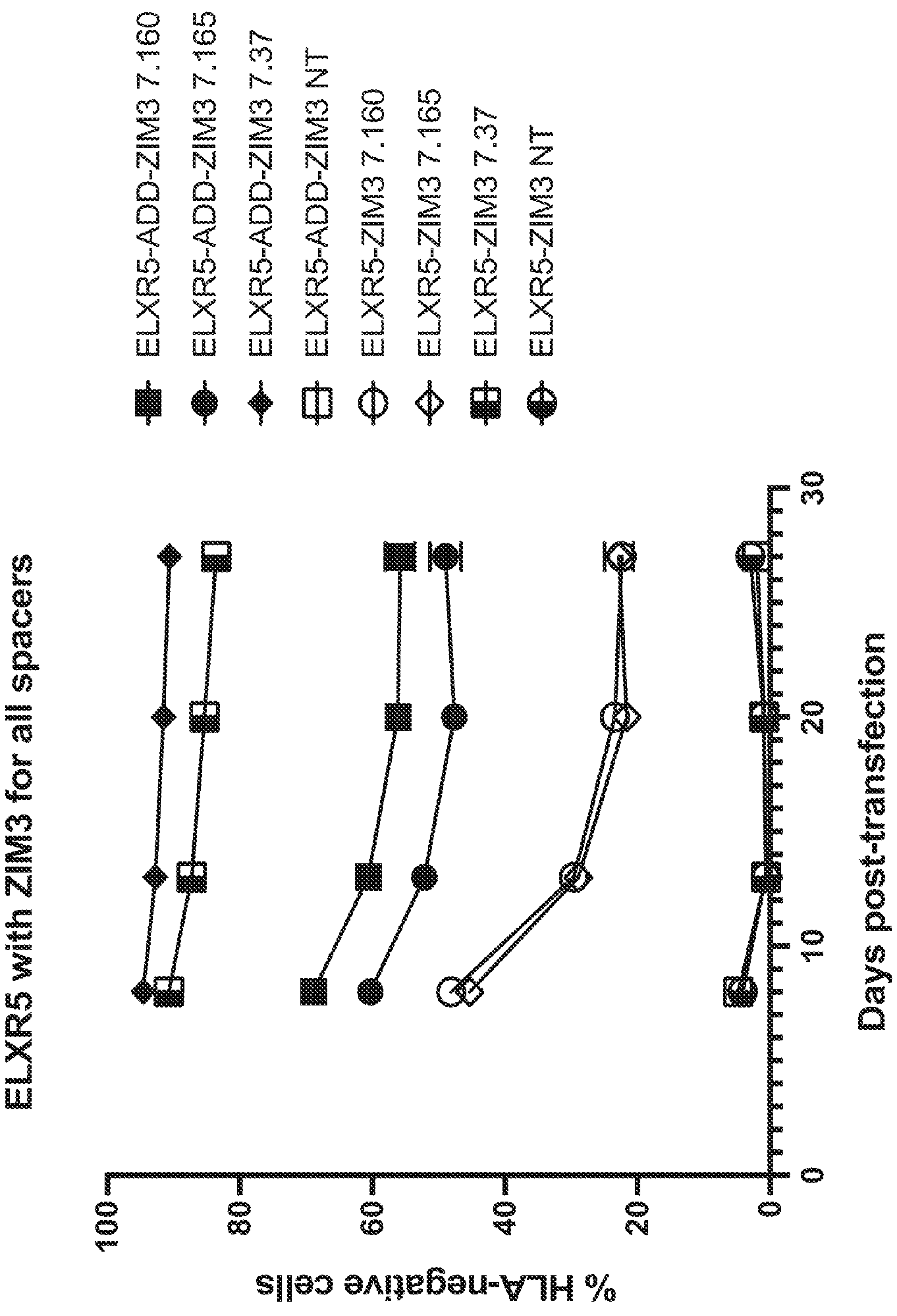
FIG. 39C is a plot showing the results of the same time-course experiment shown in FIG. 39A but illustrates B2M repression activities for ELXR5-ZIM3 with or without the DNMT3A ADD domain paired with a B2M-targeting gRNA with the indicated spacers, as described in Example 13. Data are presented as mean with standard deviation, N=3. "NT" is a gRNA with a non-targeting spacer.

| ELXR # | Domains | DNA SEQ ID NO | Protein SEQ ID NO |
|---|---|---|---|
| ELXR #1 | ZNF10-KRAB, DNMT3A ADD, DNMT3A CD, DNMT3L Interaction (ELXR #1.D) | 59488 | 59498 |
| | ZIM3-KRAB, DNMT3A ADD, DNMT3A CD, DNMT3L Interaction (ELXR #1.C) | 59489 | 59499 |
| | ZNF10-KRAB, DNMT3A CD, DNMT3L Interaction (ELXR #1.B) | 59490 | 59500 |
| | ZIM3-KRAB, DNMT3A CD, DNMT3L Interaction (ELXR #1.A) | 59491 | 59501 |
| ELXR #4 | ZNF10-KRAB, DNMT3A ADD, DNMT3A CD, DNMT3L Interaction (ELXR #4.D) | 59492 | 59502 |
| | ZIM3-KRAB, DNMT3A ADD, DNMT3A CD, DNMT3L Interaction (ELXR #4.C) | 59493 | 59503 |
| | ZNF10-KRAB, DNMT3A CD, DNMT3L Interaction (ELXR #4.B) | 59494 | 59504 |
| | ZIM3-KRAB, DNMT3A CD, DNMT3L Interaction (ELXR #4.A) | 59495 | 59507 |
| ELXR #5 | ZNF10-KRAB, DNMT3A ADD, DNMT3A CD, DNMT3L Interaction (ELXR #5.D) | 59496 | 59505 |
| | ZIM3-KRAB, DNMT3A ADD, DNMT3A CD, DNMT3L Interaction (ELXR #5.C) | 59456 | 59461 |
| | ZNF10-KRAB, DNMT3A CD, DNMT3L Interaction (ELXR #5.B) | 59497 | 59509 |
| | ZIM3-KRAB, DNMT3A CD, DNMT3L Interaction (ELXR #5.A) | 59455 | 59460 |

clearly resulted in a substantial increase in B2M repression across all the time points for all ELXR orientations containing the ZIM3-KRAB when using spacer 7.160 (FIG. 39A), and similar findings were observed when using spacers 7.165 and 7.37 (data not shown). FIG. 39B shows the resulting B2M repression upon use of ELXR #5 containing either the ZNF10 or ZIM3-KRAB when paired with a gRNA with spacer 7.160; the data demonstrate that including the ADD domain increased durable B2M repression overall, with ELXR5-ZIM3+ADD having a higher activity compared with that of ELXR5-ZNF10+ADD. Similar time course findings were observed for ELXR #1 and ELXR #4 and the other two spacers (data not shown). FIG. 39C shows the resulting B2M repression upon use of ELXR #5 containing the ZIM3-KRAB when paired with any of the three B2M-targeting gRNAs, and the data demonstrate that inclusion of the ADD domain resulted in higher B2M repression overall. Similar time course findings were also observed for ELXR #1 and ELXR #4 (data not shown).

Figure 40A:
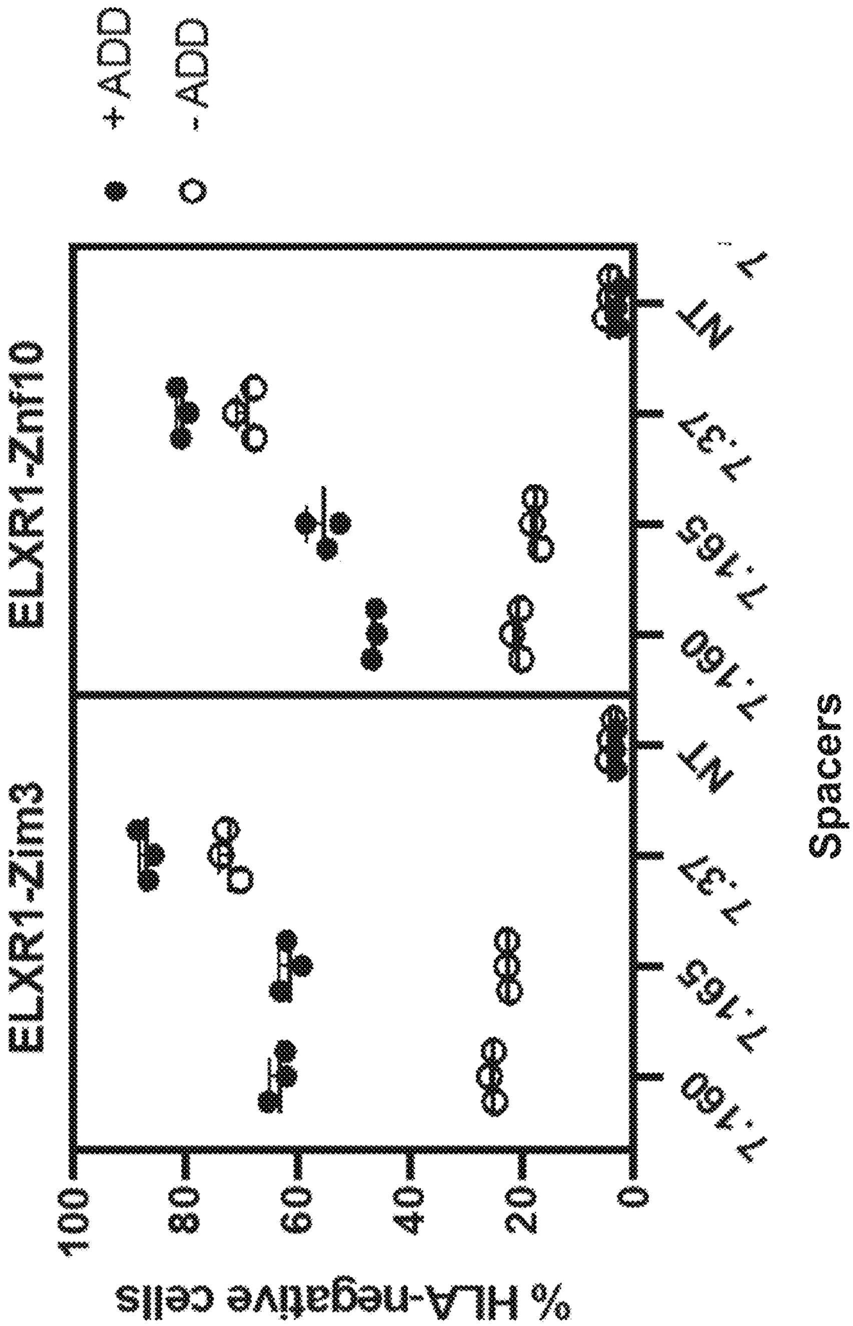
FIG. 40A is a plot illustrating the results of B2M repression activities on day 27 post-transfection for ELXRs with either the ZNF10 or ZIM3-KRAB domain having configuration #1 with or without the DNMT3A ADD domain for the indicated gRNAs, as described in Example 13. Data are presented as mean with standard deviation, N=3. "NT" is a gRNA with a non-targeting spacer.
Figure 40B:
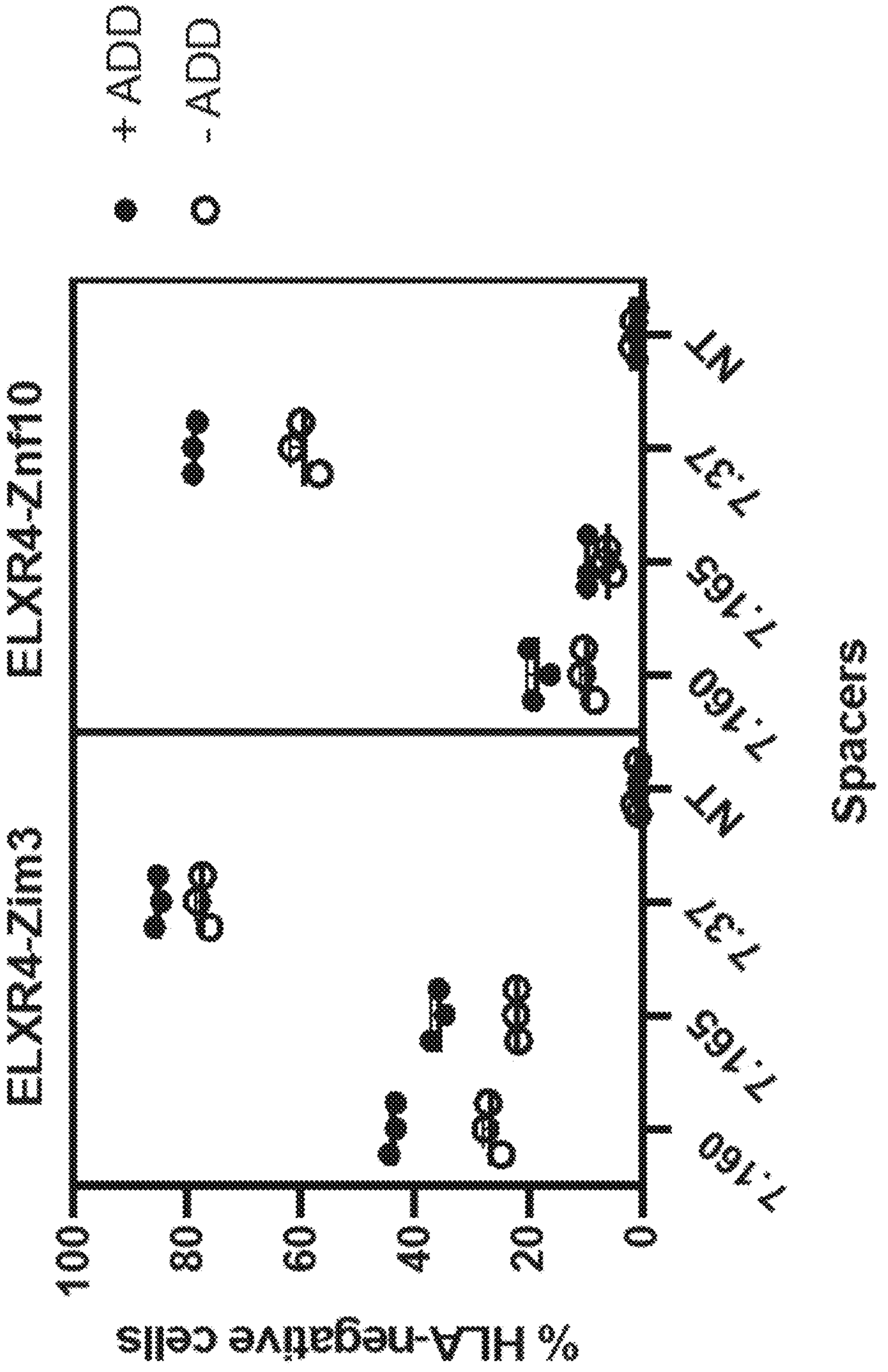
FIG. 40B is a plot illustrating the results of B2M repression activities on day 27 post-transfection for ELXRs with either the ZNF10 or ZIM3-KRAB domain having configuration #4 with or without the DNMT3A ADD domain for the indicated gRNAs, as described in Example 13. Data are presented as mean with standard deviation, N=3. "NT" is a gRNA with a non-targeting spacer.
Figure 40C:
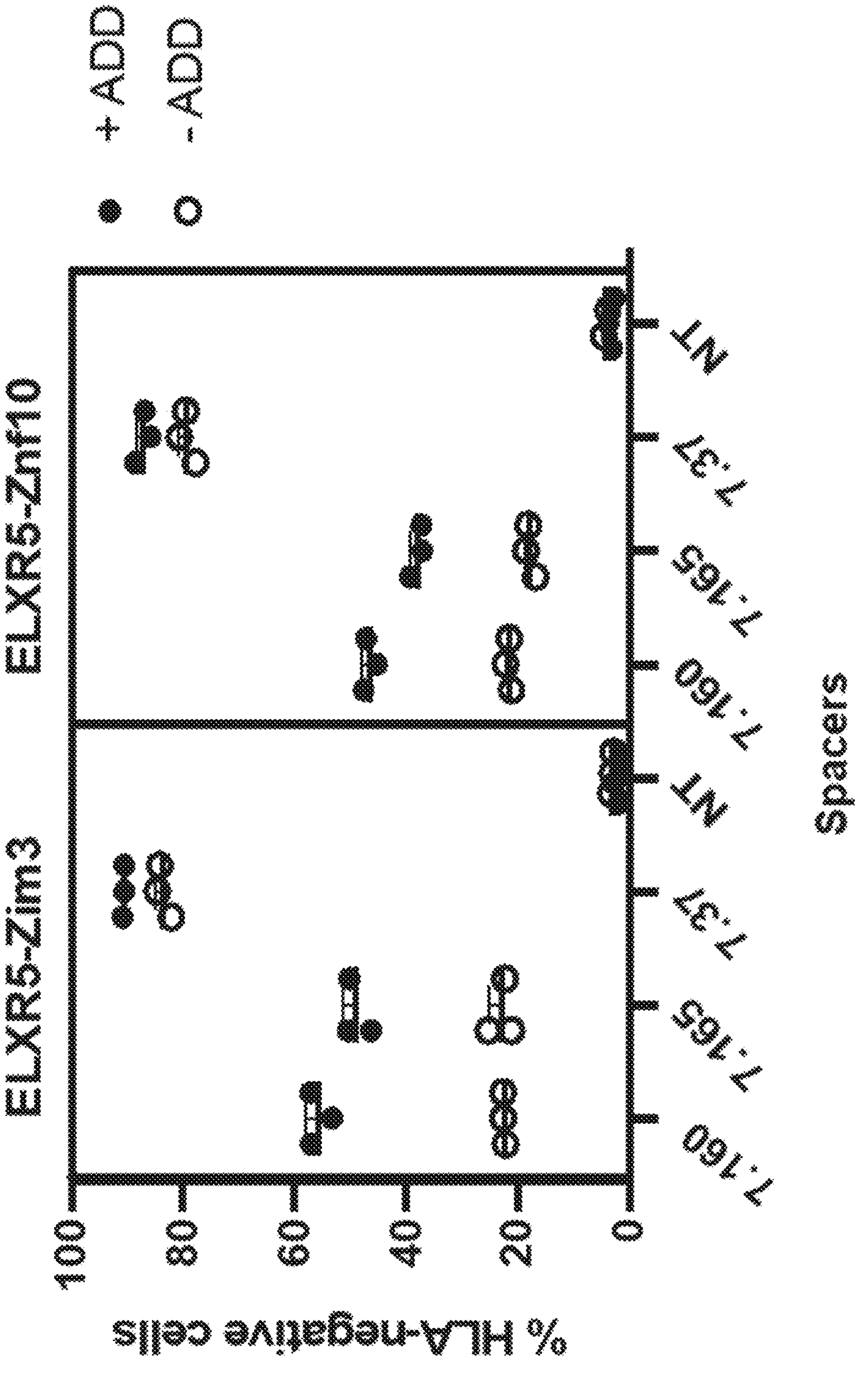
FIG. 40C is a plot illustrating the results of B2M repression activities on day 27 post-transfection for ELXRs with either the ZNF10 or ZIM3-KRAB domain having configuration #5 with or without the DNMT3A ADD domain for the indicated gRNAs, as described in Example 13. Data are presented as mean with standard deviation, N=3. "NT" is a gRNA with a non-targeting spacer.

FIGS. 40A-40C shows the resulting B2M repression at the day 27 time point for all the ELXR configurations and gRNAs tested. The results show that the increase in B2M repression activity is more prominent with use of the sub-optimal spacers 7.160 and 7.165 compared to use of spacer 7.37. Furthermore, use of ELXR #1 and ELXR #5, which contained the DNMT3A and DNMT3L domains on the N-terminus of the molecule, resulted in the highest increase in B2M repression upon addition of the DNMT3A ADD domain (FIGS. 40A-40C). Use of ELXR #4, which harbored the DNMT3A/3L domains 3' to the KRAB domain and 5' to the dCasX, resulted in lower activity gains, which may be attributable to a decreased ability of the ADD domain to interact with chromatin properly.

Figure 41A:
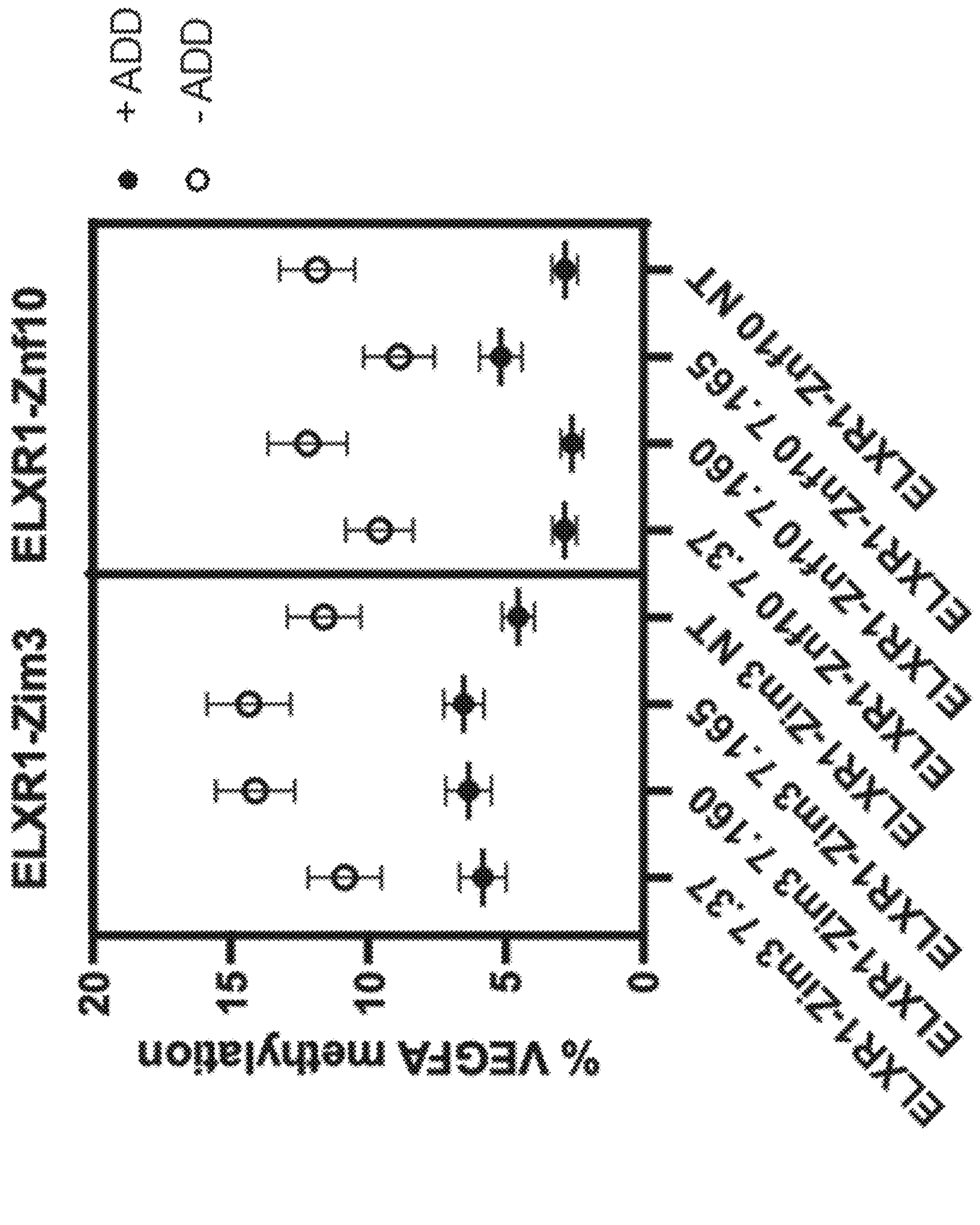
FIG. 41A is a plot illustrating the results of bisulfite sequencing used to determine off-target methylation at the VEGFA locus on day 5 post-transfection for ELXRs with either the ZNF10 or ZIM3-KRAB domain having configuration #1 with or without the DNMT3A ADD domain for the indicated gRNAs, as described in Example 13. Data are presented as mean percentage of CpG methylation for CpG sites near the VEGFA locus; standard error of the mean is also presented; N=3. "NT" is a gRNA with a non-targeting spacer.
Figure 41B:
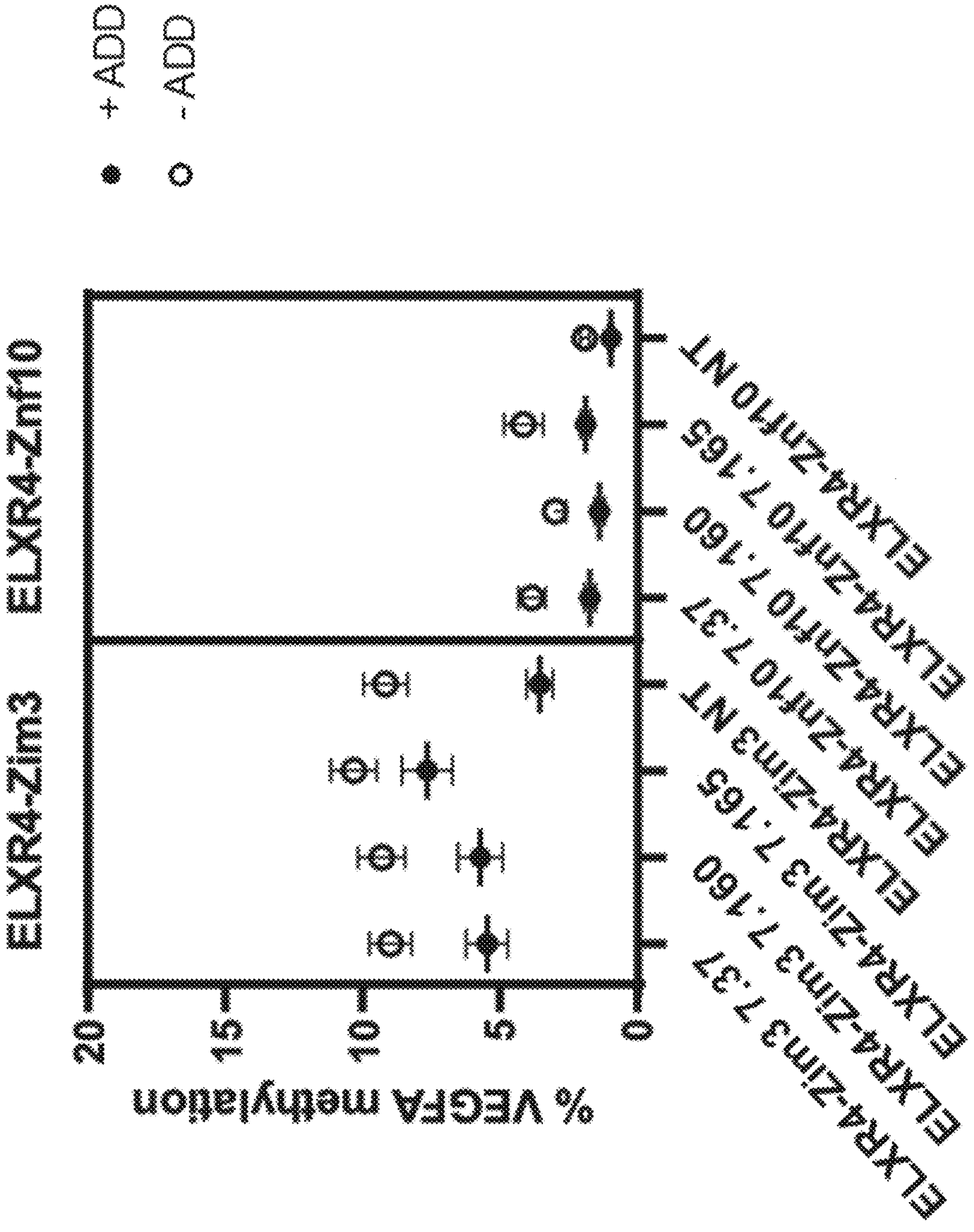
FIG. 41B is a plot illustrating the results of bisulfite sequencing used to determine off-target methylation at the VEGFA locus on day 5 post-transfection for ELXRs with either the ZNF10 or ZIM3-KRAB domain having configuration #4 with or without the DNMT3A ADD domain for the indicated gRNAs, as described in Example 13. Data are presented as mean percentage of CpG methylation for CpG sites near the VEGFA locus; standard error of the mean is also presented; N=3. "NT" is a gRNA with a non-targeting spacer.
Figure 41C:
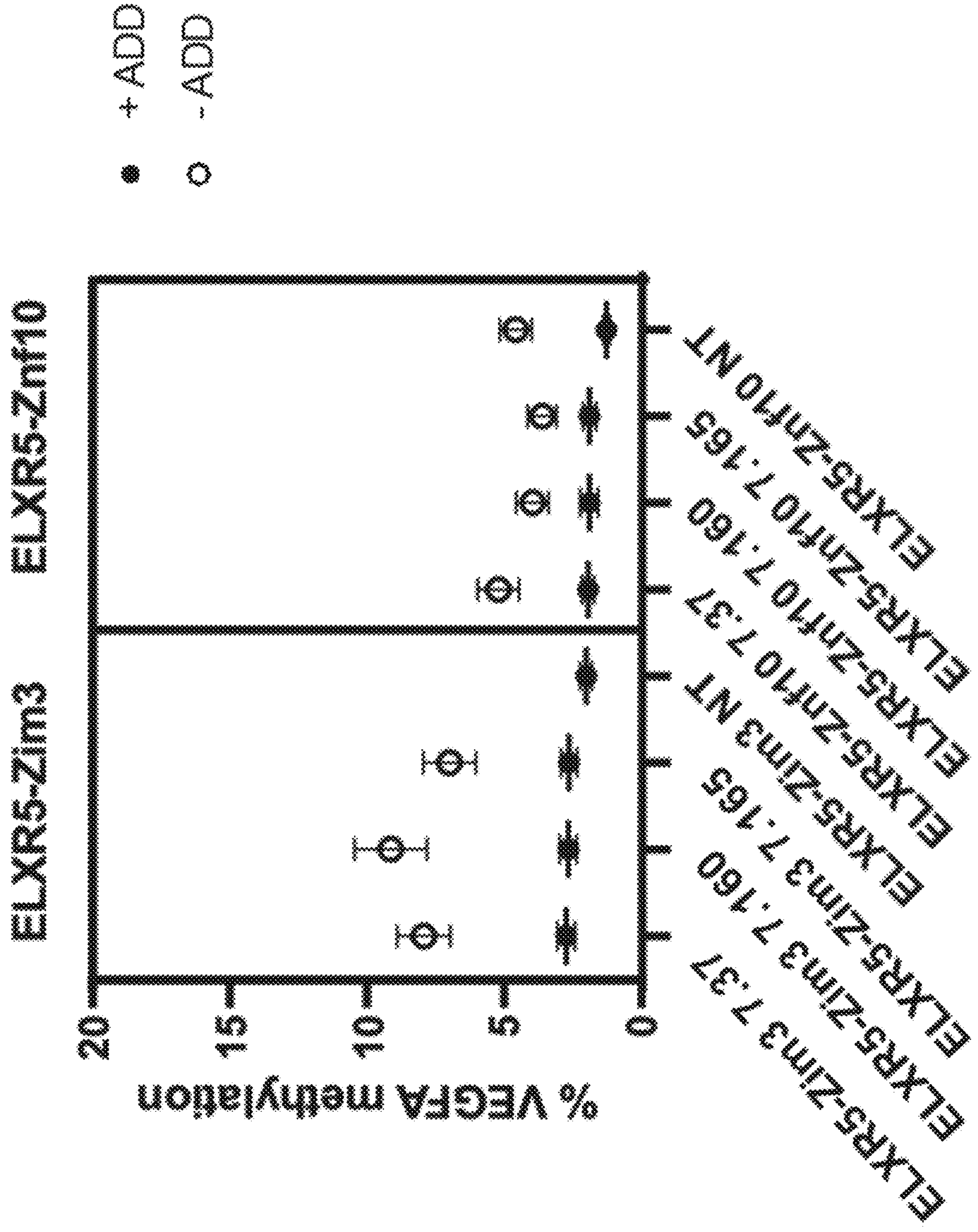
FIG. 41C is a plot illustrating the results of bisulfite sequencing used to determine off-target methylation at the VEGFA locus on day 5 post-transfection for ELXRs with either the ZNF10 or ZIM3-KRAB domain having configuration #5 with or without the DNMT3A ADD domain for the indicated gRNAs, as described in Example 13. Data are presented as mean percentage of CpG methylation for CpG sites near the VEGFA locus; standard error of the mean is also presented; N=3. "NT" is a gRNA with a non-targeting spacer.
Figure 42A:
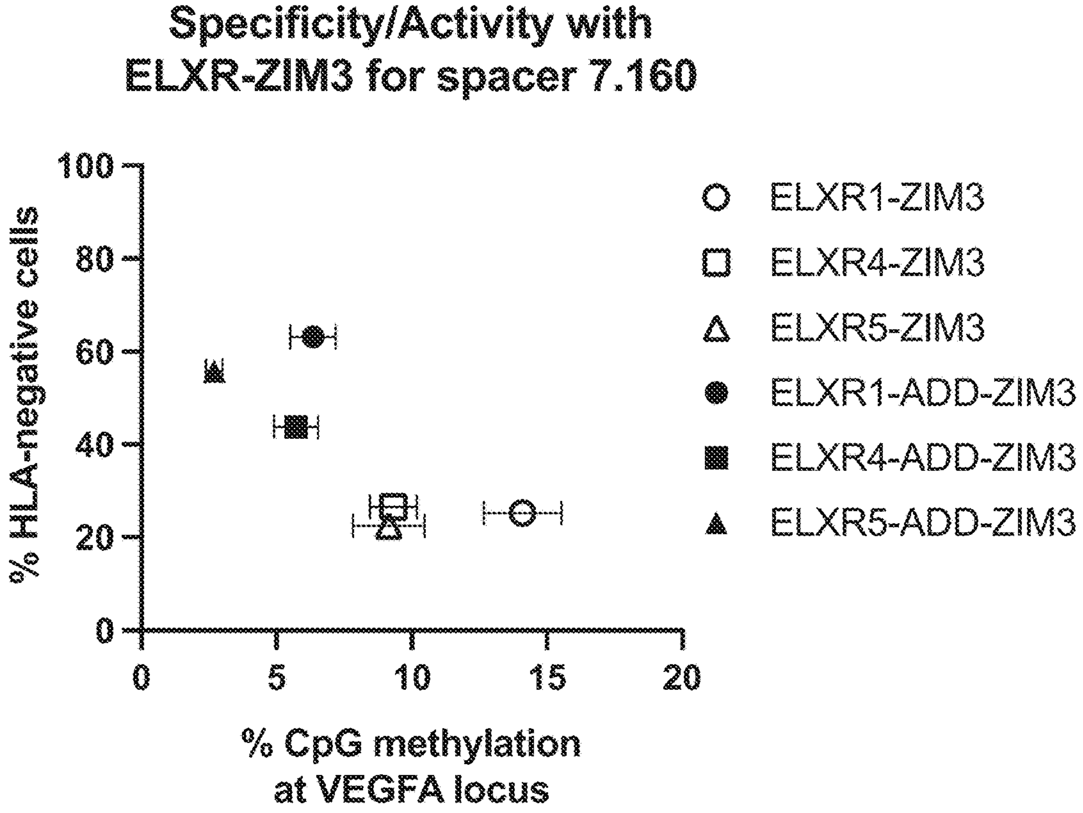
FIG. 42A is a dot plot showing the relative activity (average percentage of HLA-negative cells at day 27) versus specificity (percentage of off-target CpG methylation at the VEGFA locus quantified at day 5) for the ELXR molecules with the ZIM3-KRAB domain having configurations #1, #4, and #5, for B2M-targeting gRNA with spacer 7.160, as described in Example 13.
Figure 42B:
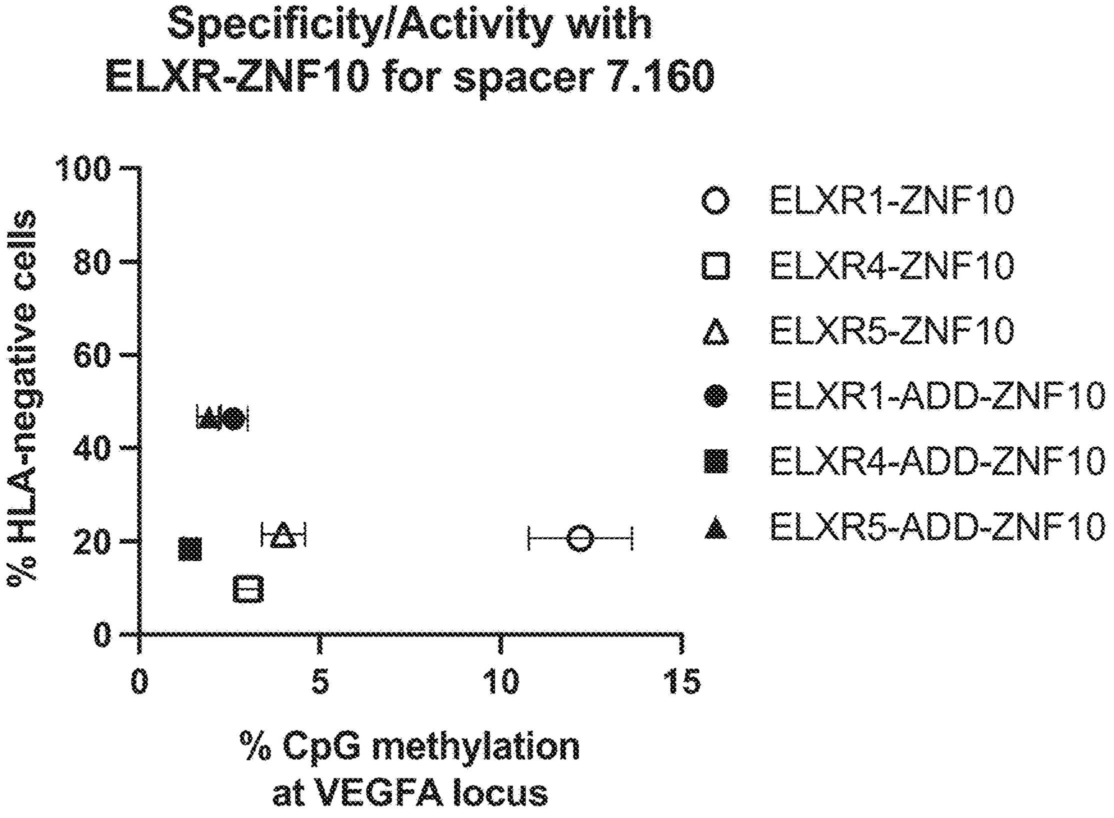
FIG. 42B is a dot plot showing the relative activity (average percentage of HLA-negative cells at day 27) versus specificity (percentage of off-target CpG methylation at the VEGFA locus quantified at day 5) for the ELXR molecules with the ZNF10-KRAB domain having configurations #1, #4, and #5, for B2M-targeting gRNA with spacer 7.160, as described in Example 13.
Figure 43A:
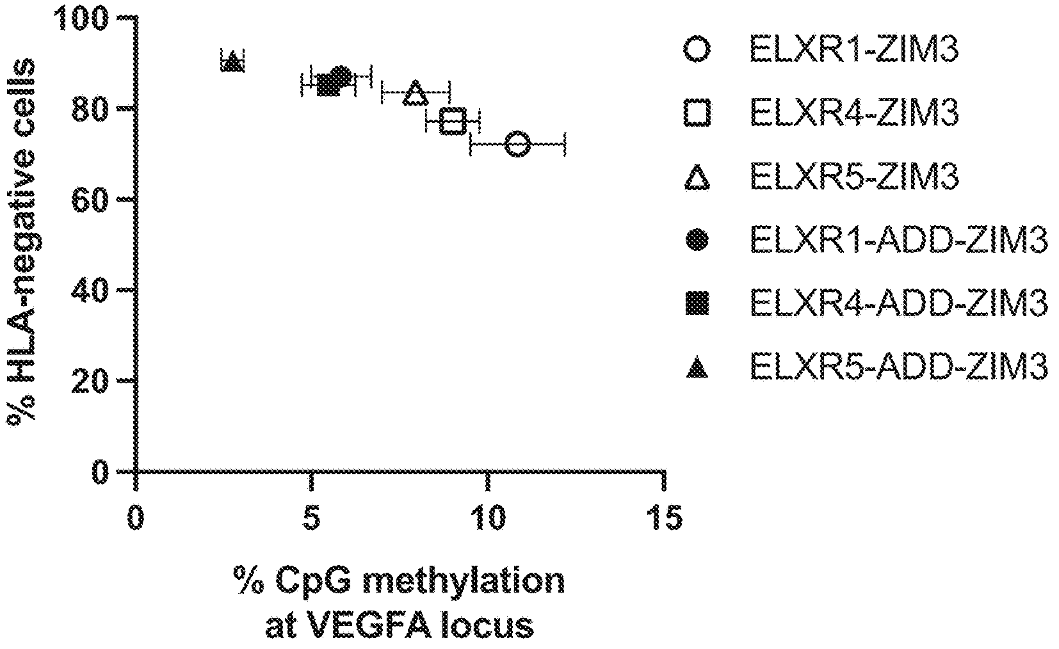
FIG. 43A is a dot plot showing the relative activity (average percentage of HLA-negative cells at day 27) versus specificity (percentage of off-target CpG methylation at the VEGFA locus quantified at day 5) for the ELXR molecules with the ZIM3-KRAB domain having configurations #1, #4, and #5, for B2M-targeting gRNA with spacer 7.37, as described in Example 13.
Figure 43B:
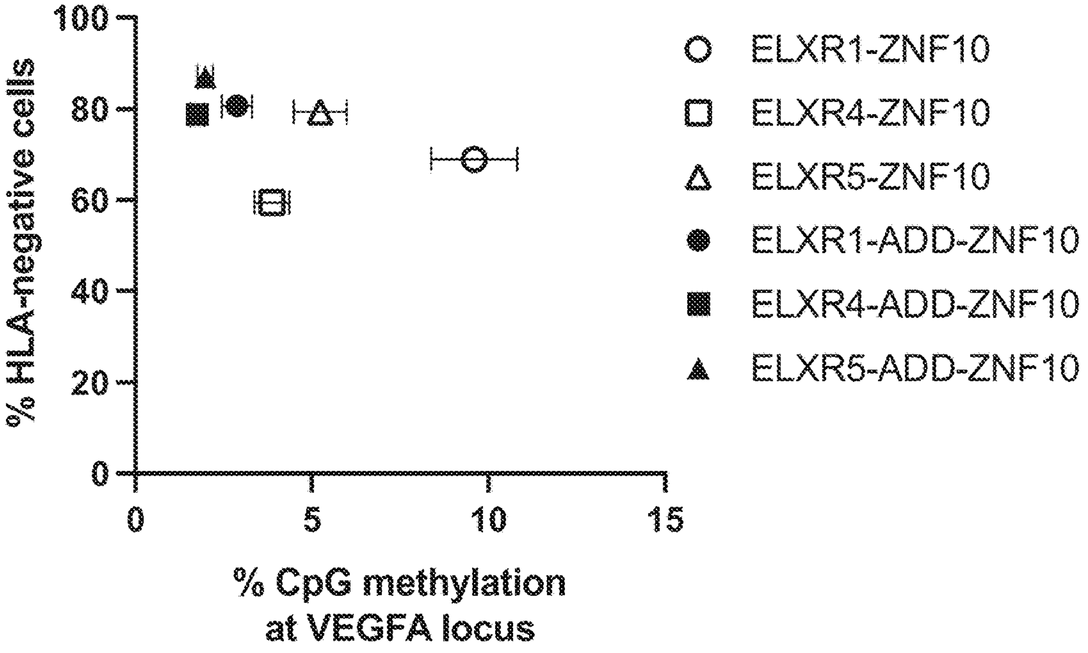
FIG. 43B is a dot plot showing the relative activity (average percentage of HLA-negative cells at day 27) versus specificity (percentage of off-target CpG methylation at the VEGFA locus quantified at day 5) for the ELXR molecules with the ZNF10-KRAB domain having configurations #1, #4, and #5, for B2M-targeting gRNA with spacer 7.37, as described in Example 13.
Figure 44A:
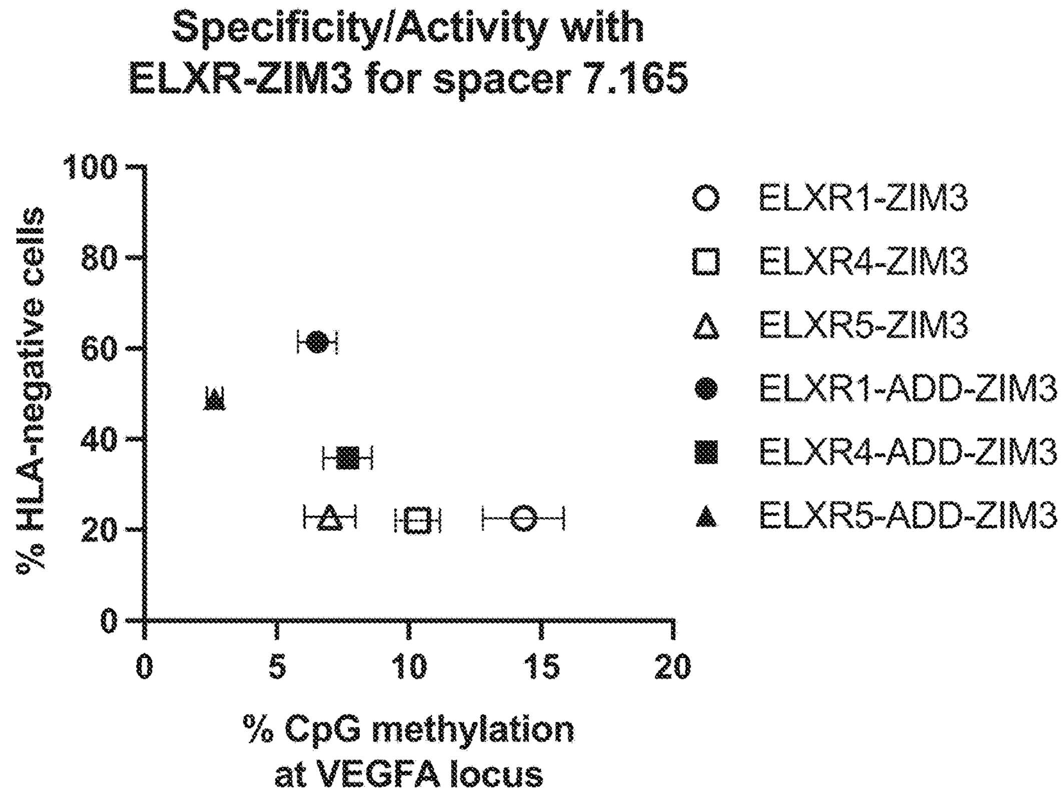
FIG. 44A is a dot plot showing the relative activity (average percentage of HLA-negative cells at day 27) versus specificity (percentage of off-target CpG methylation at the VEGFA locus quantified at day 5) for the ELXR molecules with the ZIM3-KRAB domain having configurations #1, #4, and #5, for B2M-targeting gRNA with spacer 7.165, as described in Example 13.
Figure 44B:
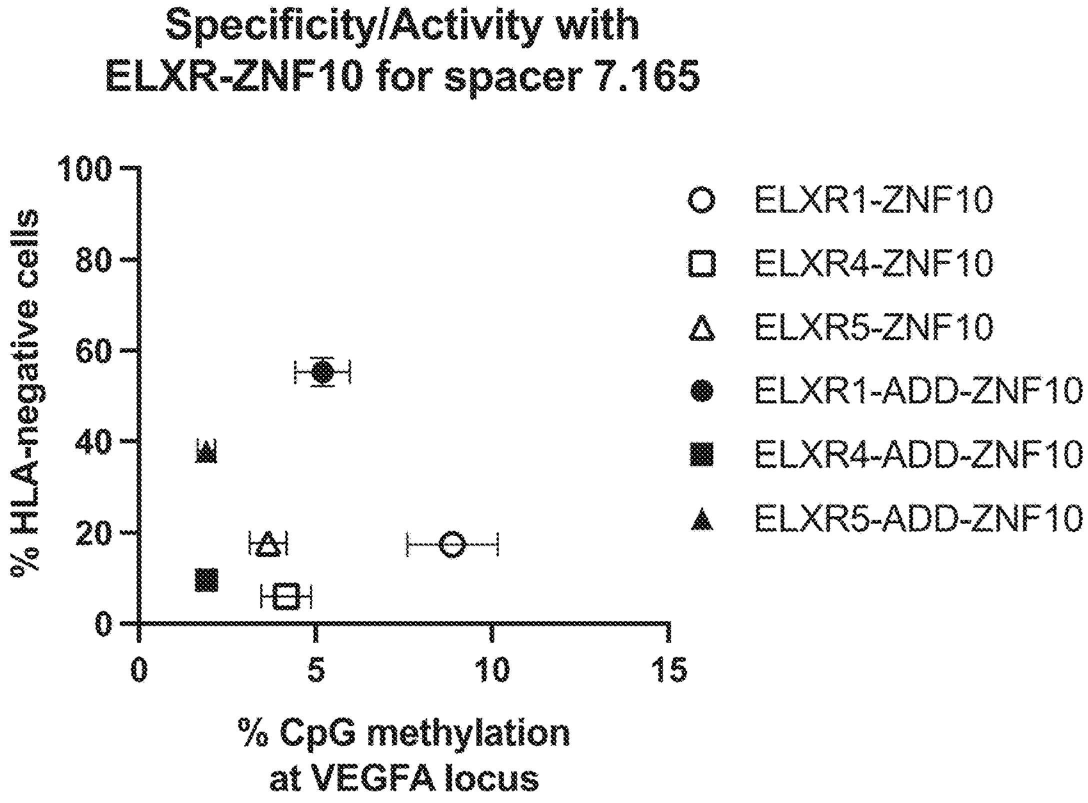
FIG. 44B is a dot plot showing the relative activity (average percentage of HLA-negative cells at day 27) versus specificity (percentage of off-target CpG methylation at the VEGFA locus quantified at day 5) for the ELXR molecules with the ZNF10-KRAB domain having configurations #1, #4, and #5, for B2M-targeting gRNA with spacer 7.165, as described in Example 13.

The specificity of ELXR molecules was determined by profiling the level of CpG methylation at the VEGFA gene, an off-target locus, using bisulfite sequencing, and the data are illustrated in FIGS. 41A-44B. The data demonstrate that inclusion of the DNMT3A ADD domain resulted in a substantial decrease in off-target methylation of the VEGFA locus across all conditions tested (FIGS. 41A-41C). Notably, the increased specificity mediated by the inclusion of the ADD domain was most prominent with the ELXR #1 and ELXR #5 configurations, both of which harbored the DNMT3A/3L domains on the N-terminal end of the molecule. Interestingly, ELXR molecules containing the ZIM3-KRAB domain led to stronger off-target methylation of the VEGFA locus. Furthermore, use of ELXR #4 and #5 configurations, even in the absence of an ADD domain, resulted in higher specificity compared to use of the ELXR #1 configuration. Compared to ELXR1-ZIM3 and ELXR4-ZIM3 configurations, inclusion of the ADD domain into ELXR5-ZIM3 resulted in the lowest off-target methylation.

FIGS. 42A-44B are a series of scatterplots mapping the activity-specificity profiles for the various ELXR molecules, where activity was measured as the average percentage of HLA-negative cells at day 27, and specificity was determined by the percentage of off-target CpG methylation at the VEGFA locus at day 5. The data demonstrate that across all three B2M-targeting spacers tested, inclusion of the ADD domain resulted in increased on-target B2M repression and decreased off-target methylation at the VEGFA locus. ELXR molecules having #1 and #5 configurations exhibited the greatest increases in activity and specificity at each spacer tested.

The results of the experiments discussed in this example support the findings in Example 11, in that the data demonstrate that inclusion of the DNMT3A ADD domain enhances both the strength of repression at early timepoints and the heritability of silencing across cell divisions, as well as decreases the off-target methylation incurred by the DNMT3A catalytic domain in the ELXR molecules. The data also confirm that different ELXR orientations have intrinsic differences in specificity, which can be exacerbated by use of a more potent KRAB domain. This decrease in specificity can be mitigated by inclusion of the DNMT3A ADD domain, which also can lead to greater on-target repression overall. The gains in repression activity are believed to be mediated by the function of the DNMT3A ADD domain to recognize H3K4me0 and subsequent recruitment to chromatin. The gains in specificity are believed to be mediated via the function of the DNMT3A ADD domain to induce allosteric inhibition of the catalytic domain of DNMT3A in the absence of binding to H3K4me0. The results also highlight that positioning of the ADD domain in the different configurations tested is important to achieve the strongest gains in both specificity and activity of ELXR molecules.

Example 14: Demonstration that Use of ELXRs can Induce Silencing of an Endogenous Locus in Mouse Hepa 1-6 Cells Experiments were performed to demonstrate the ability of ELXRs to induce durable repression of an alternative endogenous locus in mouse Hepa 1-6 liver cells, when delivered as mRNA co-transfected with a targeting gRNA.

Materials and Methods

Experiment #1: dXR1 vs. ELXR #1 in Hepa1-6 cells when delivered as mRNA Generation of dXR1 and ELXR #1 mRNA:

mRNA encoding dXR1 or ELXR #1 containing the ZIM3-KRAB domain was generated by in vitro transcription (IVT). Briefly, constructs encoding for a 5'UTR region, dXR1 or ELXR #1 harboring the ZIM3-KRAB domain with flanking SV40 NLSes, and a 3'UTR region were generated and cloned into a plasmid containing a T7 promoter and 80-nucleotide poly(A) tail. These constructs also contained a 2× FLAG sequence. Sequences encoding the dXR1 and ELXR #1 molecules were codon-optimized using a codon utilization table based on ribosomal protein codon usage, in addition to using a variety of publicly available codon optimization tools and adjusting parameters such as GC content as needed. The resulting plasmid was linearized prior to use for IVT reactions, which were carried out with CleanCap® AG and N1-methyl-pseudouridine. IVT reactions were then subjected to DNase digestion and oligodT purification on-column. For experiment #1, the DNA sequences encoding the dXR1 and ELXR #1 molecules are listed in Table 36. The corresponding mRNA sequences encoding the dXR1 and ELXR #1 mRNAs are listed in Table 37. The protein sequences of the dXR1 and ELXR #1 are shown in Table 38.

TABLE 36

Encoding sequences of the dXR1 and ELXR #1 containing the ZIM3-KRAB domain mRNA molecules assessed in experiment #1 of this example*.

| XR or ELXR ID | Component | DNA SEQ ID NO |
| --- | --- | --- |
| dXR1 (codon-optimized) | 5'UTR | 59568 |
| | START codon + NLS + linker | 59569 |
| | dCasX491 | 59570 |
| | Linker + buffer sequence | 59571 |
| | ZIM3-KRAB | 59572 |
| | Buffer sequence + NLS | 59573 |
| | Tag | 59574 |
| | STOP codon + buffer sequence | 59575 |
| | 3'UTR | 59576 |
| | Buffer sequence | 59577 |
| | Poly(A) tail | 59578 |
| ELXR #1 (codon-optimized) | 5'UTR | 59568 |
| | START codon + NLS + buffer sequence + linker | 59579 |

TABLE 36-continued

Encoding sequences of the dXR1 and ELXR #1 containing the ZIM3-KRAB domain mRNA molecules assessed in experiment #1 of this example*.

| XR or ELXR ID | Component | DNA SEQ ID NO |
| --- | --- | --- |
| | START codon + DNMT3A catalytic domain | 59580 |
| | Linker | 59581 |
| | DNMT3L interaction domain | 59582 |
| | Linker | 59583 |
| | dCasX491 | 59570 |
| | Linker | 59571 |
| | ZIM3-KRAB | 59572 |
| | Buffer sequence + NLS | 59573 |
| | Tag | 59574 |
| | STOP codons + buffer sequence | 59575 |
| | 3'UTR | 59576 |
| | Buffer sequence | 59577 |
| | Poly(A) tail | 59578 |

*Components are listed in a 5' to 3' order within the constructs

TABLE 37

Full-length RNA sequences of dXR1 and ELXR #1 containing the ZIM3-KRAB domain mRNA molecules assessed in experiment #1 of this example. Modification 'mψ' = N1-methyl-pseudouridine.

| XR or ELXR ID | RNA sequence | SEQ ID NO |
| --- | --- | --- |
| dXR1 | AAAmψAAGAGAGAAAAGAAGAGmWAAGAAGAAAmψAmψAAGAGCCACCAmψGGCC<br>CCmψAAGAAGAAGCGmψAAAGmψGAGCCGGGGCGGCAGCGGCGGCGGCAGCGCCC<br>AGGAGAmψmψAAACGGAmψCAACAAGAmψCAGAAGAAGACmψmψGmψGAAAGACA<br>GCAACACCAAGAAGGCCGGCAAGACAGGCCCCAmψGAAAACCCmψGCmψGGmψmψ<br>AGAGmψGAmψGACACCCGAmψCmψGAGAGAGCGGCmψGGAAAACCmψGAGAAAGA<br>AGCCmψGAAAAmψAmψCCCCCAGCCCAmψCAGCAAmψACAmψCmψAGAGCCAACC<br>mψGAAmψAAGCmψGCmψGACCGAmψmψACACCGAAAmψGAAGAAGGCGAmψCCmψ<br>GCAmψGmψGmψACmψGGGAAGAGmψmψCCAGAAGGACCCmψGmψGGGCCmψGAmψ<br>GAGCCGGGmψGGCCCAGCCmψGCCAGCAAGAAGAmψCGAmψCAGAACAAGCmψGA<br>AACCmψGAGAmψGGACGAGAAGGGCAACCmψGACCACCGCCGGCmψmψmψGCCmψ<br>GCmψCmψCAGmψGmψGGCCAGCCCCmψGmψmψCGmψGmψACAAGCmψGGAGCAGG<br>mψGmψCmψGAGAAGGGCAAGGCmψmψACACCAACmψACmψmψCGGACGGmψGCAA<br>mψGmψGGCCGAGCACGAAAAGCmψGAmψCCmψGCmψGGCCCAGCmψGAAGCCCGA<br>GAAGGAmψAGCGACGAAGCCGmψGACAmψAmψAGCCmψGGGAAAGmψmψmψGGGC<br>AGAGGGCCCmψGGAmψmψmψCmψACAGCAmψmψCAmψGmψGACCAAGGAGmψCCA<br>CCCACCCCGmψGAAGCCCCmψGGCCCAGAmψCGCCGGAAACAGAmψACGCCmψCC<br>GGACCmψGmψGGGAAAGGCCCmψGAGCGACGCAmψGmψAmψGGGCACAAmψCGCC<br>mψCCmψmψCCmψGmψCmψAAGmψACCAGGACAmψCAmψCAmψCGAACACCAGAAG<br>GmψGGmψGAAGGGCAACCAGAAGAGACmψGGAGAGCCmψGCGGGAGCmψGGCCGG<br>CAAGGAAAACCmψGGAAmψACCCmψAGCGmψGACCCmψGCCACCmψCAGCCmψCA<br>CACCAAGGAGGGCGmψmψGAmψGCCmψACAACGAAGmψGAmψCGCCCGGGmψGCG<br>AAmψGmψGGGmψGAACCmψGAACCmψGmψGGCAGAAGCmψGAAGCmψAAGCAGAG<br>AmψGAmψGCCAAGCCmψCmψGCmψGAGACmψGAAGGGAmψmψCCCmψmψCCmψmψ<br>mψCCmψCmψGGmψCGAGAGACAGGCCAACGAAGmψGGACmψGGmψGGGACAmψGG<br>mψGmψGmψAACGmψGAAGAAGCmψGAmψCAACGAGAAAAAGGAGGAmψGGCAAGG<br>mψGmψmψmψmψGGCAGAAmψCmψGGCmψGGCmψACAAGAGACAGGAAGCCCmψGA<br>GACCAmψACCmψGAGCAGCGAGGAAGAmψCGGAAGAAGGGAAAGAAAmψmψCGCm<br>ψCGGmψACCAGCmψGGGCGACCmψGCmψGCmψGCACCmψGGAAAAGAAGCACGGC<br>GAGGACmψGGGGAAAGGmψGmψACGACGAGGCCmψGGGAGCGGAmψmψGACAAGA<br>AAGmψGGAAGGCCmψGAGCAAGCACAmψCAAGCmψGGAAGAGGAACGGAGAAGCG<br>AGGACGCCCAGAGCAAGGCCGCCCmψGACCGACmψGGCmψGCGGGCmψAAGGCCA<br>GCmψmψCGmψGAmψCGAGGGCCmψGAAGGAGGCCGACAAGGACGAGmψmψCmψGC<br>AGAmψGCGAGCmψGAAGCmψGCAGAAGmψGGmψACGGGGACCmψGCGGGGAAAGC<br>CCmψmψCGCCAmψCGAAGCCGAGAACAGCAmψCCmψGGACAmψCAGCGGCmψmψC<br>AGCAAGCAGmψACAACmψGmψGCCmψmψCAmψCmψGGCAGAAGGACGGCGmψGAA<br>GAAGCmψGAACCmψGmψACCmψGAmψCAmψCAACmψACmψmψCAAGGGCGGCAAG<br>CmψGCGGmψmψCAAGAAGAmψCAAACCmψGAAGCCmψmψCGAAGCCAACAGAmψm<br>ψCmψACACCGmψGAmψCAACAAAAAGAGCGGCGAGAmψCGmψGCCCAmψGGAGGm<br>ψGAACmψmψCAACmψmψCGACGACCCCAACCmψGAmψCAmψCCmψGCCmψCmψGG<br>CCmψmψmψGGCAAGAGACAGGGCAGAGAAmψmψCAmψCmψGGAACGACCmψGCmψ<br>GmψCCCmψGGAAACCGGCAGCCmψGAAGCmψGGCCAACGGAAGAGmψGAmψCGAG<br>AAGACACmψGmψACAACAGAAGAACCCGGCAGGAmψGAGCCmψGCCCmψGmψmψC<br>GmψGGCCCmψGACCmψmψCGAGCGGCGGGAGGmψCCmψGGACmψCCmψCCAAmψA<br>mψCAAACCAAmψGAACCmψGAmψCGGCGmψGGCAAGAGGCGAAAACAmψCCCCGC<br>CGmψGAmψCGCCCmψGACCGACCCCGAGGGCmψGCCCACmψGAGCCGGmψmψmψA | 59584 |

TABLE 37-continued

Full-length RNA sequences of dXR1 and ELXR #1 containing the ZIM3-KRAB domain mRNA molecules assessed in experiment #1 of this example. Modification 'mψ' = N1-methyl-pseudouridine.

| XR or ELXR ID | RNA sequence | SEQ ID NO |
|---|---|---|
| | AGGAmψAGCCmψGGGAAACCCAACCCACAmψCCmψGAGAAmψCGGCGAGAGCmψA<br>mψAAGGAGAAGCAGCGGACCAmψCCAGGCCAAGAAGGAGGmψGGAGCAGCGGAGA<br>GCCGGCGGCmψACAGCCGGAAGmψACGCCAGCAAAGCCAAGAAmψCmUGGCAGAC<br>GAmψAmψGGmψGAGAAACACCGCmψAGAGAmψCmψGCmψGmψACmψACGCCGmψG<br>ACCCAGGAmψGCCAmψGCmψGAmψCmψmψCGCCAACCmψGAGCCGGGGCmψmψCG<br>GCCGGCAGGGCAAGCGGACCmψmψCAmψGGCCGAGAGACAGmψACACACGGAmψG<br>GAGGACmψGGCmψGACCGCCAAGCmψGGCCmψACGAGGGCCmψGAGCAAGACCmψ<br>ACCmψGmψCCAAGACACmψGGCCCAGmψACACCmψCCAAGACAmψGCAGCAACmψ<br>GmψGGGmψmψmψACCAmψCACCAGCGCCGACmψACGACAGGGmψGCmψGGAGAAG<br>CmψGAAGAAGACAGCAACAGGCmψGGAmψGACCACAAmψmψAACGGCAAGGAGCm<br>ψGAAGGmψGGAGGGCCAGAmψmψACCmψACmψACAACAGAmψACAAGAGACAGAA<br>CGmψAGmψCAAGGACCmψGmψCCGmψCGAGCmψGGAmψAGACmψGAGCGAAGAAm<br>ψCmψGmψGAACAACGACAmψCmψCCmψCCmψGGACAAAGGGCAGAAGCGGAGAAG<br>CmψCmψGAGCCmψCCmψGAAGAAAAGAmψmψCmψCCCAmψAGACCCGmψGCAGGA<br>GAAGmψmψCGmψGmψGCCmψGAACmψGCGGCmψmψCGAGACACACGCAGCCGAGC<br>AAGCCGCCCmψGAACAmψCGCCAGAmψCCmψGGCmψGmψmψCCmψGCGGAGCCAG<br>GAGmψACAAGAAAmψACCAGACAAACAAGACAACCGGCAACACCGAmψAAGAGAG<br>CCmψmψCGmψCGAGACCmψGGCAGmψCCmψmψmψmψACCGGAAGAAGCmψmψAAG<br>GAGGmψGmψGGAAACCmψGCCGmψGCGGmψCmψGGCGGAmψCmψGGCGGAGGCmψ<br>CCACAAGCAmψGAACAACmψCCCAGGGCAGAGmψGACCmψmψCGAGGACGmψGAC<br>CGmψGAAmψmψmψmψACACAGGGAGAGmψGGCAGAGACmψGAACCCCGAGCAGAG<br>AAACCmψGmψACCGGGAmψGmψGAmψGCmψGGAAAACmψACAGCAAmψCmψGGmψ<br>GmψCCGmψGGGCCAGGGCGAGACCACAAAGCCmψGACGmψGAmψCCmψGCGmψCm<br>ψGGAGCAGGGCAAGGAACCCmψGGCmψGGAGGAGGAGGAGGmψGCmψGGGAAGCG<br>GACGGGCCGAGAAGAACGGCGACAmψCGGCGGACAGAmψCmψGGAAGCCmψAAGG<br>ACGmψGAAAGAAAGCCmψGACCAGCCCCAAGAAAAAGAGAAAAGmψCGACmψACA<br>AGGAmψGACGAmψGACAAGGACmψACAAGGAmψGACGACGACAAGmψAAmψAGAm<br>ψAAGCGGCCGCmψmψAAmψmψAAGCmψGCCmψmψCmψGCGGGGCmψmψGCCmψmψ<br>CmψGGCCAmψGCCCmψmψCmψmψCmψCmψCCCmψmψGCACCmψGmψACCmψCmψm<br>ψGGmψCmψmψmψGAAmψAAAGCCmψGAGmψAGGAAGmψcmψagaaaaaaaaaaaa<br>aaaaaaaaaaaaaaaaaaaaaaaaaaaaaaaaaaaaaaaaaaaaaaaaaaaaaaa<br>aaaaaaaaaaaaa | |
| ELXR #1 | AAAmψAAGAGAGAAAAGAAGAGmψAAGAAGAAAmψAmψAAGAGCCACCAmψGGCC<br>CCmψAAGAAGAAGCGmψAAAGmψGAGCCGGGmψGAACGGCAGCGGCAGCGGCGGC<br>GGCAmψGAACCACGACCAGGAGmψmψCGACCCCCCmψAAGGmψGmψACCCmψCCC<br>GmψCCCCGCCGAGAAGAGAAAGCCCAmψCCGGGmψCCmψGAGCCmψGmψmψCGAm<br>ψGGCAmψCGCCACCGGmψCmψGCmψGGmψGCmψGAAGGACCmψGGGCAmψCCAGG<br>mψGGAmψAGGmψACAmψmψGCCmψCCGAGGmψGmψGCGAGGACmψCCAmψCACCG<br>mψGGGAAmψGGmψGCGmψCAmψCAGGGCAAGAmψCAmψGmψACGmψGGGCGACGm<br>ψGCGGAGCGmψGACACAGAAGCAmψAmψCCAGGAGmψGGGGCCmψmψmψCGACC<br>mψGGmψGAmψCGGCGGCAGCCCmψmψGCAAmψGACCmψGAGCAmψCGmψGAACCC<br>AGCCCGGAAGGGCCmψGmψACGAGGGAACCGGCAGACmψGmψmψCmψmψCGAGmψ<br>mψmψmψACAGACmψGCmψGCACGACGCCCGGCCmψAAGGAAGGCGACGACCGGCC<br>CmψmψCmψmψmψmψGGCmψGmψmψCGAGAAmψGmψGGmψGGCCAmψGGGAGmψCA<br>GCGACAAGCGGGAmψAmψmψAGCCGGmψmψCCmψGGAGAGCAACCCCGmψGAmψG<br>AmψCGAmψGCCAAGGAAGmψGAGCGCCGCCCACCGGGCCAGAmψACmψmψCmψGG<br>GGCAAmψCmψGCCmψGGCAmψGAACAGACCCCmψGGCCAGCACCGmψGAACGACA<br>AGCmψGGAGCmψGCAGGAGmψGCCmψGGAGCACGGCCGGAmψCGCCAAGmψmψCA<br>GCAAGGmψGAGAACCAmψCACCACCCGAAGCAACAGCAmψCAAACAAGGCAAGGA<br>CCAGCACmψmψmψCCmψGmψGmψmψCAmψGAACGAGAAGGAGGACAmψCCmψGmψ<br>GGmψGmψACCGAGAmψGGAGAGAGmψGmψmψCGGGmψmψCCCAGmψCCACmψACA<br>CAGAmψGmψCAGCAACAmψGmψCmψAGACmψGGCCAGACAGAGACmψGCmψGGGA<br>AGAAGCmψGGmψCCGmψCCCmψGmψGAmψCAGACACCmψGmψmψCGCCCCmψCmψ<br>GAAGGAGmψACmψmψCGCCmψGCGmψGAGCAGCGGCAACAGCAACGCCAACAGCC<br>GGGGCCCCAGCmψmψCmψCmψAGCGGCCmψGGmψGCCACmψGmψCCCmψGAGAGG<br>GAGCCACAmψGGGCCCCAmψGGAGAmψCmψACAAAACCGmψGAGCGCCmψGGAAG<br>CGGCAGCCmψGmψGCGCGmψGCmψGAGCCmψGmψmψmψCGGAAmψAmψCGAmψAA<br>AGmψCCmψGAAAAGCCmψGGGAmψmψCCmψGGAGAGCGGCmψCmψGGCmψCCGGC<br>GGmψGGCACCCmψGAAGmψACGmψGGAGGAmψGmψGACAAACGmψGGmψCAGACG<br>GGAmψGmψGGAGAAGmψGGGGCCCCmψmψCGAmψCmψGGmψGmψACGGCAGCACC<br>CAACCCCmψGGGCAGCmψCmψmψGmψGACCGGmψGCCCmψGGCmψGGmψACAmψG<br>mψmψmψCAGmψmψCCACCGGAmψCCmψGCAGmψACGCCCmψGCCGAGACAGGAGm<br>ψCCCAGCGGCCAmψmψCmψmψmψmψGGAmψmψmψmψCAmψGGACAACmψmψGCmψ<br>GCmψGACCGAGGAmψGACCAGGAAACmψACCACmψCGGmψmψCCmψGCAGACCGA<br>AGCCGmψGACCCmψGCAGGACGmψGAGAGGCCGGGACmψACCAGAACGCCAmψGC<br>GGGmψGmψGGmψCCAACAmψCCCmψGGACmψGAAAAGCAAGCACGCACCmψCmψG<br>ACCCCmψAAAGAAGAGGAGmψACCmψGCAGGCCCAGGmψGCGGAGCAGAAGCAAG<br>CmψGGACGCCCCmψAAGGmψGGAmψCmψGCmψGGmψGAAGAAmψmψGCCmψCCmψ<br>GCCCCmψGAGAGAGmψACmψmψCAAGmψAmψmψmψCAGCCAGAAmψAGmψCmψGC<br>CCCmψGGGCGGCCCAAGCAGCGGCGCCCCmψCCmψCCCAGCGGCGGCAGCCCAGC<br>CGGCmψCCCCAACCmψCmψACCGAGGAGGGCACCmψCmψGAGmψCCGCCACCCCC | 59585 |

TABLE 37-continued

Full-length RNA sequences of dXR1 and ELXR #1 containing the ZIM3-KRAB domain mRNA molecules assessed in experiment #1 of this example. Modification 'mψ' = N1-methyl-pseudouridine.

| XR or ELXR ID | RNA sequence | SEQ ID NO |
|---|---|---|
| | GAGAGCGGCCCmψGGCACCmψCCACCGAGCCCAGCGAGGGCAGCGCACCCGGCAG<br>CCCmψGCCGGCAGCCCCACCmψCCACAGAGGAGGGAACCAGCACCGAGCCCAGCG<br>AAGGCAGCGCCCCAGGCACCAGCACCGAGCCmψAGmψGAGGGCGGCmψCmψGGCG<br>GCGGCAGCGCCCAGGAGAmψmψAAACGGAmψCAACAAGAmψCAGAAGAAGACmψm<br>ψGmψGAAAGACAGCAACACCAAGAAGGCCGGCAAGACAGGCCCCAmψGAAAACCC<br>mψGCmψGGmψmψAGAGmψGAmψGACACCCGAmψCmψGAGAGAGCGGCmψGGAAAA<br>CCmψGAGAAAGAAGCCmψGAAAAmψAmψCCCCCAGCCCAmψCAGCAAmψACAmψC<br>mψAGAGCCAACCmψGAAmψAAGCmψGCmψGACCGAmψmψACACCGAAAmψGAAGA<br>AGGCGAmψCCmψGCAmψGmψGmψACmψGGGAAGAGmψmψCCAGAAGGACCCmψGm<br>ψGGGCCmψGAmψGAGCCGGGmψGGCCCAGCCmψGCCAGCAAGAAGAmψCGAmψCA<br>GAACAAGCmψGAAACCmψGAGAmψGGACGAGAAGGGCAACCmψGACCACCGCCGG<br>CmψmψmψGCCmψGCmψCmψCAGmψGmψGGCCAGCCCCmψGmψmψCGmψGmψACAA<br>GCmψGGAGCAGGmψGmψCmψGAGAAGGGCAAGGCmψmψACACCAACmψACmψmψC<br>GGACGGmψGCAAmψGmψGGCCGAGCACGAAAAGCmψGAmψCCmψGCmψGGCCCAG<br>CmψGAAGCCCGAGAAGGAmψAGCGACGAAGCCGmψGACAmψAmψAGCCmψGGGAA<br>AGmψmψmψGGGCAGAGGGCCCmψGGAmψmψmψCmψACAGCAmψmψCAmψGmψGAC<br>CAAGGAGmψCCACCCACCCCGmψGAAGCCCCmψGGCCCAGAmψCGCCGGAAACAG<br>AmψACGCCmψCCGGACCmψGmψGGGAAAGGCCCmψGAGCGACGCAmψGmψAmψGG<br>GCACAAmψCGCCmψCCmψmψCCmψGmψCmψAAGmψACCAGGACAmψCAmψCAmψC<br>GAACACCAGAAGGmψGGmψGAAGGGCAACCAGAAGAGACmψGGAGAGCCmψGCGG<br>GAGCmψGGCCGGCAAGGAAAACCmψGGAAmψACCCmψAGCGmψGACCCmψGCCAC<br>CmψCAGCCmψCACACCAAGGAGGGCGmψmψGAmψGCCmψACAACGAAGmψGAmψC<br>GCCCGGGmψGCGAAmψGmψGGGmψGAACCmψGAACCmψGmψGGCAGAAGCmψGAA<br>GCmψAAGCAGAGAmψGAmψGCCAAGCCmψCmψGCmψGAGACmψGAAGGGAmψmψC<br>CCmψmψCCmψmψmψCCmψCmψGGmψCGAGAGACAGGCCAACGAAGmψGGACmψGG<br>mψGGGACAmψGGmψGmψGmψAACGmψGAAGAAGCmψGAmψCAACGAGAAAAAGGA<br>GGAmψGGCAAGGmψGmψmψmψmψGGCAGAAmψCmψGGCmψGGCmψACAAGAGACA<br>GGAAGCCCmψGAGACCAmψACCmψGAGCAGCGAGGAAGAmψCGGAAGAAGGGAAA<br>GAAAmψmψCGCmψCGGmψACCAGCmψGGGCGACCmψGCmψGCmψGCACCmψGGAA<br>AAGAAGCACGGCGAGGACmψGGGGAAAGGmψGmψACGACGAGGCCmψGGGAGCGG<br>AmψmψGACAAGAAAGmψGGAAGGCCmψGAGCAAGCACAmψCAAGCmψGGAAGAGG<br>AACGGAGAAGCGAGGACGCCCAGAGCAAGGCCGCCCmψGACCGACmψGGCmψGCG<br>GGCmψAAGGCCAGCmψmψCGmψGAmψCGAGGGCCmψGAAGGAGGCCGACAAGGAC<br>GAGmψmψCmψGCAGAmψGCGAGCmψGAAGCmψGCAGAAGmψGGmψACGGGGACCm<br>ψGCGGGGAAAGCCCmψmψCGCCAmψCGAAGCCGAGAACAGCAmψCCmψGGACAmψ<br>CAGCGGCmψmψCAGCAAGCAGmψACAACmψGmψGCCmψmψCAmψCmψGGCAGAAG<br>GACGGCGmψGAAGAAGCmψGAACCmψGmψACCmψGAmψCAmψCAACmψACmψmψC<br>AAGGGCGGCAAGCmψGCGGmψmψCAAGAAGAmψCAAACCmψGAAGCCmψmψCGAA<br>GCCAACAGAmψmψCmψACACCGmψGAmψCAACAAAAAGAGCGGCGAGAmψCGmψG<br>CCCAmψGGAGGmψGAACmψmψCAACmψmψCGACGACCCCAACCmψGAmψCAmψCC<br>mψGCCmψCmψGGCCmψmψmψGGCAAGAGACAGGGCAGAGAAmψmvCAmψCmψGGA<br>ACGACCmψGCmψGmψCCCmψGGAAACCGGCAGCCmψGAAGCmψGGCCAACGGAAG<br>AGmψGAmψCGAGAAGACACmψGmψACAACAGAAGAACCCGGCAGGAmψGAGCCmψ<br>GCCCmψGmψmψCGmψGGCCCmψGACCmψmψCGAGCGGCGGGAGGmψCCmψGGACm<br>ψCCmψCCAAmψAmψCAAACCAAmψGAACCmψGAmψCGGCGmψGGCAAGAGGCGAA<br>AACAmψCCCCGCCGmψGAmψCGCCCmψGACCGACCCCGAGGGCmψGCCCACmψGA<br>GCCGGmψmψmψAAGGAmψAGCCmψGGGAAACCCAACCCACAmψCCmψGAGAAmψC<br>GGCGAGAGCmψAmψAAGGAGAAGCAGCGGACCAmψCCAGGCCAAGAAGGAGGmψG<br>GAGCAGCGGAGAGCCGGCGGCmψACAGCCGGAAGmψACGCCAGCAAAGCCAAGAA<br>mψCmψGGCAGACGAmψAmψGGmψGAGAAACACCGCmψAGAGAmψCmψGCmψGmψA<br>CmψACGCCGmψGACCCAGGAmψGCCAmψGCmψGAmψCmψmψCGCCAACCmψGAGC<br>CGGGGCmψmψCGGCCGGCAGGGCAAGCGGACCmψmψCAmψGGCCGAGAGACAGmψ<br>ACACACGGAmψGGAGGACmψGGCmψGACCGCCAAGCmψGGCCmψACGAGGGCCmψ<br>GAGCAAGACCmψACCmψGmψCCAAGACACmψGGCCCAGmψACACCmψCCAAGACA<br>mψGCAGCAACmψGmψGGGmψmψmψACCAmψCACCAGCGCCGACmψACGACAGGGm<br>ψGCmψGGAGAAGCmψGAAGAAGACAGCAACAGGCmψGGAmψGACCACAAmψmψAA<br>CGGCAAGGAGCmψGAAGGmψGGAGGGCCAGAmψmψACCmψACmψACAACAGAmψA<br>CAAGAGACAGAACGmψAGmψCAAGGACCmψGmψCCGmψCGAGCmψGGAmψAGACm<br>ψGAGCGAAGAAmψCmψGmψGAACAACGACAmψCmψCCmψCCmψGGACAAAGGGCA<br>GAAGCGGAGAAGCmψCmψGAGCCmψCCmψGAAGAAAAGAmψmψCmψCCCAmψAGA<br>CCCGmψGCAGGAGAAGmψmψCGmψGmψGCCmψGAACmψGCGGCmψmψCGAGACAC<br>ACGCAGCCGAGCAAGCCGCCCmψGAACAmψCGCCAGAmψCCmψGGCmψGmψmψCC<br>mψGCGGAGCCAGGAGmψACAAGAAAmψACCAGACAAACAAGACAACCGGCAACAC<br>CGAmψAAGAGAGCCmψmψCGmψCGAGACCmψGGCAGmψCCmψmψmψmψACCGGAA<br>GAAGCmψmψAAGGAGGmψGmψGGAAACCmψGCCGmψGCGGmψCmψGGCGGAmψCm<br>ψGGCGGAGGCmψCCACAAGCAmψGAACAACmψCCCAGGGCAGAGmψGACCmψmψC<br>GAGGACGmψGACCGmψGAAmψmψmψmψACACAGGGAGAGmψGGCAGAGACmψGAA<br>CCCCGAGCAGAGAAACCmψGmψACCGGGAmψGmψGAmψGCmψGGAAAACmψACAG<br>CAAmψCmψGGmψGmψCCGmψGGGCCAGGGCGAGACCACAAAGCCmψGACGmψGAm<br>ψCCmψGCGmψCmψGGAGCAGGGCAAGGAACCCmψGGCmψGGAGGAGGAGGAGGmψ<br>GCmψGGGAAGCGGACGGGCCGAGAAGAACGGCGACAmψCGGCGGACAGAmψCmψG<br>GAAGCCmψAAGGACGmψGAAAGAAAGCCmψGACCAGCCCCAAGAAAAAGAGAAAA | |

TABLE 37-continued

Full-length RNA sequences of dXR1 and ELXR #1 containing the ZIM3-KRAB domain mRNA molecules assessed in experiment #1 of this example. Modification 'mψ' = N1-methyl-pseudouridine.

| XR or ELXR ID | RNA sequence | SEQ ID NO |
|---|---|---|
| | GmψCGACmψACAAGGAmψGACGAmψGACAAGGACmψACAAGGAmψGACGACGACA AGmψAAmψAGAmψAAGCGGCCGCmψmψAAmψmψAAGCmψGCCmψmψCmψGCGGGG CmψmψGCCmψmψCmψGGCCAmψGCCCmψmψCmψmψCmψCmψCCCmψmψGCACCmψ GmψACCmψCmψmψGGmψCmψmvmψGAAmψAAAGCCmψGAGmψAGGAAGmψcmψag aaaaaaaaaaaaaaaaaaaaaaaaaaaaaaaaaaaaaaaaaaaaaaaaaaaaaaa aaaaaaaaaaaaaaaaaaaaaaaaa | |

TABLE 38

Full-length protein sequences of dXR1 and ELXR #1 containing the ZIM3-KRAB domain molecules assessed in experiment #1 of this example. Modification 'mψ' = N1-methyl-pseudouridine.

| XR or ELXR ID | Protein SEQ ID NO |
|---|---|
| dXR1 | 59586 |
| ELXR #1 | 59467 |

Synthesis of gRNAs:

In this experiment #1, gRNAs targeting the PCSK9 locus were designed using gRNA scaffold 174 and chemically synthesized. The sequences of the PCSK9-targeting spacers are listed in Table 39.

mouse IgG secondary antibody (Thermo Fisher). Fluorescence levels were measured using the Attune™ NxT flow cytometer, and data were analyzed using the FlowJo™ software. Cell populations were gated using the non-targeting gRNA as a negative control.

Experiment #2: ELXR #1 vs. ELXR #5 in Hepa1-6 Cells when Delivered as mRNA

Generation of mRNA:

mRNA encoding ELXR #1 or ELXR #5 containing the ZIM3-KRAB domain was generated by IVT in-house using PCR templates. Briefly, PCR was performed on plasmids encoding ELXR #1 or ELXR #5 harboring the ZIM3-KRAB domain with flanking NLSes with a forward primer containing a T7 promoter and reverse primer encoding a 120-nucleotide poly(A) tail. These constructs also contained a 2× FLAG sequence. DNA sequences encoding these molecules are listed in Table 40. The resulting PCR templates were used for IVT reactions, which were carried out with CleanCap® AG and N1-methyl-pseudouridine. IVT reactions were then subjected to DNase digestion and on-column oligo dT purification. Full-length RNA sequences encoding the ELXR mRNAs are listed in Table 41.

As experimental controls, mRNA encoding catalytically-active CasX 491 was also similarly generated by IVT using a PCR template as described. Generation of mRNAs encoding ELXR #1 containing the ZIM3-KRAB domain and dCas9-ZNF10-DNMT3A/3L (described in Example 6) by IVT by a third-party was performed as described above for experiment #1.

TABLE 39

Sequences of spacers targeting the PCSK9 locus used in this example.

| gRNA ID (scaffold-variant spacer) | Target | Targeting spacer sequence (RNA) | SEQ ID NO: |
|---|---|---|---|
| 174-6.7 | human PCSK9 | UCCUGGCUUCCUGGUGAAGA | 59587 |
| 174-27.1 | mouse PCSK9 | GCCUCGCCCUCCCCAGACAG | 59588 |
| 174-27.88 | mouse PCSK9 | CGCUACCUGCCUAAACUUUG | 59589 |
| 174-27.92 | mouse PCSK9 | CCCUCCAACAAUAUUAACUA | 59590 |
| 174-27.93 | mouse PCSK9 | GGGGUCUCCCAGCCACCCCU | 59591 |
| 174-27.94 | mouse PCSK9 | CCCCUCUUAAUCCCCACUCC | 59592 |
| 174-27.100 | mouse PCSK9 | CUCUCUCUUUCUGAGGCUAG | 59593 |
| 174-27.103 | mouse PCSK9 | UAAUCUCCAUCCUCGUCCUG | 59594 |

Transfection of mRNA and gRNA into Hepa1-6 Cells and Intracellular PCSK9 Staining:

Seeded Hepa1-6 cells treated with the NATE™ inhibitor were lipofected with 300 ng of mRNA encoding dXR1 or ELXR #1 with a ZIM3-KRAB domain (Table 37) and 150 ng of a PCSK9-targeting gRNA (Table 39). Seven different gRNAs spanning the promoter region of the mouse PCSK9 locus were tested, in addition to a non-targeting sequence complementary to the human PCSK9 gene (Table 39). Cells were harvested at 6, 13, and 25 days after transfection to measure intracellular levels of the PCSK9 protein using an intracellular flow cytometry staining protocol. Briefly, cells were fixed using 4% paraformaldehyde in PBS, permeabilized, and stained using a mouse anti-PCSK9 primary antibody (R&D Systems), followed by a fluorescent goat anti-

TABLE 40

Encoding sequences of the ELXR #1 and ELXR #5 containing the ZIM3-KRAB domain mRNA molecules assessed in experiment #2 of this example*

| ELXR ID | Component | DNA SEQ ID NO |
|---|---|---|
| ELXR #1 - ZIM3-KRAB | 5'UTR | 59595 |
| | START codon + NLS + linker | 59596 |
| | START codon + DNMT3A catalytic domain | 59597 |
| | Linker | 59598 |
| | DNMT3L interaction domain | 59445 |
| | Linker | 59599 |
| | Linker + buffer | 59600 |
| | dCasX491 | 59601 |
| | Linker + buffer | 59602 |
| | ZIM3-KRAB | 59603 |
| | Buffer + NLS | 59604 |
| | Tag | 59605 |
| | Buffer | 59606 |
| | Poly(A) tail | 59607 |

TABLE 40-continued

Encoding sequences of the ELXR #1 and ELXR #5 containing the ZIM3-KRAB domain mRNA molecules assessed in experiment #2 of this example*

| ELXR ID | Component | DNA SEQ ID NO |
|---|---|---|
| ELXR #5 - ZIM3-KRAB | 5'UTR | 59595 |
| | START codon + NLS + buffer | 59608 |
| | START codon + DNMT3A catalytic domain | 59597 |
| | Linker | 59598 |
| | DNMT3L interaction domain | 59445 |
| | Linker | 59446 |
| | ZIM3-KRAB | 59603 |
| | Linker | 59599 |
| | dCasX491 | 59601 |
| | Linker + buffer | 59602 |
| | NLS | 59609 |
| | Tag | 59605 |
| | Buffer | 59606 |
| | Poly(A) tail | 59607 |

*Components are listed in a 5' to 3' order within the constructs

TABLE 41

Full-length RNA sequences of ELXR #1 and ELXR #5 containing the ZIM3-KRAB domain mRNA molecules assessed in experiment #2 of this example. Modification 'mψ' = N1-methyl-pseudouridine.

| ELXR ID | RNA sequence | SEQ ID NO |
|---|---|---|
| ELXR #1-ZIM3-KRAB | GACCGGCCGCCACCAmψGGCCCCAAAGAAGAAGCGGAAGGmψCmψCmψAGAGmψmψAACGGAmψ<br>CAGGCmψCmψGGAGGmψGGAAmψGAACCAmψGACCAGGAAmψmψmψGACCCCCCAAAGGmψmψm<br>ψACCCACCmψGmψGCCAGCmψGAGAAGAGGAAGCCCAmψCCGCGmψGCmψGmψCmψCmψCmψmψ<br>mψGAmψGGGAmψmψGCmψACAGGGCmψCCmψGGmψGCmψGAAGGACCmψGGGCAmψCCAAGmψG<br>GACCGCmψACAmψCGCCmψCCGAGGmψGmψGmψGAGGACmψCCAmψCACGGmψGGGCAmψGGmψ<br>GCGGCACCAGGGAAAGAmψCAmψGmψACGmψCGGGGACGmψCCGCAGCGmψCACACAGAAGCAm<br>ψAmψCCAGGAGmψGGGGCCCAmψmψCGACCmψGGmψGAmψmψGGAGGCAGmψCCCmψGCAACGA<br>CCmψCmψCCAmψmψGmψCAACCCmψGCCCGCAAGGGACmψmψmψAmψGAGGGmψACmψGGCCGC<br>CmψCmψmψCmψmψmψGAGmψmψCmψACCGCCmψCCmψGCAmψGAmψGCGCGGCCCAAGGAGGGA<br>GAmψGAmψCGCCCCmψmψCmψmψCmψGGCmψCmψmψmψGAGAAmψGmψGGmψGGCCAmψGGGCG<br>mψmψAGmψGACAAGAGGGACAmψCmψCGCGAmψmψmψCmψmψGAGmψCmψAACCCCGmψGAmψG<br>AmψmψGACGCCAAAGAAGmψGmψCmψGCmψGCACACAGGGCCCGmψmψACmψmψCmψGGGGmψA<br>ACCmψmψCCmψGGCAmψGAACAGGCCmψmψmψGGCAmψCCACmψGmψGAAmψGAmψAAGCmψGG<br>AGCmψGCAAGAGmψGmψCmψGGAGCACGGCAGAAmψAGCCAAGmψmψCAGCAAAGmψGAGGACC<br>AmψmψACCACCAGGmψCAAACmψCmψAmψAAAGCAGGGCAAAGACCAGCAmψmψmψCCCCGmψC<br>mψmψCAmψGAACGAGAAGGAGGACAmψCCmψGmψGGmψGCACmψGAAAmψGGAAAGGGmψGmψm<br>ψmψGGCmψmψCCCCGmψCCACmψACACAGACGmψGmψCCAACAmψGAGCCGCmψmψGGCGAGGC<br>AGAGACmψGCmψGGGCCGGmψCGmψGGAGCGmψGCCGGmψCAmψCCGCCACCmψCmψmψCGCmψ<br>CCGCmψGAAGGAAmψAmψmψmψmψGCmψmψGmψGmψGmψCmψAGCGGCAAmψAGmψAACGCmψA<br>ACAGCCGCGGGCCGAGCmψmψCAGCAGCGGCCmψGGmψGCCGmψmψAAGCmψmψGCGCGGCAGC<br>CAmψAmψGGGCCCmψAmψGGAGAmψAmψACAAGACAGmψGmψCmψGCAmψGGAAGAGACAGCCA<br>GmψGCGGGmψACmψGAGCCmψCmψmψCAGAAACAmψCGACAAGGmψACmψAAAGAGmψmψmψGG<br>GCmψmψCmψmψGGAAAGCGGmψmψCmψGGmψmψCmψGGGGGAGGAACGCmψGAAGmψACGmψGG<br>AAGAmψGmψCACAAAmψGmψCGmψGAGGAGGGACGmψGGAGAAAmψGGGGCCCCmψmψmψGACC<br>mψGGmψGmψACGGCmψCGACGCAGCCCCmψAGGCAGCmψCmψmψGmψGAmψCGCmψGmψCCCGG<br>CmψGAGGAmψGACCAAGAGACAACmψACCCGCmψmψCCmψmψCAGACAGAGGCmψGmψGACCCm<br>GGAGAGmψCAGCGGCCCmψmψCmψmψCmψGGAmψAmψmψCAmψGGACAAmψCmψGCmψGCmψGA<br>CmψGAGGAmψGACCAAGAGACAACmψACCCGCmψmψCCmψmψCAGACAGAGGCmψGmψGACCCm<br>ψCCAGGAmψGmψCCGmψGGCAGAGACmψACCAGAAmψGCmψAmψGCGGGmψGmψGGAGCAACAm<br>ψmψCCAGGGCmψGAAGAGCAAGCAmψGCGCCCCmψGACCCCAAAGGAAGAAGAGmψAmψCmψGC<br>AAGCCCAAGmψCAGAAGCAGGAGCAAGCmψGGACGCCCCGAAAGmψmψGACCmψCCmψGGmψGA<br>AGAACmψGCCmψmψCmψCCCGCmψGAGAGAGmψACmψmψCAAGmψAmψmψmψmψmψCmψCAAAA<br>CmqCACmψmψCCmψCmψmψGGAGGGCCGAGCmψCmψGGCGCACCCCCCACCAAGmψGGAGGGmψC<br>mψCCmψGCCGGGmψCCCCAACAmψCmψACmψGAAGAAGGCACCAGCGAAmψCCGCAACGCCCGA<br>GmψCAGGCCCmψGGmψACCmψCCACAGAACCAmψCmψGAAGGmψAGmψGCGCCmψGGmψmψCCC<br>CAGCmψGGAAGCCCmψACmψmψCCACCGAAGAAGGCACGmψCAACCGAACCAAGmψGAAGGAmψ<br>CmψGCCCCmψGGGACCAGCACmψGAACCAmψCmψGAGGGCGGmψmψCCGGCGGAGGAAGCGCmψ<br>CAAGAGAmψCAAGAGAAmψCAACAAGAmψCAGAAGGAGACmψGGmψCAAGGACAGCAACACAAA<br>GAAGGCCGGCAAGACAGGCCCCAmψGAAAACCCmψGCmψCGmψCAGAGmψGAmψGACCCCmψGA<br>CCmψGAGAGAGCGGCmψGGAAAACCmψGAGAAAGAAGCCCGAGAACAmψCCCmψCAGCCmψAmψ<br>CAGCAACACCAGCAGGGCCAACCmψGAACAAGCmψGCmψGACCGACmψACACCGAGAmψGAAGA<br>AAGCCAmψCCmψGCaCGmψGmψACmψGGGAAGAGmψmψCCAGAAAGACCCCGmψGGGCCmψGAm<br>ψGAGCAGAGmψmψGCmψCAGCCmψGCCAGCAAGAAGAmψCGACCAGAACAAGCmψGAAGCCCGA<br>GAmψGGACGAGAAGGGCAAmψCmψGACCACAGCCGGCmψmψmψGCCmψGCm4Cm4CAGmψGmψG | 59610 |

TABLE 41-continued

Full-length RNA sequences of ELXR #1 and ELXR #5 containing the ZIM3-KRAB domain mRNA molecules assessed in experiment #2 of this example. Modification 'mψ' = N1-methyl-pseudouridine.

| ELXR ID | RNA sequence | SEQ ID NO |
|---|---|---|
| | GCCAGCCmψCmψGmψmψCGmψGmψACAAGCmψGGAACAGGmψGmψCCGAGAAAGGCAAGGCCmψ<br>ACACCAACmψACmψmψCGGCAGAmψGmψAACGmψGGCCGAGCACGAGAAGCmψGAmψmψCmψGC<br>mψGGCCCAGCmψGAAACCmψGAGAAGGACmψCmψGAmψGAGGCCGmψGACCmψACAGCCmψGGG<br>CAAGmψmψmψGGACAGAGAGCCCmψGGACmψmψCmψACAGCAmψCCACGmψGACCAAAGAAAGC<br>ACACACCCCGmψGAAGCCCCmGGCmψCAGAmψCGCCGGCAAmψTAGAmψACGCCmψCmψGGACC<br>mψGmψGGGCAAAGCCCmψGmψCCGAmψGCCmψGCAmψGGGAACAAmψCGCCAGCmψmψCCmψGA<br>GCAAGmψACCAGGACAmψCAmψCAmψCGAGCACCAGAAGGmψGGmψCAAGGGCAACCAGAAGAG<br>ACmψGGAAAGCCmψGAGGGAGCmψGGCCGGCAAAGAGAACCmψGGAAmψACCCCAGCGmψGACC<br>CmψGCCmψCCmψCAGCCmψCACACAAAAGAAGGCGmψGGACGCCmψACAACGAAGmψGAmψCGC<br>CAGAGmψGAGAAmψGmψGGGmψCAACCmψGAACCmψGmψGGCAGAAGCmψGAAACmψGmψCCAG<br>GGACGACGCCAAGCCmψCmψGCmψGAGACmψGAAGGGCmψmψCCCmψAGCmψmψCCCmψCmψGG<br>mψGGAAAGACAGGCCAAmψGAAGmψGGAmψmψGGmψGGGACAmψGGmψCmψGCAACGmψGAAGA<br>AGCmψGAmψCAACGAGAAGAAAGAGGAmψGGCAAGGmψmψmψmψCmψGGCAGAACCmψGGCCGG<br>CmψACAAGAGACAAGAAGCCCmψGAGGCCmψmψACCmψGAGCAGCGAAGAGGACCGGAAGAAGG<br>GCAAGAAGmψmψCGCCAGAmψACCAGCmψGGGCGACCmψGCmψGCmψGCACCmψGGAAAAGAAG<br>CACGGCGAGGACmψGGGGCAAAGmψGmψACGAmψGAGGCCmψGGGAGAGAAmψCGACAAGAAGG<br>mψGGAAGGCCmψGAGCAAGCACAmψmψAAGCmψGGAAGAGGAAAGAAGGAGCGAGGACGCCCAA<br>mψCmψAAAGCCGCmψCmψGACCGAmψmψGGCmψGAGAGCCAAGGCCAGCmψmψmψGmψGAmψCG<br>AGGGCCmψGAAAGAGGCCGACAAGGACGAGmψmψCmψGCAGAmψGCGAGCmψGAAGCmψGCAGA<br>AGmψGGmψACGGCGAmψCmψGAGAGGCAAGCCCmψmψCGCCAmψmψGAGGCCGAGAACAGCAmψ<br>CCmψGGACAmψCAGCGGCmψmψCAGCAAGCAGmψACAACmψGCGCCmψmψCAmψmψmψGGCAGA<br>AAGACGGCGmψCAAGAAACmψGAACCmψGmψACCmψGAmψCAmψCAAmψmψACmψmψCAAAGGC<br>GGCAAGCmψGCGGmψmψCAAGAAGAmψCAAACCCGAGGCCmψmψCGAGGCmψAACAGAmψmψCm<br>ψACACCGmψGAmψCAACAAAAAGmψCCGGCGAGAmψCGmψGCCCAmψGGAAGmψGAACmψmψCA<br>ACmψmψCGACGACCCCAACCmψGAmψmψAmψCCmψGCCmψCmψGGCCmψmψCGGCAAGAGACAG<br>GGCAGAGAGmψmψCAmψCmψGGAACGAmψCmψGCmψGAGCCmψGGAAACCGGCmψCmψCmψGAA<br>GCmψGGCCAAmψGGCAGAGmψGAmψCGAGAAAACCCmψGmψACAACAGGAGAACCAGACAGGAC<br>GAGCCmψGCmψCmψGmψmψmψGmψGGCCCmψGACCmψmψCGAGAGAAGAGAGGmψGCmψGGACa<br>GCAGCAACAmψCAAGCCCAmψGAACCmψGAmψCGGCGmψGGCCCGGGGCGAGAAmψAmψCCCmψ<br>GCmψGmψGAmψCGCCCmψGACAGACCCmψGAAGGAmψGCCCACmψGAGCAGAmψmψCAAGGACm<br>ψCCCmqGGGCAACCCmψACACACAmψCCmψGAGAAmψCGGCGAGAGCmψACAAAGAGAAGCAGA<br>GGACAAmψCCAGGCCAAGAAAGAGGmψGGAACAGAGAAGAGCCGGCGGAmψACmψCmψAGGAAG<br>mψACGCCAGCAAGGCCAAGAAmψCmψGGCCGACGACAmψGGmψCCGAAACACCGCCAGAGAmψC<br>mψGCmψGmψACmψACGCCGmψGACACAGGACGCCAmψGCmψGAmψCmψmψCGCGAAmψCmψGAG<br>CAGAGGCmψmψCGGCCGGCAGGGCAAGAGAACCmψmψmψAmψGGCCGAGAGGCAGmψACACCAG<br>AAmψGGAAGAmψmψGGCmψCACAGCmψAAACmψGGCCmψACGAGGGACmψGAGCAAGACCmψAC<br>CmψGmψCCAAAACACmψGGCCCAGmψAmψACCmψCCAAGACCmψGCAGCAAmψmψGCGGCmψmψ<br>CACCAmψCACCAGCGCCGACmψACGACAGAGmψGCmψGGAAAAGCmψCAAGAAAACCGCCACCG<br>GCmψGGAmψGACCACCAmψCAACGGCAAAGAGCmψGAAGGmψmψGAGGGCCAGAmψCACCmψAC<br>mψACAACAGGmψACAAGAGGCAGAACGmψCGmψGAAGGAmψCmψGAGCGmψGGAACmψGGACAG<br>ACmψGAGCGAAGAGAGCGmψGAACAACGACAmψCAGCAGCmψGGACAAAGGGCAGAmψCAGGCG<br>AGGCmψCmψGAGCCmψGCmψGAAGAAGAGGmψmψmψAGCCACAGACCmψGmψGCAAGAGAAGmψ<br>mψCGmψGmψGCCmψGAACmψGCGGCmψmψCGAGACACACGCCGCmψGAACAGGCmψGCCCmψGA<br>ACAmψmψGCCAGAAGCmψGGCmψGmψmψCCmψGAGAAGCCAAGAGmψACAAGAAGmψACCAGAC<br>CAACAAGACCACCGGCAACACCGACAAGAGGGCCmψmψmψGmψGGAAACCmψGGCAGAGCmψmψ<br>CmψACAGAAAAAAGCmψGAAAGAAGmψCmψGGAAGCCCGCCGmψGCGAmψCGGGCGGmψmψCCG<br>GCGGAGGmψmψCCACmψAGmψAmψGAACAAmψmψCCCAGGGAAGAGmψGACCmψmψCGAGGAmψ<br>GmψCACmψGmψGAACmψmψCACCCAGGGGGAGmψGGCAGCGGCmψGAAmψCCCGAACAGAGAAA<br>CmψmψGmψACAGGGAmψGmψGAmψGCmψGGAGAAmψmψACAGCAACCmψmψGmψCmψCmψGmψG<br>GGACAAGGGGAAACCACCAAACCCGAmψGmψGAmt CmψmψGAGGmψmψGGAACAAGGAAAGGAG<br>CCAmψGGmψmψGGAGGAAGAGGAAGmψGCmψGGGAAGmψGGCCGmψGCAGAAAAAAAmψGGGGA<br>CAmψmψGGAGGGCAGAmψmψmψGGAAGCCAAAGGAmψGmψGAAAGAGAGmψCmψCACmψAGmψC<br>CAAAAAAGAAGAGAAAGGmψAGAmψmψACAAAGAmψGACGAmψGACAAAGACmψACAAGGAmψG<br>AmψGAmψGAmψAAGGGAmψCCGGCmψGAAAAAAAAAAAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAA<br>AAAAAAAAAAAAAAAAAAAA | |
| ELXR #5-ZIM3-KRAB | GACCGGCCGCCACCAmψGGCCCCAAAGAAGAAGCGGAAGGmψCmψCmψAGAAmψGAACCAmψGA<br>CCAGGAAmψmψmψGACCCCCCAAAGGmψmψmψACCCACCmψGmψGCCAGCmψGAGAAGAGGAAG<br>CCCAmψCCGCGmψGCmψGmψCmψCmψCmψmψmψGAmψGGGAmψmψGCmψACAGGGCmψCCmψGG<br>mψGCmψGAAGGACCmψGGGCAmψCCAAGmψGGACCGCmψACAmψCGCCmψCCGAGGmψGmψGmψ<br>GAGGACmψCCAmψCACGGmψGGGCAmψGGmψGCGGCACCAGGGAAAGAmψCAmψGmψACGmψCG<br>GGGACGmψCCGCAGCGmψCACACAGAAGCAmψAmψCCAGGAGmψGGGGCCCAmψmψCGACCmψG<br>GmψGAmψmψGGAGGCAGmψCCCmψGCAACGACCmψCmψCCAmψmψGmψCAACCCmψGCCCGCAA<br>GGGACmψmψmψAmψGAGGGmψACmψGGCCGCCmψCmψmψCmψmψmψGAGmψmψCmψACCGCCmψ<br>CCmψGCAmψGAmψGCGCGGCCCAAGGAGGGAGAmψGAmψCGCCCCmψmψCmψmψCmψGGCmψCm<br>ψmψmψGAGAAmψGmψGGmψGGCCAmψGGGCGmψmψAGmψGACAAGAGGGACAmψCmψCGCGAmψ<br>mψmψCmψmψGAGmψCmψAACCCCGmψGAmψGAmψmψGACGCCAAAGAAGmψGmψCmψGCmψGCA<br>CACAGGGCCCGmψmψACmψmψCmψGGGGmψAACCmψmψCCmψGGCAmψGAACAGGCCmψmψmψG<br>GCAmψCCACmψGmψGAAmψGAmψAAGCmψGGAGCmψGCAAGAGmψGmψCmψGGAGCACGGCAGA<br>AmψAGCCAAGmψmψCAGCAAAGmψGAGGACCAmψmψACCACCAGGmψCAAACmψCmψAmψAAAG<br>CAGGGCAAAGACCAGCAmψmψmψCCCCGmψCmψmψCAmψGAACGAGAAGGAGGACAmψCCmψGm<br>ψGGmψGCACmψGAAAmψGGAAAGGGmψGmψmψmψGGCmψmψCCCCGmψCCACmψACACAGACGm | 59611 |

TABLE 41-continued

Full-length RNA sequences of ELXR #1 and ELXR #5 containing the ZIM3-KRAB domain mRNA molecules assessed in experiment #2 of this example. Modification 'mψ' = N1-methyl-pseudouridine.

| ELXR ID | RNA sequence | SEQ ID NO |
|---|---|---|
| | ψGmψCCAACAmψGAGCCGCmψmψGGCGAGGCAGAGACmψGCmψGGGCCGGmψCGmψGGAGCGmψ | |
| | GCCGGmψCAmψCCGCCACCmψCmψmψCGCmψCCGCmψGAAGGAAmψAmψmψmψmψGCmψmψGmψ | |
| | GmψGmψCmψAGCGGCAAmψAGmψAACGCmψAACAGCCGCGGGCCGAGCmψmψCAGCAGCGGCCm | |
| | ψGGmψGCCGmψmψAAGCmψmψGCGCGGCAGCCAmψAmψGGGCCCmψAmψGGAGAmψAmψACAAG | |
| | ACAGmψGmψCmψGCAmψGGAAGAGACAGCCAGmψGCGGGmψACmψGAGCCmψCmψmψCAGAAAC | |
| | AmψCGACAAGGmψACmψAAAGAGmψmψmψGGGCmψmψCmψmψGGAAAGCGGmψmψCmψGGmψmψ | |
| | CmψGGGGGAGGAACGCmψGAAGmψACGmψGGAAGAmψGmψCACAAAmψGmψCGmψGAGGAGGGA | |
| | CGmψGGAGAAAmψGGGGCCCCmψmψmψGACCmψGGmψGmψACGGCmψCGACGCAGCCCCmψAGG | |
| | CAGCmψCmψmψGmψGAmψCGCmψGmψCCCGGCmψGGmψACAmψGmψmψCCAGmψmψCCACCGGA | |
| | mψCCmψGCAGmψAmψGCGCmψGCCmψCGCCAGGAGAGmψCAGCGGCCCmψmψCmψmψCmψGGAm | |
| | ψAmψmψCAmψGGACAAmψCmψGCmψGCmψGACmψGAGGAmψGACCAAGAGACAACmψACCCGCm | |
| | ψmψCCmψmψCAGACAGAGGCmψGmψGACCCmψCCAGGAmψGmψCCGmψGGCAGAGACmψACCAG | |
| | AAmψGCmψAmψGCGGGmψGmψGGAGCAACAmψmψCCAGGGCmψGAAGAGCAAGCAmψGCGCCCC | |
| | mψGACCCCAAAGGAAGAAGAGmψAmψCmψGCAAGCCCAAGmψCAGAAGCAGGAGCAAGCmψGGA | |
| | CGCCCCGAAAGmψmψGACCmψCCmψGGmψGAAGAACmψGCCmψmψCmψCCCGCmψGAGAGAGmψ | |
| | ACmψmψCAAGmψAmψmψmψmψmψCmψCAAAACmψCACmψmψCCmψCmψmψGGCGGmψmψCCGGC | |
| | GGAGGAAmψGAACAAmψmψCCCAGGGAAGAGmψGACCmψmψCGAGGAmψGmψCACmψGmψGAAC | |
| | mψmψCACCCAGGGGGAGmψGGCAGCGGCmψGAAmψCCCGAACAGAGAAACmψmψGmψACAGGGA | |
| | mψGmψGAmψGCmψGGAGAAmψmψACAGCAACCmψmψGmψCmψCmψGmψGGGACAAGGGGAAACC | |
| | ACCAAACCCGAmψGmψGAmψCmvmψGAGGmψmψGGAACAAGGAAAGGAGCCAmψGGmψmψGGAG | |
| | GAAGAGGAAGmψGCmψGGGAAGmψGGCCGmψGCAGAAAAAAAmψGGGGACAmψmψGGAGGGCAG | |
| | AmψmψmψGGAAGCCAAAGGAmψGmψGAAAGAGAGmψCmψCGGAGGGCCGAGCmψCmψGGCGCAC | |
| | CCCCACCAAGmψGGAGGGmψCmψCCmψGCCGGGmψCCCCAACAmψCmψACmψGAAGAAGGCACC | |
| | AGCGAAmψCCGCAACGCCCGAGmψCAGGCCCmψGGmψACCmψCCACAGAACCAmψCmψGAAGGm | |
| | ψAGmψGCGCCmψGGmψmψCCCCAGCmψGGAAGCCCmψACmψmψCCACCGAAGAAGGCACGmψCA | |
| | ACCGAACCAAGmψGAAGGAmψCmψGCCCCmψGGGACCAGCACmψGAACCAmψCmψGAGCAAGAG | |
| | AmψCAAGAGAAmψCAACAAGAmψCAGAAGGAGACmψGGmψCAAGGACAGCAACACAAAGAAGGC | |
| | CGGCAAGACAGGCCCCAmψGAAAACCCmψGCmψCGmψCAGAGmψGAmψGACCCCmψGACCmψGA | |
| | GAGAGCGGCmψGGAAAACCmψGAGAAAGAAGCCCGAGAACAmψCCCmψCAGCCmψψAmCAGCAA | |
| | CACCAGCAGGGCCAACCmψGAACAAGCmψGCmψGACCGACmψACACCGAGAmψGAAGAAAGCCA | |
| | mψCCmψGCACGmψGmψACmψGGGAAGAGmψmψCCAGAAAGACCCCGmψGGGCCmψGAmψGAGCA | |
| | GAGmψmψGCmψCAGCCmψGCCAGCAAGAAGAmψCGACCAGAACAAGCmψGAAGCCCGAGAmψGG | |
| | ACGAGAAGGGCAAmψCmψGACCACAGCCGGCmψmψmψGCCmψGCmψCmψCAGmψGmψGGCCAGC | |
| | CmψCmψGmψmψCGmψGmψACAAGCmψGGAACAGGmψGmψCCGAGAAAGGCAAGGCCmψACACCA | |
| | ACmψACmψmψCGGCAGAmψGmψAACGmψGGCCGAGCACGAGAAGCmψGAmψmψCmψGCmψGGCC | |
| | CAGCmψGAAACCmψGAGAAGGACmψCmψGAmψGAGGCCGmψGACCmψACAGCCmψGGGCAAGmψ | |
| | mψmψGGACAGAGAGCCCmψGGACmψmψCmψACAGCAmψCCACGmψGACCAAAGAAAGCACACAC | |
| | CCCGmψGAAGCCCCmψGGCmψCAGAmψCGCCGGCAAmψAGAmψACGCCmψCmψGGACCmψGmψG | |
| | GGCAAAGCCCmψGmψCCGAmψGCCmψGCAmψGGGAACAAmψCGCCAGCmψmψCCmψGAGCAAGm | |
| | ψACCAGGACAmψCAmψCAmψCGAGCACCAGAAGGmψGGmψCAAGGGCAACCAGAAGAGACmψGG | |
| | AAAGCCmψGAGGGAGCmψGGCCGGCAAAGAGAACCmψGGAAmψACCCCAGCGmψGACCCmψGCC | |
| | mψCCmψCAGCCmψCACACAAAAGAAGGCGmψGGACGCCmψACAACGAAGmψGAmψCGCCAGAGm | |
| | ψGAGAAmψGmψGGGmψCAACCmψGAACCmψGmψGGCAGAAGCmψGAAACmψGmψCCAGGGACGA | |
| | CGCCAAGCCmψCmψGCmψGAGACmψGAAGGGCmψmψCCCmψAGCmψmψCCCmψCmψGGmψGGAA | |
| | AGACAGGCCAAmψGAAGmψGGAmψmψGGmψGGGACAmψGGmψCmψGCAACGmψGAAGAAGCmψG | |
| | AmψCAACGAGAAGAAAGAGGAmψGGCAAGGmψmψmψmψCmψGGCAGAACCmψGGCCGGCmψACA | |
| | AGAGACAAGAAGCCCmψGAGGCCmψmψACCmψGAGCAGCGAAGAGGACCGGAAGAAGGGCAAGA | |
| | AGmψmψCGCCAGAmψACCAGCmψGGGCGACCmψGCmψGCmψGCACCmψGGAAAAGAAGCACGGC | |
| | GAGGACmψGGGGCAAAGmψGmψACGAmψGAGGCCmψGGGAGAGAAmψCGACAAGAAGGmψGGAA | |
| | GGCCmψGAGCAAGCACAmψmψAAGCmψGGAAGAGGAAAGAAGGAGCGAGGACGCCCAAmψCmψA | |
| | AAGCCGCmψCmψGACCGAmψmψGGCmψGAGAGCCAAGGCCAGCmψmψmψGmψGAmψCGAGGGCC | |
| | mψGAAAGAGGCCGACAAGGACGAGmψmψCmψGCAGAmψGCGAGCmψGAAGCmψGCAGAAGmψGG | |
| | mψACGGCGAmψCmψGAGAGGCAAGCCCmψmψCGCCAmψmψGAGGCCGAGAACAGCAmψCCmψGG | |
| | ACAmψCAGCGGCmψmψCAGCAAGCAGmψACAACmψGCGCCmψmψCAmψmψmψGGCAGAAAGACG | |
| | GCGmψCAAGAAACmψGAACCmψGmψACCmψGAmψCAmψCAAmψmψACmψmψCAAAGGCGGCAAG | |
| | CmψGCGGmψmψCAAGAAGAmψCAAACCCGAGGCCmψmψCGAGGCmψAACAGAmψmψCmψACACC | |
| | GmψGAmψCAACAAAAAGmψCCGGCGAGAmψCGmψGCCCAmψGGAAGmψGAACmψmψCAACmψmψ | |
| | CCAAmψGGCAGAGmψGAmψCGAGAAAACCCmψGmψACAACAGGAGAACCAGACAGGACGAGCCm | |
| | CGACGACCCCAACCmψGAmψmψAmψCCmψGCCmψCmψGGCCmψmψCGGCAAGAGACAGGGCAGA | |
| | GAGmψmψCAmψCmψGGAACGAmψCmψGCmψGAGCCmψGGAAACCGGCmψCmψCmψGAAGCmψGG | |
| | CCAAmψGGCAGAGmψGAmψCGAGAAAACCCmψGmψACAACAGGAGAACCAGACAGGACGAGCCm | |
| | ψGCmψCmψGmψmψmψGmψGGCCCmψGACCmψmψCGAGAGAAGAGAGGmψGCmψGGACAGCAGCA | |
| | ACAmψCAAGCCCAmψGAACCmψGAmψCGGCGmψGGCCCGGGGCGAGAAmψAmψCCCmψGCmψGm | |
| | ψGAmψCGCCCmψGACAGACCCmψGAAGGAmψGCCCACmψGAGCAGAmψmψCAAGGACmψCCCmψ | |
| | GGGCAACCCmψACACACAmψCCmψGAGAAmψCGGCGAGAGCmψACAAAGAGAAGCAGAGGACAA | |
| | mψCCAGGCCAAGAAAGAGGmψGGAACAGAGAAGAGCCGGCGGAmψACmψCmψAGGAAGmψACGC | |
| | CAGCAAGGCCAAGAAmψCmψGGCCGACGACAmψGGmψCCGAAACACCGCCAGAGAmψCmψGCmψ | |
| | GmψACmψACGCCGmψGACACAGGACGCCAmψGCmψGAmψCmψmψCGCGAAmψCmψGAGCAGAGG | |
| | CmψmψCGGCCGGCAGGGCAAGAGAACCmψmψmψAmψGGCCGAGAGGCAGmψACACCAGAAmψGG | |
| | AAGAmψmψGGCmψCACAGCmψAAACmψGGCCmψACGAGGGACmψGAGCAAGACCmψACCmψGmψ | |
| | CCAAAACACmψGGCCCAGmψAmψψACCmψCCAAGACCmψGCAGCAAmψmψGCGGCmψmCACCAm | |
| | ψCACCAGCGCCGACmψACGACAGAGmψGCmψGGAAAAGCmψCAAGAAAACCGCCACCGGCmψGG | |
| | AmψGACCACCAmψCAACGGCAAAGAGCmψGAAGGmψmψGAGGGCCAGAmψCACCmψACmψACAA | |

TABLE 41-continued

Full-length RNA sequences of ELXR #1 and ELXR #5 containing the ZIM3-KRAB domain mRNA molecules assessed in experiment #2 of this example. Modification 'mψ' = N1-methyl-pseudouridine.

| ELXR ID | RNA sequence | SEQ ID NO |
|---|---|---|
| | CAGGmψACAAGAGGCAGAACGmψCGmψGAAGGAmψCmψGAGCGmψGGAACmψGGACAGACmψGA GCGAAGAGAGCGmψGAACAACGACAmψCAGCAGCmψGGACAAAGGGCAGAmψCAGGCGAGGCmψ CmψGAGCCmψGCmψGAAGAAGAGGmψmψmψAGCCACAGACCmψGmψGCAAGAGAAGmψmψCGmψ GmψGCCmψGAACmψGCGGCmψmψCGAGACACACGCCGCmψGAACAGGCmψGCCCmψGAACAmψm ψGCCAGAAGCmψGGCmψGmψmψCCmψGAGAAGCCAAGAGmψACAAGAAGmψACCAGACCAACAA GACCACCGGCAACACCGACAAGAGGGCCmψmψmψGmψGGAAACCmψGGCAGAGCmψmψCmψACA GAAAAAAGCmψGAAAGAAGmψCmψGGAAGCCCGCCGmψGCGAmψCGGGCGGmψmψCCGGCGGAG GmψmψCCACmψAGmψCCAAAAAAGAAGAGAAAGGmψAGAmψmψACAAAGAmψGACGAmψGACAA AGACmψACAAGGAmψGAmψGAmψGAmψAAGGGAmψCCGGCmψGAAAAAAAAAAAAAAAAAAAAA AAAAAAAAAAAAAAAAAAAAAAAAAAAAAAAAAAAAAAAAAAAAAAAAAAAAAAAAAAAAAA AAAAAAAAAAAAAAAAAAAAAAAAAAAAAAAAAAA | |

For experiment #2, synthesis of PCSK9-targeting gRNAs was performed as described above for experiment #1, and the sequences of the targeting spacers are listed in Table 39. For pairing with dCas9-ZNF10-DNMT3A/3L, targeting spacers were as follows: 1) 7.148 (B2M, as non-targeting control; SEQ ID NO: 57645), 27.126 (PCSK9; CACGCCACCCCGAGCCCCAU; SEQ ID NO: 60013), and 27.128 (PCSK9; CAGCCUGCGCGUCCACGUGA; SEQ ID NO: 60014).

Transfection of mRNA and gRNA into Hepa1-6 Cells and Intracellular PCSK9 Staining:

Seeded Hepa1-6 cells treated with the NATE™ inhibitor were lipofected with 300 ng of mRNA encoding ELXR #1 with the ZIM3-KRAB, ELXR #5 with the ZIM3-KRAB, catalytically-active CasX 491, or dCas9-ZNF10-DNMT3A/3L, and 150 ng of PCSK9-targeting gRNA (Table 39). Intracellular levels of PCSK9 protein were measured at day 7 and day 14 post-transfection using an intracellular staining protocol as described earlier for experiment #1.

Results

Figure 28:
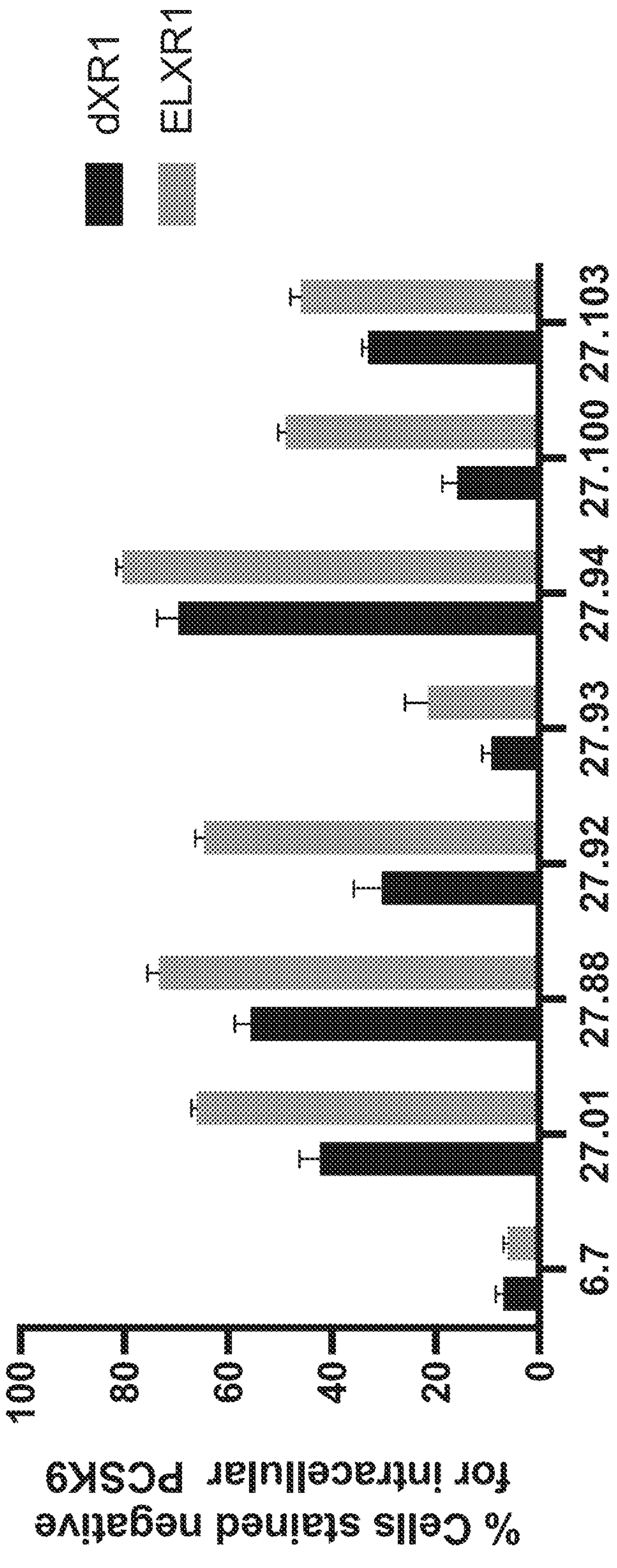
FIG. 28 is a bar plot showing the percentage of mouse Hepa1-6 cells, treated with either dXR1 or ELXR1-ZIM3 mRNA paired with the indicated PCSK9-targeting gRNAs, that stained negative for intracellular PCSK9 at day 6, as described in Example 14. Spacer 6.7 targeting the human PCSK9 locus served as a non-targeting control.
Figure 29:
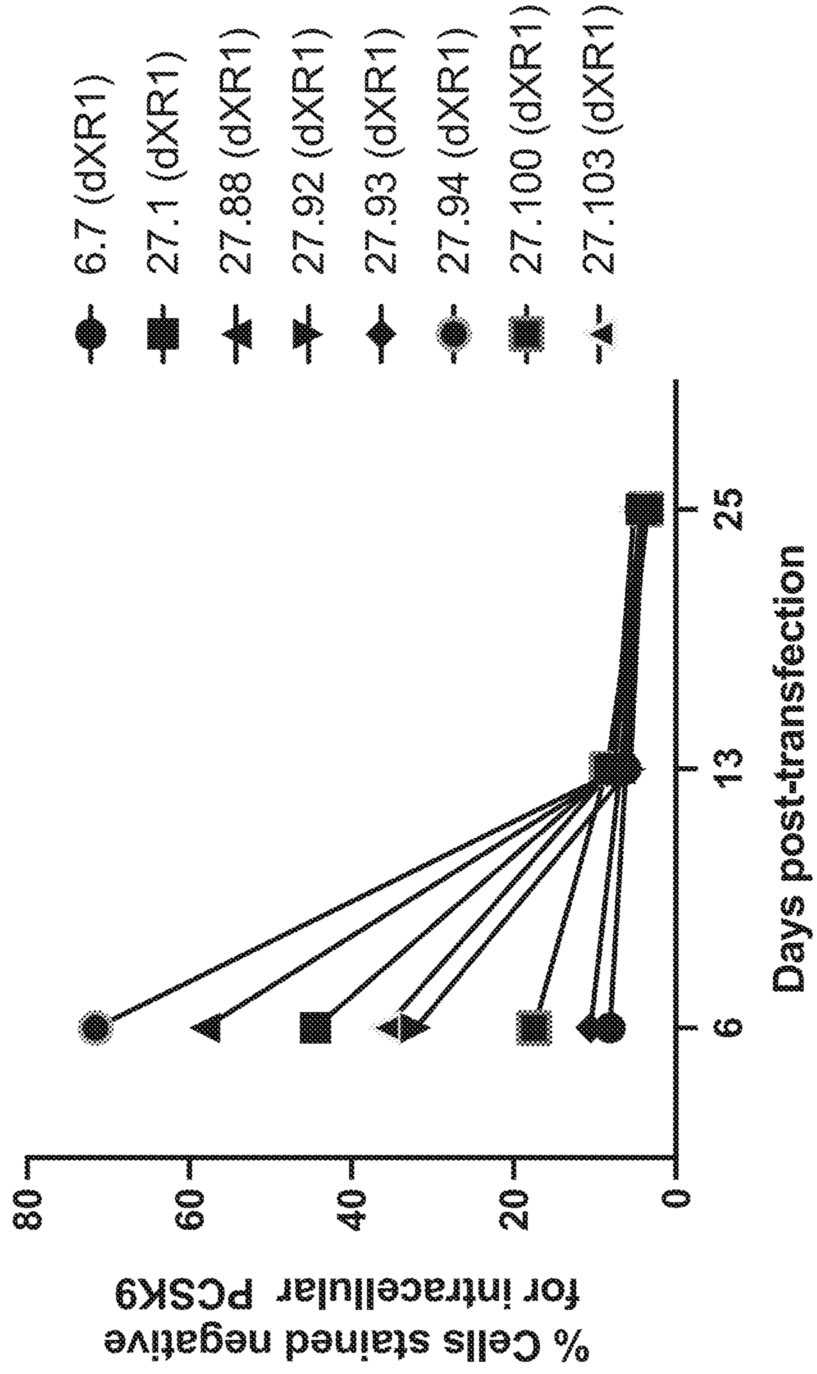
FIG. 29 is a time course plot showing the percentage of mouse Hepa1-6 cells, treated with dXR1 mRNA paired with the indicated PCSK9-targeting gRNAs, that stained negative for intracellular PCSK9 at 6, 13, and 25 days post-delivery, as described in Example 14. Spacer 6.7 targeting the human PCSK9 locus served as a non-targeting control, and treatment with water served as a negative control.
Figure 30:
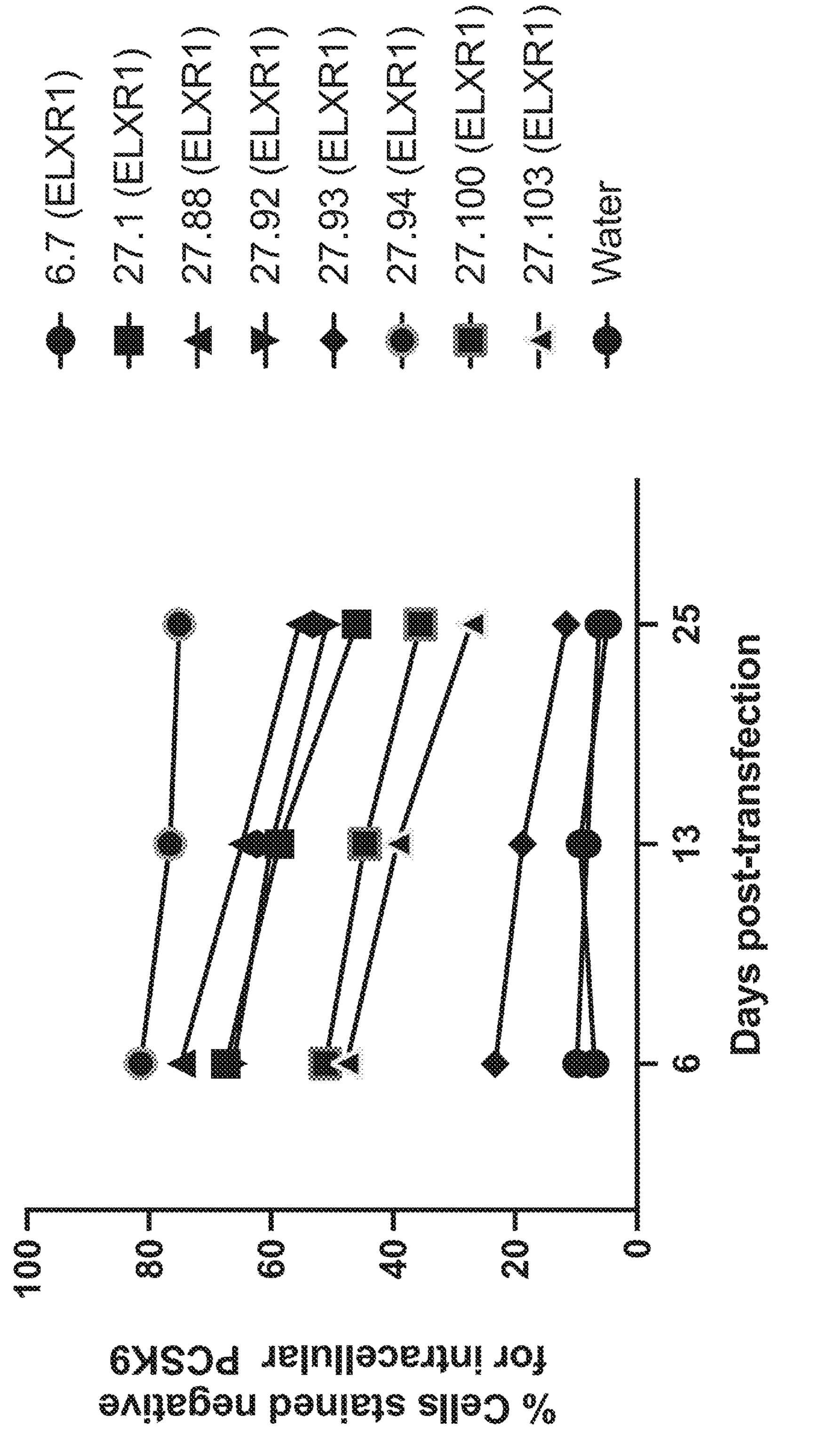
FIG. 30 is a time course plot showing the percentage of mouse Hepa1-6 cells, treated with ELXR1-ZIM3 mRNA paired with the indicated PCSK9-targeting gRNAs, that stained negative for intracellular PCSK9 at 6, 13, and 25 days post-delivery, as described in Example 14. Spacer 6.7 targeting the human PCSK9 locus served as a non-targeting control, and treatment with water served as a negative control.

In experiment #1, mRNAs encoding dXR1 or ELXR #1 containing the ZIM3-KRAB domain were co-transfected with a PCSK9-targeting gRNA into mouse Hepa1-6 cells to assess their ability to induce PCSK9 knockdown by silencing the mouse PCSK9 locus. The quantification of the resulting PCSK9 knockdown is shown in FIGS. 28-30. The data demonstrate that at day 6, use of six out of seven gRNAs targeting the mouse PCSK9 locus with ELXR #1 mRNA resulted in >50% knockdown of intracellular PCSK9, with the top spacer 27.94 achieving>80% repression level (FIG. 28). A similar trend was observed with use of dXR1 mRNA at day 6, although the degree of repression was less substantial when paired with certain spacers, such as spacer 27.92 and 27.100 (FIG. 28). The results also demonstrate that use of ELXR #1 mRNA led to sustained repression of the PCSK9 locus through at least 25 days, with use of the top spacers 27.94 and 27.88 showing the strongest permanence in silencing PCSK9 (FIG. 30). However, the PCSK9 repression mediated by dXR1 that was observed at day 6 reverted to similar levels of PCSK9 as detected with the non-targeting control (spacer 6.7) by day 13; such transient repression was noticeable for all gRNAs assayed that targeted the mouse PCSK9 gene (FIG. 29).

Figure 31:
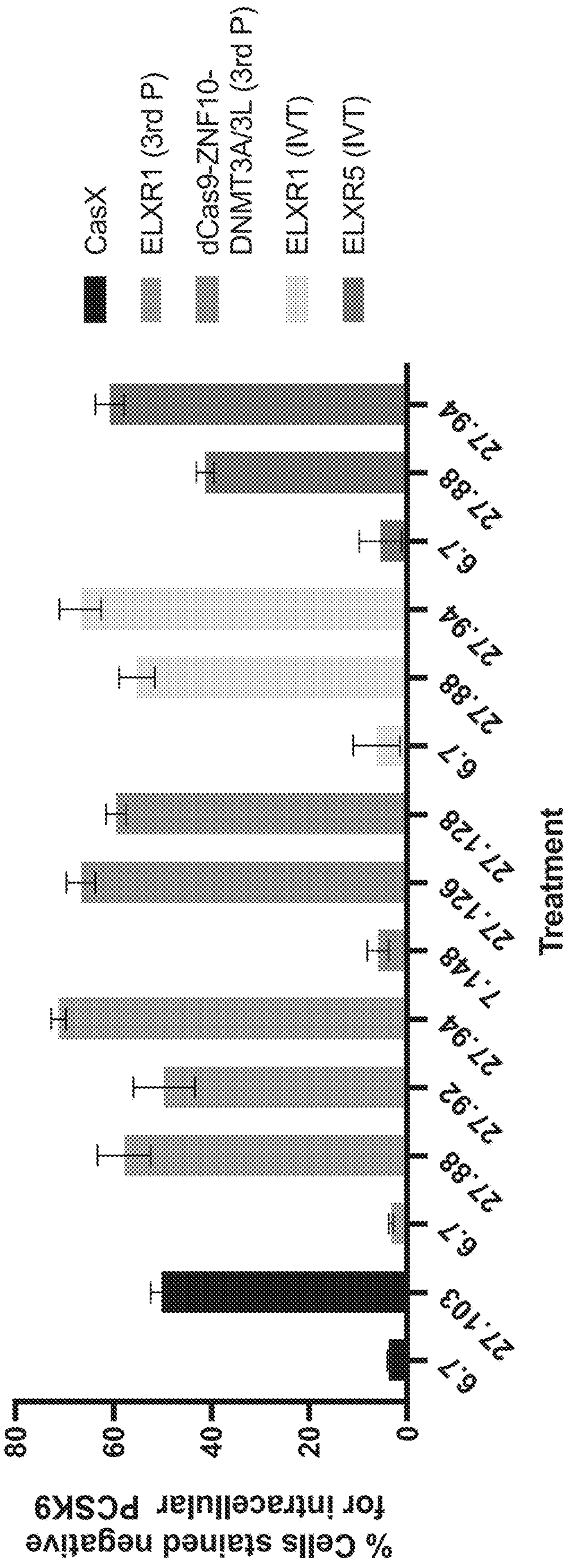
FIG. 31 is a bar plot showing the percentage of mouse Hepa1-6 cells, treated with ELXR1-ZIM3, ELXR5-ZIM3, catalytically active CasX491, or dCas9-ZNF10-DNMT3A/3L mRNA paired with the indicated PCSK9-targeting gRNAs, that stained negative for intracellular PCSK9 at day 7, as described in Example 14. Spacer 6.7 targeting the human PCSK9 locus served as a non-targeting control. Production of mRNA by in-house IVT or a third-party is indicated in parentheses.
Figure 32:
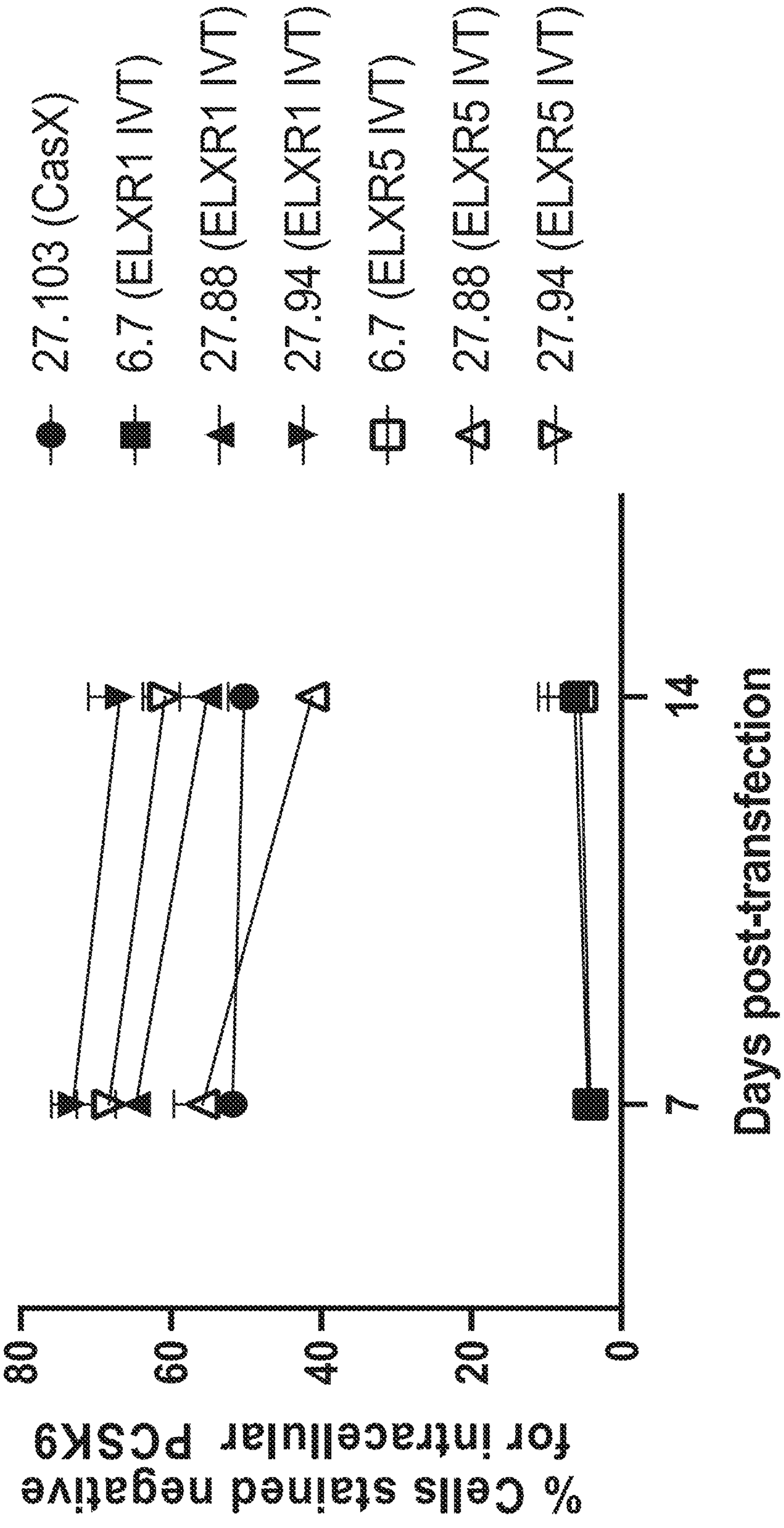
FIG. 32 is a time course plot showing the percentage of mouse Hepa1-6 cells, treated with IVT-produced ELXR1-ZIM3 vs. ELXR5-ZIM5 mRNA paired with the indicated PCSK9-targeting gRNAs, that stained negative for intracellular PCSK9 at 7 and 14 days post-delivery, as described in Example 14.
Figure 33:
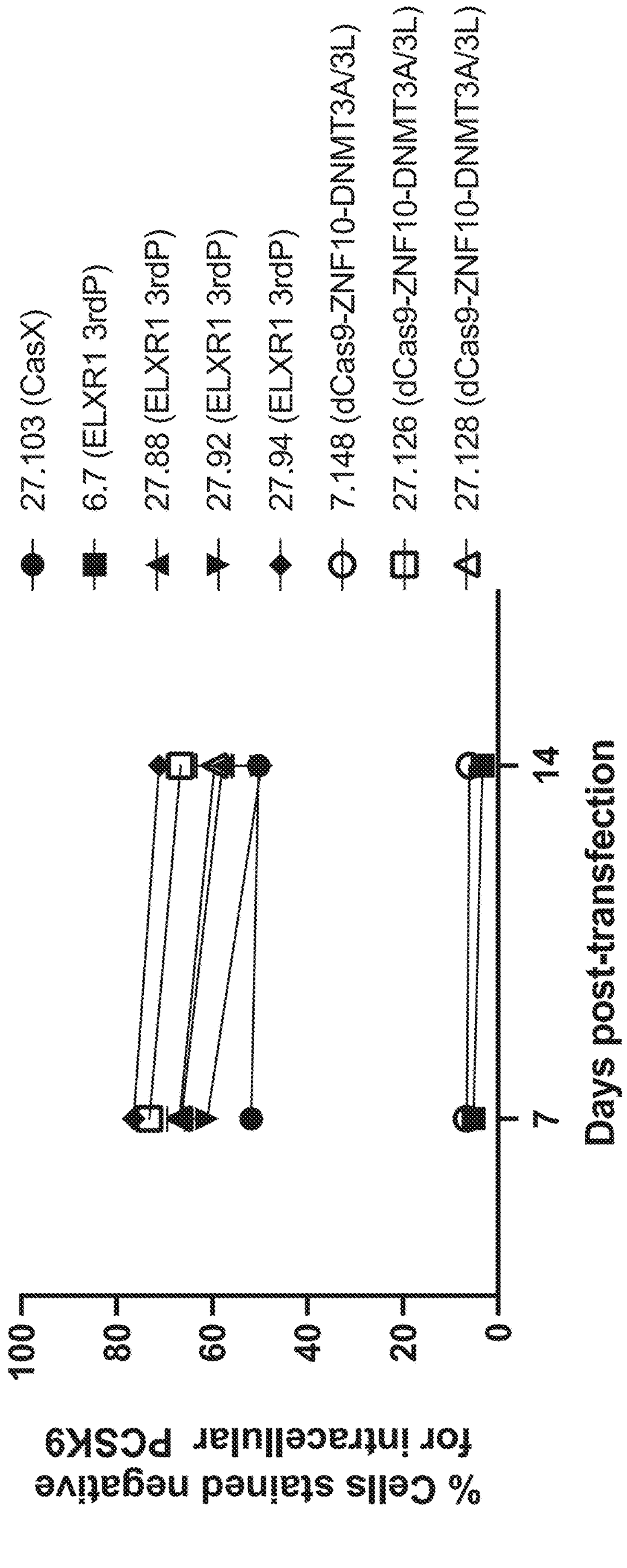
FIG. 33 is a time course plot showing the percentage of mouse Hepa1-6 cells, treated with third-party-produced ELXR1-ZIM3 vs. dCas9-ZNF10-DNMT3A/3L mRNA paired with the indicated PCSK9-targeting gRNAs, that stained negative for intracellular PCSK9 at 7 and 14 days post-delivery, as described in Example 14.

In experiment #2, mRNAs encoding ELXR #1 or ELXR #5 containing the ZIM3-KRAB domain, dCas9-ZNF10-DNMT3A/3L, or catalytically active CasX491 were co-transfected with a PCSK9-targeting gRNA into mouse Hepa1-6 cells to assess their ability to induce PCSK9 knockdown by silencing the mouse PCSK9 locus. The quantification of the resulting PCSK9 repression is shown in FIGS. 31-33. The data demonstrate that delivery of IVT-produced ELXR #1 or ELXR #5 mRNA resulted in comparable levels of sustained PCSK9 knockdown when paired with a targeting gRNA with the top spacer 27.94 (>70%), while use of gRNA with spacer 27.88 resulted in slightly higher repression with ELXR #1 than with ELXR #5 (FIGS. 31-33). Furthermore, third-party-produced mRNA encoding ELXR #1 and dCas9-ZNF10-DNMT3A/3L led to similar levels (>70%) of durable PCSK9 knockdown when paired with gRNAs containing the top spacers (FIGS. 31-33).

These experiments demonstrate that ELXR molecules, having different configurations, can induce heritable silencing of an endogenous locus in a mouse liver cell line. Meanwhile, as anticipated, use of dXR constructs result in efficient repression of the target locus at early timepoints, but their use does not lead to durable silencing. These findings also show that dXR and ELXR molecules (of different configurations) can be delivered as mRNA and co-transfected with a targeting gRNA to cells, indicating that the transient nature of this delivery modality is still sufficient to induce silencing.

Example 15: ELXR mRNA and Targeting gRNA can be Delivered Via LNPs to Achieve Repression of Target Locus In Vitro Experiments will be performed to demonstrate that delivery of lipid nanoparticles (LNPs) encapsulating ELXR mRNA and targeting gRNA will induce durable repression of a target endogenous locus in a cell-based assay.

Materials and Methods:

Generation of ELXR mRNAs:

mRNA encoding an ELXR molecule will be generated by IVT, as described earlier in Example 14. Sequences encoding the ELXR molecule will be codon-optimized as briefly described in Example 14. Examples of DNA sequences encoding ELXR mRNA are listed in Table 36 and Table 40, with the corresponding mRNA sequences listed in Table 37 and Table 41. Additional examples of DNA sequences encoding ELXR mRNA are presented in Table 42 below, with their corresponding mRNA sequences shown in Table 43.

TABLE 42

Encoding sequences of additional ELXR mRNA molecules that may be assessed*.

| ELXR ID | Component | DNA SEQ ID NO |
| --- | --- | --- |
| ELXR1-ZIM3_vs2 | 5'UTR | 59568 |
| | START codon + NLS + linker | 59612 |
| | START codon + DNMT3A catalytic domain | 59580 |
| | Linker | 59581 |
| | DNMT3L interaction domain | 59582 |
| | Linker | 59583 |
| | dCasX491 | 59570 |
| | Linker | 59571 |
| | ZIM3-KRAB | 59572 |
| | Buffer sequence + NLS | 59613 |
| | STOP codons + buffer sequence | 59575 |
| | 3'UTR | 59576 |
| | Buffer sequence | 59577 |
| | Poly(A) tail | 59578 |
| ELXR5-ZIM3 | 5'UTR | 59568 |
| | START codon + NLS + linker | 59614 |
| | START codon + DNMT3A catalytic domain | 59580 |
| | Linker | 59581 |
| | DNMT3L interaction domain | 59582 |
| | Linker | 59615 |
| | ZIM3-KRAB | 59572 |
| | Linker | 59616 |
| | dCasX491 | 59570 |
| | Buffer + linker | 59617 |
| | NLS + STOP codon + buffer sequence | 59618 |
| | 3'UTR | 59576 |
| | Buffer sequence | 59577 |
| | Poly(A) tail | 59618 |
| ELXR5-ZIM3 + ADD | 5'UTR | 59568 |
| | START codon + NLS + linker | 59614 |
| | START codon + DNMT3A ADD domain | 59620 |
| | DNMT3A catalytic domain | 59621 |
| | Linker | 59581 |
| | DNMT3L interaction domain | 59582 |
| | Linker | 59615 |
| | ZIM3-KRAB | 59572 |
| | Linker | 59616 |
| | dCasX491 | 59570 |
| | Buffer + linker | 59617 |
| | NLS + STOP codon + buffer sequence | 59618 |
| | 3'UTR | 59576 |
| | Buffer sequence | 59577 |
| | Poly(A) tail | 59619 |

*Components are listed in a 5' to 3' order within the constructs

TABLE 43

Full-length RNA sequences of additional ELXR mRNA molecψles in Table 42 for assessment. Modification 'mψ' = N1-methyl-pseudouridine.

| ELXR ID | RNA sequence | SEQ ID NO |
| --- | --- | --- |
| ELXR 1-ZIM3_vs2 | AAAmψAAGAGAGAAAAGAAGAGmψAAGAAGAAAmψAmψAAGAGCCACCAmψGGCCCCCGCCGCCAAGAGAGmψGAAGCmψGGAmψmψCCCGGGmψGAAmψGGCAGCGGCAGCGGGGGCGGCAmψGAACCACGACCAGGAGmψmψCGACCCCCCmψAAGGmψGmψACCCmψCCCGmψCCCCGCCGAGAAGAGAAAGCCCAmψCCGGGmψCCmψGAGCCmψGmψmψCGAmψGGCAmψCGCCACCGGmψCmψGCmψGGmψGCmψGAAGGACCmψGGGCAmψCCAGGmψGGAmψAGGmψACAmψmψGCCmψCCGAGGmψGmψGCGAGGACmψCCAmψCACCGmψGGGAAmψGGmψGCGmψCAmψCAGGGCAAGAmψCAmψGmψACGmψGGGCGACGmψGCGGAGCGmψGACACAGAAGCAmψAmψCCAGGAGmψGGGGCCCmψmψmψCGACCmψGGmψGAmψCGGCGGCAGCCCmψmψGCAAmψGACCmψGAGCAmψCGmψGAACCCAGCCCGGAAGGGCCmψGmψACGAGGGAACCGGCAGACmψGmψmψCmψmψCGAGmψmψmψmψACAGACmψGCmψGCACGACGCCCGGCCmψAAGGAAGGCGACGACCGGCCCmψmψCmψmψmψmψGGCmψGmψmψCGAGAAmψGmψGGmψGGCCAmψGGGAGmψCAGCGACAAGCGGGAmψAmψmψAGCCGGmψmψCCmψGGAGAGCAACCCCGmψGAmψGAmψCGAmψGCCAAGGAAGmψGAGCGCCGCCCACCGGGCCAGAmψACmψmψCmψGGGGCAAmψCmψGCCmψGGCAmψGAACAGACCCCmψGGCCAGCACCGmψGAACGACAAGCmψGGAGCmψGCAGGAGmψGCCmψGGAGCACGGCCGGAmψCGCCAAGmψmψCAGCAAGGmψGAGAACCAmψCACCACCCGAAGCAACAGCAmψCAAACAAGGCAAGGACCAGCACmψmψmψCCmψGmψGmψmψCAmψGAACGAGAAGGAGGACAmψCCmψGmψGGmψGmψACCGAGAmψGGAGAGAGmψGmψmψCGGGmψmψCCCAGmψCCACmψACACAGAmψGmψCAGCAACAmψGmψCmψAGACmψGGCCAGACAGAGACmψGCmψGGGAAGAAGCmψGGmψCCGmψCCCmψGmψGAmψCAGACACCmψGmψmψCGCCCCmψCmψGAAGGAGmψACmψmψCGCCmψGCGmψGAGCAGCGGCAACAGCAACGCCAACAGCCGGGGCCCCAGCmψmψCmψCmψAGCGGCCmψGGmψGCCACmψGmψCCCmψGAGAGGGAGCCACAmψGGGCCCCAmψGGAGAmψCmψACAAAACCGmψGAGCGCCmψGGAAGCGGCAGCCmψGmψGCGCGmψGCmψGAGCCmψGmψmψmψCGGAAmψAmψCGAmψAAAGmψCCmψGAAAAGCCmψGGGAmψmψCCmψGGAGAGCGGCmψCmψGGCmψCCGGCGGmψGGCACCCmψGAAGmψACGmψGGAGGAmψGmψGACAAACGmψGGmψCAGACGGGAmψGmψGGAGAAGmψGGGGCCCCmψmψCGAmψCmψGGmψGmψACGGCAGCACCCAACCCCmψGGGCAGCmψCmψmψGmψGACCGGmψGCCCmψGGCmψGGmψACAmψGmψmψmψCAGmψmψCCACCGGAmψCCmψGCAGmψACGCCCmψGCCGAGACAGGAGmψCCCAGCGGCCAmψmψCmψmψmψmψGGAmψmψmψmψCAmψGGACAACmmψGCmψGCmψGACCCGAGGAmψGACCAGGAAACmψACCACmψCGGmψmψCCmψGCaGACCGAAGCCGmψGACCCmψGCAGGACGmψGAGAGGCCGGGACmψACCAGAACGCCAmψGCGGGmψGmψGGmψCCAACAmψCCCmψGGACmψGAAAAGCAAGCACGCACCmψCmψGACCCCmψAAAGAAGAGGAGmψACCmψGCAGGCCCAGGmψGCGGAGCAGAAGCAAGCmψGGACGCCCCmψAAGGmψGGAmψCmψGCmψGGmψGAAGAAmψmψGCCmψCCmψGCCCCmψGAGAGAGmvACmψmψCAAGmψAmψmψmψCAGCCAGAAmψAGmψCmψGCCCCmψGGGCGGCCCAAGCAGCGGCGCCCCmψCCmψCCCAGCGGCGGCAGCCCAGCCGGCmψCCCCAACCmψCmψACCGAGGAGGGCACCmψCmψGAGmψCCGCCACCCCCGAGAGCGGCCCmψGGCACCmψCCACCGAGCCCAGCGAGGGCAGCGCACCCGGCAGCCCmψGCCGGCAGCCCCACCmψCCACAGAGGAGGGAACCAGCACCGAGCCCAGCGAAGGCAGCGCCCCAGGCACCAGCACCGAGCCmψAGmψGAGGGCGGCmψCmψGGCGGCGGCAGCGCCCAGGAGAmψmψAAACGGAmψCAACAAGAmψCAGAAGAAG | 59622 |

TABLE 43-continued

| Full-length RNA sequences of additional ELXR mRNA molecψles in Table 42 for assessment. Modification 'mψ' = N1-methyl-pseudouridine. | | |
|---|---|---|
| ELXR ID | RNA sequence | SEQ ID NO |
| | ACmψmψGmψGAAAGACAGCAACACCAAGAAGGCCGGCAAGACAGGCCCCAmψGAAAACCCmψGC<br>mψGGmψmψAGAGmψGAmψGACACCCGAmψCmψGAGAGAGCGGCmψGGAAAACCmψGAGAAAGAA<br>GCCmψGAAAAmψAmψCCCCCAGCCCAmψCAGCAAmψACAmψCmψAGAGCCAACCmψGAAmψAAG<br>CmqGCmψGACCGAmψmψACACCGAAAψGAAGAAGGCGAmψCCmψGCAmψGmψψGmψACmψGGGA<br>AGAGmψmψCCAGAAGGACCCmψGmψGGGCCmψGAmψGAGCCGGGmψGGCCCAGCCmψGCCAGCA<br>AGAAGAmψCGAmψCAGAACAAGCmψGAAACCmψGAGAmψGGACGAGAAGGGCAACCmψGACCAC<br>CGCCGGCmψmψmψGCCmψGCmψCmψCAGmψGmψGGCCAGCCCCmψGmψmψCGmψGmψACAAGCm<br>ψGGAGCAGGmψGmψCmψGAGAAGGGCAAGGCmψmψACACCAACmψACmψmψCGGACGGmψGCAA<br>mψGmψGGCCGAGCACGAAAAGCmψGAmψCCmψGCmψGGCCCAGCmψGAAGCCCGAGAAGGAmψA<br>GCGACGAAGCCGmψGACAmψAmψAGCCmψGGGAAAGmψmψmψGGGCAGAGGGCCCmψGGAmψmψ<br>mψCmψACAGCAmψmψCAmψGmψGACCAAGGAGmψCCACCCACCCCGmψGAAGCCCCmψGGCCCA<br>GAmψCGCCGGAAACAGAmψACGCCmψCCGGACCmψGmψGGGAAAGGCCCmψGAGCGACGCAmψG<br>mψAmψGGGCACAAmψCGCCmψCCmψmψCCmψGmψCmψAAGmψACCAGGACAmψCAmψCAmψCGA<br>ACACCAGAAGGmψGGmψGAAGGGCAACCAGAAGAGACmψGGAGAGCCmψGCGGGAGCmψGGCCG<br>GCAAGGAAAACCmψGGAAmψACCCmψAGCGmψGACCCmψGCCACCmψCAGCCmψCACACCAAGG<br>AGGGCGmψmψGAmψGCCmψACAACGAAGmψGAmψCGCCCGGGmψGCGAAmψGmψGGGmψGAACC<br>mψGAACCmψGmψGGCAGAAGCmψGAAGCmψAAGCAGAGAmψGAmψGCCAAGCCmψCmψGCmψGA<br>GACmψGAAGGGAmψmψCCCmψmψCCmψmψmψCCmψCmψGGmψCGAGAGACAGGCCAACGAAGmψ<br>GGACmψGGmψGGGACAmψGGmψGmψGmψAACGmψGAAGAAGCmψGAmψCAACGAGAAAAAGGAG<br>GAmψGGCAAGGmψGmψmψmψmψGGCAGAAmψCmψGGCmψGGCmψACAAGAGACAGGAAGCCCmψ<br>GAGACCAmψACCmψGAGCAGCGAGGAAGAmψCGGAAGAAGGGAAAGAAAmψmψCGCmψCGGmψA<br>CCAGCmψGGGCGACCmψGCmψGCmψGCACCmψGGAAAAGAAGCACGGCGAGGACmψGGGGAAAG<br>GmψGmψACGACGAGGCCmψGGGAGCGGAmψmψGACAAGAAAGmψGGAAGGCCmψGAGCAAGCAC<br>AmψCAAGCmψGGAAGAGGAACGGAGAAGCGAGGACGCCCAGAGCAAGGCCGCCCmψGACCGACm<br>ψGGCmψGCGGGCmψAAGGCCAGCmψmψCGmψGAmψCGAGGGCCmψGAAGGAGGCCGACAAGGAC<br>GAGmψmψCmψGCAGAmψGCGAGCmψGAAGCmψGCAGAAGmψGGmψACGGGGACCmψGCGGGGAA<br>AGCCCmψmψCGCCAmψCGAAGCCGAGAACAGCAmψCCmψGGACAmψCAGCGGCmψmψCAGCAAG<br>CAGmψACAACmψGmψGCCmψmψCAmψCmψGGCAGAAGGACGGCGmψGAAGAAGCmψGAACCmψG<br>mψACCmψGAmψCAmψCAACmψACmψmψCAAGGGCGGCAAGCmGCGGmψψmψCAAGAAGAmψCAA<br>ACCmψGAAGCCmψmψCGAAGCCAACAGAmψmψCmψACACCGmψGAmψCAACAAAAAGAGCGGCG<br>AGAmψCGmψGCCCAmψGGAGGmψGAACmψmψCAACmψmψCGACGACCCCAACCmψGAmψCAmψC<br>CmψGCCmψCmψGGCCmψmψmψGGCAAGAGACAGGGCAGAGAAmψmψCAmψCmψGGAACGACCmψ<br>GCmψGmψCCCmψGGAAACCGGCAGCCmψGAAGCmψGGCCAACGGAAGAGmψGAmψCGAGAAGAC<br>ACmψGmψACAACAGAAGAACCCGGCAGGAmψGAGCCmψGCCCmψGmψmψCGmψGGCCCmψGACC<br>mψmψCGAGCGGCGGGAGGmψCCmψGGACmψCCmψCCAAmψAmψCAAACCAAmψGAACCmψGAmψ<br>CGGCGmψGGCAAGAGGCGAAAACAmψCCCCGCCGmψGAmψCGCCCmψGACCGACCCCGAGGGCm<br>ψGCCCACmψGAGCCGGmψmψmψAAGGAmψAGCCmψGGGAAACCCAACCCACAmψCCmψGAGAAm<br>ψCGGCGAGAGCmψAmψAAGGAGAAGCAGCGGACCAmψCCAGGCCAAGAAGGAGGmψGGAGCAGC<br>GGAGAGCCGGCGGCmψACAGCCGGAAGmψACGCCAGCAAAGCCAAGAAmψCmψGGCAGACGAmψ<br>AmψGGmψGAGAAACACCGCmψAGAGAmψCmψGCmψGmψACmψACGCCGmψGACCCAGGAmψGCC<br>AmψGCmψGAmψCmψmψCGCCAACCmψGAGCCGGGGCmψmψCGGCCGGCAGGGCAAGCGGACCmψ<br>mψCAmψGGCCGAGAGACAGmψACACACGGAmψGGAGGACmψGGCmψGACCGCCAAGCmψGGCCm<br>ψACGAGGGCCmψGAGCAAGACCmψACCmψGmψCCAAGACACmψGGCCCAGmψACACCmψCCAAG<br>ACAmψGCAGCAACmψGmψGGGmψmψmψACCAmψCACCAGCGCCGACmψACGACAGGGmψGCmψG<br>GAGAAGCmψGAAGAAGACAGCAACAGGCmψGGAmψGACCACAAmψmψAACGGCAAGGAGCmψGA<br>AGGmψGGAGGGCCAGAmψmψACCmψACmψACAACAGAmψACAAGAGACAGAACGmψAGmψCAAG<br>GACCmψGmψCCGmψCGAGCmψGGAmψAGACmψGAGCGAAGAAmψCmψGmψGAACAACGACAmψC<br>mψCCmψCCmψGGACAAAGGGCAGAAGCGGAGAAGCmψCmψGAGCCmψCCmψGAAGAAAAGAmψm<br>ψCmψCCCAmψAGACCCGmψGCAGGAGAAGmψmψCGmψGmψGCCmψGAACmψGCGGCmψmψCGAG<br>ACACACGCAGCCGAGCAAGCCGCCCmψGAACAmψCGCCAGAmψCCmψGGCmψGmψmψCCmψGCG<br>GAGCCAGGAGmψACAAGAAAmψACCAGACAAACAAGACAACCGGCAACACCGAmψAAGAGAGCC<br>mψmψCGmψCGAGACCmψGGCAGmψCCmψmψmψmψACCGGAAGAAGCmψmψAAGGAGGmψGmψGG<br>AAACCmψGCCGmψGCGGmψCmψGGCGGAmψCmψGGCGGAGGCmψCCACAAGCAmψGAACAACmψ<br>CCCAGGGCAGAGmψGACCmψmψCGAGGACGmψGACCGmψGAAmψmψmψmψACACAGGGAGAGmψ<br>GGCAGAGACmψGAACCCCGAGCAGAGAAACCmψGmψACCGGGAmψGmψGAmψGCmψGGAAAACm<br>ψACAGCAAmψCmψGGmψGmψCCGmψGGGCCAGGGCGAGACCACAAAGCCmψGACGmψGAmψCCm<br>ψGCGmψCmψGGAGCAGGGCAAGGAACCCmψGGCmψGGAGGAGGAGGAGGmψGCmψGGGAAGCGG<br>ACGGGCCGAGAAGAACGGCGACAmψCGGCGGACAGAmψCmψGGAAGCCmψAAGGACGmψGAAAG<br>AAAGCCmψGGGCmψCmψCCCGCCGCCAAGAGAGmψGAAGCmψGGACmψAAmψAGAmψAAGCGGC<br>CGCmψmψAAmψmψAAGCmψGCCmψmψCmψGCGGGGCmψmψGCCmψmψCmψGGCCAmψGCCCmψm<br>ψCmψmψCmψCmψCCCmψmψGCACCmψGmψACCmψCmψmψGGmψCmψmψmψGAAmψAAAGCCmψG<br>AGmψAGGAAGmψCmψAGAAAAAAAAAAAAAAAAAAAAAAAAAAAAAAAAAAAAAAAAAAAAAAAA<br>AAAAAAAAAAAAAAAAAAAAAAAAAAAAAAAAA | |
| ELXR 5-ZIM3 | AAAmψAAGAGAGAAAAGAAGAGmψAAGAAGAAAmψAmψAAGAGCCACCAmψGGCCCCmψAAGAA<br>GAAGCGmψAAAGmψGAGCCGGAmψGAACCACGACCAGGAGmψmψCGACCCCCCmψAAGGmψGmψ<br>ACCCmψCCCGmψCCCCGCCGAGAAGAGAAAGCCCAmψCCGGGmψCCmψGAGCCmψGmψmψCGAm<br>ψGGCAmψCGCCACCGGmψCmψGCmψGGmψGCmψGAAGGACCmψGGGCAmψCCAGGmψGGAmψAG<br>GmψACAmψmψGCCmψCCGAGGmψGmψGCGAGGACmψCCAmψCACCGmψGGGAAmψGGmψGCGmψ<br>CAmψCAGGGCAAGAmψCAmψGmψACGmψGGGCGACGmψGCGGAGCGmψGACACAGAAGCAmψAm<br>ψCCAGGAGmψGGGGCCCmψmψmψCGACCmψGGmψGAmψCGGCGGCAGCCCmvmψGCAAmψGACC<br>mψGAGCAmψCGmψGAACCCAGCCCGGAAGGGCCmψGmψACGAGGGAACCGGCAGACmψGmψmψC<br>mψmψCGAGmψmψmψmψACAGACmψGCmψGCACGACGCCCGGCCmψAAGGAAGGCGACGACCGGC | 59623 |

TABLE 43-continued

Full-length RNA sequences of additional ELXR mRNA molecψles in Table 42 for assessment. Modification 'mψ' = N1-methyl-pseudouridine.

| ELXR ID | RNA sequence | SEQ ID NO |
|---|---|---|
| | CCmψmψCmψmψmψmψGGCmψGmψmψCGAGAAmψGmψGGmψGGCCAmψGGGAGmψCAGCGACAAG | |
| | CGGGAmψAmψmψAGCCGGmψmψCCmψGGAGAGCAACCCCGmψGAmψGAmψCGAmψGCCAAGGAA | |
| | GmψGAGCGCCGCCCACCGGGCCAGAmψACmψmψCmψGGGGCAAmψCmψGCCmψGGCAmψGAACA | |
| | GACCCCmψGGCCAGCACCGmψGAACGACAAGCmψGGAGCmψGCAGGAGmψGCCmψGGAGCACGG | |
| | CCGGAmψCGCCAAGmψmψCAGCAAGGmψGAGAACCAmψCACCACCCGAAGCAACAGCAmψCAAA | |
| | CAAGGCAAGGACCAGCACmψmψmψCCmψGmψGmψmψCAmψGAACGAGAAGGAGGACAmψCCmψG | |
| | mψGGmψGmψACCGAGAmψGGAGAGAGmψGmψmψCGGGmψmψCCCAGmψCCACmψACACAGAmψG | |
| | mψCAGCAACAmψGmψCmψAGACmψGGCCAGACAGAGACmψGCmψGGGAAGAAGCmψGGmψCCGm | |
| | ψCCCmψGmψGAmψCAGACACCmψGmψmψCGCCCCmψCmψGAAGGAGmψACmψmψCGCCmψGCGm | |
| | ψGAGCAGCGGCAACAGCAACGCCAACAGCCGGGGCCCCAGCmψmψCmψCmψAGCGGCCmψGGmψ | |
| | GCCACmψGmψCCCmψGAGAGGGAGCCACAmψGGGCCCCAmψGGAGAmψCmψACAAAACCGmψGA | |
| | GCGCCmψGGAAGCGGCAGCCmψGmψGCGCGmψGCmψGAGCCmψGmψmψmψCGGAAmψAmψCGAm | |
| | ψAAAGmψCCmψGAAAAGCCmψGGGAmψmψCCmψGGAGAGCGGCmψCmψGGCmψCCGGCGGmψGG | |
| | CACCCmψGAAGmψACGmψGGAGGAmψGmψGACAAACGmψGGmψCAGACGGGAmψGmψGGAGAAG | |
| | mψGGGGCCCCmψmψCGAmψCmψGGmψGmψACGGCAGCACCCAACCCCmψGGGCAGCmψCmψmψG | |
| | mψGACCGGmψGCCCmψGGCmψGGmψACAmψGmψmψmψCAGmψmψCCACCGGAmψCCmψGCAGmψ | |
| | ACGCCCmψGCCGAGACAGGAGmψCCCAGCGGCCAmψmψCmψmψmψmψGGAmψmψmψmψCAmψGG | |
| | ACAACmψmψGCmψGCmψGACCGAGGAmψGACCAGGAAACmψACCACmψCGGmψmψCCmψGCAGA | |
| | CCGAAGCCGmψGACCCmψGCAGGACGmψGAGAGGCCGGGACmψACCAGAACGCCAmψGCGGGmψ | |
| | GmψGGmψCCAACAmψCCCmψGGACmψGAAAAGCAAGCACGCACCmψCmψGACCCCmvAAAGAAG | |
| | AGGAGmψACCmψGCAGGCCCAGGmψGCGGAGCAGAAGCAAGCmψGGACGCCCCmψAAGGmψGGA | |
| | mψCmψGCmψGGmψGAAGAAmψmψGCCmψCCmψGCCCCmψGAGAGAGmψACmψmψCAAGmψAmψm | |
| | ψmψCAGCCAGAAmψAGmψCmψGCCCCmψGGGAGGCAGCGGCGGCAmψGAACAACmψCCCAG | |
| | GGCAGAGmψGACCmψmψCGAGGACGmψGACCGmψGAAmψmψmψmψACACAGGGAGAGmψGGCAG | |
| | AGACmψGAACCCCGAGCAGAGAAACCmψGmψACCGGGAmψGmψGAmψGCmψGGAAAACnψACAG | |
| | CAAmψCmψGGmψGmψCCGmψGGGCCAGGGCGAGACCACAAAGCCmψGACGmψGAmψCCmψGCGm | |
| | ψCmψGGAGCAGGGCAAGGAACCCmψGGCmψGGAGGAGGAGGAGGmψGCmψGGGAAGCGGACGGG | |
| | CCGAGAAGAACGGCGACAmψCGGCGGACAGAmψCmψGGAAGCCmψAAGGACGmψGAAAGAAAGC | |
| | CmψGGGCGGCCCAAGCAGCGGCGCCCCmψCCmψCCCAGCGGCGGCAGCCCAGCCGGCmψCCCCA | |
| | ACCmψCmψACCGAGGAGGGCACCmψCmψGAGmψCCGCCACCCCCGAGAGCGGCCCmψGGCACCm | |
| | ψCCACCGAGCCCAGCGAGGGCAGCGCACCCGGCAGCCCmψGCCGGCAGCCCCACCmψCCACAGA | |
| | GGAGGGAACCAGCACCGAGCCCAGCGAAGGCAGCGCCCCAGGCACCAGCACCGAGCCmψAGmψG | |
| | AGCAGGAGAmψmψAAACGGAmCAACAAGAmψCAGAAGAAGACmψmψψGmψGAAAGACAGCAACA | |
| | CCAAGAAGGCCGGCAAGACAGGCCCCAmψGAAAACCCmψGCmψGGmψmψAGAGmψGAmψGACAC | |
| | CCGAmψCmψGAGAGAGCGGCmψGGAAAACCmψGAGAAAGAAGCCmψGAAAAm;AmψCCCCCAGC | |
| | CCAmψCAGCAAmψACAmψCmψAGAGCCAACCmψGAAmψAAGCmψGCmψGACCGAmψmψACACCG | |
| | AAAmψGAAGAAGGCGAmψCCmψGCAmψGmψGmψACmψGGGAAGAGmψmψCCAGAAGGACCCmψG | |
| | mψGGGCCmψGAmψGAGCCGGGmψGGCCCAGCCmψGCCAGCAAGAAGAmψCGAmψCAGAACAAGC | |
| | mψGAAACCmψGAGAmψGGACGAGAAGGGCAACCmψGACCACCGCCGGCmψmψmψGCCmψGCmψC | |
| | mψCAGmψGmψGGCCAGCCCCmψGmψmψCGmψGmψACAAGCmψGGAGCAGGmψGmψCmψGAGAAG | |
| | GGCAAGGCmψmψACACCAACmψACmψmψCGGACGGmψGCAAmψGmψGGCCGAGCACGAAAAGCm | |
| | ψGAmψCCmψGCmψGGCCCAGCmψGAAGCCCGAGAAGGAmψAGCGACGAAGCCGmψGACAmψAmψ | |
| | AGCCmψGGGAAAGmψmψmψGGGCAGAGGGCCCmψGGAmψmψmψCmψACAGCAmψmψCAmψGmψG | |
| | ACCAAGGAGmψCCACCCACCCCGmψGAAGCCCCmψGGCCCAGAmψCGCCGGAAACAGAmψACGC | |
| | CmψCCGGACCmψGmψGGGAAAGGCCCmψGAGCGACGCAmψGmψAmψGGGCACAAmψCGCCmψCC | |
| | mψmψCCmψGmψCmψAAGmψACCAGGACAmψCAmψCAmψCGAACACCAGAAGGmψGGmψGAAGGG | |
| | CAACCAGAAGAGACmψGGAGAGCCmψGCGGGAGCmψGGCCGGCAAGGAAAACCmψGGAAmψACC | |
| | CmψAGCGmψGACCCmψGCCACCmψCAGCCmψCACACCAAGGAGGGCGmψmψGAmψGCCmψACAA | |
| | CGAAGmψGAmψCGCCCGGGmψGCGAAmψGmψGGGmψGAACCmψGAACCmψGmψGGCAGAAGCmψ | |
| | GAAGCmψAAGCAGAGAmψGAmψGCCAAGCCmψCmψGCmψGAGACmψGAAGGGAmψmψCCCmψmψ | |
| | CCmψmψmψCCmψCmψGGmψCGAGAGACAGGCCAACGAAGmψGGACmψGGmψGGGACAmψGGmψG | |
| | mψGmψAACGmψGAAGAAGCmψGAmψCAACGAGAAAAAGGAGGAmψGGCAAGGmψGmψmψmψmψG | |
| | GCAGAAmψCmψGGCmψGGCmψACAAGAGACAGGAAGCCCmψGAGACCAmψACCmψGAGCAGCGA | |
| | GGAAGAmψCGGAAGAAGGGAAAGAAAmψmψCGCmψCGGmψACCAGCmψGGGCGACCmψGCmψGC | |
| | mψGCACCmψGGAAAAGAAGCACGGCGAGGACmψGGGGAAAGGmψGmψACGACGAGGCCmψGGGA | |
| | GCGGAmψmψGACAAGAAAGmψGGAAGGCCmψGAGCAAGCACAmψCAAGCmψGGAAGAGGAACGG | |
| | AGAAGCGAGGACGCCCAGAGCAAGGCCGCCCmψGACCGACmψGGCmψGCGGGCmψAAGGCCAGC | |
| | mψmψCGmψGAmψCGAGGGCCmψGAAGGAGGCCGACAAGGACGAGmψmψCmψGCAGAmψGCGAGC | |
| | mψGAAGCmψGCAGAAGmψGGmψACGGGGACCmψGCGGGGAAAGCCCmψmψCGCCAmψCGAAGCC | |
| | GAGAACAGCAmψCCmψGGACAmψCAGCGGCmψmψCAGCAAGCAGmψACAACmψGmψGCCmψmψC | |
| | AmψCmψGGCAGAAGGACGGCGmψGAAGAAGCmψGAACCmψGmψACCmψGAmψCAmψCAACmψAC | |
| | mψmψCAAGGGCGGCAAGCmψGCGGmψmψCAAGAAGAmψCAAACCmψGAAGCCmψmψCGAAGCCA | |
| | ACAGAmψmψCmψACACCGmψGAmψCAACAAAAAGAGCGGCGAGAmψCGmψGCCCAmψGGAGGmψ | |
| | GAACmψmψCAACmψmψCGACGACCCCAACCmψGAmψCAmψCCmψGCCmψCmψGGCCmψmψmψGG | |
| | CAAGAGACAGGGCAGAGAAmψmψCAmψCmψGGAACGACCmψGCmψGmψCCCmψGGAAACCGGCA | |
| | GCCmψGAAGCmψGGCCAACGGAAGAGmψGAmψCGAGAAGACACmψGmψACAACAGAAGAACCCG | |
| | GCAGGAmψGAGCCmψGCCCmψGmψmψCGmψGGCCCmψGACCmψmψCGAGGCGGGGGAGGmψCCm | |
| | ψGGACmψCCmψCCAAmψAmψCAAACCAAmψGAACCmψGAmψCGGCGmψGGCAAGAGGCGAAAAC | |
| | AmψCCCCGCCGmGAmψCGCCCmψGACCGACCCCGAGGGCmψGCCCACmψGAGCCGGmψψmψmψA | |
| | AGGAmψAGCCmψGGGAAACCCAACCCACAmψCCmψGAGAAmψCGGCGAGAGCmψAmψAAGGAGA | |
| | AGCAGCGGACCAmψCCAGGCCAAGAAGGAGGmψGGAGCAGCGGAGAGCCGGCGGCmψACAGCCG | |
| | GAAGmψACGCCAGCAAAGCCAAGAAmψCmψGGCAGACGAmψAmψGGmψGAGAAACACCGCmψAG | |
| | AGAmψCmψGCmψGmψACmψACGCCGmψGACCCAGGAmψGCCAmψGCmψGAmψCmψmψCGCCAAC | |

TABLE 43-continued

Full-length RNA sequences of additional ELXR mRNA molecψles in Table 42 for assessment. Modification 'mψ' = N1-methyl-pseudouridine.

| ELXR ID | RNA sequence | SEQ ID NO |
|---|---|---|
| | CmψGAGCCGGGGCmψmψCGGCCGGCAGGGCAAGCGGACCmψmψCAmψGGCCGAGAGACAGmψAC ACACGGAmψGGAGGACmψGGCmψGACCGCCAAGCmψGGCCmψACGAGGGCCmψGAGCAAGACCm ψACCmψGmψCCAAGACACmψGGCCCAGmψACACCmψCCAAGACAmψGCAGCAACmψGmψGGGmψ mψmψACCAmψCACCAGCGCCGACmψACGACAGGGmψGCmψGGAGAAGCmψGAAGAAGACAGCAA CAGGCmψGGAmψGACCACAAmψmψAACGGCAAGGAGCmψGAAGGmψGGAGGGCCAGAmψmψACC mψACmψACAACAGAmψACAAGAGACAGAACGmψAGmψCAAGGACCmψGmψCCGmψCGAGCmψGG AmψAGACmψGAGCGAAGAAmψCmψGmψGAACAACGACAmψCmψCCmψCCmψGGACAAAGGGCAG AAGCGGAGAAGCmψCmψGAGCCmψCCmψGAAGAAAAGAmψmψCmψCCCAmψAGACCCGmψGCAG GAGAAGmψmψCGmψGmψGCCmψGAACmψGCGGCmψmψCGAGACACACGCAGCCGAGCAAGCCGC CCmψGAACAmψCGCCAGAmψCCmψGGCmψGmψmψCCmψGCGGAGCCAGGAGmψACAAGAAAmψA CCAGACAAACAAGACAACCGGCAACACCGAmTAAGAGAGCCmψmψCGmψCGAGACCmψGGCAGm ψCCmψmψmψmψACCGGAAGAAGCmψmψAAGGAGGmψGmψGGAAACCmψGCCGmψGCGGmψCmψG GCGGAmψCmψGGCGGAGGCmψCCACCAGCCCCAAGAAAAAGAGAAAAGmψCmψAAmψAGAmψAA GCmψGCCmψmψCmψGCGGGGCmψmψGCCmψmψCmψGGCCAmψGCCCmψmψCmψmψCmψCmψCCC mψmψGCACCmψGmψACCmψCmψmψGGmψCmψmψmψGAAmψAAAGCCmψGAGmψAGGAAGmψCmψ AGAAAAAAAAAAAAAAAAAAAAAAAAAAAAAAAAAAAAAAAAAAAAAAAAAAAAAAAAAA AAAAAAAAAAAAAAAA | |
| ELXR 5-ZIM3 + ADD | AAAmψAAGAGAGAAAAGAAGAGmψAAGAAGAAAmψAmψAAGAGCCACCAmψGGCCCCmψAAGAA GAAGCGmψAAAGmψGAGCCGGAmψGGAACGCCmψCGmψCmψACGAGGmψGCGGCAGAAGmψGCA GAAACAmψCGAGGACAmψCmψGCAmψCmψCCmψGCGGAmCmψψCmψGAACGmψGACCCmψGGAG CACCCACmψGmψmψCAmψCGGCGGCAmψGmψGCCAGAACmψGmψAAAAACmψGmψmψmψmψCmψ GGAGmψGmψGCCmψAmψCAAmψACGACGAmψGACGGCmψACCAGAGCmψACmψGCACCAmψCmψ GmψmψGCGGCGGAAGAGAGGmψGCmψGAmψGmψGmψGGAAAmψAACAACmψGCmψGCCGGmψGC mψmψCmψGCGmψGGAAmψGCGmψGGACCmψGCmψGGmψGGGCCCCGGCGCCGCCCAGGCCGCmψ AmψmψAAGGAAGAmψCCmψmψGGAACmψGCmψACAmψGmψGCGGCCACAAGGGCACAmψACGGC CmψGCmψGAGACGGAGAGAGGACmψGGCCmψAGCAGACmψGCAGAmψGmψmψCmψmψCGCCAAm ψAACCACGACCAGGAGmψmψCGACCCCCmψAAGGmψGmψACCCmψCCCGmψCCCCGCCGAGAA GAGAAAGCCCAmψCCGGGmψCCmψGAGCCmψGmψmψCGAmψGGCAmψCGCCACCGGmψCmψGCm ψGGmψGCmψGAAGGACCmψGGGCAmψCCAGGmψGGAmψAGGmψACAmψmψGCCmψCCGAGGmψG mψGCGAGGACmψCCAmψCACCGmψGGGAAmψGGmψGCGmψCAmψCAGGGCAAGAmψCAmψGmψA CGmψGGGCGACGmψGCGGAGCGmψGACACAGAAGCAmψAmψCCAGGAGmψGGGGCCCmψmψmψC GACCmψGGmψGAmψCGGCGGCAGCCCmψmψGCAAmψGACCmψGAGCAmψCGmψGAACCCAGCCC GGAAGGGCCmψGmψACGAGGGAACCGGCAGACmψGmψmψCmψmψCGAGmψmψmψmψACAGACmψ GCmψGCACGACGCCCGGCCmψAAGGAAGGCGACGACCGGCCCmψmψCmψmψmψmψGGCmψGmψm ψCGAGAAmψGmψGGmψGGCCAmψGGGAGmψCAGCGACAAGCGGGAmψAmψmψAGCCGGmψmψCC mψGGAGAGCAACCCCGmψGAmψGAmψCGAmψGCCAAGGAAGmψGAGCGCCGCCCACCGGGCCAG AmψACmψmψCmψGGGGCAAmψCmψGCCmψGGCAmψGAACAGACCCCmψGGCCAGCACCGmψGAA CGACAAGCmψGGAGCmψGCAGGAGmψGCCmψGGAGCACGGCCGGAmψCGCCAAGmψmψCAGCAA GGmψGAGAACCAmψCACCACCCGAAGCAACAGCAmψCAAACAAGGCAAGGACCAGCACmψmψmψ CCmψGmψGmψmψCAmψGAACGAGAAGGAGGACAmψCCmψGmψGGmψGmψACCGAGAmψGGAGAG AGmψGmψmψCGGGmψmψCCCAGmψCCACmψACACAGAmψGmψCAGCAACAmψGmψCmψAGACmψ GGCCAGACAGAGACmψGCmψGGGAAGAAGCmψGGmψCCGmψCCCmψGmψGAmψCAGACACCmψG mψmψCGCCCCmψCmψGAAGGAGmψACmψmψCGCCmψGCGmψGAGCAGCGGCAACAGCAACGCCA ACAGCCGGGGCCCCAGCmψmψCmψCmψAGCGGCCmψGGmψGCCACmψGmψCCCmψGAGAGGGAG CCACAmψGGGCCCCAmψGGAGAmψCmψACAAAACCGmψGAGCGCCmψGGAAGCGGCAGCCmψGm ψGCGCGmψGCmψGAGCCmψGmψmψmψCGGAAmψAmψCGAmψAAAGmψCCmψGAAAAGCCmψGGG AmψmψCCmψGGAGAGCGGCmψCmψGGCmψCCGGCGGmψGGCACCCmψGAAGmψACGmψGGAGGA mψGmψGACAAACGmψGGmψCAGACGGGAmψGmψGGAGAAGmψGGGGCCCmψmψCGAmψCmψGG mψGmψACGGCAGCACCCAACCCCmψGGGCAGCmψCmψmψGmψGACCGGmψGCCCmψGGCmψGGm ψACAmψGmψmψmψCAGmψmψCCACCGGAmψCCmψGCAGmψACGCCCmψGCCGAGACAGGAGmψC CCAGCGGCCAmψmψCmψmψmψmψGGAmψmψmψmψCAmψGGACAACmψmψGCmψGCmψGACCGAG GAmψGACCAGGAAACmψACCACmψCGGmψmψCCmψGCAGACCGAAGCCGmψGACCCmψGCAGGA CGmψGAGAGGCCGGGACmψACCAGAACGCCAmψGCGGGmψGmψGGmψCCAACAmψCCCmψGGAC mψGAAAAGCAAGCACGCACCmψCmψGACCCCmψAAAGAAGAGGAGmψACCmψGCAGGCCCAGGm ψGCGGAGCAGAAGCAAGCmψGGACGCCCCmψAAGGmψGGAmψCmψGCmψGGmψGAAGAAmψmψG CCmψCCmψGCCCCmψGAGAGAGmψACmψmψCAAGmψAmψmψmψCAGCCAGAAmψAGmψCmψGCC CCmψGGGAGGCAGCGGCGGCGGCAmψGAACAACmψCCCAGGGCAGAGmψGACCmψmψCGAGGAC GmψGACCGmψGAAmψmψmψmψACACAGGGAGAGmψGGCAGAGACmψGAACCCCGAGCAGAGAAA CCmψGmψACCGGGAmψGmψGAmψGCmψGGAAAACmψACAGCAAmψCmψGGmψGmψCCGmψGGGC CAGGGCGAGACCACAAAGCCmψGACGmψGAmψCCmψGCGmψCmψGGAGCAGGGCAAGGAACCCm ψGGCmψGGAGGAGGAGGAGGmψGCmψGGGAAGCGGACGGGCCGAGAAGAACGGCGACAmψCGGC GGACAGAmψCmψGGAAGCCmψAAGGACGmψGAAAGAAAGCCmψGGGCGGCCCAAGCAGCGGCGC CCCCmψCCmψCCCAGCGGCGGCAGCCCAGCCGGCmψCCCCAACCmψCmψACCGAGGAGGGCACCm ψCmψGAGmψCCGCCACCCCCGAGAGCGGCCCmψGGCACCmψCCACCGAGCCCAGCGAGGGCAGC GCACCCGGCAGCCCmψGCCGGCAGCCCCACCmψCCACAGAGGAGGGAACCAGCACCGAGCCCAG CGAAGGCAGCGCCCCAGGCACCAGCACCGAGCCmψAGmψGAGCAGGAGAmψmψAAACGGAmψCA ACAAGAmψCAGAAGAAGACmψmψGmψGAAAGACAGCAACACCAAGAAGGCCGGCAAGACAGGCC CCAmψGAAAACCCmψGCmψGGmψmψAGAGmψGAmψGACACCCGAmψCmψGAGAGAGCGGCmψGG AAAACCmψGAGAAAGAAGCCmψGAAAAmψAmψCCCCCAGCCCAmψCAGCAAmψACAmψCmψAGA GCCAACCmψGAAmψAAGCmψGCmψGACCGAmψmψACACCGAAAmψGAAGAAGGCGAmψCCmψGC AmψGmψGmψACmψGGGAAGAGmψmψCCAGAAGGACCCmψGmψGGGCCmψGAmψGAGCCGGGmψG GCCCAGCCmψGCCAGCAAGAAGAmψCGAmψCAGAACAAGCmψGAAACCmψGAGAmψGGACGAGA | 59624 |

TABLE 43-continued

Full-length RNA sequences of additional ELXR mRNA molecψles in Table 42 for assessment. Modification 'mψ' = N1-methyl-pseudouridine.

| ELXR ID | RNA sequence | SEQ ID NO |
|---|---|---|
| | AGGGCAACCmψGACCACCGCCGGCmψmψmψGCCmψGCmψCmψCAGmψGmψGGCCAGCCCCmψGm<br>ψmψCGmψGmψACAAGCmψGGAGCAGGmψGmψCmψGAGAAGGGCAAGGCmψmψACACCAACmψAC<br>ψmψmψCGGACGGmψGCAAmψGmψGGCCGAGCACGAAAAGCmψGAmψCCmψGCmψGGCCCAGCmG<br>AAGCCCGAGAAGGAmψAGCGACGAAGCCGmψGACAmψAmψAGCCmψGGGAAAGmψmψmψGGGCA<br>GAGGGCCCmψGGAmψmψmψCmψACAGCAmψmψCAmψGmψGACCAAGGAGmψCCACCCACCCCGm<br>ψGAAGCCCCmψGGCCCAGAmψCGCCGGAAACAGAmψACGCCmψCCGGACCmψGmψGGGAAAGGC<br>CCmψGAGCGACGCAmψGmψAmψGGGCACAAmψCGCCmψCCmψmψCCmψGmψCmψAAGmψACCAG<br>GACAmψCAmψCAmψCGAACACCAGAAGGmψGGmψGAAGGGCAACCAGAAGAGACmψGGAGAGCC<br>mψGCGGGAGCmψGGCCGGCAAGGAAAACCmψGGAAmψACCCmψAGCGmψGACCCmψGCCACCmψ<br>CAGCCmψCACACCAAGGAGGGCGmψmψGAmψGCCmψACAACGAAGmψGAmψCGCCCGGGmψGCG<br>AAmψGmψGGGmψGAACCmψGAACCmψGmψGGCAGAAGCmψGAAGCmψAAGCAGAGAmψGAmψGC<br>CAAGCCmψCmψGCmψGAGACmψGAAGGGAmψmψCCCmψmψCCmψmψmψCCmψCmψGGmψCGAGA<br>GACAGGCCAACGAAGmψGGACmψGGmψGGGACAmψGGmψGmψGmψAACGmψGAAGAAGCmψGAm<br>ψCAACGAGAAAAAGGAGGAmψGGCAAGGmψGmψmψmψmψGGCAGAAmψCmψGGCmψGGCmψACA<br>AGAGACAGGAAGCCCmψGAGACCAmψACCmψGAGCAGCGAGGAAGAmψCGGAAGAAGGGAAAGA<br>AAmψmψCGCmψCGGmψACCAGCmψGGGCGACCmψGCmψGCmψGCACCmψGGAAAAGAAGCACGG<br>CGAGGACmψGGGGAAAGGmψGmψACGACGAGGCCmψGGGAGCGGAmψmψGACAAGAAAGmψGGA<br>AGGCCmψGAGCAAGCACAmψCAAGCmψGGAAGAGGAACGGAGAAGCGAGGACGCCCAGAGCAAG<br>GCCGCCCmψGACCGACmψGGCmψGCGGGCmψAAGGCCAGCmψmψCGmψGAmψCGAGGGCCmψGA<br>AGGAGGCCGACAAGGACGAGmψmψCmψGCAGAmψGCGAGCmψGAAGCmψGCAGAAGmψGGmψAC<br>GGGGACCmψGCGGGGAAAGCCCmψmψCGCCAmψCGAAGCCGAGAACAGCAmψCCmψGGACAmψC<br>AGCGGCmψmψCAGCAAGCAGmψACAACmψGmψGCCmψmψCAmψCmψGGCAGAAGGACGGCGmψG<br>AAGAAGCmψGAACCmψGmψACCmψGAmψCAmψCAACmψACmψmψCAAGGGCGGCAAGCmψGCGG<br>mψmψCAAGAAGAmψCAAACCmψGAAGCCmψmψCGAAGCCAACAGAmψmψCmψACACCGmψGAmψ<br>CAACAAAAAGAGCGGCGAGAmψCGmψGCCCAmψGGAGGmψGAACmψmψCAACmψmψCGACGACC<br>CCAACCmψGAmψCAmψCCmψGCCmψCmψGGCCmψmψmψGGCAAGAGACAGGGCAGAGAAmψmψC<br>AmψCmψGGAACGACCmψGCmψGmψCCCmψGGAAACCGGCAGCCmψGAAGCmψGGCCAACGGAAG<br>AGmψGAmψCGAGAAGACACmψGmψACAACAGAAGAACCCGGCAGGAmψGAGCCmψGCCCmψGmψ<br>mψCGmψGGCCCmψGACCmψmψCGAGCGGCGGGAGGmψCCmψGGACmψCCmψCCAAmψAmψCAAA<br>CCAAmψGAACCmψGAmψCGGCGmψGGCAAGAGGCGAAAACAmψCCCCGCCGmψGAmψCGCCCmψ<br>GACCGACCCCGAGGGCmψGCCCACmψGAGCCGGmψmψmψAAGGAmψAGCCmψGGGAAACCCAAC<br>CCACAmψCCmψGAGAAmψCGGCGAGAGCmψAmψAAGGAGAAGCAGCGGACCAmψCCAGGCCAAG<br>AAGGAGGmψGGAGCAGCGGAGAGCCGGCGGCmψACAGCCGGAAGmψACGCCAGCAAAGCCAAGA<br>AmψCmψGGCAGACGAmψAmψGGmψGAGAAACACCGCmψAGAGAmψCmψGCmψGmψACmψACGCC<br>GmψGACCCAGGAmψGCCAmψGCmψGAmψCmψmψCGCCAACCmψGAGCCGGGGCmψmψCGGCCGG<br>CAGGGCAAGCGGACCmψmψCAmψGGCCGAGAGACAGmψACACACGGAmψGGAGGACmψGGCmψG<br>ACCGCCAAGCmψGGCCmψACGAGGGCCmψGAGCAAGACCmψACCmψGmψCCAAGACACmψGGCC<br>CAGmψACACCmψCCAAGACAmψGCAGCAACmψGmψGGGmψmψmψACCAmψCACCAGCGCCGACm<br>ψACGACAGGGmψGCmψGGAGAAGCmψGAAGAAGACAGCAACAGGCmψGGAmψGACCACAAmψmψ<br>AACGGCAAGGAGCmψGAAGGmψGGAGGGCCAGAmmψACCmψψACmψACAACAGAmψACAAGAGA<br>CAGAACGmψAGmψCAAGGACCmψGmψCCGmψCGAGCmψGGAmψAGACmψGAGCGAAGAAmψCmψ<br>GmψGAACAACGACAmψCmψCCmψCCmψGGACAAAGGGCAGAAGCGGAGAAGCmψCmψGAGCCmψ<br>CCmψGAAGAAAAGAmψmψCmψCCCAmψAGACCCGmψGCAGGAGAAGmψmψCGmψGmψGCCmψGA<br>ACmψGCGGCmψmψCGAGACACACGCAGCCGAGCAAGCCGCCCmψGAACAmψCGCCAGAmψCCmψ<br>GGCmψGmψmψCCmψGCGGAGCCAGGAGmψACAAGAAAmψACCAGACAAACAAGACAACCGGCAA<br>CACCGAmψAAGAGAGCCmψmψCGmψCGAGACCmψGGCAGmψCCmψmψmψmψACCGGAAGAAGCm<br>ψmψAAGGAGGmψGmψGGAAACCmψGCCGmψGCGGmψCmψGGCGGAmψCmψGGCGGAGGCmψCCA<br>CCAGCCCCAAGAAAAAGAGAAAAGmψCmψAAmψAGAmψAAGCmψGCCmψmψCmψGCGGGGCmψm<br>ψGCCmψmψCmvGGCCAmψGCCCmψmψCmψmψCmψCmψCCCmψmψGCACCmψGmψACCmψCmψmψ<br>GGmψCmψmψmψGAAmψAAAGCCmψGAGmψAGGAAGmψCmψAGAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAAAA | |

Synthesis of targeting gRNAs (e.g., targeting the endogenous B2M locus) will be performed as described above in Example 14.

LNP formulations will be performed as described in Example 16.

Delivery of LNPs encapsulating ELXR mRNA and targeting gRNAs into mouse liver Hepa1-6 cells:

Hepa1-6 cells will be seeded in a 96-well plate. The next day, seeded cells will be treated with varying concentrations of LNPs, which will be prepared in six 2-fold serial dilutions starting at 250 ng. These LNPs will be formulated to encapsulate an ELXR mRNA and a B2M-targeting gRNA. Media will be changed 24 hours after LNP treatment, and cells will be cultured before being harvested at multiple timepoints (e.g., 7, 14, 21, 28, and 56 days post-treatment) for gDNA extraction for editing assessment at the B2M locus by NGS and for bisulfite sequencing to assess off-target methylation at the VEGFA locus as described in Example 6.

The results from this experiment are expected to show that ELXR mRNA and targeting gRNA can be co-encapsulated within LNPs to be delivered to target cells to induce heritable silencing of a target endogenous locus.

Example 16: Formulation of Lipid Nanoparticles (LNPs) to Deliver XR or ELXR mRNA and gRNA Payloads to Target Cells and Tissue Experiments will be performed to encapsulate XR or ELXR mRNA and gRNA into LNPs for delivery to target cells and tissue. Here, XR or ELXR mRNA and gRNA will be encapsulated into LNPs using GenVoy-ILM™ lipids using the Precision NanoSystems Inc. (PNI) Ignite™ Benchtop System, following the manufacturer's guidelines. GenVoy-ILM™ lipids are a composition of ionizable lipid: DSPC:cholesterol:stabilizer at 50:10:37.5:2.5 mol %. Briefly, to formulate LNPs, equal mass ratios of XR or ELXR mRNA and gRNA will be diluted in PNI Formulation Buffer, pH 4.0. GenVoy-ILM™ lipids will be diluted 1:1 in anhydrous ethanol. mRNA/gRNA co-formulations will be performed using a predetermined N/P ratio. The RNA and lipids will be run through a PNI laminar flow cartridge at a predetermined flow rate ratio on the PNI Ignite™ Benchtop System. After formulation, the LNPs will be diluted in PBS, pH 7.4, to decrease the ethanol concentration and increase the pH, which increases the stability of the particles. Buffer exchange of the mRNA/sgRNA-LNPs will be achieved by overnight dialysis into PBS, pH 7.4, at 4° C. using 10k Slide-A-Lyzer™ Dialysis Cassettes (Thermo Scientific™). Following dialysis, the mRNA/gRNA-LNPs will be concentrated to >0.5 mg/mL using 100 kDa Amicon®-Ultra Centrifugal Filters (Millipore) and then filter-sterilized. Formulated LNPs will be analyzed on a Stunner (Unchained Labs) to determine their diameter and polydispersity index (PDI). Encapsulation efficiency and RNA concentration will be determined by RiboGreen™ assay using Invitrogen's Quant-iT™ RiboGreen™ RNA assay kit. LNPs will be used in various experiments to deliver XR or ELXR mRNA and gRNA to target cells and tissue.

Example 17: Members of the Top 95 KRAB Domains Increase ELXR5 Activity

As described in Example 4, KRAB domains were identified that were superior repressors in the context of dXR constructs. As described herein, experiments were performed to test whether the KRAB domains identified in Example 4 were also superior transcriptional repressors in Example 4 in the context of ELXR5.

Materials and Methods:

Representative KRAB domains identified in Example 4 and determined to be members of the top 95 performing repressors were cloned into an ELXR5 construct (see FIG. 7 for ELXR #5 configuration). The ELXR5 constructs were constructed as described in Example 6 (Table 25 and Table 26), except that an SV40 NLS was present downstream of the KRAB domains. An ELXR5 molecule with a KRAB domain derived from ZIM3 was used as a control. A separate plasmid was used to encode guide scaffold 316 (SEQ ID NO: 59352) with spacer 7.165 (UCCCUAUGUCC-UUGCUGUUU; SEQ ID NO: 59667) targeting the B2M locus. Additional controls included a dXR molecule with a KRAB domain derived from ZIM3 with the same guide and spacer, and ELXR5 and dXR molecules with KRAB domains derived from ZIM3 and non-targeting 0.0 spacers (SEQ ID NO: 57646). Notably, spacer 7.165 was chosen because it is known to be a relatively inefficient spacer which would therefore increase the dynamic range of the assay for discerning differences between the various ELXR molecules tested.

HEK293T cells were transfected as described in Example 11, except that the cells were transfected with 50 ng each of a plasmid encoding the ELXR construct and a plasmid encoding the sgRNA. Repression analysis was conducted by analyzing B2M protein expression via HLA immunostaining followed by flow cytometry seven days following transfection, as described in Example 6.

Results

The results of the 1B2M assay are provided in Table 44, below.

TABLE 44

Levels of B2M repression mediated by XR and ELXR constructs with various KRAB domains quantified at seven days post-transfection.

| Repressor construct | KRAB domain | Spacer | Mean % HLA negative cells | Standard deviation | Sample size |
|---|---|---|---|---|---|
| ELXR5 | ZIM3 | 0.0 | 6.703333 | 1.169031 | 3 |
| XR | ZIM3 | 7.165 | 7.36 | 1.626346 | 2 |
| XR | ZIM3 | 0.0 | 7.786667 | 0.721757 | 3 |
| ELXR5 | DOMAIN_27811 | 7.165 | 22.63333 | 0.64291 | 3 |
| ELXR5 | DOMAIN_17317 | 7.165 | 25.93333 | 0.585947 | 3 |
| ELXR5 | DOMAIN_17358 | 7.165 | 27.76667 | 3.06159 | 3 |
| ELXR5 | DOMAIN_18258 | 7.165 | 29.13333 | 0.776745 | 3 |
| ELXR5 | DOMAIN_8503 | 7.165 | 29.7 | 0.888819 | 3 |
| ELXR5 | DOMAIN_4968 | 7.165 | 30.13333 | 2.804164 | 3 |
| ELXR5 | DOMAIN_15126 | 7.165 | 30.33333 | 0.305505 | 3 |
| ELXR5 | DOMAIN_28803 | 7.165 | 30.36667 | 0.90185 | 3 |
| ELXR5 | DOMAIN_19949 | 7.165 | 31.96667 | 2.510644 | 3 |
| ELXR5 | DOMAIN_22270 | 7.165 | 32.5 | 1.1 | 3 |
| ELXR5 | DOMAIN_5463 | 7.165 | 32.53333 | 0.404145 | 3 |
| ELXR5 | DOMAIN_24125 | 7.165 | 32.66667 | 1.289703 | 3 |
| ELXR5 | ZIM3 | 7.165 | 32.9 | 0.43589 | 3 |
| ELXR5 | DOMAIN_23723 | 7.165 | 33.4 | 2.170253 | 3 |
| ELXR5 | DOMAIN_11029 | 7.165 | 33.46667 | 1.289703 | 3 |
| ELXR5 | DOMAIN_19229 | 7.165 | 33.96667 | 0.321455 | 3 |
| ELXR5 | DOMAIN_21603 | 7.165 | 34.36667 | 0.404145 | 3 |
| ELXR5 | DOMAIN_8790 | 7.165 | 34.9 | 0.608276 | 3 |
| ELXR5 | DOMAIN_11386 | 7.165 | 35.63333 | 1.677299 | 3 |
| ELXR5 | DOMAIN_16806 | 7.165 | 35.66667 | 1.450287 | 3 |
| ELXR5 | DOMAIN_6248 | 7.165 | 36 | 2.351595 | 3 |
| ELXR5 | DOMAIN_16444 | 7.165 | 36.36667 | 1.703917 | 3 |
| ELXR5 | DOMAIN_11486 | 7.165 | 36.66667 | 1.320353 | 3 |
| ELXR5 | DOMAIN_4806 | 7.165 | 36.76667 | 1.747379 | 3 |
| ELXR5 | DOMAIN_17905 | 7.165 | 36.93333 | 1.446836 | 3 |
| ELXR5 | DOMAIN_14755 | 7.165 | 37.35 | 0.070711 | 2 |
| ELXR5 | DOMAIN_5066 | 7.165 | 37.83333 | 1.02632 | 3 |
| ELXR5 | DOMAIN_21247 | 7.165 | 37.86667 | 2.218859 | 3 |
| ELXR5 | DOMAIN_14659 | 7.165 | 37.93333 | 1.767295 | 3 |
| ELXR5 | DOMAIN_10331 | 7.165 | 38.3 | 1.30767 | 3 |
| ELXR5 | DOMAIN_11348 | 7.165 | 38.43333 | 1.28582 | 3 |
| ELXR5 | DOMAIN_25289 | 7.165 | 38.53333 | 0.945163 | 3 |
| ELXR5 | DOMAIN_21755 | 7.165 | 38.66667 | 1.497776 | 3 |
| ELXR5 | DOMAIN_13331 | 7.165 | 38.7 | 2.163331 | 3 |
| ELXR5 | DOMAIN_24663 | 7.165 | 39.43333 | 6.047589 | 3 |
| ELXR5 | DOMAIN_27506 | 7.165 | 39.46667 | 1.504438 | 3 |
| ELXR5 | DOMAIN_6807 | 7.165 | 39.5 | 0.43589 | 3 |
| ELXR5 | DOMAIN_28640 | 7.165 | 39.9 | 1.276715 | 3 |
| ELXR5 | DOMAIN_11683 | 7.165 | 40.26667 | 0.152753 | 3 |
| ELXR5 | DOMAIN_12631 | 7.165 | 40.3 | 0.6245 | 3 |
| ELXR5 | DOMAIN_23394 | 7.165 | 40.73333 | 2.285461 | 3 |
| ELXR5 | DOMAIN_13539 | 7.165 | 40.8 | 2.306513 | 3 |
| ELXR5 | DOMAIN_2380 | 7.165 | 41.1 | 1.276715 | 3 |
| ELXR5 | DOMAIN_16643 | 7.165 | 41.13333 | 1.205543 | 3 |
| ELXR5 | DOMAIN_18216 | 7.165 | 41.4 | 0.818535 | 3 |
| ELXR5 | DOMAIN_737 | 7.165 | 41.46667 | 3.257811 | 3 |
| ELXR5 | DOMAIN_16688 | 7.165 | 41.8 | 0.264575 | 3 |
| ELXR5 | DOMAIN_19804 | 7.165 | 42.06667 | 1.913984 | 3 |
| ELXR5 | DOMAIN_10948 | 7.165 | 42.73333 | 0.92376 | 3 |
| ELXR5 | DOMAIN_26322 | 7.165 | 42.76667 | 4.66083 | 3 |
| ELXR5 | DOMAIN_17759 | 7.165 | 43.23333 | 0.92376 | 3 |
| ELXR5 | DOMAIN_9114 | 7.165 | 43.26667 | 1.501111 | 3 |
| ELXR5 | DOMAIN_5290 | 7.165 | 43.4 | 1.135782 | 3 |
| ELXR5 | DOMAIN_221 | 7.165 | 43.43333 | 0.750555 | 3 |
| ELXR5 | DOMAIN_881 | 7.165 | 43.53333 | 1.858315 | 3 |
| ELXR5 | DOMAIN_7255 | 7.165 | 43.56667 | 0.450925 | 3 |
| ELXR5 | DOMAIN_24458 | 7.165 | 43.56667 | 1.331666 | 3 |
| ELXR5 | DOMAIN_19896 | 7.165 | 43.6 | 0.6245 | 3 |
| ELXR5 | DOMAIN_13468 | 7.165 | 43.7 | 1.571623 | 3 |
| ELXR5 | DOMAIN_9960 | 7.165 | 43.96667 | 2.362908 | 3 |
| ELXR5 | DOMAIN_17432 | 7.165 | 43.96667 | 0.907377 | 3 |
| ELXR5 | DOMAIN_18137 | 7.165 | 44.03333 | 0.404145 | 3 |

TABLE 44-continued

Levels of B2M repression mediated by XR and ELXR constructs with various KRAB domains quantified at seven days post-transfection.

| Repressor construct | KRAB domain | Spacer | Mean % HLA negative cells | Standard deviation | Sample size |
|---|---|---|---|---|---|
| ELXR5 | DOMAIN_15507 | 7.165 | 44.06667 | 0.907377 | 3 |
| ELXR5 | DOMAIN_20505 | 7.165 | 45.36667 | 0.568624 | 3 |
| ELXR5 | DOMAIN_6445 | 7.165 | 45.66667 | 2.730079 | 3 |
| ELXR5 | DOMAIN_6802 | 7.165 | 45.76667 | 1.887679 | 3 |
| ELXR5 | DOMAIN_25379 | 7.165 | 46.46667 | 3.868247 | 3 |
| ELXR5 | DOMAIN_22153 | 7.165 | 46.83333 | 0.64291 | 3 |
| ELXR5 | DOMAIN_10123 | 7.165 | 47.83333 | 0.665833 | 3 |
| ELXR5 | DOMAIN_8853 | 7.165 | 48.1 | 4.457578 | 3 |
| ELXR5 | DOMAIN_29304 | 7.165 | 51.7 | 1.4 | 3 |
| ELXR5 | DOMAIN_7694 | 7.165 | 52.4 | 0.43589 | 3 |
| ELXR5 | DOMAIN_30173 | 7.165 | 53.9 | 0.1 | 3 |

As shown in Table 44, constructs with many of the KRAB domains in the top 95 KRAB domains produced higher levels of B2M repression in the context of an ELXR5 molecule with spacer 7.165 compared to an ELXR5 construct with a KRAB domain derived from ZIM3. The highest level of repression was achieved by an ELXR5 molecule with KRAB domain ID 30173, which produced a 35% stronger repression than ELXR5 with a KRAB domain derived from ZIM3. Later timepoints will be assessed to measure the durability of the repression.

Accordingly, the experiments described herein demonstrate that the KRAB domains identified in Example 4 support improved levels of transcriptional repression both in the context of a dXR construct and an ELXR construct.

Example 18: Exemplary Sequences of dXR and ELXR Constructs

Table 45 provides exemplary amino acid sequences of components of dXR and ELXR constructs. In Table 45, the protein domains are shown without starting methionines.

TABLE 45

Exemplary protein sequences of components of dXR and ELXR constructs.

| Key component | Protein sequence | SEQ ID NO |
|---|---|---|
| ZNF10 KRAB domain | DAKSLTAWSRTLVTFKDVFVDFTREEWKLLDTAQQIVYRNVMLENYKNLVSLGYQL TKPDVILRLEKGEEP | 59626 |
| ZIM3 KRAB domain | NNSQGRVTFEDVTVNFTQGEWQRLNPEQRNLYRDVMLENYSNLVSVGQGETTKPDV ILRLEQGKEPWLEEEEVLGSGRAEKNGDIGGQIWKPKDVKESL | 59627 |
| DNMT3A catalψtic domain (CD) | NHDQEFDPPKVYPPVPAEKRKPIRVLSLFDGIATGLLVLKDLGIQVDRYIASEVCE DSITVGMVRHQGKIMYVGDVRSVTQKHIQEWGPFDLVIGGSPCNDLSIVNPARKGL YEGTGRLFFEFYRLLHDARPKEGDDRPFFWLFENVVAMGVSDKRDISRFLESNPVM IDAKEVSAAHRARYFWGNLPGMNRPLASTVNDKLELQECLEHGRIAKFSKVRTITT RSNSIKQGKDQHFPVFMNEKEDILWCTEMERVFGFPVHYTDVSNMSRLARQRLLGR SWSVPVIRHLFAPLKEYFACV | 59450 |
| DNMT3L interaction domain | GPMEIYKTVSAWKRQPVRVLSLFRNIDKVLKSLGFLESGSGSGGGTLKYVEDVTNV VRRDVEKWGPFDLVYGSTQPLGSSCDRCPGWYMFQFHRILQYALPRQESQRPFFWI FMDNLLLTEDDQETTTRFLQTEAVTLQDVRGRDYQNAMRVWSNIPGLKSKHAPLTP KEEEYLQAQVRSRSKLDAPKVDLLVKNCLLPLREYFKYFSQNSLPL | 59625 |
| dCasX491 | QEIKRINKIRRRLVKDSNTKKAGKTGPMKTLLVRVMTPDLRERLENLRKKPENIPQ PISNTSRANLNKLLTDYTEMKKAILHVYWEEFQKDPVGLMSRVAQPASKKIDQNKL KPEMDEKGNLTTAGFACSQCGQPLFVYKLEQVSEKGKAYTNYFGRCNVAEHEKLIL LAQLKPEKDSDEAVTYSLGKFGQRALDFYSIHVTKESTHPVKPLAQIAGNRYASGP VGKALSDACMGTIASFLSKYQDIIIEHQKVVKGNQKRLESLRELAGKENLEYPSVT LPPQPHTKEGVDAYNEVIARVRMWVNLNLWQKLKLSRDDAKPLLRLKGFPSFPLVE RQANEVDWWDMVCNVKKLINEKKEDGKVFWQNLAGYKRQEALRPYLSSEEDRKKGK KFARYQLGDLLLHLEKKHGEDWGKVYDEAWERIDKKVEGLSKHIKLEEERRSEDAQ SKAALTDWLRAKASFVIEGLKEADKDEFCRCELKLQKWYGDLRGKPFAIEAENSIL DISGFSKQYNCAFIWQKDGVKKLNLYLIINYFKGGKLRFKKIKPEAFEANRFYTVI NKKSGEIVPMEVNFNFDDPNLIILPLAFGKRQGREFIWNDLLSLETGSLKLANGRV IEKTLYNRRTRQDEPALFVALTFERREVLDSSNIKPMNLIGVARGENIPAVIALTD PEGCPLSRFKDSLGNPTHILRIGESYKEKQRTIQAKKEVEQRRAGGYSRKYASKAK NLADDMVRNTARDLLYYAVTQDAMLIFANLSRGFGRQGKRTFMAERQYTRMEDWLT AKLAYEGLSKTYLSKTLAQYTSKTCSNCGFTITSADYDRVLEKLKKTATGWMTTIN GKELKVEGQITYYNRYKRQNVVKDLSVELDRLSEESVNNDISSWTKGRSGEALSLL KKRFSHRPVQEKFVCLNCGFETHAAEQAALNIARSWLFLRSQEYKKYQTNKTTGNT DKRAFVETWQSFYRKKLKEVWKPAV | 18 |
| Linker 1 | GGPSSGAPPPSGGSPAGSPTSTEEGTSESATPESGPGTSTEPSEGSAPGSPAGSPT STEEGTSTEPSEGSAPGTSTEPSE | 57621 |
| Linker 2 | SSGNSNANSRGPSFSSGLVPLSLRGSH | 57623 |
| Linker 3A' | GGSGGG | 59451 |
| Linker 3B | GGSGGGS | 57626 |
| Linker 4 | GSGSGGG | 57628 |

TABLE 45-continued

Exemplary protein sequences of components of dXR and ELXR constructs.

| Key component | Protein sequence | SEQ ID NO |
|---|---|---|
| SV40NLS | PKKKRKV | 57631 |
| cMYC NLS | PAAKRVKLD | 33291 |
| DNMT3A | ERLVYEVRQKCRNIEDICISCGSLNVTLEHPLFIGGMCQNCKNCFLECAYQYDDDG | 59452 |
| ADD domain | YQSYCTICCGGREVLMCGNNNCCRCFCVECVDLLVGPGAAQAAIKEDPWNCYMCGH KGTYGLLRRREDWPSRLQMFFAN | |

Table 46 provides exemplary full-length ELXR constructs (including dCaX, NLS, linkers, and repressor domains) in configurations 1, 4, or 5, with or without the ADD domain, with each of the top ten KRAB domains: DOMAIN_737, DOMAIN_10331, DOMAIN_10948, DOMAIN_11029, DOMAIN_17358, DOMAIN_17759, DOMAIN_18258, DOMAIN_19804, DOMAIN_20505, and DOMAIN_26749. Further exemplary full-length ELXR sequences are provided in SEQ ID NOs: 59673-60012.

TABLE 46

Exemplary protein sequences of ELXR molecules containing the top ten KRAB domains with or without the ADD domain and having the #1, #4, or #5 configurations.

| ELXR # | Domains | KRAB domain ID | SEQ ID NO |
|---|---|---|---|
| ELXR #1 | KRAB, DNMT3A CD, DNMT3L Interaction | DOMAIN_737 | 59508 |
| | | DOMAIN_10331 | 59509 |
| | | DOMAIN_10948 | 59510 |
| | | DOMAIN_11029 | 59511 |
| | | DOMAIN_17358 | 59512 |
| | | DOMAIN_17759 | 59513 |
| | | DOMAIN_18258 | 59514 |
| | | DOMAIN_19804 | 59515 |
| | | DOMAIN_20505 | 59516 |
| | | DOMAIN_26749 | 59517 |
| | KRAB, DNMT3A ADD, DNMT3A CD, DNMT3L Interaction | DOMAIN_737 | 59518 |
| | | DOMAIN_10331 | 59519 |
| | | DOMAIN_10948 | 59520 |
| | | DOMAIN_11029 | 59521 |
| | | DOMAIN_17358 | 59522 |
| | | DOMAIN_17759 | 59523 |
| | | DOMAIN_18258 | 59524 |
| | | DOMAIN_19804 | 59525 |
| | | DOMAIN_20505 | 59526 |
| | | DOMAIN_26749 | 59527 |
| ELXR #4 | KRAB, DNMT3A CD, DNMT3L Interaction | DOMAIN_737 | 59528 |
| | | DOMAIN_10331 | 59529 |
| | | DOMAIN_10948 | 59530 |
| | | DOMAIN_11029 | 59531 |
| | | DOMAIN_17358 | 59532 |

TABLE 46-continued

Exemplary protein sequences of ELXR molecules containing the top ten KRAB domains with or without the ADD domain and having the #1, #4, or #5 configurations.

| ELXR # | Domains | KRAB domain ID | SEQ ID NO |
|---|---|---|---|
| | | DOMAIN_17759 | 59533 |
| | | DOMAIN_18258 | 59534 |
| | | DOMAIN_19804 | 59535 |
| | | DOMAIN_20505 | 59536 |
| | | DOMAIN_26749 | 59537 |
| | KRAB, DNMT3A ADD, DNMT3A CD, DNMT3L Interaction | DOMAIN_737 | 59538 |
| | | DOMAIN_10331 | 59539 |
| | | DOMAIN_10948 | 59540 |
| | | DOMAIN_11029 | 59541 |
| | | DOMAIN_17358 | 59542 |
| | | DOMAIN_17759 | 59543 |
| | | DOMAIN_18258 | 59544 |
| | | DOMAIN_19804 | 59545 |
| | | DOMAIN_20505 | 59546 |
| | | DOMAIN_26749 | 59547 |
| ELXR #5 | KRAB, DNMT3A CD, DNMT3L Interaction | DOMAIN_737 | 59548 |
| | | DOMAIN_10331 | 59549 |
| | | DOMAIN_10948 | 59550 |
| | | DOMAIN_11029 | 59551 |
| | | DOMAIN_17358 | 59552 |
| | | DOMAIN_17759 | 59553 |
| | | DOMAIN_18258 | 59554 |
| | | DOMAIN_19804 | 59555 |
| | | DOMAIN_20505 | 59556 |
| | | DOMAIN_26749 | 59557 |
| | KRAB, DNMT3A ADD, DNMT3A CD, DNMT3L Interaction | DOMAIN_737 | 59558 |
| | | DOMAIN_10331 | 59559 |
| | | DOMAIN_10948 | 59560 |
| | | DOMAIN_11029 | 59561 |
| | | DOMAIN_17358 | 59562 |
| | | DOMAIN_17759 | 59563 |
| | | DOMAIN_18258 | 59564 |
| | | DOMAIN_19804 | 59565 |
| | | DOMAIN_20505 | 59566 |
| | | DOMAIN_26749 | 59567 |

SEQUENCE LISTING

The patent contains a lengthy sequence listing. A copy of the sequence listing is available in electronic form from the USPTO web site (https://seqdata.uspto.gov/docdetail?docId=US12553037B2). An electronic copy of the sequence listing will also be available from the USPTO upon request and payment of the fee set forth in 37 CFR 1.19(b)(3).

What is claimed is:

1. A gene repressor system comprising:

a) an RNA encoding a fusion protein, the fusion protein comprising:

i) a catalytically-dead Cas12e (dCasX) protein, wherein the dCasX protein comprises the sequence of SEQ ID NOS: 18, 25, 59355, 59356, 59357 or 59358;

ii) a first transcription repressor domain comprising the sequence of SEQ ID NO: 57755, or a sequence having at least 95% identity thereto;

iii) a second transcription repressor domain; and iv) a third transcription repressor domain, and b) a guide ribonucleic acid (gRNA) capable of forming ribonucleoprotein (RNP) with the fusion protein, wherein the gRNA comprises a targeting sequence complementary to a target nucleic acid sequence of a gene targeted for repression, silencing, or downregulation.

2. The gene repressor system of claim 1, wherein the second transcription repressor domain comprises a DNMT3 A catalytic domain (DNMT3A CD).

3. The gene repressor system of claim 2, wherein the DNTM3A CD comprises the sequence of SEQ ID NO: 59450, or a sequence having at least 95% identity thereto.

4. The gene repressor system of claim 1, wherein the third transcription repressor domain comprises a DNMT3L interaction domain (DNMT3L ID).

5. The gene repressor system of claim 4, wherein the DNMT3L ID comprises the sequence of SEQ ID NO: 59625, or a sequence having at least 95% identity thereto.

6. The gene repressor system of claim 1, wherein the fusion protein comprises a fourth transcription repressor domain, and wherein the fourth transcription repressor domain comprises an ATRX-DNMT3-DNMT3L (ADD) domain.

7. The gene repressor system of claim 6, wherein the C-terminus of the ADD domain is linked to the N-terminus of the second transcription repressor domain, and wherein the second transcription repressor domain comprises a DNMT3A catalytic domain.

8. The gene repressor system of claim 6, wherein the ADD domain comprises the sequence of SEQ ID NO: 59452 or a sequence having at least 95% identity thereto.

9. The gene repressor system of claim 6, wherein the fusion protein comprises, from N to C terminus:

a) a nuclear localization signal (NLS), the ADD domain, the second transcription repressor domain, the third transcription repressor domain, the dCasX protein, the first transcription repressor domain and a second NLS; or b) an NLS, the ADD domain, the second transcription repressor domain, the third transcription repressor domain, the first transcription repressor domain, the dCasX protein, and a second NLS, wherein the first transcription repressor domain, the second transcription repressor domain, the third transcription repressor domain, and the dCasX protein are separated by linker sequences, and wherein:

i) the second transcription repressor domain comprises a DNMT3A catalytic domain (DNMT3A CD); and ii) the third transcription repressor domain comprises a DNMT3L interaction domain (DNMT3L ID).

10. The gene repressor system of claim 1, wherein the fusion protein comprises one or more nuclear localization signals.

11. The gene repressor system of claim 1, wherein the fusion protein comprises one or more linker sequences.

12. The gene repressor system of claim 1, wherein the fusion protein comprises, from N to C terminus:

a) a nuclear localization signal (NLS), the second transcription repressor domain, the third transcription repressor domain, the dCasX protein, the first transcription repressor domain and a second NLS; or b) an NLS, the second transcription repressor domain, the third transcription repressor domain, the first transcription repressor domain, the dCasX protein, and a second NLS, wherein the first transcription repressor domain, the second transcription repressor domain, the third transcription repressor domain, and the dCasX protein are separated by linker sequences, and wherein:

i) the second transcription repressor domain comprises a DNMT3A catalytic domain (DNMT3A CD); and ii) the third transcription repressor domain comprises a DNMT3L interaction domain (DNMT3L ID).

13. A lipid nanoparticle comprising the gene repressor system of claim 1.

14. A method of repressing transcription of a target nucleic acid sequence in a cell, comprising introducing into the cell a gene repressor system comprising:

a) an RNA encoding a fusion protein, the fusion protein comprising:

i) a catalytically-dead Cas12e (dCasX) protein, wherein the dCasX protein comprises the sequence of SEQ ID NO: 18, 25, 59355, 59356, 59357 or 59358;

ii) a first transcription repressor domain comprising the sequence of SEQ ID NO: 57755, or a sequence having at least 95% identity thereto;

iii) a second transcription repressor domain; and iv) a third transcription repressor domain, and b) a guide ribonucleic acid (gRNA) capable of forming ribonucleoprotein (RNP) with the fusion protein, wherein the gRNA comprises a targeting sequence complementary to a target nucleic acid sequence of a gene targeted for repression, silencing, or downregulation.

15. The method of claim 14, wherein the second transcription repressor domain comprises a DNMT3A catalytic domain (DNMT3A CD).

16. The method of claim 15, wherein the DNTM3A CD comprises the sequence of SEQ ID NO: 59450, or a sequence having at least 95% identity thereto.

17. The method of claim 14, wherein the third transcription repressor domain comprises a DNMT3L interaction domain (DNMT3L ID).

18. The method of claim 17, wherein the DNMT3L ID comprises the sequence of SEQ ID NO: 59625, or a sequence having at least 95% identity thereto.

19. The method of claim 14, wherein the dCasX protein comprises the sequence of SEQ ID NO: 18.

20. The method of claim 14, wherein the fusion protein comprises a fourth transcription repressor domain, and wherein the fourth transcription repressor domain comprises an ATRX-DNMT3-DNMT3L (ADD) domain.

21. The method of claim 20, wherein the C-terminus of the ADD domain is linked to the N-terminus of the second transcription repressor domain, and wherein the second transcription repressor domain comprises a DNMT3A catalytic domain.

22. The method of claim 21, wherein the ADD domain comprises the sequence of SEQ ID NO: 59452 or a sequence having at least 95% identity thereto.

23. The method of claim 20, wherein the fusion protein comprises, from N to C terminus:

a) a nuclear localization signal (NLS), the ADD domain, the second transcription repressor domain, the third transcription repressor domain, the dCasX protein, the first transcription repressor domain and a second NLS; or b) an NLS, the ADD domain, the second transcription repressor domain, the third transcription repressor domain, the first transcription repressor domain, the dCasX protein, and a second NLS, wherein the first transcription repressor domain, the second transcription repressor domain, the third transcription repressor domain, and the dCasX protein are separated by linker sequences, and wherein:

i) the second transcription repressor domain comprises a DNMT3A catalytic domain (DNMT3A CD); and ii) the third transcription repressor domain comprises a DNMT3L interaction domain (DNMT3L ID).

24. The method of claim 14, wherein the fusion protein comprises one or more nuclear localization signals.

25. The method of claim 14, wherein the fusion protein comprises one or more linker sequences.

26. The method of claim 14, wherein the fusion protein comprises, from N to C terminus:

a) a nuclear localization signal (NLS), the second transcription repressor domain, the third transcription repressor domain, the dCasX protein, the first transcription repressor domain and a second NLS; or b) an NLS, the second transcription repressor domain, the third transcription repressor domain, the first transcription repressor domain, the dCasX protein, and a second NLS, wherein the first transcription repressor domain, the second transcription repressor domain, the third transcription repressor domain, and the dCasX protein are separated by linker sequences, and wherein:

i) the second transcription repressor domain comprises a DNMT3A catalytic domain (DNMT3A CD); and ii) the third transcription repressor domain comprises a DNMT3L interaction domain (DNMT3L ID).

* * * * *